(12) United States Patent
Nova et al.

(10) Patent No.: US 6,329,139 B1
(45) Date of Patent: *Dec. 11, 2001

(54) AUTOMATED SORTING SYSTEM FOR MATRICES WITH MEMORY

(75) Inventors: Michael P. Nova, Rancho Santa Fe; John E. Lillig, Alamo; Kanchana Sanjaya Gunesekera Karunaratne, San Diego; William Ewing, San Diego; Yozo Satoda, San Diego, all of CA (US); Hanan Potash, Austin, TX (US)

(73) Assignee: Discovery Partners International, San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/912,998

(22) Filed: Aug. 11, 1997

Related U.S. Application Data

(63) Continuation-in-part of application No. 08/826,253, filed on Mar. 27, 1997, now abandoned, which is a continuation-in-part of application No. 08/857,800, filed on Jan. 22, 1997, now abandoned, which is a continuation-in-part of application No. 08/741,685, filed on Oct. 31, 1996, now abandoned, which is a continuation-in-part of application No. 08/743,984, filed on Oct. 28, 1996, which is a continuation-in-part of application No. 08/726,703, filed on Oct. 7, 1996, now abandoned, which is a continuation-in-part of application No. PCT/US96/15999, filed on Oct. 3, 1996, and a continuation-in-part of application No. 08/723,423, filed on Sep. 30, 1996, now Pat. No. 5,961,923, which is a continuation-in-part of application No. 08/709,435, filed on Sep. 6, 1996, now Pat. No. 6,017,496, which is a continuation-in-part of application No. 08/711,426, filed on Sep. 5, 1996, which is a continuation-in-part of application No. 08/669,252, filed on Jun. 24, 1996, which is a continuation-in-part of application No. 08/633,410, filed on Jun. 10, 1996, now Pat. No. 6,100,026, which is a continuation-in-part of application No. PCT/US96/06145, filed on Apr. 25, 1996, which is a continuation-in-part of application No. 08/639,813, filed on Apr. 2, 1996, now abandoned, which is a continuation-in-part of application No. 08/567,746, filed on Dec. 5, 1995, and a continuation-in-part of application No. 08/639,813, filed on Apr. 2, 1996, now abandoned, which is a continuation-in-part of application No. 08/567,746, filed on Dec. 5, 1995, which is a continuation-in-part of application No. 08/538,387, filed on Oct. 3, 1995, now Pat. No. 5,874,214, each is a continuation-in-part of application No.08/480,147, filed on Jun. 7, 1995, and a continuation-in-part of application No. 08/484,486, filed on Jun. 7, 1995, and a continuation-in-part of application No. 08/484,504, filed on Jun. 7, 1995, now Pat. No. 5,751,629, and a continuation-in-part of application No. 08/480,196, filed on Jun. 7, 1995, now Pat. No. 5,925,562, and a continuation-in-part of application No. 08/473,660, filed on Jun. 7, 1995, which is a continuation-in-part of application No. 08/428,662, filed on Apr. 25, 1995, now Pat. No. 5,741,462.

(51) Int. Cl.[7] .................................................. C12Q 1/68

(52) U.S. Cl. .............................. 435/6; 209/597; 209/604; 364/130

(58) Field of Search .................................. 209/597, 604; 364/130; 435/6

(56) References Cited

U.S. PATENT DOCUMENTS

| Re. 34,936 | 5/1995 | Campbell et al. ................... 606/117 |
|---|---|---|
| 2,866,723 | 12/1958 | West ................................. 117/138.8 |
| 3,017,025 | 1/1962 | Stephen ................................. 209/81 |
| 3,047,421 | 7/1962 | Taylor ................................. 117/709 |

(List continued on next page.)

FOREIGN PATENT DOCUMENTS

| 2344930 | 4/1974 | (DE) . |
|---|---|---|
| 2503684 | 8/1976 | (DE) . |
| 4313807 | 4/1993 | (DE) . |

(List continued on next page.)

OTHER PUBLICATIONS

Baldwin et al., Synthesis of a small molecule combinatorial library encoded with molecular tags, *J. Am. Chem. Soc.* 117:5588 (1995).

Campbell et al., A transition state analogue inhibitor combinatorial library, *J. Am. Chem. Soc.* 117:5381 (1995).

Combinatorial chemistry—playing electronic tag, *Chem, & Indust. Magaz. News,* Nov. 6, 1995.

Czarnik et al., No static at all, *Chemistry in Britain,* pp. 39–41 (Oct., 1996).

(List continued on next page.)

*Primary Examiner*—Kenneth R. Horlick
*Assistant Examiner*—Jeffrey Siew
(74) *Attorney, Agent, or Firm*—Kilpatrick Stockton LLP

(57) ABSTRACT

Automated drug discovery protocols, or partially automated protocols, in which matrices with memories serve as the platform on which all manipulations are performed or serve as the repository of information that is transferred to other memories as the synthesized compounds are processed and screened. Also provided are automated drug discovery units for use in the protocols. The units provide a means for seamless data tracking and include instrumentation and vials with memories for information transfer to other memories in a unit. The units, which are provided herein, include some or all of the following: an automated or manual sorter, microvessels, which contain memories, an automated or semi-automated synthesizer, a microvessel washer/dryer, a manual or automated cleaver for removing compounds from the matrix with memory microvessels, and associated software. The memories may be any of any type, including electromagnetically encodable memories and optical memories, or combinations thereof. The memories may be pre-encoded or may be encodabie during, after or before processing. Also provided are manual and automated methods for sorting matrices with memories.

58 Claims, 79 Drawing Sheets

Microfiche Appendix Included
(23 Microfiche, 1236 Pages)

U.S. PATENT DOCUMENTS

| | | | |
|---|---|---|---|
| 3,119,099 | 1/1964 | Biernat | 365/151 |
| 3,288,728 | 11/1966 | Gorham et al. | 260/2 |
| 3,342,754 | 9/1967 | Gorham et al. | 260/2 |
| 3,429,739 | 2/1969 | Tittmann et al. | 117/106 |
| 3,469,848 | 9/1969 | Mulay | 274/41 |
| 3,692,498 | 9/1972 | Frank et al. | 23/292 |
| 3,704,952 | 12/1972 | Bird | 356/87 |
| 3,715,856 | 2/1973 | Borel | 53/41 |
| 3,781,120 | 12/1973 | Engelhardt | 356/244 |
| 3,843,443 | 10/1974 | Fishman | 105/63 |
| 3,867,517 | 2/1975 | Ling | 424/1 |
| 3,920,124 | 11/1975 | Patterson | 209/111.7 |
| 3,930,924 | 1/1976 | Oka et al. | 156/268 |
| 3,935,427 | 1/1976 | Geul | 235/61.7 R |
| 3,939,123 | 2/1976 | Matthews et al. | 260/77.5 |
| 4,000,252 | 12/1976 | Kosak | 424/1 |
| 4,006,117 | 2/1977 | Merrifield et al. | 260/45.9 |
| 4,006,403 | 2/1977 | Olsen et al. | 324/15 |
| 4,020,830 | 5/1977 | Johnson et al. | 128/2 |
| 4,133,642 | 1/1979 | Nosaka et al. | 422/67 |
| 4,154,795 | 5/1979 | Thorne | 422/99 |
| 4,162,355 | 7/1979 | Tsibris | 526/293 |
| 4,171,412 | 10/1979 | Coupek et al. | 525/329 |
| 4,175,183 | 11/1979 | Ayers | 536/57 |
| 4,176,260 | 11/1979 | Ward et al. | 235/475 |
| 4,177,038 | 12/1979 | Biebricher et al. | 8/192 |
| 4,177,253 | 12/1979 | Davies et al. . | |
| 4,178,439 | 12/1979 | Ayers et al. | 536/59 |
| 4,179,402 | 12/1979 | Kim et al. | 252/431 |
| 4,180,524 | 12/1979 | Reusser et al. | 585/644 |
| 4,241,537 | 12/1980 | Wood | 47/77 |
| 4,271,139 | 6/1981 | Hart | 424/1 |
| 4,282,287 | 8/1981 | Giese | 428/407 |
| 4,297,337 | 10/1981 | Mansfield et al. | 424/1 |
| 4,305,496 | 12/1981 | Hoppmann et al. | 198/420 |
| 4,318,658 | 3/1982 | McIntyre | 414/480 |
| 4,321,069 | 3/1982 | Ritter | 55/161 |
| 4,333,072 | 6/1982 | Beigel | 340/825.54 |
| 4,351,337 | 9/1982 | Sidman | 128/260 |
| 4,376,110 | 3/1983 | David et al. | 436/513 |
| 4,382,074 | 5/1983 | Hart | 436/537 |
| 4,387,297 | 6/1983 | Swartz et al. | 235/462 |
| 4,388,296 | 6/1983 | Hart | 424/1 |
| 4,409,470 | 10/1983 | Shepard et al. | 235/472 |
| 4,424,579 | 1/1984 | Roesner | 365/105 |
| 4,439,585 | 3/1984 | Gould et al. | 525/127 |
| 4,442,507 | 4/1984 | Roesner | 365/100 |
| 4,450,150 | 5/1984 | Sidman | 424/1.1 |
| 4,452,773 | 6/1984 | Molday | 424/1.1 |
| 4,476,149 | 10/1984 | Poppe et al. | 427/2 |
| 4,485,227 | 11/1984 | Fox | 528/61 |
| 4,507,230 | 3/1985 | Tam et al. | 260/112.5 |
| 4,530,840 | 7/1985 | Tice et al. | 514/179 |
| 4,542,025 | 9/1985 | Tice et al. | 424/78 |
| 4,542,102 | 9/1985 | Dattagupta et al. | 435/6 |
| 4,562,157 | 12/1985 | Lowe et al. | 435/291 |
| 4,568,649 | 2/1986 | Bertoglio-Matte | 436/534 |
| 4,569,981 | 2/1986 | Wenzel et al. | 528/67 |
| 4,588,698 | 5/1986 | Gruner et al. | 436/535 |
| 4,588,880 | 5/1986 | Hesser | 235/376 |
| 4,598,386 | 7/1986 | Roesner et al. | 365/105 |
| 4,631,211 | 12/1986 | Houghten | 428/35 |
| 4,646,266 | 2/1987 | Ovshinsky et al. | 365/105 |
| 4,651,598 | 3/1987 | Warheit | 81/407 |
| 4,652,528 | 3/1987 | Domkowski | 436/56 |
| 4,654,512 | 3/1987 | Gardosi | 235/376 |
| 4,657,543 | 4/1987 | Langer et al. | 604/891 |
| 4,662,252 | 5/1987 | Warheit | 81/341 |
| 4,680,268 | 7/1987 | Clark, Jr. | 435/291 |
| 4,681,870 | 7/1987 | Balint, Jr. et al. | 502/403 |
| 4,683,202 | 7/1987 | Mullis | 435/91 |
| 4,687,636 | 8/1987 | Hart | 422/57 |
| 4,702,732 | 10/1987 | Powers et al. | 604/20 |
| 4,703,756 | 11/1987 | Gough et al. | 123/635 |
| 4,705,503 | 11/1987 | Dorman et al. | 604/50 |
| 4,721,677 | 1/1988 | Clark, Jr. | 435/291 |
| 4,723,661 | 2/1988 | Hoppmann et al. | 209/658 |
| 4,745,072 | 5/1988 | Ekins et al. | 436/500 |
| 4,762,881 | 8/1988 | Kauer | 525/54.11 |
| 4,764,573 | 8/1988 | Myers | 526/90 |
| 4,777,019 | 10/1988 | Dandekar | 422/68 |
| 4,777,128 | 10/1988 | Lippa | 435/5 |
| 4,779,806 | 10/1988 | Langer et al. | 241/1 |
| 4,783,776 | 11/1988 | Ishigaki et al. | 269/109 |
| 4,784,162 | 11/1988 | Ricks et al. | 128/903 |
| 4,786,277 | 11/1988 | Powers et al. | 604/20 |
| 4,791,285 | 12/1988 | Ohki | 235/449 |
| 4,796,074 | 1/1989 | Roesner | 357/51 |
| 4,807,140 | 2/1989 | Saulnier | 364/468 |
| 4,816,513 | 3/1989 | Bridgham et al. . | |
| 4,821,920 | 4/1989 | Lin et al. | 221/167 |
| 4,828,100 | 5/1989 | Hoppmann et al. | 198/392 |
| 4,848,559 | 7/1989 | Saulnier | 364/468 |
| 4,854,328 | 8/1989 | Pollack | 128/736 |
| 4,855,583 | 8/1989 | Fraser et al. | 235/492 |
| 4,855,909 | 8/1989 | Vincent et al. | 364/413.01 |
| 4,857,893 | 8/1989 | Carroll . | |
| 4,870,574 | 9/1989 | Limisimaque | 364/300 |
| 4,876,668 | 10/1989 | Thakoor et al. | 365/163 |
| 4,885,250 | 12/1989 | Eveleigh et al. | 435/181 |
| 4,889,800 | 12/1989 | Shinnick et al. | 435/7 |
| 4,908,405 | 3/1990 | Bayer et al. | 525/61 |
| 4,908,694 | 3/1990 | Hidaka et al. | 357/74 |
| 4,908,813 | 3/1990 | Ojima et al. | 369/94 |
| 4,909,921 | 3/1990 | Ito | 204/403 |
| 4,915,564 | * 4/1990 | Eror et al. | 414/217 |
| 4,927,879 | 5/1990 | Pidgeon | 525/54.1 |
| 4,927,923 | 5/1990 | Mathis et aol. | 540/456 |
| 4,931,498 | 6/1990 | Pidgeon | 525/54.1 |
| 4,933,285 | 6/1990 | Patton | 435/181 |
| 4,938,591 | 7/1990 | Anderson et al. | 356/73 |
| 4,952,531 | 8/1990 | Cherukuri | 501/69 |
| 4,952,913 | 8/1990 | Pauley et al. | 340/573 |
| 4,952,928 | 8/1990 | Carroll et al. | 340/825.54 |
| 4,954,444 | 9/1990 | Eveleigh et al. | 435/181 |
| 4,958,452 | 9/1990 | Tate | 40/301 |
| 4,960,983 | 10/1990 | Inoue | 235/449 |
| 4,966,154 | 10/1990 | Cooper et al. | 128/671 |
| 4,973,493 | 11/1990 | Guire | 427/2 |
| 4,975,647 | 12/1990 | Downer et al. | 324/425 |
| 4,990,756 | 2/1991 | Hoeman | 235/462 |
| 4,991,719 | 2/1991 | Butcher et al. | 209/3.3 |
| 4,993,425 | 2/1991 | Kronberg | 128/748 |
| 4,995,467 | * 2/1991 | Niemann et al. | 177/25.18 |
| 5,002,548 | 3/1991 | Campbell et al. | 606/116 |
| 5,004,606 | 4/1991 | Frincke et al. | 424/85.8 |
| 5,012,236 | 4/1991 | Troyk et al. | 340/825.54 |
| 5,024,727 | 6/1991 | Campbell et al. | 156/663 |
| 5,028,918 | 7/1991 | Giles et al. | 340/825.54 |
| 5,029,214 | 7/1991 | Hollander | 381/51 |
| 5,030,807 | 7/1991 | Landt et al. | 235/375 |
| 5,033,623 | 7/1991 | Grecksch et al. | 209/3.3 |
| 5,043,222 | 8/1991 | Cherukuri | 428/432 |
| 5,044,623 | 9/1991 | Munz et al. | 271/223 |
| 5,046,496 | 9/1991 | Betts et al. | 128/635 |
| 5,047,134 | 9/1991 | Weinberger et al. | 204/299 |
| 5,047,371 | 9/1991 | Cherukuri | 501/21 |
| 5,050,612 | 9/1991 | Matsumura | 128/670 |
| 5,053,115 | 10/1991 | Weinberger et al. | 204/299 |
| 5,055,659 | 10/1991 | Hendrick et al. | 235/439 |

| | | | | | | | |
|---|---|---|---|---|---|---|---|
| 5,056,056 | 10/1991 | Gustin | 364/900 | 5,232,831 | 8/1993 | Milliman et al. | 435/6 |
| 5,063,417 | 11/1991 | Hopfield | 357/8 | 5,235,326 | 8/1993 | Beigel et al. | 340/825.54 |
| 5,064,767 | 11/1991 | Le et al. | 436/89 | 5,236,355 | 8/1993 | Brizzolara et al. | 433/80 |
| 5,066,382 | 11/1991 | Weinberger et al. | 204/299 | 5,241,160 | 8/1993 | Bashan et al. | 235/390 |
| 5,073,703 | 12/1991 | Wehrmacher | 235/492 | 5,242,974 | 9/1993 | Holmes et al. | 525/54.11 |
| 5,074,318 | 12/1991 | Campbell et al. | 128/899 | 5,246,869 | 9/1993 | Potter et al. | 436/518 |
| 5,075,077 | 12/1991 | Durley, III et al. | 422/56 | 5,248,632 | 9/1993 | Tung et al. | 437/195 |
| 5,082,550 | 1/1992 | Rishpon et al. | 204/403 | 5,250,459 | 10/1993 | Lee | 437/52 |
| 5,087,570 | 2/1992 | Weissman et al. | 435/240.1 | 5,250,944 | 10/1993 | Urbas et al. | 340/870.31 |
| 5,088,488 | 2/1992 | Markowitz et al. | 128/419 | 5,252,743 | 10/1993 | Barrett et al. | 548/303.7 |
| 5,089,391 | 2/1992 | Buechler et al. | 435/7.24 | 5,252,962 | 10/1993 | Urbas et al. | 340/870.17 |
| 5,089,877 | 2/1992 | Queyssac et al. | 357/70 | 5,253,198 | 10/1993 | Birge et al. | 365/106 |
| 5,092,466 | 3/1992 | Anderson | 206/438 | 5,256,469 | 10/1993 | Cherukuri et al. | 428/901 |
| 5,092,992 | 3/1992 | Crane et al. | 210/198.2 | 5,257,011 | 10/1993 | Beigel | 340/572 |
| 5,093,240 | 3/1992 | Inouye et al. | 435/69.1 | 5,258,289 | 11/1993 | Davis et al. | 435/69.6 |
| 5,093,982 * | 3/1992 | Gussman et al. | 29/705 | 5,260,203 | 11/1993 | Ladner et al. | 435/172.3 |
| 5,095,362 | 3/1992 | Roesner | 357/23.4 | 5,261,615 | 11/1993 | Cuttelod | 242/7.02 |
| 5,099,226 | 3/1992 | Andrews | 340/572 | 5,262,035 | 11/1993 | Gregg et al. | 204/403 |
| 5,100,626 | 3/1992 | Levin | 422/100 | 5,262,305 | 11/1993 | Heller et al. | 435/28 |
| 5,105,190 | 4/1992 | Kip et al. | 340/825.54 | 5,262,772 | 11/1993 | Urbas et al. | 340/825.54 |
| 5,108,819 | 4/1992 | Heller et al. | 428/195 | 5,264,104 | 11/1993 | Gregg et al. | 204/403 |
| 5,110,424 | 5/1992 | Chin | 204/180 | 5,264,105 | 11/1993 | Gregg et al. | 204/403 |
| 5,112,457 | 5/1992 | Marchant | 204/165 | 5,265,610 | 11/1993 | Darrow et al. | 128/653.1 |
| 5,114,719 | 5/1992 | Sabel et al. | 424/422 | 5,266,926 | 11/1993 | Beigel | 340/572 |
| 5,119,163 | 6/1992 | Ishihara et al. | 357/51 | 5,267,151 | 11/1993 | Ham et al. | 364/413.09 |
| 5,119,813 | 6/1992 | Cohen | 128/419 | 5,268,371 | 12/1993 | Mauclaire et al. | 514/185 |
| 5,120,642 | 6/1992 | Schlossman et al. | 435/7.24 | 5,268,862 | 12/1993 | Rentzepis | 365/151 |
| 5,121,748 | 6/1992 | Ditz et al. | 128/631 | 5,270,170 | 12/1993 | Schatz et al. | 435/7.37 |
| 5,128,528 | 7/1992 | Heninger . | | 5,270,251 | 12/1993 | Cohen | 437/173 |
| 5,130,362 | 7/1992 | Prasad et al. | 524/265 | 5,271,400 | 12/1993 | Dumoulin et al. | 128/653.2 |
| 5,134,277 | 7/1992 | Yerbury et al. | 250/214 | 5,272,666 | 12/1993 | Tsang et al. | 365/96 |
| 5,136,572 | 8/1992 | Bradley | 369/108 | 5,273,715 | 12/1993 | Bridgham et al. . | |
| 5,139,937 | 8/1992 | Inouye et al. | 435/69.1 | 5,273,905 | 12/1993 | Muller et al. . | |
| 5,143,854 | 9/1992 | Pirrung et al. | 436/518 | 5,273,927 | 12/1993 | Gnadinger | 437/52 |
| 5,145,051 | 9/1992 | Hoppmann | 198/396 | 5,277,724 | 1/1994 | Prabhu | 428/210 |
| 5,147,608 | 9/1992 | Hudson et al. | 422/63 | 5,279,943 | 1/1994 | Mathis et al. | 435/7.32 |
| 5,148,256 | 9/1992 | Potash et al. | 357/45 | 5,281,540 | 1/1994 | Merkh et al. | 436/530 |
| 5,148,404 | 9/1992 | Hilferink et al. | 367/2 | 5,281,855 | 1/1994 | Hadden et al. | 257/784 |
| 5,149,629 | 9/1992 | Rishpon et al. | 435/7.9 | 5,282,158 | 1/1994 | Lee | 365/96 |
| 5,152,758 | 10/1992 | Kaetsu et al. | 604/890.1 | 5,284,140 | 2/1994 | Allen et al. | 128/634 |
| 5,153,583 | 10/1992 | Murdoch | 340/825.54 | 5,284,747 | 2/1994 | Milliman | 435/6 |
| 5,156,810 | 10/1992 | Ribi | 422/82.01 | 5,288,291 | 2/1994 | Teoh | 604/60 |
| 5,157,262 | 10/1992 | Marsoner et al. | 250/458.1 | 5,288,476 | 2/1994 | Pasqualini et al. | 424/1.65 |
| 5,162,227 | 11/1992 | Cormier | 435/252.33 | 5,288,514 | 2/1994 | Ellman | 427/2 |
| 5,162,508 | 11/1992 | Lehn et al. | 534/15 | 5,288,622 | 2/1994 | Gray et al. | 435/69.4 |
| 5,165,406 | 11/1992 | Wong | 128/635 | 5,290,734 | 3/1994 | Boardman et al. | 437/195 |
| 5,171,695 | 12/1992 | Ekins | 436/501 | 5,292,814 | 3/1994 | Bayer et al. | 525/243 |
| 5,184,003 | 2/1993 | McMillan et al. | 235/454 | 5,292,874 | 3/1994 | Milliman | 536/24.32 |
| 5,186,336 * | 2/1993 | Pippin et al. | 209/583 | 5,296,122 | 3/1994 | Katsube et al. | 204/298.04 |
| 5,186,898 | 2/1993 | Bridgham et al. | 422/102 | 5,296,722 | 3/1994 | Potash et al. | 257/50 |
| 5,198,670 | 3/1993 | VanCauter et al. | 250/328 | 5,300,278 | 4/1994 | Pasqualini et al. | 534/14 |
| 5,200,051 | 4/1993 | Cozzette et al. | 204/403 | 5,300,456 | 4/1994 | Tigelaar et al. | 437/195 |
| 5,209,231 | 5/1993 | Cote et al. | 128/633 | 5,304,498 | 4/1994 | Ekins | 436/501 |
| 5,211,129 | 5/1993 | Taylor et al. | 119/3 | 5,306,466 | 4/1994 | Goldsmith et al. | 422/58 |
| 5,212,050 | 5/1993 | Mier et al. | 430/320 | 5,307,808 | 5/1994 | Dumoulin et al. | 128/653.2 |
| 5,212,315 | 5/1993 | Jones et al. | 546/257 | 5,308,967 | 5/1994 | Jurisch | 235/492 |
| 5,214,409 | 5/1993 | Beigel | 340/572 | 5,310,686 | 5/1994 | Sawyers et al. | 428/552 |
| 5,215,899 | 6/1993 | Dattagupta | 435/6 | 5,311,039 | 5/1994 | Kimura et al. | 257/50 |
| 5,216,143 | 6/1993 | Hogan et al. | 536/24.32 | 5,311,426 | 5/1994 | Donohue et al. | 364/413.09 |
| 5,217,743 | 6/1993 | Farah | 427/2 | 5,314,058 * | 5/1994 | Graham | 198/753 |
| 5,217,870 | 6/1993 | Hession et al. | 435/7.24 | 5,314,829 | 5/1994 | Coles | 436/165 |
| 5,217,875 | 6/1993 | Karpf et al. | 435/34 | 5,316,922 | 5/1994 | Brown et al. | 435/69.7 |
| 5,218,189 | 6/1993 | Hutchinson | 235/439 | 5,316,971 | 5/1994 | Chiang et al. | 437/170 |
| 5,218,343 | 6/1993 | Stobbe et al. | 340/572 | 5,318,354 | 6/1994 | Tyler | 303/3 |
| 5,223,408 | 6/1993 | Goeddel et al. | 435/69.3 | 5,318,676 | 6/1994 | Sailor et al. | 204/129.3 |
| 5,223,409 | 6/1993 | Ladner et al. | 435/69.7 | 5,319,181 | 6/1994 | Shellhammer et al. | 235/462 |
| 5,223,851 | 6/1993 | Hadden et al. | 343/873 | 5,319,363 | 6/1994 | Welch et al. | 340/825 |
| 5,225,229 | 7/1993 | Martin et al. | 423/629 | 5,320,725 | 6/1994 | Gregg et al. | 204/153.12 |
| 5,226,926 | 7/1993 | Matsuzaki | 44/530 | 5,320,808 | 6/1994 | Holen et al. | 422/64 |
| 5,227,042 | 7/1993 | Zawodzinski | 204/403 | 5,322,812 | 6/1994 | Dixit et al. | 437/60 |
| 5,228,001 | 7/1993 | Birge et al. | 365/215 | 5,323,704 | 6/1994 | Fraczek | 101/375 |

| | | | |
|---|---|---|---|
| 5,324,324 | 6/1994 | Vachon et al. ......................... 607/120 |
| 5,324,483 | 6/1994 | Cody et al. ........................... 422/131 |
| 5,324,591 | 6/1994 | Georger et al. ....................... 528/552 |
| 5,324,633 | 6/1994 | Fodor et al. ............................. 435/6 |
| 5,325,324 | 6/1994 | Rentzepis et al. .................... 365/127 |
| 5,326,449 | 7/1994 | Cunningham ......................... 204/403 |
| 5,326,696 | 7/1994 | Chang .................................. 435/7.24 |
| 5,328,603 | 7/1994 | Velander et al. .................... 210/198.2 |
| 5,329,153 | 7/1994 | Dixit ..................................... 257/530 |
| 5,330,513 | 7/1994 | Nichols et al. ........................ 607/32 |
| 5,333,675 | 8/1994 | Mullis et al. ........................... 165/12 |
| 5,333,716 | 8/1994 | Hoppmann et al. ................. 198/380 |
| 5,334,640 | 8/1994 | Desai et al. ............................ 524/56 |
| 5,334,880 | 8/1994 | Abadeer et al. ..................... 307/219 |
| 5,335,219 | 8/1994 | Ovshinsky et al. .................. 369/288 |
| 5,338,665 | 8/1994 | Schatz et al. ............................. 435/6 |
| 5,342,633 | 8/1994 | Cully et al. ............................ 426/47 |
| 5,342,692 | 8/1994 | Ribi ..................................... 428/420 |
| 5,342,772 | 8/1994 | Arenzen et al. ..................... 435/181 |
| 5,342,789 | 8/1994 | Chick et al. .......................... 436/501 |
| 5,343,869 | 9/1994 | Pross et al. ........................... 128/700 |
| 5,345,231 | 9/1994 | Koo et al. ............................ 340/870 |
| 5,346,789 | 9/1994 | Lewis et al. ............................ 430/19 |
| 5,347,263 | 9/1994 | Carroll et al. ........................ 340/572 |
| 5,347,283 | 9/1994 | Krizek et al. ........................ 342/201 |
| 5,348,705 | 9/1994 | Koreyasu et al. ..................... 422/67 |
| 5,348,867 | 9/1994 | Georgiou et al. .................... 435/69.7 |
| 5,349,173 | 9/1994 | Scheckel et al. ..................... 235/492 |
| 5,350,645 | 9/1994 | Lake et al. ........................... 429/124 |
| 5,351,052 | 9/1994 | D'Hont et al. ......................... 342/42 |
| 5,352,579 | 10/1994 | Milliman ................................. 435/6 |
| 5,353,795 | 10/1994 | Souza et al. ....................... 128/653.2 |
| 5,354,977 | 10/1994 | Roustaei .............................. 235/472 |
| 5,356,786 | 10/1994 | Heller et al. .......................... 535/14 |
| 5,358,691 | 10/1994 | Clark et al. ........................... 422/64 |
| 5,359,115 | 10/1994 | Campbell et al. ................... 558/110 |
| 5,359,250 | 10/1994 | Toda .................................... 310/313 |
| 5,360,728 | 11/1994 | Prasher ................................ 435/189 |
| 5,361,385 | 11/1994 | Bakalash ............................. 395/124 |
| 5,362,899 | 11/1994 | Campbell ............................ 558/108 |
| 5,364,797 | 11/1994 | Olson et al. ......................... 436/501 |
| 5,366,733 | 11/1994 | Brizzolara et al. .................. 424/426 |
| 5,368,040 | 11/1994 | Carney ................................ 128/700 |
| 5,371,809 | 12/1994 | Desieno ................................ 182/15 |
| 5,374,718 | 12/1994 | Hammond et al. ............... 536/24.32 |
| 5,375,604 | 12/1994 | Kelly et al .......................... 128/671 |
| 5,376,313 | 12/1994 | Kanewske, III et al. ............. 264/1.1 |
| 5,376,692 | 12/1994 | Park et al. ............................ 522/87 |
| 5,377,678 | 1/1995 | Dumoulin et al. ................. 128/653.1 |
| 5,378,432 | 1/1995 | Bankert et al. .................... 422/82.07 |
| 5,380,589 | 1/1995 | Goodman et al. ................. 428/36.92 |
| 5,381,035 | 1/1995 | Chen et al. .......................... 257/530 |
| 5,382,513 | 1/1995 | Lam et al. ............................ 435/7.1 |
| 5,383,873 | 1/1995 | Hoey et al. ........................ 604/891.1 |
| 5,384,028 | 1/1995 | Ito ....................................... 204/403 |
| 5,384,261 | 1/1995 | Winkler et al. ..................... 436/518 |
| 5,384,481 | 1/1995 | Holzworth et al. .................. 257/530 |
| 5,386,024 | 1/1995 | Kacian et al. ....................... 536/25.4 |
| 5,389,449 | 2/1995 | Afeyan et al. ...................... 428/523 |
| 5,389,534 | 2/1995 | von gentzkow et al. ........... 435/180 |
| 5,389,769 | 2/1995 | Yamashita et al. ................. 235/375 |
| 5,391,463 | 2/1995 | Ligler et al. ......................... 430/272 |
| 5,395,587 | 3/1995 | Brigham-Burke et al. ......... 422/68.1 |
| 5,395,750 | 3/1995 | Dillion et al. ............................ 435/5 |
| 5,397,939 | 3/1995 | Gordon et al. ........................ 326/38 |
| 5,399,339 | 3/1995 | Pasqualini et al. ................. 424/1.53 |
| 5,399,486 | 3/1995 | Cathey et al. ........................ 435/7.9 |
| 5,400,136 | 3/1995 | Vo-Dinh .............................. 356/301 |
| 5,401,378 | 3/1995 | King et al. ........................... 204/418 |
| 5,403,484 | 4/1995 | Ladner et al. ..................... 435/235.1 |
| 5,403,750 | 4/1995 | Braatz et al. ........................ 436/531 |
| 5,405,510 | 4/1995 | Betts et al. ......................... 204/153.1 |
| 5,405,783 | 4/1995 | Pirrung et al. ....................... 436/518 |
| 5,406,042 | 4/1995 | Engelfriet et al. ............... 219/121.68 |
| 5,407,699 | 4/1995 | Myers ................................. 427/121 |
| 5,408,037 | 4/1995 | Smith et al. ......................... 530/308 |
| 5,410,155 | 4/1995 | Thomson et al. ................... 250/364 |
| 5,411,537 | 5/1995 | Munshi et al. ........................ 607/33 |
| 5,411,647 | 5/1995 | Johnson et al. ................... 204/153.1 |
| 5,412,593 | 5/1995 | Magel et al. ........................ 365/96 |
| 5,414,405 | 5/1995 | Hogg et al. ......................... 340/321 |
| 5,415,839 | 5/1995 | Zaun et al. ............................ 422/64 |
| 5,415,999 | 5/1995 | Saul et al. ............................ 435/7.9 |
| 5,416,071 | 5/1995 | Igari et al. ............................... 514/8 |
| 5,416,193 | 5/1995 | Desai .................................. 530/334 |
| 5,416,486 | 5/1995 | Koert et al. ............................ 342/42 |
| 5,420,328 | 5/1995 | Campbell ............................ 558/110 |
| 5,420,579 | 5/1995 | Urbas et al. ..................... 340/870.31 |
| 5,421,816 | 6/1995 | Lipkovker ............................. 604/20 |
| 5,422,266 | 6/1995 | Cormier et al. ................... 435/252.3 |
| 5,422,636 | 6/1995 | Urbas et al. ..................... 340/825.54 |
| 5,424,037 | 6/1995 | Zimmermann et al. .............. 422/64 |
| 5,424,186 | 6/1995 | Fodor et al. ............................. 435/6 |
| 5,424,483 | 6/1995 | Pfund et al. ........................ 800/200 |
| 5,425,361 | 6/1995 | Fenzlein et al. .................... 128/635 |
| 5,425,915 | 6/1995 | Phillips et al. ........................ 422/58 |
| 5,427,915 | 6/1995 | Ribi et al. ........................... 435/7.92 |
| 5,430,150 | 7/1995 | Trova et al. ........................ 546/139 |
| 5,431,691 | 7/1995 | Snell et al. . |
| 5,432,018 | 7/1995 | Dower et al. ........................... 435/5 |
| 5,432,171 | 7/1995 | Harrison et al. .................... 128/698 |
| 5,435,937 | 7/1995 | Bell et al. ....................... 252/301.18 |
| 5,437,277 | 8/1995 | Dumoulin et al. ............... 128/653.1 |
| 5,437,284 | 8/1995 | Trimble .............................. 128/673 |
| 5,438,439 | 8/1995 | Mok et al. ............................. 359/10 |
| 5,440,511 | 8/1995 | Yamamoto et al. ............ 365/189.05 |
| 5,442,212 | 8/1995 | Eimori ................................. 257/303 |
| 5,442,584 | 8/1995 | Jeong et al. ........................ 365/149 |
| 5,442,940 | 8/1995 | Secker et al. ....................... 128/670 |
| 5,443,066 | 8/1995 | Dumoulin et al. ............... 128/653.1 |
| 5,443,816 | 8/1995 | Zamora et al. ..................... 424/1.69 |
| 5,443,953 | 8/1995 | Hansen et al. ...................... 424/1.49 |
| 5,444,223 | 8/1995 | Blama ................................. 235/435 |
| 5,445,150 | 8/1995 | Dumoulin et al. ............... 128/653.1 |
| 5,446,447 | 8/1995 | Carney et al. ...................... 340/572 |
| 5,447,533 | 9/1995 | Vachon et al. ...................... 607/120 |
| 5,449,941 | 9/1995 | Yamazaki et al. .................. 257/411 |
| 5,451,528 | 9/1995 | Raymoure et al. ................. 436/533 |
| 5,451,683 | 9/1995 | Barrett et al. ..................... 548/302.7 |
| 5,451,896 | 9/1995 | Mori .................................... 327/543 |
| 5,452,251 | 9/1995 | Akaogi et al. ...................... 365/200 |
| 5,452,311 | 9/1995 | Wells et al. ......................... 371/51.1 |
| 5,453,633 | 9/1995 | Yun ..................................... 257/306 |
| 5,457,184 | 10/1995 | Lehn et al. ............................ 534/15 |
| 5,458,123 | 10/1995 | Unger .................................. 128/696 |
| 5,463,564 | 10/1995 | Agrafiotis et al. .................. 364/496 |
| 5,476,094 | 12/1995 | Allen et al. ......................... 128/634 |
| 5,482,861 | 1/1996 | Clark et al. .......................... 438/48 |
| 5,482,863 | 1/1996 | Knobel ................................. 436/54 |
| 5,482,864 | 1/1996 | Knobel ................................. 436/54 |
| 5,482,867 | 1/1996 | Barrett et al. . |
| 5,489,678 | 2/1996 | Fodor et al. ........................ 536/22.1 |
| 5,491,074 | 2/1996 | Aldwin et al. ...................... 435/69.7 |
| 5,492,806 | 2/1996 | Drmanac et al. ...................... 435/5 |
| 5,498,530 | 3/1996 | Schatz et al. ........................ 435/69.1 |
| 5,498,545 | 3/1996 | Vestal ................................... 436/47 |
| 5,499,547 | 3/1996 | Nagai et al. ........................ 74/89.15 |
| 5,503,805 | 4/1996 | Sugarman et al. .................. 422/131 |
| 5,507,290 | 4/1996 | Kelly et al. .......................... 128/640 |
| 5,507,410 | 4/1996 | Clark et al. .......................... 221/171 |
| 5,508,030 | 4/1996 | Bierman .............................. 424/85.1 |
| 5,508,200 | 4/1996 | Tiffany et al. ........................ 436/44 |

| | | | |
|---|---|---|---|
| 5,517,194 | 5/1996 | Carroll et al. ............ 342/50 |
| 5,521,601 | 5/1996 | Kandlur et al. . |
| 5,521,602 | 5/1996 | Carroll et al. ............ 342/50 |
| 5,525,463 | 6/1996 | Drmanac et al. ............ 435/6 |
| 5,525,464 | 6/1996 | Drmanac et al. ............ 435/6 |
| 5,527,681 | 6/1996 | Holmes ............ 435/6 |
| 5,528,222 | 6/1996 | Moskowitz et al. ............ 340/572 |
| 5,530,702 | 6/1996 | Palmer et al. ............ 370/85.3 |
| 5,537,126 | 7/1996 | Kayser et al. ............ 345/1 |
| 5,541,061 | 7/1996 | Fodor et al. . |
| 5,545,531 | 8/1996 | Rava et al. . |
| 5,547,839 | 8/1996 | Dower et al. ............ 435/6 |
| 5,549,974 | 8/1996 | Holmes ............ 428/403 |
| 5,552,270 | 9/1996 | Khrapko et al. ............ 435/6 |
| 5,556,762 | 9/1996 | Pinella et al. ............ 435/7.21 |
| 5,565,324 | 10/1996 | Still et al. ............ 435/6 |
| 5,572,410 | 11/1996 | Gustafson ............ 361/807 |
| 5,583,819 | 12/1996 | Roesner et al. ............ 365/225.7 |
| 5,609,826 | 3/1997 | Cargill et al. . |
| 5,624,711 | 4/1997 | Sundberg et al. ............ 427/261 |
| 5,634,562 * | 6/1997 | Isaacs ............ 209/583 |
| 5,639,603 | 6/1997 | Dower et al. ............ 435/6 |
| 5,641,634 | 6/1997 | Mandecki . |
| 5,679,773 | 10/1997 | Holmes ............ 530/334 |
| 5,684,711 | 11/1997 | Agrafiotis et al. . |
| 5,708,153 | 1/1998 | Dower et al. . |
| 5,751,629 * | 5/1998 | Nova et al. ............ 365/151 |

FOREIGN PATENT DOCUMENTS

| | | |
|---|---|---|
| 4310169 | 9/1993 | (DE) . |
| 4210365 A1 | 10/1993 | (DE) . |
| 4213065 A1 | 10/1993 | (DE) . |
| 4301401 A1 | 7/1994 | (DE) . |
| 4306563 | 9/1994 | (DE) . |
| 9416270 | 1/1995 | (DE) . |
| 0074428 | 9/1981 | (EP) . |
| 0351891 B1 | 1/1984 | (EP) . |
| 0127958 B1 | 8/1984 | (EP) . |
| 0540063 A1 | 4/1985 | (EP) . |
| 0154734 A1 | 9/1985 | (EP) . |
| 0154734 B1 | 9/1985 | (EP) . |
| 0196174 A2 | 3/1986 | (EP) . |
| 0196174 A3 | 3/1986 | (EP) . |
| 196174 B1 | 3/1986 | (EP) . |
| 0226979 A2 | 12/1986 | (EP) . |
| 0245093 A1 | 5/1987 | (EP) . |
| 0245093 B1 | 6/1987 | (EP) . |
| 0252471 A2 | 1/1988 | (EP) . |
| 0252471 A3 | 1/1988 | (EP) . |
| 0252471 B1 | 1/1988 | (EP) . |
| 0301769 A2 | 2/1989 | (EP) . |
| 0301769 A3 | 2/1989 | (EP) . |
| 0378059 A1 | 7/1990 | (EP) . |
| 0420177 A1 | 9/1990 | (EP) . |
| 0410688 A2 | 1/1991 | (EP) . |
| 0194084 B1 | 6/1991 | (EP) . |
| 0502638 A2 | 9/1992 | (EP) . |
| 0526173 A2 | 2/1993 | (EP) . |
| 0526173 A3 | 2/1993 | (EP) . |
| 0534640 A1 | 3/1993 | (EP) . |
| 0276302 B1 | 4/1993 | (EP) . |
| 0535242 | 4/1993 | (EP) . |
| 0541340 A2 | 5/1993 | (EP) . |
| 0554955 A1 | 8/1993 | (EP) . |
| 0556006 A1 | 8/1993 | (EP) . |
| 0378059 B1 | 9/1993 | (EP) . |
| 0569215 A3 | 11/1993 | (EP) . |
| 9308204.5 | 1/1994 | (EP) . |
| 0633468 | 5/1994 | (EP) . |
| 0125137 B1 | 8/1994 | (EP) . |
| 0637750 A2 | 2/1995 | (EP) . |
| 0640826 A1 | 3/1995 | (EP) . |
| 2110030 | 5/1972 | (FR) . |
| 2526169 | 4/1983 | (FR) . |
| 2555744 | 5/1985 | (FR) . |
| 2129551 | 5/1984 | (GB) . |
| 2194176 | 3/1988 | (GB) . |
| 2306484 | 5/1997 | (GB) . |
| 57016359 | 5/1992 | (JP) . |
| 8603840 | 7/1986 | (WO) . |
| 8801302 | 2/1988 | (WO) . |
| 8901157 | 2/1989 | (WO) . |
| 8908264 | 2/1989 | (WO) . |
| 9003844 | 4/1990 | (WO) . |
| 9011524 | 10/1990 | (WO) . |
| 9015070 | 12/1990 | (WO) . |
| 9108489 | 6/1991 | (WO) . |
| 9116718 | 10/1991 | (WO) . |
| 9201225 | 1/1992 | (WO) . |
| 9201268 | 1/1992 | (WO) . |
| 9207093 | 4/1992 | (WO) . |
| 9209300 | 6/1992 | (WO) . |
| 9210092 | 6/1992 | (WO) . |
| 9210588 | 6/1992 | (WO) . |
| 9213271 | 8/1992 | (WO) . |
| 9215105 | 9/1992 | (WO) . |
| 9216655 | 10/1992 | (WO) . |
| 9305049 | 3/1993 | (WO) . |
| 9306121 | 4/1993 | (WO) . |
| 9308472 | 4/1993 | (WO) . |
| 9312513 | 6/1993 | (WO) . |
| 9319175 | 9/1993 | (WO) . |
| 9400602 | 1/1994 | (WO) . |
| WO 9400602 | 1/1994 | (WO) . |
| 9402634 | 2/1994 | (WO) . |
| 9405394 | 3/1994 | (WO) . |
| 9408051 | 4/1994 | (WO) . |
| 9410901 | 5/1994 | (WO) . |
| 9411388 | 5/1994 | (WO) . |
| 9413402 | 6/1994 | (WO) . |
| 9413623 | 6/1994 | (WO) . |
| 9414980 | 7/1994 | (WO) ............ C12Q/1/68 |
| 9417208 | 8/1994 | (WO) . |
| 9422889 | 10/1994 | (WO) . |
| 9424642 | 10/1994 | (WO) . |
| 9426413 | 11/1994 | (WO) . |
| 9428424 | 12/1994 | (WO) . |
| 9500530 | 1/1995 | (WO) . |
| 9501569 | 1/1995 | (WO) . |
| 9502566 | 1/1995 | (WO) . |
| WO 9501569 | 1/1995 | (WO) . |
| 9505601 | 2/1995 | (WO) . |
| 9509925 | 4/1995 | (WO) . |
| 9510629 | 4/1995 | (WO) . |
| 9516270 | 6/1995 | (WO) . |
| 9519567 | 7/1995 | (WO) . |
| 9529473 | 11/1995 | (WO) . |
| WO 9529473 | 11/1995 | (WO) . |
| 9533246 | 12/1995 | (WO) . |
| 9501700 | 2/1996 | (WO) . |
| 9611878 | 4/1996 | (WO) . |
| 9616078 | 5/1996 | (WO) . |
| 9621156 | 7/1996 | (WO) . |
| 9623749 | 8/1996 | (WO) . |
| 9624061 | 8/1996 | (WO) . |
| WO 9624061 | 8/1996 | (WO) . |
| 9636436 | 11/1996 | (WO) . |
| 9712680 | 4/1997 | (WO) . |
| 0720074 | 6/1997 | (WO) . |
| 9719959 | 6/1997 | (WO) . |
| 9720073 | 6/1997 | (WO) . |
| WO 9720073 | 6/1997 | (WO) . |

WO 9720074   6/1997 (WO).
   9735198   9/1997 (WO).
   9737953  10/1997 (WO).

OTHER PUBLICATIONS

Eckes, "Binary encoding of compound libraries", *Angew. Chem. Int. Ed. Engl. 33(15)*:1573–1575 (1994).
Ohlmeyer et al., "Complex synthetic chemical libraries indexed with molecular tags", *Proc. Natl. Acad. Sci. 90*:10922–10926, 1993).
Service, Memory enhanced microreactor chemistry, *Science 270*:577 (1995).
Brandt et al., High–through put screening; an overview 21–26 (1995).
Koutny et al., Microchip electrophoretic immunoassay for serum cortisol, *Anal. Chem. 68*:18–22, (1996).
Xiao–Yi et al., Combinatorial chemistry with laser optical encoding, *Angew Chem. Int. Ed. Engl. 36(7)*: 780–782 (1997).
Armstrong et al., Microchip encoded combinatorial libraries; Generation of a spatially encoded library from a pool synthesis *CHIMIA 50(6)*: 258–260 (1996).
Bock–Sickinger, et al., Semiautomated T–Bag peptide synthesis . . . *Peptide Research 4(2)*: 88–94, Mar. 1991–Apr. 1991.
Gordon, et al., Applications of combinatorial technologies to drug discovery (2) *J. Med Chem. 37 (10)*: 1385–1401 (1994).
Callop; et al. Applications of combinatorial technologies to drug discovery (1) *J.Med. Chem.* 37(9): 1233–1251.
Armstrong et al., Microchip encoded combinatorial libraries: Generation of a spatially encoded library from a pool synthesis, *CHIMIA 50(6)*:258–260 (1996).
Derwent #001509407 WPI Acc. No. 76–H2335X/197633 (citing German Patent No. DE 2503684, published Aug. 5, 1976).
Albretsen, et al., "Applications of magnetic beads with covalenty attached oligonucleotides in hybridization: Isolation and detection of specific measles virus mRNA from a crude cell lysate", *Anal. Biochem.,* 189:40–50, 1990.
Alper J., "Drug discovery on the assembly line", *Science*, 264:1399–1401, 1994.
Maskos and Southern, "Oligonucleotide hybridisations on glass supports: a novel linker for oligonucleotide synthesis and hybridisation properties of oligonucleotides synthesised in situ", *Nucl. Acids Resh.,* 20(7):1679–1684, 1992.
Urdea, et al., "A comparison of non–radioisotopic hybridization assay methods using fluorescent, chemiluminescent and enzyme labled synthetic oligodeoxyribonucleotide probes", *Nucl. Acids. Resh.,* 16(11):4937–4957, 1988.
IUPAC–IUB commission on biochemical nomenclature, *Biochem. 11(5)*:942–944 (1972).
AccuTag™—100 Combinatorial chemistry system, *IRORI Quantum Microchemistry,* Aug. 1, 1996.
AccuTag™—100 Combinatorial chemistry system Price List, *IRORI Quantum Microchemistry,* Aug. 1, 1996.
AccuTag System Site License, *IRORI Quantum Microchemistry,* Jul. 22, 1996.
AccuTag™—100 Product Specifications, *IRORI Quantum Microchemistry.*
Baldwin et al., Synthesis of a small molecule combinatorial library encoded with molecular tags, *J. Am. Chem. Soc. 117*:5588 (1995).

Baum, Combinatorial approaches provide fresh leads for medicinal chemistry, *C&EN*: pp. 20–26 (1994).
Borman, Combinatorial chemists focus on small molecules, molecular recognition, and automation, *C&EN,* pp. 29–54 (1996).
Brandt et al., High–throughput screening: an overview, 21–26 (1995).
Brown et al., "A single–bead decode strategy using electrospray ionization mass spectrometry and a new photolabile linker: 3–Amino–3–(2–nitrophenyl)propionic acid", *Mol. Diversity 1*:4–12 (1995).
Brummel et al., "A Mass spectrometric solution to the address problems of combinatorial libraries", *Sci 264*:399–401, (1994).
Burgess et al. Combinatorial technologies involving reiterative division/ coupling/recombination: Statistical considerations, *J. Med. Chem. 37*:2985 (1994).
Clackson et al., Making antibody fragments using phage display libraries, *Nature 352*:624–628 (1991).
Combinatorial chemistry—playing electronic tag, *Chem. & Indust. Magaz. News,* Nov. 6, 1995.
Devlin et al., Random peptide libraries: A source of specific protein binding molecules, *Science 249*:404–406 (1990).
Dower et al., Chapter 28. The search for molecular diversity (II): recombinant and synthetic randomized peptide libraries, *Ann. Rep. Med. Chem. 26*:271–280 (1991).
Dulac et al., A novel family of genes encoding putative pheromone receptors in mammals, *Cell 83*:195–206 (1995).
Eckes, "Binary encoding of compound libraries", *Angew. Chem. Int. Ed. Engl. 33(15)*:1573–1575, (1994).
Ekins et al., Multinalyte immunoassay: The immunological 'compact disk' of the future, *J. Clin. Immunol. 13(4)*:169–181 (1990).
Gallop, et al., Applications of combinatorial technologies to drug discovery. 1. background and peptide combinatorial libraries, *J. Med. Chem. 37(9)*:1233–1251 (1994).
Gordon et al., Applications of combinatorial technologies to drug discovery. 2. Combinatorial organic synthesis, library screening strategies, and future directions, *J. Med. Chem. 37(10)*1385–1401 (1994).
Janda, Tagged versus untagged libraries: Methods for the generation and screening of combinatorial chemical libraries, *Proc. Natl. Acad. Sci USA 91*:19779–10785 (1994).
Jung et al., Multiple peptide synthesis methods and their applications, *Angew, Chem. Int. Ed. Engl.,* 31(4):367–486 (1992).
Jurisch, Identifikation: kontaktlos via hochfrequenz, *Elektronik 42 (9)*:86–92 (1993).
LED Indicator Accessory for The AccuTag™—100 System, *IRORI Quantum Microchemistry.*
Mjalli and Toyonaga, Solid support combinatorial chemistry in lead discovery and SAR optimization, *Net Sci 1(1)* (1995).
Moran et al., A radio frequency tag encoding combinatorial library method for the discovery of cinnamite amide inhibitors of the protein tyrosine phosphatase PTP1B, 31st Annual American Chemical Society Western Regional Meeting & 4th Annual San Diego Biotech Exposition. 117 (Oct. 19, 1995).
Ecker and Crook, Combinatorial drug discovery: Which method will produce the greatest value? *Biotechnology 13*: 351–360 (1995).
Bill Ewing, Source Code—Overview of the AccuTag Synthesis Manager Software, Sep.2 7, 1996.

Martin et al., Measuring diversity: Experimental design of combinatorial libraries for drug discovery, *J. Med. Chem.* 38:1431 (1995).

Metzger et al., "Electrospray mass spectrometery and tandem mass spectrometry of synthetic multicomponent peptide mixtures: determination of composition and purity", *Analytical Biochem.* 219:261–277, (1994).

Moran et al., Radiofrequency tag encoded combinatorial library method for the discovery of tripeptide–substituted cinnamic acid inhibitors of the protein tyrpsine phosphatase PTP1B, *J. Am. Chem. Soc.* 117:10787–10788.

Needels, et al., "Generation and screening of an oligonucleotide–encoded synthetic peptide library", *Proc. Natl. Acad. Sci. USA* 90:10700–10704, (1993).

New US combinatorial company, *Scrip* (Dec. 15, 1995) p. 11.

Ni et al., "Versatile approach to encoding combinatorial organic syntheses using chemically robust secondary amine tags", *J. Med. Chem.* 39:1601–1608, (1996).

Nicolaou et al., Radiofrequency combinatorial chemistry, *Agnew. Chem. 34*: 2289–2291 (1995).

Nicolaou et al., Radiofrequenz–verschlüsselte kombinatorische Chemie. *Agnew. Chem.* 107(20):2476–2479, (1995) (translation provided).

Nova et al., Memory enhanced microreactor chemistry, *Science* (1995) (in press).

Ohlmeyer et al., "Complex synthetic chemical libraries indexed with molecular tags", *Proc. Natl. Acad. Sci.* 90:10922–10926, (1993).

Pavia et al., The generation of molecular diversity, *Bioorg. & Med. Chem. Lettrs.* 3(3):387–396 (1993).

Radio frequency encoded combinatorial chemistry (RECC) kit (available at http://www.irori.com/products.html on May 24, 1996.

Roland et al., Even smaller radar tags on insects, *Nature* 381:120, (1996).

Scott et al., Searching for peptide ligands with an epitope library, *Science* 249:386–390 (1990).

Service, Memory enhanced microreactor chemistry, *Science* 270:577 (1995).

Synthesis Manager™ Software License, IRORI, Jul. 22, 1996

Toyanaga et al., Application of solid phase synthesized small molecules libraries in drug discovery. First Annual Conference of The Society For BioMolecular Screening (1995).

Xiang et al., A combinatorial approach to materials discovery, *Science* 268: 1738–1740 (1995).

Youngquist et al., "Generation and screening of combinatorial peptide libraries designed for rapid sequencing by mass spectrometry", *J. Am. Chem. Soc.* 117:3900–3906, (1995).

Zuckermann et al., Identification of highest–affinity ligands by affinity selection from equimolar peptide mixtures generated by robotic synthesis, *Proc. Natl. Acad. Sci. USA* 89:4505–4509 (1992).

IRORI Price List, IRORI Quantum Microchemistry, Jul. 23, 1997.

IRORI AutoSort®–10K—Microreactor Sorting System.

Czarnik et al., No static at all, *Chemistry in Britain*, pp. 39–41 (Oct., 1996).

Barany et al., Solid–phase peptide synthesis: A silver anniversary report, *Int. J. Pept Protein Res.* 30:705–739 (1987).

Beck–Sickinger, et al., Semiautomated T–Bag peptide synthesis using 9–Fluorenyl–Methoxyearbonyl strategy and Benzotriazol–1–yl–Tetramethyl–Uronium Tetrafluoroborate activation, *Peptide Research*, 4(2):88–94, Mar. 1991–Apr. 1991.

Cambell et al., A transition state analogue inhibitor combinatorial library, *J. Am. Chem. Soc.* 117:5381 (1995).

Cwirla et al., Peptides on phage: A vast library of peptides for identifying ligands, *Proc. Natl. Acad. Sci. USA* 87:6378–6382 (1990).

Furka et al., General method for rapid synthesis of multi-component peptide mixtures, *Int. J. Pept. Protein Res.* 37:487–493 (1991).

Kessler, Peptoids—A new approach to the development of pharmaceuticals, *Agnew. Chem. Int. Ed. Engl.* 32(4): 543–544 (1993).

Geysen et al., Strategies for epitope analysis using peptide synthesis, *J. Immunol. Meth.* 102:259–274 (1987).

Geysen et al., Small peptides induce antibodies with a sequence and structural requirement for binding antigen comparable to antibodies raised against the native protein, *Proc. Natl. Acad. Sci. U.S.A.* 82:178–182 (1985).

Houghten et al., The use of synthetic peptide combinatorial libraries for the identification of bioactive peptides, *BioTechniques* 313(3):412–421 (1992).

Houghten et al., Generation and use of synthetic peptide combinatorial libraries for basic research and drug discovery, *Nature* 354:84–86 (1991).

Maeji et al., Grafted supports used with the multipin method of peptide synthesis, *Reactive Polymer* 22:203–212 (1994).

Nikolaiev et al., Peptide–encoding for structure determination of nonsequencable polymers within libraries synthesized and tested on solid–phase supports, *Peptide Research* (1992).

Salmon et al., Discovery of biologically active peptides in random libraries: Solution–phase testing after staged orthagonal release from resin in beads, *Proc. Natl. Acad. Sci. U.S.A.* 90:11708–11712 (1993).

Sebestyén et al., Chemical synthesis of peptide libraries, *Bioorg. Med. Chem. Lettrs.* 3:413–418 (1993).

Simon, et al., Peptoids: A modular approach to drug discovery, *Proc. Natl. Acad. Sci USA* 89:9367–9371 (1992).

Scott et al., Random peptide libraries, *Current Opin. Biotechnol.* 5:40–48 (1994).

Moussy et al., Prevention of the rapid degradation of subcutaneously implanted Ag/AgCl reference electrodes using polymer coatings, *Anal. Chem.* 66:674–679, (1994).

Usmani, Chap. 1: Diagnostic Polymers and Coatings: "Chemistry, technology, and applications" in *Diagnostic Biosensors Polymers:* 2–19, ACS Symp. Series 556, Usmani et al. Eds. American Chemical Society, Washington D.C. (1994).

Brenner et al., Encoded combinatorial chemistry, *Proc. Natl. Acad. Sci. USA* 89: 5381–5383 (1992).

Brown et al., Modern machine–aided methods of oligodeoxyribonucleotide synthesis, *Oligonucleotides and Analogues: A Practical Approach*, Eckstein et al., eds., IRL, Oxford UK, 1:1–24 (1991).

Fodor et al., Light–directed, spatially addressable parallel chemical synthesis, *Science* 251:767–773 (1991).

Houghten, General method for the rapid solid–phase synthesis of large numbers of peptides; Specificity of antigen–antibody interaction at the level of individual amino acids, *Proc. Natl. Acad. Sci. USA* 82:5131, (1985).

Kieleczawa, Jan, et al., DNA sequencing by primer walking with strings of contingous hexamers, *Science* 258:1787–1791, (1992).

McCombie, W. Richard, et al., Automated DNA sequencing using 4–Color fluorescent detection of reactions primed with hexamer strings, *Biotechniques* 17:(3)574–579 (1994).

Lam et al., A new type of synthetic peptide library for identifying ligand–binding activity, *Nature* 354:82–83.

Ruiz–Martinex, M.C., et al., DNA sequencing by capillary electrophoresis using short oligonucleotide primer Libraries, *Biotechniques* 20:(6)1058–1069, (1996).

Spatola, Peptide backbond modifications: A structure–activity analysis of peptides containing amide bond surrogates. Conformations constraints, and related backbone replacements, *Chem. Biochem. Amino Acids, Pept, Proteins* 7:267–357 (1983).

Szelke et al., Novel transition–state analogue inhibitors of renin, in *Peptides: Structure and Function. Proceedings of the Eighth American Peptide Symposium* (1983) pp. 579–582.

Zuckerman et al., Efficient method for the preparation of peptoids [oligo(N–substituted glycines)] by submonomer solid phase synthesis, *J. Am. Chem. Soc.* 114:106460–10647 (1992).

Zuckerman et al., Discovery of nanomolar ligands for 7–transmembrane g–protein–coupled receptors from a diverse N–(substituted)glycine peptoid library, *J. Med. Chem.* 37:2678–2685 (1994).

Saha et al., Diisopropylsilyl–linked oligonucleotide analogs: solid–phase synthesis and physiochemical properties, *J. Org. Chem* 58: 7827–7831.

Aoki et al., Effect of quaternization on electron diffusion for redox hydrogels based on poly(4–vinylpyridine), *J. Phys. Chem.* 99:(14)5102–5110, (1995).

Bunin et al., The combinatorial synthesis and chemical and biological evaluation of a 1,4–benzodiazepine library, *Proc. Natl. Acad, Sci. USA* 91:4708–4712 (1994).

Bunin et al., A general method for the solid–phase synthesis of 1,4–benzodiazepine derivatives, *J. Am. Chem. Soc.* 114:10997–10998 (1992).

Chen et al., 'Analogous' organic synthesis of small–compound libraries: Validation of combinatorial chemistry in small–molecule synthesis, *J. Am. Chem. Soc.* 116:2661–2662 (1994).

Czarnik et al., Parke–Davis' Diversomers™ technology: A practical approach to simultaneous, parallel organic synthesis, *Polym. Prepr. (Am. Chem. Soc., Div. Polym. Chem.)* 35(2):985 (1994).

DeWitt et al., 'Diversomers': An approach to nonpeptide, nonligomeric chemical diversity, *Proc. Natl. Acad. Sci. USA* 90:6909–6913 (1993).

DeWitt et al., Diversomers: An approach to nonpeptide nonoligomeric chemical diversity, *Proc. Natl. Acad. Sci. USA* 90:6909–6913 (1993).

DeWitt et al., Diversomers™ technology: Solid phase synthesis, automation, and integration for the generation of chemical diversity, *Drug Develop. Res.* 33:116–124 (1994).

Eichler and Houghten, Identification of substrate–analog trypsin inhibitors through the screening of synthetic peptide combinatorial libraries, *Biochemistry* 32:11035–11041 (1993).

Goldmacher et al., Photoactivation of toxin conjugates, *Bioconjugate Chem.* 3:3:104–107 (1992).

Hazum et al., A photocleavalble protecting group for the thiol function of cysteine, *Pept.,* Proc. Eur. Pept. Symp., 16th, Brunfeldt, K (Ed), pp. 105–110 (1981).

Kennedy et al., Amperometric monitoring of chemical secretions from individual pancreatic β–Cells, *Anal. Chem.,* 65:(14)1882–1887, (1993).

Kick et al., Expedient method for the solid–phase synthesis of aspartic acid protease inhibitors directed toward the generation of libraries, *J. Med. Che.* 38:1427 (1995).

Kulys et al., Kinetics of glucose oxidase catalyzed electron transfer mediated by sulfur and selenium compounds, *Febs. Lett.* 329:(1,2)205–209, (1993).

Liskamp. Opportunities for new chemical libraries: unnatural biopolymers and diversomers, *Agnew. Chem. Int. Ed. Engl.* 33(6):633–636 (1994).

Mitchell et al., tert–Butyloxycarbonylaminoacyl–4–(oxymethyl)phenylacetamidomethyl–resin, an improved support for solid–phase peptide synthesis, *J. Org. Chem.* 43(14):2845–2852 (1978).

Nogrady, Pro–drugs and soft drugs, *Medicinal Chemistry: A Biochemical Approach,* Oxford Univ. Press, N.V. (1985) pp. 388–392.

Padwa et al., Intramolecular reorganization of some unsaturated 2H–azirines, *J. Org. Chem.* 41(3):543–549 (1976).

Padwa et al., Thermal arrangement of allyl substituted 2H–azirines to 3–azabicyclo[3.1.0]hex–2–enes, *J. Org. Chem.,* 41(1):180–182 (1976).

Padwa et al., Photoelimination of a β–keto sulfide with a low–lying $\pi$—$\pi^*$ triplet state, *J. Org. Chem.* 36:3550–3552 (1971).

Pátek et al., All–cis cyclopentane scaffolding for combinatorial solid phase synthesis of small non–peptide compounds, *Tetrahedron LEtt.* 35:9169, (1994).

Pétek et al., Solid–phase synthesis of "small" organic molecules based on thiazolidine scaffold, *Tetrahedron Letter.* 36:2227, (1995).

Polymer lights up with voltage, *Chemical and Engineering News,* Oct. 7,1996, p. 30.

Randolph et al., Major simplifications in oligosaccharide syntheses arising from a solid–phase based method: An application to the synthesis of the Lewis b antigen, *J. Am. Chem. Soc.* 117:5712, (1995).

Sakai et al., Local detection of photoelectrochemically produced $H_2O_2$ with a "wired" horseradish peroxidase microsensor, *J. Phys. Chem.* 99:(31)11896–11900, (1995).

Stankovic et al., Diversomers™ libraries: A novel approach to chemical diversity, in *Innovation and Perspectives in Solid Phase Synthesis,* R. Epton, ed. (SPCC Ltd. Birmingham, 1993) pp. 391–396.

Sucholeiki, Solid–phase photochemical C–S Bond cleavage of thioethers—A New approach to the solid–phase production of non–peptide molecules, *Tetrahedron Letter.* 35:7307 (1994).

Tarkka et al., Electrically generated intramolecular proton transfer: electroluinescence and stimulated emission from polymers, *J. Am. Chem. Soc.* 118, 9438–9439 (1996).

Vedejs et al., A method for mild photochemical oxidation: Conversion of phenacyl sulfides into carbonyl compounds, *J. Org. Chem.* 49:5730575 (1984).

Wang, Solid phase synthesis of protected peptides via photolytic cleavage of the α–methylpenacyl ester anchoring linkage, *J. Org. Chem.* 41(20):3258–3261 (1976).

Yang et al., Applications of "wired" peroxidase electrodes for peroxide determinatio in liquid chromatography coupled to oxidase immobilized enzyme reactors, *Anal. Chem.* 67:1326–1331, (1995).

Yen et al., Optically controlled ligand delivery, 1. Synthesis of water–soluble copolymers containing photocleavable bonds, *Makromol. Chem. 190*:69–82 (1989).

Ames et al., Methods for detecting carcinogens and mutagens with the Salmonella/mammalian–microsome mutaggenicity test, *Mutation Res. 31*:347–364 (1975).

Ames et al., An improved bacterial test system for the detection and classification of mutagens and carcinogens, *Proc. Natl. Acad. Sci. U.S.A. 70*:782–786 (1973).

Ames, The detection of chemical mutagens with enteric bacteria, *Chemical Mutagens, Principles and Methods for their Detection,* vol. 1, Plenum PRess, New York, 971, pp 267–282.

Baxendale et al., Development of scintillation proximity assays for prostaglandins and related compounds, *Advances in Prostaglandin, Thromboxane, and Leukotriene Research 21*:303–6, B. Sameulsson et al., Eds., Raven Press, Ltd., New York (1990).

Benjamin et al. X–rays induce interallelic homologous recombination at the human thymidine kinase gene, *Mol. Cell. Biol. 12*(6):2730–2738 (1992).

Berry et al., Scintillation proximity assay: Competitive binding studies with [$^{125}$I]endothelin–1 in human placenta and porcine lung, *J. Cardiovasc Oharmacol. 17 (Suppl. 7)*:S143–S145 (1991).

Birge, Photophysics and molecular electronic applications of the rhodpsins,*Ann. Rev. Phys. Chem. 41*:683–733 (1990).

Bosworth et al., Scintillation proximity assay, *Nature 341*:167–168 (1989).

Bourdillon et al., A fully active monolayer enzyme electrode derivatized by antigen–antibody attachment, *J. Am. Chem. Soc. 115*:(26)12254–12269, (1993).

Bourdillon et al., Step–by–step immunological construction of a fully active multilayer enzyme electrode, *J. Am. Chem. Soc. 116*:(2)10328–10329, (1994).

Buechler et al., Simultaneous detection of seven drugs of abuse by the triage™ panel for drugs of abuse, *Clin. Chem. 38*(9):1678–1684 (1992).

Butz et al., Immunization and affinity purification of antibodies using resin–immobilized lysine–branched synthetic peptides, *Peptide Res. 71(1)*:20–23 (1994).

Cardullo et al., Detection of nucleic acid by hybridization by nonradiative fluorescence resonance energy transfer, *Proc. Natl. Acad. Sci. USA 85*:8790–8794 (1998).

Chen, Digoxin immunoassay using capillary electrophoresis with laser–induced fluorescence detection (available at http://wwn.beckman . . . les/a1778/a/1778.htm on Jun. 13, 1996).

Cook et al., Scintillation proximity enzyme assay. A rapid and novel assay technique applied to HIV proteinase, *Structure and Function of an Aspartic Proteinases,* pp. 525–528, B.M. Dunn, Ed., Plenum Press, NY (1991).

Duan et al., Separation–free sandwich enzyme immunoassays using microporous gold electrodes and self–assembled monolayer/immobilized capture antibodies, *Anal. Chem. 66*:1369–1377, (1994).

Fenwick et al., Application of the scintillation proximity assay technique to the determination of drugs, Analytical Proceedings Including Analytical Communications, Mar. 1994, vol. 31 (presented at the Eurupanalysis VIII Conference held Sep. 5–11, 1993, University of Edinburgh).

Gee, et al., detection and classification of mutagens: A set of base–specific Salmonnela tester strains, *Proc. Natl. Acad. Sci. USA 91*:11606–11610 (1994).

Hart et al., Scintillation proximity assay (SPA)—A new method of immunoassay. Direct and inhibition mode detection with human albumin and rabbit antihuman albumin, *Molec. Immunol. 16*:265–267 (1979).

Heath et al., A note on cAMP [$^{125}$I] scintillation proximity assay (SPA)—A homogeneous radioimmunoassay for cAMP, *Method. Surv. Biochem. Anal. 21*:193–194 (1991).

Hildebrand et al., Comparison of bioanalytical determinations of lloprost, a chemically stable $PGI_2$ memetic, by conventional radioimmunoassay (RIA) and scintillation proximity assay (SPA), *Eicosanoids 5*:5–8 (1992).

Horrocks et al., Scanning electrochemical microscopy. 24. Enzyme ultramicroelectrodes for the measurement of hydrogen peroxide at surfaces, *Anal. Chem. 65*:3605–3614, (1993).

Ill et al., A COOH–terminal peptide confers regiospecific orientation and facilitates atomic force microscopy of an $IgG_1$. *Biohys J. 64*:919 (1993).

Jiang et al., Capillary enzyme immunoassay with electochemical detection for the determination of atrazine in water, *J. Agric. Food Chem. 43*:1098–1104, (1995).

Kabat et al., *Experimental Immunochemistry,* Chapter 40. Equilibrium Dialysis, Charles C. Thomas, Springfield, Illinois. pp. 715–718 (1961).

Katakis et al., Electrostatic control of the electron transfer enabling binding of recombinant glucose oxidase and redox olyelectrolyte, *J. Am. Chem. Soc. 116*:3617–3618, (1994).

Ketner et al., Integrated simina virus 40 sequences in transformed cell DNA: Analysis using restriction endonucleases, *Proc. Nat. Acad. Sci. USA 73(4)*:1102–1106 (1976).

Khrapko et al., An oligonucleotide hybridization approach to DNA sequencing. *FEBS Lett. 255*:118–122 (1989).

Kirk et al., Encapsulated scintillators monitor $^3$H–solute concentrations, *IEEE Transactions on Nuclear Science NS–29 (1)* (Feb. 1982).

Koutney et al., Microchip electrophoretic immunoassay for serum cortisol, *Anal. Chem. 68*:18–2, (1996).

Kowalski et al., Characterization and applications of the disc angiogenesis system, *Exp. Exp. Mol. Path. 56*:1–19, (1992).

Mansfield, Scintillation proximity assay using polymeric membranes, *Health Sciences, Pharmacy,* Dissertation Abstracts Int'l. (1992).

Maron et al., Revised methods for the Salmonella mutagenicity test, *Mutation research 113*:173–215 (1983).

Mathis, Probing molecular interactions with homogeneous techniques based on rare earth cryptates and fluorescence energy transfer, *Clin. Chem. 41(9)*:1391–7 (1995).

Matsumura et al., A Simple method for measurement of phosphoramindon–sensitive endothelin converting enzyme activity, *Life Sci. 51*:1603–1611 (1992).

Mattingly et al., Membrane–based scintillation proximity assays. I. Detection and quantification of $^{13}CO_2$, *J. Memb. Sci. 98*:275–280 (1995).

Nelson, A Novel method for the detection of receptors and membrane proteins by scintillation proximity radioassay, *Anal. Biochem. 165*:287–293 (1987).

Nguyen et al., Quantitation of angiogenesis and antiangiogenesis in the chick embryo chorioallantoic membrane, *Microvasc. Res. 47*:31–40, (1994).

Nowak, Entering the postgenome era, *Science 270*:368–371 (1993).

Peerce, Distance between substrate sites on the Na–glucose cotransporter by fluorscence energy transfer, *Proc. Natl. Acad. Sci. USA 83*:8092–8096 (1986).

Pernelle et al., An efficient screening assay for the rapid and precise determination of affinities between leucine zipper domains, *Biochemistry 32*:11682–11687 (1993).

Riklin et al., Improving enzyme–electrode contacts by redox modification of cofactors, *Nature 376*:672–675, (1995).

Schena et al., Quantitative monitoring of gene expression patterns with a complementary DNA microarray, *Science 270*:467–470 (1995).

Schiestl et al., Effect of peroxisome proliferators on intrachromosomal and interchromosomal recombination in yeast, *Carcinogenesis 11*(1):173–176 (1990).

Sherwood et al., Controlled antibody delivery systems, *Bio/Technology 10*:1446–1449 (1992).

Skinner et al., Direct measurement of the binding of RAS to neurofibromin using a scintillation proximity assay, *Anal. Biochem. 223*:259–265 (1994).

Southern, Detection of Specific sequences among DNA fragments separated by gel electrophoresis, *J. Mol. Biol. 98*:503–517 (1975).

Takeuchi, Scintillation proximity assay, from *Lab. Pract.* (Sep. 1992).

Towbin et al., Electrophoretic transfer of proteins from polyacrylamide gels to nitrocellulose sheets: Procedure and some applications, *Proc. Natl. Acad. Sci. USA, 76*(9):4350–4354 (1979).

Towers et al., Scintillation proximity assay, 9th Joint Meeting of British Endocrine Societies, Glasgow, Scotland, UK, Mar. 19–22, 1990, *J. Endocrinol. 124*(Suppl.) (1990).

Udenfriend et al., Scintillation proximity assay: A Sensitive and continuous isotropic method for monitoring ligand/receptor and antigen/antibody interactions, *Anal. Biochem. 161*:494–500 (1987).

Udenfriend et al., Scintillation proximity assay: A sensitive and continuous isotropic method for monitoring ligand/receptor and antigen/antibody interactions, *Anal. Biochem. 151*:494–500 (1987).

Velculescu et al., Serial Analysis of gene expression, *Science 270*:484–487 (1995).

Vreeke et al., Direct electrical detection of dissolved biotinylated horseradish peroxidase, biotin, and avidin, *Anal. Chem. 67*:303–306, (1995).

Whitford et al., An homogeneous radioimmunoassay for abscisic acid using a scintillation proximity assay technique, *Phytochemical Anal. 2*:134–136 (1991).

Wood et al., Radioligand binding to technology which eliminates the requirement for separation of free and bound radiolabel, Meeting of the British Pharmacological Society, Sheffield, England, UK, Apr. 18–20, 1990 *Br. J. Pharmacol. 100*(Proc. Suppl. Jun.) p. 492 (1990).

Device would detect drugs in sweat, *NASATECH* (May 1996).

DIALOG Abstract 003670011, citing: EP 0074428.
DIALOG Abstract 004334295, citing: FR 2 555 744.
DIALOG Abstract 003812858, citing: FR 2 526 169.
DIALOG Abstract 010167274, citing: EP 637 750 A2.
DIALOG Abstract 009968074, citing: DE 43 01401 A1.
DIALOG Abstract 009619322, citing: DE 43 10169 A1.
DIALOG Abstract 009659308, citing: DE 43 13807 A1.
European Patent Office, Patent Abstracts of Japan, citing: JP 57016359.

Harmon et al., "Reading between the lines—an introduction to bar code technology", Elmers Publishing, Inc., (1989).

Herbreteau et al., Analysis of oligosaccharides using aminobonded silica gel and a ternary eluent with evaporative light scattering detection, *J. Anal. Chem. 351*:246–250, (1995).

Kovacs et al., Silicon micromachining—sensors to systems, *Anal. Chem. News & Features,* pp. 407A–412A (1996).

Maier et al., Possible correlation between blood glucose concentration and the reduced scattering coefficient of tissues in the near infrared, *Optics Lett. 19*:(24)2062–2064, (1994).

Nadis, All–in–one detectors for the faintest objects, *Science 274*: 36–38 (1996).

Peacock et al., Single optical photon detection with a superconducting tunnel junction, *Nature 381*: 135–137 (1996).

Sodickson et al., Kromoscopic™ Analysis: A possible Alternatiave to spectroscopic analysis for noninvasive measurement of analytes in vivo, *Clin Chem 30*:(9) 1838–1844, (1994).

Vellacott, CMOS in camera, *IEE Review,* p. 111 (May 1994).

Wang et al., A high density two dimensional bar code, SPIE Proceedings vol. 1384, High Speed Architectures, Bar Coding and Character Recognition, pp. 169–175 (1990).

Batteries Chemistry 411/511 Oregon State University, (available at http://www/chem.orst.edu/classes/ch411/rest/scbatt.htm#1: on Sep. 18, 1996).

Biboulet et al., Haemodynamic effects of moderate normovolaemic haemodilution in conscious and anaesthetized patents, *Brit. J. Anaes. 76*:81–84, (1996).

Bloom, A memory to remember, *Electronics Systems Design Magazine* (1989) pp. 5–9.

Brecht et al., Transducer–based approaches for parallel binding assays in HTS, *J. of Biomolecular Screening 1*:(4)191–201, (1996).

Cohen et al., A flat–aluminum based voltage–programmable link for field–programmable devices, *IEEE Transactions on Electron Devices,* 41(5):721–725 (1994).

Cook and Keller, Amorrhous silicon antifuse technology for bipolar PROMS, *Proc. IEEE Bipolar Circuits Technol. Meet.* (1986) pp. 99–100.

Czosnyka et al., Laboratory testing of three intracranial pressure microtransducers: technical report (available at http://www/wwilkins . . . babr.htm/#Santbrink on Sep. 28, 1996).

Dandrige et al., Optical fiber sensor technology, in *Applications of Optoelectronics in Lightwave Systems,* pp. 600–649.

DIALOG Abstract 008591601, citing: EP 4213065 A1.
DIALOG Abstract 008591601, citing: EP 420177 A1.

Greve, Programming mechanism of polysilicon resistor fuses,*IEEE Transactions on Electron Devices ED–29(4)*:719–724 (1982).

Gu et al., Cross talk–limited storage capacity of volume holographic memory, Reprinted with permission from *J. Optical Soc. America A,* vol. 9(11), pp. 1978–1983 (Nov. 1992), in Selected Papers on Holographic Storage.

Gu et al., Noise grating formed during the multiple exposure schedule in photorefractive media, Reprinted with permission from *Optics Commun.*, vol. 93, pp. 213–218 (1992), in Selected Papers on Holographic Storage.

Haarer, Photochemical hole burning: A high density storage scheme, Proc. Int. Symp. on Optical Memory, 1987; in *Jap. J. Appl. Phys. Supplement* 26–4:227–232 (1987).

Hamici et al., Une etude preliminaire d'un dispositif implantable alimente par liaison inductive pour la telemesure de l'electrocardiogramme epicardique et de l'activite radio–isotopique du ventricule gauche, *Phys. Med. Biol.* 40:609–627, (1995).

Hong et al., Volume holographic memory systems: techniques and architectures, *Optical Engineering* 34(8):2193–2203 (1995).

Isailović, Optical Memories, *Videodisc and Optical Memory Systems,* Prentice–Hall, Inc. (1985) pp. iii, 292–293.

Li et al., Three–dimensional holographic disks, *Applied Optics* 33(7)3764–3774 (1994).

Martens et al., An assessment of mediators as oxidants for glucose oxidase in the presence of oxygen, *Biosensors & Bioelectronics* 10:393–403, (1995).

Martin, Unique symbol for marking and tracking very small semiconductor products, SPIE Proceedings vol. 1598, *Lasers in Microelectronic Manufacturing,* pp. 206–220.

Mobius et al., Chap. 25: Solid–State electrochemical potentiometric sensors for gas analysis, in *Sensors—A Comprehensive Survey,* Ed. W. Gopel, J. Hesse, and J.N. Zernel, VCH, New York, pp. 1106–1154 (1991).

Mok, Angel–multiplexed storage of 5000 holograms in lithium niobate, *Optics Lett.* 18(11):915–917 (1993).

Moussy et al., A miniaturized nafion–based glucose sensor: in vitro and in vivo evaluation in dogs, *Int. J. Artif. Organs* 17:88–94, (1994).

Moussy et al., In vitro and in vivo performance and lifetime of perfluorinated Ionomer–coated glucose sensors after high–temperature curing, *Anal. Chem.* 66:3882–3888, (1994).

Pein and Plummer, A 3–D sidewall flash EPROM cell and memory array, *IEEE Transactions on Electronic Devices* 40(11) (1993).

Pokrowsky et al., Reading and writing of photochemical holes using GaAlAs–diode lasers, *Optics Lettrs* 8(6):280–282 (1983).

Prabhu et al., Co–fired ceramic on metal multilayer circuit board technology for multichip module packaging, Proc. SPIE–Int. Soc. Opt. Eng. (Proc. 1992 Intl. Symposium on Microelectronics) 1847:601–606 (1992).

Psaltis, Parallel optical memories, *Byte* pp. 179–182 (Sep. 1992).

Psaltis et al., Holographic memories, *Scientific American* pp.70–76 (Nov. 1995).

Pitsillides et al., Biotelemetry of cardiovascular hemodynamic measurements in miniswine, *IEEE Transactions on Biomedical Engineering* 39(9):982–986, (1992).

Qiao et al., Electrical fixing of photorefractive holograms in $Sr_{0.75}Ba_{0.25}Nb_2O_6$, Reprinted with permission from *Optics Lett.,* vol. 18(12), pp. 1004–1006 (Jun. 1993), in Selected Papers on Holographic Storage.

Qiao et al., Sampled dynamic holographic memory, Reprinted with permission from *Optics Lett.,* vol. 17(1), pp. 1376–1378 (Oct. 1992), in Selected Papers on Holographic Storage.

Sandia Poineers Breakthroughs in Long–life Lithium Battery Technology (available at http://www.sandia.gov/elecomcen/fffs26.html on Sep. 18, 1996).

Shacham–Diamand et al., IPEL—A novel ion–implanted electrically programmable element, *IEEE Electron Device Lett.* 10(5):180–182 (1989).

Summaries of FY 1995 Research in the Chemical Science, Advanced Batteries (available at http://www.er.doe.g . . . n/bes/chm/jabos.html on Sep. 18, 1996.

Surampudi et al., High Performance, Low Temperature Batteries, (available at Abstract http://137.79.14197/Hiplot-b.html on Sep. 18, 1996).

Tanimoto et al., A novel MOS PROM using a highly resistive poly–Si resistor, *IEEE Transactions on Electron Devices* ED–27(3):517–520 (1980).

Truett et al., Validation of a radiotelemetry system for continuous blood pressure and heart rate monitoring in dogs, *Laboratory Animal Science* 45(3):299–302, (1995).

Wild et al., Hole Buring, Stark–Effect and Holographic Image Storage, Proc. Int. Symp. on Optical Memory, 1987; in *Jap. J. Appl. Phys. Supplement* 26–4:233–236 (1987).

Woakes et al., Implantable data logging system for heart rate and body temperature: its application to the estimation of field metabolic rates in Antarctic predators, *Med. & Biol. Eng. & Comput.* 145–151, (1995).

Yoshimura et al., Ultra–high density optical memory by photochemical hole burning (PHB) and multi–layered PHB system, *SPIE 1078,* Optical Data Storage Topical Meeting (1989).

Berg, Peptide oligomers used to store holograms, *Chem. and Engin. News,* Oct. 14, 1996, p. 28.

Berg et al., Peptide oligomers for holographic data storage, *Nature 383:* 505–508 (1996).

Xiao–yi et al., Combinatorial chemistry with laser optical encoding, *Angew Chem. Int. Ed. Engl.* 36(7): 780–782 (1997).

Aylott et al., Development of optical biosensors using sol–gel technology, *3rd European Conference on Optical Chemical Sensors and Biosensors,* Mar. 31, 1996–Apr. 3, 1996, Zurich, Switzerland (1996).

Barisci et al., Conducting Polymer Sensors, *TRIP* 4(9):307–311, (1996).

Barnikol et al., Experiments aimed at developing an implantable and continuously functioning glucose sensors based on polarimetry, *Biomed. Tech. 40*:(5)114–120, Berlin (1995).

Bindra et al., Design and in vitro studies of a neelde–type glucose sensor for subcutaneous monitoring, *Anal. Chem,* 64:1692–1696, (1991).

Charbonneau et al., Amino acid sequence of the calcium–dependent photoprotein aequorin, *Biochemistry* 24:6762–6771, (1985).

Claremont et al., Potentially–implantable, ferrocene–mediated glucose sensor, *J. Biomed. Engr.* 5:272–274, (1986).

Clark, Jr. et al., Implanted electroenzymataic glucose sensors, *Diabetes Care* 5(3):174–180, (1982).

Clark, Jr. et al., Theoretical and practical bases for implantable glucose sensors with special reference to the peritoneum, *IEEE/NSF Symposium on Biosensors,* pp. 69–74, (1984).

Csoregi et al., Design, characterization, and one–point in vivo calibration of a subcutaneously implanted glucose electrode, *Anal. Chem.* 66:3131–3138, (1994).

Csoregi et al., Design and optimization of a selective subcutaneously implantable glucose electrode based on "wired" glucose oxidase, *Anal. Chem.* 67:1240–1244, (1995).

Czarnik et al., Desperately seeking sensors, *Current Biology* 2:423–428, (1995).

Dave et al., Sol–gel encapsulation methods for biosensors, *Anal. Chem.* 77(22):1120A–1127A (1994).

Dialog Abstract 010113714, citing: EP 0633468 A1.

Eastman et al., Clinical review 51 implications of the diabetes control and complications trial, *J. Clin. Endocrinol. Metabol.* 77(5):1105–1107, (1993).

Foulds et al., Chap. 4, Immunoelectrodes, in *Biosensors—A Practical Approach*, Ed. A.E.G. Cass, IRL Press, pp. 97–124, (1990).

Gopel et al., Part I—Chemical and biochemical sensors in *Sensors—A Comprehensive Survey*, Ed. W. Gopel. J. Hesse, and J.N. Zernel, VCH, New York, pp. 1–27, (1991).

Gopel et al., Chapter 4: Specific molecular interactions and detection principles, in *Sensors—A Comprehensive Survey*, Ed. W. Gopel, J. Hesse, and J.N. Zernel, VCH, New York, pp. 120–157 (1991).

Gough et al., Perspectives in diabetes—development of the implantable glucose sensor—what are the prospects and why is it taking so long? *Diabetes* 44:1005–1008, (1995).

Heller, Amperometric Biosensors, Dept. of Chemical Engineering, The University of Texas at Austin, Austin, Texas 78712–10962.

Hu et al., A needle–type enzyme–based lactate sensor for in vivo monitoring, *Analyt. Chem. Acta* 281:503–511, (1993).

Inouye et al., Cloning and sequence analysis of cDNA for the luminescent protein aequorin, *Proc. Natl. Acad. Sci. USA:* 82:3154–3158, (1985).

Inouye et al., Expression or apoaequorin complmentary DNA in *Escherichia coli, Biochem.* 25:8425–8429, (1986).

Inouye et al., Overexpression and purification of the recombinant $Ca^2$–Binding Protein, Apoaequorin, *J. Biochem,* 105:473–477, (1989).

Johnson et la., Chap. 7: Reproducible electodeposition technique for immobilizing glucose oxidase, in *Diagnostic Biosensor Polymers ACS* Symp. Ser. 556, Usmani et al., Eds., American Chemical Society, Washington, D.C., pp. 84–95, (1994).

Kohama et al., Molecular weight of the photoprotein aequorin, *Biochem.* 10:(22):4149–4152, (1971).

Koudelka et al., In–vivo behaviour of hypodermically implanted microfabricated Glucose sensors, *Biosensors Bioelectronics* 6:31–36, (1991).

Millan et al., Sequence–selective biosensor for DNA based on electroactive hybridization indicators, *Anal. Chem.* 65:2317–2323, (1993).

Millan et al., Voltammetric DNA biosensor for cystic fibrosis based on a modified carbon paste electrode, *Anal. Chem.* 66:2943–2948, (1994).

Moatti–Sirat et al., Towards continuous glucose monitoring: in vivo evaluation of a miniaturized glucose sensor implanted for several days in rat subcutaneous tissue, *Diabetologia* 35:224–230, (1992).

Moatti–Sirat et al., Reduction of acetaminophen interference in blucose sensors by a composite Nafion membrane: demonstration in rats and man, *Diabetologia* 37:610–616, (1994).

Morgan et al., Immunosensors: technology and opportunities in laboratory medicine, *Clin. Chem.* 42(2):193–209, (1996).

Piek, Pressure–controlled drainage of cerebrospinal fluid: clinical experience with a new type of ventricular catheter (ventcontrol MTC) and an integrated piezo–resistive Sensor at its tip: Technical Note, (available at http://www/wwilkins . . . Gabs.html#Santbrink on Sep. 28, 1996).

Piskin et al., *Diagnostic Biosensor Polymers,* ACS Symposium Series No. 556, Chap. 18 (1994).

Poitout et al., A glucose monitoring system for on line estimation in man of blood glucose concentration using a miniaturized glucose sensor implanted in the subcutaneous tissue and a wearable control unit, *Diabetologia* 36:658–663, (1993).

Prasher et al., Cloning and expession of the cDNA coding for aequorin—bioluminescent calcium–bonding protein, *Biochem. and Biophy. Res. Comm.* 126(3):1259–1268, (1985).

Prasher et al., Isolation and expression of cDNA coding for aequorin, the $Ca^{2+}$–activated photoprotein from *Aequorea victoria, Bioluminescence* 288–297, (1986).

Prasher et al., Sequence comparisons of complementry DNAs encoding aequorin isotypes, *Biochem.* 26:1326–1332, (1987).

Prendergast et al., Chemical and physical properties of aequorin and the green fluorescent protein isolated from *Aequorea Forskalea, Bioch,.* 17(17):3448–3453, (1978).

Quinn et al., Kinetics of glucose delivery to subcutaneous tissue in Rats measured with 0.3–mm amperometric microsensors, *Am. J. Physiol.* 269:E155–E–161, (1995).

Raftopoulos et al., Prospective analysis by computed tomography and long–term outcome of 23 adult patients with chronic idiopathic hydrocephalus, available at http://www/wwilkins . . . 6abs.html#Santbrink on Sep. 26, 1996.

Reach et al., Can continuous glucose monitoring be used for the treatment of diabetes? *Anal. Chem.* 64(6):381–386, (1992).

Scheper et al., Chap. 22: Sensors in Biotechnology, in *Sensors—A Comprehensive Survey,* Ed. W. Gopel, J. Hesse, and J.N. Zernel, VDH, New York, pp. 1024–1046 (1991).

Schmidt et al., Chapter 14: Specific Features of Biosensors, in *Sensors—A Comprehensive Survey,* Ed. W. Gopel. J. Hesse, and J.N. Zernel, VCH, New York, pp. 720–817 (1991).

Stability of AquaLite: Lyophilized and In Solution in SeaLite Sciences Technical Report Sealite Sciences, Inc., Bogart, GA, pp. 1–11, (1994).

Shimomura et al., Extraction, purification and properties of aequorin, a bioluminescent protein from the luminous hydromedusan aequorea[1], *J. Cell. Comp. Physiol.* 59:223–239, (1962).

Shimomura et al., Properties of the bioliminescent protein aequorin, *Biochem.* 8:(10)3991–3997, (1969).

Shimomura et al., Structure of the light–emitting moiety of aequorin, *Biochem.* 11:(9)1604–1608, (1972).

Shimomura et al., Resistivity to denaturation of the aprprotein of aequorin and reconstitution of the luminescent photoprotein from teh partially denatured aproprotein, *Biochem. J.* 199:825–828, (1981).

The effect of intensive treatment of diabetes on the development and progresion of long–term complications in insulin–dependent diabetes mellitus, *New Engl. J. Med.* 329(14):977–986, (1993).

Tsuji et al., Site–specific mutagenesis of the calcium–binding photoprotein aequorin, *Proc. Natl. Acad. Sci. USA* 86:8107–8111, (1986).

van Santbrink et al., Continuous monitoring of partial pressure of brain tissue oxygen in patients with severe head injury, (available at http://www.wwilkins . . . abs.html#Santbrink on Sep. 28, 1996).

Wang et la., Highly selective and sensitive amperometric biosensing of glucose at ruthenium–dispersed carbon paste enzyme electrodes, *Anal. Lett.* 26:(9)1819–1830, (1993).

Wilson et al., Progress toward the development of an implantable sensor for glucose, *Clin. Chem.* 38:(9)1613–1617, (1992).

Wilson, Bioanalytical Chemistry, (available at http://www/chem/uka . . . wilson/gwilson.html on Oct. 1, 1996).

Winquist and Danielsson, Semiconductor filed effect devices, *Biosensors. A Practical Approach,* Chap. 7, Cass, Ed., IRL Press at Oxford University Press (1990).

Wrotnowski, C–053U: Biosensors and chemical biosensors (available at http://www.buscom.com/biotech/CO53U.html on Oct. 1, 1996).

Zhang et al., Elimination of the acetaminiophen interference in an implantable glucose sensor, *Anal. Chem.* 66:(7)1183–1188, (1994).

Ang et al., Chap. 10: Application of Radiation Grafting in Reagent Insolubilization, 223–247.

Berg et al., Long–chain polystyrene–grafted polyethylene film matrix: A new support for solid–phase peptide synthesis, *J. Am. Chem, Soc. 111*:8024–8026 (1989).

Berg et al., Peptide synthesis on polystyrene–grafted polyethylene sheets, Pept., Proc. Eur. Pept. Symp., 20th, Jung et al. (Eds.), pp. 196–198.

Berg et al., Polystyrene–grafted polyethylene: design of film and felt matrices for solid–phase peptide synthesis, *Innovation Perspect. Solid Phase Synth. Collect. Pap.,* Int. Symp., 1st, Epton (ed.), (1990) pp. 453–459.

Chapter 11, "Tape and Disk Materials" from *The Complete Handbook of Magnetic Recording,* 3rd Edition, by Finn Jorgenson, Tab Books (1988).

Charych et al., A 'litmus test' for molecular recognition using artificial membrances, *Chem. & Biol 3*:113–120, (1996).

Dagani et al., Two photons shine in 3–D data storage, *Chem. & Eng. News:,* Sep. 23, 1996, 68–70.

Dvornikov et al., Studies on 3D volume memory, *SPIE: 1662*: 197–204, (1992).

Dvornikov et al., Nonlinear properties of photochromic materials for use in optical devices, *SPIE 1852*:243–252, (1993).

Dvornikov et al., Spectroscopy and kinetics of photochromic materials for 3D optical memory devices, *J. Phys. Chem.* 98:6746–6752, (1994).

Dvornikov et al., Photochromism: Non–linear picosecond kinetics and 3D computer memory, *Mol. Cryst. Liq. Cryst. 246*:379–388, (1994).

Dvornikov et al., Materials for 3D Memory Devices, *SPIE 2297*:447–451, (1994).

Dvornikov et al., Molecular transformation as a means for 3D optical memory devices, *Optics Commun. 128*205–210, (1996).

Dvornikov et al., Anthracene monomer–dimer photochemistry: high density 3D optical storage memory, *Res. Chem. Intermed. 22*:(2)115–128, (1996).

Ford et al., 3–D two photon memory materials and systems, *SPIE 1853*:5–13, (1993).

Ford et al., Write/read performance in 2 photon 3–D memories, *SPIE 2026*:604–613, (1993).

Kent et al. Preparation and properties of tert–butyloxycarbonylaminoacyl–4–(oxymethyl)phenylacetamidomethyl–(Kel F–g–styrene) resin, an insoluble, noncrosslinked support for solid phase peptide synthesis, *Isr. J. Chem.* 17:243–247 (1979).

Kleine et al., Lipopeptide–polyoxyethylene conjugates as mitogens and adjuvants, *Immunobiol. 190*:53–66 (1994).

Loading MicoKan™ Reactors with Solid Phase Resin—Recommended Procedures, *Irori,* Sep. 26, 1996.

Malkin et al., Photocemistry of molecular systems for optical 3D storage memory, *Research of Chemical Intermediates, 19*:(2)159–189, (1993).

Merrifield, Solid–phase peptide synthesis. III. An improved synthesis of bradykinin, *Biochem. 3(9)*:1385–1390 (1964).

Mitchell et al., A new synthetic route to tert–butyloxycarbonylaminoacyl–4–(oxymethyl)phenylacetamidomethyl–resin, an improved support for solid–phase peptide synthesis, *J. Org. Chem. 43(14)*:2845–2852 (1978).

Mitchell et al., Preparation of aminomethyl–polystyrene resin by direct amidomethylation, *Tetrahedron Lett. 42*:3795–3798 (1976).

*Pierce Chemical Co. Catalog & Handbook,* selected pages which describe the preparation of and use of such reagents and provides a commerical source for such reagents, (1994).

*Polymeric Materials for Microelectronic Applications: Science and Technology,* ACS Symposium Series No. 579, Ito et al., (Eds.), Chaps. 17–23, 27–29, 35 and 36 (1995).

Prassad et al., Multiphasic nanostructured composites for photonics, Mat. Res. Soc. Symp. Proc. 413:203–213, (1996).

Quinn et al., Photo–crosslinked copoymers of 2–hrdroxyethyl methacrylate, poly)ethylene glycol) tetra–acrylate and ethylene dimetharylate for improving biocompatibility of biosensors, *Biomaterials 16*:389–396, (1995).

Reaction Reproducibility Using MicroKan™ Reactors, *Irori Quantum Microchemistry.*

Solid Phase Synthesis using MicroKan™ Reactors—Recommended Procedures, *Irori,* Sep. 26, 1996.

Solid Phase Chemistries—Performed in MicroKan Reactors, *Irori Quantum Microchemistry.*

To Fill MicroKan—Tips for Using the Electronic Pipette, *Irori Quantum Microchemistry.*

The MicroKan™ Filling Kit—Recommended Procedures, *Irori Quantum Microchemistry.*

Wilkins et al., Biomaterials for implanted closed loop insulin delivery system: A review, *Biosensors and Bioelectronics* 5:167–213, (1990).

Moerner et al., Polymeric photorefractive materials, *Chem. Rev. 94*: 127–155 (1994).

IRORI Unisphere®–200 Resins—optimized for use with MicroKan®Reactors.

Amstein et al., Adaptation of plastic surfaces for tissue culture by glow discharge, *J. Clinical Microbiol.* 2:46–54 (1975).

Basch et al., Cell separation using positive immunoselective techniques, *J. Immunol. Meth.* 56:269–280 (1983).

Batra et al., Insertion of constant region domains of human $JgG_1$ into CD4–PE40 increases its plasma half–life, *Mol. Immunol.* 30(4):379–386 (1993).

Bayer et al., Pept.: Struct. Funct., Proc. Am. Pept. Symp, 8th, Hruby et al., Eds., pp. 87–90 (1983).

Bayer, E. et al., New polymer and strategy for the solid–phase synthesis of protected peptide fragments, Peptides: Chemistry Structural Biology, Proc. Amer. Peptide Symp., 13th, Hodges et al. eds., pp. 156–158 (1994).

Bayer et al., New polymer supports for solid–liquid–phase synthesis, *Chem. Pept. Proteins* 3:3–8 (1986).

Bayer et al., Polystyrene–immobilized PEG chains, *Poly-(Ethylene Glycol) Chem.* Harris, ed. (1992) pp. 325–345.

Boldt, Fractionation of human lymphocytes with plant lectins. II *Lens culinaris* lectin and wheat germ agglutinin Identify distinct lymphocytes subclasses, *J. Immunol.* 123(2):808–816 (1979).

Dormán et al., Benzophenone photophores in biochemistry, *Biochem.* 33(19):5661–5673 (1994).

Freshney, *Culture of Animal Cells. A Manual of Basic Technique,* Alan R. Liss, Inc., New York, pp. 141–143, 217–244 (1983).

Gilham, Immobilized Polynucleotides and Nucleic Acids, in Immobilized Bichemicals and Affinity Chromatography, Ed. R. Bruce Dunlap, Plenum Press, N.Y., pp. 173–184 (1973).

Hale, Irreversible, oriented immobilization of antibodies to cobalt–iminodiacetate resin for sse as immunoaffinity media, *Anal. Biochem.* 231:46–49 (1995).

Harlow et al., *Antibodies. A Laboratory Manual,* Cold Spring Harbor Laboratory Chap. 14 (1988).

Ilg et al., Investigation of the diffusion process in cross–linked polystyrenes by means of MNR imaging and solid–state NMR spectroscopy, *Macromolecules,* pp., 2778–2783 (1994).

*Immobilized Enzyme, Antigens, Antibodies and Peptides. Preparation and Characterization,* Howard H. Weetall, Ed., Marcel Dekker, Inc., N.Y. (1975).

Ishikawa et al., Enzyme–Labeling of antibodies and their fragments for enzyme immunoassay and immunohistochemical Staining, *J. Immunoassay* 4(3):209–327 (1983).

Johansson et al., Immobilized enzymes in microcalorimetry, *Meth. Enzymol.* 44:659–667 (1976).

Kaji, Molecular design of epoxy resins for microelectronics packaging, Chap. 17, *American Chemical Society* (1994).

Kennedy et al., Immobilized Enzymes, *Solid Phase Biochemistry, Analytical and Synthetic Aspects,* Scouten, Ed., 7:253–391 (1983).

Kleinman et al., Use of extracellular matrix components for cell culture, *Analytical Biochem,* 166:1–13 (1987).

Kwoh et al., Transcription–based amplification system and detection of amplified human immunodeficiency virus type 1 with a bead–based sandwich hybridization format, *Proc. Natl. Acad. Sci. USA,* 86:1173–1177 (1989).

Loetscher et al., Immobilization of monoclonal antibodies for affinity chromatography using a chelating peptide, *J. Chromatography* 595:113–119 (1882).

Loetscher et al., Immobilization of monoclonal antibodies for affinity chromatography, *J. Chromatography* 595:113–(1992).

Mage et al., Mouse lymphocytes with and without surface immunoglobulin: Preparative Scale Separation in Polystyrene tissue culture dishes coated with specifically purified anti–immunoglobulin, *J. Immunol. Methods* 15:47–56 (1977).

Mage et al., Preparative nonlytic separation of Lyt2[30] and Lyt2[31] T lymphocytes, functional analysis of the separated cells and demonstration of synergy in graft– vs.– host reaction of Lyt2[+] and Lyt2[30] cells, *Eur. J. Immunol.* 11:228–235 (1981).

McKeehan et al., Stimulation of clonal growth of normal fibroblasts with substrata coated with basic polymers, *J. Cell Biol.* 71:727–734 (1976).

Miles & Hales, Labelled antibodies and immunological assay systems, *Nature* 219:186–189 (1968).

Mosbach, AMP and NAD as 'general ligands', Affinity Techniques. Enzyme Purification: Part B. *Methods in Enzymology,* vol. 34, W. B. Jakoby, et al., Eds., Acad. Press, N.Y. (1974).

Nokihara et al., Superior support for solid–phase peptide synthesis, *Shimadzu Hyoron* 50:25–31 (1993).

Padwa et al., Photocycloaddition of arylazirenes with electron–deficient olefins, *J. Am. Chem. Soc.* 93(2):548–550 (1971).

Pidgeon et al., Solid phase membrane mimetics, *Enzyme Microb. Technol.* 12:149 (1990).

Powell et al., Protein purification by affinity binding to unilamellar vesicles, *Biotech. & Bioeng.,* 33:173–182 (1989).

Rapp et al., Polystyrene–polyoxyethylene graftcopolymers for high speed peptide synthesis, Pept., Proc. Eur. Pept, Symp., 20th, Jung et al., eds., pp. 199–201 (1989).

Rapp et al., Continuous flow peptide synthesis of PSPOE–graft copolymers, *Innovation Perspect. Solid Phase Synth. Collect. Pap.,* Int. Symp., 1st, Epton, ed., pp. 205–210 (1990).

Rapp et al., Peptide screening and optimization by using monosized 25μm tentacle microspheres, in *Pept. Chem, 1992,* Proc. Jpn. Symp., 2nd, Yanaihara, ed., pp. 7–10 (1992).

Rapp et al., Monosized 15 micron grafted microspheres for ultra high speed peptide synthesis, Pept.: Chem, Biol., Proc. Am. Pept. Symp., 12th, Smith et al., eds., pp. 529–530 (1992).

Sakakibara, *The Use of Hydrogen Fluoride in Peptide Chemistry,* Chap. 3, Institute for Protein Research, Osaka Univ., Osaka, Japan.

Senter et al., Novel photocleavable protein crosslinking reagents and their use in the preparation of antibody–toxin conjugates, *Photochem. and Photobiol.* 42(3):231–237 (1985).

Slomkowski et al., Two–dimensional latex assemblies and their potential application in diagnosis, *TRIP* 3:(9)297–303, (1995).

Smith et al., Kinetically inert Co(III) linkage through an engineered metal binding site: Specific orientation of recombinant human papillomavirus type 16 E7 protein on a solid support, *Methods: A companion to Methods in Enzymology,* 4:73–78 (1992(.

Stewart and Young, *Solid Phase Peptide Synthesis,* 2d Ed., Pierce Chemical Co., pp. 53–73 (1984).

Thiele et al., The immunosuppressive activity of L–leucyl–L–leucine methyl ester: Selective ablation of cytotoxic lymphocytes and monocytes, *J. Immunoassay* 136(3):1038–1048 (1986).

Tsao et al., Clonal growth of normal human epidermal keratinocytes in a defined medium, *J. Cell. Physiol.* 110:219–229 (1982).

Wong. Conjugation of proteins to solid matrices, *Chemistry of Protein Conjugation and Cross Linking,* 12:295–317 (1993).

Wright et al., Large scale synthesis of oligonucleotides via phosphoramidite nucleosides and a high loaded polystyrene support, *Tetrahedron Lett.* 34:3373–3376 (1993).

Wysocki et al., 'Planning' for lymphocytes: A method for cell seclection, *Proc. Natl. Acad. Sci. USA* 75(6):2844–2848 (1978).

Zeppezauer et al., Hydrophilic polystyrene–polyoxyethylene graft polymer beads as carrier of antigenic peptides for in vivo and in vitro immunization techniques, *Z. Naturforsch., B: Chem. Sci.* 48 1801–1806 (1993).

Zhang et al., Scale–up continuous–flow peptide synthesis of a partial sequence of tyrosine kinase using tentacle polymers, Pept. 1992, Proc. Eur. Pept. Symp., 22nd, Schneider, et al., Eds., pp. 432–433 (1993).

* cited by examiner

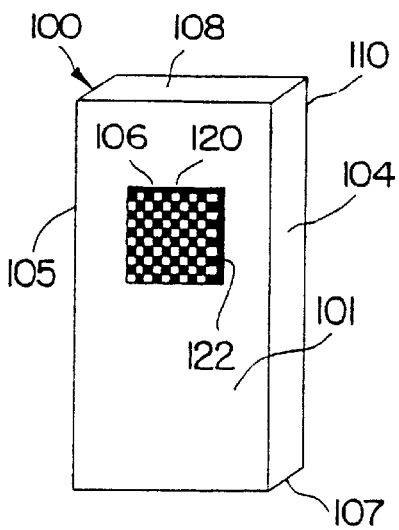
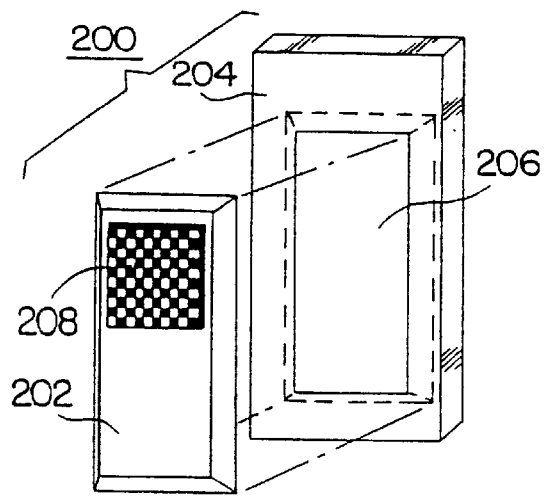
FIG. 22   FIG. 23
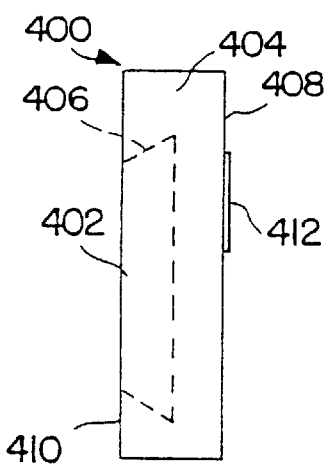 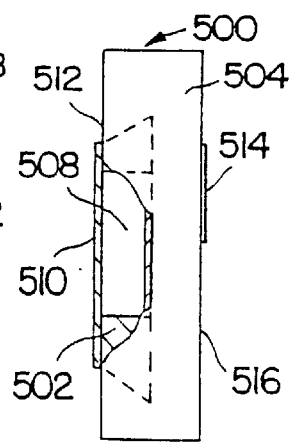 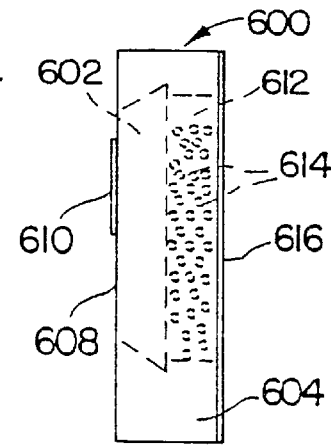
FIG. 25   FIG. 26   FIG. 27
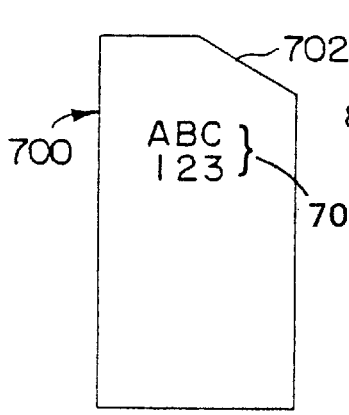 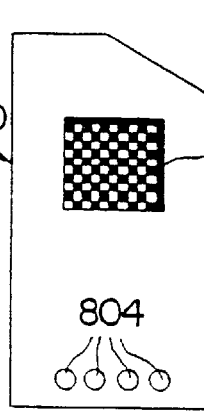 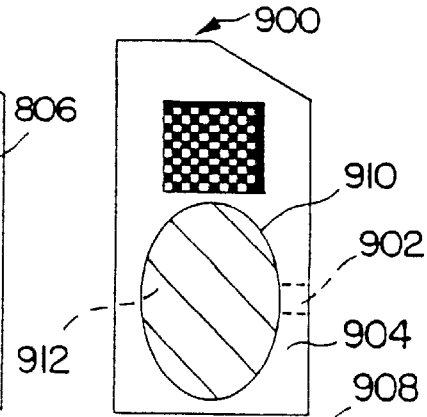
FIG. 28   FIG. 29   FIG. 30

SCHEME 2

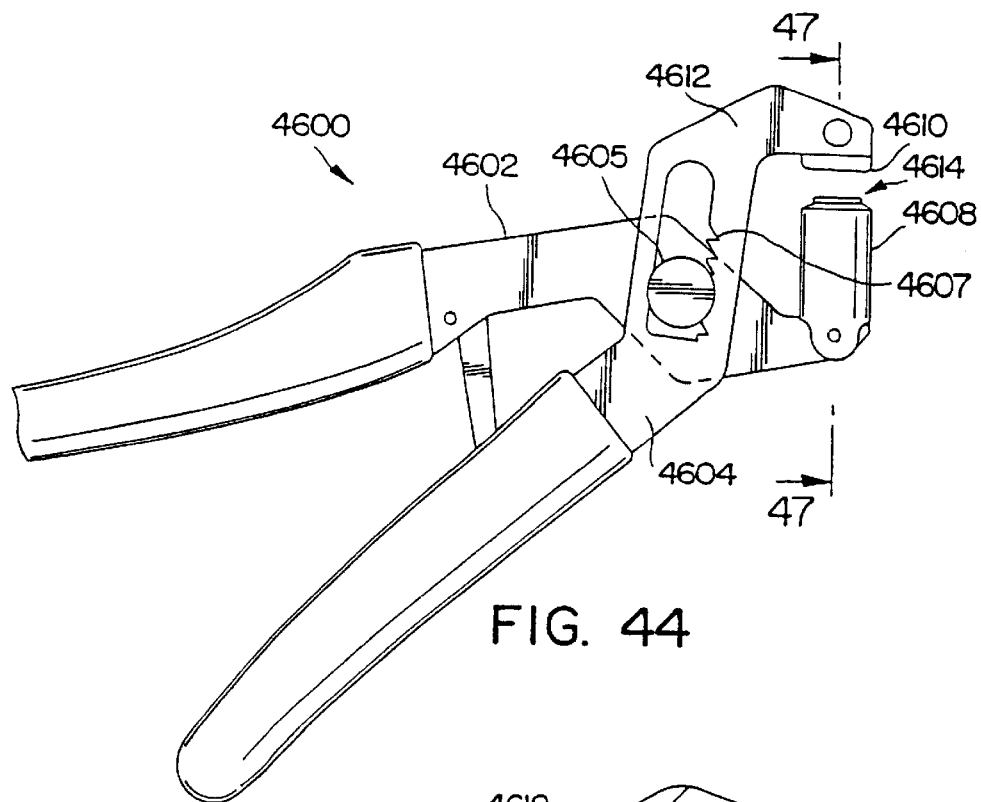
FIG. 44
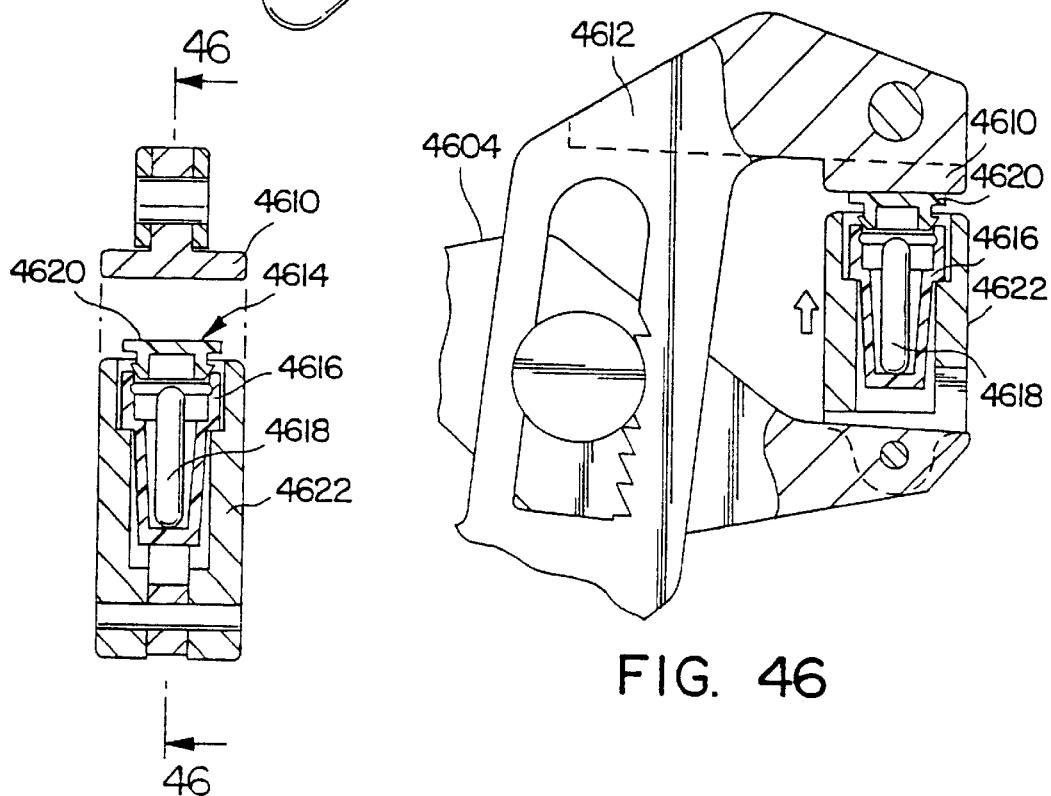
FIG. 45
FIG. 46

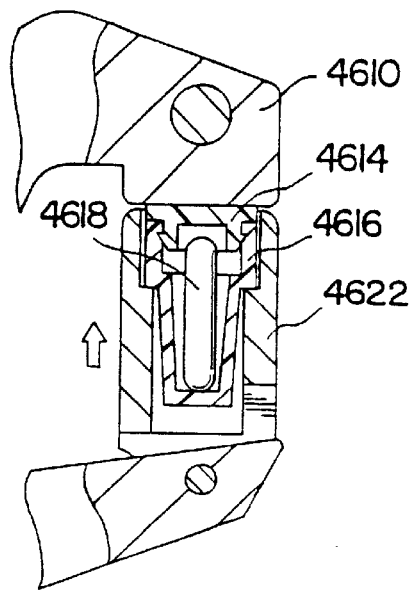
FIG. 47
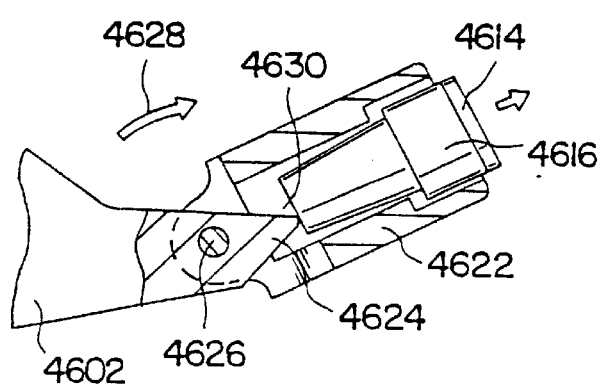
FIG. 48
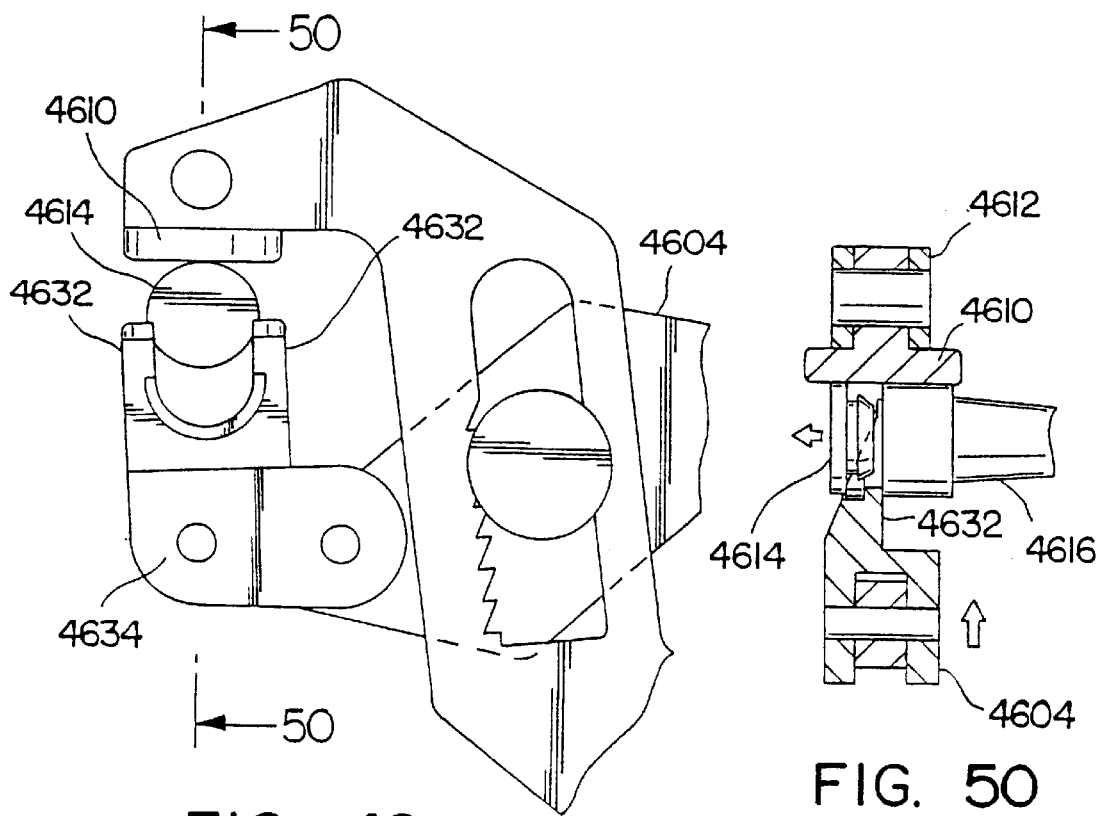
FIG. 49
FIG. 50

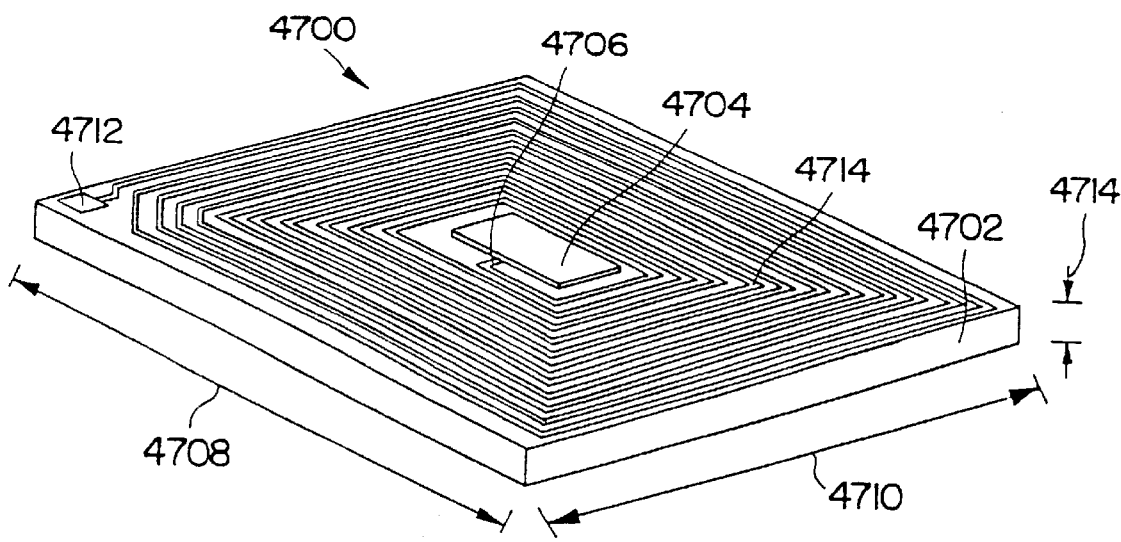
FIG. 51
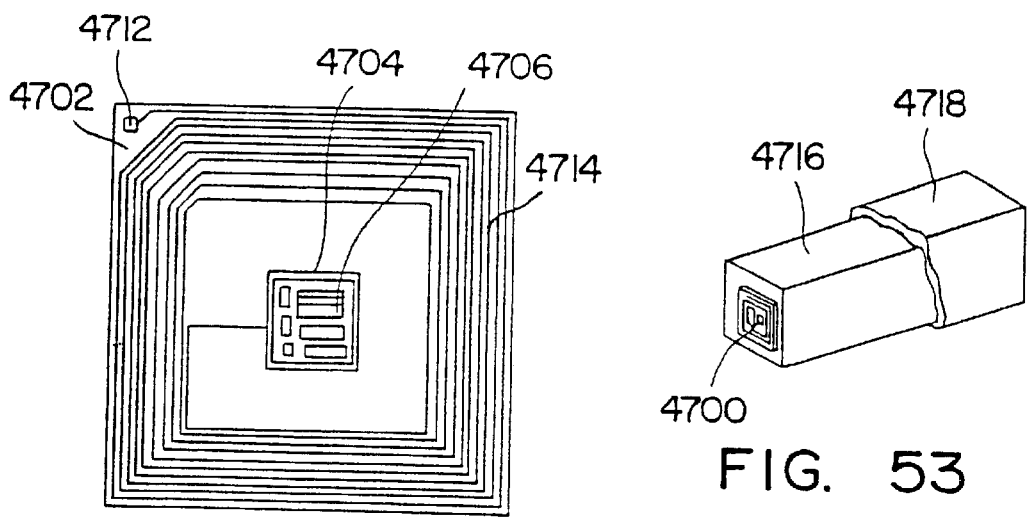
FIG. 52
FIG. 53

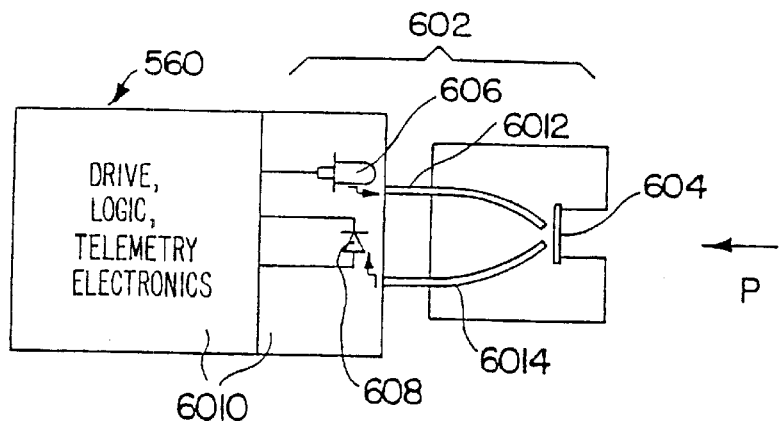
FIG. 60
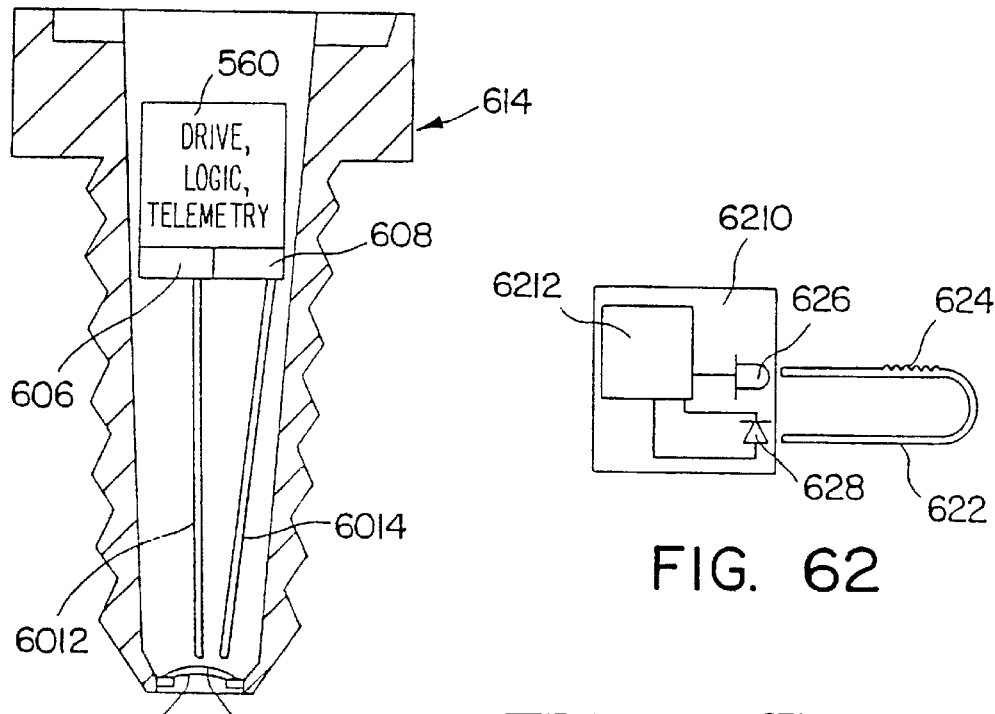
FIG. 61
FIG. 62
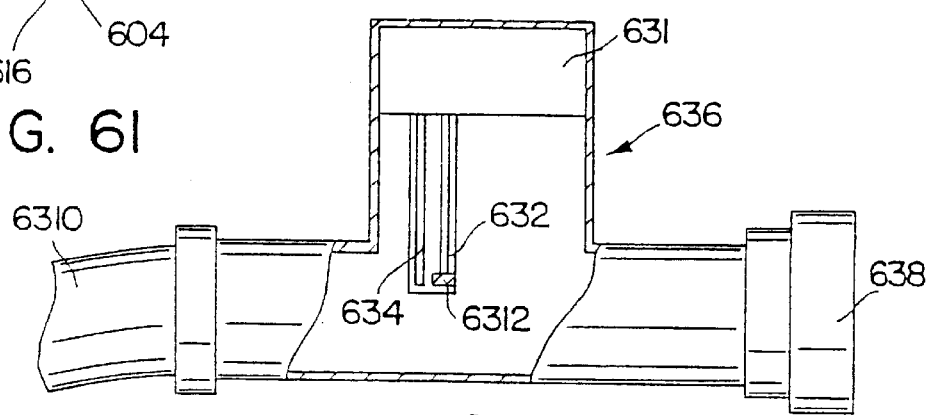
FIG. 63

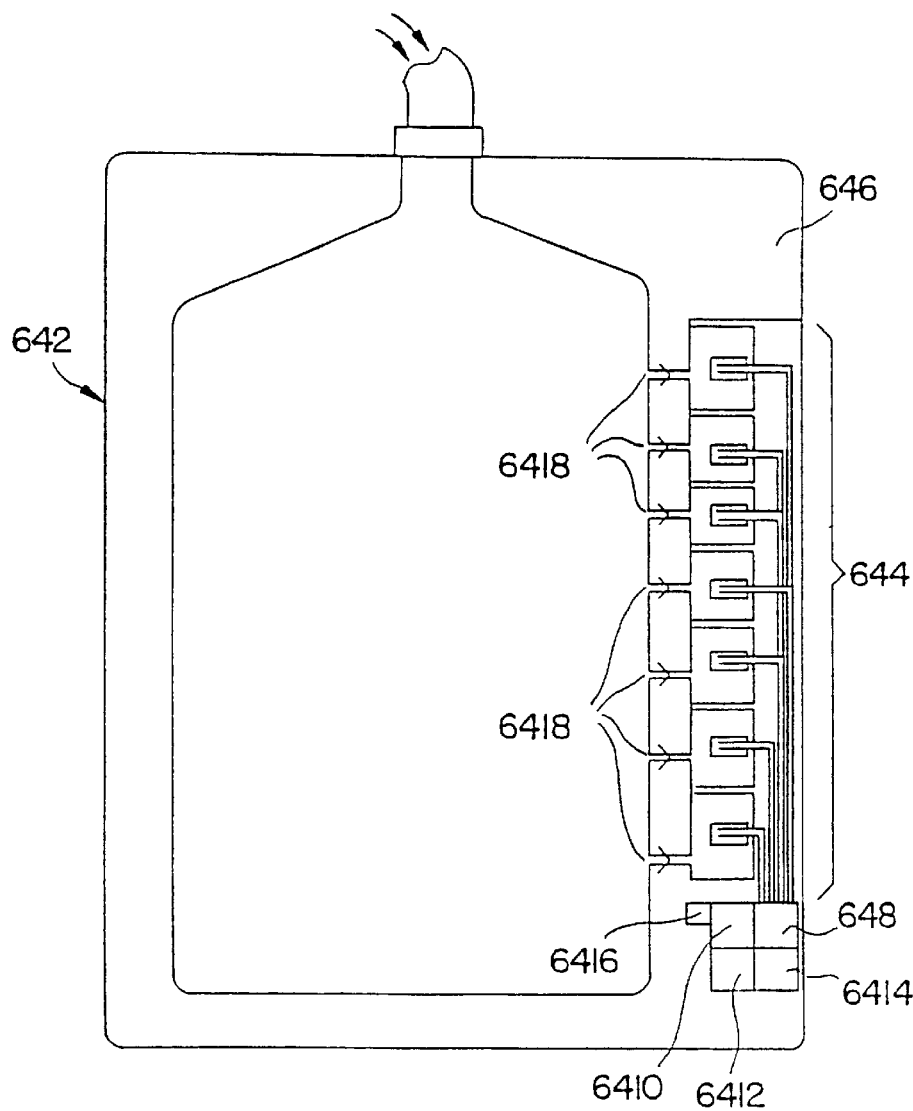
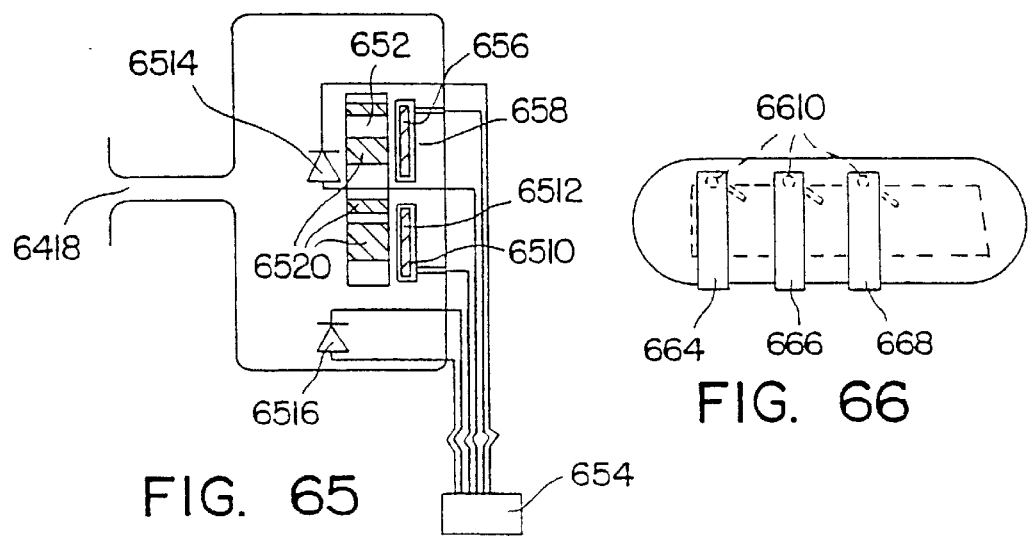
FIG. 64
FIG. 65
FIG. 66

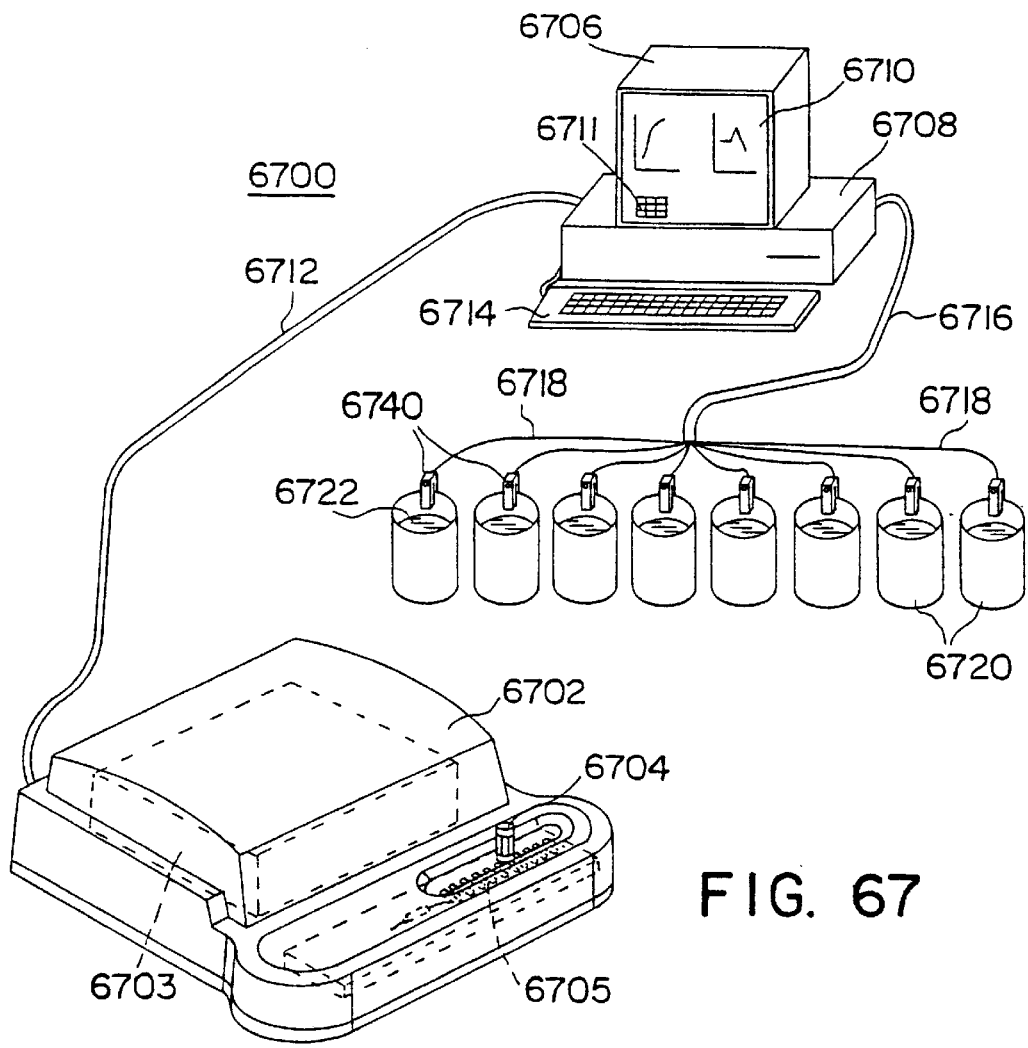
FIG. 67
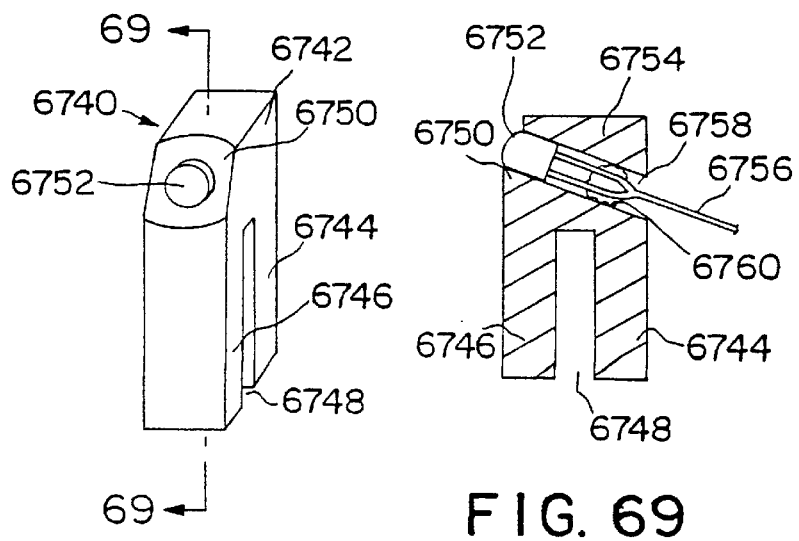
FIG. 68
FIG. 69

* VERIFY THAT COMPOUNDS DESIGNED = COMPOUNDS GENERATED

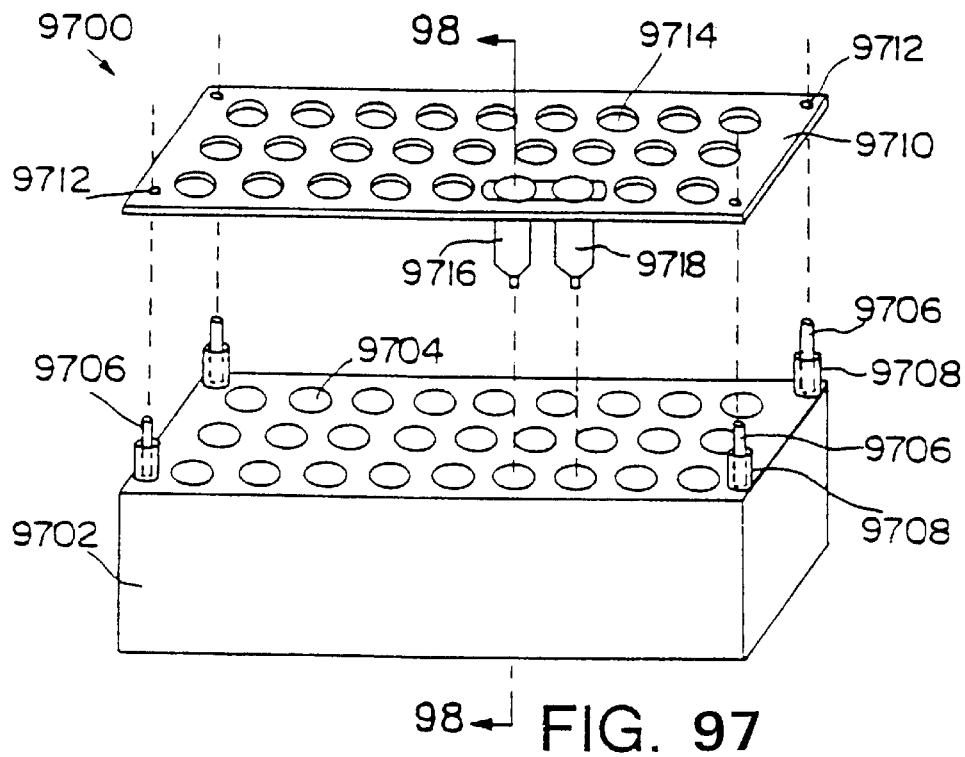
FIG. 97
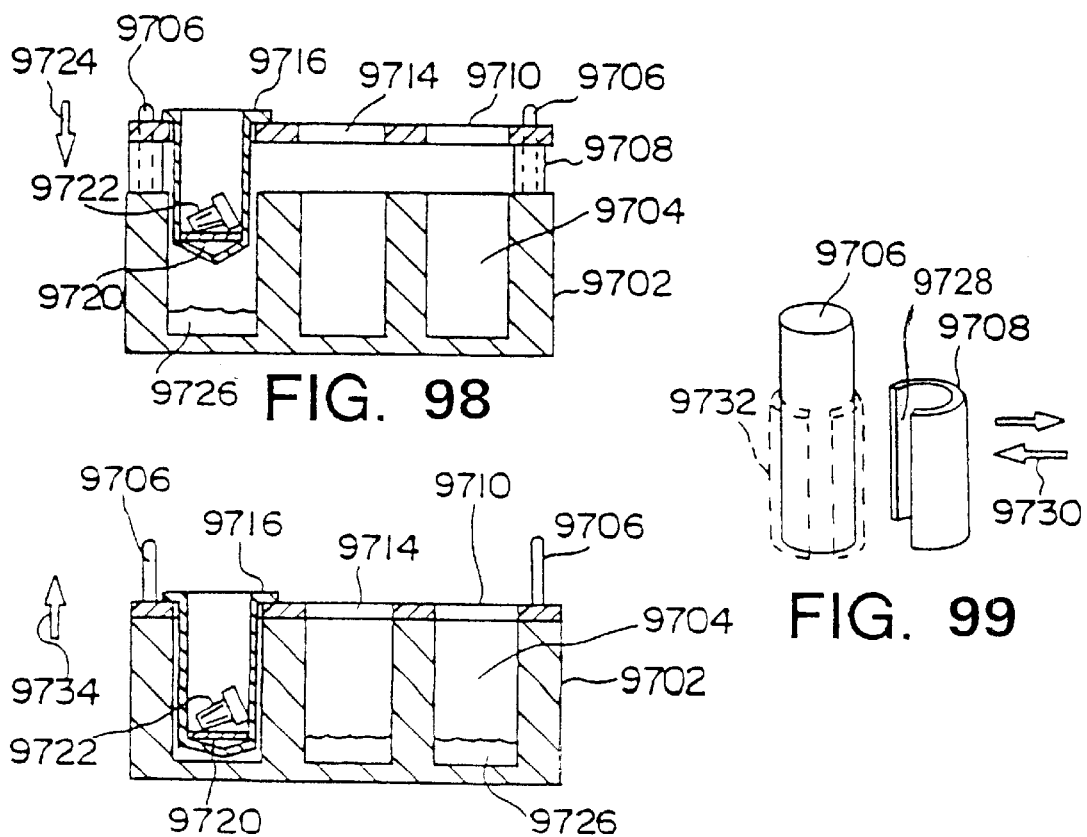
FIG. 98
FIG. 99
FIG. 100

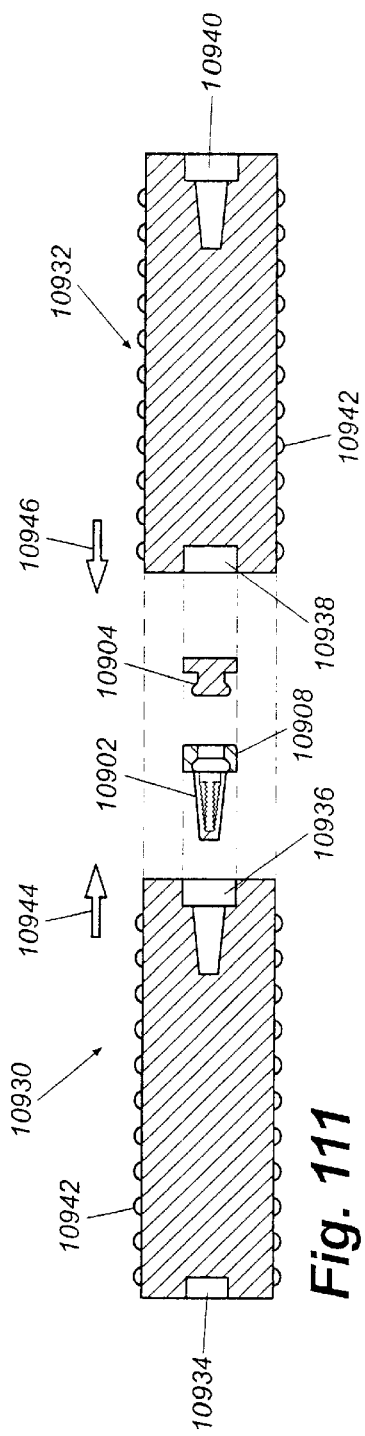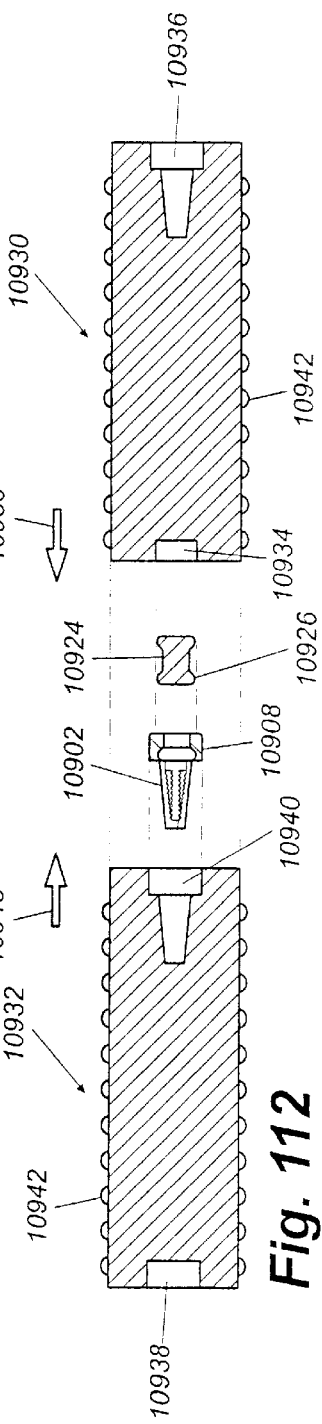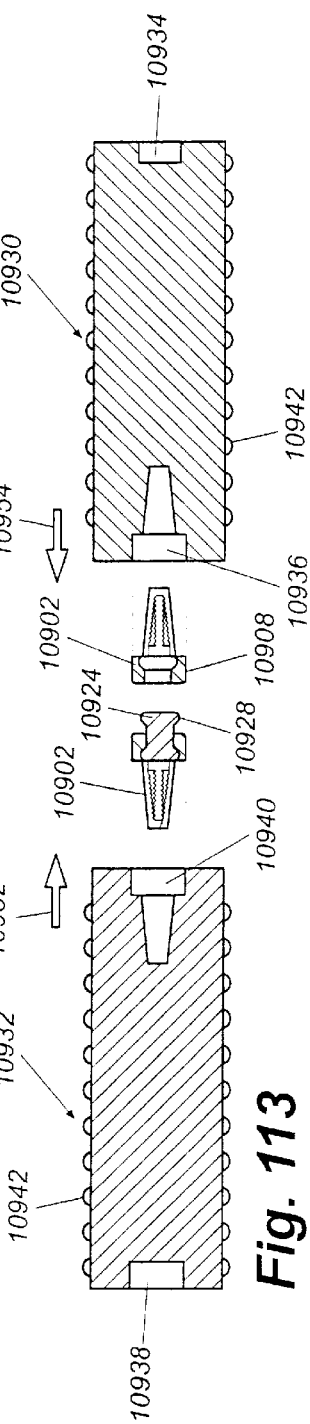

FIG. 135

AUTOMATED SORTING SYSTEM FOR MATRICES WITH MEMORY

The disclosure of the invention includes a microfiche appendix, referred to herein as "Microfiche Appendices I through VIII", containing source code for computer programs described herein. The appendix consists of twenty-three (23) fiche in which Microfiche Appendix I consists of two fiche (#1–2) with 104 frames; Microfiche Appendix II consists of one fiche (#1 of 1) with 4 frames; Microfiche Appendix III consists of four fiche (#1–4) with 279 frames; Microfiche Appendix IV consists of one fiche (#1 of 1) with 7 frames; Microfiche Appendix V consists of one fiche (#1 of 1) with 16 frames; Microfiche Appendix VI consists of eleven fiche (#1–11) with 722 frames; Microfiche Appendix VII consists of two fiche (#1–2) with 81 frames; and Microfiche Appendix VIII consists of one fiche (#1 of 1) with 23 frames.

Thus, a portion of the disclosure of this patent document contains material that is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

RELATED APPLICATIONS

This application is a continuation-in-part of U.S. application Ser. No. 08/826,253, filed Mar. 27, 1997, now abandoned which is a continuation-in-part of U.S. application Ser. No. 08/857,800, filed Jan. 22, 1997, now abandoned which is a continuation-in-part of U.S. application Ser. No. 08/741,685, filed Oct. 31, 1996, now abandoned which is a continuation-in-part of U.S. application Ser. No. 08/743,984 filed Oct. 28, 1996 which is a continuation-in-part of U.S. application Ser. No. 08/726,703, filed Oct. 7, 1996, now abandoned, which is a continuation-in-part of each of application Ser. No. 08/723,423, filed Sep. 30, 1996, now issued as U.S. Pat. No. 5,961,923 and International PCT application No. PCT/US96/15999, filed in the US/RO on Oct. 3, 1996 and published as WO 97/12680, which are continuations-in-part of U.S. application Ser. No. 08/709,435, filed on Sep. 6, 1996, now issued as U.S. Pat. No. 6,017,496 which is a continuation-in-part of U.S. application Ser. No. 08/711,426, filed on Sep. 5, 1996, which is a continuation-in-part of U.S. application Ser. No. 08/669,252, filed on Jun. 24, 1996, which is a continuation-in-part of U.S. application Ser. No. 08/633,410, now issued as U.S. Pat. No. 6,100,026 filed on Jun. 10, 1996, which is a continuation-in-part of International PCT application No. PCT/US96/06145 which designates the U.S. and which was filed on Apr. 25, 1996 and published as WO 96/36436, and U.S. application Ser. No. 08/639,813, filed Apr. 2, 1996, now abandoned, which is a continuation-in-part of U.S. application Ser. No. 08/567,746, filed Dec. 5, 1995, which is a continuation-in-part of U.S. application Ser. No. 08/538,387, filed Oct. 3, 1995, now issued as U.S. Pat. No. 5,874,214, which is a continuation-in-part of each of U.S. application Serial Nos. 08/480,147, 08/484,486, 08/484,504, now issued as U.S. Pat. No. 5,751,629, Ser. No. 08/480,196, now issued as U.S. Pat. No. 5,925,562 and Ser. No. 08/473,660, all filed on Jun. 7, 1995, which are all continuations-in-part of U.S. application Ser. No. 08/428,662, filed Apr. 25, 1995, now issued as U.S. Pat. No. 5,741,462.

This application is also related to U.S. application Ser. No. 08/881,248, filed Jun. 24, 1997.

The subject matter of each of above-noted U.S. applications and International PCT applications is incorporated herein by reference in its entirety.

FIELD OF THE INVENTION

The present invention relates to the application of information and data storage and retrieval technology to drug discovery, including molecular tracking and identification and to biological, chemical, immunological and biochemical assays. The methods, combinations, and devices provided herein permit synthetic chemistry to be linked to analysis and high throughput screening on the same platform with seamless remote informatics management.

BACKGROUND OF THE INVENTION

Drug Discovery

Drug discovery relies on the ability to identify compounds that interact with a selected target, such as cells, an antibody, receptor, enzyme, transcription factor or the like. Traditional drug discovery relied on collections or "libraries" obtained from proprietary databases of compounds accumulated over many years, natural products, fermentation broths, and rational drug design. Recent advances in molecular biology, chemistry and automation have resulted in the development of rapid, High throughput screening (HTS) protocols to screen these collection. In connection with HTS, methods for generating molecular diversity and for detecting, identifying and quantifying biological or chemical material have been developed. These advances have been facilitated by fundamental developments in chemistry, including the development of highly sensitive analytical methods, solid state chemical synthesis, and sensitive and specific biological assay systems.

Analyses of biological interactions and chemical reactions, however, require the use of labels or tags to track and identify the results of such analyses. Typically biological reactions, such as binding, catalytic, hybridization and signaling reactions, are monitored by labels, such as radioactive, fluorescent, photoabsorptive, luminescent and other such labels, or by direct or indirect enzyme labels. Chemical reactions are also monitored by direct or indirect means, such as by linking the reactions to a second reaction in which a colored, fluorescent, chemiluminescent or other such product results. These analytical methods, however, are often time consuming, tedious and, when practiced in vivo, invasive. In addition, each reaction is typically measured individually, in a separate assay. There is, thus, a need to develop alternative and convenient methods for tracking and identifying analytes in biological interactions and the reactants and products of chemical reactions.

Combinatorial libraries

The provision and maintenance of compounds to support HTS have become critical. New methods for the lead generation and lead optimization have emerged to address this need for diversity. Among these methods is combinatorial chemistry, which has become a powerful tool in drug discovery and materials science. Methods and strategies for generating diverse libraries, primarily peptide- and nucleotide-based oligomer libraries, have been developed using molecular biology methods and/or simultaneous chemical synthesis methodologies [see, e.g., Dower et al. (1991) *Annu. Rep. Med. Chem.* 26:271–280; Fodor et al. (1991) *Science* 251:767–773; Jung et al. (1992) *Angew. Chem. Ind. Ed. Engl.* 31:367–383; Zuckerman et al. (1992) *Proc. Natl. Acad. Sci. USA* 89:4505–4509; Scott et al. (1990) *Science* 249:386–390; Devlin et al. (1990) *Science* 249:404–406; Cwirla et al. (1990) *Proc. Natl. Acad. Sci. USA* 87:6378–6382; and Gallop et al. (1994) *J. Medicinal*

Chemistry 37:1233–12511. The resulting combinatorial libraries potentially contain millions of pharmaceutically relevant compounds and that can be screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads [see, e.g., Lam et al. (1991) *Nature* 354:82–84] and cotton supports [see, e.g., Eichler et al. (1993) *Biochemistry* 32:11035–11041]; and methods in which the compounds are used in solution [see, e.g., Houghten et al. (1991) *Nature* 354:84–86, Houghten et al. (1992) *BioTechniques* 313:412–421; and Scott et al. (1994) *Curr. Opin. Biotechnol.* 5:40–48]. There are numerous examples of synthetic peptide and oligonucleotide combinatorial libraries. The present direction in this area is to produce combinatorial libraries that contain non-peptidic small organic molecules. Such libraries are based on either a basis set of monomers that can be combined to form mixtures of diverse organic molecules or that can be combined to form a library based upon a selected pharmacophore monomer.

There are three critical aspects in any combinatorial library: (i) the chemical units of which the library is composed; (ii) generation and categorization of the library, and (iii) identification of library members that interact with the target of interest, and tracking intermediary synthesis products and the multitude of molecules in a single vessel. The generation of such libraries often relies on the use of solid phase synthesis methods, as well as solution phase methods, to produce collections containing tens of millions of compounds that can be screened in diagnostically or pharmacologically relevant in vitro assay systems. In generating large numbers of diverse molecules by stepwise synthesis, the resulting library is a complex mixture in which a particular compound is present at very low concentrations, so that it is difficult or impossible to determine its chemical structure. Various methods exist for ordered synthesis by sequential addition of particular moieties, or by identifying molecules based on spacial positioning on a chip. These methods are cumbersome and ultimately impossible to apply to highly diverse and large libraries. Identification of library members that interact with a target of interest, and tracking intermediary synthesis products and the multitude of molecules in a single vessel is also a problem. While considerable efforts have been devoted to the development of solid support chemistry, the choice of methods for structural elucidation has been limited to spatial addressing, mixture deconvolution, direct microanalysis and chemical tagging [see, e.g., Metzger et al. (1994) *Jung, Anal. Biochem.* 219:261; Brown et al. (1995) *Mol. Diversity* 1:4; Youngquist et al. (1995) *J. Am. Chem. Soc.* 177:3900; Brummel et al. (1994) *Science* 264:399; Brenner et al. (1992) *Proc. Natl. Acad. Sci. U.S.A.* 89: 5381; Needles et al. (1993) *Proc. Natl. Acad. Sci. U.S.A.* 90:10700; Ohimeyer et al. *Proc. Natl. Acad. Sci. U.S.A.* 90: 10922; Eckes (1994) *Angew. Chem. Int. Ed. Engl.* 33:1573; Ni et al. (1996) *J. Med. Chem.* 39:1601]. Tagging, especially non-chemical, non-invasive tagging, is potentially the most efficient and reliable structural tracking method.

High Throughput Screening

In addition, exploitation of this diversity requires development of methods for rapidly screening compounds. Advances in instrumentation, molecular biology and protein chemistry and the adaptation of biochemical activity screens into microplate formats, has made it possible to screen of large numbers of compounds. Also, because compound screening has been successful in areas of significance for the pharmaceutical industry, high throughput screening (HTS) protocols have assumed importance. Presently, there are hundreds of HTS systems operating throughout the world, which are used, not only for compound screening for drug discovery, but also for immunoassays, cell-based assays and receptor-binding assays.

An essential element of high throughput screening for drug discovery process and areas in which molecules are identified and tracked, is the ability to extract the information made available during synthesis and screening of a library, identification of the active components of intermediary structures, and the reactants and products of assays. While there are several techniques for identification of intermediary products and final products, nanosequencing protocols that provide exact structures are only applicable on mass to naturally occurring linear oligomers such as peptides and amino acids. Mass spectrographic [MS] analysis is sufficiently sensitive to determine the exact mass and fragmentation patterns of individual synthesis steps, but complex analytical mass spectrographic strategies are not readily automated nor conveniently performed. Also, mass spectrographic analysis provides at best simple connectivity information, but no stereoisomeric information, and generally cannot discriminate among isomeric monomers. Another problem with mass spectrographic analysis is that it requires pure compounds; structural determinations on complex mixtures is either difficult or impossible. Finally, mass spectrographic analysis is tedious and time consuming. Thus, although there are a multitude of solutions to the generation of libraries and to screening protocols, there are no ideal solutions to the problems of identification, tracking and categorization.

These problems arise in any screening or analytical process in which large numbers of molecules or biological entities are screened. In any system, once a desired molecule (s) has been isolated, it must be identified. Simple means for identification do not exist. Because of the problems inherent in any labeling procedure, it would be desirable to have alternative means for tracking and quantitating chemical and biological reactions during synthesis and/or screening processes, and for automating such tracking and quantitating.

Therefore, it is an object herein to provide methods for identification, tracking and categorization of the components of complex mixtures of diverse molecules. It is also an object herein to provide products for such identification, tracking and categorization and to provide assays, diagnostics and screening protocols that use such products. It is of particular interest herein to provide means to track and identify compounds and to perform HTS protocols.

SUMMARY OF THE INVENTION

Combinations of matrix materials with programmable data storage or recording devices or other memory means, herein referred to as memories, and assays using these combinations are provided. The combinations are referred to herein as matrices with memories. These combinations serve as a common platform for all aspects of drug discovery, including synthesis, screening and storage. Protocols in which all steps, including synthesis and screening or assaying, are performed on a single platform are provided herein. In addition protocols in which a series of matrices with memories are used and information is transferred from one memory to another are also provided.

Of particular interest herein, are automated protocols, or partially automated protocols, in which the matrices with memories serve as the platform on which all manipulations are performed or that serve as the repository of information that is transferred to other memories as the synthesized compounds are processed and screened. Automated drug discovery units for effecting these protocols are also provided. Thus, an automated drug discovery unit provides a means for seamless data tracking between and among the components of the units in which all critical components, including instrumentation and vials include memories for seamless transfer information to other memories in a unit. The units [see, e.g., FIG. 75 for diagrammatic representations], which are provided herein, include some or all of the following: an automated or manual sorter, microvessels, which contain memories, an automated or semi-automated synthesizer, a microvessel washer/dryer, a manual or automated cleaver for removing compounds from the matrix with memory microvessels, and associated software. The memories may be any of any type, including electromagnetically encodable memories and optical memories, or combinations thereof. The memories may be pre-encoded or may be encodable during, after or before processing. Remotely addressable memories are presently preferred. Although in some embodiments, memories associate with certain of the components, such as instrumentation or vials used therewith, for convenience and ease of reuse, they may be pre-encoded.

By virtue of the memory with matrix combination, molecules, such as antigens, antibodies, ligands, proteins and nucleic acids, and biological particles, such as phage and viral particles and cells, that are associated with, such as in proximity to or in physical contact with the matrix combination or linked via information stored in a remote computer, can be electromagnetically tagged by programming the memory with data corresponding to identifying information or can be tagged by imprinting or encoding the matrix with identifying information.

The memories with matrices may also include a sensing function that records information related to the sample and/or source of the sample and/or to detect or sense and store information about events in proximity the memory. In particular, sensors with memories are provided. Thus, also provided herein are sensors that combine memories with matrices and sensors. Programming and reading the memory is effected remotely, preferably electromagnetic radiation, particularly radio frequency [RF] or radar, microwave, or microwave or energies between RF and microwave, or by reading the imprinted information. These memories with matrices may further include identifying symbology on the matrix material or container holding or supporting the matrix.

Optical memories, either bar coded information, particularly the 2-D bar codes provided herein, or optically encoded memories, such as memories that rely on changes in chemical or physical properties of particular molecules are contemplated herein. Memories may also be remote from the matrix, such as instances in which the memory device is precoded [or pre-encoded] with a mark or identifier or the matrix is encoded with a bar code. The identity [i.e., the mark or code] of each device is written to a memory, which may be a computer or a piece of paper or any recording device, and information associated with each matrix is stored in the remote memory and linked to or associated with the code or other identifier.

For example, matrices with memories in which the matrices have an engraved code are contemplated for use in the units provided herein. These matrices with memories are herein referred to as matrices with codes or optical memory devices [OMDs] or optical memory microreactors. The memories are remote recording devices, such as a remote computer memory in which information associated with the codes is stored. The materials are encoded with identifying information and/or any other information of interest. Synthetic protocols and assays using encoded matrix materials are provided. By virtue of this code on the matrix, molecules, such as antigens, antibodies, ligands, proteins and nucleic acids, and biological particles, such as phage and viral particles and cells, that are associated with, such as in proximity to or in physical contact with the matrix, can be tagged by programming a memory, such as a memory in a computer, with data corresponding to the encoded identifying information. The identity [i.e., the mark or code] of each device is written to a memory, which may be a computer or a piece of paper or any recording device, and information associated with each matrix is stored in the remote memory and linked to the code or other identifier.

The molecules and biological particles that are associated with the matrix combination, such as in proximity to or in physical contact or with the matrix combination, can be identified and the results of the assays determined by retrieving the stored data points from the memories. Querying the memory will identify associated molecules or biological particles that have reacted.

In certain embodiments of the matrices with memories, reactions, assays and other events or external parameters, such as temperature and/or pH, can be monitored because occurrence of a reaction or an event can be detected and such detection sent to the recording device when proximate to the matrix and recorded in the memory.

The combinations provided herein thus have a multiplicity of applications, including combinatorial chemistry, isolation and purification of target macromolecules, capture and detection of macromolecules for analytical purposes, high throughput screening, selective removal of contaminants, enzymatic catalysis, drug delivery, chemical modification, information collection and management and other uses. As a result, they can serve as a platform for all aspects of the drug discovery process These combinations are particularly advantageous for use in multianalyte analyses, assays in which a electromagnetic signal is generated by the reactants or products in the assay, for use in homogeneous assays, and for use in multiplexed protocols. All are intended for use in the units and drug discovery protocols provided herein.

In preferred embodiments, the matrix with memory combinations contain (i) a recording device that includes one or more programmable data storage devices [memories] and/or an engraved or imprinted optically readable code or a 3-D optical memory, that can be remotely read and in preferred embodiments also remotely programmed; and (ii) a matrix, such as a particulate support used in chemical syntheses. These matrix with memory combinations or the memories also are combined with sensors.

The matrix materials [matrices] are any materials that are routinely used in chemical and biochemical synthesis. The matrix materials are typically polymeric materials that are compatible with chemical and biological syntheses and assays, and include, glasses, silicates, celluloses, polystyrenes, polysaccharides, polypropylenes, sand, and synthetic resins and polymers, including acrylamides, particularly cross-linked polymers, cotton, and other such materials. The matrices may be in the form of particles or may be continuous in design, such as a test tube or microplate, 96 well or 384 well or higher density formats or other such microplates and microtiter plates. The matrices may contain one or a plurality of recording devices. For example, each well or selected wells in the microplate include a memory device in contact therewith or embedded therein. The plates may further contain embedded scintillant or a coating of scintillant [such as FlashPlate™, available from DuPont NEN®, and plates available from Packard, Meriden, Conn. and Cytostar-T plates available from Amersham International plc, U.K.]. Automated robotic protocols will incorporate such plates for automated multiplexing [performing a series of coupled synthetic and processing steps, typically, though not necessarily on the same platform, i.e. coupling of the chemistry to the biology] including one or more of the following, synthesis, preferably accompanied by writing to the linked memories to identify linked compounds, screening, including using protocols with matrices with memories, and compound identification by querying the memories of matrices associated with the selected compounds.

The matrices are either particulate of a size that is roughly about 1 to 20 $mm^3$ [or 1–20 mm in its largest dimension], preferably about 10 $mm^3$ or smaller, preferably 1 $mm^3$ or smaller, such as minute particulates, or a continuous medium, such as a microtiter plate, or other multi-well plate, or plastic or other solid polymeric vial or glass vial or catheter-tube [for drug delivery] or such container or device conventionally used in chemistry and biological syntheses and reactions.

In instances in which the matrix is continuous, the data storage device [memory] may be placed in, on, or under the matrix medium or may be embedded in the material of the matrix or removably attached, such as in a sleeve designed to fit on the matrix.

Plates that include a bar code, particularly the two-dimensional optical bar code provided herein on the base of each well or elsewhere. The two-dimensional bar code or other such code is particularly suited for application to each well in a microplate, such as a microtiter plate, that contain 96, 384, 1536 or higher density formats. The bar code may also be used in combination with modules that are fitted into the frames of 96 wells, or higher density formats [such as those available from NUNC, such as NUNC-Immuno Modules, and also sources, such as COSTAR plate strips, Cytostar-T plates from Amersham International plc, U.K., and Octavac Filter Strips]. Separate containers or strips of containers are designed to fit into microplate frames. Each such container may be encoded with a bar code so that, upon removal from the strip, the container, and thereby, its contents or history, may be identified.

In embodiments herein in which the matrices with memories are used in assays, such as scintillation proximity assays [SPA], FP [fluorescence polarization] assays, FET [fluorescent energy transfer] assays, FRET [fluorescent resonance energy transfer] assays and HTRF [homogeneous time-resolved fluorescence] assays, the matrices may be coated with, embedded with or otherwise combined with or in contact with assay material, such as scintillant, fluophore or other fluorescent label. The resulting combinations are called luminescing memories with matrices. When used in SPA formats they are referred to as scintillating matrices with memories and when used in non-radioactive energy transfer formats [such as HTRF] they are referred to as fluorescing memories with matrices.

The recording device used in proximity to the matrix is preferably a miniature device or is part of the support, such as an optical memory, typically less than 10–20 $mm^3$ [or 10–20 mm in its largest dimension] in size, preferably smaller, such as 1 to 5 mm, that includes at least one data storage unit that includes a remotely programmable and remotely readable, preferably non-volatile, memory. This device with remotely programmable memory is in proximity to, associated with or in contact with the matrix. In particular, the recording device includes a memory device, preferably having memory means, preferably non-volatile, for storing a plurality of data points and means for receiving a transmitted signal that is received by the device and for causing a data point corresponding to the data signal to be permanently stored within the memory means. If needed, the recording device further includes a shell [coating] that is non-reactive with and impervious to any processing steps or solutions in which the combination of matrix with recording device [matrix with memory] is placed, and that is transmissive of read or write signals transmitted to the memory. The device may also include at least one support matrix disposed on an outer surface of the shell for retaining molecules or biological particles. The shell and support matrix may be the same. In such instances, the shell must be treated or derivatized such that molecules, particularly amino acids and nucleic acids, can be linked, preferably either electrostatically or covalently, thereto. Thus, a transponder enclosed in plastic, must be further treated or coated to render it suitable for linkage of the molecule or biological particle. In preferred embodiments provided herein, the device also includes a photodetector to detect events and means to write a record of the event to the memory.

The data storage device or memory is programmed with or encoded with information that identifies molecules or biological particles, either by their process of preparation, their identity, their batch number, category, physical or chemical properties, combinations of any of such information, or other such identifying information. The molecules or biological particles are in physical contact, direct or indirect, or in proximity with the matrix, which in turn is in physical contact or in the proximity of the recording device that contains the data storage memory. The molecule or biological particle may also be associated, such that a molecule or biological particle that had been linked to or in proximity with a matrix with memory may be identified [i.e., although the matrix particle and biological particle or molecule are not linked or in proximity, the identify of the matrix that had been linked to the molecule or particle is known]. Typically, the matrix is on the surface of the recording device and the molecules and biological particles are in physical contact with the matrix material. In certain embodiments, the memory device may be linked to or in proximity to more than one matrix particle.

The data storage device or memory can also be programmed by virtue of a reaction in proximity to or in the vicinity of the matrix with memory. In particular, the recording devices include memories and also additional components that detect occurrence of external events or to monitor the status of external parameters, such as EM emissions, changes in temperature or pH, ion concentrations and other such solution parameters. For example, recording devices include memories and also include a photodectector can detect the occurrence of fluorescence or other optical emission. Coupling this emission with an amplifier and providing a voltage to permit data storage in the matrix with memory during the reaction by way of, for example an RF signal transmitted to and received by an antenna/rectifier combination within the data storage device or providing voltage sufficient to write to memory from a battery [see, e.g., U.S. Pat. No. 5,350,645 and U.S. Pat. No. 5,089,877], permits occurrence of the emission to be recorded in the memory.

The recording device [containing the memory] is associated with the memory. Typically, the recording device is coated with at least one layer of material, such as a protective polymer or a glass, including polystyrene, heavy metal-free glass, plastic, ceramic, and may be coated with more than one layers of this and other materials. It must be treated to render it suitable for linking molecules or biological particles when it is used as a support. For example, it may be coated with a ceramic or glass that is suitably derivatized or then coated with or linked to the matrix material. Alternatively, the glass or ceramic or other coating may serve as the matrix. In other embodiments the recording device and the matrix material are in proximity, such as in a container of a size approximately that of the device and matrix material. In yet other embodiments the recording device and matrix material are associated, such that the molecule or biological particle that was linked to the matrix or that was in proximity thereto may be identified.

The matrix combinations [the matrices with memories], thus, contain a matrix material, typically in particulate form, in physical contact with a tiny device containing one or more remotely programmable data storage units [memories]. Contact can be effected by placing the recording device with memory on or in the matrix material or in a solution that is in contact with the matrix material or by linking the device, either by direct or indirect covalent or non-covalent interactions, chemical linkages or by other interactions, to the matrix. Alternatively, matrices with memories carry a code, such as a bar code, preferably a two-dimensional bar code, on typically one surface and the memory is remote, such as a memory in a computer or any written record by which the code can be deciphered and information stored and associated therewith.

For example, when the memories are proximate to the matrix, contact can be effected chemically, by chemically coupling the recording device with memory to the matrix, or physically by coating the recording device with the matrix material or another material, by physically inserting or encasing the device in the matrix material, by placing the device onto the matrix or by any other means by which the device can be placed in contact with or in proximity to the matrix material. The contact may be direct or indirect via linkers. The contact may be effected by absorption or adsorption.

Since matrix materials have many known uses in conjunction with molecules and biological particles, there are a multitude of methods known to artisans of skill in this art for linking, joining or physically contacting the molecule or biological particle with the matrix material. In some embodiments, the recording device with data storage unit is placed in a solution or suspension of the molecule or biological particle of interest. In some of such instances, the container, such as the microtiter plate or test tube or other vial, is the matrix material. The recording device is placed in or on the matrix or is embedded, encased or dipped in the matrix material or otherwise place in proximity by enclosing the device and matrix material in a sealed pouch or bag or container [MICROKAN™ microreactor] fabricated from, preferably, porous material, such as polytetrafluoroethylene [marketed under the trademark TEFLON® (Trademark, E.I. DuPont)] or polypropylene prepared with pores, that is inert to the reaction of interest and that have pores of size permeable to desired components of the reaction medium.

The "microreactors" provided herein permit the advantageous productivity gains of the split-and-pool technique, without any of its limitations.

More than one data storage device or engraved coded or combination thereof may be in proximity to or contact with a matrix particle, or more than one matrix particle may be in contact with on device. For example, microplates, such as microtiter y plates or other such high density format [i.e. 96, 384 1536 or more wells per plate, such as those available from Nunc, Naperville, Ill., Costar, Cambridge Mass., and Millipore, Bedford, Mass.] with the recording device containing the data storage unit [remotely programmable memory] embedded in each well or vials [typically with a 1.5 ml or smaller capacity] with an embedded recording device may be manufactured.

In a preferred embodiment, the recording device is a semiconductor that is approximately 10 mm or less in its largest dimension and the matrix material is a particle, such as a polystyrene bead. The device and a plurality of particles, referred to as "beads", typically about 1 mg to about 50 mg, but larger size vessels and amounts up to 1000 mg, preferably 50 to about 200 mg, are sealed in chemically inert porous supports, such as polypropylene formed so that it has pores of a selected size that excludes the particles but permits passage of the external medium. For example, a single device and a plurality of particles may be sealed in a porous or semi-permeable inert material to produce a microvessel [such as the MICROKAN™ microreactor] such as a TEFLON® [polytetrafluoroethylene] or polypropylene or membrane that is permeable to the components of the medium, or they may be contained in a small closable container that has at least one dimension that is porous or is a semi-permeable tube. Typically such a tube will have an end that can be opened and sealed or closed tightly.

These microvessels preferably have a volume of about 200–500 mm$^3$, but can have larger volumes, such as greater than 500 mm$^3$ [or 1000 mm$^3$] at least sufficient to contain at least 200 mg of matrix particles, such as about 500–3000 mm$^3$, such as 1000–2000 or 1000 to 1500, with preferred dimensions of about 1–10 mm in diameter and 5 to 20 mm in height, more preferably about 5 mm by 15 mm, or larger, such as about 1–6 cm by 1–6 cm. The porous wall should be non-collapsible with a pore size in the range of 70 $\mu$M to about 100 $\mu$M, but can be selected to be semi-permeable for selected components of the medium in which the microvessel is placed. The preferred geometry of these combinations is cylindrical. These porous microvessels may be sealed by heat or may be designed to snap or otherwise close. In some embodiments they are designed to be reused. In other embodiments, the microvessel MICROKAN™ microreactor with closures may be made out of non-porous material, such as a tube in the conical shape or other geometry.

Such vessels thus are relatively rigid containers with mesh side walls. Typically, a single compound is synthesized in each one, and each one contains a unique memory with encoded information or a read/write memory and are designed to be loaded with solid phase resin. Syntheses takes place by allowing reagents to flow through the outer mesh walls. The preferred embodiment has a volume of about 330 $\mu$l of which approximately 200 $\mu$l is available for resin with the remainder of the space being occupied by the RF tag. In other embodiments the microvessel is engraved with the 2-D optical code provided herein. Typically about 30 mg of most commercial resins can be loaded into this volume leaving enough space available for the resin to swell and still remain loose within the walls.

Also provided herein are tubular devices [or other geometry of a hollow container] in which the recording device is enclosed or encased in a solid polymer, such as a polypropylene, which is then suitably treated, such as by radiation grafting with selected monomers to produce a surface suitable for chemical synthesis and linkage of molecules or biological particles. The tubes may be sealed or open and retain the device by friction or by virtue of crimps in the surface.

These tubular hollow devices [or other geometry], such as the MICROTUBE™ microvessels (or microreactors) may contain a recording device and/or may include a code engraved, such as by a laser, or otherwise imprinted on the surface or combinations thereof The tubular devices are preferably TEFLON® [polytetrafluoroethylene (PTFE)], polyethylene, high density polyethylene, polypropylene, polystyrene, polyester, ceramic, composites of any of these materials and other such materials.

In certain embodiments, the tubes are hollow and retain any memory by virtue of friction, or alternatively the ends or insides are crimped to retain any memory device. In other embodiments, the tubes are designed to serve as a reaction "flask", storage vial, and microtiter plate well. This is effected by having the tube differentially loaded and/or include different materials in the coating. One part of the tube includes a scintillant, but can be designed or grafted in such a manner that it is lightly loaded; another part is loaded with as much compound as possible. For example, relatively very long tubes [cms, for example about 1–3 cms] or other convenient shapes, such as star shaped or other shape from which pieces can be conveniently removed, are provided. The tag is inserted or a bar code is located at one end. After synthesis, small [millimeter] pieces can be cut off the other end and run through various assays. Synthesis is performed on the tube and then small segments of the tube are cut off or clipped off and the product cleaved into a microplate well. In other embodiments, the tube may be relatively long or relatively large and of any geometry, but coated uniformly. In these embodiments, the MICROTUBE becomes a permanent or semi-permanent storage and information device for the compounds linked thereto, and is stored as such. Wherever material is required for an assay, a small piece of the tube can be cut off and tested.

A method for radiation grafting of monomers to fluoropolymers, such as PTFE and ETFE is provided herein. Also provided herein is a method for increasing radiation grafting [50–200% increase in the amount of polymer grafted] loading by including a mineral acid, such as sulfuric acid and nitric acid [typically at concentrations of from about 0.01–0.5M]. A method for further increasing loading by machining (i.e., using a lathe to render the surface ridged or making the surface rough) the grafted surface.

The devices may also be formed from a ball with a screw cap [MICROBALLS®] or with other type of cap to permit access to the inside, or may be hollow and of such size or geometry to retain a memory inside or to include an optical memory. These types of memories with matrices are, for example, polypropylene or fluoropolymer tubes with a radiation grafted functionalized polystyrene surface that completely enclose a selected memory, such as an RF tag. The surface may also include an identifying symbology. Syntheses are performed on the functionalized polystyrene allowing solid phase chemistry to be performed without the need to load solid phase resins.

Other devices of interest are polymeric supports, particularly polypropylene supports, generally about 5–10 mm in the largest dimension, and preferably a cube or other such shape, that are marked with a code, and tracked using a remote memory. The code can be a bar code, alphanumeric code, the 2-D optical bar code provided herein, or other identifying mark.

It was found that washing the grafted tubes following synthesis in PBS containing about 0.75% SDS with or without 35% charcoal for about 2 days significantly improved the signal/noise ratio in subsequent assays, such as scintillation proximity assays. Increases in signal to noise ratios of 2/1 to 47/1 have been observed. Such improvement should be observed with any solid support. Thus, a method for increasing the performance of assays on solid supports in provided by washing the solid support with linked biological particle or molecule with PBS containing 0.75% SDS with or without 35% charcoal for about 2 days.

The surface of the matrix material that is treated or adapted for linking biological particles or molecules may include linkers for effecting the linker. In certain embodiments, a variety of linkers with differential cleavage properties may be used, thereby providing a means to selectively cleave linked molecules after synthesis and/or screening and linked biological particles before or after screening.

The combination of matrix with memory is used by contacting it with, linking it to, or placing it in proximity with a molecule or biological particle, such as a virus or phage particle, a bacterium or a cell, to produce a second combination of a matrix with memory and a molecule or biological particle. In certain instances, such combinations of matrix with memory or combination of matrix with memory and molecule or biological particle may be prepared when used or may be prepared before use and packaged or stored as such for future use. The matrix with memory when linked or proximate to a molecule or biological particle is herein referred to as a microreactor.

The recording device containing the data storage unit(s) with remotely programmable memory, includes, in addition to the remotely programmable memory, means for receiving information for storage in the memory and for retrieving information stored in the memory. Such means is typically an antenna, which also serves to provide power in a passive device when combined with a rectifier circuit to convert received energy, such as RF, into voltage that can be tuned to a desired electromagnetic frequency to program the memory. Power for operation of the recording device may also be provided by a battery attached directly to the recording device, to create an active device, or by other power sources, including light and chemical reactions, including biological reactions, that generate energy.

Preferred frequencies are any that do not substantially alter the molecular and biological interactions of interest, are not substantially absorbed by the molecules or biological particles linked to the matrix or in proximity of the matrix, and do not alter the support properties of the matrix. Radio frequencies are presently preferred, but other frequencies, such as microwave or the higher end of the radiofrequency range (300 MHz–800 MHz) that approaches the microwave range are also preferred. Other frequencies include radar and infrared. Optical lasers will be used, as long as the selected frequency or optical laser does not interfere with the interactions of the molecules or biological particles of interest. Thus, information in the form of data points corresponding to such information is stored in and retrieved from the data storage device by application of a selected electromagnetic radiation frequency, which preferably is selected to avoid interference from any background electromagnetic radiation.

The preferred recording device for use in the combinations herein is a single substrate of a size preferably less than about 10 to 20 mm³ [or 10–20 mm in its largest dimension, most preferably 2 mm or less], that includes a remotely programmable data storage unit(s) [memory], preferably a non-volatile memory, and an antenna for receiving or transmitting an electromagnetic signal [and in some embodiments for supplying power in passive devices when combined with a rectifier circuit] preferably a radio frequency signal; the antenna, rectifier circuit, memory and other components are preferably integrated onto a single substrate, thereby minimizing the size of the device. An active device, i.e., one that does not rely on external sources for providing voltage for operation of the memory, may include a battery for power, with the battery attached to the substrate, preferably on the surface of the substrate. Vias through the substrate can then provide conduction paths from the battery to the circuitry on the substrate. The device is rapidly or substantially instantaneously programmable, preferably in less than 5 seconds, more preferably in about 1 second, and more preferably in about 50 to 100 milliseconds or less, and most preferably in about 1 millisecond or less. In a passive device that relies upon external transmissions to generate sufficient voltage to operate, write to and read from an electronic recording device, the preferred memory is non-volatile, and may be permanent. Such memories may rely antifuse-based architecture or flash memory. Other memories, such as electrically programmable erasable read only memories [EEPROMs] based upon other architectures also can be used in passive devices. In active recording devices that have batteries to assure continuous power availability, a broader range of memory devices may be used in addition to those identified above. These memory devices include dynamic random access memories [DRAMS, which refer to semiconductor volatile memory devices that allow random input/output of stored information; see, e.g., U.S. Pat. Nos. 5,453,633, 5,451,896, 5,442,584, 5,442,212 and 5,440,511], that permit higher density memories, and EEPROMs.

Monolithic devices, such as that described herein are among the preferred electromagnetically programmable memories. The monolithic devices are designed to be addressable and programmable in the microwave range or in the higher radiofrequency range. Thus, devices that are programmable in the gigahertz and microwave range are among the preferred devices.

Containers, such as vials, tubes, microtiter plates, reagent bottles, sample and collection vials, autosampler carousels, HPLC columns and other chromatography columns, such as GC columns, electrophoresis and capillary electrophoresis equipment, plate readers, reagent carriers, blood bags, fraction collectors, capsules and the like, which are in contact with a recording device that includes a data storage unit with programmable memory or include an optical memory, such as a 3-D optical memory or the 2-D optical bar codes provided herein, incorporated into the material or attached to the container or instrument or other analytical tool or engraved thereon are also provided. The memories may also be used in combination with instruments, including, but not limited to HPLC, gas chromatographs (GC), mass spectrometers (MS), NMR instruments, GC-MS, stir bars spectrometers, including fluorimeters, luminometers, and capillary electrophoresis and electrophoresis instruments and tubes and plates used therefor. Thus, an entire laboratory may be augmented with memories linked to or proximate to every container, instrument, and device, from reagent bottle to collected fraction, used in a particular protocol, whereby a sample may be tracked. Software that integrates and provides communication links among the devices and instruments will also be included. The information that is stored will include information regarding the identity of a sample and/or source of the sample.

These instruments and devices may also include a remotely programmable electronic device and a symbology, such as the 2-D optical bar code. In addition, as described herein, information from one device may be written to another or associated with the identifier of another, such as in a remote computer, either manually or automatically, as the sample is processed and assayed.

A container is typically of a size used in immunoassays or hybridization reactions, generally a liter or less, typically less than 100 ml, and often less than about 10 ml in volume, typically 100 $\mu$l–500 $\mu$l, particularly 200–250 $\mu$l. Alternatively the container can be in the form of a plurality of wells, such as a microtiter plate, each well having about 1 to 1.5 ml or less in volume. The container is transmissive to the electromagnetic radiation, such as radio frequencies, infrared wavelengths, radar, ultraviolet wavelengths, microwave frequencies, visible wavelengths, X-rays or laser light, used to program the recording device.

The memories have also been combined with stirring bars, particularly magnetic stir bars, thereby permitting remote identification of any beakers, bottles, and other containers in which stir bars are used.

Methods for electromagnetically tagging molecules or biological particles are provided. Such tagging is effected by placing the molecules or biological particles of interest in proximity with the recording device or with the matrix with memory, and programming or encoding the identity of the molecule or synthetic history of the molecules or batch number or other identifying information into the memory.

The, thus identified molecule or biological particle is then used in the reaction or assay of interest and tracked by virtue of its linkage to the matrix with memory, its proximity to the matrix with memory or its having been linked or in proximity to the matrix [i.e., its association with], which can be queried at will to identify the molecule or biological particle. The tagging and/or reaction or assay protocols may be automated. Automation may use robotics [see, U.S. Pat. No. 5,463,564, which provides an automated iterative method of drug design]. In addition, methods for addressing such memories in individually among a group are provided.

Methods for tagging constituent members of combinatorial libraries and other libraries or mixtures of diverse molecules and biological particles are provided. These methods involve electromagnetically tagging or optically imprinting molecules, particularly constituent members of a library, by contacting the molecules or biological particles or bringing such molecules or particles into proximity with a matrix with memory and programming the memory [by writing to it or by imprinting the matrix with an optical bar code or by associating a pre-engraved code with identifying information] with retrievable information from which the identity, synthesis history, batch number or other identifying information can be retrieved. The contact is preferably effected by coating, completely or in part, the recording device with memory with the matrix and then linking, directly or via linkers, the molecule or biological particle of interest to the matrix support. The memories can be coated with a protective coating, such as a glass or silicon, which can be readily derivatized for chemical linkage or coupling to the matrix material. In other embodiments, the memories can be coated with matrix, such as for example dipping the memory into the polymer prior to polymerization, and allowing the polymer to polymerize on the surface of the memory.

In other embodiments, the memory is part of the container that contains the sample or is part of the instrument. As a sample is moved, for example, from container to container or from instrument to container to a plate, the information from one memory is transferred by reading one memory and writing to the next so the identity of the contents is tracked as it is processed. Such movement and tracking can be automated.

If the matrices are used for the synthesis of the constituent molecules, the memory of each particle is addressed and the identity of the added component is encoded in the memory at [before, during, or preferably after] each step in the synthesis. At the end of the synthesis, the memory contains a retrievable record of all of the constituents of the resulting molecule, which can then be used, either linked to the support, or following cleavage from the support in an assay or for screening or other such application. If the molecule is cleaved from the support with memory, the memory must remain in proximity to the molecule or must in some manner be traceable [ie., associated with] to the molecule. Such synthetic steps may be automated.

In preferred embodiments, the matrix with memory with linked molecules [or biological particles] are mixed and reacted with a sample according to a screening or assay protocol, and those that react are isolated. The identity of reacted molecules can then be ascertained by remotely retrieving the information stored in the memory and decoding it to identify the linked molecules. Such steps can be performed on a single platform or on a series of platforms in which with each transfer information from one memory is transferred to a subsequent memory that is in contact with the sample.

Compositions containing combinations of matrices with memories and compositions of matrices with memories and molecules or biological particles are also provided. In particular, optically coded or electronically tagged libraries of oligonucleotides, peptides, proteins, non-peptide organic molecules, phage display, viruses and cells are provided. Particulate matrices, such as polystyrene beads, with attached memories, and continuous matrices, such as microtiter plates or slabs or polymer, with a plurality of embedded or attached memories are provided.

These combinations of matrix materials with memories and combinations of matrices with memories and molecules or biological particles may be used in any application in which support-bound molecules or biological particles are used. Such applications include, but are not limited to diagnostics, such as immunoassays, drug screening assays, combinatorial chemistry protocols and other such uses. These matrices with memories can be used to tag cells for uses in cell sorting, to identify molecules in combinatorial syntheses, to label monoclonal antibodies, to tag constituent members of phage displays, affinity separation procedures, to label DNA and RNA, in nucleic acid amplification reactions [see, e.g., U.S. Pat. No. 5,403,484; U.S. Pat. No. 5,386,024; U.S. Pat. No. 4,683,202 and, for example International PCT Application WO/94 02634, which describes the use of solid supports in connection with nucleic acid amplification methods], to label known compounds, particularly mixtures of known compounds in multianalyte analyses], to thereby identify unknown compounds, or to label or track unknowns and thereby identify the unknown by virtue of reaction with a known. Thus, the matrices with memories are particularly suited for high throughput screening applications and for multianalyte analyses.

Systems and methods for recording and reading or retrieving the information in the data storage devices regarding the identity or synthesis of the molecules or biological particles are also provided. The systems for recording and reading data include: a host computer or other encoder/decoder instrument having a memory for storing data relating to the identity or synthesis of the molecules, and a transmitter means for receiving a data signal and generating a signal for transmitting a data signal; and a recording device that includes a remotely programmable, preferably non-volatile, memory and transmitter means for receiving a data signal and generating at least a transmitted signal and for providing a write signal to the memory in the recording device. The host computer stores transmitted signals from the memories with matrices, and decodes the transmitted information.

In particular, the systems include means for writing to and reading from the memory device to store and identify each of the indicators that identify or track the molecules and biological particles. The systems additionally include the matrix material in physical contact with or proximate to the recording device, and may also include a device for separating matrix particles with memory so that each particle or memory can be separately programmed.

Methods for tagging molecules and biological particles by contacting, either directly or indirectly, a molecule or biological particle with a recording device; transmitting from a host computer or decoder/encoder instrument to the device electromagnetic radiation representative of a data signal corresponding to an indicator that either specifies one of a series of synthetic steps or the identity or other information for identification of the molecule or biological particle, whereby the data point representing the indicator is written into the memory, are provided. Where optical memories are used the memories are optically scanned and the encoded information read.

Methods for reading identifying information from recording devices linked to or in contact with or in proximity to or that had been in contact with or proximity to a electromagnetically tagged molecule or electromagnetically tagged biological particles are provided. These methods include the step of exposing the recording device containing the memory in which the data are stored to electromagnetic radiation [EM]; and transmitting to a host computer or decoder/encoder instrument an indicator representative of a the identity of a molecule or biological particle or identification of the molecule or biological particle linked to, in proximity to or associated with the recording device.

One, two, three and N-dimensional arrays of the matrices with memories are also provided. Each memory includes a record [or for pre-encoded memories with matrices, the record is associated with code in a remote memory] of its position in the array. Such arrays may be used for blotting, if each matrix particle is coated on one at least one side with a suitable material, such as nitrocellulose. For blotting, each memory is coated on at least one side with the matrix material and arranged contiguously to adjacent memories to form a substantially continuous sheet. After blotting, the matrix particles may be separated and reacted with the analyte of interest [e.g., a labeled antibody or oligonucleotide or other ligand], after which the physical position of the matrices to which analyte binds may be determined. The amount of bound analyte, as well as the kinetics of the binding reaction, may also be quantified. Southern, Northern, Western, dot blot and other such assays using such arrays are provided. Dimensions beyond three can refer to additional unique identifying parameters, such as batch number, and simultaneous analysis of multiple blots.

Assays that use combinations of (i) a memory, such as a 2-D optical bar code or a miniature recording device that contains one or more programmable data storage devices [memories] that can be remotely programmed and read; and (ii) a matrix, such as a particulate support used in chemical syntheses, are provided. The remote programming and reading is preferably effected using electromagnetic radiation.

Also provided are scintillation proximity assays, HTRF, FP, FET and FRET assays in which the memories are in proximity with or are in physical contact with the matrix that contains scintillant for detecting proximate radionucleotide signals or fluorescence. In addition, embodiments that include a memory device that also detects occurrence of a reaction are provided.

Molecular libraries, DNA libraries, peptide libraries, biological particle libraries, such as phage display libraries, in which the constituent molecules or biological particles are combined with a solid support matrix that is combined with a data storage unit with a programmable memory are provided.

Affinity purification protocols in which the affinity resin is combined with a recording device containing a data storage unit with a programmable memory are also provided.

Immunological, biochemical, cell biological, molecular biological, microbiological, and chemical assays in which memory with matrix combinations are used are provided. For example immunoassays, such as enzyme linked immunosorbent assays [ELISAs] in which at least one analyte is linked to a solid support matrix that is combined with a recording device containing a data storage unit with a programmable, preferably remotely programmable and non-volatile, memory are provided.

Of particular interest herein, are multiprotocol applications [such as multiplexed assays or coupled synthetic and assay protocols] in which the matrices with memories are used in a series [more than one] of reactions, a series [more than one] of assays, and/or a series of one or more reactions and one or more assays, typically on a single platform or coupled via automated analysis instrumentation. As a result synthesis is coupled to screening, including compound identification and analysis, where needed.

As noted above, where sample is transferred, for example, from vial or tubes to plates, etc., the vials, plates, reagent bottles and columns and other items used in drug discovery or for collecting and analyzing samples, screening and analysis equipment and instrumentation include memory, such as an RF tag, optical memory, such as a 3-D optical memory, or 2-D optical bar code. As a sample is synthesized or obtained and processed, the information is transferred from one memory to the next, thereby providing a means to track the sample and identity from synthesis to screening to analysis.

Methods for engraving bar codes, bar codes and bar-code engraved devices are also provided herein. In particular OMDs are provided and methods for writing to the surface of these devices and reading the engraved symbology are provided. The OMDs are fabricated from a suitable material, such as black, white or colored glass, TEFLON® [polytetrafluoroethylene], polyethylene, high density polyethylene, polypropylene, polystyrene, polyester, ceramic, composites of any of these materials and other such materials. The typical OMD is 10 mm or smaller in its largest dimension and is encoded by direct deposit, dot matrix deposit, direct laser write or dot matrix scan laser write. They may be precoded or coded prior to or even during use. For use in the applications provided herein, at least one surface or a portion of a surface is treated to render it suitable for use as a support, such as by grafting, ion implant, vacuum deposit, oxidation, combinations thereof, suitable derivatization or any other means known to those of skill in the art by which materials are treated to render them suitable for use as supports. The OMDs also have applications as a data pad for recording information about linked molecules or biological particles, or for monitoring storage and location, or in clinical labs for recording relevant information. The OMDs may be in the form of microplates in which each well is encoded or in combination with any instrumentation used in biological and chemical processing and screening.

Also of particular interest herein, are combinations of vials, tubes or other containers with sleeves [see, e.g., FIGS. 35–38], in which vial [such as a Hewlett Packard or Waters HPLC vial] is inserted into a fitted sleeve that contains the memory. These may be those used for patient samples or HPLC samples or other samples, such as samples from fraction collectors.

In one embodiment a carousel (such as those sold by Hewlett Packard) equipped with a reader and linked to a computer with software is also provided. Also provided herein is the carousel that houses a plurality of such vials or vessels, which are each equipped with a memory device. The carousel is mounted on a rotating seat that is designed to be rotated either manually, or by electrical, mechanical or other suitable control. This seat is mounted to a housing and is positioned such that the carousel rotates with the memory device [i.e., a read/write device] coming in proximity to a read/write controller. This read/write controller is located within the housing and positioned such that a detector head for the read/write controller is adjacent to the read/write device as held in the carousel. In order to assist the accurate positioning of the carousel, a plunger is oriented on the surface of the housing to strike the carousel at the location of the vial which helps to prevent further rotation of the carousel while the read/write device is communicating with the read/write controller. The read/write controller is a micro-controller based instrument that generates a selected frequency, such as 125 kHz radio frequency (RF) signal, when RF devices are used, which is transmitted to the read/write controller head which includes an antenna element that is designed to transmit the particular RF signal. It will be appreciated that other electromagnetic frequencies, such as microwave, radar, x-ray, UV, and IR may be used.

Also included in the read/write controller is an oscillator and EEPROM memory which, in combination, control a transmitter and receiver for the RF signals. The read/write device includes a semiconductor that is attached to a similarly shaped antenna designed to receive the signals transmitted from the read/write controller head. The signal from the read/write device antenna is filtered and a portion of the signal is rectified to create the power required to drive the semiconductor. Once the power is created, the semiconductor transmits through the same antenna information, such as identifying information, that has been programmed previously. This allows each vial to be attached to a read/write device, and programmed with a particular identification code or other information.

In alternative embodiments, the read/write device is pre-programmed or the container, such as the vial, reagent bottle, etc. is engraved with the 2-D optical bar code provided herein and using the methods herein. The vial can be attached to the read/write device either before or after the vial is filled. Once the vial is attached to a read/write device, the vial can be inserted into the carousel with a number of other vials similarly attached to the read/write devices.

The information that is transmitted from the read/write device is received by the antenna in the read/write device head or is scanned with an optical reader. This received information is then analyzed by the micro-controller within the read/write device and the identification code is determined. This identification code is then output from the read/write controller via a serial data line which can be fed to a computer. This output of the read/write controller is fed from the read/write controller to a computer system which identifies the particular read/write device, and may combine the identification information with the other information such as information regarding the contents or source of the contents of the vial. Such information could be used to track the contents of the vial from location to location within a lab, or to specifically identify a particular vial when the contents of the vial are in question. Moreover, because of the virtually unlimited number of identification codes which could be programmed into the read/write devices, an unlimited number of vials may be so identified.

Devices specially adapted for opening and closing the microvessels, such as the MICROKAN microvessels, are also provided.

Also provided herein are sensors in which matrices with memories are adapted to detect environmental parameters or changes or to be implanted in a mammal to detect internal parameters. Sensors containing memories, and coated with polymers and other materials that are responsive to the environment are also provided. In particular, sensors with memories that are coated with electrically conducting polymers are provided.

Also provided are manual system and automated systems for directing synthesis and screening and other protocols. In particular apparatus and software are provided that provide protocols and implement the protocols. These apparatus and software are used in conjunction with manual and automated systems. For example, a manual system includes a device for reading and, in instances in which the memories are encodable, writing to the memories, a computer for storing a database with identifying information and for containing and implementing the software, and also a sorter. A manual sorter will include, for example, an apparatus that assists the user in identifying a particular matrix with memory, such as the MICROKAN microreactors and MICROTUBE microreactors, identifying the destination of that matrix, and providing an indication, such as a visual or audio cue that identifies the destination as a means simplify, expedite, and increase the accuracy of the synthetic and screening protocols.

For example, a manual sorter provided herein, includes an identification station that identifies a particular matrix with memory, a host computer having a database that stores identifying information and software for directing the selected protocol(s). Such identifying information includes the source of the particular matrix with memory, the identity of linked molecules or biological particles, and the destination of that matrix with memory. Once the destination of the matrix with memory has been determined, the computer system provides the user with a cue, such as an audio cue, visual cue, or a combination of the two, that identifies the destination of the matrix with memory. For example, a manual system that includes a device for reading and, in instances in which the memories are encodable, writing to the memories, a computer for storing a database with identifying information and for containing and implementing the software, and also a sorter is provided.

Automated sorting devices, systems using the devices and methods of sorting are also provided herein. In one embodiment, for example, a sorting device that is fully automated to load, read from and write to the matrix with memory device, and automatically place the matrix with memory device in the properly selected location of the sorting device is provided. Exemplary software for use with the sorter is also provided. Automated and manual cleaving stations are also provided. In particular an automated sorter for sorting a plurality of matrices-with-memories into a plurality of containers that includes:

a feeder having a vessel for receiving the plurality of matrices-with-memories and a vessel outlet for feeding the plurality of matrices-with-memories one at a time out of the vessel;

a singulator means connected to vessel outlet for receiving the plurality of matrices-with-memories and dispensing after a pre-determined delay a matrix-with-memory of the plurality of matrices-with-memories;

a positioning means disposed for receiving the matrix-with-memory dispensed from the singulator means, wherein the positioning means holds the matrix-with-memory until a release signal is received;

a gating means within the positioning means responsive to the release signal for retaining the matrix-with-memory within the positioning means and releasing the matrix-with-memory when the release signal is received;

a read/write station disposed within a reading distance of the positioning means for reading data stored within the matrix-with-memory when the matrix-with memory is held within the positioning means, wherein the read/write station generates a data signal comprising information corresponding to the matrix-with-memory;

a translator for moving the positioning means in response to a positioning signal for positioning the matrix-with-memory over a pre-determined container; and a controller including software for receiving the data signal and associating the information therein with a pre-determined process, for identifying a location of the pre-determined container corresponding to the pre-determined process, for generating the positioning signal for moving the positioning means to the pre-determined container, and for generating the release signal for releasing the matrix-with-memory from the positioning means into the pre-determined container is provided.

Automated cleavers for cleaving compounds and molecules from the matrices with memories are provided. In one embodiment, the cleaver includes a cleaving block formed with at least one vessel, the vessel having a drain;

a vacuum chamber attached to the cleaving block and sized to enclose a container having at least one well; and a fluid communication means extending from the drain to the well wherein creating a partial vacuum within the vacuum chamber draws any fluid within the vessel through the fluid communication means and into the well.

The fluid communication means includes:

a U-tube which has a first end attached to the drain, and a second end positioned above the well, wherein a fluid trap is formed to prevent fluid from flowing through the u-tube in the absence of a partial vacuum within the vacuum chamber. Software for operating the cleaver and for integrating the operation of the sorter and cleaver is also contemplated herein.

Also provided are robotic methods for synthesizing and screening compounds using the memories with matrices provided herein for supports and the assays provided herein for screening. The robotic methods incorporate the automated sorting device and software such as that provided herein. The robotic methods also can incorporate the methods in which one memory with matrix is used to transmit information to another memory. Also provided herein, is the fully automated and communicating laboratory in which all aspects of synthesis and screening are automated and/or communicated from one container or instrument to another, thereby tracking and following the synthesis, screening and storage and subsequent use of compounds synthesized on matrices with memories as provided herein.

In particular, an improvement of the robotic methods for synthesis and screening, such as the methods set forth in U.S. Pat. No. 5,463,564, is provided herein. As provided herein, all instrumentation and devices include memory devices, such as RF tags or optical memories, 2-D optical bar codes or combinations thereof, whereby identifying information is stored. All vials, glassware, flasks, beakers, tubes and other containers in which the compounds are synthesized and assayed and all synthesis and assays are performed as provided herein by coupling each vial and assay step to a memory The information can be transferred, manually or, preferably automatically, from one memory device to another as a sample is processed. In particular, automated methods for generating and screening a plurality of compounds are provided. The methods include the steps of robotically synthesizing, in accordance with robotic synthesis instructions, a plurality of chemical compounds linked to a memory with matrix; and (2) robotically analyzing the chemical compounds to obtain structure-activity data pertaining thereto. The matrices with memories will be sorted preferably using the automated sorting methods and systems provided herein. Software integrating all steps in the synthesis and processing steps will be used, and substantially all instrumentation and containers will include memories to store information regarding the associated compounds. The methods can also include one or more of the steps of comparing, under computer control, the structure-activity data of the chemical compounds against the prescribed set of properties to identify any of the chemical compounds substantially conforming to the prescribed set of properties; classifying, under computer control, the identified chemical compounds as lead compounds; analyzing, under computer control, the structure-activity data of the compounds and historical structure-activity data pertaining to compounds synthesized and analyzed in the past to derive structure-activity models having enhanced predictive and discriminating capabilities; identifying, under computer control and in accordance with the structure-activity models, reagents from a reagent database that, when combined, will produce a set of compounds predicted to exhibit activity/properties more closely matching the prescribed set of properties; generating, under computer control, robotic synthesis instructions that, when executed, enable robotic synthesis of the set of compounds; (8) repeating steps (1)–(7), where step (1) is repeated using the generated robotic synthesis instructions. At all steps, relevant information and/or parameters will be stored in the memories associated with each compound.

DESCRIPTION OF THE DRAWINGS

FIG. 22 is a perspective view of a first embodiment of an optical memory device;

FIG. 23 is an exploded perspective view of a second embodiment of the optical memory device;

FIG. 25 is a side elevation of a third embodiment of the optical memory device;

FIG. 26 is a side elevation of a fourth embodiment of the optical memory device;

FIG. 27 is a side elevation of a fifth embodiment of the optical memory device;

FIG. 28 is a front elevation of a sixth embodiment of the optical memory device;

FIG. 29 is a front elevation of a seventh embodiment of the optical memory device;

FIG. 30 is a front elevation of an eighth embodiment of the optical memory device;

FIGS. 33 A–E depict the OMDs with optical symbology provided herein.

FIGS. 34 A–D depict a protocol for radiation grafting of polymers to the inert surfaces to render them suitable for use as matrices.

FIG. 44 is a side elevation view of the capsule sealing tool mounted on a plier type tool.

FIG. 45 is an enlarged sectional view taken on line 47—47 of FIG. 46.

FIG. 46 is a sectional view taken along line 48—48 of FIG. 47, showing the initial cap engagement.

FIG. 47 is a view similar to a portion of FIG. 46, showing the cap fully seated.

FIG. 48 is a view similar to a portion view of FIG. 46, showing ejection of the sealed capsule.

FIG. 49 is a side elevation view of the uncapping tool.

FIG. 50 is a sectional view taken on line 52—52 of FIG. 49, showing the cap separated from the capsule.

FIG. 51 is a perspective view of a monolithic identification tag with the antenna formed on the substrate.

FIG. 52 is a plane view of the monolithic identification tag as shown in FIG. 51, showing generally the outline of the circuitry on the substrate, and the formation of the antenna on encircling that circuitry; and FIG. 53 is a perspective view of a typical stirring bar with portions of the encapsulation removed to show the positioning of a monolithic identification tag against the metal of the stirring bar.

FIG. 60 is a block diagram of the components of an exemplary intracranial pressure monitor.

FIG. 61 is a diagrammatic view of an exemplary optical intracranial pressure monitor.

FIG. 62 is a diagrammatic view of an alternate optical sensor for use in the intracranial pressure monitor.

FIG. 63 is a diagrammatic view of an exemplary urea sensor located in line with a hemodialysis system.

FIG. 64 is a diagrammatic view of an exemplary embodiment of a "smart" blood bag.

FIG. 65 is a diagrammatic view of an alternate optical sensor for use in a "smart" blood bag.

FIG. 66 is a diagrammatic view of electrode construction for an alternate embodiment of a glucose sensor.

FIG. 67 is a perspective view of a preferred embodiment of a manual sorting device, including an identification station, a computer, and a visual cue for each destination.

FIG. 68 is a perspective view of the LED bracket showing the LED and the slot positionable over the rim of a beaker.

FIG. 69 is a cross-sectional view of the LED bracket taken along line 69—69 in FIG. 68 showing the orientation of the LED within the bracket, and the electrical connections extending out the rear portion of the bracket.

FIGS. 75(*a–c*) schematically depict the manner in which the matrices with memories are used as a single platform to link all aspects of the drug discovery process.

FIG. 97 is a perspective view of a manual cleaving station.

FIG. 98 is a cross-sectional view of the manual cleaving station of FIG. 97 taken along line 98—98, and showing the top plate separated from the cleaving block.

FIG. 99 is a detail view of the standoff of FIG. 97, detailing the operation of the standoff to suspend the top plate from the cleaving block.

FIG. 100 is a cross sectional view of the manual cleaving station of FIG. 97, showing the top plate adjacent to the cleaving block to rinse the MICROKAN microreactor.

FIG. 111 is a cross-sectional view of a two-part hand tool set for assembling both the MICROKAN microreactor and the back-to-back MICROKAN microreactors, with the tool being shown as used to assemble a MICROKAN microreactor;

FIG. 112 is a cross-sectional view of the two-part hand tool set being used in the first step to assemble a back-to-back MICROKAN microreactor;

FIG. 113 is a cross-sectional view of the two-part hand tool set being used in the second step in the assembly of a back-to-back MICROKAN microreactor;

FIG. 119 is a perspective view of a speed-vacuum chamber with portions cut away for clarity, where the individual vial racks are speed-vacuumed;

FIG. 120 is a top view of a typical collection rack showing the positioning and keying of the individual vial racks;

FIG. 121 is an enlarged view of a typical collection rack showing one embodiment of keying the individual vial racks for placement on a unique position within the collection rack;

FIG. 122 is a cross-sectional view of an alterative embodiment of an automated cleaving station showing a U-tube having a valve assembly for use in inhibiting the flow of fluid through the U-tube, and a resistive heater for assisting in the maintenance of a particular temperature within the cleaving block;

FIG. 123 is an enlarged view of the U-tube having a valve showing the valve in its open state allowing fluid to flow freely through the U-tube;

FIG. 124 is an enlarged view of the U-tube having a valve showing the valve in its closed state inhibiting the flow of fluid through the U-tube;

FIG. 125 is a side view of an alternative embodiment of an orientator within the automated sorting device which is intended for use with single-bodied MICROKAN microreactors;

FIG. 126 is a side view of yet another alternative embodiment of an orientator for use with the double-bodied MICROKAN microreactors;

FIG. 127 is a schematic view of a fourth embodiment of the automated sorting system;

FIG. 128 is a perspective view of a second embodiment of the cleaving assembly for use with the automated sorting system;

FIG. 129 is an enlarged side view, partially cut away, of the singulator for use in the automated sorting system shown in FIG. 127;

FIG. 130 is a side view of the cleaving assembly with its external housing indicated in broken line and a portion in section to show the relationship between the various components;

Figure 130:
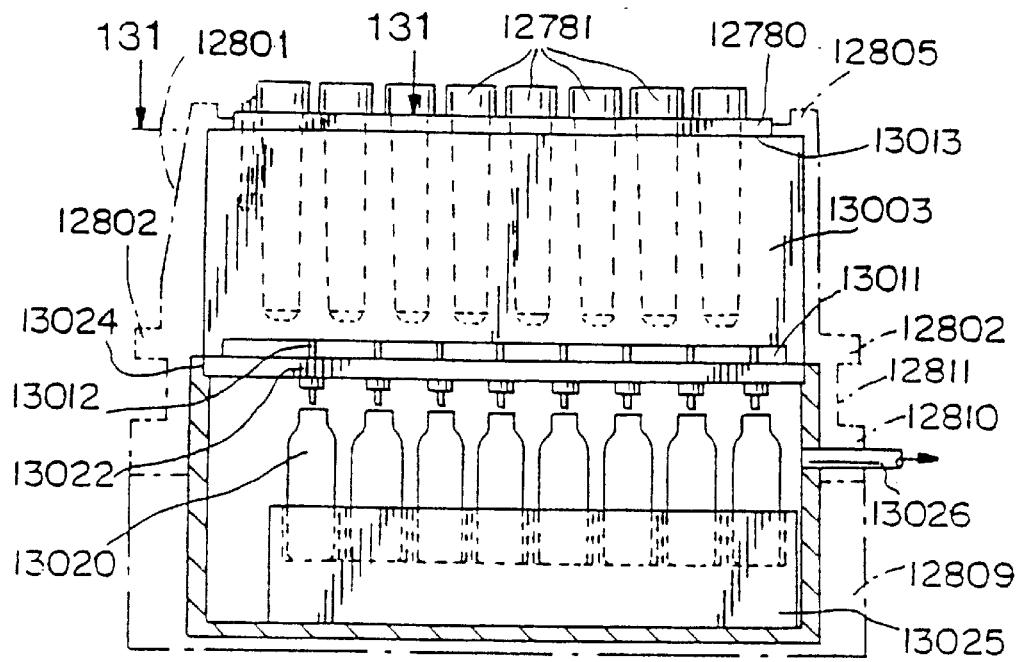
Figure 131:
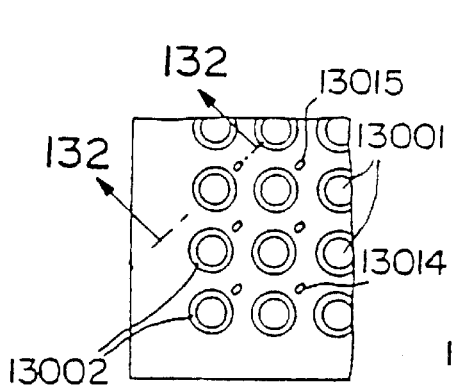
Figure 132:
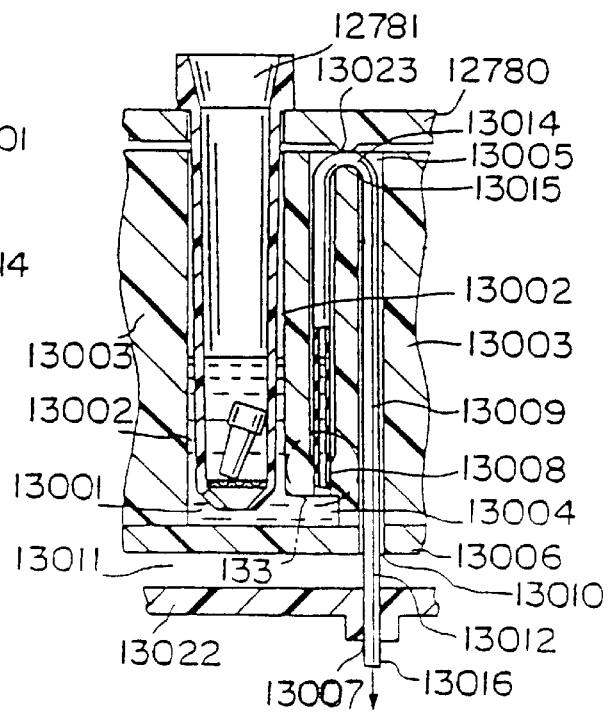
Figure 133:
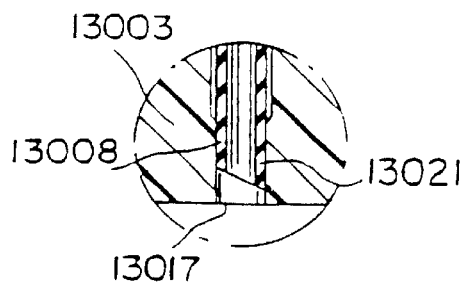
Figure 134:
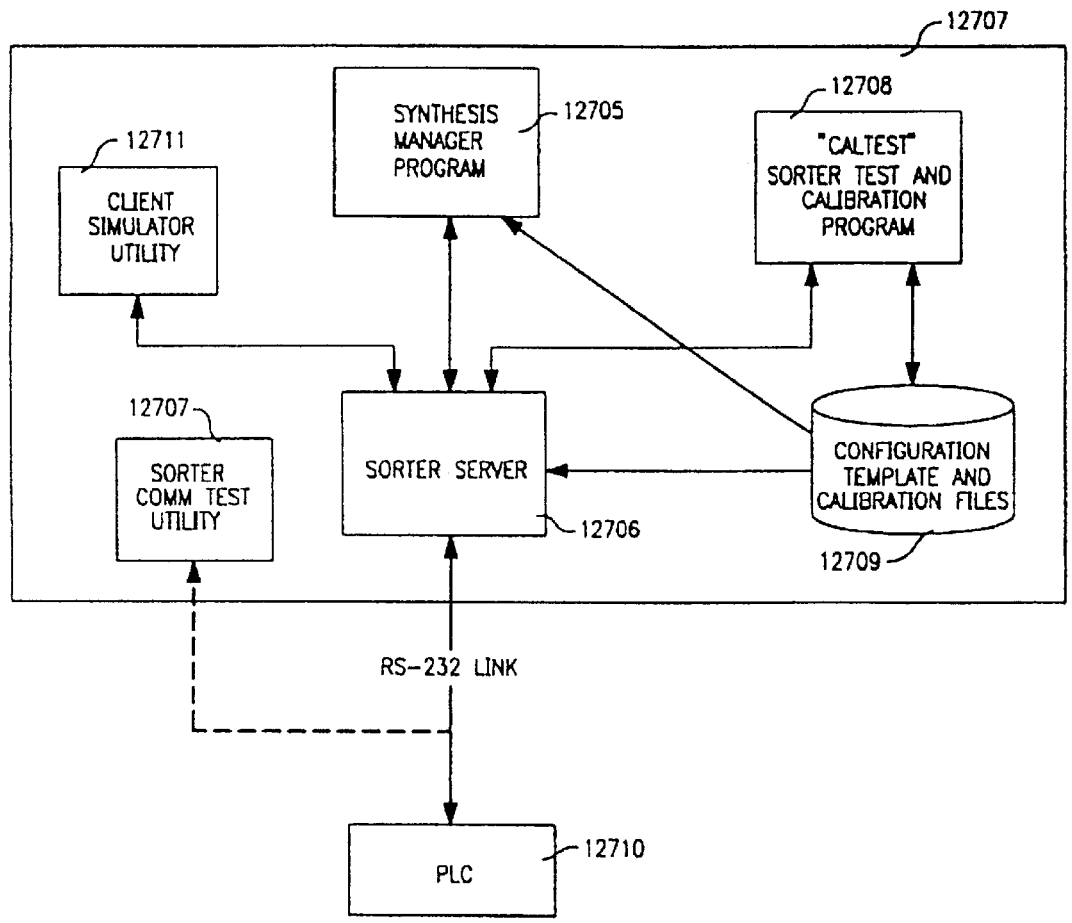
Figure 136:
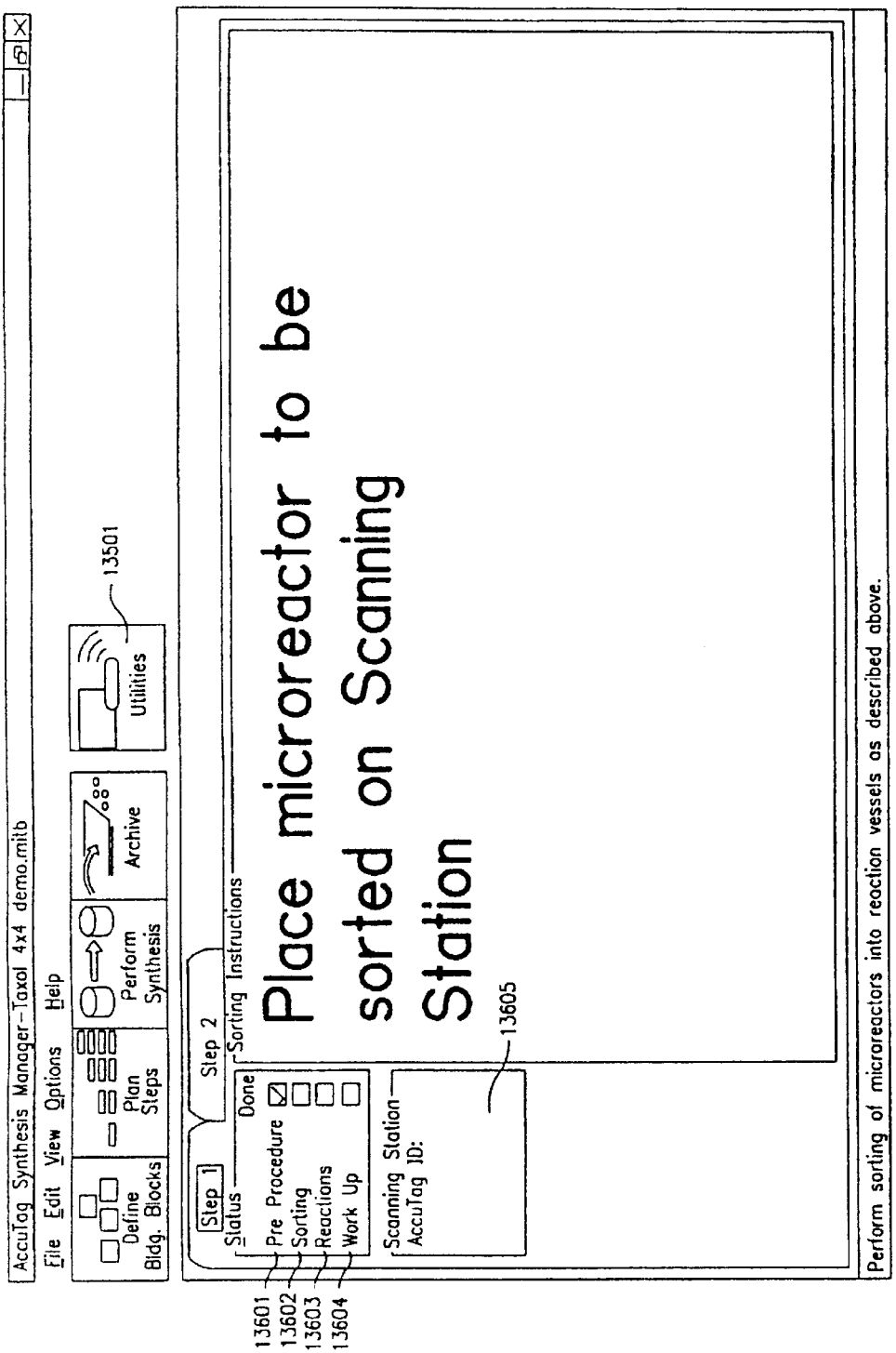
Figure 137:
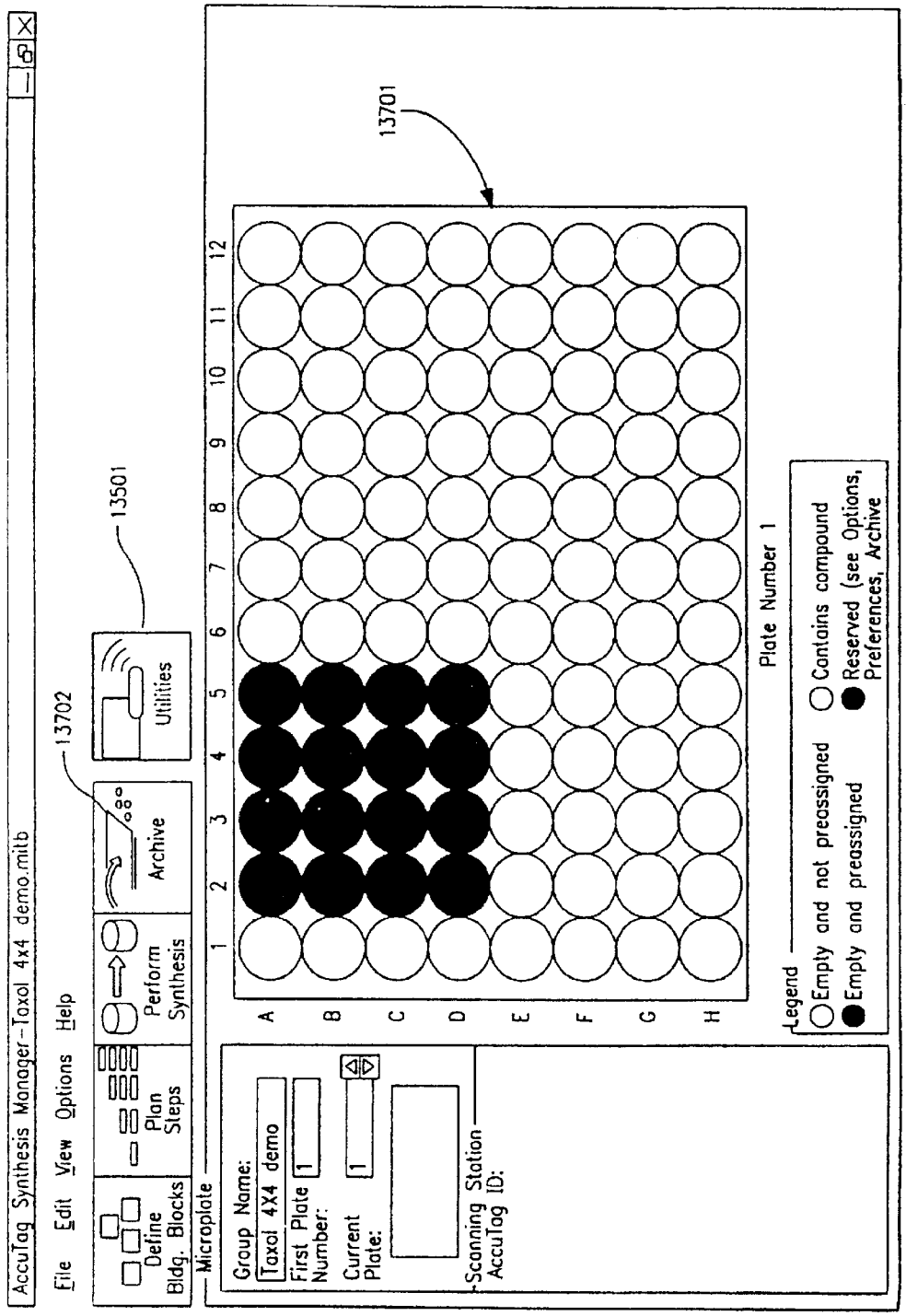
Figure 138:
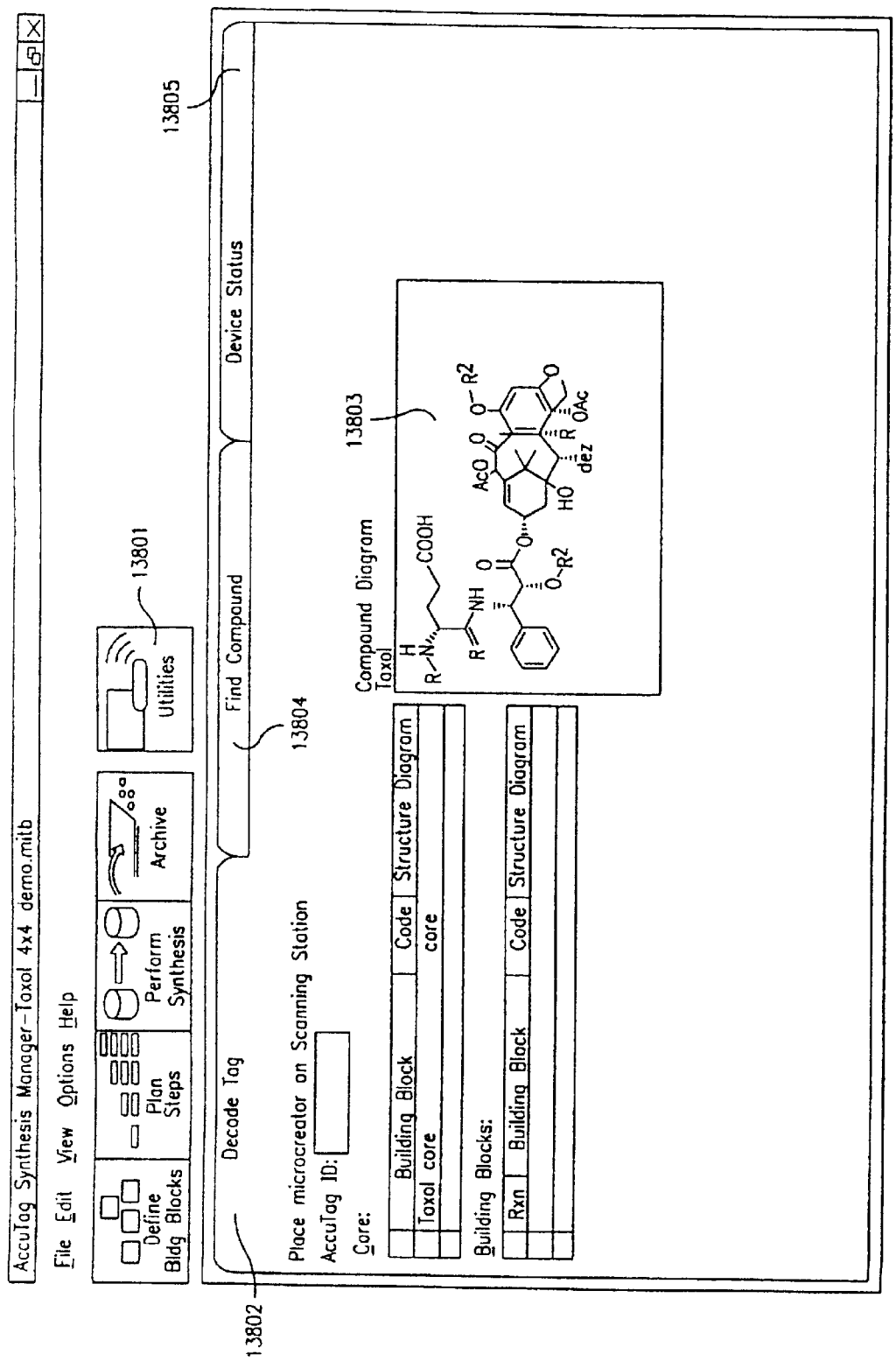

FIG. 131 is a sectional view of the cleaving block taken along line 131—131 of FIG. 130;

FIG. 132 is an enlarged sectional view taken on line 132—132 of FIG. 131;

FIG. 133 is an enlargement of the portion circled on FIG. 132;

FIG. 134 is a block diagram of the software architecture for the automated sorter system;

Figure 135:
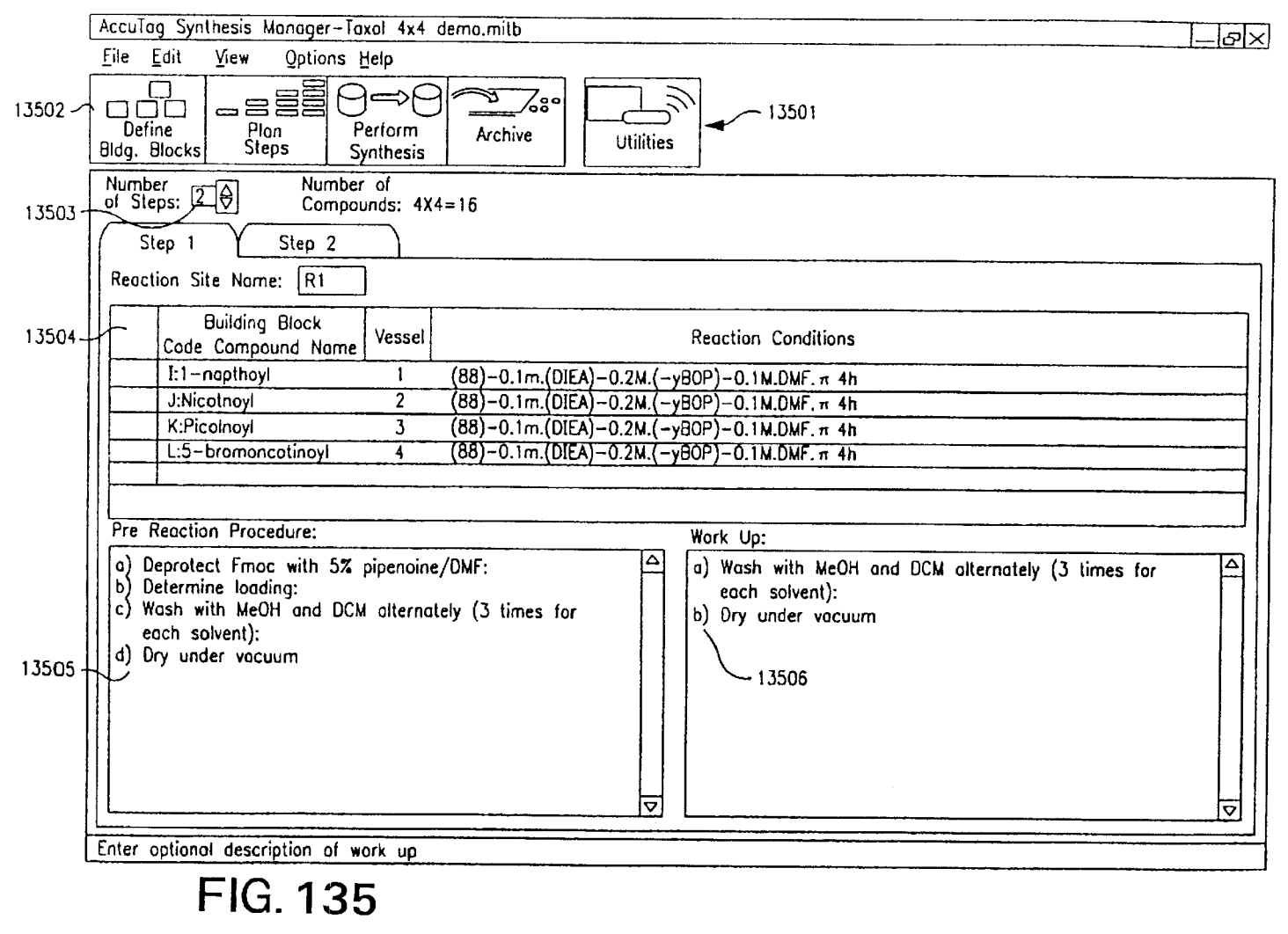

FIG. 135 is a diagram of an exemplary view screen produced by the SYNTHESIS MANAGER™ software for the step of defining building blocks;

FIG. 136 is a diagram of an exemplary view screen produced by the SYNTHESIS MANAGER™ software for the step of performing synthesis operations;

FIG. 137 is a diagram of an exemplary view screen produced by the SYNTHESIS MANAGER™ software for the step of producing a map and archiving information relative to specific compounds in an array of containers; and FIG. 138 is a diagram of an exemplary view screen produced by the SYNTHESIS MANAGER™ software for the utility function of decoding information stored on a memory device and displaying the associated compound.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are, unless noted otherwise, incorporated by reference in their entirety. In the event a definition in this section is not consistent with definitions elsewhere, the definition set forth in this section will control.

As used herein, a bar codes refers any array optically readable marks of any desired size and shape that are arranged in a reference context or frame of, preferably, although not necessarily, one or more columns and one or more rows. For purposes herein, the bar code refers to any symbology, not necessarily restricted to "bars" but may include dots, characters or any symbol or symbols.

As used herein, an optical memory refers to the symbology and the surface on which it is engraved or otherwise imprinted or refers to other optical devices. For purposes herein, an optical memory also includes from optical recording media that may be appropriate for use in the recording devices and combinations herein and include, but are not limited to, optical discs, magneto-optical materials, photochromic materials, photoferroelectric materials, and photoconductive electro-optic materials. Optical memories also include memories, such as 2-D and 3-D optical memories that use optics, such as lasers, for writing and/or reading.

As used herein, an optical memory device [OMD] refers to a surface that is encoded with a code, preferably the 2-D bar code provided herein. For use herein, such devices include at least two surfaces, one of which is treated or formed from a matrix material treated to render it suitable for use as a support to which molecules or biological particles are linked, such as in chemical syntheses or as supports in assays, and the other that includes a code that can be optically read and then compared with information in a computer or other memory to interpret its meaning.

As used herein, symbology refers to the code, such as a bar code, that is engraved or imprinted on the OMD. The symbology is any code known or designed by the user. The symbols are associated with information stored in a remote computer or memory or other such device or means. For example, each OMD can be uniquely identified with an encoded symbology. The process steps or additions or manipulations to the associated molecules or biological particles can be recorded in a remote memory and associated with the code.

As used herein, a matrix refers to any solid or semisolid or insoluble support on which a code is to which the memory device and/or the molecule of interest, typically a biological molecule, organic molecule or biospecific ligand is linked or contacted. Typically a matrix is a substrate material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or other such topology. Matrix materials include any materials that are used as affinity matrices or supports for chemical and biological molecule syntheses and analyses, such as, but are not limited to: polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrylamide non-covalent composite, polystyrene-polyacrylamide covalent composite, polystyrene-PEG [polyethyleneglycol] composite, silicon, rubber, and other materials used as supports for solid phase syntheses, affinity separations and purifications, hybridization reactions, immunoassays and other such applications. The matrix herein may be particulate or may be in the form of a continuous surface, such as a microtiter dish or well, a glass slide, a silicon chip with a surface adapted for linking of biological particles or molecules, a nitrocellulose sheet, nylon mesh, or other such materials. When particulate, typically the particles have at least one dimension in the 5–10 mm range or smaller. Such particles, referred collectively herein as "beads", are often, but not necessarily, spherical. Such reference, however, does not constrain the geometry of the matrix, which may be any shape, including random shapes, needles, fibers, elongated, etc. The "beads" may include additional components, such as magnetic or paramagnetic particles [see, e.g., Dyna beads (Dynal, Oslo, Norway)] for separation using magnets, fluophores and other scintillants, as long as the additional components do not' interfere with chemical reactions, data entry or retrieval from the memory.

Also contemplated herein, are the combination of "chips" or arrays that contain hundreds of thousands of probes [see, e.g., U.S. Pat. No. 5,525,531] linked to a matrix with a surface suitable for linking probes or other selected molecules or biological particles.

Significantly, it is noted, however, that many surfaces, such as glass, require modification to render them suitable for use as supports. Any such surface must be treated to render it suitable for chemical syntheses or for adsorption of biological particles. Chemical syntheses require a support that not only has the proper surface characteristics (organic solvent wettability, chemical kinetics, etc.), but that also has a high density of functional groups. An untreated glass surface contains only a very small amount [less than 1 nmol/sq. mm] of hydroxy groups. It is also very hydrophilic and not very suitable for reactions in organic media. Therefore, the glass surface has to be modified to achieve high functional group density ("$>10$ nmol/mm$^2$) and proper hydrophobicity. Thus, as used herein, matrix refers to materials that have been so-treated. Therefore, a transponder in which the memory device is encased in a glass capsule for instance is not usable as is, but must be treated, either by coating at least one surface with a polymer, such as by grafting, derivatizing or otherwise activating the surface.

As used herein, scintillants include, 2,5-diphenyloxazole [PPO], anthracene, 2-(4'-tert-butylphenyl)-5-(4"-biphenyl)-1,3,4-oxadiazole [butyl-PBD]; 1-phenyl-3-mesityl-2-pyrazoline [PMP], with or without frequency shifters, such as 1,4,-bis[5-phenyl(oxazolyl)benzene] [POPOP]; p-bis-o-methylstyrylbenzene [bis-MSB]. Combinations of these fluors, such as PPO and POPOP or PPO and bis-MSB, in suitable solvents, such as benzyltoluene [see, e.g., U.S. Pat. No. 5,410,155], are referred to as scintillation cocktails.

As used herein a luminescent moiety refers to a scintillant or fluophor used in scintillation proximity assays or in non-radioactive energy transfer assays, such as HTRF assays.

As used herein, fluorescent resonance energy transfer [FRET] is an art-recognized term meaning that one fluorophore [the acceptor] can be promoted to an excited electronic state through quantum mechanical coupling with and receipt of energy from an electronically excited second fluorophore [the donor]. This transfer of energy results in a decrease in visible fluorescence emission by the donor and an increase in fluorescent energy emission by the acceptor. Significant energy transfer can only occur when the donor and acceptor are sufficiently closely positioned since the efficiency of energy transfer is highly dependent upon the distance between donor and acceptor fluorophores.

As used herein, matrix particles refer to matrix materials that are in the form of discrete particles. The particles have any shape and dimensions, but typically have at least one dimension that is 100 mm or less, preferably 50 mm or less, more preferably 10 mm or less, and typically have a size that is 100 mm$^3$ or less, preferably 50 mm$^3$ or less, more preferably 10 mm$^3$ or less, and most preferably 1 mm$^3$ or less. The matrices may also be continuous surfaces, such as microtiter plates [e.g., plates made from polystyrene or polycarbonate or derivatives thereof commercially available from Perkin Elmer Cetus and numerous other sources, and Covalink trays [Nunc], microtiter plate lids or a test tube, such as a 1 ml Eppendorf tube or smaller versions, such as 500 $\mu$l, 200 $\mu$l or smaller. Matrices that are in the form of containers refers to containers, such as test tubes and microplates and vials that are typically used for solid phase syntheses of combinatorial libraries or as pouches, vessels, bags, and microvessels for screening and diagnostic assays or as containers for samples, such as patient samples. Thus, a container used for chemical syntheses refers to a container that typically has a volume of about 1 liter, generally 100 ml, and more often 10 ml or less, 5 ml or less, preferably 1 ml or less, and as small as about 50 $\mu$l–500 $\mu$l, such as 100 $\mu$l or 250 $\mu$l or 200 $\mu$l. This also refers to multi-well plates, such as microtiter plates [96 well, 384 well, 1536 well or other higher density format]. Such microplate will typically contain a memory device in, on, or otherwise in contact with in each of a plurality of wells.

As used herein, a matrix with a memory refers to a combination of a matrix with any means for storing information. Such memories include, a miniature recording device that stores multiple bits of data by which the matrix may be identified, preferably in a non-volatile memory that can be written to and read from by transmission of electromagnetic radiation from a remote host, such as a computer. By miniature is meant of a size less than about 10–20 mm$^3$ [or 10–20 mm in the largest dimension]. Preferred memory devices or data storage units are miniature and are preferably smaller than 10–20 mm$^3$ [or 10–20 mm in its largest dimension] dimension, more preferably less than 5 mm$^3$, most preferably about 1 mm$^3$ or smaller. Alternatively, the memory may be fabricated as part of the matrix material or may be a chemical or biological-based memory means, such as those described herein, including the rhodopsin based memories and 3-D optical memories based on photochromic materials [see, e.g., U.S. Pat. Nos. 5,268,862, 5,130,362, 5,325,324; see, also, Dvornikov et al. (1996) *Opt. Commun.* 128:205–210; Dvornikov et al. (1996) *Res. Chem. Intermed.* 22:115–28; Dvornikov et al. (1994) *Proc. SPIE-Int. Soc. Opt. Eng.* 2297:447–51; Dvornikov et al. (1994) *Mol. Cryst. Lic. Cryst. Sci. Technol., Sect. A* 246:379–88; Dvornikov et al. (1994) *J. Phys. Chem.* 98:6746–52; Ford et al. (1993) *Proc. SPIE-Int. Soc. Opt.* 2026:604–613; Ford et al. *Proc. SPIE-Int. Soc. Opt. Eng.* 1853:5–13; Malkin et al. *Res. Chem. Intermed.* 19:159–89; Dvornikov et al. (1993) *Proc.*

SPIE-Int. Soc. Opt. Eng. 1852:243–52; Dvornikov et al. (1992) Proc. SPIE-Int. Soc. Opt. Eng. 1662:197–204; Prasad et al. (1996) Mater. Res. Soc. Symp. Proc. 413:203–213]. Alternatively, the memory may be an optical bar code, such as the 2-D optical bar codes described herein. Thus, the term memory with matrix refers generically to any combination [association] between a matrix and any means for storing information.

As used herein, a microreactor refers to combinations of matrices with memories with associated, such as linked or proximate, biological particles or molecules. It is produced, for example, when the molecule is linked thereto or synthesized thereon. It is then used in subsequent protocols, such as immunoassays and scintillation proximity assays.

As used herein, a combination herein called a microvessel [e.g., a microvessel such as those designated presently designated a MICROKAN™ microreactor] refers to a combination in which a single device [or more than one device] and a plurality of particles are sealed in a porous or semipermeable inert material, such as polytetrafluoroethylene or polypropylene or membrane that is permeable to the components of the medium, but retains the particles and memory, or are sealed in a small closable container that has at least one dimension that is porous or semi-permeable. Typically such microvessels, which preferably have at least one end that can be opened and sealed or closed tightly, has a volume of about 200–500 mm$^3$, with preferred dimensions of about 1–10 mm in diameter and 5 to 20 mm in height, more preferably about 5 mm by 15 mm. The porous wall should be non-collapsible with a pore size in the range of 70 $\mu$M to about 100 $\mu$M, but can be selected to be semi-permeable for selected components of the reaction medium.

As used herein, a memory is a data storage unit [or medium] with programmable memory, preferably a non-volatile memory; or alternatively is a symbology on a surface, such as a bar code, whose identity and as for which associate information is stored in a remote memory, such as a computer memory.

As used herein, programming refers to the process by which data or information is entered and stored in a memory. A memory that is programmed is a memory that contains retrievable information.

As used herein, remotely programmable, means that the memory can be programmed (read from and written to) without direct physical or electrical contact or can be programmed from a distance, typically at least about 10 mm, although shorter distances may also be used, such as instances in which the information comes from surface or proximal reactions or from an adjacent memory or in instances, such as embodiments in which the memories are very close to each other, as in microtiter plate wells or in an array.

As used herein, a recording device [or memory device] is an apparatus that includes the data storage unit with programmable memory, and, if necessary, means for receiving information and for transmitting information that has been recorded. It includes any means needed or used for writing to and reading from the memory. The recording devices intended for use herein, are miniature devices that preferably are smaller than 10–20 mm$^3$ [or 10–20 mm in their largest dimension], and more preferably are closer in size to 1 mm$^3$ or smaller that contain at least one such memory and means for receiving and transmitting data to and from the memory. The data storage device also includes optical memories, such as bar codes, on devices such as OMDs.

As used herein, a data storage unit with programmable memory includes any data storage means having the ability to record multiple discrete bits of data, which discrete bits of data may be individually accessed [read] after one or more recording operations. Thus, a matrix with memory is a combination of a matrix material with a data storage unit.

As used herein, programmable means capable of storing unique data points. Addressable means having unique locations that may be selected for storing the unique data points.

As used herein, reaction verifying and reaction or event detecting are interchangeable and refer to the combination that also includes elements that detect occurrence of a reaction or event of interest between the associated molecule or biological particle and its environment [i.e., detects occurrence of a reaction, such as ligand binding, by virtue of emission of EM upon reaction or a change in pH or temperature or other parameter].

As used herein, a host computer or decoder/encoder instrument is an instrument that has been programmed with or includes information [i.e., a key] specifying the code used to encode or decode the memory devices. This instrument or one linked thereto transmits the information and signals to the recording device and it, or another instrument, receives the information transmitted from the recording device upon receipt of the appropriate signal. This instrument thus creates the appropriate signal to transmit to the recording device and can interpret transmitted signals. For example, if a "1" is stored at position 1,1 in the memory of the recording device means, upon receipt of this information, this instrument or computer can determine that this means the linked molecule is, for example, a peptide containing alanine at the N-terminus, an organic group, organic molecule, oligonucleotide, or whatever this information has been predetermined to mean. Alternatively, the information sent to and transmitted from the recording device can be encoded into the appropriate form by a person.

Figure 17:
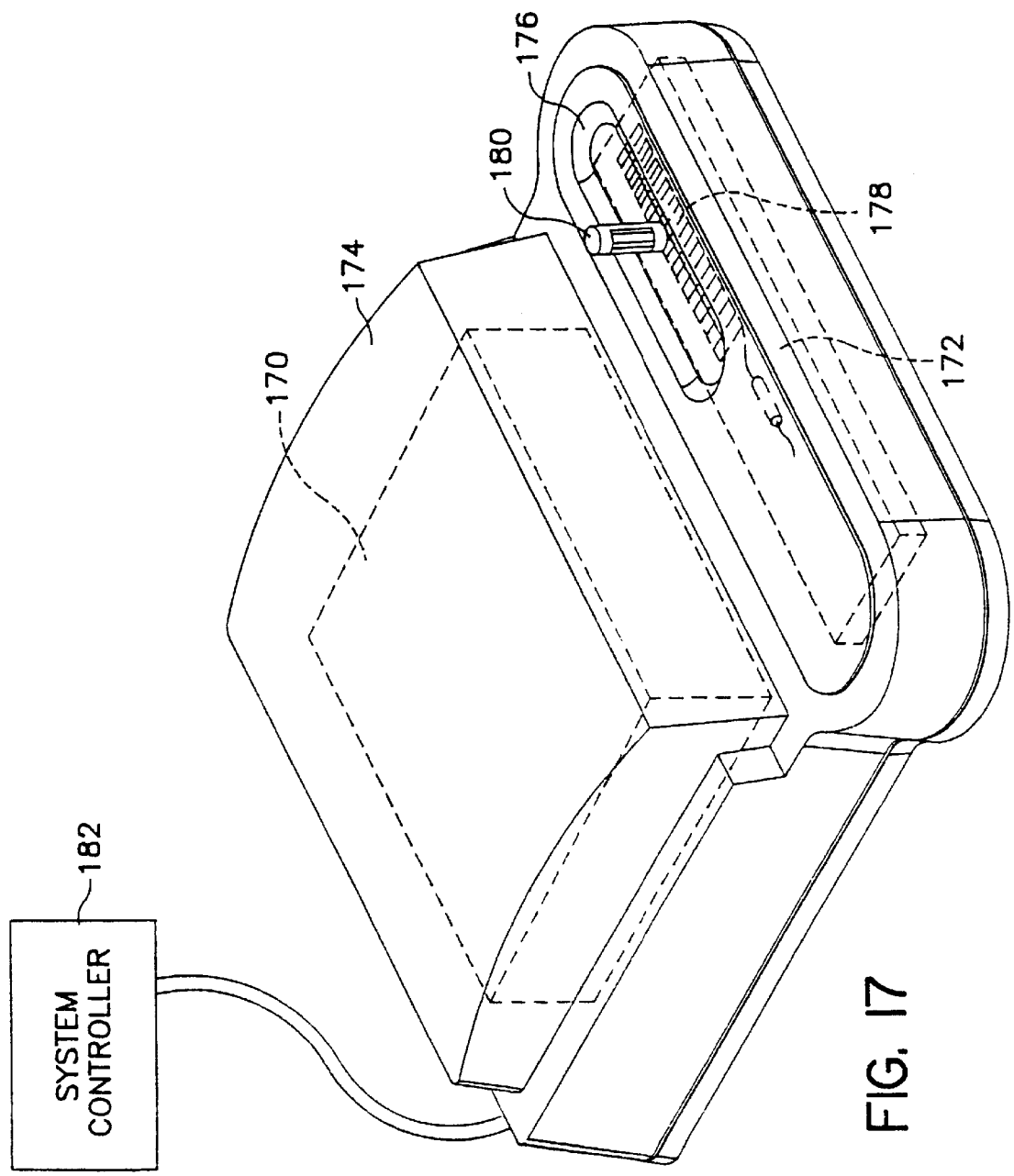
FIG. 17 is a perspective view of an exemplary write/read station.

As used herein, an identification station refers to a device that reads memories and includes any such components and software necessary to effect such reading and communication of information to the user or to other devices, such as a host computer. An exemplary identification station is depicted in FIGS. 17 and 67.

As used herein, an electromagnetic tag or electronic tag is a recording device that has a memory that contains unique data points that correspond to information that identifies molecules or biological particles linked to, directly or indirectly, in physical contact with or in proximity [or associated with] to the device. Thus, electromagnetic tagging is the process by which identifying or tracking information is transmitted [by any means and to any recording device memory, including optical and magnetic storage media] to the recording device.

As used herein, a cue refers to any detectable signal, such as an audio, visual, electronic or other signal, generated in the automated and manual sorting systems provided herein. In the manual system, the signal is detected by the user; and in the automated system, by means that transport matrices with memories to their destination.

As used herein, proximity means within a very short distance, generally less than 0.5 inch, typically less than 0.2 inches. In particular, stating that the matrix material and memory, or the biological particle or molecule and matrix with memory are in proximity means that, they are at least or at least were in the same reaction vessel or, if the memory is removed from the reaction vessel, the identity of the vessel containing the molecules or biological particles with which the memory was proximate or linked is tracked or otherwise known.

As used herein, associated with means that the memory must remain in proximity to the molecule or biological particle or must in some manner be traceable to the molecule or biological particle. For example, if a molecule is cleaved from the support with memory, the memory must in some manner be identified as having been linked to the cleaved molecule. Thus, a molecule or biological particle that had been linked to or in proximity to a matrix with memory is associated with the matrix or memory if it can be identified by querying the memory.

As used herein, antifuse refers to an electrical device that is initially an open circuit that becomes a closed circuit during programming, thereby providing for non-volatile memory means and, when accompanied by appropriate transceiver and rectification circuitry, permitting remote programming and, hence identification. In practice, an antifuse is a substantially nonconductive structure that is capable of becoming substantially conductive upon application of a predetermined voltage, which exceeds a threshold voltage. An antifuse memory does not require a constant voltage source for refreshing the memory and, therefore, may be incorporated in a passive device. Other memories that may be used include, but are not limited to: EEPROMS, DRAMS and flash memories.

As used herein, flash memory is memory that retains information when power is removed [see, e.g., U.S. Pat. No. 5,452,311, U.S. Pat. No. 5,452,251 and U.S. Pat. No. 5,449,941]. Flash memory can be rewritten by electrically and collectively erasing the stored data, and then by programming.

As used herein, passive device refers to an electrical device which does not have its own voltage source and relies upon a transmitted signal to provide voltage for operation.

As used herein, electromagnetic [EM] radiation refers to radiation understood by skilled artisans to be EM radiation and includes, but is not limited to radio frequency [RF; low kilohertz (80 KHz) up to about 800 MHz–1 GHz], infrared [IR], visible, ultraviolet [UV], radiation, microwave [i.e., 800 MHz–300 GHz (corresponding to wavelengths of 1 meter to 1 mm), preferably just beyond the RF range], sonic waves, X-rays, and laser light.

As used herein, information identifying or tracking a biological particle or molecule, refers to any information that identifies the molecule or biological particle, such as, but not limited to the identity particle [i.e. its chemical formula or name], its sequence, its types its class, its purity, its properties, such as its binding affinity for a particular ligand. Tracking means the ability to follow a molecule or biological particle through synthesis and/or process steps. The memory devices herein store unique indicators that represent any of this information.

As used herein, combinatorial chemistry is a synthetic strategy that produces diverse, usually large, chemical libraries. It is the systematic and repetitive, covalent connection of a set, the basis set, of different monomeric building blocks of varying structure to each other to produce an array of diverse molecules [see, e.g., Gallop et al. (1994) *J. Medicinal Chemistry* 37:1233–1251]. It also encompasses other chemical modifications, such as cyclizations, eliminations, cleavages, etc., that are carried in manner that generates permutations and thereby collections of diverse molecules.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials.

As used herein, a molecule refers to any molecule that is linked to the solid support. Typically such molecules are compounds or components or precursors thereof, such as peptides, amino acids, small organics, oligonucleotides or monomeric units thereof. A monomeric unit refers to one of the constituents from which the resulting compound is built. Thus, monomeric units include, nucleotides, amino acids, and pharmacophores from which small organic molecules are synthesized.

As used herein, the molecules in the combinations include any molecule, including nucleic acids, amino acids, other biopolymers, and other organic molecules, including peptidomimetics and monomers or polymers of small organic molecular constituents of non-peptidic libraries, that may be identified by the methods here and/or synthesized on matrices with memories as described herein.

As used herein, the term "bio-oligomer" refers to a biopolymer of less than about 100 subunits. A bio-oligomer includes, but is not limited to, a peptide, i.e., containing amino acid subunits, an oligonucleotide, i.e., containing nucleoside subunits, a peptide-oligonucleotide chimera, peptidomimetic, and a polysaccharide.

As used herein, the term "sequences of random monomer subunits" refers to polymers or oligomers containing sequences of monomers in which any monomer subunit may precede or follow any other monomer subunit.

As used herein, the term "library" refers to a collection of substantially random compounds or biological particles expressing random peptides or proteins or to a collection of diverse compounds. Of particular interest are bio-oligomers, biopolymers, or diverse organic compounds or a set of compounds prepared from monomers based on a selected pharmacophore.

As used herein, an analyte is any substance that is analyzed or assayed in the reaction of interest. Thus, analytes include the substrates, products and intermediates in the reaction, as well as the enzymes and cofactors.

As used herein, multianalyte analysis is the ability to measure many analytes in a single specimen or to perform multiple tests from a single specimen. The methods and combinations herein provide means to identify or track individual analytes from among a mixture of such analytes.

As used herein, a fluophore or a fluor is a molecule that readily fluoresces; it is a molecule that emits light following interaction with radiation. The process of fluorescence refers to emission of a photon by a molecule in an excited singlet state. For scintillation assays, combinations of fluors are typically used. A primary fluor that emits light following interaction with radiation and a secondary fluor that shifts the wavelength emitted by the primary fluor to a higher more efficiently detected wavelength.

As used herein, a peptidomimetic is a compound that mimics the conformation and certain stereochemical features of the biologically active form of a particular peptide. In general, peptidomimetics are designed to mimic certain desirable properties of a compound but not the undesirable features, such as flexibility leading to a loss of the biologically active conformation and bond breakdown. For example, methylenethio bioisostere [$CH_2S$] has been used as an amide replacement in enkephalin analogs [see, e.g., Spatola, A. F. *Chemistry and Biochemistry of Amino Acids, Peptides, and Proteins* [Weinstein, B, Ed., Vol. 7, pp. 267–357, Marcel Dekker, New York (1983); and Szelke et al. (1983) *In Peptides: Structure and Function, Proceedings of the Eighth American Peptide Symposium*, Hruby and Rich, Eds., pp. 579–582, Pierce Chemical Co., Rockford, Ill.].

As used herein, complete coupling means that the coupling reaction is driven substantially to completion despite or regardless of the differences in the coupling rates of individual components of the reaction, such as amino acids In addition, the amino acids, or whatever is being coupled, are coupled to substantially all available coupling sites on the solid phase support so that each solid phase support will contain essentially only one species of peptide.

As used herein, the biological activity or bioactivity of a particular compound includes any activity induced, potentiated or influenced by the compound in vivo or in vitro. It also includes the abilities, such as the ability of certain molecules to bind to particular receptors and to induce [or modulate] a functional response. It may be assessed by in vivo assays or by in vitro assays, such as those exemplified herein.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, substantially pure means sufficiently homogeneous to appear free of readily detectable impurities as determined by standard methods of analysis, such as thin layer chromatography [TLC], mass spectrometry [MS], size exclusion chromatography, gel electrophoresis, particularly agarose and polyacrylamide gel electrophoresis [PAGE] and high performance liquid chromatography [HPLC], used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, adequately pure or "pure" per se means sufficiently pure for the intended use of the adequately pure compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound [see, e.g., Nogrady (1985) *Medicinal Chemistry A Biochemical Approach*, Oxford University Press, New York, pages 388–392].

As used herein, amino acids refer to the naturally-occurring amino acids and any other non-naturally occurring amino acids, and also the corresponding D-isomers. It is also understood that certain amino acids may be replaced by substantially equivalent non-naturally occurring variants thereof, such as D-Nva, D-Nle, D-Alle, and others listed with the abbreviations below or known to those of skill in this art.

As used herein, hydrophobic amino acids include Ala, Val, Leu, lle, Pro, Phe, Trp, and Met, the non-naturally occurring amino acids and the corresponding D isomers of the hydrophobic amino acids, that have similar hydrophobic properties; the polar amino acids include Gly, Ser, Thr, Cys, Tyr, Asn, Gln, the non-naturally occurring amino acids and the corresponding D isomers of the polar amino acids, that have similar properties, the charged amino acids include Asp, Glu, Lys, Arg, His, the non-naturally occurring amino acids and the corresponding D isomers of these amino acids.

As used herein, Southern, Northern, Western and dot blot procedures refer to those in which DNA, RNA and protein patterns, respectively, are transferred for example, from agarose gels, polyacrylamide gels or other suitable medium that constricts convective motion of molecules, to nitrocellulose membranes or other suitable medium for hybridization or antibody or antigen binding are well known to those of skill in this art [see, e.g., Southern (1975) *J. Mol. Biol.* 98:503–517; Ketner et al. (1976) *Proc. Natl. Acad. Sci. U.S.A.* 73:1102–1106; Towbin et al. (1979) *Proc. Natl. Acad. Sci. U.S.A.* 76:4350.

As used herein, a receptor refers to a molecule that has an affinity for a given ligand. Receptors may be naturally-occurring or synthetic molecules. Receptors may also be referred to in the art as anti-ligands. As used herein, the terms, receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases;

c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, antibody includes antibody fragments, such as Fab fragments, which are composed of a light chain and the variable region of a heavy chain.

As used herein, complementary refers to the topological compatibility or matching together of interacting surfaces of a ligand molecule and its receptor. Thus, the receptor and its ligand can be described as complementary, and furthermore, the contact surface characteristics are complementary to each other.

As used herein, a ligand-receptor pair or complex formed when two macromolecules have combined through molecular recognition to form a complex.

As used herein, an epitope refers to a portion of an antigen molecule that is delineated by the area of interaction with the subclass of receptors known as antibodies.

As used herein, a ligand is a molecule that is specifically recognized by a particular receptor. Examples of ligands, include, but are not limited to, agonists and antagonists for cell membrane receptors, toxins and venoms, viral epitopes, hormones [e.g., steroids], hormone receptors, opiates, peptides, enzymes, enzyme substrates, cofactors, drugs, lectins, sugars, oligonucleotides, nucleic acids, oligosaccharides, proteins, and monoclonal antibodies.

As used herein, a sensor is a device or apparatus that monitors external (or internal) parameters (i.e., conditions), such as ion concentrations, pH, temperatures, and events. Internal parameters refer to conditions, concentrations, such as electrolyte and glucose concentration, in an animal. Biosensors are sensors that detect biological species. Sensors encompass devices that rely on electrochemical, optical, biological and other such means to monitor the environment.

As used herein, multiplexing refers to performing a series of synthetic and processing steps and/or assaying steps on the same platform [i.e. solid support or matrix] or coupled together as part of the same automated coupled protocol, including one or more of the following, synthesis, preferably accompanied by writing to the linked memories to identify linked compounds, screening, including using protocols with matrices with memories, and compound identification by querying the memories of matrices associated with the selected compounds. Thus, the platform refers system in which all manipulations are performed. In general it means that several protocols are coupled and performed sequentially or simultaneously.

As used herein, a platform refers to the instrumentation or devices in which on which a reaction or series of reactions is(are) performed.

As used herein a protecting group refers to a material that is chemically bound to a monomer unit that may be removed upon selective exposure to an activator such as electromagnetic radiation and, especially ultraviolet and visible light, or that may be selectively cleaved. Examples of protecting groups include, but are not limited to: those containing nitropiperonyl, pyrenylmethoxy-carbonyl, nitroveratryl, nitrobenzyl, dimethyl dimethoxybenzyl, 5-bromo-7-nitroindolinyl, o-hydroxy- alpha -methyl cinnamoyl, and 2-oxymethylene anthraquinone.

Also protected amino acids are readily available to those of skill in this art. For example, Fmoc and Boc protected amino acids can be obtained from Fluka, Bachem, Advanced Chemtech, Sigma, Cambridge Research Biochemical, Bachem, or Peninsula Labs or other chemical companies familiar to those who practice this art.

As used herein, the abbreviations for amino acids and protective groups are in accord with their common usage and the IUPAC-IUB Commission on Biochemical Nomenclature [see, (1972) *Biochem.* 11: 942–944]. Each naturally occurring L-amino acid is identified by the standard three letter code or the standard three letter code with or without the prefix "L-"; the prefix "D-" indicates that the stereoisomeric form of the amino acid is D. For example, as used herein, Fmoc is 9-fluorenylmethoxycarbonyl; BOP is benzotriazol-1-yloxy-tris(dimethylamino) phosphonium hexafluorophosphate, DCC is dicyclohexyl-carbodiimide; DDZ is dimethoxydimethylbenzyloxy; DMT is dimethoxytrityl; FMOC is fluorenylmethyloxycarbonyl; HBTU is 2-(1H-benzotriazol-1-yl)-1,1,3,3-tetramethyluronium; hexafluorophosphate NV is nitroveratryl; NVOC is 6-nitroveratryloxycarbonyl and other photoremovable groups; TFA is trifluoroacetic acid; DMF for N,N-dimethylformamide; Boc is tert-butoxycarbonyl; ACN is acetonitrile, TFA for trifluoroacetic acid; HF for hydrogen fluoride; HFIP for hexafluoroisopropanol; HPLC for high performance liquid chromatography; FAB-MS for fast atom bombardment mass spectrometry; DCM is dichloromethane, Bom is benzyloxymethyl; Pd/C is palladium catalyst on activated charcoal; DIC is diisopropylcarbodiimide; DCC is N,N'-dicyclohexylcarbodiimide; [For] is formyl; PyBop is benzotriazol-1-yl-oxy-trispyrrolidino-phosphonium hexafluorophosphate; POPOP is 1,4,-bis[5-phenyl(oxazolyl) benzene]; PPO is 2,5-diphenyloxazole; butyl-PBD is [2-(4'-tert-butylphenyl)-5-(4'-biphenyl)-1,3,4-oxadiazole]; PMP is (1-phenyl-3-mesityl-2-pyrazoline) DIEA is diisopropylethylamine; EDIA is ethyidiisopropylethylamine; NMP is N-methylpyrrolidone; NV is nitroveratryl PAL is pyridylalanine; HATU is O(7-azabenzotriaol-1-yl)-1,1,3,3-tetramethyluronium hexafluorophosphate; TFA is trifluoracetic acid, THF is tetrahydrofuran; and EDT is 1,2-ethanedithiol.

A. Matrices

For purposes herein matrices refer to supports used to retain molecules and biological particles, such as for chemical synthesis and to containers, such as microplates and test tubes. Matrices used for supports will be derivatized or otherwise suitable for retaining molecules or biological particles. Containers will either be derivatized or otherwise suitable for retaining molecules or biological particles or will be suitable for containing molecules and biological particles. In the embodiments of interest herein, the matrices are engraved with an optical bar code, include a memory and are associated with a sensor or are associated with containers, laboratory equipment and other such devices.

Matrices, which are generally insoluble materials used to immobilize ligands and other molecules, have application in many chemical syntheses and separations. Matrices are used in affinity chromatography, in the immobilization of biologically active materials, and during chemical syntheses of biomolecules, including proteins, amino acids and other organic molecules and polymers. The preparation of and use of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols.

Matrices include any material that can act as a support matrix for attachment of the molecules or biological particles of interest and can be in contact with or proximity to or associated with, preferably encasing or coating, the data storage device with programmable memory. Any matrix composed of material that is compatible with and upon or in which chemical syntheses are performed, including biocompatible polymers, is suitable for use herein. The matrix material should be selected so that it does not interfere with the chemistry or biological reaction of interest during the time which the molecule or particle is linked to, or in proximity therewith [see, e.g., U.S. Pat. No. 4,006,403]. These matrices, thus include any material to which the data storage device with memory can be attached, placed in proximity thereof, impregnated, encased or otherwise connected, linked or physically contacted. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass that is derivatized to render it suitable for use a support, silica gels, polystyrene, gelatin, polyvinyl pyrrolidone, co-polymers of vinyl and acrylamide, polystyrene cross-linked with divinylbenzene or the like [see, Merrifield (1964) Biochemistry 3:1385–1390], polyacrylamides, latex gels, polystyrene, dextran, polyacrylamides, rubber, silicon, plastics, nitrocellulose, celluloses, natural sponges, and many others. It is understood that the matrix materials contemplated are those that are suitable for use a s support matrix for retaining molecules or biological particles during syntheses or reactions.

Among the preferred matrices are polymeric beads, such as the TENTAGEL™ resins and derivatives thereof [sold by Rapp Polymere, Tubingen, Germany; see, U.S. Pat. No. 4,908,405 and U.S. Pat. No. 5,292,814; see, also Butz et al. (1994) *Peptide Res.* 7:20–23; Kleine et al. (1994) *Immunobiol.* 190:53–66; see, also Piskin et al. (1994), Chapter 18 "Nondegradable and Biodegradable Polymeric Particles" in *Diagnostic Biosensor Polymers*, ACS Symp. Series 556, Usmani et al. Eds, American Chemical Society, Washington, D.C.], which are designed for solid phase chemistry and for affinity separations and purifications. See, also Bayer et al. (1994) in *Pept.: Chem., Struct. Biol., Proc. Am. Pept. Symp.*, 13th; Hodges, et al. eds., pp.156–158; Zhang et al. (1993) *Pept. 1992, Proc. Eur. Pept. Symp.*, 22nd, Schneider, et al., eds. pp. 432–433; llg et al. (1994) *Macromolecules*, pp. 2778–83; Zeppezauer et al. (1993) *Z. Naturforsch., B: Chem. Sci.* 48:1801–1806; Rapp et al. (1992) *Pept. Chem. 1992, Proc. Jpn. Symp.*, 2nd, Yanaihara, ed., pp. 7–10; Nokihara et al. (1993) *Shimadzu Hyoron* 50:25–31; Wright et al. (1993) *Tetrahedron Lett.* 34:3373–3376; Bayer et al. (1992) *Poly(Ethylene Glycol) Chem.* Harris, ed., pp. 325–45; Rapp et al. (1990) *Innovation Perspect. Solid Phase Synth. Collect. Pap., Int. Symp.*, 1st, Epton, ed., pp. 205–10; Rapp et al. (1992) *Pept.: Chem. Biol., Proc. Am. Pept. Symp.*, 12th, Smith et al., eds., pp. 529–530; Rapp et al. (1989) *Pept., Proc. Eur. Pept. Symp.*, 20th, Jung et al., ed., pp. 199–201; Bayer et al. (1986) *Chem. Pept. Proteins* 3: 3–8; Bayer et al. (1983) *Pept.: Struct. Funct., Proc. Am. Pept. Symp.*, 8th, Hruby et al. eds., pp. 87–90 for descriptions of preparation of such beads and use thereof in synthetic chemistry. Matrices that are also contemplated for use herein include fluophore-containing or -impregnated matrices, such as microplates and beads [commercially available, for example, from Amersham, Arlington Heights, Ill.; plastic scintillation beads from NE (Nuclear Technology, Inc., San Carlos, Calif.), Packard, Meriden, Conn.]. It is understood that these commercially available materials will be modified by combining them with memories, such as by methods described herein.

Figure 21:
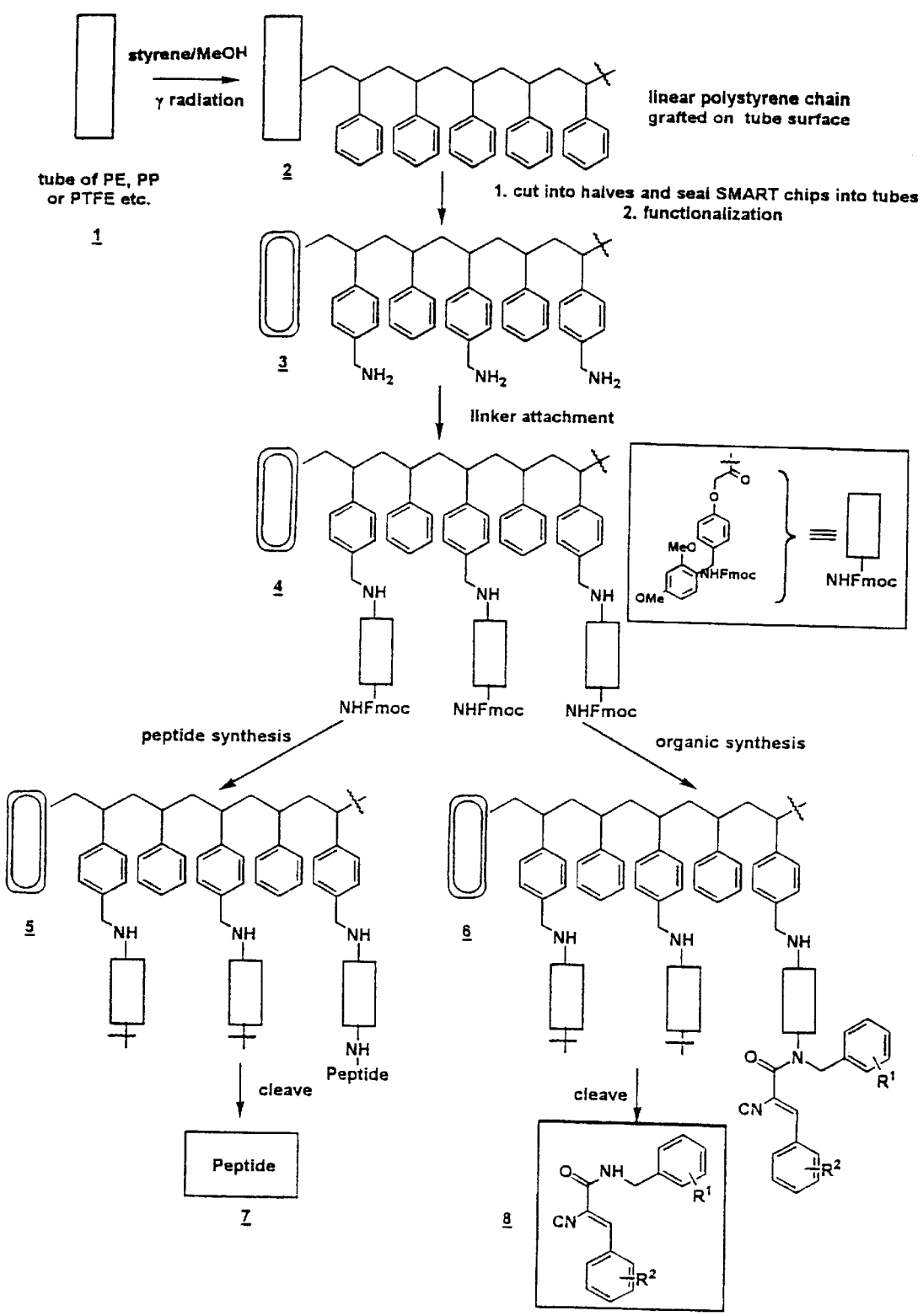
FIG. 21 Show the preparation and use of a tubular microvessel in which the container is radiation grafted with monomers or otherwise activated for use as a support matrix. As with the supports and "beads", these "beads" will include either an electromagnetically programmable memory, or an optical memory on the surface, such as the 2-D optical bar code provided herein, or combinations thereof.

The matrix may also be a relatively inert polymer, which can be grafted by ionizing radiation [see, e.g., FIG. 21, which depicts a particular embodiment] to permit attachment of a coating of polystyrene or other such polymer that can be derivatized and used as a support. Radiation grafting of monomers allows a diversity of surface characteristics to be generated on plasmid supports [see, e.g., Maeji et al. (1994) *Reactive Polymers* 22:203–212; and Berg et al. (1989) *J. Am. Chem. Soc.* 111:8024–8026]. For example, radiolytic grafting of monomers, such as vinyl monomers, or mixtures of monomers, to polymers, such as polyethylene and polypropylene, produce composites that have a wide variety of surface characteristics. These methods have been used to graft polymers to insoluble supports for synthesis of peptides and other molecules, and are of particular interest herein. The recording devices, which are often coated with a plastic or other insert material, can be treated with ionizing radiation so that selected monomers can be grafted to render the surface suitable for chemical syntheses. As set forth in the EXAMPLES, methods for increasing the loading of polymer on surfaces are provided, as are methods for effectively grafting PTFE and ETFE surfaces.

Where the matrix particles are macroscopic in size, such as about at least 1 mm in at least one dimension, such bead or matrix particle or continuous matrix may contain one or more memories. Where the matrix particles are smaller, such as NE particles [PVT-based plastic scintillator microsphere], which are about 1 to 10 $\mu$m in diameter, more than one such particle will generally be associated with one memory. Also, the "bead" or plate or container may include additional material, such as scintillant or a fluophore impregnated therein. In preferred embodiments, the solid phase chemistry and subsequent assaying may be performed on the same bead or matrix with memory combination. All procedures, including synthesis on the bead and assaying and analysis, can be automated and performed robotically using appropriate software.

The matrices are typically insoluble substrates that are solid, porous, deformable, or hard, and have any required structure and geometry, including, but not limited to: beads, pellets, disks, capillaries, hollow fibers, needles, solid fibers, random shapes, thin films and membranes. Typically, when the matrix is particulate, the particles are at least about 10–2000 $\mu$M, but may be smaller, particularly for use in embodiments in which more than one particle is in proximity to a memory. For purposes herein, the support material will typically encase or be in contact with the data storage device, and, thus, will desirably have at least one dimension on the order of 1 mm [1000 $\mu$M] or more, although smaller particles may be contacted with the data storage devices, particularly in embodiments in which more than one matrix particle is associated, linked or in proximity to one memory or matrix with memory, such as the microvessels [see, e.g., FIGS. 11–16]. Each memory will be in associated with, in contact with or proximity to at least one matrix particle, and may be in contact with more than one. As smaller semiconductor and electronic or optical devices become available, the capacity of the memory can be increased and/or the size of the particles can be decreased. For example, presently, 0.5 micron semiconductor devices are available. Integrated circuits 0.25-micron in size have been described and are being developed using a technology called the Complementary Metal Oxide-Semiconductor process (see, e.g., Investor's Business Daily May 31, 1995).

Also of interest herein, are devices that are prepared by inserting the recording device into a "tube" [see, e.g., FIG. 21] or encasing them in an inert material [with respect to the media in which the device will be in contact]. This material is fabricated from a plastic or other inert material. Preferably prior to introducing [and preferably sealing] the recording device inside, the tube or encasing material is treated with ionizing radiation to render the surface suitable for grafting selected monomers, such as styrene [see, e.g., Maeji et al. (1994) *Reactive Polymers* 22:203–21 2; Ang et al. in Chapter 10: Application of Radiation Grafting in Reagent Insolubilization, pp 223–247; and Berg et al. (1989) *J. Am. Chem. Soc.* 111:8024–8026].

Recording device(s) is(are) introduced inside the material or the material is wrapped around the device and the resulting matrix with memory "tubes" [MICROTUBE™ microreactors, see, FIG. 21] are used for chemical synthesis or linkage of selected molecules or biological particles. These "tubes" are preferably synthesized from an inert resin, such as a polypropylene resin [e.g., a Moplen resin, V29G PP resin from Montell, Newark Del., a distributor for Himont, Italy]. Any inert matrix that can then be functionalized or to which derivatizable monomers can be grafted is suitable. Preferably herein, polypropylene tubes are grafted and then formed into tubes or other suitable shape and the recording device inserted inside. These tubes [MICROTUBE™ microreactors] with grafted monomers are then used as synthesis, and/or for assays or for multiplexed processes, including synthesis and assays or other multistep procedures. Although denoted a "tube", the device may be any shape formed from a continuous surface fabricated from an inert polymer, enclosing a hollow space comprising about 5 ml or less and including at least one orifice. Thus, the microvessel is hollow with an interior volume of less than about 5 ml, typically less than 1 or 2 mls; and the inert polymer is inert with respect to solvents used for protein synthesis, oligonucleotide synthesis, or organic synthesis or any assays for biological or pharmacological activity.

Such tubes may also have snap on or screw lids or caps so that, in embodiments in which the memory device is, for example, a chip, the memory device or chip is removable. For example, they may be conical tubes like Eppendorf tubes, with a snap on top, preferably a flat top. The tubes will be of a size to accommodate a memory device and thus may be as small as about 2 mm×2 mm×0.1 to hold the small 2 mm×2 mm×0.1 mm device described herein. They will be fabricated from polypropylene or other suitable material and radiation grafted, see above, and Examples, below, preferably prior to introduction of the memory device.

The "tubes" may have no lids and instead retain any memory device by virtue of friction. Hollow and open "tubes" are presently preferred. They may have a nonuniform coating on the surface so that differential loading may be achieved or so different portions are suitable for different assays. They may be designed to be readily chopped or cut into pieces so the portion with a memory serves to store the linked molecules or biological particles as bits or pieces of the device are introduced into various assays or used for other purposes.

Figure 83:
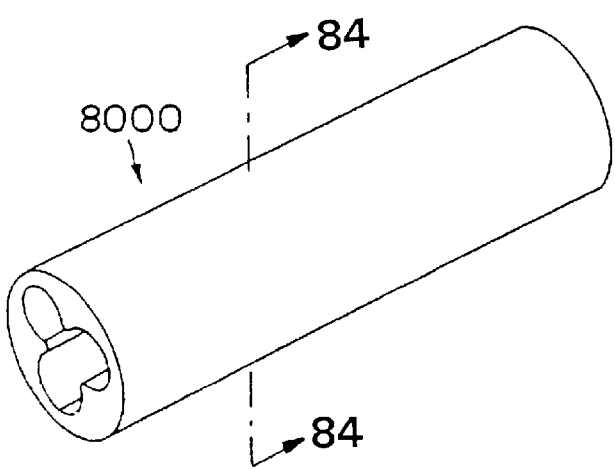
FIG. 83 is a perspective view of an alternative embodiment of a MICROTUBE microreactor.
Figure 84:
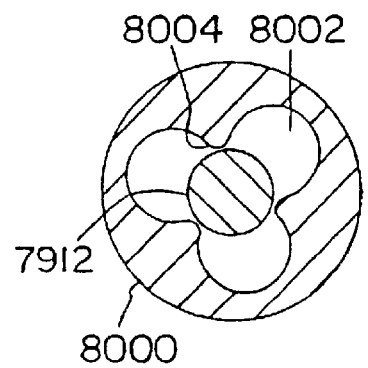
FIG. 84 is a cross-sectional view of the MICROTUBE microreactor of FIG. 83 taken along line 84—84.

Referring now to FIGS. 83 and 84, an alternative embodiment of a MICROTUBE microreactor is shown and generally designated 8000. MICROTUBE microreactor 8000 is shown having a microtag 7912 inserted within the MICROTUBE microreactor and held in place by friction between ridges 8004 and the outside surface of the microtag 7912. This three-point design provides for three flow channels 8002 through the MICROTUBE microreactor which increases the surface area of the MICROTUBE microreactor to exposure to solutions during synthesis and screening protocols.

Figure 85:
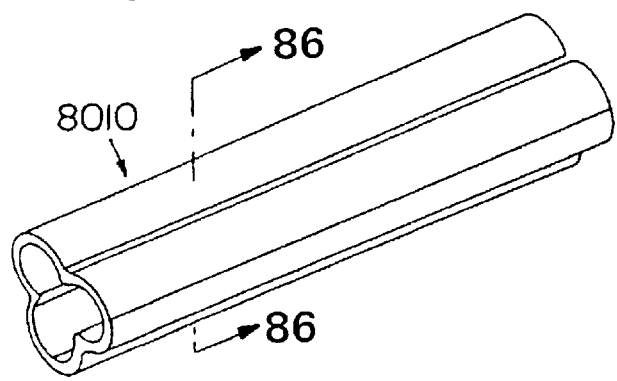
FIG. 85 is a perspective view of an alternative embodiment of a MICROTUBE microreactor.
Figure 86:
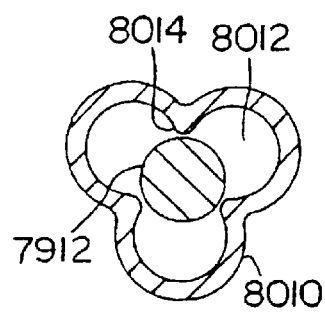
FIG. 86 is a cross-sectional view of the MICROTUBE microreactor of FIG. 85 taken along line 86—86.

FIGS. 85 and 86 show yet another alternative embodiment of a MICROTUBE microreactor generally designated 8010. MICROTUBE microreactor 8010 is similar to MICROTUBE microreactor 8000, yet having an outside surface which parallels the inside surface defining the flow channels 8012. The microtag 7912 in this embodiment is also retained in place by the frictional forces exerted by ridges 8014.

Figure 87:
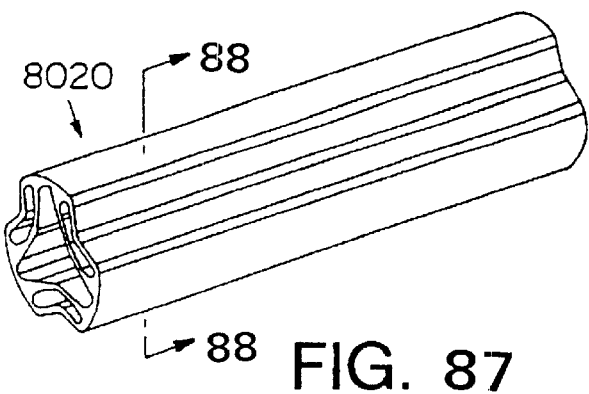
FIG. 87 is a perspective view of an alternative embodiment of a MICROTUBE microreactor.
Figure 88:
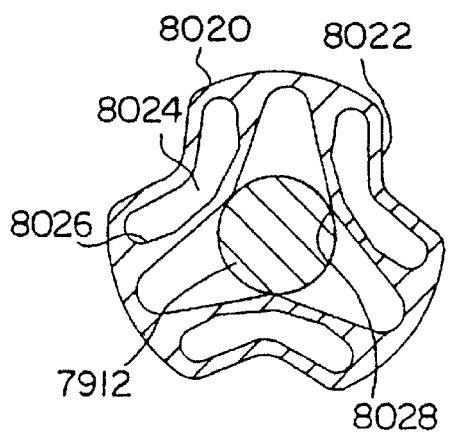
FIG. 88 is a cross-sectional view of the MICROTUBE microreactor of FIG. 87 taken along line 88—88.

Another alternative embodiment of a MICROTUBE microreactor is shown in FIGS. 87 and 88, and generally designated 8020. MICROTUBE microreactor 8020 is formed with a number of flow chambers 8024 defining an interior surface 8026, and an exterior surface 8022 which provides an increase in the overall surface area of the MICROTUBE microreactor. Microtag 7912 is retained within the MICROTUBE microreactor 8020 by frictional forces exerted on its outer surface by ridges 8028.

Figure 89:
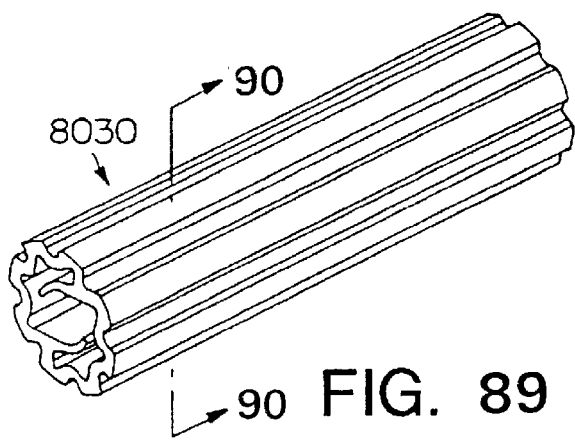
FIG. 89 is a perspective view of an alternative embodiment of a MICROTUBE microreactor.
Figure 90:
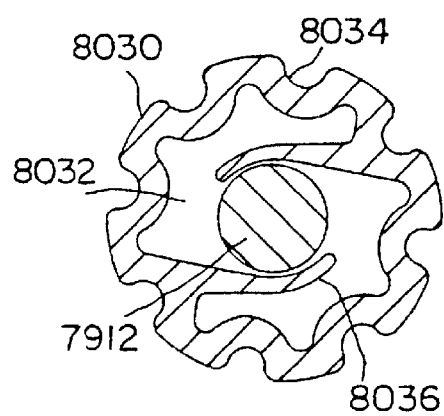
FIG. 90 is a cross-sectional view of the MICROTUBE microreactor of FIG. 89 taken along line 90—90.

Yet another alternative embodiment of a MICROTUBE microreactor is shown in FIGS. 89 and 90, and is generally designated 8030. MICROTUBE microreactor 8030 includes a pair of arms 8036 which are designed to securely hold the microtag 7912 firmly within the MICROTUBE microreactor. Flow chambers 8032, which in combination with the corrugated exterior surface 8034, provide a substantial surface area for MICROTUBE microreactor 8030.

Figure 91:
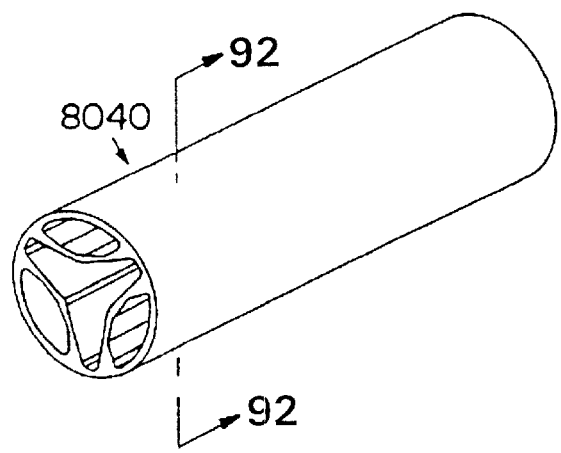
FIG. 91 is a perspective view of an alternative embodiment of a MICROTUBE microreactor.
Figure 92:
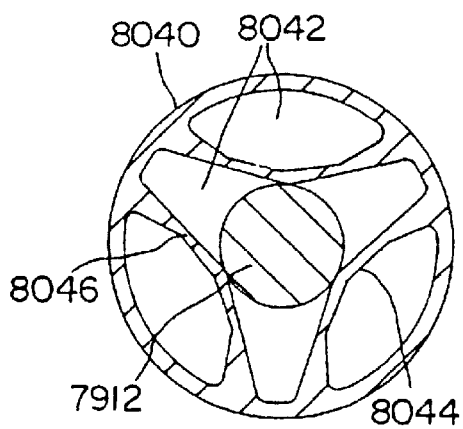
FIG. 92 is a cross-sectional view of the MICROTUBE microreactor of FIG. 91 taken along line 92—92.

Still another alternative embodiment of a MICROTUBE microreactor is shown in FIGS. 91 and 92, and is generally designated 8040. MICROTUBE microreactor 8040 retains microtag 7912 within the tube by applying frictional force between members 8046 and the exterior surface of the microtag. Flow channels 8042 provide an interior surface 8044 which substantially increases the surface area of the MICROTUBE microreactor 8040.

Figure 93:
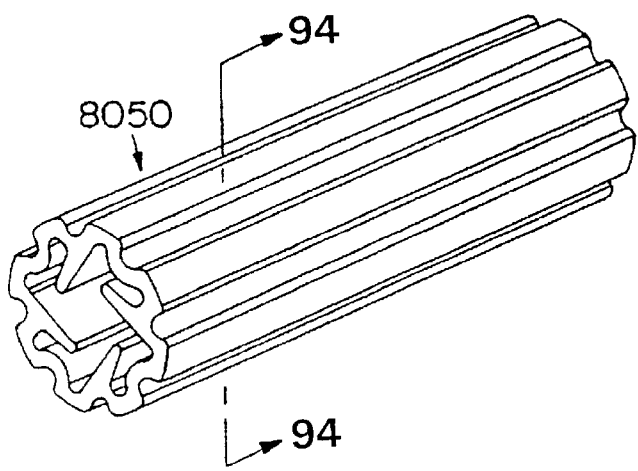
FIG. 93 is a perspective view of an alternative embodiment of a MICROTUBE microreactor.
Figure 94:
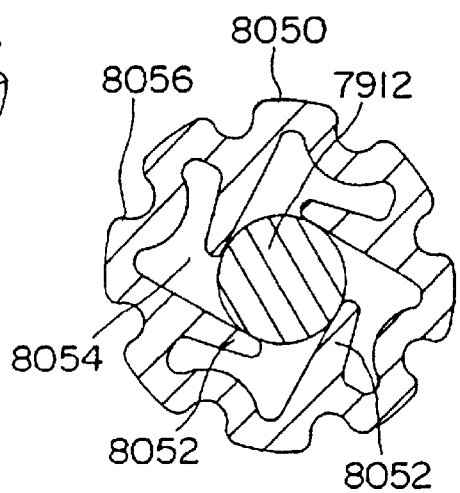
FIG. 94 is a cross-sectional view of the MICROTUBE microreactor of FIG. 93 taken along line 94—94.

Referring now to FIGS. 93 and 94, still another alternative embodiment of a MICROTUBE microreactor is shown and generally designated 8050. MICROTUBE microreactor 8050 includes four arms 8052 which exert a force on the microtag 7912 to hold it within the MICROTUBE microreactor. As a result of the arm structures 8052 forming flow channels 8054, in combination with the corrugated exterior surface 8056, MICROTUBE microreactor 8050 has a large surface area.

Figure 95:
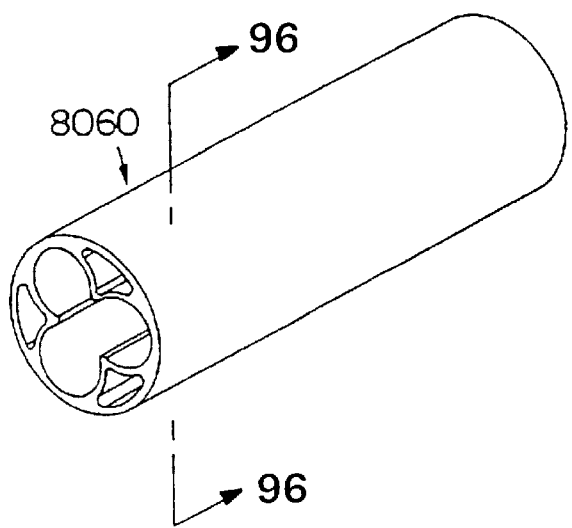
FIG. 95 is a perspective view of an alternative embodiment of a MICROTUBE microreactor.
Figure 96:
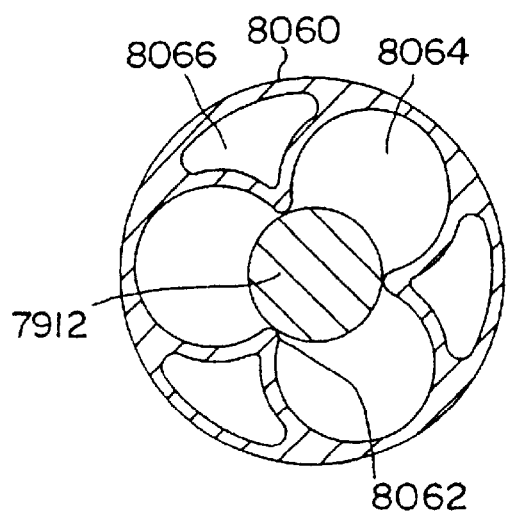
FIG. 96 is a cross-sectional view of the MICROTUBE microreactor of FIG. 95 taken along line 96—96.

Referring to FIGS. 95 and 96, another alternative embodiment of a MICROTUBE microreactor is shown and generally designated 8060. MICROTUBE microreactor 8060 includes three ridges 8062 which frictionally grip microtag 7912 for holding therein. Ridges 8062 form flow channels 8064 and 8066 which provide an increase in the surface area of the MICROTUBE microreactor.

The MICROTUBE microreactors shown in FIGS. 83 through 95 represent alternative shapes for a microtag-compatible MICROTUBE microreactor. These alternative shapes, however, exemplary and are not intended to be limiting. It is to be appreciated that any number of designs could be used with the MICROTUBE microreactor assembly system to achieve the same results.

Each of the MICROTUBE microreactors described above typically has a 7 millimeter outer diameter, and is manufactured from a polypropylene material, or a TEFZEL material, or any other suitable material. Additionally, each of these MICROTUBE microreactors may have synthesis resin grafted onto its inner and outer surfaces. The MICROTUBE microreactors are formed by extruding the material from an extrusion mold and allowing the material to cool. Typically, an extrusion process includes melting the material to be extruded and forcing the molten material through a mold. The various interior characteristics of the MICROTUBE microreactors are formed by inserting a mandrel within the center portion of the mold such that when the material is forced through the mold, the mold forms the outside surface of the MICROTUBE microreactor, and the mandrel forms the inside surface of the MICROTUBE microreactor. Extrusion of materials is well known in the art, and only described generally herein for reference.

Extrusion is one of the most inexpensive methods of forming plastic, or plastic-like materials. As a result, by forming the MICROTUBE microreactors using extrusion, the cost of each MICROTUBE microreactor is dramatically decreased. Additionally, because the MICROTUBE microreactors discussed herein are capable of being loaded and un-loaded with a microtag, the MICROTUBE microreactor may be discarded after use, and the microtags may be reused several times, requiring only a thorough cleaning. Thus, the decrease of operating a laboratory which utilizes a microtube assembly system 7900 is significant, including a decrease in number of microtags which must be purchased, as well as an overall decrease in the cost of the extruded MICROTUBE microreactors themselves. Further, because existing MICROTUBE microreactors are substantially tubular, having smooth inner and outer surfaces, the microtag is retained by crimping the ends of the MICROTUBE microreactor closed. While this is effective, such crimping increases the effort needed to recycle the microtag, as well as minimizes the flow of solution through the MICROTUBE microreactor.

The areas within each MICROTUBE microreactor are sized to receive a microtag which is forcibly inserted, or swaged, into the center portion of the MICROTUBE microreactor. In order to retain the microtag within the MICROTUBE microreactor, the portions of the tube which contact the microtag should be at least slightly pliable to provide the necessary contact force. Such pliability is a natural characteristic of polypropylene and TEFZEL, resulting in a MICROTUBE microreactor which exhibits sufficient contact force to retain the microtag.

In addition to accepting a microtag, the MICROTUBE microreactors discussed herein are also capable of receiving any other identification device disclosed herein. For example, the two-dimensional bar coded tags may also be easily utilized with these MICROTUBE microreactors.

Grafting

Solid hollow tubular (or other geometry) embodiments, such as the MICROTUBE microreactors made of tubes [or other geometry] have been coated or grafted with suitable materials are used as a solid support for any other methods disclosed herein, including organic syntheses and assays. Fluorophores, scintillants and other such compounds may also be incorporated into the surface or linked thereto [see, EXAMPLES below]. These tubes include those that contain the memory encased either permanently or removably or that include an imprinted symbology.

Briefly, for radiation-induced graft copolymerization, for example, of styrene to polypropylene (PP), polyethylene (PE), Teflon (PTFE), and ethylenetetrafluoroethylene copolymer (ETFE; such as that sold under the trade mark TEFZEL by Dupont), poly(chlorotrifluoroethylene) resin (PCTFE), tetrafluoroethylene-perfluoroalkylvinylether copolymer (PFA), ethylene-chlorotrifluoroethylene copolymer (ECTFE), tetrafluoroethylene-perfluoroalkylvinylether copolymer (PFA), polyvinyl fluoride(PVF) and tetrafluoroethylene-hexafluoropropylene copolymer (FEP) tubes (or other geometries), the diameter or dimensions of the tube can be any desired size, with 0.1 mm to 20 mm presently preferred and 2 mm to 5 mm more preferred. It has been found that dilution of styrene with methanol enhances the rate of grafting, thereby permitting use of PTFE tubes. Dilutions, which can be determined empirically for each material, from 5% to 70% have been tested. PTFE and PE tubes have the highest styrene grafting at a 50% dilution, and polypropylene tubes have the best performance when grafted at a 35% dilution. To effect grafting the polymer tubes are irradiated under a $Co^{60}$ source. The dose rate can be empirically determined. Rates of $0.01 \times 10^6$ to $1 \times 10^6$ rads (r)/h are typical and the most effective rate was $0.1 \times 10^6$ r/h. A total dose of $0.5$–$10 \times 10^6$ rads was typical and the most effective dose was $2.6$–$2.9 \times 10^6$ rads. It has also been found that inclusion of a mineral acid in the grafting reaction increases the amount of grafting. An exemplary protocol, particularly useful for increasing loading on fluoropolymers, which heretofore had not been achieved, is provided in the Examples.

Functional groups are introduced by selection of the monomers, such as styrene, choloromethylstyrene, methylacrylate, 2-hydroxymethylacrylate and/or other vinyl monomers containing one or more functional groups. For example (see, e.g., FIGS. 33) aminomethyl functional groups been introduced by first radiation grafting polystyrene onto the surface of tubes or other geometry devices fabricated from any of the above-noted polymers tubes followed by functionalization using N-(hydroxymethyl) phthalimide with trifluoromethanesulfonic acid as a catalyst. The polystyrene grafted polymer tube is thoroughly washed before use to remove residual monomer, non-attached polystyrene and additives remaining from the radiation grafting. The amidoalkylation proceeds smoothly at room temperature in 50% (v/v) trifluoroacetic acid-dichloromethane solvent for 24 hours. Loading can be controlled by changing the concentrations of reagent, catalyst and/or reaction time. Hydrazinolysis in refluxing ethanol gives the aminomethyl polystyrene grafted polymer tube. Adjustable loading range is on the order of 0.5–100 $\mu$mol per tube, depending the size of the tube and the polymer.

A carboxylic acid group was introduced by using acrylate acid or functionalization of polystyrene. The polystyrene grafted tube was functionalized using n-butyllithium and N,N N',N'-tetramethylethylendiamine in hexane at 60° C., after which the polymer tube was bubbled with $CO_2$. The carboxylic acid loading was about 1–20 $\mu$mol per tube.

Also larger matrix particles, which advantageously provide ease of handling, may be used and may be in contact with or proximity to more than one memory [i.e., one particle may have a plurality of memories in proximity or linked to it; each memory may programmed with different data regarding the matrix particle, linked molecules, synthesis or assay protocol, etc.]. Thus, so-called macro-beads (Rapp Polymere, Tubingen, Germany), which have a diameter of 2 mm when swollen, or other matrices of such size, are also contemplated for use herein. Particles of such size can be readily manipulated and the memory can be readily impregnated in or on the bead. These beads (available from Rapp) are also advantageous because of their uniformity in size, which is useful when automating the processes for electronically tagging and assaying the beads.

The matrices may also include an inert strip, such as a polytetrafluoroethylene [TEFLON®] strip or other material to which the molecules or biological particles of interest do not adhere, to aid in handling the matrix, such as embodiments in which a matrix with memory and linked molecules or biological particle are introduced into an agar-containing plate for immunoassays or for antibiotic screening.

Selection of the matrices will be governed, at least in part, by their physical and chemical properties, such as solubility, functional groups, mechanical stability, surface area swelling propensity, hydrophobic or hydrophilic properties and intended use.

The data storage device with programmable memory may be coated with a material, such as a glass or a plastic, that can be further derivatized and used as the support or it may be encased, partially or completely, in the matrix material, such as during or prior to polymerization of the material. Such coating may be performed manually or may be automated. The coating can be effected manually or using instruments designed for coating such devices. Instruments for this purpose are available [see, e.g., the Series C3000 systems for dipping available from Specialty Coating Systems, Inc., Indianapolis, Ind.; and the Series CM 2000 systems for spray coating available from Integrated Technologies, Inc. Acushnet, Mass.].

The data storage device with memory may be physically inserted into the matrix material or particle. It also can be manufactured with a coating that is suitable for use as a matrix or that includes regions in the coating that are suitable for use as a matrix. If the matrix material is a porous membrane, it may be placed inside the membrane. It is understood that when the memory device is encased in the matrix or coated with protective material, such matrix or material must be transparent to the signal used to program the memory for writing or reading data. More than one matrix particle may be linked to each data storage device.

In some instances, the data storage device with memory is coated with a polymer, which is then treated to contain an appropriate reactive moiety or in some cases the device may be obtained commercially already containing the reactive moiety, and may thereby serve as the matrix support upon which molecules or biological particles are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropylsilane, and other organic moieties; N-[3-(triethyoxysilyl)propyl]phthelamic acid; and bis-(2-hydroxyethyl)aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art [e.g., the TENTAGEL® Resins are available with a multitude of functional groups, and are sold by Rapp Polymere, Tubingen, Germany; see, U.S. Pat. No. 4,908,405 and U.S. Pat. No. 5,292,814; see, also Butz et al. (1994) *Peptide Res.* 7:20–23; Kleine et al. (1994) *Immunobiol.* 190:53–66].

The data storage device with memory, however, generally should not or cannot be exposed to the reaction solution, and, thus, must be coated with at least a thin layer of a glass or ceramic or other protective coating that does not interfere with the operation of the device. These operations include electrical conduction across the device and transmission of remotely transmitted electromagnetic radiation by which data are written and read. It is such coating that may also serve as a matrix upon which the molecules or biological particles may be linked.

The data storage devices with memory may be coated either directly or following coating with a ceramic, glass or other material, may then be coated with agarose, which is heated, the devices are dipped into the agarose, and then cooled to about room temperature. The resulting glass, silica, agarose or other coated memory device, may be used as the matrix supports for chemical syntheses and reactions.

Conventional integrated circuit manufacturing and packaging methods include methods and means for encapsulating integrated circuits to protect the devices from the environment and to facilitate connection to external devices. Also, there are numerous descriptions for the preparation of semiconductor devices and wires, particularly for use as sensors [see, e.g., U.S. Pat. No. 4,933,285; see, also Cass, Ed. (1990) *Biosensors A Practical Approach*, IRL Press at Oxford University Press, Oxford; chemosensors are sensors that can include a biological or chemical detection system, generally biologically active substances, such as enzymes, antibodies, lectins and hormone receptors, which are immobilized on the surface of the sensor electrode or in a thin layer on the sensor electrode; biosensors are sensors that detect biological species and for purposes herein can be implanted in an animal], which measure electrochemical solution parameters, such as pH. Despite differences in the components of biosensors and recording devices used herein, certain of the methods for coating electrodes and wires in the biosensor art may be adapted for use herein [see, e.g., U.S. Pat. Nos. 5,342,772, 5,389,534, 5,384,028, 5,296,122, 5,334,880, 5,311,039, 4,777,019, 5,143,854, 5,200,051, 5,212,050, 5,310,686, 5,324,591; see, also Usmani et al., ed. (1994) *Diagnostic Biosensor Polymers*, ACS Symposium Series No. 556].

It is, however, emphasized that the combinations herein of matrix with memory are not sensors, which measure external parameters and can include electrodes that must be in contact with the solution such that molecules in solution directly contact the electrode, and which measure solution parameters. Data regarding the combination, particularly the linked or associated biological particle or matrix is written into the memory, and thus records information about itself. Sensors monitor what is going outside of the device. The combinations herein of matrices with memories can be enhanced by addition of sensor elements for the measurement of external conditions, information about the external conditions can be recorded into the combination's memory. Of particular interest herein, are sensors that comprise matrix with memories and photosensors.

The combinations herein are matrix materials with recording devices that contain data storage units that include remotely programmable memories; the recording devices used in solution must be coated with a material that prevents contact between the recording device and the medium, such as the solution or air or gas [e.g., nitrogen or oxygen or $CO_2$]. The information is introduced into the memory by addressing the memory to record information regarding molecules or biological particles linked thereto. Except in the reaction detecting [verifying] embodiment, in which the memory can be encoded upon reaction of a linked molecule or biological particle, solution parameters are not recorded in the memory.

In certain embodiments herein, the matrices with memories herein, however may be combined with devices or components or biosensors or other such sensor devices and used in connection therewith to monitor solution or external parameters. For example, the combination may be electronically or otherwise linked to a biosensor and information obtained by the biosensor can be encoded in memory, or the combination can transmit information to the biosensor or, when used internally in an animal, to monitor the location of a biosensor or to transmit information from the biosensor. For example, transponder memory devices exemplified herein, include circuitry for measuring and recording solution temperature. These transponders can be modified to read and record pH, instead of or in addition to temperature. Thus, during synthesis or other processing steps of linked or proximate molecules or biological particles, RF or other EM radiation will be used to encode information in the memory and at the same time pH and/or temperature in the external solution can be measured and recorded in the memory.

1. Natural matrix support materials

Naturally-occurring supports include, but are not limited to agarose, other polysaccharides, collagen, celluloses and derivatives thereof, glass, silica, and alumina. Methods for isolation, modification and treatment to render them suitable for use as supports is well known to those of skill in this art [see, e.g., Hermanson et al. (1992) *Immobilized Affinity Ligand Techniques*, Academic Press, Inc., San Diego]. Gels, such as agarose, can be readily adapted for use herein. Natural polymers such as polypeptides, proteins and carbohydrates; metalloids, such as silicon and germanium, that have semiconductive properties, as long as they do not interfere with operation of the data storage device may also be adapted for use herein. Also, metals such as platinum, gold, nickel, copper, zinc, tin, palladium, silver, again as long as the combination of the data storage device with memory, matrix support with molecule or biological particle does not interfere with operation of the device with memory, may be adapted for use herein. Other matrices of interest include oxides of the metal and metalloids, such as, but not limited to, Pt—PtO, Si—SiO, Au—AuO, TiO2 and Cu—CuO. Also compound semiconductors, such as lithium niobate, gallium arsenide and indium-phosphide, and nickel-coated mica surfaces, as used in preparation of molecules for observation in an atomic force microscope [see, e.g., III et al. (1993) *Biophys J.* 64:919] may be used as matrices. Methods for preparation of such matrix materials are well known.

For example, U.S. Pat. No. 4,175,183 describes a water insoluble hydroxyalkylated cross-linked regenerated cellulose and a method for its preparation. A method of preparing the product using near stoichiometric proportions of reagents is described. Use of the product directly in gel chromatography and as an intermediate in the preparation of ion exchangers is also described.

2. Synthetic matrices

There are innumerable synthetic matrices and methods for their preparation known to those of skill in this art. Synthetic matrices are typically produced by polymerization of functional matrices, or copolymerization from two or more monomers of from a synthetic monomer and naturally occurring matrix monomer or polymer, such as agarose. Before such polymers solidify, they are contacted with the data storage device with memory, which can be cast into the material or dipped into the material. Alternatively, after preparation of particles or larger synthetic matrices, the recording device containing the data storage unit(s) can be manually inserted into the matrix material. Again, such devices can be pre-coated with glass, ceramic, silica or other suitable material.

Synthetic matrices include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers [see, e.g., Merrifield (1964) *Biochemistry* 3:1385–1390; Berg et al. (1990) in *Innovation Perspect. Solid Phase Synth. Collect. Pap.*, Int. Symp., 1st, Epton, Roger (Ed), pp. 453–459; Berg et al. (1989) in *Pept. Proc. Eur. Pept. Symp.*, 20th, Jung, G. et a. (Eds), pp. 196–198; Berg et al. (1989) *J. Am. Chem. Soc.* 111 :8024–8026; Kent et al. (1979) *Isr. J. Chem.* 17:243–247; Kent et al. (1978) *J. Org. Chem.* 43:2845–2852; Mitchell et al. (1976) *Tetrahedron Lett.* 42:3795–3798; U.S. Pat. No. 4,507,230; U.S. Pat. No. 4,006,117; and U.S. Pat. No. 5,389,449]. Methods for preparation of such matrices are well-known to those of skill in this art.

Synthetic matrices include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride, polypropylene-co-maleic anhydride and the like, and fluoropolymers. Liposomes have also been used as solid supports for affinity purifications [Powell et al. (1989) *Biotechnol. Bioeng.* 33:173].

For example, U.S. Pat. No. 5,403,750, describes the preparation of polyurethane-based polymers. U.S. Pat. No. 4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers containing poly(ethyleneoxy) glycols with up to 35% of a poly (propyleneoxy) glycol or a poly(butyleneoxy) glycol. In producing these polymers, an organic polyamine is used as a crosslinking agent. Other matrices and preparation thereof are described in U.S. Pat. Nos. 4,177,038, 4,175,183, 4,439, 585, 4,485,227, 4,569,981, 5,092,992, 5,334,640, 5,328,603

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halo-methyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylimide and vinyl compound is a chloromethyl styrene.

U.S. Pat. No. 4,171,412 describes specific matrices based on hydrophilic polymeric gels, preferably of a macroporous character, which carry covalently bonded D-amino acids or peptides that contain D-amino acid units. The basic support is prepared by copolymerization of hydroxyalkyl esters or hydroxyalkylamides of acrylic and methacrylic acid with crosslinking acrylate or methacrylate comonomers are modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier.

U.S. Pat. No. 4,178,439 describes a cationic ion exchanger and a method for preparation thereof. U.S. Pat. No. 4,180,524 describes chemical syntheses on a silica support.

Immobilized Artificial Membranes [IAMs; see, e.g., U.S. Pat. Nos. 4,931,498 and 4,927,879] may also be used. IAMs mimic cell membrane environments and may be used to bind molecules that preferentially associate with cell membranes [see, e.g., Pidgeon et al. (1990) *Enzyme Microb. Technol.* 12:149].

3. Immobilization and activation

Numerous methods have been developed for the immobilization of proteins and other biomolecules onto solid or liquid supports [see, e.g., Mosbach (1976) *Methods in Enzymology* 44; Weetall (1975) *Immobilized Enzymes, Antigens, Antibodies, and Peptides*; and Kennedy et al. (1983) *Solid Phase Biochemistry, Analytical and Synthetic Aspects*, Scouten, ed., pp. 253–391; see, generally, *Affinity Techniques, Enzyme Purification: Part B. Methods in Enzymology*, Vol. 34, ed. W. B. Jakoby, M. Wilchek, Acad. Press, N.Y. (1974); *Immobilized Biochemicals and Affinity Chromatography, Advances in Experimental Medicine and Biology*, vol. 42, ed. R. Dunlap, Plenum Press, New York (1974)].

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art [see, e.g., the PIERCE CATALOG, ImmunoTechnology Catalog & Handbook, 1992–1993, which describes the preparation of and use of such reagents and provides a commercial source for such reagents; and Wong (1993) *Chemistry of Protein Conjugation and Cross Linking*, CRC Press; see, also DeWitt et al. (1993) *Proc. Natl. Acad. Sci. U.S.A.* 90:6909; Zuckermann et al. (1992) *J. Am. Chem. Soc.* 114:10646; Kurth et al. (1994) *J. Am. Chem. Soc.* 116:2661; Ellman et al. (1994) *Proc. Natl. Acad. Sci. U.S.A.* 91:4708; Sucholeiki (1994) *Tetrahedron Lttrs.* 35:7307; and Su-Sun Wang (1976) *J. Org. Chem.* 41:3258; Padwa et al. (1971) *J. Org. Chem.* 41:3550 and Vedejs et al. (1984) *J. Org. Chem.* 49:575, which describe photosensitive linkers]

To effect immobilization, a solution of the protein or other biomolecule is contacted with a support material such as alumina, carbon, an ion-exchange resin, cellulose, glass or a ceramic. Fluorocarbon polymers have been used as supports to which biomolecules have been attached by adsorption [see, U.S. Pat. No. 3,843,443; Published International PCT Application WO/86 03840].

A large variety of methods are known for attaching biological molecules, including proteins and nucleic acids, molecules to solid supports [see. e.g., U.S. Pat. No. 5,451,683]. For example, U.S. Pat. No. 4,681,870 describes a method for introducing free amino or carboxyl groups onto a silica matrix. These groups may subsequently be covalently linked to other groups, such as a protein or other anti-ligand, in the presence of a carbodiimide. Alternatively, a silica matrix may be activated by treatment with a cyanogen halide under alkaline conditions. The anti-ligand is covalently attached to the surface upon addition to the activated surface. Another method involves modification of a polymer surface through the successive application of multiple layers of biotin, avidin and extenders [see, e.g., U.S. Pat. No. 4,282,287]; other methods involve photoactivation in which a polypeptide chain is attached to a solid substrate by incorporating a light-sensitive unnatural amino acid group into the polypeptide chain and exposing the product to low-energy ultraviolet light [see, e.g., U.S. Pat. No. 4,762,881]. Oligonucleotides have also been attached using a photochemically active reagents, such as a psoralen compound, and a coupling agent, which attaches the photoreagent to the substrate [see, e.g., U.S. Pat. No. 4,542,102 and U.S. Pat. No. 4,562,157]. Photoactivation of the photoreagent binds a nucleic acid molecule to the substrate to give a surface-bound probe.

Covalent binding of the protein or other biomolecule or organic molecule or biological particle to chemically activated solid matrix supports such as glass, synthetic polymers, and cross-linked polysaccharides is a more frequently used immobilization technique. The molecule or biological particle may be directly linked to the matrix support or linked via linker, such as a metal [see, e.g., U.S. Pat. No. 4,179,402; and Smith et al. (1992) *Methods: A Companion to Methods in Enz.* 4:73–78]. An example of this method is the cyanogen bromide activation of polysaccharide supports, such as agarose. The use of perfluorocarbon polymer-based supports for enzyme immobilization and affinity chromatography is described in U.S. Pat. No. 4,885,250]. In this method the biomolecule is first modified by reaction with a perfluoroalkylating agent such as perfluorooctylpropylisocyanate described in U.S. Pat. No. 4,954,444. Then, the modified protein is adsorbed onto the fluorocarbon support to effect immobilization.

The activation and use of matrices are well known and may be effected by any such known methods [see, e.g., Hermanson et al. (1992) *Immobilized Affinity Ligand Techniques*, Academic Press, Inc., San Diego]. For example, the coupling of the amino acids may be accomplished by techniques familiar to those in the art and provided, for example, in Stewart and Young, 1984, *Solid Phase Synthesis*, Second Edition, Pierce Chemical Co., Rockford.

Molecules may also be attached to matrices through kinetically inert metal ion linkages, such as Co(III), using, for example, native metal binding sites on the molecules, such as IgG binding sequences, or genetically modified proteins that bind metal ions [see, e.g., Smith et al. (1992) *Methods: A Companion to Methods in Enzymology* 4, 73 (1992); III et al. (1993) *Biophys J.* 64:919; Loetscher et al. (1992) *J. Chromatography* 595:113–199; U.S. Pat. No. 5,443,816; Hale (1995) *Analytical Biochem.* 231:46–49].

Other suitable methods for linking molecules and biological particles to solid supports are well known to those of skill in this art [see, e.g., U.S. Pat. No. 5,416,193]. These linkers include linkers that are suitable for chemically linking molecules, such as proteins and nucleic acid, to supports include, but are not limited to, disulfide bonds, thioether bonds, hindered disulfide bonds, and covalent bonds between free reactive groups, such as amine and thiol groups. These bonds can be produced using heterobifunctional reagents to produce reactive thiol groups on one or both of the moieties and then reacting the thiol groups on one moiety with reactive thiol groups or amine groups to which reactive maleimido groups or thiol groups can be attached on the other. Other linkers include, acid cleavable linkers, such as bismaleimideothoxy propane, acid labile-transferring conjugates and adipic acid diihydrazide, that would be cleaved in more acidic intracellular compartments; cross linkers that are cleaved upon exposure to UV or visible light and linkers, such as the various domains, such as $C_H 1$, $C_H 2$, and $C_H 3$, from the constant region of human $IgG_1$ (see, Batra et al. (1993) *Molecular Immunol.* 30:379–386).

Presently preferred linkages are direct linkages effected by adsorbing the molecule or biological particle to the surface of the matrix. Other preferred linkages are photocleavable linkages that can be activated by exposure to light [see, e.g., Baldwin et al. (1995) *J. Am. Chem. Soc.* 117:5588; Goldmacher et al. (1992) *Biocon. Chem.* 3:104–107]. The photocleavable linker is selected such that the cleaving wavelength that does not damage linked moieties. Photocleavable linkers are linkers that are cleaved upon exposure to light [see, e.g., Hazum et al. (1981) in *Pept., Proc. Eur. Pept. Symp.*, 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Biocon. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxy-carbonyl chloride cross linking reagents that produce photocleavable linkages]. Other linkers include fluoride labile linkers [see, e.g., Rodolph et al. (1995) *J. Am. Chem. Soc.* 117:5712], and acid labile linkers [see, e.g., Kick et al. (1995) *J. Med. Chem.* 38:1427]. Many linkers and conditions for linking and cleaving are well known to those of skill in this art. Any such linkers may be used in the methods and devices herein. The selected linker will depend upon the particular application and, if needed, may be empirically selected. A plurality of linkers may be used to link a compound to a support, such as the MICROTUBE microreactor so that the portions of the compound can be selectively cleaved.

Differential linkage for sequential release of compounds and biological particles from memories with matrices Sequential release of compounds can be used by attaching compounds to the support with linkers that are cleaved under different conditions [see, e.g., Salmon et al. (1993) *Proc. Natl. Acad. Sci. U.S.A.* 90:11708–11712; Krchnak et al. (1995) Chapter 2: Combinatorial Libraries of Synthetic Structures: Synthesis, Screening, and Structure Determination, pp. 27–36 in *Combinatorial Libraries Synthesis, Screening and Application Potential*. Riccardo Cortese, Ed., Walter de Gruyter & Co., D-10785 Berlin]. For examples, compounds are linked to the support using several different linkers, such as a linker that is cleaved at neutral pH, another at high pH, and another that does not get cleaved. After synthesis, a portion of the compounds are released for screening by treating the support with neutral pH, for example. In practice, for example, beads with linked compounds are distributed into 96 well plates, and about one third of the compounds are released and assayed. Beads from positive wells are redistributed into individual wells and the second portion of the compound is released and assayed. The remaining compound in the positive wells can then be used for structural and other analytical assays.

Figure 75A:
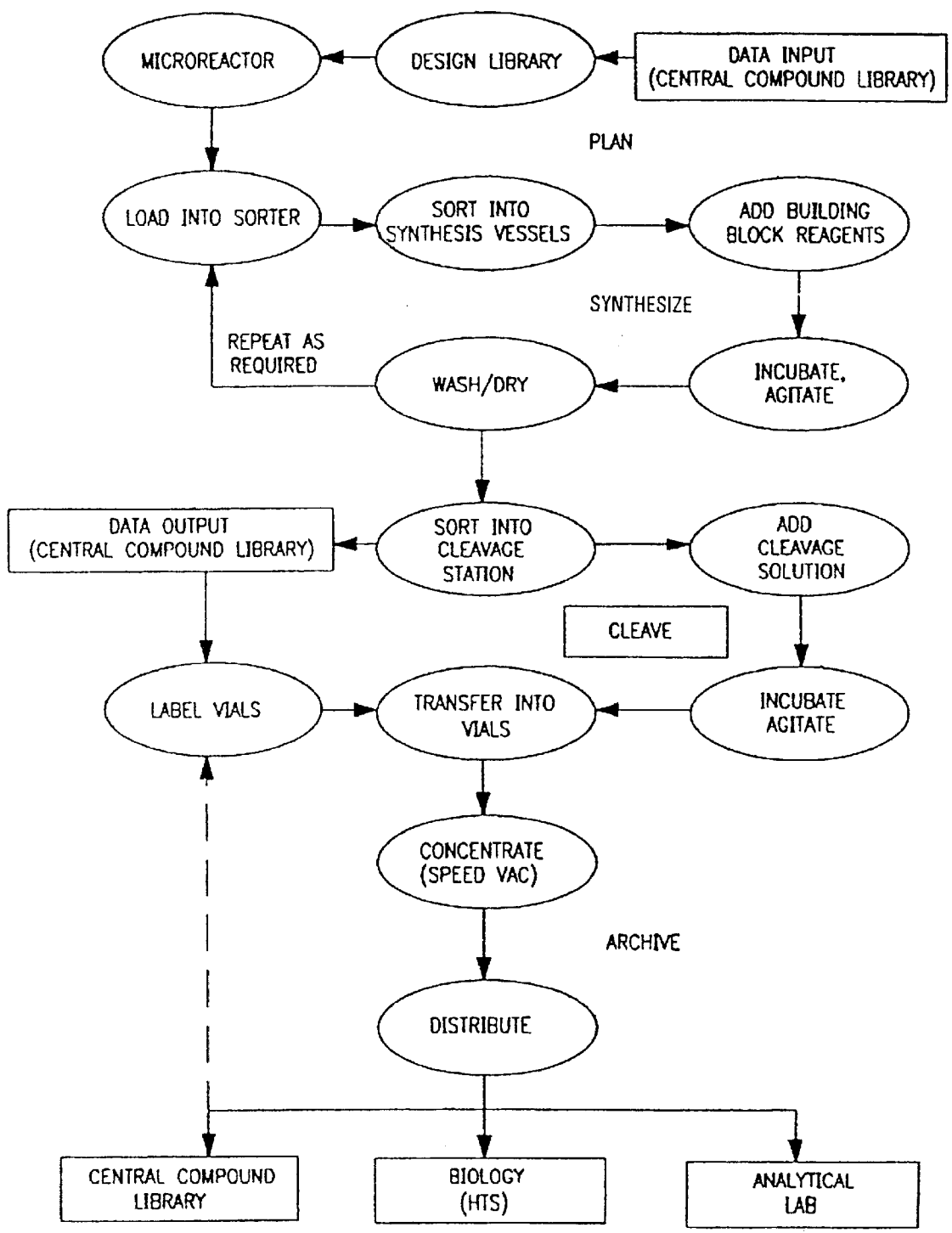
FIG. 75*a* depicts an automated drug discovery unit, which provides a means for seamless data tracking between and among the components of the units in which all critical components, including instrumentation and vials include memories for seamless transfer information to other memories in a unit. The units include some or all of the following: an automated or manual sorter, microvessels, which contain memories, an automated or semi-automated synthesizer, a microvessel washer/dryer, a manual or automated cleaver for removing compounds from the matrix with memory microvessels, and associated software. The microreactor is any of the memory with matrices used for solid support provided herein. Preferred are resin-loaded MICROKAN microreactors and MICROTUBE microreactors. In addition to memories with matrices upon which synthesis is performed, all instrumentation, vials, plates, sorters, robots, and other components, will also include memories. Information from one memory will be transferred to another as a protocol proceeds.
Figure 75B:
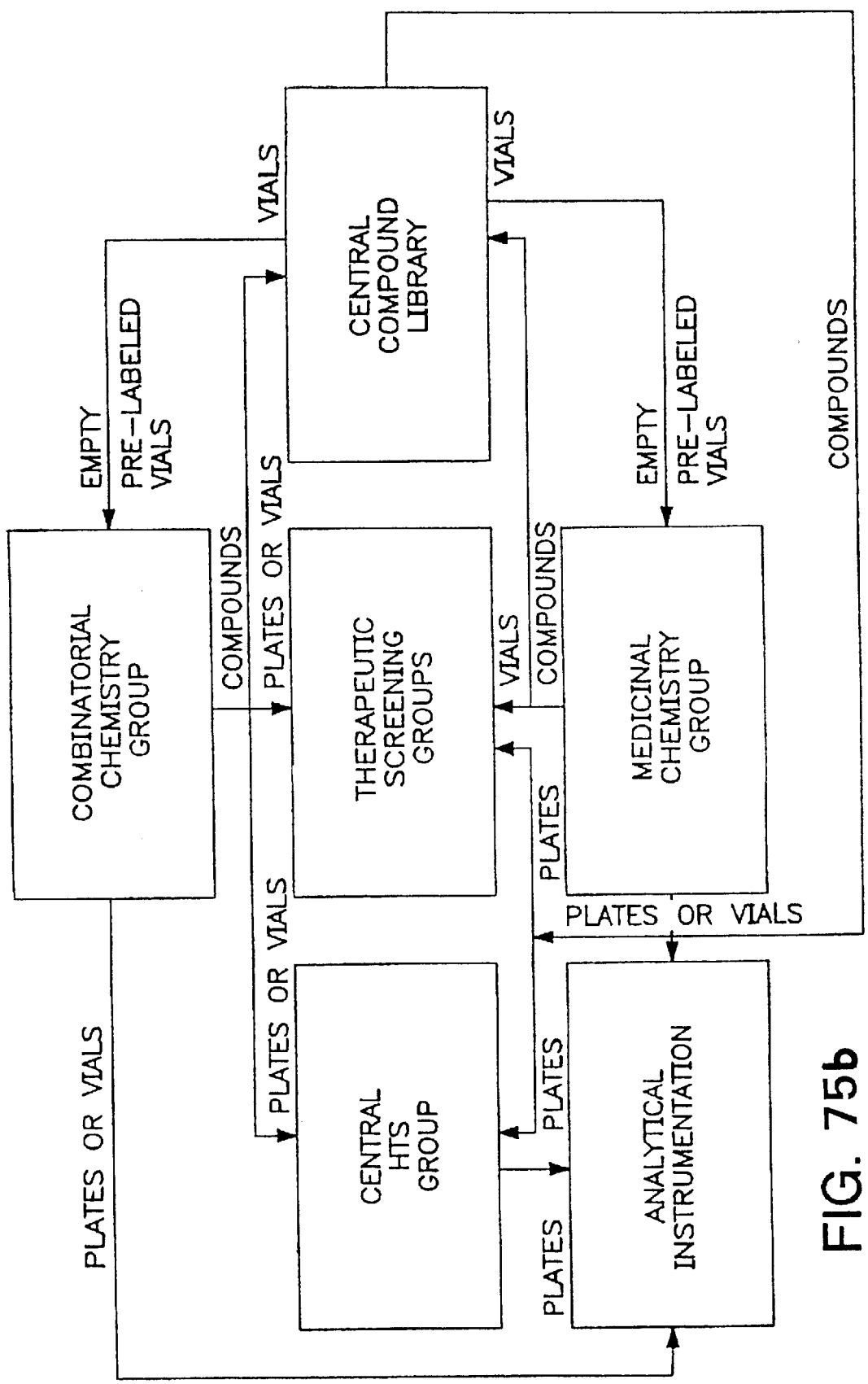
FIG. 75*b* presents a flow chart of the automated drug discovery laboratory provided herein, including analytical instruments and workflow, in which the entire process is based on a single platform, the matrices with memories provided herein. The libraries on synthesized and stored on the memories with matrices, which can then be used for a variety of applications. In addition to memories with matrices upon which synthesis is performed, all instrumentation, vials, plates, sorters, robots, and other components, will also include memories. Information from one memory will be transferred to another as a protocol proceeds.
Figure 75C:
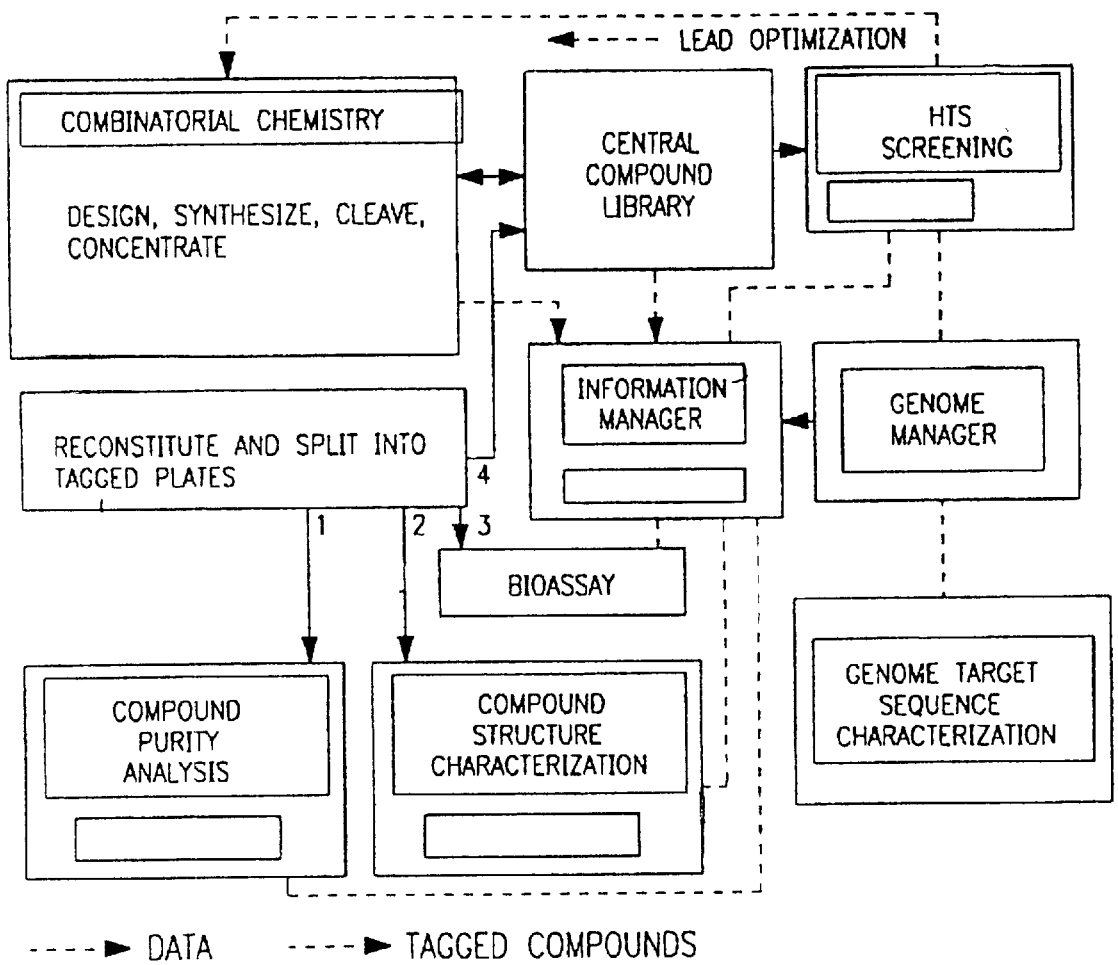
FIG. 75C shows how the entire drug discovery process is linked by the memory with matrix platform. The compounds are synthesized on the matrix, sorted, cleaved and concentrated as described herein. The compounds can then be assayed, characterized, analyzed, used for high throughput screening and tracked throughout using the memories for identification. The resulting information will be accumulated in databases. The box designated combinatorial chemistry refers to hardware, software, and consumables using the micromemory (electronic tags, optical memories, etc., or combinations thereof) technology provided herein for synthesis, cleavage, concentration and design of libraries of molecules and biological particles. The final product is a library of discrete multimilligram quantities of compounds ready for further processing, including screening and other analyses, that can remain linked to the matrix with memory or can be cleaved. The micromemories and associated software will provide the means to transfer information as the compounds are processed and moved from location to location. The central compound library refers to compounds as stored in racks, vials, microtiter plates, and other such vessels, using the memories for tracking. High throughput screening (HTS) refers to on bead or off bead screening, while the memories and databases relate back to the compound/library/synthesis/analysis data. Information on targets can come from genomics databases and other such sources. Genome manager software refers to software, databases and drivers that deal with genomic information. This can be linked to the software provided herein, such as the Synthesis Manager software, and the Information manager software. Information Manager software is a software platform that runs the entire drug discovery process by providing multiple links to HTS, genomics databases, combinatorial chemistry and analysis, and that relies on the micromemory technology to track the information. Compound analysis and structural information, includes results of structural and physical analyses, including HPLC results, mass spectrometry results, NMR and any other analytical procedure. This database is linked to synthesis manager, assay manager (HTS) software via the information manager software.

Sequential release is particularly adaptable for use in the methods herein in which matrix with memories with linked molecules or biological particles may be used for various applications [see, e.g., FIG. 75].

B. Optically Encoded Memory Devices

The matrices or strips attached thereto may be encoded with a preprogrammed identifying bar code, such as an optical bar code that will be encoded on the matrix and read by laser. Such pre-coded devices may be used in embodiments in which parameters, such as location in an automated synthesizer, are monitored. The identity of a product or reactant determined by its location or path, which is monitored by reading the chip or memory in each device and storing such information in a remote computer.

Thus, it is contemplated herein, that the memory is not proximate to the matrix, but is separate, such a memory in a remote computer or other recording device. In these embodiments, the matrices are marked with a unique code or mark of any sort. The identity of each mark is saved in the remote memory, and then, each time something is done to a molecule or biological particle linked to each matrix, the information regarding such event is recorded and associated with the coded identity. After completion of, for example, a synthetic protocol, each matrix is examined or read to identify the code. Retrieving information that from the remote memory that is stored with the identifying code will permit identification or retrieval of any other saved information regarding the matrix.

For example, simple codes, including bar codes, alphanumeric characters or other visually or identifiable codes or marks on matrices are also contemplated for use herein. When bar codes or other precoded devices are used, the information can be written to an associated but remote memory, such as a computer or even a piece of paper. The computer stores the bar code that a identifies a matrix particle or other code and information relating to the molecule or biological particle linked to the matrix or other relevant information regarding the linked materials or synthesis or assay. Instead of writing to an on-board memory, information is encoded in a remote memory that stores information regarding the precoded identity of each matrix with bar code and linked molecules or biological particles. Thus, the precoded information is associated with, for example, the identity of the linked molecule or a component thereof, or a position (such as X-Y coordinates in a grid). This information is transmitted to a memory for later retrieval. Each treatment or synthetic step that is performed on the linked molecule or biological particle is transmitted to the remote memory and associated with the precoded ID.

For example, an amino acid is linked to a matrix particle that is encoded with or marked with a bar code or even a letter such as "A" or other coded mark. The identity the amino acid linked to the matrix particle "A" is recorded into a memory. This particle is mixed with other particles, each with a unique identifier or mark, and this mixture is then treated to a synthetic step. Each particle is individually scanned or viewed to see what mark is on each particle and the remote memory is written to describe the synthetic step, which is then associated with each unique identifier in the memory, such as the computer or piece of paper. Thus, in the remote memory the original amino acid linked to particle A is stored. After the synthetic step, the identify of the next amino acid is stored in the memory associated with "A" as is the identity of the next amino acid added. At the end of the synthesis, the history of each particle can be read by scanning the particle or visually looking at the particle and noting its bar code or mark, such as A. The remote memory is then queried to determine what amino acids are linked to the particle identified as "A" [see, e.g., FIG. 20].

Figure 20:
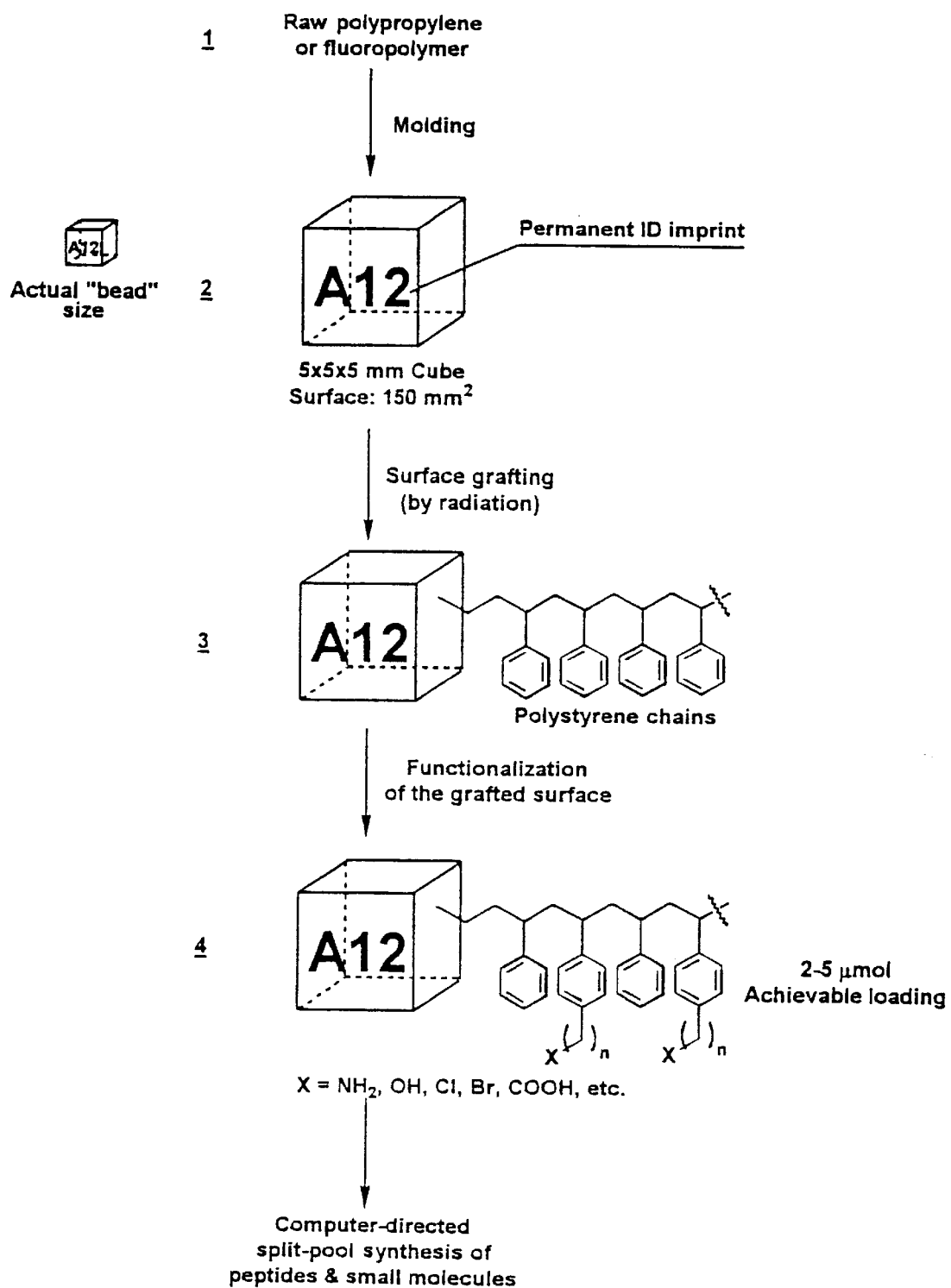
FIG. 20 depicts coded macro "beads" for efficient combinatorial synthesis. As with the supports, these "beads" will include either an electromagnetically programmable memory, or an optical memory engraved on the surface, such as the 2-D optical bar code provided herein.

For example, many combinatorial libraries contain a relatively small number of discrete compounds [$10^2$–$10^4$] in a conveniently manipulable quantity, rather than millions of members in minute quantities. These small libraries are ideal for use with the methods and matrices with memories herein. They may also be used in methods in which the memory is not in proximity to the matrix, but is a remote memory, such as a computer or a table of information stored even on paper. The system depicted in FIG. 20 is ideal for use in these methods. Polypropylene or other inert polymer, including fluoropolymers or scintillating polymers are molded into a convenient geometry and size, such an approximately 5 mm×5 mm×5 mm cube [or smaller or larger] with a unique identifying code imprinted, preferably permanently, on one side of each cube. If, for example, a three element code is used, based on all digits (0 to 9) and all letters of the alphabet, a collection of 46,666 unique three element codes are available for imprinting on the cubes. Also, commercially available polypropylene or fluoropolymer beads (0.5–5 mm diameter) may be used. These can be radiation grafted as described herein and used either singly or by inserting in mesh containers [i.e., the MICROKAN microreactors]. When used singly they can be linked to the smaller chips or encoded with a symbology, such as a 2-D optical bar code.

The cubes are surface grafted with a selected monomer [or mixture of monomer], such as styrene. Functionalization of the resulting polymer provides a relatively large surface area for chemical syntheses and subsequent assaying [on a single platform]. For example, a 5×5×5 mm$^3$ cube has a surface area of 150 mm$^2$, which is equivalent to about 2–5 μmol achievable loading, which is about 1–2.5 mg of compounds with a molecular weight of about 500. A computer program, described below [see, e.g., Appendix III and Examples], provides a protocol that directs split and pool during synthesis. The information regarding each building block of the linked molecules on each cube is recorded in the memory [i.e., computer] at each step in the synthesis.

Since the cubes [herein called MACROCUBES™] are relatively large, they can be read by the eye or any suitable device during synthesis and the associated data can be manually entered into a computer or even written down. The cubes can include scintillant or fluorophore or label and used in any of the assay formats described herein or otherwise known to those of skill in the art.

For example, with reference to FIG. 20, polypropylene, polyethylene or fluophore raw material [any such material described herein, particularly the Moplen resin e.g., V29G PP resin from Montell, Newark Del., a distributor for Himont, Italy] 1 is molded, preferably into a cube, preferably about 5×5×5 mm$^3$ and engraved, using any suitable imprinting method, with a code, preferably a three element alphanumeric code, on one side. The cube can be weighted or molded so that it all cubes will orient in the same direction. The engraved cubes 2 are then surface-grafted 3 and functionalized using methods described herein or known to those of skill in this art, to produce cubes [MACROCUBES™] or devices any selected geometry 4.

1. Encoded memory devices with two-dimensional bar codes a. Matrices with optical memories In another exemplary embodiment, illustrated in FIG. 22, the optical memory device ["OMD"] 100 is a preferably a rectangular parallelepiped that provides a broad face upon which encoded information can be inscribed. Any geometry that is suitable for a particular application and that provides at least one surface for encoding information. The OMDs may also be containers used for chemical synthesis, such as microtiter plates, tubes, tubes adapted for use with microtiter-type plates. The two-dimensional bar code described herein is ideally suited for incorporation onto the outside surface of each well of a microtiter plate or on the outside of a small test tube or other such tube, particularly, tubes intended for use with a microplate frame, such as those available from NUNC and COSTAR. This two-dimensional bar code as wells as the method for reading and writing may also be used to track and identify other laboratory equipment, such as chromatography tubes, test tubes, beakers, flasks and other such items.

The OMDs may also be fabricated as tubes, such as the MICROTUBE™ microreactors provided herein. When used with such tubular devices, they will be engraved on the outer surface, preferably the top or bottom of the device.

The material of which the OMDs are fabricated will depend upon the monitored processes. The materials that may be used include, but are not limited to, black, white or colored glass, TEFLON®, polyethylene, high density polyethylene, polypropylene, polystyrene, polyester, ceramic, such as alumina or zirconia, metal, or any composite of the above materials or any material that is physically or chemically structured to produce optical contrast as the result of exposure to the write process, which is described below. For use in the methods herein, these materials may be suitable or at least one surface there may have been treated to render them suitable for retaining molecules and biological particles for use as matrices as described herein.

For the first exemplary embodiment of OMD 100 shown in FIG. 22, if the OMD is formed from a ceramic material, it may have exemplary dimensions of 280 mil (L)×140 mil (W)×50 mil (T) [7 mm×3.5 mm×1.3 mm]. The dimensions of the face can be varied as needed to provide the appropriate size for recording data, providing sufficient chemical binding surface area, and to facilitate handling. The presently preferred minimum size for use with commercial feeding systems is on the order of 0.5 mm×0.5 mm×0.5 mm.

If the OMD 100 is formed from polypropylene, it may have exemplary dimensions of 280 mil (L)×140 mil (W)× 100 mil (T) [7 mm×3.5 mm×2.6 mm], although smaller dimensions are contemplated. Since OMDs made from polypropylene may be read by transmission of light through the device, the thickness must be sufficiently thin to permit transmission of light through the OMD, except where there are darkened areas of a bar code symbol. Where reflected light is to be used, as with the ceramic OMDs, thickness need not be so limited.

For OMDs used for chemical binding or other processes for which surfaces must be specially prepared in order to assure adsorption or absorption or any means of binding of molecules or biological particles, it may be desirable to separate the binding surfaces from the data storage surface 101. In this case, one or more of sides 104 and 105, bottom 107, top 108, and back 110 may be treated to enhance binding using radiation, mechanical or chemical abrasion, or other processes as appropriate. By segregation of the binding and information surfaces, possible activation or modification of certain bound compounds by the high intensity light source used in the write process is avoided. In addition, degradation of the bar code contrast may be less on a surface that is not derivatized for binding.

If needed, segregation of the binding and information surfaces can be achieved by coating portions of the OMD with films formed from a dielectric material such as polyethylene, MYLAR, TEFLON®, KAPTON, polycarbonate, or, preferably, the para-xylylene polymers sold under the trade name Parylene [see, e.g., U.S. Pat. Nos. 3,288,728, 3,342,754 and 3,429,739], or any other such materials that are commonly used in the electronics industry to passivate electronic components and circuit boards, and as a coating for medical devices, especially implants, catheters, probes and needles. [Parylene is the trade name for members of a series of polymers which are commercially available from Specialty Coating Systems, Inc., of Indianapolis, Ind. and originally from Union Carbide Corporation, Greenville, S.C., see, U.S. Pat. Nos. 3,288,728, 3,342,754 and Gorham 3,429,739; see, also brochures distributed by the manufacturer, entitled "Parylene Conformal Coatings Specifications and Properties" (© 1984, Specialty Coating Systems, Inc.), and "Parylene, A Biostable Coating for Medical Applications" (© 1984, Specialty Coating Systems, Inc.]. These polymers provide a conformal biostable coating which electrically and chemically isolates the protected surface from its environment.

The Parylene or other such polymeric coating can be treated to form a chemically functional substrate by methods such as beta or gamma radiation, and mechanical or chemical roughening. Alternatively, polystyrene microspheres can be bonded [glued or welded] to selected surface(s) of the OMD, either on the Parylene or similar coating, or directly to the ceramic or polypropylene.

The encoded information may be stored in any optically writable and readable format. As shown printed on data storage surface 101, symbologies 106 are two-dimensional bar codes, which can be stacked rows of one-dimensional bar codes, checkerboards, or dot matrices. Other symbologies that can be used include one-dimensional bar codes, target codes, alphanumeric characters or other optically readable characters which are well known in the art. [See, e.g., Wang, et al. (1990) A High Density Two Dimensional Bar Code *SPIE Proceedings* Vol. 1384, High-Speed Inspection Architectures, Bar Coding, and Character Recognition, pp. 169–175; Martin (1991) Unique Symbol for Marking and Tracking Very Small Semiconductor Products, *SPIE Proceedings* Vol. 1598, Lasers in Microelectronic Manufacturing, pp. 206–220.]

In the exemplary embodiment, the two-dimensional bar code [e.g., symbol 106] includes an orientation indicator in the form of solid black lines across the top 120 and down the right side 122 of the symbol. Upon acquisition of the image of the symbol by the image sensing means, the image processor will utilize the orientation indicator to provide information about the rotation of the OMD relative to the sensor, and can compensate in its software by rotating the image to the appropriate orientation for decoding the image. Other types of orientation indicators as are known in the art, such as those described in the above-identified references relating to bar codes, may also be used such that physical precise orientation of the OMD within the read area is not critical. For reflection-type readers, it is only necessary for the OMD to be right side up and the symbol is fully within the field of view of the detector, so that the symbol 106 is exposed to the image sensor. Even where reading is accomplished by transmission of light through the OMD, as in certain polypropylene embodiments, an orientation indicator in the symbol in combination with a distinctive physical or optical feature, such as described below, can provide information sufficient to determine whether the OMD is face up or face down so that appropriate compensation, such as reversal of the image, can be performed by the software in order to enable decoding.

An alternative means for recording and reading information involves the formation of a magnetic film on at least a portion of the surface of the OMD. Creation of thin magnetic films by sputtering, electroplating, or other deposition techniques are well known in magnetic recording technology. [See, e.g., Chapter 11, "Tape and Disk Materials" from *The Complete Handbook of Magnetic Recording*, 3rd Edition, by Finn Jorgenson, Tab Books, 1988.] Recording and reading of data on the magnetic film can utilize conventional magnetic recording techniques.

The OMD 200 of FIG. 23 is a variation on the embodiment of FIG. 22 that provides a information recording section that is formed from a separate material from that of the binding surface(s) [i.e., the chemistry surface(s) or the surface(s) to which molecules or biological particles are linked]. In this embodiment, the OMD contains two sections that are linked together. Here, OMD 200 is formed from the assembly of information unit 202 and binding unit 204, with unit 202 fitting within a cavity or well 206 formed in unit 204. This embodiment provides the advantage of selecting the optimal material for each of the binding and recording processes, and also permits the information unit 202 to be assembled with the binding unit 204 after the binding unit has been treated to enhance adhesion. For example, binding unit 204 can be formed from a polymer, e.g., polypropylene, functionalized by radiation and/or chemical processes, or can be modified by bonding polystyrene microspheres to its surface(s). Information unit 202 can be formed from plastic, ceramic or glass, and mounted within well 206 by adhesive or other bonding process, or may be press fit into the well. Since pre-treatment of the binding unit to enhance binding could possibly discolor the information unit, or otherwise make it less readable by modifying the surface, e.g., pitting or etching, separate formation could be advantageous. The outer dimensions of unit 202 are preferably selected to closely fit the inside dimensions of well 206 to prevent the intrusion of chemicals, or even air, into spaces between the units. In the illustrated example, unit 204 has outer dimensions of 280 mil (L)×140 mil (W)×100 mil (T) [7 mm×3.5 mm×2.6 mm] and unit 202 has maximum dimensions of 210 mil (L)×115 mil (W)×50 mil (T) [5.3 mm×2.9 mm×1.3 mm]. Since, as shown, the sides of unit 202 are beveled to form a trapezoidal cross-section to conform to a corresponding shape of the well 206, and also to assist in forming a tight seal between the two units, the actual exposed face of the information unit is on the order of 105 mil×200 mil [2.7 mm×5 mm]. When the two units are assembled, the combined face surface of the information and binding units are preferably flush. As can be seen, the encoded information, shown as a two-dimensional bar code symbol 208, is inscribed on information unit 202 only. With regard to the magnetic recording alternative method, the use of a separate information unit is ideal since it would generally be preferred to avoid exposure of magnetic recording media to the radiation or corrosive chemicals used for enhancement of the binding process.

Variations on the two-part OMD of FIG. 23 are illustrated in FIGS. 25–27. In FIG. 25, OMD 400 is illustrated where insert unit 402 is the binding unit formed, for example, from polymer functionalized by radiation and/or derivatized by suitable chemical processes or grafted to render the surface suitable for binding biological particles and molecules. Base unit 404, which may be formed from plastic, polymer, ceramic or glass, has a well 406 corresponding to the exterior shape of the binding unit 402, so that they will interfit closely. The encoded information, shown, again, as a two-dimensional bar code symbol 412, is inscribed on the back 408 of base unit 404, opposite the face 410 at which binding unit 402 is exposed.

In FIG. 26 [an embodiment of a microvessel], insert unit 502 has a cavity 508 covered by mesh 510 [porous material] for retaining particles but permitting chemical materials and biological particles to pass through, to form OMD 500. The chemicals pass through mesh 510 to be within cavity 508, or some material contained therein, such as microspheres, or are retained on the strands of mesh 510. As in the embodiment of FIG. 25, base unit 504, which is encoded with the symbology, receives the binding [chemistry] unit so that it is exposed on one face 512, with the encoded information 514 located on the opposite face 516.

In the embodiment of FIG. 27, insert unit 602 is formed from polypropylene or ceramic or other suitable material and provides the information storage face 608 for writing symbology, preferably a bar code symbol 610 on OMD 600. Base unit 604 provides the means for binding of chemical materials, which contains cavity 612 which is filled with microspheres 614 and covered with polypropylene screen 616 or other suitable porous material. The base material is preferably polypropylene or other such material. In this embodiment, the information storage face 608 is on the opposite side of the OMD from the screen 616.

In yet another embodiment, OMD 700, which is illustrated in FIG. 28, an orientation indicator is provided in the form of a notched or cut-corner 702. In this embodiment, the corner cut-out 702 will provide information as to the rotation and inversion of OMD 700, since, even if the OMD is face down, it will be apparent due to the unique outline of the face. The use of a physically detectable orientation indicator allows the handling equipment to readily detect improper positioning, for example, by placement of mechanical or optical edge detectors within the handling system. An improperly positioned OMD can be removed from the imaging position and placed back at the entry point into the reading handler, or mechanical means, such as a retractable blade, can be provided to flip the OMD over if it is presented face down within the field of view of the reader. An alternative symbology 706 is illustrated which is, in this case, an alphanumeric code, which can be read and decoded using known optical character recognition (OCR) techniques.

Other types of orientation indicators that can be used include chamfers, holes and protrusions. Several different and distinctive shapes can be included on a single OMD to assist in orientation, positioning and separation of the OMDs. For example, a group of OMDs can have a cut corner for orientation of each OMD, with some of those OMDs having a tab extending from one of its sides, so that those with tabs can be separated from those without tabs, which facilitates division of the group for diversion to different containers.

Additional test media can be included in the OMD in the embodiment of FIG. 29. Here, the OMD 800 has a plurality of wells or recesses 804 into which can be placed gels, beads, or the like for retaining additional chemical [molecules] or biological materials [biological particles], and/or chemical, biological or temperature sensors, or other such devices. Where such materials are placed in the wells 804, the bar code symbol 806 can include information about the nature of these materials.

The embodiment of FIG. 30 is a variation on that of FIG. 29. Here, the OMD 900 is partially hollow, and a plug 902 is formed in the side to permit access to the cavity 912. The front 904 and/or back 908 walls of the OMD have a mesh insert 910 which provides limited access to the cavity 912 in the OMD. A chemically- or biologically-functional material [biolgocial particle or molecule], or microspheres, for example, can be placed within the cavity 912 through plug 902 so that it is exposed to the chemical or biological materials to which the OMD is exposed without allowing direct contact between the material in the cavity and the environment in which the OMD is placed. The mesh [porous material] 910 can be polypropylene or other such suitable polymer, and of a size that makes it semi-permeable, admitting the external solution without allowing the interior material to escape. Generally, the pore size will be within the range of 20 $\mu$m to 200 $\mu$m, preferably less than 80 $\mu$m, and more preferably between about 30 $\mu$m to about 50 $\mu$m.

The use of OMDs and protocols therefor are flexible and can employ a variety of shapes, configurations, and polymeric synthesis supports. The ceramic 2-D bar codes will have at least 8-bytes of information content. When etched on ceramics, they are inert to the vast majority of organic synthesis conditions, easy and reliable to use, inexpensive, and very amenable to mass production. The low crosslinking polystyrene surface graft (and other polymer grafts) on the stable and inert base polymer provides an ideal solid support for chemical synthesis with excellent functionalizability and chemokinetics. This technology can also be applied to the synthesis of other types of compounds, especially small organic molecules. Among the advantages of this technology over existing combinatorial techniques are a) low manufacturing cost; b) non-invasive encoding; c) high encoding reliability and capacity; d) total chemistry flexibility; e) excellent chemokinetics; f) easy and clean washing between reactions; g) utilization of the highly efficient directed sorting strategy; h) delivery of pure, discrete compounds in multi-milligram scale; and i) very amenable to full automation. Integration of the laser optical synthesis OMD technology with automation will further enhance its applications in high throughput chemical synthesis and biological screening.

These devices have a wide variety of applications. For example, with reference to FIG. 33E, the bar-coded OMDs devices are functionalized with amino groups to give functionalized OMDs devices 3 and used in the synthesis of oligomers. The first set of nucleosides modified with a succinic acid linker are coupled onto the matrices using DNA synthesizer with modified reaction vessels [suitable for use with the OMD-linked nascent oligonucleotides]. Five cycles of TCA de-blocking, sorting, tetrazole activation, coupling, capping, and oxidation are performed automatically on the machine [except the sorting] to yield oligonucleotides [hexamers] on the matrices 6. Cleavage and deprotection under standard conditions give the oligonucleotide hexamer library 7. The identity of each oligonucleotide is associated with the unique code in a remote memory, such as by manually entry before, during or after synthesis.

b. Reading and writing to matrices with optical memories

Figure 24:
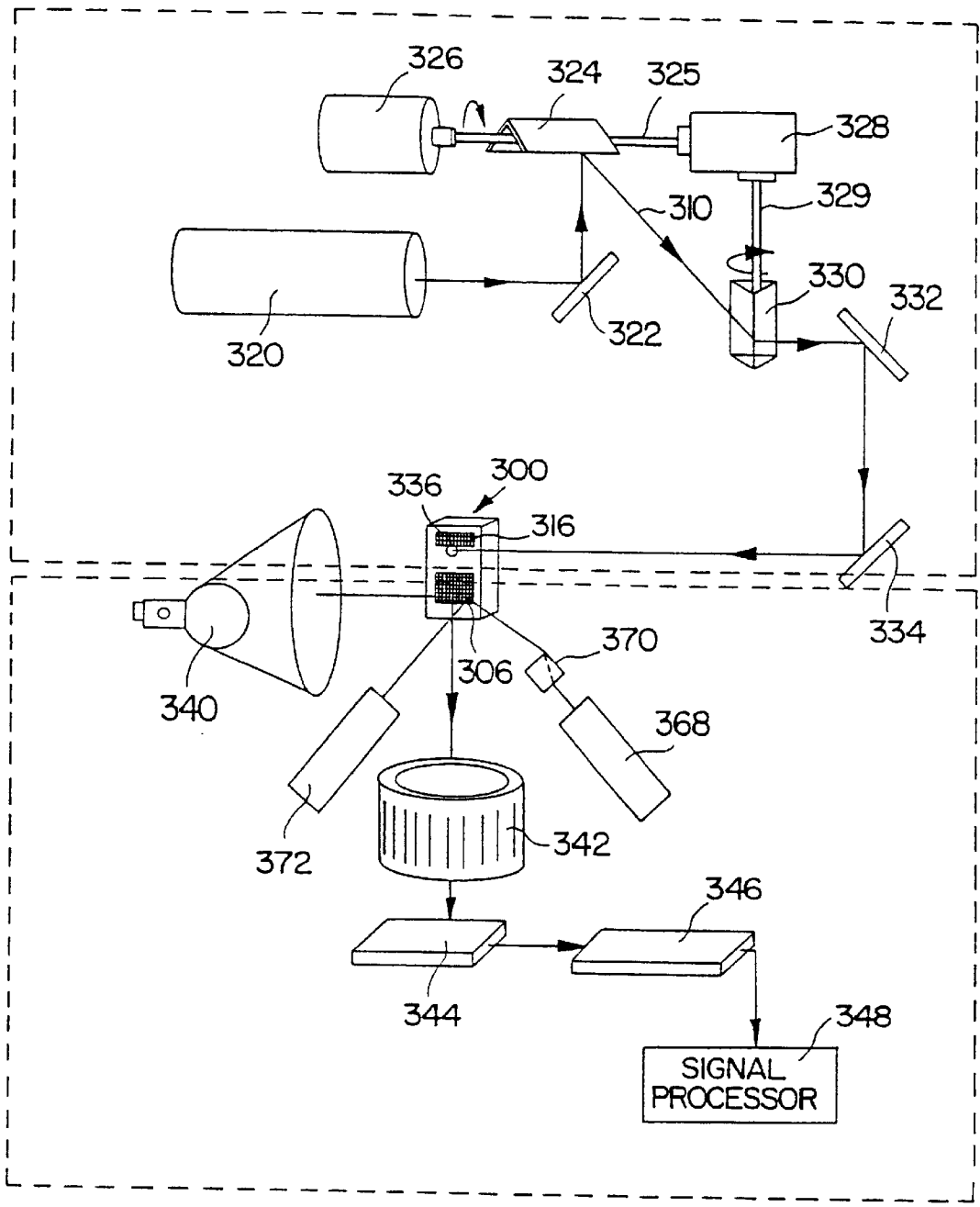
FIG. 24 is a diagrammatic view of the optical write and read for the optical memory devices.

An exemplary read/write system is illustrated in FIG. 24. The write system includes laser 320, mirror 322, and prism 324 mounted on drive shaft 325 connected at a first end to drive motor 326. Drive shaft 325 is connected at its second end to geared linkage 328 which rotates drive shaft 329 and prism 330 in synchrony with prism 324. The beam emitted by laser 320 follows optical path 310 to mirror 322, where it is reflected toward prism 324. Prism 324 rotates to scan the beam along the y-axis, i.e., up and down, so that the beam effectively shifts top to bottom by reflection from the prism faces in succession as it rotates. This beam is similarly scanned along the x-axis from left to right by reflection from the faces of prism 330 in succession as prism 330 rotates. Either or both prisms can be replaced with rotating or oscillating mirrors to achieve the same scanning pattern, in a manner similar to the scanning mechanisms used in conventional laser-based bar code scanners [see, e.g., U.S. Pat. No. 4,387,297 to Swartz, et al., entitled "Portable Laser Scanning System and Scanning Methods", and U. S. Pat. No. 4,409,470 to Shepard, et al., entitled "Narrow Bodied, Single- and Twin-Windowed Portable Laser Scanning Head for Reading Bar Code Symbols"]. Mirrors 332 and 334 provide means for directing the beam toward the OMD 300 at the appropriate level, and, thus, are positioned in consideration of the guide means, so that the beam impinges upon the desired recording surface.

As illustrated in FIG. 24, OMD 300 has already been inscribed during an earlier process step, evidenced by the fact that symbology 306 is present and complete. Also as illustrated, symbology 316 is currently being written by the progression of laser spot 336 across the write surface, as scanned by prisms 324 and 330. The contrasting dark and light areas of the symbologies 306,316 are created by pulsing the laser 320 according to a signal provided by system controller 338.

In an exemplary embodiment, laser 320 is a $CO_2$ laser, which emits light in the infrared at a wavelength of 10.6 $\mu$m. The writing process is accomplished by using a sufficiently high power beam to burn the surface of the OMD, formed of ceramic, white polypropylene or the like, to produce a dark carbon build-up corresponding to the dark lines of the symbology on the lighter colored background. The exemplary laser power is 25 W, with a spot size of 0.03 mm, burning a dot in the write surface of 0.13 mm, to create a two-dimensional bar code using a dot matrix pattern. Mirrors 322, 332 and 334, and prisms 324 and 330 must be coated with an appropriate IR-reflective film to avoid damage to the optics by the laser. In read systems which utilize transmission of light through the OMD, the carbon build-up will block the light, appearing as darkened areas to a sensor on the opposite side of the OMD from the light source. In read systems which utilize back-reflection, the carbon build-up will absorb light, while the other areas will reflect the light, again creating a contrast between the inscribed and untouched areas of the surface.

Since the IR write beam is not visible, it may be desirable to use an optically-visible laser 336, for example, He—Ne or a diode laser which emits within the visible spectrum, or other focused light source, to emit a beam along optical path 310 to permit visual alignment. Optically-visible laser 339 may also be used as a proximity detector to send a signal to the system controller to indicate the presence of the OMD in the write position to trigger the write process, either by reflection or by blocked transmission using conventional optical sensors. Alternatively, a separate optical detector system may also be used to detect and indicate the presence of an OMD in the write or read position.

For OMDs formed from glass or ceramic, a beam from a $CO_2$ laser can be used to etch the glass to produce contrasting lines by modifying the surface finish of the glass. For example, the glass can be frosted or otherwise roughened, which may assist in the binding of compounds, and which has a reduced reflectivity. Upon exposure to the high power write beam, the glass surface is partly flowed, i.e., partly melted, so that a smooth, highly reflective surface remains after the surface cools. Contrast between the frosted and flowed glass can be enhanced for reading by selecting a read wavelength which maximizes the differences in reflectivity between the two surface finishes.

Other types of lasers which may be used include neodymium-YAG [yttrium-aluminum-garnet], excimer, or any other laser capable of emitting a sufficiently high power beam to modify the material surface to produce an optically-readable contrast. Alternative lasers for the writing process include diode lasers, such as those made by Coherent, Inc. of Santa Barbara, Calif. Among those that are suitable are Model No. S-98-2000C-200-C, T or H, which emit light at 980 nm with a CW power of 2000 mW, Model No. B1-81-10C-19-30-A or W, which emit light at 808 nm with a CW power of 10,000 mW, or Model No. B1-81-15C-19-30-A or W, which emit light at 808 nm with a CW power of 15,000 mW.

Selection of the laser will depend on the material of which the OMDs are formed. For example, if an optically-reactive material is encased within a transparent glass or plastic shell, any laser capable of inducing the readable change in the optically-reactive material would be acceptable. Photochemically-reactive media, known to those of skill in the art [see, e.g., U.S. Pat. No. 5,136,572 to Bradley, entitled "Optical Data Storage System"] can be selectively activated and read by use of wavelength tunable diode lasers, such that a lesser power and/or visible light laser can be used with a more reactive recording media.

Figure 32:
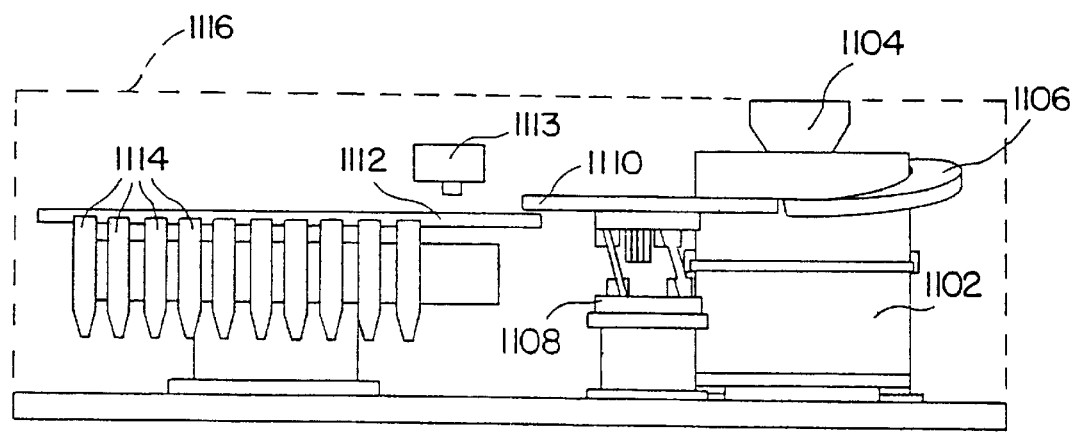
FIG. 32 is a diagrammatic view of an exemplary handling system for feeding, reading and distributing the optical memory devices.

The range of movement of the laser spot 336 is limited, generally to the area of the write surface, so that the OMDs must be moved past a target area within which laser spot 336 is projected. Movement of the OMDs can be achieved by one or more sets of conveyor belts 370, chutes or guide rollers, each of which can be fed by a commercial-type centrifugal feeder, such as those available from Hoppmann Corporation of Chantilly, Va. and Kirchlintein, Germany. Feeders of this type are known in industry for mass handling of parts and products, including foods, pharmaceuticals, containers and hardware. Linear and vibratory feeders are also known and may be used for handling the OMDs. An exemplary handling system is illustrated in FIG. 32 and will be discussed in more detail below.

Included in the proximity location process to detect the presence of an OMD within the write position can be a detector 372 for locating the next available area on the write surface for writing. In the example illustrated in FIG. 24, for a write surface having four available locations, position #1 is already filled with symbology 306, and position #2 is in the process of being filled with symbology 316. A light source 368, such as a visible laser, emits a beam which is directed by scanning optics 370 toward the write surface of the OMD. As the write surface is scanned by the beam, the next available area detector 372 can look sequentially at each OMD as its presence is detected, first at position #1, then at subsequent positions until it finds an area on which no symbology is written, i.e., no contrasting markings are detected, or a "white" area of a pre-determined width is detected which is wider than the "quiet Zone" which is commonly included in bar codes. [See, e.g., Wang, et al., "A High Density Two Dimensional Bar Code," SPIE Proceedings Vol. 1384, High-Speed Inspection Architectures, Bar Coding, and Character Recognition (1990) pp. 169–175.] This location process permits multiple uses of OMDs, and takes into consideration that some OMDs may be exposed to a greater number of process steps than others before being combined into the string in which they are presently included.

The detector 372 can also be used for indication of the presence of OMDs to be read. In the case of reading, the detector 372 can also be used to identify the presence of all symbologies to be scanned for reading, which is particularly important if a laser beam or other relatively narrow beam of light is scanned over the written surface to read the symbology. Where an incoherent light source is used to flood the entire write surface with light, such as a lamp 340, the ability to detect the presence of individual symbologies is not critical, since the entire write surface will be viewed and recorded at once using frame grabbing techniques.

During the read process, after the presence of an OMD is indicated, the lamp 340 is activated to illuminate the write surface. The light reflected from the surface is modulated by the symbology printed thereon due to the selective reflection and absorption of the contrasting areas. Optics 342, which will typically be an assembly of lenses and filters, which remove stray light, focus the reflected light onto detector 344. Selection of optics can be performed in a using methods known to those of skill in the art [see, e.g., U.S. Pat. No. 5,354,977 of Roustaei, which describes an optical bar code scanner using a CCD [charge-coupled device] detector and associated optics. In the same reference, a detailed description of CCD detectors for use in bar code scanners is provided, as well as steps for processing the signal generated by the CCD detector.

In the exemplary embodiment illustrated in FIG. 24, the CCD detector 344 comprises an array of discrete devices, each of which is a "pixel", capable of storing charge impinging upon it representative of reflected light from the write surface, then reading out the charge as a serial analog waveform. A typical CCD array for bar code scanning has 2048 pixels, however, CCD arrays of other dimensions may be used. In the preferred embodiment, a CCD array of 640×480 pixels is used. Using the CCD array, a "snap shot" of the OMD surface is created using known image or frame grabbing techniques, and an analog electrical representative of the snap shot is conducted to the signal processing function 348 within the system controller, which includes an analog-to-digital converter, to convert the signal into an output of the data written on the OMD.

In a preferred embodiment, the detector is a commercially-available, PC-interfaceable CCD camera sold under the trademark QuickCam™ by Connectix Corporation of San Mateo, Calif., which has a resolution of 640×480 pixels. Any other such camera may be used. The camera has a manually-adjustable focus lens, but image acquisition is otherwise controlled by the system controller 348, which, as part of its software, initializes the camera for frame grabbing. Any such PC-interfaceable CCD camera with a similar or better resolution may be used. For example, other types of detector arrays are known within the bar code scanning technology, including CMOS sensors [see, e.g., "CMOS in camera", IEE Review, May 1994, p. 111], which are also capable of generating "snap shots" of the data written on the OMD and could be used in place of the CCD detector array 344.

Processing of the image grabbed by the image detector is a significant aspect of the system in that it provides the flexibility to manipulate the image to enhance readability. The steps of the exemplary image processor are provided in the flow diagram of FIG. 31, and the image signal generated by the detector is checked for completeness, validity and orientation, among other things. As discussed above, if systems where physical orientation and positioning of the OMD is not assured by the handling hardware, one aspect of the image processing software is to determine skew or rotation of the image as seen by the detector.

Figure 31:
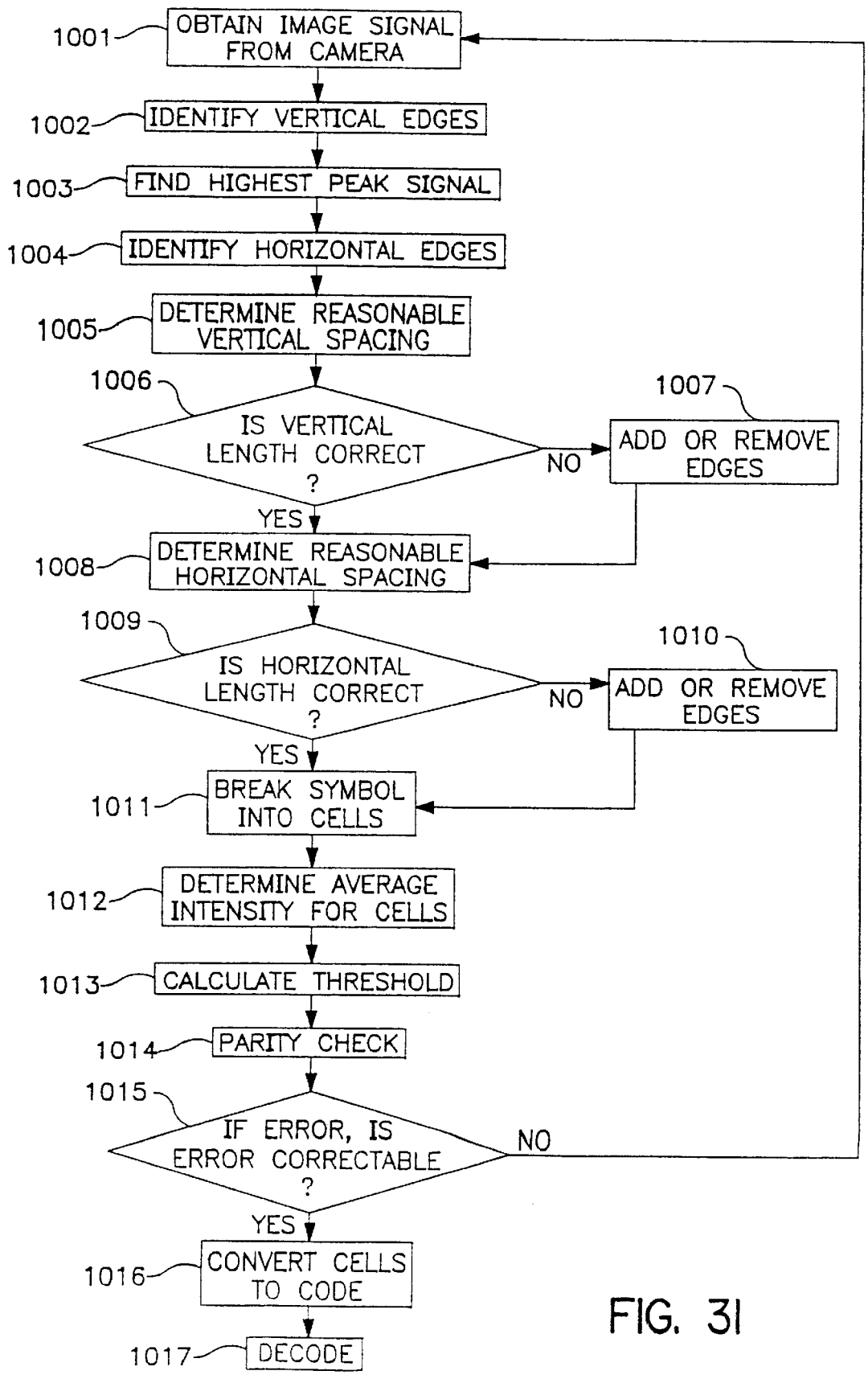
FIG. 31 is a flow diagram of the image processing sequence for a two-dimensional bar code on an optical memory device.

The following steps are provided in detail in the system processor's software, the code for which is provided as a Microfiche Appendix I, and a portion of which is depicted in the flow diagram of FIG. 31. [Note that the actual image obtained from the camera can be displayed on a system monitor as it is being modified to permit decoding.] First, after obtaining the image from the camera [step 1001], in steps 1002 and 1003, the edges of the symbol in the vertical direction are identified, looking for the highest peak signal to provide a reference, then the horizontal edges are found [step 1004]. Knowing the boundaries of the symbol, the reasonable spacing is determined [step 1005] to correct for missing or extra vertical edges using a neural network approach. Based on the reasonable spacing, it is determined if the length of the vertical edge is appropriate [step 1006]; if not, adjustments are made by adding or removing edges [step 1007]. A similar procedure is used for the horizontal edges [steps 1008–1010], allowing skew to be determined. Having determined the orientation and spacing of the symbol, the symbol is broken into sections [step 1011], or cells, and the average intensity for each cell is determined [step 1012] to permit calculation of the threshold [step 1013] for distinguishing a dark from a light area of the code. Following this, parity checks are performed [step 1014] to provide an indication of whether the complete symbol was detected, i.e., the correct number of bits was obtained, or whether the signal was corrupted. In the preferred embodiment, 17 bits of the data contained within the two-dimensional bar code are dedicated to parity checking. At this point, if a corrupted signal is indicated, and the error is not corrected [step 1015], rather than proceeding with an attempt to decode, the image processor initiates a new scan of the symbol [step 1001]. If the signal is good, the cells are converted to code [step 1016] which is decoded [step 1017].

The image processing system converts the stored image into a series of rows [and columns for two-dimensional codes] containing binary data, with dark lines indicating highs, or ones, and white lines indicating lows, or zeroes [or vice versa]. To enhance accuracy, a number of processing steps may be performed, and the resulting data can be the average of all processing steps for that particular image.

Although efforts are taken initially to avoid modification of the surface on which the information is written, because each OMD is presumably being subjected to a significant number of process steps, the appearance of the symbol may degrade with time due to accumulation of chemicals or surface roughening, resulting in decreased contrast between the light and dark lines of the code. This issue can be addressed with software, which can compensate for the deterioration of the symbol. In a preferred embodiment, the software includes neural network algorithms which can be trained to learn the specific cumulative effects of chemical processing and compensate by either recalibrating the detector, for example, to increase the exposure time, to modify the illumination, to increase the number of verification decode steps used for averaging, or to adjust the threshold between "dark" and "light". Any methodology that applies some sort of history based correction, such as an expert system or neural net, is suitable. For example, two appropriate commercially-available neural network programs are Thinks™ and ThinksPro™ [published by Logical Designs Consulting, Inc. La Jolla, Calif.; see, U.S. Pat. No. 5,371,809], which are designed to run on personal computers, and provide numerous different and well known training algorithms and methods. Other neural network software products are commercially available, including Neural Works Professional™ by NeuralWare, Neuro-Shell2™ by Ward Systems, BrainMaker Professional™ by California Scientific, and Neural Net Tool Kit™ by Math Works. Each could be used for training of the signal processor to compensate for degraded contrast in the symbol, and selection of the appropriate program or creation of an appropriate program would be within the level of skill in the art.

FIG. 32 provides a diagram of an exemplary handling system for separating and reading and/or writing to an OMD, particularly those in the shape of a parallelopiped. Such handlers, such as vibratory feeders, are commercially available [e.g., from Hoppmann Corporation, Chantilly, Va., see, U.S. Pat. Nos. 5,333,716, 5,236,077, 5,145,051, 4,848,559 4,828,100, 4,821,920, 4,723,661 and 4,305,496]. The OMDs are placed in vibratory feeder 1102 by way of supply hopper 1104. Vibratory feeder 1102 includes rings and ramps [not shown] which support the OMDs as they move within the feeder, driven by the feeder's vibration in a direction toward exit chute 1106. An orientation rim, bar, or other feature [not shown] may be included in the internal ramps or exit chute to rotate the OMDs when a physical orientation indicator, such as the cut corner, is provided. Exit chute 1106 feeds the OMDs to ramp 1110 of linear feeder 1108. The reciprocating motion of the ramp 1110 causes the OMDs to move forward [to the left in the figure] toward walking beam 1112 and within the field of view of camera 1114. [Where a write operation is to be performed, the write laser and optics can be positioned in place of or nearby the camera.] Movement of the walking beam 1112 is stepped so as to pause advance motion of the OMD to allow writing and/or reading of the appropriate information.

After completion of the writing or reading step, the OMD is advanced along the walking beam 1112 toward one or more vials or flasks 1114 containing chemical or biological solutions Ramps [not shown] leading from the walking beam to the vials or flasks 1114 can be selected by opening gates, or by tilting the walking beam 1112 in front of the selected vial, thus feeding the OMD into the desired vial for the next process step. The vials or flasks 1114 can be fixed within a tray or rack that allows it to be removed after the processing has finished so that the OMDs can be dumped into the hopper of the same or another feeder to repeat the above steps for handling, writing, reading, and distributing the OMDs to the next process step.

It may be desirable to include a protective enclosure 1116, such as a polycarbonate and polyphenylene oxide resins, preferably the polycarbonate resin sold under the name LEXAN™ [the well known polycarbonate resin commercially available from General Electric Corp, Waterford, N.Y., or MERLON™ made by Mobey Chemical Co., Pittsburg, Pa.] or the resin sold under the tradename NORYL [from General Electric Corp] other such polymer such as polyethylene, lucite, bakelite and other such resins that have high tensile and impact strength over a broad temperature range, are virtually shatter-proof and are extrudable as transparent sheets, over the handling system to prevent contamination of the OMDs and solutions as well as for the safety of the system operator.

3. Devices coded with "electronic ink"

The devices, such as the MICROTUBE microreactors, are encoded with "electronic ink" [see, Jacobson (1997) Wired Jan. issue]. The "ink" is fabricated by providing a thin coating on the device or on tag placed on the device with a coating of tiny black and white "balls" that rotate electronically to display either a black side or a white side.

4. Pre-coded memory devices

Alternatively, the matrices attached thereto may be encoded with a pre-programmed identifying bar code, such as the 2-D optical bar code that will be encoded on the matrix and read by laser. Such pre-coded devices may be used in embodiments in which parameters, such as location in an automated synthesizer, are monitored. The identity of a product or reactant determined by its location or path, which is monitored by reading the chip in each device and storing such information in a remote computer.

C. Data Storage Units with Memory

In embodiments in which OMDs are used, the programmable devices are remote memories, such as computers into which information regarding the encoded information and linked molecules and biological particles is stored. The OMDs are read/write devices or are precoded devices.

For use with the matrices in which the memory, rather than a code, is linked to the device, any remotely programmable data storage device that can be linked to or used in proximity to the solid supports and molecules and biological particles as described herein is intended for use herein. Preferred devices are rapidly and readily programmable using penetrating electromagnetic radiation, such as radio frequency or visible light lasers, operate with relatively low power, have fast access [preferably 1 sec or less, more preferably $10^2$–$10^3$ sec], and are remotely programmable so that information can be stored or programmed and later retrieved from a distance, as permitted by the form of the electromagnetic signal used for transmission. Presently preferred devices are on the order of 1–10 mm in the largest dimension and are remotely programmable using RF, microwave frequencies or radar [see, e.g., Roland et al. (1996) Nature 381:120].

Recording devices may be active, which contain a power source, such as a battery, and passive, which does not include a power source. In a passive device, which has no independent power source, the transmitter/receiver system, which transfers the data between the recording device and a host computer and which is preferably integrated on the same substrate as the memory, also supplies the power to program and retrieve the data stored in the memory. This is effected by integrating a rectifier circuit onto the substrate to convert the received signal into an operating voltage.

Alternatively, an active device can include a battery [see, e.g., U.S. Pat. No. 5,442,940, U.S. Pat. No. 5,350,645, U.S. Pat. No. 5,212,315, U.S. Pat. No. 5,029,214, U.S. Pat. No. 4,960,983] to supply the power to provide an operating voltage to the memory device. When a battery is used the memory can be an EEPROM, a DRAM, or other erasable memory requiring continuous power to retain information. It may be desirable to combine the antenna/rectifier circuit combination with a battery to create a passive/active device, with the voltages supplied by each source supplementing each other. For example, the transmitted signal could provide the voltage for writing and reading, while the battery, in addition to supplementing this voltage, provides a refresh voltage for a DRAM memory so that data is retained when the transmitted signal is removed.

The remotely programmable device can be programmed sequentially to be uniquely identifiable during and after stepwise synthesis of macromolecules or before, or during, or after selection of screened molecules. In certain embodiments herein, the data storage units are information carriers in which the functions of writing data and reading the recorded data are empowered by an electromagnetic signal generated and modulated by a remote host controller. Thus, the data storage devices are inactive, except when exposed to the appropriate electromagnetic signal. In an alternative embodiment, the devices may be optically or magnetically programmable read/write devices.

1. Electromagnetically programmable devices

The programmable devices intended for use herein, include any device that can record or store data. A preferred device will be remotely programmable and will be small, typically on the order of 10–20 mm$^3$ [or 10–20 mm in its largest dimension] or, preferably smaller. Any means for remote programming and data storage, including semiconductors and optical storage media are intended for use herein. These include Yagi chips [see, e.g., Roland et al. (1996) *Nature* 381:120 and other references that describe the simple miniature diodes are powered by radar or microwave and emit in the radar range and are used for tracking insects, such as bees and butterflies], diodes, magnetic tapes, and any other medium for storing information. The small Yagi diodes and similar device can be used as pre-encoded devices, which is then associated with identifying information in a database. These chips may be particularly useful because of they are very small [small (2 mm or less) and light enough to glue to a butterfly without interfering with its ability to fly].

Also intended for use herein, are commercially available precoded devices, such as identification and tracking devices for animals and merchandise, such those used with and as security systems [see, e.g., U.S. Pat. Nos. 4,652,528, 5,044,623, 5,099,226, 5,218,343, 5,323,704, 4,333,072, 4,321,069, 4,318,658, 5,121,748, 5,214,409, 5,235,326, 5,257,011 and 5,266,926], and devices used to tag animals. These devices may also be programmable using an RF signal. These device can be modified, such as by folding it, to change geometry to render them more suitable for use in the methods herein. Of particular interest herein are devices sold by BioMedic Data Systems, Inc, New Jersey [see, e.g., the IPTT-100 purchased from BioMedic Data Systems, Inc., Maywood, N.J.; see, also U.S. Pat. Nos. 5,422,636, 5,420,579, 5,262,772, 5,252,962, 5,250,962, and see, also, U.S. application Ser. No. 08/322,644, filed Oct. 13, 1994]. ID tags available from IDTAG™ Inc, particularly the IDT150 read/write transponder [ITDAG™ Ltd. Bracknell, Berks RG12 3XQ, UK, fabricated using standard procedures and the method for coil winding, bonding and packaging described in International PCT application Nos. WO95/33246, WO95/16270, WO94/24642, WO93/12513, WO92/15105, WO91/16718; see, also U.S. Pat. Nos. 5,572,410, 5,223,851, 5,261,615 and 5,281,855] are also preferred herein. The IDT150 is a CMOS device that provides a kilobit of EEPROM. This transponder also includes a 32 bit fixed code serial number that uniquely identifies each chip. The IDTAG™ transponder transmits data to a transceiver system by amplitude modulating its coil and generating an EM field. It receives data and commands from a transceiver by demodulating the field received by the coil and decoding the commands. The transponder derives its power source from a frequency emitted in the signal from the reader, to which the transponder emits a response. A smaller version [that has 16 bit EEPROM] and is about 11 mm×4 mm×3 mm of this transponder is also among preferred devices. These transponders are packaged in glass or polystyrene or other such material. Also preferred herein, are tags fabricated by and available from MIKRON under the name HITAG® [see, e.g., U.S. Pat. No. 5,345,231 for a description of the systems for reading and writing].

In a preferred embodiment herein, the data storage unit includes a semi-conductor chip with integrated circuits formed thereon including a memory and its supporting circuitry. These devices can be written to and interrogated from a distance. A radio frequency transmitter/receiver system supplies power to program and retrieve data. In particular, the data storage unit preferably includes a programmable read only semiconductor memory [PROM], preferably a non-volatile memory or other memory that can store data for future retrieval, that will have information describing or identifying the molecules or biological particles linked to or in proximity to the matrix. This information either identifies the molecule or biological particles including a phage and viral particles, bacteria, cells and fragments thereof, provides a history of the synthesis of the molecule, or provides information, such as a batch number, quality control data, reaction number, and/or identity of the linked entity. The memory is programmed, before, during or, preferably, after, each step of synthesis and can thereafter be read, thereby identifying the molecule or its components and order of addition, or process of synthesis.

While many well known read only memory devices use fuse structures that are selectively "blown" to store data points, with a fuse located at each possible data address in an array, among the devices of interest herein are those that rely on antifuse programming technology, in which short circuits are selectively created through an insulating layer separating word and bit lines in an array. Due to the relatively low level of voltage supplied by the transmitted signal when the memory device is passive, antifuse memories are readily used because of the lower voltage requirements for writing.

Thus, suitable memory devices, are about 1–20 mm in the smallest dimension [or smaller], are rapidly programmable [1 sec, preferably 1 msec or less], can be interrogated from a distance [distances of about a centimeter up to about an inch are presently preferred], and are programmable using electromagnetic radiation, preferably frequencies, such as those within the radio frequency range, that do not alter the assessed activities and physical properties of the molecules and biological particles of interest.

Devices that rely on programmable volatile memories are also intended for use herein. For example, a battery may be used as to supply the power to provide an operating voltage to the memory device. When a battery is used the memory can be an EEPROM, a DRAM, or other erasable memory requiring continuous power to retain information. It may be advantageous to combine the antenna/rectifier circuitry with a battery to create a passive/active device, in which the voltages supplied by each source supplement each other. For example, the transmitted signal could provide the voltage for writing and reading, while the battery, in addition to supplementing this write/read voltage, provides a refresh voltage for a DRAM memory so that data is retained when the transmitted signal is removed. A 2 mm×2 mm×0.1 mm chip [or 3 mm×3 mm×0.1 mm–1 mm, preferably 0.9 mm] is presently among the preferred chips [fabricated by Sokymat]. This chip has monolithic antenna. Such chips addressable [read/write] using high radiofrequency range to microwave [GHz] range frequencies.

a. Antifuses

An antifuse contains a layer of antifuse material sandwiched between two conductive electrodes. The antifuse device is initially an open circuited device in its unprogrammed state and can be irreversibly converted into an essentially short circuited device by the application of a programming voltage across the two electrodes to disrupt the antifuse material and create a low resistance current path between the two electrodes.

An exemplary antifuse structure for use herein is formed by defining a word line of heavily N-doped polysilicon on an insulating substrate, depositing an antifuse layer of lightly N-doped semiconductor over the polysilicon, and defining a metal address [or bit] line upon and in electrical contact with the antifuse layer. The semiconductor material used for the antifuse layer is typically selected from among silicon, germanium, carbon and alpha-tin. The properties of the semiconductor material are such that the material is essentially non-conductive as long as the voltage across it does not exceed a threshold level. Once the threshold voltage is exceeded, a conductive filament is formed through the semiconductor so that the resistance between the metal and polysilicon lines at the points at which they cross irreversibly switches from a high resistance state to a relatively low resistance state.

To program or change the resistance of the antifuse from a very high level [greater than 100,000,000 ohms] to a low level [less than 1000 ohms], a voltage of sufficiently high electrical field strength is placed across the antifuse film to create a short circuit. The voltage level required to induce breakdown is determined by the level of dopant in the antifuse layer. As breakdown occurs electrical current will flow through one small region of the film. The current is limited by the resistance of the filament itself as well as any series resistance of conductive layers or logic devices [transistors] in series with the antifuse.

Examples of the antifuse and its use as a memory cell within a Read-Only Memory are discussed in Roesner et al., "Apparatus and Method of Use of Radio frequency Identification Tags", U.S. Pat. No. 5,583,819, Roesner, "Method of Fabricating a High Density Programmable Read-Only Memory", U.S. Pat. No. 4,796,074 (1989) and Roesner, "Electrically Programmable Read-Only Memory Stacked above a Semiconductor Substrate", U.S. Pat. No. 4,442,507 (1984). A preferred antifuse is described in U.S. Pat. No. 5,095,362. "Method for reducing resistance for programmed antifuse" (1992) [see, also U.S. Pat. No. 5,412,593 and 5,384,481] and U.S. Pat. No. 5,583,810.

U.S. Pat. No. 5,095,362 provides a method for fabricating a layer of programmable material within an antifuse that exhibits relatively lower than normal resistance in its programmed state and also provides a semiconductor device containing an antifuse film of the type composed of semiconductor material having a first electrical state that is characterized by high electrical resistivity and a second electrical state that is characterized by low electrical resistivity.

The means for selectively decreasing resistivity includes nonactivated conductive dopants that are ion implanted within the otherwise highly resistive semiconductor material The dopants as implanted are in a nonactivated state so that the dopants do not enhance the conduction of carriers in the film. Once activated, the dopants enhance the conduction of carriers in the film. Activation of the dopants occurs upon application of a threshold voltage across a predetermined and selected portion of the material in which the dopants are disposed. The selected portion is defined by the crossover point of selected word and bit [or address] lines. The dopants are N-type, selected from among antimony, phosphorous, arsenic, and others to provide additional charge carriers. The implant dosage is used to determine the threshold voltage level that will be required to induce formation of the conductive filament. P-type dopants, such as boron, may also be used to affect a change in programming voltage.

b. A recording device with non-volatile memory

Figure 5:
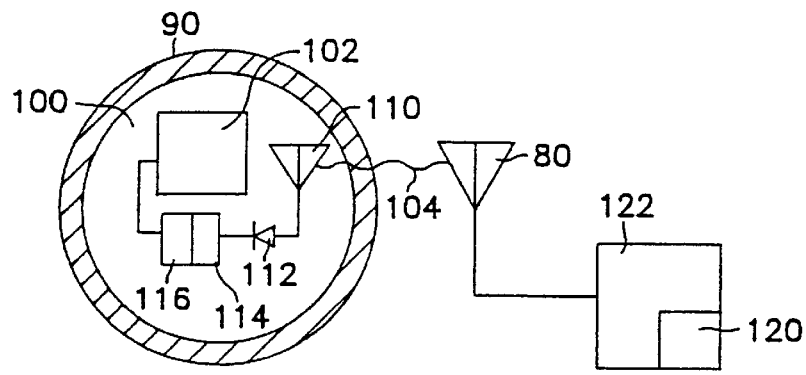
FIG. 5 is a block diagram of the data storage means and supporting electrical components of a preferred embodiment.

FIG. 5 depicts a recording device containing a non-volatile electrically-programmable read-only memory [ROM] 102 that utilizes antifuse technology [or EEPROM or other suitable memory] is combined on a single substrate 100 with a thin-film planar antenna 110 for receiving/ transmitting an RF signal 104, a rectifier 112 for deriving a voltage from a received radio frequency [RF] signal, an analog-to-digital converter [ADC] 114 for converting the voltage into a digital signal for storage of data in the memory, and a digital-to-analog converter [DAC] 116 for converting the digital data into a voltage signal for transmission back to the host computer is provided. A single substrate 100 is preferred to provide the smallest possible chip, and to facilitate encapsulation of the chip with a protective, polymer shell [or shell +matrix or matrix material] 90. Shell 90 must be non-reactive with and impervious to the various processes that the recording device is being used to track in order to assure the integrity of the memory device components on the chip. Materials for the shell include any such materials that are known to those of skill in the art [see, e.g., Hiroshi et.al., eds. (1995) *Polymeric Materials for Microelectronic Applications: Science and Technology*, ACS Symposium Series No. 579], including glasses, ceramics, plastics and other inert coatings.

Based on current semiconductor integrated circuit fabrication process capabilities, in a preferred embodiment the finished chip on which all of the listed components are integrated is on the order of 1 mm×1 mm [~40 mils×40 mils], with a memory capacity of about 1024 bits, but can have greater or lesser capacity as required or desired. Greater memory capacity, where needed, and smaller chips, however, will be preferred.

The chip may be larger to accommodate more memory if desired, or may be smaller as design rules permit smaller transistors and higher device densities, i.e., greater memory capacity.

The antifuse ROM structure described herein, and the method for fabricating the same, are based upon the know devices [see, e.g., U.S. Pat. No. 4,424,579, issued Jan. 3, 1984, No. 4,442,507, issued Apr. 10, 1984, No. 4,796,074, issued Jan. 3, 1989, and No. 5,095,362, issued Mar. 10, 1992, all of Roesner, No. 4,598,386, issued Jul. 1, 1986, of Roesner et al., and No. 5,148,256, issued Sep. 15, 1992 and No. 5,296,722, issued Mar. 22, 1994, to Potash, et al., and also U.S. application Ser. No. 08/379,923, filed Jan. 27, 1 995, to Roesner et al.].

In an antifuse-type memory device, the individual memory cells are arranged in arrays of orthogonal conductive word and bit lines to obtain the smallest possible memory array size. For example, for 1024 bits of memory, there are 32 word lines and 32 bit lines for a square array. Memories with greater capacity may also be used. Schottky diodes are formed generally corresponding to the points at which the word and bit lines cross. The word and bit lines are separated by an undoped or lightly-doped semiconductor layer with interstitial doping. The semiconductor layer may also be amorphous silicon with implanted dopants in a nonactivated state. Each of these crossover points is a memory cell and is the equivalent of a programmable switch in series with a Schottky diode. Data are stored by the switch being ON or OFF. As fabricated, an antifuse memory device has all of its switches in the OFF state. A switch is turned on by applying a voltage in excess of a pre-determined threshold voltage to one of the word lines while setting a selected bit line to a low logic level. The threshold voltage is determined by the impedance of the semiconductor layer, i.e., its doping level. According to the process for fabricating the antifuse memory of the preferred embodiment, the impedance can be less than 200 ohms with a threshold voltage for programming as low as 3 volts. Since in the embodiment described herein the programming voltage is provided solely by the rectified RF signal, a low threshold is preferred. Application of voltage exceeding the threshold activates the interstitial dopant in the semiconducting film at the point corresponding to the cross-over between the two lines, causing a short between the word and bit lines and irreversibly turning on that particular switch or memory cell. Address decoders, as are known in the art, are used to selectively address the word and bit lines for purposes of writing information to and reading stored information from the memory array. [See, e.g., U.S. Pat. No. 5,033,623, 5,099,226, 5,105,190, 5,218,343, 5,323,704]. Exemplary means for decoding information to be stored in memory and to be read from memory are provided in Pat. No. 4,442,507 and No. 4,598,386.

Information to be written into the memory need not be detailed since the data stored in the memory is primarily acting as an identification marker that is traceable to a more detailed record stored in the host computer memory 120, independent of the memory associated with the matrix support or tagged molecule or biological particle. In this manner, the RF signal from transmitter 80 that is used to provide the power and the signal to the matrix particle memory need only address a single memory cell to indicate that a nascent oligomer linked to or in proximity to the memory device has been subjected to a given process step or to identify a molecule or biological particle. In other words, a conventional "push-pull" type of address decoder, where only one bit line and one word line are driven high and low, respectively, at any given time, may be used. Thus, a sophisticated memory addressing system need not be provided on the matrix particle memory chip, and shift registers may be used to control memory addressing. Alternatively, a microprocessor which is mask-programmed during the fabrication process for controlling an address bus which connects the ADC 114 and the DAC 116 to the memory array may also be built onto the same substrate on which the memory and other components are integrated. Other integrated means for selectively addressing locations within the memory are known and will be apparent to the practitioner skilled in the art.

As described above, antifuse memories are well known in the art. These memories include structures in which the word and bit lines may be made of either N+ polysilicon or metal [aluminum or aluminum-silicon], separated by silicon dioxide ($SiO_2$), silicon nitride ($Si_3N_4$), combinations thereof, or amorphous silicon alone or in combination with $SiO_2$ and/or $Si_3N_4$. In each case, a short circuit is created at locations in the antifuse material corresponding to the crossover location of selected word and bit lines by applying a voltage in excess of a pre-determined threshold voltage.

Examples of alternate means for forming an antifuse memory are provided in the following U.S. Pat. Nos.: No. 5,248,632, issued Sep. 28, 1993, of Tung et al.; U.S. Pat. No. 5,250,459, issued Oct. 5, 1993, of Lee, U.S. Pat. No. 5,282,158, issued Jan. 25, 1994, of Lee; U.S. Pat. No. 5,290,734, issued Mar. 1, 1994, of Boardman, et al.; U.S. Pat. No. 5,300,456, issued Apr. 5, 1994, of Tigelaar et al.; U.S. Pat. No. 5,311,039, issued May 10, 1994, of Kimura, et al.; U.S. Pat. No. 5,316,971, issued May 31, 1994, of Chiang et al.; U.S. Pat. No. 5,322,812, issued Jun. 21, 1994, of Dixit, et al.; U.S. Pat. No. 5,334,880, issued Aug. 2, 1994, of Abadeer, et al., and others.

Generally for use in the methods herein, non-volatility of the memory or the ability to lock or prevent erasure is preferred since power is applied to the chip only when it is subjected to the RF or other transmission signal for reading or reading and writing. Further considerations are the voltage levels required for writing into memory, since the threshold voltage must be less than the maximum voltage of the rectified RF signal in order to assure that sufficient voltage is always available during the writing process. The write voltage may be enhanced by supplementing the RF-supplied voltage with optically-generated voltage, such as a photocell. Photocells on semiconductor substrates are well known in the art and could be easily integrated onto the chip. A laser or other light source could be readily included in the write apparatus to illuminate the chip coincident with transmission of the RF write signal. Similarly, other forms of electromagnetic radiation may be used to provide additional power, if needed. Although antifuse memories are not designed to be erasable, it may be desirable to re-use the devices if the memory becomes full. In such instances, conventional electrically programmable erasable read only memories [EEPROMs] may be used instead. Since EEPROMs require higher write voltage levels, it may be desirable to supplement the RF-supplied voltage as described above. In EEPROMs, stored data can be erased by exposing the device to UV light.

Signal rectifier 112 may be one or more Schottky diode(s), making it readily incorporated into the fabrication process used for the memory array. Other means for signal rectification may be used as are known. The ADC 114 and DAC 116 are well-known devices and are readily integrated onto the substrate 100 using the fabrication process described in the references for the memory array. Radio frequency modulation techniques, which are known in the art, for example, pulse code modulation, may be adapted to permit direct digital transmission, in which case the ADC and DAC may not be required.

Antenna 110 is formed during the fabrication process using conventional photolithographic techniques to provide one or more metal structures, such as aluminum, to receive a pre-determined wavelength RF transmission. The antenna may be a simple straight line half-wave antenna which is created by patterning a structure during the second metal process steps so that the structure has a length equal to one-half of the wavelength of the selected RF transmission frequency in free space. Another option for formation of the antenna is as a small loop, either on a dedicated portion of the chip, or encircling the other components of the chip, also formed during the second metal step of the fabrication process. It is noted that, in a typical semiconductor fabrication process, such as would be compatible with the preferred antifuse memory, the first and second metal steps include depositing a layer of aluminum, then patterning the aluminum photolithographically followed by a plasma etch to define the desired features. Except where vias are formed, the two metal layers are separated by a dielectric film. Dipole antennas may be formed by patterning the second metal in a similar manner, with the dimensions of the antenna being selected for the appropriate RF frequency. The two metal layers may also be used to form a microstrip antenna structure by selecting the dielectric film between the metal layers such that it has a dielectric constant and thickness appropriate so that the microstrip is resonant at one-half of the RF wavelength. [The first metal layer provides the ground plane.] The metal structures, which may be square patches, circles, lines, or other geometries, are defined photolithographically during the normal masking steps of the first and second metal processes. Other antenna structures which can be configured as a thin film device for integration onto a common substrate with the memory structure and other components may be used and will be apparent to those skilled in the art. Similarly, a resonant circuit [inductor-capacitor] can be readily integrated onto the chip, with the resonant circuit being tuned to the RF carrier signal of the transmitter.

Frequency tuning of either an antenna or resonant circuit can provide additional coding capability. For example, a first group of memory devices can be tuned to receive a carrier wave of a first RF frequency, e.g., $f_1$, and a second group could be tuned to receive a second frequency $f_2$, and so on. The separate carrier frequencies could provide additional means for tracking or providing information to the devices, even if the groups become intermixed.

The RF antenna may, in an alternate embodiment, be formed external to the semiconductor substrate. In this configuration, a separate conductive wire, which acts as an antenna, will be attached to a bond pad formed on the chip using methods known to those skilled in the art. The wire will then be stabilized when the chip is encased in the protective shell, so that the antenna extends at some angle to the chip.

Also, as an alternative to signal transmission via RF, the antifuse or other semiconductor memory and supporting circuitry can receive the addressing commands and device power by optical transmission. In this embodiment, the RF antenna 110 would be replaced by a photocell that generates sufficient write voltage to exceed the threshold voltage. For the addressing commands, the RF transmitter 80 is replaced by a light source, and the commands may be transmitted digitally by pulsing the optical transmitter, which can be a laser, flash lamp or other high intensity light source. It is noted that the light intensity must be sufficient to generate adequate voltage, either singly or in conjunction with a second power generating device, in the photocell to write into memory, but not so high that it damages the metal interconnect on the chip. With digital data transmission analog-to-digital and digital-to-analog conversion circuitry can be eliminated.

c. Other memory devices

Other types of electrically-programmable read-only memories, preferably non-volatile memories, which are known in the art, may be used [see, e.g., U.S. Pat. No. 5,335,219]. Chips, such as those sold by Actel, Mosaic, Lattice Semiconductor, AVID, Anicare, Destron, Rayethon, Altera, ICT, Xilinix, Intel and Signetics [see, e.g., U.S. Pat. Nos. 4,652,528, 5,044,623, 5,099,226, 5,218,343, 5,323,704, 4,333,072, 4,321,069, 4,318,658, 5,121,748, 5,214,409, 5,235,326, 5,257,011 and 5,266,926] may be used herein. Preprogrammed remotely addressable identification tags, such as those used for tracking objects or animals [see, e.g., U.S. Pat. Nos. 5,257,011, 5,235,326, 5,226,926, 5,214,409, 4,333,072, available from AVID, Norco, Calif.; see, also U.S. Pat. No. 5,218,189, 5,416,486, 4,952,928, 5,359,250] and remotely writable versions thereof are also contemplated for use herein. Preprogrammed tags may be used in embodiments, such as those in which tracking of linked molecules is desired. Devices sold by XCI [San Jose, Calif.] that operate in the lower frequency ["900 MHz] range are also preferred herein.

d. Pre-coded memory devices

Alternatively, the matrices or strips attached thereto may be encoded with a pre-programmed identifying bar code, such as an optical bar code that will be encoded on the matrix and read by laser. Such pre-coded devices may be used in embodiments in which parameters, such as location in an automated synthesizer, are monitored. The identity of a product or reactant determined by its location or path, which is monitored by reading the chip in each device and storing such information in a remote computer. Read/write tags such as the IPTT-100 [BioMedic Data Systems, Inc., Maywood, N.J.; see, also U.S. Pat. Nos. 5,422,636, 5,420,579, 5,262,772, 5,252,962, 5,250,962, and U.S. application Ser. Nos. 08/497,349 and 08/322,644, published as GB 2,297,227] are also contemplated for use herein.

Among the particularly preferred devices are the chips [particularly, the IPTT-100, Bio Medic Data Systems, Inc., Maywood, N.J.; see, also U.S. Pat. Nos. 5,422,636, 5,420,579, 5,262,772, 5,252,962 and 5,250,962 and U.S. application Ser. Nos. 08/497,349 and 08/322,644, published as GB 2,297,227] that can be remotely encoded and remotely read. These devices, such as the IPTT-100 transponders that are about 8 mm long, include a recording device, an EEPROM, a passive transponder for receiving an input signal and transmitting an output signal in response. In some embodiments here, the devices are modified for use herein by altering the geometry. They are folded in half and the antenna wrapped around the resulting folded structure. This permits convenient insertion into the microvessels and formation of other combinations.

These devices include a power antenna means [see, e.g., U.S. Pat. No. 5,250,944 and U.S. Pat. No. 5,420,579] for receiving the input signal, frequency generator and modulator means for receiving the input signal the receive antenna means and for generating the output signal. The output signal has a frequency different from the input frequency, outputs the output signal in response the input signal. The input signal having a first frequency, the output signal has a second frequency that is a multiple of the first frequency, and is greater that the first frequency. It also includes a transmitting antenna means for receiving the output signal from the frequency generator and modulator means and that transmit the output signal. Data are stored within the transponder within a reprogrammable memory circuit that is programmed by the user [see, e.g., U.S. Pat. No. 5,422,636 and EP 0 526 173 A3]. A transponder scanner for scanning and programming the transponder is also available [Bio Medic Data Systems Inc. DAS-5001 CONSOLE™ System, e.g., U.S. Pat. No. 5,252,962 and U.S. Pat. No. 5,262,772].

e. Other memories

Another such device is a 4 mm chip with an onboard antenna and an EEPROM [Dimensional Technology International, Germany]. This device can also be written to and read from remotely.

ID tags available from IDTAG™ Inc, particularly the IDT150 read/write transponder [ITDAG™ Ltd. Bracknell, Berks RG12 3XQ, UK], discussed above, are also preferred herein.

Among other tags for use herein are magnetoelastic tags, which contain a metallic glass whose nuclei resonate and give off a radio signal when the tag passes through an oscillating magnetic field. Such tags are manufactured by Sensormatic Electronics Corporation, Deerfield Beach, Fla. [see, e.g., U.S. Pat. Nos. 5,594,420, 5,321,412, 5,218,371, 5,051,726, 5,517,195, 4,999,641, 5,006,856].

f. Monolithic semiconductors

Additionally, smaller monolithic devices are of interest herein. Monolithic tags can be smaller than RF tags and are faster. A 2.45 GHz tag can communicate 360 times faster than a 6.78 MHz tag and 20 K faster than a 125 KHz (RF) tag. A microwave tag contains an antenna, which is a dipole or loop or a monolithically etched into the chip or bonded to the chip; a rectifier circuit that converts the incoming microwave signal to a DC level to power the chip; a power capacitor that stores the charge to hold power during chip communication; analog circuitry that detects code transitions and amplifies signals up to proper digital communication levels; digital circuitry that provides digital processing, modulates communication codes, communicates and controls memory; EPROM to store permanent information, and RAM to hold variable information, such as write information that is transmitted to the chip form external transmission sources. For example, in a particular embodiment of an electromagnetically programmable tag, such as, for exemplification purposes an RF tag or microwave tag, a single chip tag is formed entirely on a single substrate [about 2 mm×2 mm×0.1 mm or less]. More specifically, referring to FIG. 51, a monolithic tag, such as an RF tag, preferably a microwave tag, is shown and generally designated 4700. This monolithic tag is sized such that the substrate has following overall external dimensions: width 4710 of 2 mm wide, length 4708 of 2 mm, and a height 4714 of 0.1 mm. As a result of this miniaturization of the tag, a variety of shapes and sizes of the tags may be created [see, e.g., U.S. Pat. No. 4,857,893 issued to Carroll in 1989, entitled "Single Chip Transponder Device", which describes a single substrate (monolithic) RF transponder which, due to its single substrate, is simple to manufacture].

In FIG. 51, the tag 4700 is shown having a substrate 4702 is formed with an antenna 4714. This antenna is preferably formed on the substrate using a metalization process wherein a metal is placed on a pattern on the top surface of the substrate to create a particular antenna. As shown, the antenna is substantially square, tracing out a coiled antenna beginning at pad 4712, and ending at conductor 4706 which attaches back to the circuitry 4704. It should be appreciated that while the antenna is shown to be square, any other shapes could be used. In particular, a circular antenna could be formed just as easily on the surface of the substrate. It should be appreciated, however, that the functionality of the antenna are likely very similar between a square antenna and a circular antenna. In addition to the antenna as shown, there may be a second antenna on the back side of the substrate (not shown) which could be used to increase the number of windings or, as an alternative, be tuned for a different frequency range than the antenna patterned on the upper surface of the substrate 4702.

Referring to FIG. 52, the tag is shown in plan view and has circuitry 4704 which includes specific logic and control electronics generally denoted 4706. The pattern of the antenna 4714 is easily appreciated from this view. Moreover, the circular equivalent can be easily envisioned on the substrate 4702 to spiral around the circuitry 4704 to create a similarly sized antenna.

The specific electronic circuitry that is contained in circuitry 4704 is known and well described [see, e.g., U.S. Pat. No. 4,857,893, and U.S. Pat. No. 5,345,231, discussed above] For example, U.S. Pat. No. 5,345,231, entitled "Contactless Inductive Data-Transmission System" discloses circuitry capable of communicating identification information across a wireless communication system which employs an inductive coupling. Specifically, with reference to FIG. 2 of that reference, this inductive coupling provides the power to run the tag electronics, as well as provides the communication channel with which the identification information travels. The circuitry includes a rectifier attached to the antenna to receive an electromagnetically coupled signal, and to create its own power from the signal. In addition to the rectifier, a clock extractor and demodulator also receive the antenna's signal. The clock extractor recreates a communication clock, and the demodulator decodes the signal received from the antenna using that clocking information. This information is provided to a control unit which either programs or downloads the contents of a memory bank. In the particular tag discussed herein, the memory bank can include a single data bit, or may be easily expanded as is generally known in the art to a variety of memory sizes, up to several kilobytes. Once the memory has been accessed, the control unit can communicate with the base transmitter/receiver by sending data to the modulator which is also electrically connected to the antenna. In that manner, the antenna can be used to either receive a signal from the transmitter, or to transmit a signal to the receiver.

The antenna for use with these particular electronics is tuned for a resonant frequency of approximately 125 kHz. It is to be appreciated, as discussed above, that the antenna can be tuned to receive a variety of frequencies, including 125 kHz, but also in the higher frequency RF-microwave range (300 MHz and higher) and preferably microwave range (800 MHz to 300 GHz, corresponding to wavelengths of 1 meter to 1 mm). In preferred embodiments herein, the monolithic-antenna etched silicon remote memory is powered by about a 900 MHz, 1.25 GHz or 2.45 GHz microwave band field.

It should be noted, however, that depending on the frequencies to be received, the antenna shape and size can be altered. In fact, a single antenna that is capable of receiving a number of frequencies can be created by having electrical leads attached to a number of points along the length of the antenna. As a result, a single antenna could be used to receive a number of frequencies, where the frequency to be received could be set by an initial communication with the tag. Because of such frequency specification, a number of tags could be addressed simultaneously in a "batch" read or write process.

A batch read/write process permits a single transmitter station to address more than one tag at the same time which is appropriate when programing a number of tags with the same or similar information. Thus, by batch writing the information to a number of tags, the programming process is shortened and simplified, while at the same time, minimizing the opportunity for error. Batch reading can be effected with RF and microwave chips. In a batch read, the reader sends out an ID signal to all of the tags in the batch asking all other tags to turn off, thereby permitting the reader to extract information from the identified tag. The reader will then readdress the batch looking for the next tag and extract its information. Thus, the faster tags, such as the microwave tags can be advantageously employed for batch reading.

The ability to batch access the tags permits the transmitter/receiver to identify any number of tags within an area by one access process instead of having to access each tag individually. In addition to accessing all tags at one time, there could be a variety of signal types which could narrow the field of access. One manner of restricting the access to tags, such as an RF tag, could be to make any interrogation either code or frequency discriminating. Such discrimination would occur, for example, by selecting only the particular RF tags within a frequency range. On the other hand, the specific address code of a number of RF tags could be programmed such that by identifying, for example, the first four of an eight bit address scheme, only a portion of the RF tags identifiable with those eight addressing bits could be addressed.

Figure 2:
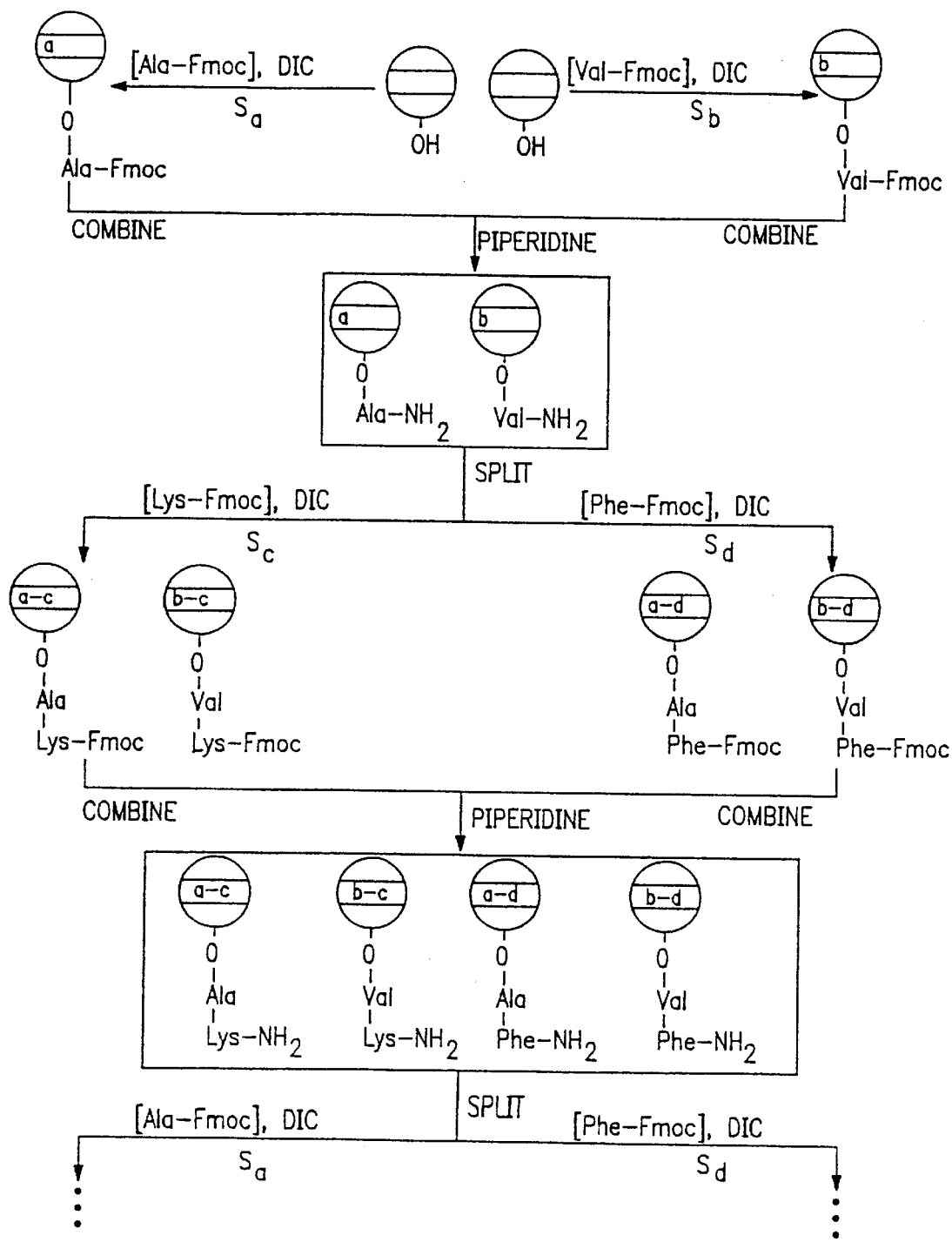
FIG. 2 depicts combinatorial synthesis of peptides on a matrix with memory. Each amino acid has a corresponding code, a,b, c . . . , in the matrix memory, and L represents a Linker between the memory device and the pharmacophore. Again as in FIG. 1, the matrix supports may be engraved with a code or symbology associated with information stored in a remote memory.

The circuitry for communication with a transmitting and receiving base is known [see, e.g., U.S. Pat. No. 4,857,893, entitled "Single Chip Transponder Device", see esp. FIG. 2 of that reference]. Briefly, an antenna receives a carrier signal which is provided to a rectifier and demodulator, as well as a timing decoder. The rectifier captures a portion of the carrier signal to derive dc power to drive the RF tag itself. The timing decoder uses the remaining portion of the antenna signal to derive the timing signals necessary to control the data storage and generation of the RF tag. Once accessed, the data generator creates a data signal which is modulated and supplied to the antenna for retransmit back to the transmitter/receiver unit.

Referring now to FIG. 53, the single substrate tag shown in FIGS. 51 and 52 is shown attached to a stirring bar, which is commonly known in the industry. The stirring bar includes a material which is capable of magnetic interaction. This material is then encapsulated in an inert material such as a polymer which insulates the material from the environment. As shown partially cut away for clarity, the insulation material 4718 covers the entire outer surface of the material 4716. Prior to encapsulation, the monolithic RF tag 4700 is attached to the material such that, once encapsulated, the RF tag is also encapsulated.

Once a stirring bar is equipped with an RF tag, the stirring bar may be placed in a container and the container may then be easily tracked through any environment by placing the container over an identification station. Moreover, by placing a number of stirring bars in different containers, with each stirring bar having its own identification number, virtually an unlimited number of containers may be tracked. This would be particularly useful in environments where there is a need to manipulate a large number of containers, such as a biomedical laboratory. It should be appreciated, however, that in addition to placing the monolithic RF tag on a stirring bar, the tag may be attached to any other commonly used devices to facilitate tracking those devices. For instance, as described elsewhere herein, each container may be manufactured with the monolithic tags embedded in the container or in sleeve that is removable attached to a container. This permits tracking of the container throughout its environment, without the need to add any device or item to the contents of the container.

In addition to allowing the simple tracking of various containers, it is possible to place a plurality of tags, such as different RF tags, within a container that is already tagged. More specifically, it is possible to place a tag in a container that is already identified with one tag. This combining of multiple tags would enable a greater level of tracking of the container. For instance, a beaker could be formed with a RF tag integral to its structure. Once identified, the beaker may be filled with a variety of materials, each having its own identification number. Thus, when solution B is added to beaker A, an RF tag indicating the material B can be dropped into the beaker A. Likewise, when solution C is added to beaker A, an RF tag indicating the material C can be dropped in the beaker. As a result of this marking method, it would be possible to verify the exact contents of a container. Specifically, by reading the various RF tags within the beaker A (solution B and solution C) the entire contents of the container would be identified.

Alternatively, in addition to, or instead of, identifying the contents of a container, it would also be possible to track the whereabouts of a container by adding identifying RF tags at various locations in its path. For instance, a beaker could be marked with an identifying RF tag A, and an identifying RF tag B could be added when a particular process is performed on the contents of the beaker A. Similarly, an identifying RF tag C could be added to the beaker at the next process step. Thus, the RF tags in the beaker would indicate the exact historical location of the container A by decoding the contents of the RF tags contained therein.

In addition, the RF tags could be used to provide a combination of the above described contents and location based information. This combination would provide a means to analyze a "chain of possession" for various contents of a container. In other words, the contents of a beaker could be determined by identifying the RF tags. This information would provide a history of the contents of the container, as well as location of the processes which were performed on the container.

2. Optically or magnetically programmed devices

In addition to electrically-programmable means for storing information on the matrix particles, and the 2-D bar codes, described above, other optical and magnetic means may be used. Such optical storage means are known [see, e.g., U.S. Pat. No. 5,136,572, issued Aug. 4, 1992, to Bradley]. Here, an array of stabilized diode lasers emits fixed wavelengths, each laser emitting light at a different wavelength. Alternatively, a tunable diode laser or a tunable dye laser, each of which is capable of emitting light across a relatively wide band of wavelengths, may be used. The recording medium is photochemically active so that exposure to laser light of the appropriate wavelength will form spectral holes.

Figure 7:
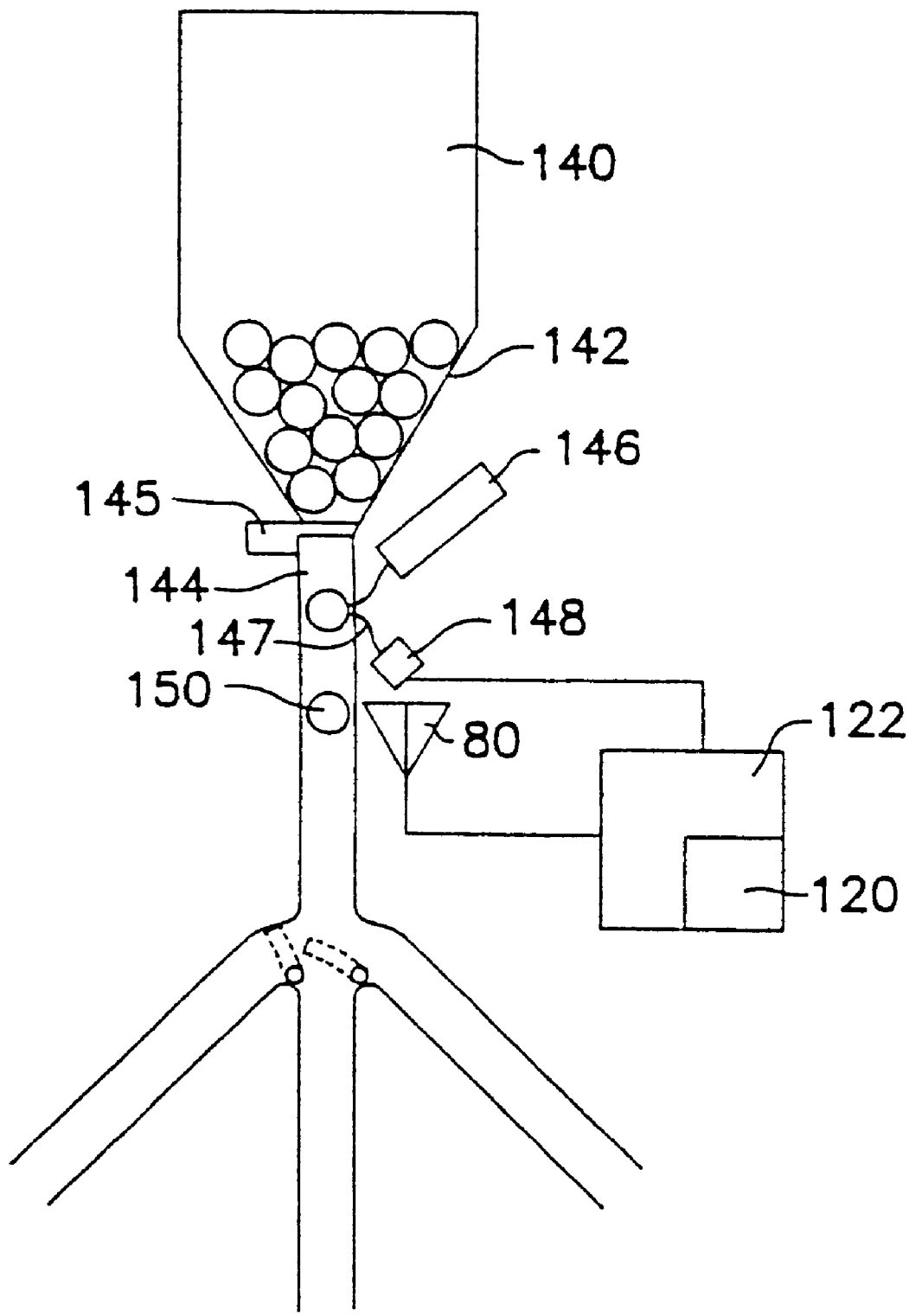
FIG. 7 is an illustration of an exemplary apparatus for separating the matrix particles with memories for individual exposure to an EM signal.
Figure 8:
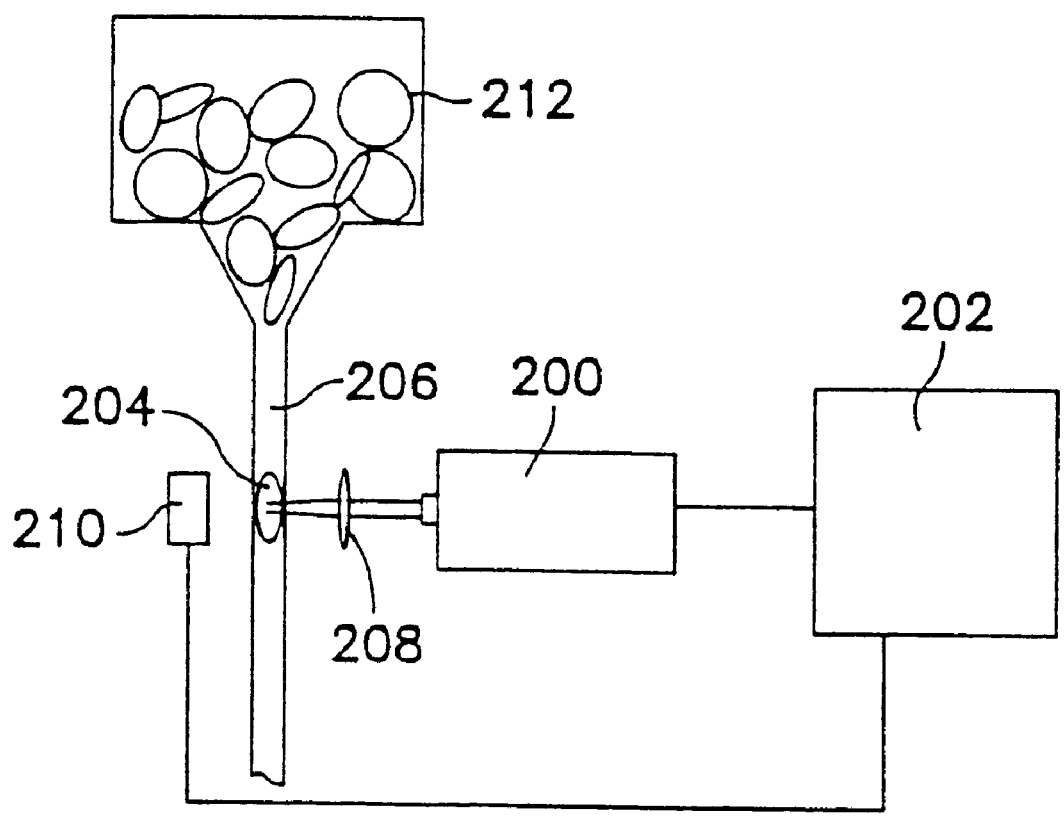
FIG. 8 is an illustration of a second exemplary embodiment of an apparatus for separating matrix particles for individual exposure to an optical signal.

As illustrated In FIG. 8, an optical write/read system is configured similar to that of the embodiment of FIG. 7, with a vessel 212 containing a number of the particles which are separated and oriented by passing through a constricted outlet into a write/read path 206 that has an optically-transparent tube [i.e., optically transparent to the required wavelength(s)] with a cross-section which orients the particles as required to expose the memory surface to the laser 200 which is capable of emitting a plurality of discrete, stable wavelengths. Gating and detection similar to that described for the previous embodiment may be used and are not shown Computer 202 controls the tuning of laser 200 so that it emits light at a unique wavelength to record a data point. Memory within computer 202 stores a record indicating which process step corresponds to which wavelength. For example, for process A, wavelength $\lambda_1$, e.g., 630 nm [red], for process C, $\lambda_2$, e.g., 550 nm [yellow], and for process E, $\lambda_3$, e.g., 480 nm [blue], etc. The recording medium 204 is configured to permit orientation to repeatably expose the recording side of the medium to the laser beam each time it passes through tube 206. One possible configuration, as illustrated here, is a disc.

Other sorting devices are also provided herein [see, e.g., FIGS. 67–69].

To write onto the recording medium 204, the laser 200 emits light of the selected wavelength to form a spectral hole in the medium. The light is focused by lens 208 to illuminate a spot on recording medium 204. The laser power must be sufficient to form the spectral hole. For reading, the same wavelength is selected at a lower power. Only this wavelength will pass through the spectral hole, where it is detected by detector 210, which provides a signal to computer 202 indicative of the recorded wavelength. Because different wavelengths are used, multiple spectral holes can be superimposed so that the recording medium can be very small for purposes of tagging. To provide an analogy to the electrical memory embodiments, each different wavelength of light corresponds to an address, so that each laser writes one bit of data. If a large number of different steps are to performed for which each requires a unique data point, the recording media will need to be sufficiently sensitive, and the lasers well-stabilized, to vary only within a narrow band to assure that each bit recorded in the media is distinguishable. Since only a single bit of information is required to tag the particle at any given step, the creation of a single spectral hole at a specific wavelength is capable of providing all of the information needed. The host computer then makes a record associating the process performed with a particular laser wavelength.

For reading, the same wavelength laser that was used to create the spectral hole will be the only light transmitted through the hole. Since the spectral holes cannot be altered except by a laser having sufficient power to create additional holes, this type of memory is effectively non-volatile. Further, the recording medium itself does not have any operations occurring within its structure, as is the case in electrical memories, so its structure is quite simple. Since the recording medium is photochemically active, it must be well encased within an optically transmissive [to the active optical wavelength(s)], inert material to prevent reaction with the various processing substances while still permitting the laser light to impinge upon the medium. In many cases, the photochemical recording media may be erased by exposure to broad spectrum light, allowing the memory to be reused.

Writing techniques can also include the formation of pits in the medium. To read these pits, the detector 210 with be positioned on the same side of the write/read tube 206 as the laser 200 to detect light reflected back from the medium. Other types of optical data storage and recording media may be used as are known in the art. For example, optical discs, which are typically plastic-encapsulated metals, such as aluminum, may be miniaturized, and written to and read from using conventional optical disc technology. In such a system, the miniature discs must be aligned in a planar fashion to permit writing and reading. A modification of the funnel system, described above, will include a flattened tube to insure the proper orientation. Alternatively, the discs can be magnetically oriented. Other optical recording media that may be appropriate for use in the recording devices and combinations herein include, but are not limited to, magneto-optical materials, which provide the advantage of erasability, photochromic materials, photoferroelectric materials, photoconductive electro-optic materials, all of which utilize polarized light for writing and/or reading, as is known in the art. When using any form of optical recording, however, considerations must be made to insure that the selected wavelength of light will not affect or interfere with reactions of the molecules or biological particles linked to or in proximity to matrix particles.

a. Three dimensional optical memories

3-D memory storage devices include persistent hole burning, phase holograms, and two photon optical 3-D memories that use organic materials and biomolecules. Any such devices are intended for use herein. Of particular interest are those that use organic materials and biomolecules. Such memories can be incorporated into the matrix materials or inert polymeric materials that are derivatized for use as matrices.

Other types of polymeric materials, such as polymeric photorefractive materials (see, e.g., Moerner et al. (1994) *Chem. Rev.* 94:127–155) that are used for information storage may also be used. The photorefractive effect is spacial modulation of the index of refraction due to charge redistribution in an optically nonlinear material. The effect arises when charge carriers, photogenerated by a spatially modulated light intensity, separate by drift and diffusion processes and become trapped to produce a nonuniform space-charge distribution. The resulting space-charge electric field then modulates the refractive index to create a phase grating that can diffract a light beam. These materials may be used for high-density optical data storage, and, thus, be combined with or integrated into the matrices.

Peptide oligomers with azobenzene side chains are used as a medium for holographic data storage [see, e.g., (1996) *Nature* 383:505]. In these materials, light-sensitive azobenzene units are linked to a peptide-like backbone that appears to organize the azobenzenes in a helical stack. When these molecules interact with polarized light, they become uniformly oriented, which leads to refractive index changes in the film, thereby provided an optical storage medium. These holograms are stable at room temperature and are heat stable.

b. 3-D Optical memories and apparatus therefor

Optical memory systems are based on light-induced changes in the optical chemical or physical properties of materials. As such these memories are ideally suited for use in the methods herein and in combination with matrices, since the materials that form the memory may be incorporated into or part of the material from which the matrix is fabricated.

Polymer-based photonic materials that can store 1 trillion bytes of date per cc have been developed [see, e.g., U.S. Pat. Nos. 5,268,862, 5,130,362, 5,325,324; see, also, Dvornikov et al. (1996) *Opt. Commun.* 128:205–210; Dvornikov et al. (1996) *Res. Chem. Intermed.* 22:115–28; Dvornikov et al. (1994) *Proc. SPIE-Int. Soc. Opt. Eng.* 2297:447–51; Dvornikov et al. (1994) *Mol. Cryst. Liq. Cryst. Sci. Technol., Sect. A* 246:379–88; Dvornikov et al. (1994) *J. Phys. Chem.* 98:6746–52; Ford et al. (1993) *Proc. SPIE-Int. Soc. Opt.* 2026:604–613; Ford et al. *Proc. SPIE-Int. Soc. Opt. Eng.* 1853:5–13; Malkin et al. *Res. Chem. Intermed.* 19:159–89; Dvornikov et al. (1993) *Proc. SPIE-Int. Soc. Opt. Eng.* 1852:243–52; Dvornikov et al. (1992) *Proc. SPIE-Int. Soc. Opt. Eng.* 1662:197–204; Prasad et al. (1996) *Mater. Res. Soc. Symp. Proc.* 413:203–213; and Dagani in *Chemical and Eng. News* Sep. 23, 1996, pp. 68–69]. This technology involves using a laser to encode information in a polymeric medium containing dye molecules that have a nonlinear optical property known to those of skill in the art as two-photon absorption. When the dye molecule is irradiated with light of sufficiently high intensity, it absorbs two photons of light simultaneously; the molecule then emits a photon of higher energy. This means that the material can be irradiated with lower energy penetrating light, such infrared or near infrared and produce a higher energy emission in the visible.

In these methods, the writing beam "photobleaches" spots in the recording medium so that those spots when subsequently illuminated with a reading beam will emit either no light or less light than the surrounding medium [see, eg., U.S. Pat. No. 5,325,324; see, also U.S. Pat. No. 5,130,362]. By varying the intensity of the writing laser, the extent of photobleaching can be varied to get a gray-scale, thereby permitting storage of information in analog as well as digital form. Dyes have been developed that are particularly suitable for use in these methods. For example, a stilbene derivative with substituted amino and sulfonyl groups [APSS] has been developed that has very strong 2-photon absorption. The dye is dispersed in a polymer, such as a methacrylate polymer, which then serves as a read/write medium.

Memories based on photochromaic materials, such as 1-nitro-2-naphthaldehyde and the colorless base form of the laser dye rhodamine B, are also available [see, e.g., Dvornikov et al. (1996) *Res. Chem. Intermed.* 22:115–28].

As noted above, incorporation of the these dyes or other such molecules into the polymeric supports used in the syntheses and assays described herein will permit the supports [or portions thereof] to serve as memories to which information can be written and from which it can be read. Thus, for example, instead of using a symbology as described in the embodiments herein, the polymer from which support is made will contain a dye molecule or other molecule that exhibits 2-photon absorption, and thereby serve as a storage medium that can be read or can be a read/write medium. The other portion of the device can be radiation grafted and used as a support for chemical syntheses and assays.

c. Rhodopsins

Another memory means that is suitable for use in the matrix with memory combinations are optical memories that employ rhodopsins, particularly bacteriorhodopsin [BR], or other photochromic substances that change between two light absorbing states in response to light of each of two wavelengths [see, e.g., U.S. Pat. Nos. 5,346,789, 5,253,198 and 5,228,001; see, also Birge (1990) *Ann. Rev. Phys. Chem* 41:683–733]. These substances, particularly BR, exhibit useful photochromic and optoelectrical properties. BR, for example, has extremely large optical nonlinearities, and is capable of producing photoinduced electrical signals whose polarity depends on the prior exposure of the material to light of various wavelengths as well as on the wavelength of the light used to induce the signal. There properties are useful for information storage and computation. Numerous applications of this material have been designed, including its use as an ultrafast photosignal detector, its use for dynamic holographic recording, and its use for data storage, which is of interest herein.

The rhodopsins include the visual rhodopsins, which are responsible for the conversion of light into nerve impulses in the image resolving eyes of mollusks, anthropods, and vertebrates, and also bacteriorhodopsin [BR]. These proteins also include a class of proteins that serve photosynthetic and phototactic functions The best known BR is the only protein found in nature in a crystalline membrane, called the "purple membrane" of Halobacterium Halobium. This membrane converts light into energy via photon-activated transmembrane proton pumping. Upon the absorption of light, the BR molecule undergoes several structural transformations in a well-defined photocycle in which energy is stored in a proton gradient formed upon absorption of light energy. This proton gradient is subsequently utilized to synthesize energy-rich ATP.

The structural changes that occur in the process of light-induced proton pumping of BR are reflected in alterations of the absorption spectra of the molecule. These changes are cyclic, and under usual physiological conditions bring the molecule back to its initial BR state after the absorption of light in about 10 milliseconds. In less than a picosecond after BR absorbs a photon, the BR produces an intermediate, known as the "J" state, which has a red-shifted absorption maximum. This is the only light-driven event in the photocycle; the rest of the steps are thermally driven processes that occur naturally. The first form, or state, following the photon-induced step is called "K", which represents the first form of light-activated BR that can be stabilized by reducing the temperature to 90° K. This form occurs about 3 picoseconds after the J intermediate at room temperature. Two microseconds later there occurs an "L" intermediate state which is, in turn, followed in 50 microseconds by an "M" intermediate state.

There are two important properties associated with all of the intermediate states of this material. The first is their ability to be photochemically converted back to the basic BR state. Under conditions where a particular intermediate is made stable, illumination with light at a wavelength corresponding to the absorption of the intermediate state in question results in regeneration of the BR state. In addition, the BR state and intermediates exhibit large two-photon absorption processes which can be used to induce interconversions among different states.

The second important property is light-induced vectorial charge transport within the molecule. In an oriented BR film, such a charge transport can be detected as an electric signal. The electrical polarity of the signal depends on the physical orientation of molecules within the material as well as on the photochemical reaction induced. The latter effect is due to the dependence of charge transport direction on which intermediates [including the BR state] are involved in the photochemical reaction of interest. For example, the polarity of an electrical signal associated with one BR photochemical reaction is opposite to that associated with a second BR photochemical reaction. The latter reaction can be induced by light with a wavelength around 412 nm and is completed in 200 ns.

In addition to the large quantum yields and distinct absorptions of BR and M, the BR molecule [and purple membrane] has several intrinsic properties of importance in optics. First, this molecule exhibits a large two-photon absorption cross section. Second, the crystalline nature and adaptation to high salt environments makes the purple membrane very resistant to degeneration by environmental perturbations and thus, unlike other biological materials, it does not require special storage. Dry films of purple membrane have been stored for several years without degradation. Furthermore, the molecule is very resistant to photochemical degradation.

Thus, numerous optical devices, including recording devices have been designed that use BR or other rhodopsin as the recording medium [see, e.g., U.S. Pat. Nos. 5,346,789, 5,253,198 and 5,228,001; see, also Birge (1990) *Ann. Rev. Phys. Chem* 41:683–733]. Such recording devices may be employed in the methods and combinations provided herein.

3. Event-detecting embodiment and sensors

Combinations of the matrices with memories and sensors, such as biosensors and devices that measure external parameters are provided. Combinations of memories with sensors are also provided. Various embodiments of the sensors are set forth in the Examples. See, also FIG. 9 and the description below. Examples of glucose sensors, calcium sensors, urea sensors, and intracranial pressure monitors are provided herein. In each embodiment, a memory is included as a means to track patient history and/or to store or record sensed information.

In particular, the memories and memories with matrices provided herein may be advantageously used in combination with sensors, which are devices that measure external parameters, such as pH, temperature, ion concentrations in solutions, and also biosensors, particularly implantable biosensors, which are used to measure internal parameters, such as electrolytes, blood glucose, to monitor blood pressure, and intracranial pressure.

The memories will be combined with sensors known to those of skill in the art as described herein to detect reactions or event, to detect and store the detected information, and to permit remote monitoring of patients or samples.

Also provided herein, are embodiments of matrices with memories in which the matrix is a sol-gel. The sol-gels, which are used to encapsulate biological molecules, such as molecules used as sensors, will include a memory device For example, sol-gel biosensors are known. The improvement herein provides a means to store information regarding the sensed event or detect the event.

a. Event-detecting embodiments and sensors therefor

The reaction- or event-detecting embodiments may be advantageously used in assays, such as the SPA, HTRF, FET, FRET and FP assays described below. In these assays, reaction, such as receptor binding, produces a detectable signal, such as light, in the matrix. If a matrix with memory with a photodetection circuit is used, occurrence of the binding reaction will be recorded in memory. These embodiments may also be used in combination with sensors.

Figure 9:
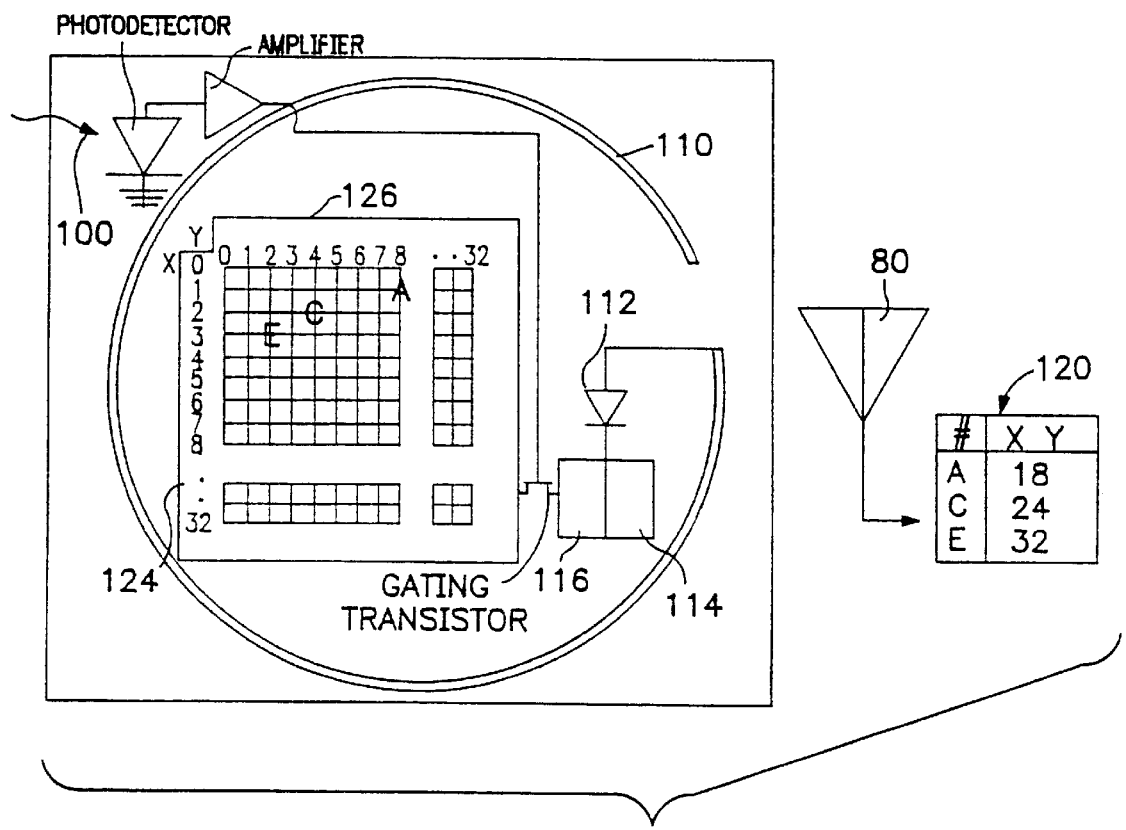
FIG. 9 is a diagrammatic view of the memory array within the recording device, the corresponding data stored in the host computer memory, and included photodetector with amplifier and gating transistor.
Figure 10:
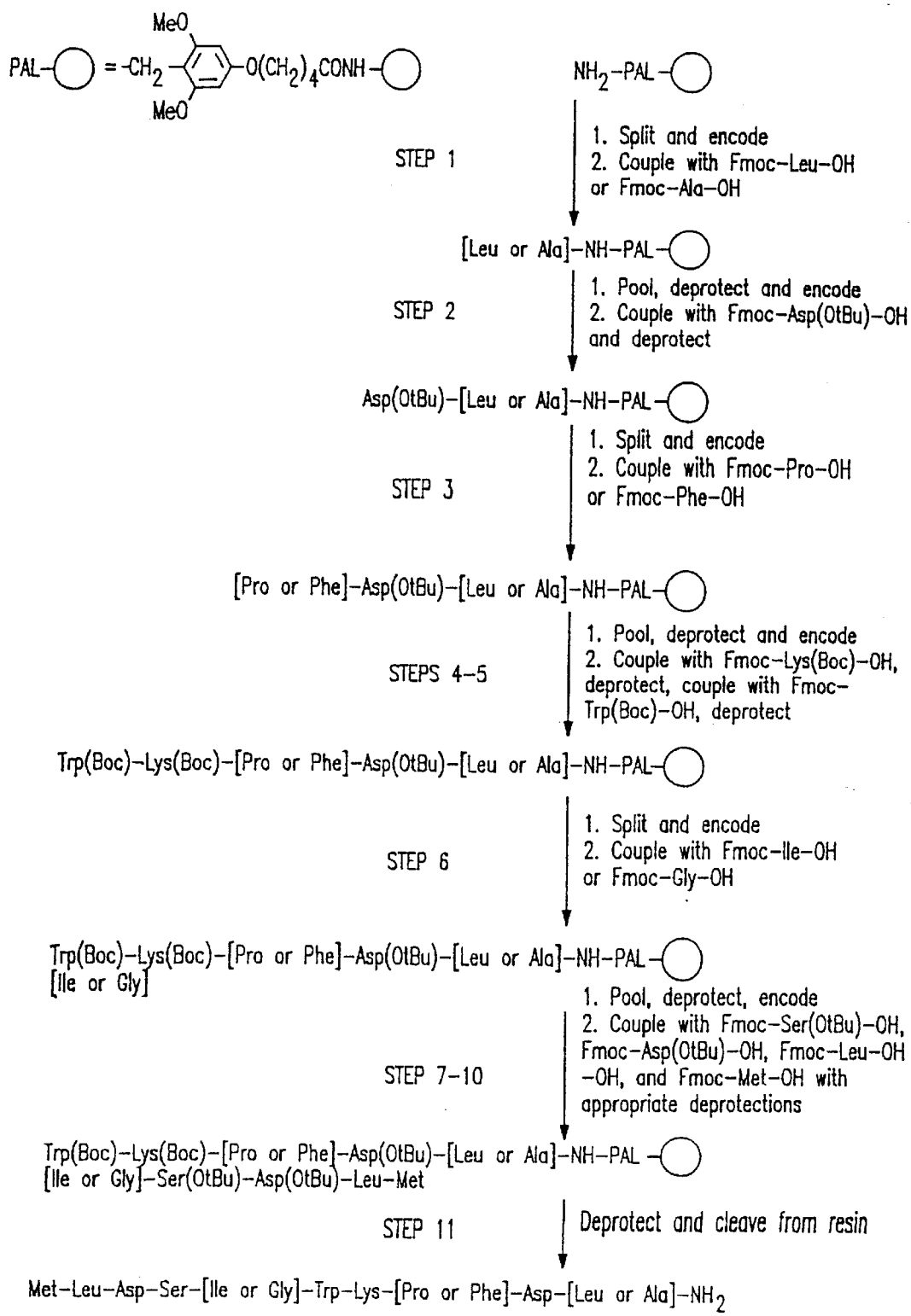
FIG. 10 is a scheme for the synthesis of the 8 member RF encoded combinatorial decameric peptide library described in EXAMPLE 4. All couplings were carried out in DMF at ambient temperature for 1 h [two couplings per amino acid], using PyBOP and EDIA or DIEA. Deprotection conditions: 20% piperidine in DMF, ambient temperature, 30 min; Cleavage conditions: 1,2-ethanedithiol:thioanisole:water:phenol:trifluoroacetic acid [1.5:3:3:4.5:88, w/w], ambient temperature, 1.5 h.

1) Another embodiment of the combinations herein uses a recording device that can detect the occurrence of a reaction or event or the status of any external parameter, such as pH or temperature, and record such occurrence or parameter in the memory, such embodiment is herein referred to as a sensor. Any of the above-described matrices with memories or memories may be modified to permit such detection. For example, the chip with the memory array with decoder, rectifier components and antenna, such as RF antenna, can be modified by addition of a photodetector and accompanying amplifier components as shown in FIG. 9. The photodetector will be selected so that it is sensitive to the frequencies of expected photoemissions from reactions of interest. To maintain the chip's passive operation, the photodetector circuitry may use voltage supplied by the same RF signal that is used to write other data to memory, so that no detection of photoemission will occur unless RF or other power is applied to provide bias and drain voltage. If an active device is used, the power supplied by the battery can provide operational voltage to the photodetector circuitry, independent of any transmitted signal. The voltage supplied by the photodetector can be used in a number of different ways. For example:

1) The threshold voltage for writing to memory will exceed the voltage supplied by the RF signal, which will still contain the address information. In order to write, additional voltage must be provided by the photodetector so that the sum of the voltages exceeds the threshold. ($V_{RF}<V_T<V_{RF}+V_{PD}$). This permits the RF supplied voltage to go to the correct address, however, no writing will occur unless a photoemission has been detected by the detector. Therefore, there will be no record of exposure to a particular process step unless a sufficient reaction has occurred to generate the required photoemission. Since the address signal can still get to the memory array without the extra voltage, reading of recorded data can be achieved without any special circuitry. If the memory device is an active device, a similar mechanism can be used in which only the sum of the voltages is sufficient to record an occurrence.

2) The threshold voltage for writing to memory will be provided by the RF signal alone, and the RF signal will include address information. ($V_T<V_{RF}$). Unless voltage from the photodetector is supplied to a "gating" transistor, however, access to the memory array is prevented so that no writing occurs unless a photoemission is detected. (This embodiment is illustrated.) This will require a special provision for opening the gate during read operations to permit access to the memory array. Since the gating transistor will conduct a signal only in the event of photoemission, this embodiment will work equally well with passive and active memory devices.

3) The RF signal provides sufficient voltage to exceed the threshold voltage. ($V_T<V_{RF}$). Voltage from the photodetector is used to create a write potential difference at an additional address location which is carried in the RF signal. For example, if the RF signal is addressing column 3, row 3, column 32 could be connected only to the photodetector circuit's output so that, when a photoemission occurs, the write signal will create antifuses [or in the case of EEPROM, standard fuses] at addresses 3,3 and 32,3. If no photoemission occurs, only address 3,3 will have an antifuse formed, providing a record of exposure of the matrix to a particular process step even without the occurrence of a detectable reaction. Special provisions, such as software within the host computer in combination with mask-programmed interconnections within the decode circuitry of the memory device, must be made to assure that more than one column in a single row of the array is polled during read operations so that both memory locations are read.

In addition to the above-described methods for recording the occurrence of photo-emitting reactions, the photodetector, while still integrated on the same substrate with the basic memory matrix for recording transmitted signals, can be connected to its own independent memory matrix. In this embodiment, the photodetector's memory matrix can be connected to separate transceiver circuitry with an antenna tuned to a different frequency from that of the basic memory. During the read operation, the memory device will be exposed to two different radio frequency signals, one for the basic memory, the other for the photo-detection circuit memory. If only the photoemission information is required, only the corresponding frequency signal need be provided during the read operation.

Depending on the type of energy release that occurs during a reaction, other types of sensors may be used in addition to photodetectors or in place thereof. In addition changes in ion concentration may also be detected. Many such sensors will be capable of generating an electrical signal that can be used as described above for the photodetectors. These sensing devices may also be incorporated onto the substrate and electrically connected to the memory device, providing data points within the device's memory under the appropriate write conditions. For example, temperature sensing elements can be made from semiconductor liquid crystal and fluorescent crystals, and addition to conventional thermocouples created by placing two different metals in contact at the detection point. It is also possible to include radiation, pH and $pCO_2$ sensors in a similar manner, using materials that respond to the detected variables by generating a voltage potential that can be conducted to the memory device and recorded.

2) Also contemplated herein, are event or reaction-detecting embodiments, wherein all or a portion of the matrix changes color by virtue of a color-generating reaction or glows by virtue of luminescence, such as chemiluminescence or, particularly electrically-generated luminescence [see, e.g., Chemical & Eng. News Oct. 7, 1996, p. 30 and Jenekhe et al. (1996) *J. Am. Chem. Soc.* 118:9438, which describe a new polymer that displays electrically generated luminescence].

The matrix with memory combinations, such as the MICROTUBE microvessels, may be assayed using a colorimetric-based assay, whereby positive compounds [or derivatives thereof], linked to the matrix, will form a colored or chemiluminescent product. The colored or chemiluminescent microvessels will be selected.

Also, contemplated herein, are the use of polymers, such as hydroxylated poly(benzothiadiazole phenylene) derivatives [see, *Chemical & Eng. News*, Oct. 7, 1996, p. 30 and Jenekhe et al. (1996) *J. Am. Chem. Soc.* 118:943] that luminescence when a voltage is applied and display stimulated emission by virtue of a light-producing proton-transfer reaction. Energy produced by virtue of a reaction can be coupled to the light producing transfer-reaction and produce the electroluminescence. A photodetector can be used to identify the positive microvessels.

Any photodetector that can detect the generated light in any of the embodiments described herein may be used. Of interest are superconducting tunnel junction [STJ] detectors [see, Tone et al. (1996) *Nature* (9 May, p. 135); (1996) *Science* 274:36–38] that can detect individual photons and measure the photon's energy. These detectors that are fabricated from niobium operate at very low temperatures.

b. Devices for drug delivery and sensors for detecting changes in internal conditions in the body Memories may also be combined with biocompatible supports and polymers that are used internally in the bodies of animals, such as drug delivery devices [see, e.g., U.S. Pat. Nos. 5,447,533, 5,443,953, 5,383,873, 5,366,733, 5,324,324, 5,236,355, 5,114,719, 4,786,277, 4,779,806, 4,705,503, 4,702,732, 4,657,543, 4,542,025, 4,530,840, 4,450,150 and 4,351,337] or other biocompatible support [see, U.S. Pat. No. 5,217,743 and U.S. Pat. No. 4,973,493, which provide methods for enhancing the biocompatibility of matrix polymers]. Such biocompatible polymers include matrices of poly(ethylene-co-vinyl acetate) and matrices of a polyanhydride copolymer of a stearic acid dimer and sebacic acid [see, e.g., Sherwood et al. (1992) *Bio/Technology* 10:1446–1449].

The biocompatible drug delivery device in combination with the memory is introduced into the body. The device, generally by virtue of combination with a biosensor or other sensor, also monitors pH, temperature, electrolyte concentrations and other such physiological parameters and in response to preprogrammed changes, directs the drug delivery device to release or not release drugs or can be queried, whereby the change is detected and drug delivered or administered.

Alternatively, the device provided in combination with a biocompatible support and biosensor, such that the information determined by the biosensor can be stored in the device memory. The combination of device and biosensor is introduced into the body and is used to monitor internal conditions, such as glucose level, which level is written to memory. The internal condition, such as glucose level, electrolytes, particularly potassium, pH, hormone levels, and other such level, can then be determined by querying the device.

In one embodiment, the device, such as one containing a memory that is read to and written using RF, linked to a biosensor [see, e.g., U.S. Pat. No. 5,384,028 which provides a biosensor with a data memory that stores data] that can detect a change in an internal condition, such as glucose or electrolyte, and store or report that change via RF to the linked matrix with memory, which records such change as a data point in the memory, which can then be queried. The animal is then scanned with RF and the presence of the data point is indicative of a change. Thus, instead of sampling the body fluid, the memory with matrix with linked biosensor is introduced into a site in the body, and can be queried externally. For example, the sensor can be embedded under the skin and scanned periodically, or the scanner is worn on the body, such as on the wrist, and the matrix with memory either periodically, intermittently, or continuously sends signals; the scanner is linked to an infusion device and automatically, when triggered triggers infusion or alters infusion rate.

A well-known problem that can rapidly render a sensing implant ineffective is the body's natural response to "wall-off" encapsulate the implant such that the concentration of any analyte in this poorly vascularized tissue surrounding the implant does not properly reflect the analyte concentration in tissue as a whole. A method for solving this problem is provided herein. Any implantable biosensor may be modified by including an angiogenic material in the matrix that surrounds the implant. The angiogenic material will promote the growth of new vascularization into the tissue immediately surrounding the implant and thus improve transport of analyte to the sensor implant. Examples of angiogenic factors, include, but are not limited to basic fibroblast growth factor (bFGF), acidic fibroblast growth factor (aFGF), epidermal growth factor (EGF), vascular endothelial growth factor (VEGF), platelet-derived growth factor (PDGF), heparin, prostaglandin E1, and interleukins, such as IL-1a and IL-8, among others.

Also, the implant may be coated with collagen and/or heparin to which the angiogenic factor, such as bFGF, is adsorbed, thereby presenting the factor in a configuration that mimics its in vivo presentation. In addition, these factors may be provided in a time release format, such as by containing the angiogenic factor within a collagen gel in conjunction with, for example, an aluminum sucrose octasulfate suspension.

4. Reading and writing to memory a. Embodiments using a proximate memory, such as a non-volatile memory device The operation of programming the memory to record the process steps to which the linked or adjacent matrix particle or support and linked or proximate molecule or biological particle is exposed involves placing the memory device reasonably close [a distance on the order of about 1 inch [25.4 mm] is presently contemplated, but longer distances should be possible and shorter distances are also contemplated [suitable distances can be determined empirically] to RF transmitter 80, The RF transmitter 80 emits a carrier wave modulated by a signal generated by host computer 122 using conventional RF technology. The carrier wave itself can provide the power to the generate the programming voltage and the operating voltage for the various devices via the rectifier, while the modulation signal provides the address instructions.

Figure 1:
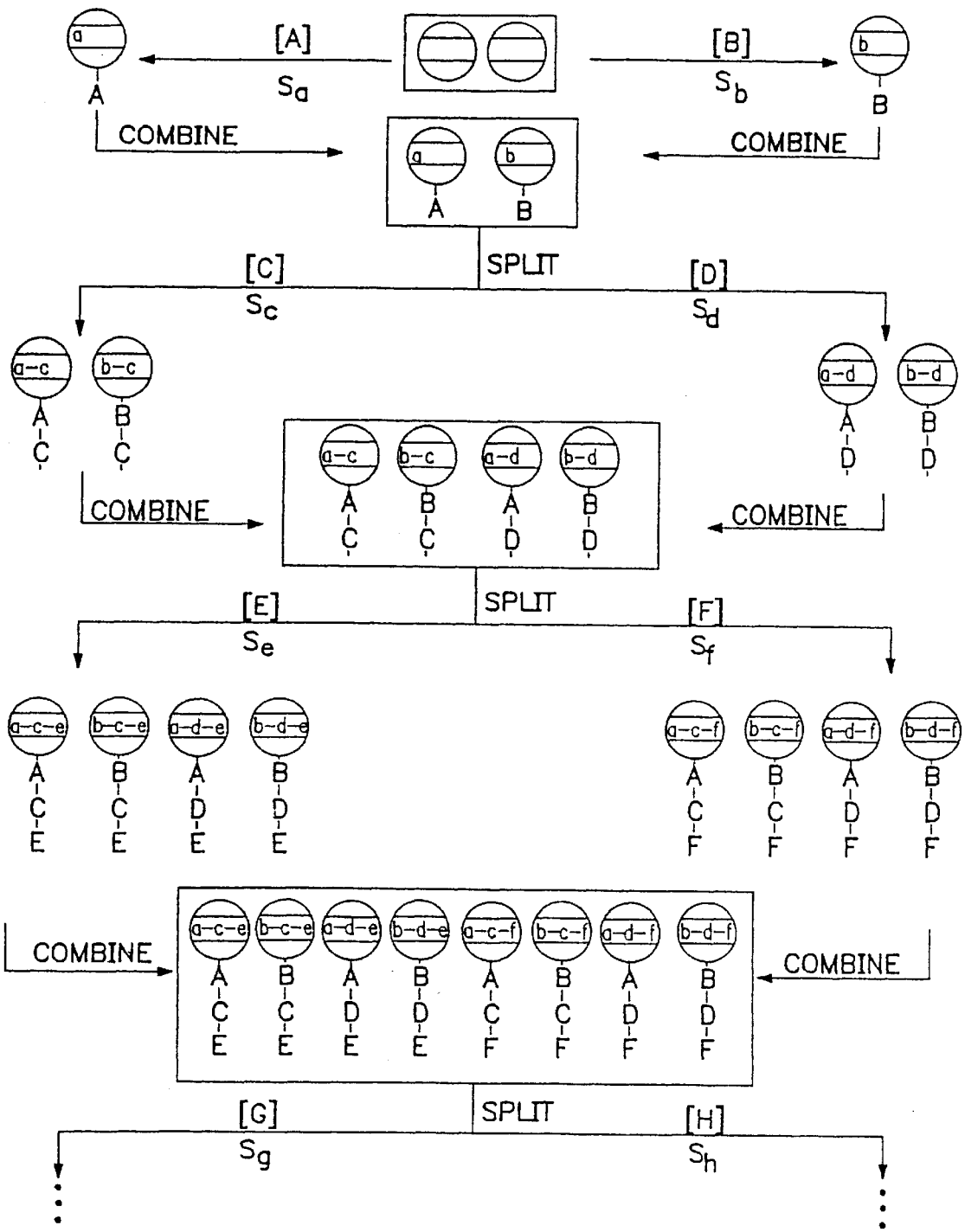
FIG. 1 depicts combinatorial synthesis of chemical libraries on matrix supports with memories. A, B, C . . . represent the chemical building blocks; a, b, c . . . represent the codes stored in memory that correspond to each of A, B, C, . . . , respectively. $S_a$, $S_b$, $S_c$ . . . represent respective signals sent to memory. Alternatively, the matrix supports are OMDs [optical memory devices] that are encoded with symbology associated with information stored in a remote memory, such as a computer. The symbology may be precoded or encoded prior to or during synthesis.
Figure 6:
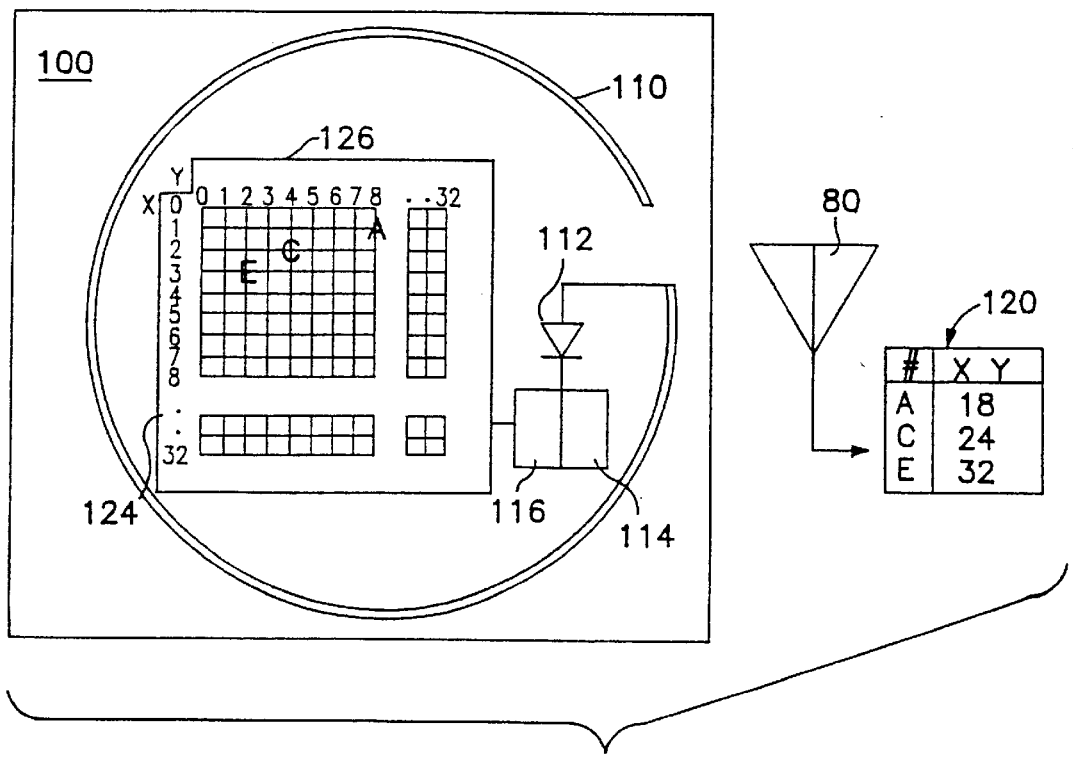
FIG. 6 is a diagrammatic view of the memory array within the recording device, and the corresponding data stored in the host computer memory.

As stated previously, since the memory only has to be "tagged" to record the exposure of the proximate or linked molecule or biological particle to a given process, the address signal only has to carry information to turn on a single memory location, while the host computer 122 stores into memory 120 the information linking the process information with the single memory location that was "tagged" to record exposure to the process step. Referring to FIG. 1, in which chemical building blocks A, C, and E are added to a molecule linked to a matrix with memory, and to FIG. 6, an illustrative example of how information is written onto a particle is provided in Table 1.

TABLE 1

| PROCESS STEP | X-REGISTER ADDRESS | Y-REGISTER ADDRESS |
|---|---|---|
| A | 1 | 8 |
| C | 2 | 4 |
| E | 3 | 2 |

For the step in which A is added, the address signal would increment the x-register 124 one location and increment the y-register 126 eight locations, and then apply the programming voltage. The activation of this switch is indicated by an "A" at the selected address, although the actual value stored will be a binary "1", indicating ON. [As described, for example, in U.S. Pat. No. 4,424,579; the manner in which the programming voltage is applied depends on whether the decoders have depletion or enhancement transistors.] The host computer 122 would write into its memory 120 that for process A, the x-, y-address is 1,8. Upon removal of the RF signal after recording process A, the voltage is removed and the registers would reset to 0. For the step in which C is added, the address signal would increment the x-register 124 two locations and the y-register 126 four locations, then apply the programming voltage, as indicated by the letter "C". The host computer 120 would similarly record in memory that an indication of exposure to process C would be found at x-, y-address 2,4. Again, upon removal of the RF signal, the registers reset to 0 so that when the matrix particle's memory is again exposed to RF following addition of block E, the registers increment 3 and 2 locations, respectively, and the programming voltage is applied to turn on the switch, indicated by "E". Desirably all processing steps are automated.

After processing is completed, to read the information that has been recorded in the memory of the data storage unit, the host computer 122 will inquire into the identity of the particle by generating a command signal to the registers to select the appropriate address locations to determine whether the switch is on or off. If the switch is on, i.e., a voltage drop occurs at that point, the computer will create a record that the particle received a particular process step. Alternatively, the host computer can generate an inquiry signal to sequentially look at all memory locations to determine which switches have been turned on, recording all locations at which voltage drops occurred. The computer will then compare the "on" locations to the process steps stored in its memory to identify the steps through which the subject particle was processed.

If desired, individual particles can be identified by reserving certain memory locations for identification only, for example, the first two rows of the x-register. In this case, particles will be passed separately through the RF signal while the x-register is incremented to turn on switches at address locations 0,0, 1,0, 2,0, etc. With individual identification, the host computer 122 can first generate a signal to query a matrix particle memory to detel mine its identity, then write the information with regard to the process performed, saving the process and particle information in the host computer memory 120.

Ideally, the tagging of particles which are exposed to a particular process would be performed in the process vessel containing all of the particles. The presence, however, of a large number of particles may result in interference or result in an inability to generate a sufficiently high voltage for programming all of the particles simultaneously. This might be remedied by providing an exposure of prolonged duration, e.g., several minutes, while stirring the vessel contents to provide the greatest opportunity for all particles to receive exposure to the RF signal. On the other hand, since each particle will need to be read individually, a mechanism for separating the particles may be used in write and read operations. Also, in instances in which each particle will have a different molecule attached, each particle memory must be addressed separately.

b. Embodiments using OMDs

When precoded OMDs are used, each OMD (or group thereof) has a unique identifier is optically scanned and entered into a remote memory. Thereafter, after each synthesis, processing or assaying step, information regarding such for each device identified by its encoded symbology is entered into a remote memory. Upon completion of the synthesis, processing, assay or other protocol, each device can be scanned and identified. Reference to the information stored in the remote memory provides information regarding the linked molecules or biological particles or the assay or other information. When read/write OMDs are used, identifying symbology is encoded on the device and the decrypting information is stored in a remote memory.

D. The Combinations and Preparation Thereof

Combinations of a memory, such as an optical memory, a magnetic memory or a miniature recording device, that contains or is a data storage unit linked to or in proximity with matrices or supports used in chemical and biotechnical applications, such as combinatorial chemistry, peptide synthesis, nucleic acid synthesis, nucleic acid amplification methods, organic template chemistry, nucleic acid sequencing, screening for drugs, particularly high throughput screening, phage display screening, cell sorting, drug delivery, tracking of biological particles and other such methods, are provided. These combinations of matrix material with data storage unit [or recording device including the unit] are herein referred to as matrices with memories. These combinations have a multiplicity of applications, including combinatorial chemistry, isolation and purification of target macromolecules, capture and detection of macromolecules for analytical purposes, high throughput screening protocols, selective removal of contaminants, enzymatic catalysis, drug delivery, chemical modification, scintillation proximity assays, FET, FRET and HTRF assays, immunoassays, receptor binding assays, drug screening assays, information collection and management and other uses. These combinations are particularly advantageous for use in multianalyte analyses. These combinations may also be advantageously used in assays in which a electromagnetic signal is generated by the reactants or products in the assay. These combinations may be used in conjunction with or may include a sensor element, such as an element that measures a solution parameter, such as pH. Change in such parameter, which is recorded in the memory will indicate a reaction event of interest, such as induction of activity of a receptor or ion channel, has occurred. The combination of matrix with memory is also advantageously used in multiplex protocols, such as those in which a molecule is synthesized on the matrix, its identity recorded in the matrix, the resulting combination is used in an assay or in a hybridization reaction. Occurrence of the reaction can be detected externally, such as in a scintillation counter, or can be detected by a sensor that writes to the memory in the matrix. Thus, combinations of matrix materials, memories, and linked or proximate molecules and biological materials and assays using such combinations are provided.

The combinations contain (i) a miniature recording device that contains one or more programmable data storage devices [memories] that can be remotely read and in preferred embodiments also remotely programmed or an engraved symbology or both a data storage device and an engraved coed; and (ii) a matrix as described above, such as a particulate support used in chemical syntheses or the MICROTUBE microreactor body or MICROKAN microreactor as described herein [see EXAMPLES below]. The remote programming and reading is preferably effected using electromagnetic radiation, particularly radio frequency or radar, microwave (1–2 GHz range), X-rays. Depending upon the application the combinations will include additional elements, such as scintillants, photodetectors, pH sensors and/or other sensors, and other such elements.

1. Preparation of matrix-memory combinations

In preferred embodiments, the recording device is cast in a selected matrix material during manufacture. Alternatively, the devices can be physically inserted into the matrix material, the deformable gel-like materials, or can be placed on the matrix material and attached by a connector, such as a plastic or wax or other such material. Alternatively, the device or device(s) may be included in an inert container in proximity to or in contact with matrix material.

2. Non-linked matrix-memory combinations

The recording device with memory can be placed onto the inner or outer surface of a vessel, such as a microtiter plate or vial or tube in which the reaction steps are conducted, fractions collected or samples stored. Alternatively, the device can be incorporated into the vessel material, such into the a wall of each microtiter well or vial or tube in which the reaction is conducted. As long as the molecules or biological particles remain associated with the well, tube or vial, such as a vial used to collect HPLC fractions, or a vial containing a patient sample, their identity can be tracked. The memory will be a programmable electronic memory or a bar code. These memories can also be associated with reagent containers.

The RF tag or other electronic tag may be combined with an liquid crystal display (LCD) or other display that displays the information in stored in the memory. Thus each microtiter plate or container, for example, will include a tag and a display that displays identifying the contents of the plate or other information. Each microtiter plate may include one or more of such displays. The LCD will provide a visual account of what is in the plate. The display will be linked to the electronic RF tag. Upon writing to the tag the information is transmitted to the display.

A bar code reader, transponder reader or other such device can be used to enter the desired information building block name by reading the reagent container. Such information will be entered in to matrix memory or remote computer memory. Software for doing so can be integrated into the systems used, such as the bar code reader described herein or the transponders and encoders described herein.

Also of interest herein are the multiwell "chips" [such as those available from Orchid Biocomputer, Inc. Princeton, N.J., see, e.g., U.S. Pat. Nos. 5,047,371, 4,952,531, 5,043,222, 5,277,724, 5,256,469 and Prabhu et al. (1992) *Proc. SPIE-Int. Soc. Opt. Eng.* 1847 NUMBER: Proceedings of the 1992 International Symposium on Microelectronics, pp.601–6], that are silicone based chips that contain 10,000 microscopic wells connected by hair-thin glass tubes to tiny reservoirs containing reagents for synthesis of compounds in each well. Each well can be marked with a code and the code associated with the identity of the synthesized compound in each well. Ultimately, a readable or read/write memory may be incorporated into each well, thus permitting rapid and ready identification of the contents of each well.

In a particularly preferred embodiment, one or more recording devices with memory and matrix particles are sealed in a porous non-reactive material, such as polypropylene or TEFLON net, with a pore size smaller than the particle size of the matrix and the device. Typically one device per about 1 to 50 mg, preferably 5 to 30, more preferably 5 to 20 mg of matrix material, or in some embodiments up to gram, generally 50 to 250 mg, preferably 150 mg to about 200 mg, and one device is sealed in a porous vessel a microvessel [MICROKAN™ microreactor]. The amount of matrix material is a function of the size of the device and the application in which the resulting matrix with memory is used, and, if necessary can be empirically determined. Generally, smaller sizes are desired, and the amount of material will depend upon the size of the selected recording device.

The resulting microvessels are then encoded, reactions, such as synthetic reactions, performed, and read, and if desired used in desired assays or other methods.

3. Combinations of memories with sensors and matrices with memories and sensors

As discussed above, below, and exemplified below, combinations of sensors with memories and sensors with matrices with memories are provided. Also provided are sol-gels with memories, coated sensors and other embodiments.

4. Preparation of matrix-memory-molecule or biological particle combinations

In certain embodiments, combinations of matrices with memories and biological particle combinations are prepared. For example, libraries [e.g., bacteria or bacteriophage, or other virus particles or other particles that contain genetic coding information or other information] can be prepared on the matrices with memories, and stored as such for future use or antibodies can be linked to the matrices with memories and stored for future use.

5. Combinations for use in proximity assays

In other embodiments the memory or recording device is coated or encapsulated in a medium, such as a gel, that contains one or more fluophors or one or more scintillants, such as 2,5-diphenyloxazole [PPO] and/or 1,4-bis-[5-phenyl-(oxazolyl)]benzene [POPOP] or FlexiScint [a gel with scintillant available from Packard, Meriden, Conn.] or yttrium silicates. Any fluophore or scintillant or scintillation cocktail known to those of skill in the art may be used. The gel coated or encased device is then coated with a matrix suitable, such as glass or polystyrene, for the intended application or application(s). The resulting device is particularly suitable for use as a matrix for synthesis of libraries and subsequent use thereof in scintillation proximity assays.

Similar combinations in non-radioactive energy transfer proximity assays, such as HTRF, FP, FET and FRET assays, which are described below. These luminescence assays are based on energy transfer between a donor luminescent label, such as a rare earth metal cryptate [e.g., Eu trisbipyridine diamine (EuTBP) or Tb tribipyridine diamine (TbTBP)] and an acceptor luminescent label, such as, when the donor is EuTBP, allopycocyanin (APC), allophycocyanin B, phycocyanin C or phycocyanin R, and when the donor is TbTBP, a rhodamine, thiomine, phycocyanin R, phycoerythrocyanin, phycoerythrin C, phycoerythrin B or phycoerythrin R. Instead of including a scintillant in the combination, a suitable fluorescent material, such as allopycocyanin (APC), allophycocyanin B, phycocyanin C, phycocyanin R; rhodamine, thiomine, phycocyanin R, phycoerythrocyanin, phycoerythrin C, phycoerythrin B or phycoerythrin R is included. Alternatively, a fluorescent material, such a europium cryptate is incorporated in the combination.

6. 2-D Bar codes, other symbologies and application thereof

Any application and combination described herein in which a recording device in proximity with a matrix may include a code or symbology in place of or in addition to the recording device. The information associated with the code is stored in a remote recording device, such as a computer. Thus, by electro-optically scanning the symbol on the combination and generating a corresponding signal, it is possible in an associated computer whose memory has digitally stored therein the full range of codes, to compare the signal derived from the scanned symbol with the stored information. When a match is found, the identity of the item and associated information, such as the identity of the linked molecule or biological particle or the synthetic steps or assay protocol, can be retrieved.

The symbology can be engraved on any matrix used as a solid support for chemical syntheses, reactions, assays and other uses set forth herein, for identification and tracking of the linked or proximate biological particles and molecules. Particularly preferred is the two-dimensional bar code and system used therewith for reading and writing the codes on matrix materials.

7. Other variations and embodiments

The combination of matrix particle with memory may be further linked, such as by welding using a laser or heat, to an inert carrier or other support, such as a TEFLON strip. This strip, which can be of any convenient size, such as 1 to 10 mm by about 10 to 100 $\mu$M will render the combination easy to use and manipulate. For example, these memories with strips can be introduced into 10 cm culture dishes and used in assays, such as immunoassays, or they can be used to introduce bacteria or phage into cultures and used in selection assays. The strip may be encoded or impregnated with a bar code to further provide identifying information.

Microplates containing a recording device in one or a plurality of wells are provided. The plates may further contain embedded scintillant or a coating of scintillant [such as FlashPlate™, available from DuPont NEN®, Cytostar-T plates from Amersham International plc, U.K., and plates available from Packard, Meriden, Conn.] FLASHPLATE™ is a 96 well microplate that is precoated with plastic scintillant for detection of β-emitting isotopes, such as $^{125}I$, $^{3}H$, $^{35}S$, $^{14}C$ and $^{33}P$. A molecule is immobilized or synthesized in each well of the plate, each memory is programmed with the identify of each molecule in each well. The immobilized molecule on the surface of the well captures a radiolabeled ligand in solution results in detection of the bound radioactivity. These plates can be used for a variety of radioimmunoassays [RIAs], radioreceptor assays [RRAs], nucleic acid/protein binding assays, enzymatic assays and cell-based assays, in which cells are grown on the plates.

Figure 19:
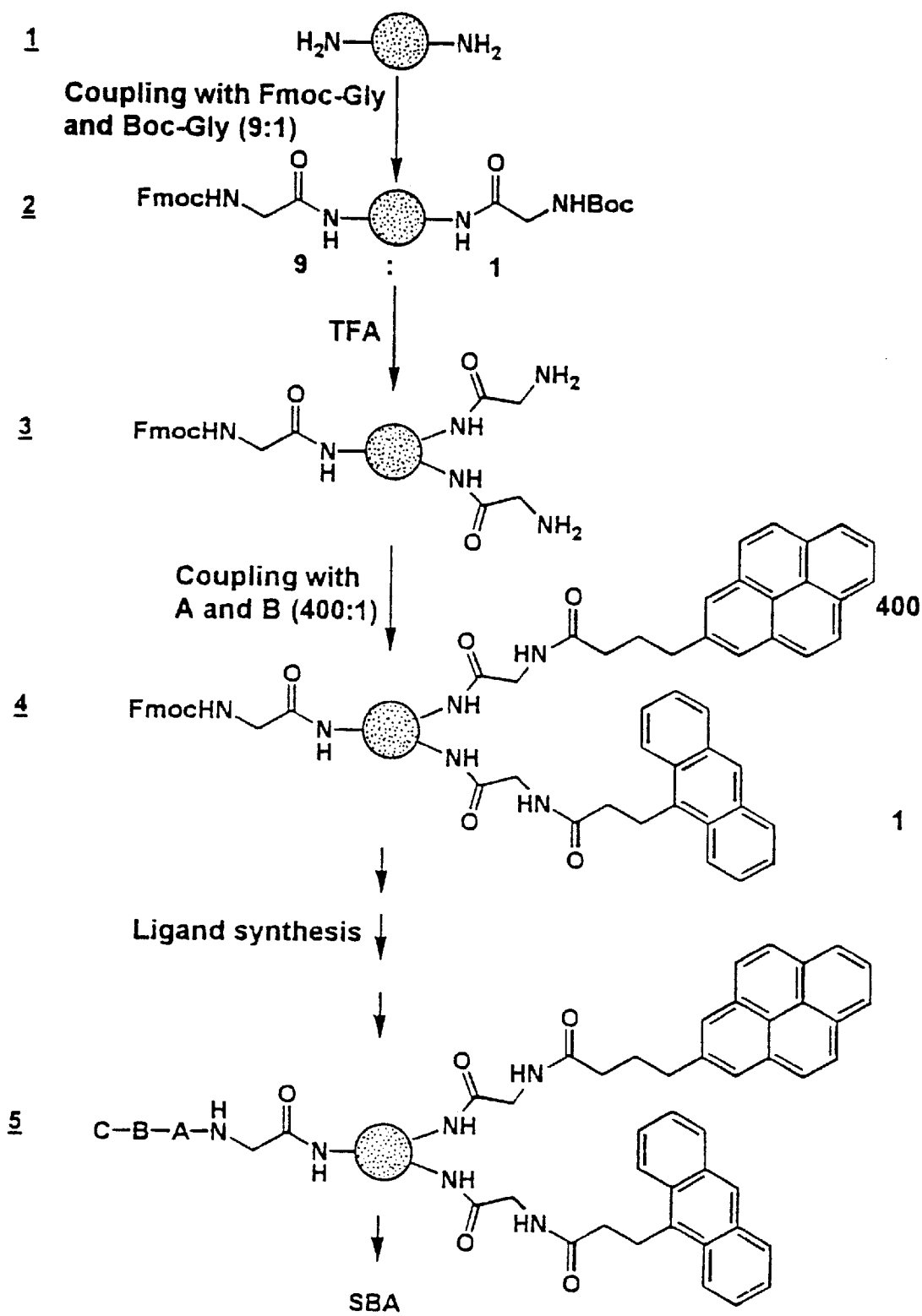
FIG. 19 shows fluorescent solid supports: and their application in solid phase synthesis of direct SPA. The supports will include a either an electromagnetically programmable memory, or an optical memory engraved on the surface, such as the 2-D optical bar code provided herein.

Another embodiment is depicted in FIG. 19. The reactive sites, such as amines, on a support matrix [1 in the FIGURE] in combination with a memory [a MICROKAN™, a MICROTUBE™, a MACROBEAD™, a MICROCUBE™ microreactor or other matrix with memory combination] are differentiated by reacting them with a selected reaction of Fmoc-glycine and Boc-glycine, thereby producing a differentiated support [2]. The Boc groups on 2 are then deprotected with a suitable agent such as TFA, to produce 3. The resulting fee amine groups are coupled with a fluophore [or mixture A and B], to produce a fluorescent support 4, which can be used in subsequent syntheses or for linkage of desired molecules or biological particles, and then used in fluorescence assays and SPAs.

E. The Recording and Reading and Systems

Systems for recording and reading information are provided. The systems include a host computer or decoder/encoder instrument, a transmitter, a receiver and the data storage device. The systems also can include a funnel-like device and other sorting devices for use in separating and/or tagging single memory devices. In practice, an EM signal or other signal is transmitted to the data storage device. The antenna or other receiver means in the device detects the signal and transmits it to the memory, whereby the data are written to the memory and stored in a memory location. As provided herein, methods for addressing individual memories in a batch are provided, thereby eliminating the need for sorting.

Mixtures of the matrix-with-memory-linked molecules or biological particles may be exposed to the EM signal, or each matrix-with-memory [either before, after or during linkage of the biological particles or molecules] may be individually exposed, using a device, such as that depicted herein, to the EM signal. Each matrix-with-memory, as discussed below, will be linked to a plurality of molecules or biological particles, which may be identical or substantially identical or a mixture of molecules or biological particles depending, upon the application and protocol in which the matrix-with-memory and linked [or proximate] molecules or biological particles is used. The memory can be programmed with data regarding such parameters.

The location of the data, which when read and transmitted to the host computer or decoder/encoder instrument, corresponds to identifying information about linked or proximate molecules or biological particles. The host computer or decoder/encoder instrument can either identify the location of the data for interpretation by a human or another computer or the host computer or the decoder/encoder can be programmed with a key to interpret or decode the data and thereby identify the linked molecule or biological particle.

As discussed above, the presently preferred system for use is the IPTT-100 transponder and DAS-5001 CONSOLE™ [Bio Medic Data Systems, Inc., Maywood, N.J.; see, e.g., U.S. Pat. Nos. 5,422,636, 5,420,579, 5,262,772, 5,252,962 and 5,250,962, 5,252,962 and 5,262,772].

Any of the systems may be automated or may be manual.

F. Units for Drug Discovery, Including Manual and Automated Systems for Combinatorial Syntheses and Other Protocols Of particular interest herein, are automated protocols, or partially automated protocols, in which the matrices-with-memories serve as the platform on which all manipulations are performed or that serve as the repository of information that is transferred to other memories as the synthesized compounds are processed and screened [see, e.g., FIG. 75]. Thus, an automated drug discovery unit provides a means for seamless data tracking between and among the components of the units in which all critical components, including instrumentation and vials include memories for seamless transfer information to other memories in a unit. The units, which are provided herein, include some or all of the following: an automated or manual sorter, microvessels, which contain memories, an automated or semi-automated synthesizer, a microvessel washer/dryer, a manual or automated cleaver for removing compounds from the matrix-with-memory microvessels, and associated software to direct the instrumentation as well as the user.

The memories may be any of any type, including electromagnetically encodable memories and optical memories, or combinations thereof. The memories may be pre-encoded or may be encodable during, after or before processing. Remotely addressable memories are presently preferred. Although in some embodiments, memories associated with certain of the components, such as instrumentation or vials used therewith, for convenience and ease of reuse, may be pre-encoded.

1. Units for drug discovery using matrices-with-memories as the platform: Single platform automated drug discovery A completely automated synthesis process [see, e.g., FIGS. 75] may be accomplished by using the apparatus described herein. For example, matrices-with-memories, such as the MICROKAN or MICROTUBE microreactor, can be fed to an automated sorting device, which sorts the microreactors into their respective microreactor carriers in a microreactor carrier tray, keeping records as to the location of each matrix within the microreactor carrier tray. The microreactor carrier tray may then be placed on a cleaving assembly where a cleaving agent is added to each microreactor carrier within the microreactor carrier tray, thereby initiating the cleaving process which is accelerated by placing the cleaving assembly onto a shaker. Alternatively, a shaker can be integrated into the cleaving assembly. Once the initial cleaving process is completed cleaved, the cleaving assembly is disposed so that it abuts and seals a vacuum chamber with the assembly in a pre-determined orientation to ensure that the location of each matrix and its associated cleaved compound is known. Then, by activating the vacuum within the vacuum chamber, the cleaved compounds are drawn from each microreactor carrier into a corresponding vial located within each vial rack in the vacuum chamber. Because the orientation and position of each vial rack within the vacuum chamber is known, and the mapping configuration from each microreactor carrier in the microreactor carrier tray to each vial location is also known, the compound within each vial in a vial rack is identifiable, such as by accessing an identification tag embedded therein or attached thereon.

a. Synthesis and/or linkage of compounds (molecules) or biological particles to matrices with memory microvessels Synthesis will be performed in reaction vessels, made of glass or other suitable material, that have internal fins that will tumble microvessels, while minimizing the amount of synthesis, i.e., building block, solution required. Each reaction vessel preferably has a capacity of about 250 to 500 or more microvessels, such as the MICROKAN™ and MICROTUBE™ microvessels.

In embodiments in which pre-synthesized molecules or other molecules or biological particles are linked within the vessels. At each step in the synthesis, and where needed thereafter, the microvessels may be sorted using either a manual, or preferably automated, sorter. In the automated sorter microvessels, such as MICROKAN™ or MICROTUBE™ microvessels, are automatically sorted into output reservoirs. The reservoirs preferably have a capacity of up to 10,000 [or more] microvessels, with throughput rate of, for example, 1000 microvessels per hour. The sorter includes output reservoirs: about 50, 100 or multiples thereof, with each capable of holding up to 1000 microvessels each. Exemplary embodiments of the sorter are provided in the EXAMPLES and FIGURES.

A semi- or fully- automated synthesizer includes reaction vessels containing the microvessels, such as the MICROKAN™ or MICROTUBE™ microvessels, and modules that hold the reaction vessels, heating and cooling elements, and reagent adding means, all components can be run manually or automatically under control of a computer with appropriate software [see Appendices].

Sorted microvessels are loaded, either manually or robotically, into reaction vessels, containing a stir bar, preferably a stir bar with memory, that can be heated, cooled, and agitated per computer controlled methods. Each module will hold a selected number, presently preferably six, reaction vessels [each reaction vessel containing preferably up to 500 microvessels.] Each module will hold six reaction vessels, each of which can hold, preferably at least 250 microvessels, such as MICROKAN™ or MICROTUBE™ microvessels, so that there will be, for example, 1500 MICROKAN™ or MICROTUBE™ microvessels per module. The synthesizer includes computer controllable heating and cooling means [temperature range about −80° C. up to at least 120° C.] and timing means for each reaction vessel, each of can be separately heated and timed. The materials, such as TEFLON™ and glass, should withstand temperatures from about −80° C. up to at least 120° C.

Following synthesis and between steps microvessels are washed, and, if desired, dried in a microvessel washer/dryer [preferably fabricated from TEFLON™ and glass] that has a capacity of up to, for example, 10,000 MICROKAN™ or MICROTUBE™ microvessels or other microvessels or memories with matrices in other formats. Microvessels are washed, rinsed and dried.

An improved washing protocol for washing memory with matrix microreactors and other solid supports following synthesis and prior to any assays is provided herein. In the method, the support or microreactor is washed with buffer (pH about 7 to 7.5, preferably 7.2) containing about 0.75% (0.5% to 0.1%) SDS for about 2 days. The buffer, preferably PBS (pH 7.2) may also contain about 25–50% charcoal (preferably about 35%).

b. Cleavage

When desired, the compounds (molecules) or biological particles are cleaved from the microvessels. Typically, when cleaved, they will be introduced into a microplate well or vial, each including memories. Information from the microvessel memory will be written to or associated with the memories in the microplate wells, vials or other vessels [i.e., cleavage vessels].

(i) Manual cleaver

Matrices with memory microvessels with synthesized compounds or linked biological particles are manually sorted into individual cleavage vessels that are organized into microplate size modules; cleavage solution is added: heating, cooling, and agitation is manually performed, cleavage effluent is collected in individually identified vials or microplates, each vial and microplate including a memory or plurality of memories, preferably remotely programmable and preferably electronically, such as RF.

Each cleavage station will handle one microplate containing 24, 48, 96 wells or other density of wells. Output reservoirs are preferably vials or deep well microplates. Again, each output reservoir will preferably include a memory or a plurality of memories to which information regarding the cleaved compounds is read or associated [in the case of pre-encoded memories] within a remote memory device, such as in a computer. An exemplary manual cleaver is described in the EXAMPLES and set forth in FIGS. 97–100.

(ii) Automated cleaver

Matrices with memory microvessels with synthesized compounds or linked biological particles are automatically or manually sorted into individual cleavage vessels that are organized into microplate size modules; cleavage solution is added; heating, cooling and agitation is programmable, preferably as a batch; cleavage effluent is collected in individually identified vials or microplates. The capacity is, for example, u to 50 microplates containing 24 or 46 cleavage wells each [i.e., 1200 or 2400 MICROKAN™ or MICROTUBE™ microvessels]. The throughput is high, typically 4 hours for 1200 or 2400 microvessels. Output reservoirs are individual vials or microplates; again, each vial or microplate contains a memory or plurality of memories. FIGS. 101–108 and the Examples provide an exemplary automated cleaving station.

c. Software

Software, such as that provided herein, (see, e.g., Appendices III–VIII and the description herein) seamlessly ties all processing and analytical steps together.

d. Assays

Following cleavage, compounds are assayed as described elsewhere herein. Alternatively, assays can be performed, where appropriate, without cleaving the compounds or biological particles from the matrix. In addition, following synthesis the compounds or biological particles may be stored on the matrix-with-memory support for subsequent assays. The larger microvessels, such as the MICROTUBE microvessels that are designed to be chopped into pieces, may be used for storage and as a repository for the synthesized compounds and linked biological molecules, to provide, for example, libraries of compounds.

2. Matrix-with-memory device-to-matrix-with-memory device communication and programming-the automated laboratory In accordance with the methods provided herein, communication among multiple matrices with memories is contemplated. In particular, matrices-with-memories that can be programmed to interrogate neighboring matrix-with-memory devices and effectively communicate and program that neighboring device are contemplated. More specifically, the matrix-with-memory device which is programmed to reprogram other devices, called a master memory, is placed within an electromagnetic field, whereby its operating power can be derived for example, as discussed above with respect to the event-detecting embodiment. Once powered, the master memory can emit an interrogation signal whereby other matrix-with-memory devices or memory devices receiving the interrogation signal can respond with their identify. In the case where the responding identity is one of a class that is to be programmed, the master memory can send a programming signal to the neighboring matrix-with-memory device which effectively writes information into the neighboring matrix-with-memory device. In this manner, a number of matrix-with-memory devices can be programmed serially by programming a master matrix-with-memory device, and placing the master matrix-with-memory device in close proximity to other matrix-with-memory devices, while all of the memories are within an electromagnetic field, such as an RF field. Other methods for powering the devices whereby communication among and between devices can be effected are also contemplated herein.

3. Manual and automated sorting devices and methods using these devices are provided herein.

a. Manual sorting

The manual system includes memories-with-matrices, a device for reading from and writing thereto, including a controller, and software for controlling the read/write function. The system also includes an apparatus and associated means, which may include software, processor(s) for running the software, and a user-interface/display, for assisting the user in identifying a particular matrix-with-memory and for identifying the destination of a given matrix, providing means for simplifying, expediting, and increasing the accuracy of the transferring procedure.

Figure 18:
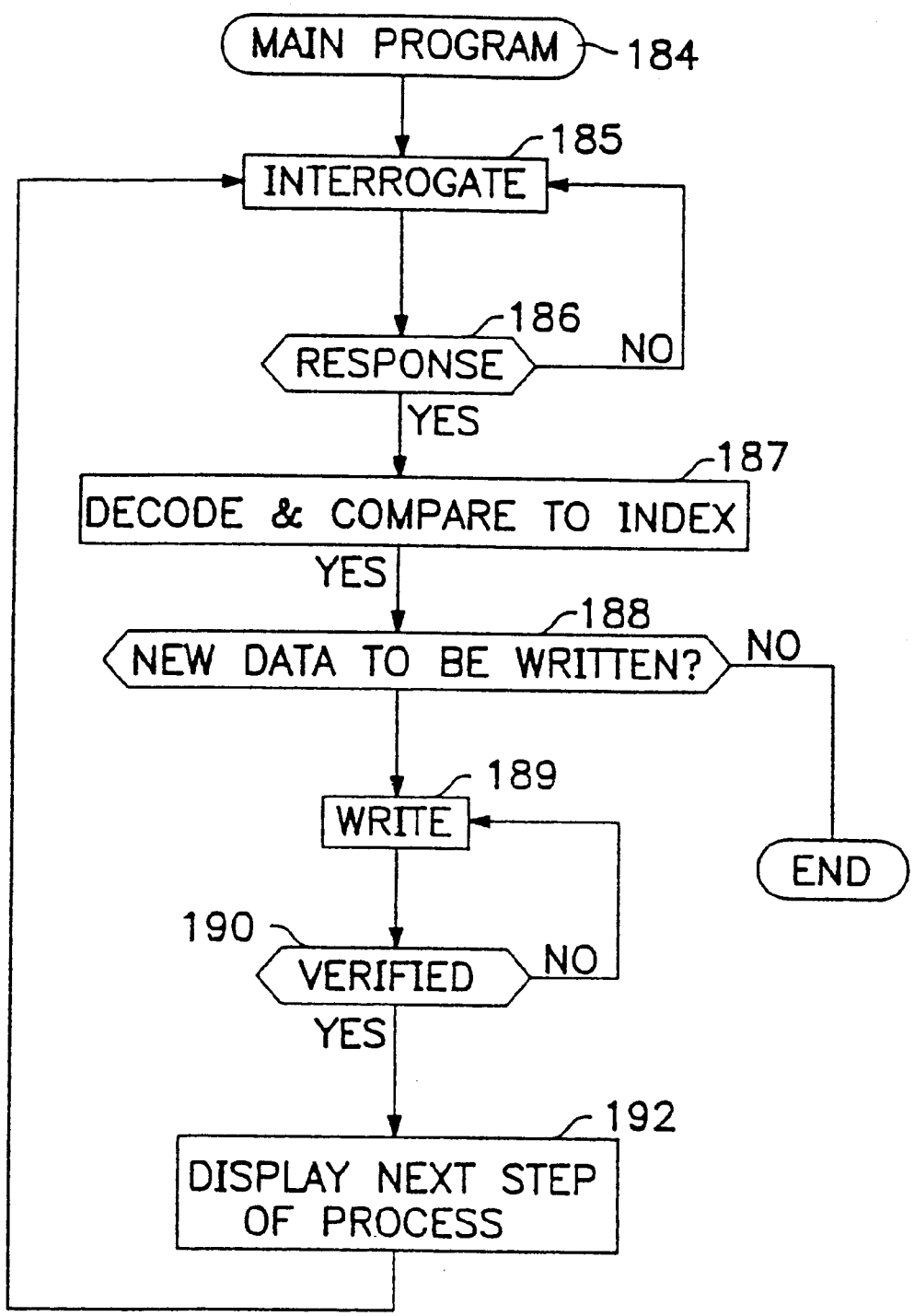
FIG. 18 is a flow diagram of the operation of the system of FIG. 17.

The presently preferred manual system in which the matrices-with-memories have electromagnetically programmable memories, includes a transponder, particularly the BMDS transponder described below or an IDTAG™ transponder or the monolithic chip provided herein, or any suitable read or read/write memory device and uses the corresponding reading and writing device, which has been reconfigured and repackaged, such as in FIG. 17, described in the EXAMPLES. An example of the operation of the system of FIG. 17 is illustrated in FIG. 18 and described in EXAMPLE 4. Briefly, the user manually places a microvessel 180 with memory within the recessed area 176 so that the interrogation signal 185 provides a response to the controllers indicating the presence of the microvessel, and information is read from or written to the transponder. Similar methods may be employed with the optically-encoded matrices-with-memories.

This manual system will include microvessels, such as MICROKAN™, MICROTUBE™, MICROBEAD™, or MICROBALL™ microreactors, read/write hardware [such as that available from BMDS or IDTAG™] connected to a PC and software running on the PC which performs a user interface and system control function. The software is designed to facilitate a number of aspects of synthetic combinatorial chemistry libraries., including: organization, planning and design, synthesis compound formula determination, molecular weight computation, reporting of plans, status and results.

In particular, for each chemical library or group of matrices-with-memories or each matrix-with-memory, the software creates a data base file. The data base file contains all of the information pertinent to the library, including chemical building blocks to be used, the design of the library in terms of steps and splits, and what synthesis has been performed. This file-oriented approach allows as number of different chemical library projects to be conducted simultaneously. The software allows the user to specify what chemical building blocks are to be used and their molecular weights. The user specifies the number of steps, the number of "splits" at each step, and what chemical building blocks are to be used at each split. The user may also enter the name of the pharmacophore and its molecular weight. Additionally, the user may specify graphical chemical diagrams for the building blocks and the pharmacophore, which information may be useful in displaying resulting compounds. The software directs all of the above "design" information to be stored in memory. The software includes algorithms for computing and displaying the size of the library. It may also include operations for predicting the range of molecular weights of the resulting compounds.

For example, the user may specify that there will be eight chemical building blocks. The names of the eight selected chemical building blocks are entered into the system controller via the user interface, and the user enters a unique letter codes for each: A, B, C, D, E, F, G and H. The user then specifies the number of steps which, in the present example, is specified as three steps. Step one will have four splits, appending the A, B, C and D building blocks. Step two will also have four splits, adding the B, D, E and H building blocks. Step three will have six splits, adding the B, C, D, E, F and G building blocks. Using a library size algorithm, the software computes the number of compounds that the library will contain, which in this case is 96 (4×6×5=96) unique compounds. Once the planning and design are completed, the software generates an output for guiding the user in performing the synthesis steps. The user-guidance function is done in concert with the read/write hardware [transceiver or a scanner, such as the BMDS-DAS 5003] or a similar device available form IDTAG Ltd [Bracknell, Berks RG12 3XQ, UK] and devices, such as a MICROKAN™ or MICROTUBE™ microvessel with memory devices. Before the synthesis begins, the microvessels are filled with polymer resin. The microvessel devices are placed upon the scanner one at a time so that the reading/writing device and its associated software can read the contents of data encoded in the recording device/transponder, such as the BMDS tag or the IDTAG™ tag, contained in each microvessel. The software includes algorithms for selecting which building block is to be added to the compound contained in each microvessel. The software directs the transceiver of the reading/writing device to write encoded data to the transponder which includes the designation of the selected building block. The software causes a message to be displayed for directing the user to place the microvessel in the appropriate reaction vessel so that the chosen building block will be added. This process is repeated a plurality of times with each microvessel and for each synthetic step in the preparation of the library.

The software directs the read/write scanner to read a tag and receive its encoded information. Using the user-entered compound names stored in the library's data base, the software translates the encoded information into the names of the chemical building blocks. The software can also produce a graphic display of compounds, using graphical information specified by the user. The software may include algorithms for calculating the molecular weight of compounds from the data provided for the pharmacophore and building blocks.

The use of software within the sorting devices facilitates creation of a record of progress through the above process. The software provides for generation of displays and reports for illustrating steps of the process as well as providing means for displaying and/or reporting the planning, design, compound data, and graphical representations of compounds. An example of the software, which is to be commercialized under the name SYNTHESIS MANAGER™, and use thereof, is set forth in Appendix 3 and in the Examples below. Using the description of the functions that is provided herein, software for performing similar functions can readily be developed by one skilled in the art.

Briefly, in the first step in building a library, the individual building blocks [i.e., the monomers, nucleotides or amino acids or other small molecules] and the steps in which they will be used are defined. The software then performs operations for automatically creating a data base record for each compound to be synthesized. Pre-reaction procedures, reaction conditions, and work-up procedures are stored for each step. When the synthesis begins, the step "Perform Synthesis" is selected. The software generates a display of the procedure for review by the user, then reads each of the memories in each microreactor and sorts them for the next reaction step. When the sorting is complete, the reaction condition information and work-up procedure are also displayed to the user.

When the chemical synthesis is complete, compounds are cleaved from the microreactors and archived. The software provides archival capability for either individual vials or a 96-well format, or may be adapted for other formats. Specific columns, rows, or individual wells can be protected to accommodate the need for standards and controls in virtually any screening format.

The software provides several utilities that permit one tag to be read at any time, displaying the corresponding building block names and structures, and the current synthesis status of that compound. A search may be conducted for a specific compound or compounds that contain certain building blocks. For compounds that have already been archived, the archive location [i.e., microplate group name, number, and well] will be displayed.

Also provided are manual system and automated systems for directing synthesis, screening and other protocols. In particular, apparatus are provided that, with associated software [including that provided herein or that may be generated based upon the disclosure herein] provide protocols and implement the protocols by directing each matrix-with-memory to a particular reaction vessel. These apparatus and software are used in conjunction with manual and automated systems.

For example, a manual sorting system [see Examples] may include a device for reading and, in instances in which the memories are encodable, writing to the memories, a computer, including a user interface, for storing a database with identifying information and for containing and implementing the software, and a sorter, which may be manual or automatic. A manual sorter may include, for example, an apparatus that assists the user in identifying a particular matrix-with-memory, such as the MICROKAN™ microreactors and MICROTUBE™ microreactors, identifying the destination of that matrix, and providing an indication, such as a visual or audio cue that identifies the destination as a means simplify, expedite, and increase the accuracy of the synthetic and screening protocols.

A manual system provided herein, for example, includes the identification station [such as that discussed above] that identifies a particular matrix-with-memory, a computer having a database that stores identifying information and software for directing the protocol. Such information includes the source of the particular matrix-with-memory, the identity of linked molecules or biological particles, any desired historical information about the matrix-with-memory, such as batch number, and the destination of that matrix-with-memory. Once the destination of the matrix-with-memory has been determined, the computer system provides the user with a cue, such as an audio cue, visual cue, a combination of the two, or other cue, that identifies the destination of the matrix-with-memory. In a particular embodiment [see, e.g., FIGS. 67–69], the visual cue is created by identifying one in a number of light emitting diodes (LEDs) that are physically attached to a series of containers, such as beakers containing a particular solution. The attachment of the LEDs to the containers is accomplished using an inverted U-shaped bracket with a LED mounted so that it is observable by the user. The bracket is sufficiently heavy that, once the bracket is placed on the rim of the beaker, the weight of the bracket will hold itself in place. In use, the matrix-with-memory is presented to the identification station which accesses the memory of the matrix and, by decoding the identification information provided by the matrix memory, identifies the matrix-with-memory. Once identified, the computer accesses the data base and determines the relevant information pertaining to the particular matrix-with-memory, and the destination of that matrix-with-memory. Once the matrix-with-memory destination has been determined, the computer generates a visual cue over the proper beaker by illuminating the LED attached to that beaker. Once the beaker is identified, the user can look for the visual cue, and place the matrix-with-memory in the identified beaker. Audio cues could be used instead of, or in addition to, the visual cues. Further description and exemplification of these devices and methods is set forth in Example 3.

The methods for sorting matrices-with-memories using the manual system [or automated system] include the steps of programming the memories, either at the time of sorting, or at an earlier time, with the information required for tracking and identifying the source and destination of the memory device. A library is created to define each of the matrices-with-memory, microreactors, or other suitable vessel or container, with the compounds which will be synthesized therein. This library will most preferably reside in the data base which can then be used to coordinate the movement of all, or part of, the matrices-with-memories in a particular laboratory. Once the library is created, the data base will be capable of identifying the particular memory device, the particular matrix-with-memory associated with the memory device, and will be capable of indicating where the matrix-with-memory should be placed to continue the necessary process steps for synthesis.

In order to simplify the assignment of a particular visual or audio indicator to a particular container, it is possible to have the computer dynamically assign any indicator to the container. This is accomplished by instructing the computer to assign an indicator to a beaker containing a compound XYZ, for example. The computer, in response, will search its data base for the unused or unassigned indicators, and selecting one, will begin flashing or beeping the particular indicator so that the user can grab the activated indicator and place it on the appropriate beaker, thus minimizing the required setup procedure for the automatic sorter. Risk of error is greatly reduced by using the computer to direct the entire sorting process—from assignment of the indicators to certain containers to the placement of the various memory devices into each of those containers.

Once the library has been created and the computer data base is enabled to coordinate the movement of the matrices with memory, the manual sorter may be utilized. The manual sorting process begins with the passing of the memory device within the field of detection of the identification station. Specifically, if the identification station is an optical bar code reading station, the matrix-with-memory must be passed within its field of view of the scanning laser, or other optical scanning device. If the identification station is an RF communicating identification station, such as for the IDTAG™ memory device, the memory device must be passed through the electromagnetic field to induce an energy level sufficient to excite the RF device and to solicit a response from the device.

Once the memory device is accessed, the device transmits back to the identification station, by either RF transmission, RF or optical reflection, or any other manner of communication discussed herein, the particular identification number, and any other relevant information stored in the memory system. This information is then modified to fit a standard serial data format by the controller 6703 of the identification station, and provided to the computer system with cable 6712. The computer receives the serial data and matches that information to the data library contained within the data base. The specific characteristics of the matrix-with-memory associated with the memory are then determined by indexing the data base to find the identification number corresponding to the particular memory device. Once the memory device record is identified, the computer may determine the proper next step for the synthesis on the matrix-with-memory, and corresponding destination. Once the destination is determined, the computer activates the proper indicator device corresponding to the destination of that memory device. Once the destination indicator device is activated, the user can look for the LED indicator which is activated, and deposit the matrix-with-memory inside. This step may be repeated until all of the matrices with memory have been properly distributed to their respective destinations.

In light of the disclosure herein, it will be apparent to those skilled in the art that numerous alternative means are available which may be used to identify a particular destination for the matrix-with-memory. Such other indicators may include, for example, an audible tone, a light source, a mechanical pointing device, an electromechanical indicator, such as a flag or solenoid, or any other indicator known in the art, or any combination of one or more or such indicators, such as audio and visual indicators. The identification station discussed above and described in detail for the electronic memory device, such as RF tag, is exemplary only. Generally, any combination of readable memory device and memory identifying station may be used in conjunction with the manual sorting device as provided herein.

b. Automated sorting

In addition to the manual sorting device discussed above, an automated sorting device is contemplated. Such device will combine a means for conveying the memory devices past the identification station, with a means for distributing the memory devices to various destinations.

Automated sorting devices, systems incorporating such devices and methods of sorting are provided. For example, an automated sorting device which includes a lower frame with a drawer having a number of addressable container positions may be used. Positioned above the drawer is an X-Y positioning device that can move in two directions, effectively covering the entire area above the drawer. Mounted to the lower frame is an upper frame which supports a matrix-with-memory device feeder. The feeder holds a large number of matrix-with-memory devices, feeding one of the matrix-with-memory devices at a time to a supply tube. The supply tube , which is oriented in a generally vertical configuration, leads downward to a turnstile that is formed with at least one slot having dimensions for receiving a single matrix-with-memory device. Once a matrix-with-memory device is captured in the slot, the turnstile rotates to dispense the matrix-with-memory device to a positioning tube. The positioning tube is equipped with a stopping solenoid for temporarily retaining the gravity-fed matrix-with-memory device in a position adjacent to an antenna coil of a read/write Once the memory device is in position, the antenna is activated to access the matrix-with-memory device to be read and identified, and, if appropriate, write to the device. Once the matrix-with-memory is identified, a host computer determines the proper container into which the matrix-with-memory device should be released after which the positioning device is moved to the position of the specified container. The stopping solenoid is opened to permit the matrix-with-memory device to slide down the positioning tube and drop into the appropriate container. A proximity sensor located near the solenoid tests for the presence of the matrix-with-memory device to confirm that the matrix-with-memory device has dropped. After placement of a first matrix-with-memory device, the turnstile is rotated to allow the next matrix-with-memory device waiting in the supply tube to be accessed and identified, written to as necessary, and placed in the proper container. This process can be repeated in rapid succession, with a positioning time of less than one second for a drawer which has dimensions of approximately thirty inches by fifty inches and contains fifty separate containers.

The automated sorting device can place matrix-with-memory devices into a variety of containers, including various sized beakers, fleakers, vials, tubes or other containing devices. The X-Y positioning device is accurate to within 0.1 inch, resulting in a device capable of placing matrix-with-memory devices in a dense arrangement of containers, with the quantity of containers being limited only by the size of the drawer and the range of travel of the positioning device in both the X and Y directions. The automated sorting device is controlled by a host computer that communicates with a Programmable Logic Controller (PLC), which has all the necessary digital and analog control lines for the control of the positioning device, the turnstile, and read/write station. An exemplary device and use thereof is set forth in FIGS. 70–74 and described in the Examples.

4. Combination of the sorter and cleaver devices for seamless data tracking

For example, FIGS. 114–119 illustrate the seamless nature of the data tracking provided by the units herein. FIGS. 114–119 depict an automated sorting and cleaving process, the requisite apparatus and linkage between the processes, incorporating an automated sorting device and an automated cleaving station. For example, in FIG. 114, an automated sorting device is shown and generally designated 11000. Sorting device 11000, which includes a hopper 11002, is attached to a computer 11004 which, in accordance with the description of the automated sorting devices herein, sorts matrices-with-memories into the appropriate microreactor carriers 11014 in the microreactor carrier tray 11012. In a preferred embodiment, after synthesis, the tagged microreactors are sorted, preferably using the automatic sorter provided herein. In embodiments in which MICROKAN™ microreactors are used, they are decapped prior to cleavage. The Sorter holds 12 carriers of 96 tagged microreactors (1152 total). Higher density carriers (and larger sorters) may be used.

Figure 115:
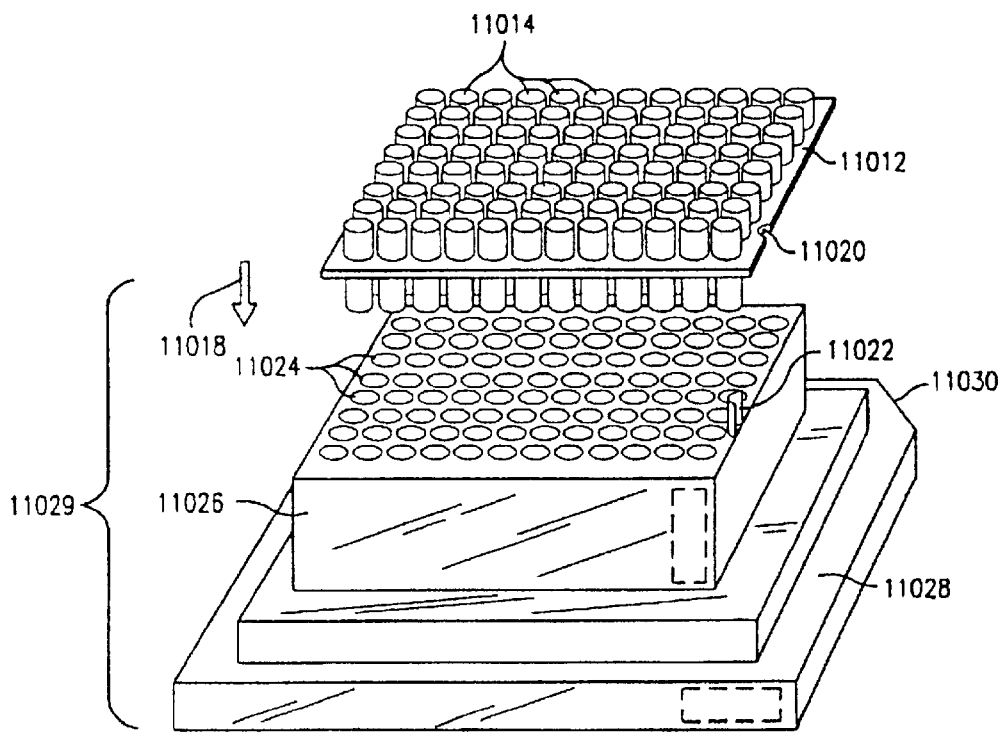
FIG. 115 is a perspective view of a microreactor carrier tray being installed in a cleaving block having an integral nozzle array interface.

Referring to FIG. 115, carriers 11014 are placed in a carrying tray 11012 which is disposed on cleaving block 11026, which is part of cleaving assembly 11029. First, a reagent such as TFA is added. Using the cleaving assembly 11029, solutions are drawn into racks of vials within a vacuum chamber. Each rack includes means for physically distinguishing it from other racks and is designed to fit into a single pre-determined location within the cleaving assembly. Also, each rack preferably includes one or more memory means, such as an electronic tag or an optically-readable code. After cleavage, the carriers and racks are scanned, their identities stored, and the contents of the tubes in the vials or tubes in the racks concentrated or lyophillized for storage. The memory means on each carrier (or each position in the rack) can be scanned to readily identify the contents for further processing, such as screening and analysis, following reconstitution.

Figure 114:
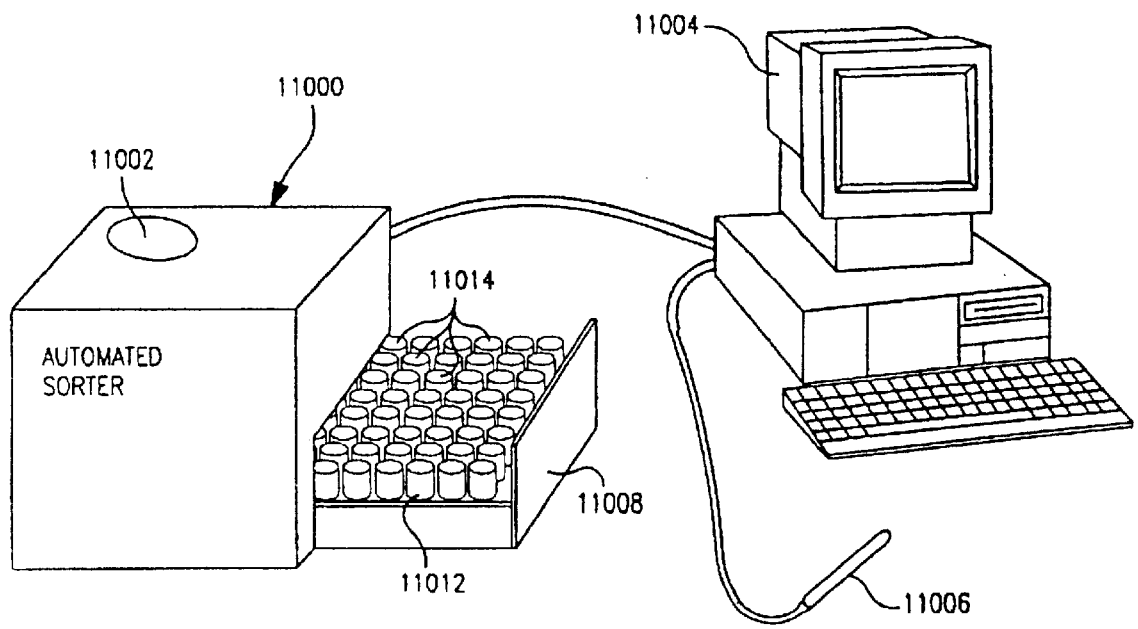
FIG. 114 is a perspective view of an automated sorting device and its associated computer and RF or microwave wand, where the microreactor carrier tray is partially inserted into the automated sorting device.

Referring to FIG. 114, the automated sorting device may have a removable portion 11008, such as a drawer, sliding tray or shelf, or an autoloader, which facilitates the insertion and removal of the microreactor carrier tray 11012. As described above in conjunction with FIGS. 67 and 70–78, each microreactor in the microreactor carrier is loaded with a matrix-with-memory, allowing the unique identification of the matrix, microreactor, and microreactor carrier 11014. The automated sorting device 11000 places one or more matrices-with-memory into each of the microreactor carriers 11014 which are oriented in an array, such as an 8 by 12 array for a 96 position microreactor carrier tray, e.g., tray 11012, allowing the automated sorting device 11000 to maintain records of the location of a specific matrix within a microreactor carrier tray. These records would typically be maintained digitally within a memory associated with computer 11004, however it may also be desirable maintain supplemental records in a tangible format, such as printed records, and to maintain back-up or permanent records on conventional data storage media such as floppy disks, CD/ROM, or data tapes.

Each microreactor carrier tray 11012 may be equipped with an identification tag, such as an RF tag, a microwave tag, or an optical tag, to facilitate the tracking and maintenance of the group of individual microreactors. For example, when an individual microreactor is placed in a microreactor carrier 11014 in a first position of the microreactor carrier tray 11012 and is loaded with a matrix having an RF or microwave tag, the individual matrix may be identified by its position within the carrier tray 11012 as well as by accessing the individual memory associated with the microreactor. Once the matrices-with-memory have been placed in their respective microreactor carriers 11014 at a known position within a microreactor carrier tray 11012, the individual microreactors may be located simply by identifying the microreactor carrier tray.

Computer 11004 may be equipped with an hand-held identification wand 11006 which is capable of reading and identifying individual matrices-with-memories and other items identified by the methods described herein. For example, the identification wand 11006 may be an RF or microwave wand, an optical scanning wand, or any other suitable identification apparatus. By moving the identification wand 11006 to a position within the detection range of the selected scanning technique, the individual matrix-with-memory may be identified. The ability to move a scanning device to the object to be scanned is permits ready access to identification tags which are associated with larger or heavier objects, such as the microreactor carrier trays 11012, cleaving blocks 11026, vial collection racks, microplates, or other objects within the laboratory environment that have a size or weight, or contain materials which should not be moved, which would make movement to an identification station impractical.

Referring to FIG. 114, once the matrices with memory have been positioned within the microreactor carriers 11014 in the microreactor carrier tray 11012, the microreactor carrier tray 11012 is removed from the automated sorting device 11000, and placed on a cleaving block 11026, as shown in FIG. 115.

In FIG. 115, microreactor carrier tray 11012 is shown positioned over cleaving block 11026, so that alignment pin 11022 is aligned with alignment hole, notch or groove 11020 in carrier tray 11012. Alignment pin 11022, which is shown extending upward from cleaving block 11026, mates with alignment notch 11020 in only one orientation to ensure correct orientation of the microreactor carrier tray 11012 on cleaving block 11026. The ability to limit the relative positions of the tray 11012 and cleaving block 11026 to only one possible position eliminates the need to separately identify each of the matrices-with-memory within the tray. Thereafter, each matrix may be identified simply by identifying microreactor carrier tray 11012, and accessing the record associated with carrier tray 11012 to identify a matrix within a particular location within the carrier tray 11012. Once positioned above the cleaving block 11026, the microreactor carrier tray 11012 may be lowered in direction 11018 onto the cleaving block 11026 so that microreactor carriers 11014 are inserted into bores 11024.

Figure 116:
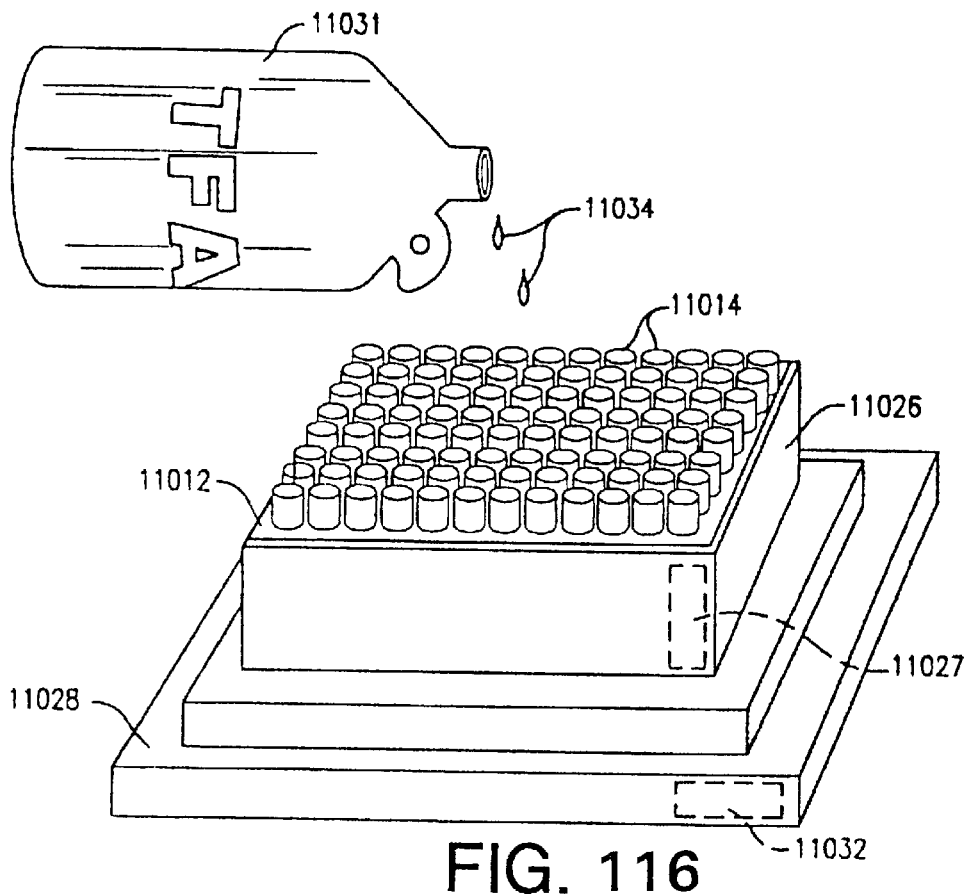
FIG. 116 is a perspective view of the nozzle array interface with the microreactor carrier tray installed, and the addition of TFA to the microreactor carriers.
Figure 117:
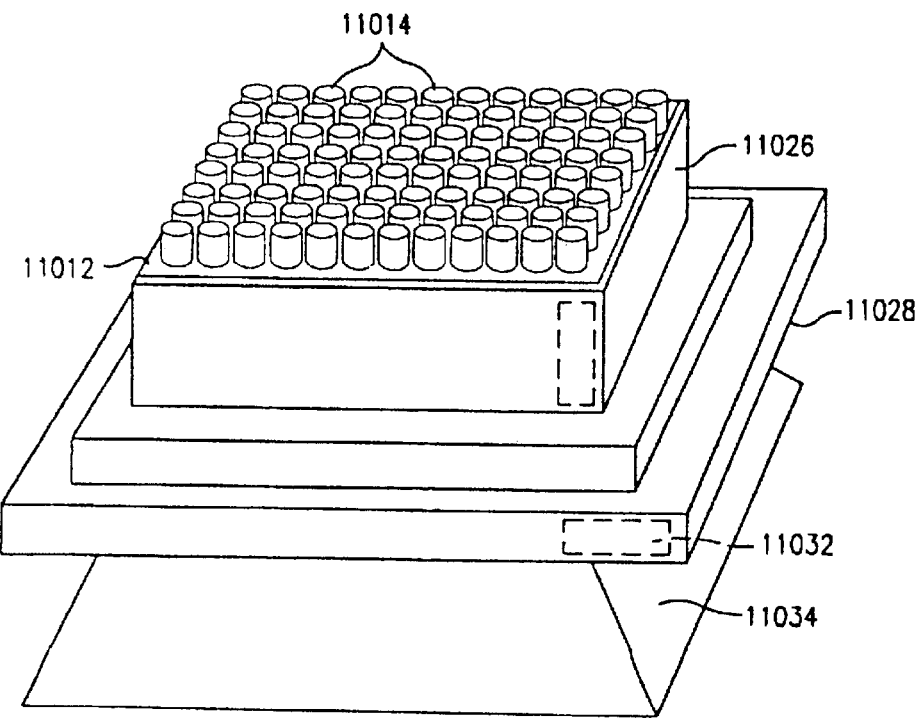
FIG. 117 is a perspective view of the microreactor carrier tray on the cleaving assembly and positioned on a shaking table to facilitate the cleaving process.

In addition to the identification of each microreactor carrier tray 11012 with its own identification tag, cleaving block 11026 may also have a dedicated identification tag 11027, as shown in FIG. 116, which facilitates tracking and maintenance of cleaving block 11026 and microreactor carrier tray 11012. The cleaving block 11026 may also have an integral nozzle array interface, or manifold, 11028. While the cleaving block 11026 and nozzle array interface 11028 have previously been discussed as separate components of an automated cleaving station, it will be apparent that such components may be combined, and collectively referred to as cleaving assembly 11029. The combination of these components reduces the need for addition of new components after the cleaving or synthesis process has begun. The nozzle array interface 11028 may also be optionally identified with an identification tag 11032. To facilitate the proper orientation of the cleaving assembly 11029. the nozzle array interface 11028 may be formed with an orientation key 11030 which will allow the cleaving assembly to be uniquely positioned for further processing in the cleaving and synthesis operation. Here, orientation key 11030 is shown as a notch in one corner of the interface, however, as will be apparent, any of a number of orientation indicators may be used to limit the relative positioning options to one.

Figure 118:
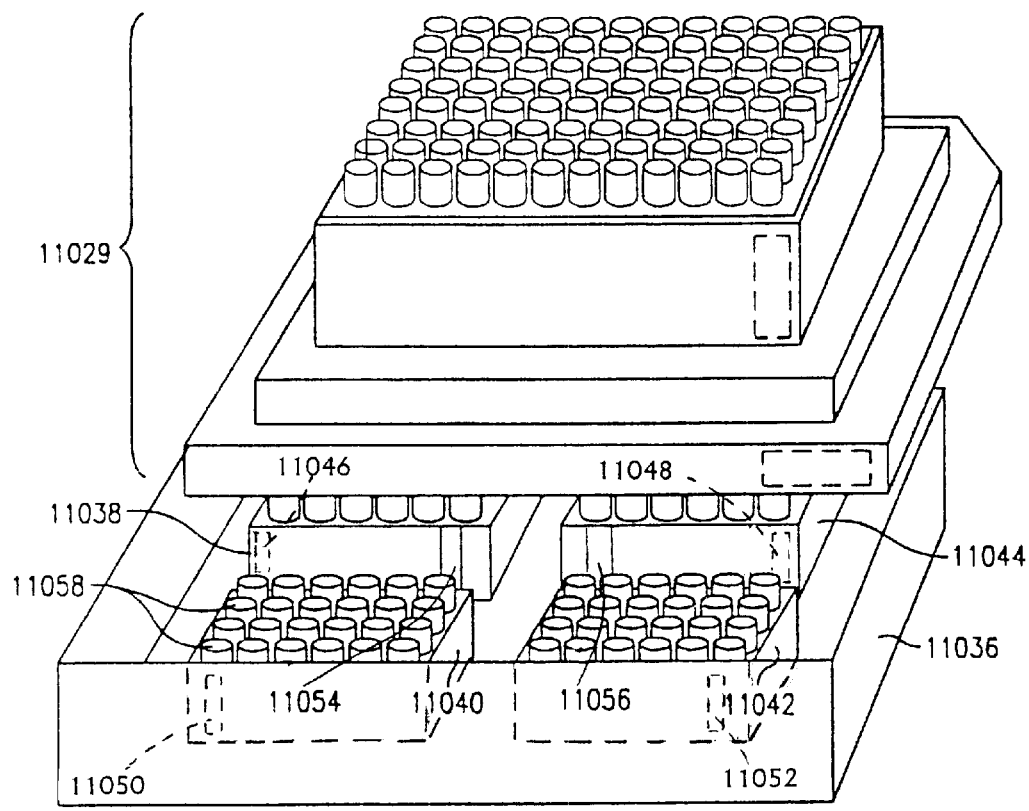
FIG. 118 is a perspective view of the nozzle array assembly positioned on a vacuum chamber with portions cut away for clarity, showing a collection rack having four 24 vessel vial racks.

Referring still to FIG. 116, cleaving assembly 11029 is shown with microreactor carrier tray 11012 in position on cleaving block 11026. Each microreactor carrier is filled with a cleavage reagent 11034, such as TFA 11031, to facilitate the cleaving of molecules (compounds) or biological particles from the matrices within the microreactors. To expedite the cleaving process, the cleaving assembly 11029 may be placed on a shaker 11034 of the type well known in the art, and shown generally in FIG. 117. Following agitation by shaker 11034, the cleaving assembly 11029 is positioned over a vacuum chamber 11036, as shown in FIG. 118, so that vacuum chamber 11036 is fully closed with a sufficient seal to retain a vacuum. Vacuum chamber 11036 is equipped with a keying mechanism which accepts the cleaving assembly only when the orientation key 11030 of the nozzle array interface is properly positioned. In the case of key 11030, which is a cut-off corner, the corresponding keying mechanism could be one or more pins projecting upward from the back, right corner of the top of vacuum chamber 11036, or it could be a solid raised area on the top of vacuum chamber 11036 which completes the missing area corner 11030. Such keying permits only one orientation of the cleaving assembly 11029 on top of vacuum chamber 11036.

Figure 106:
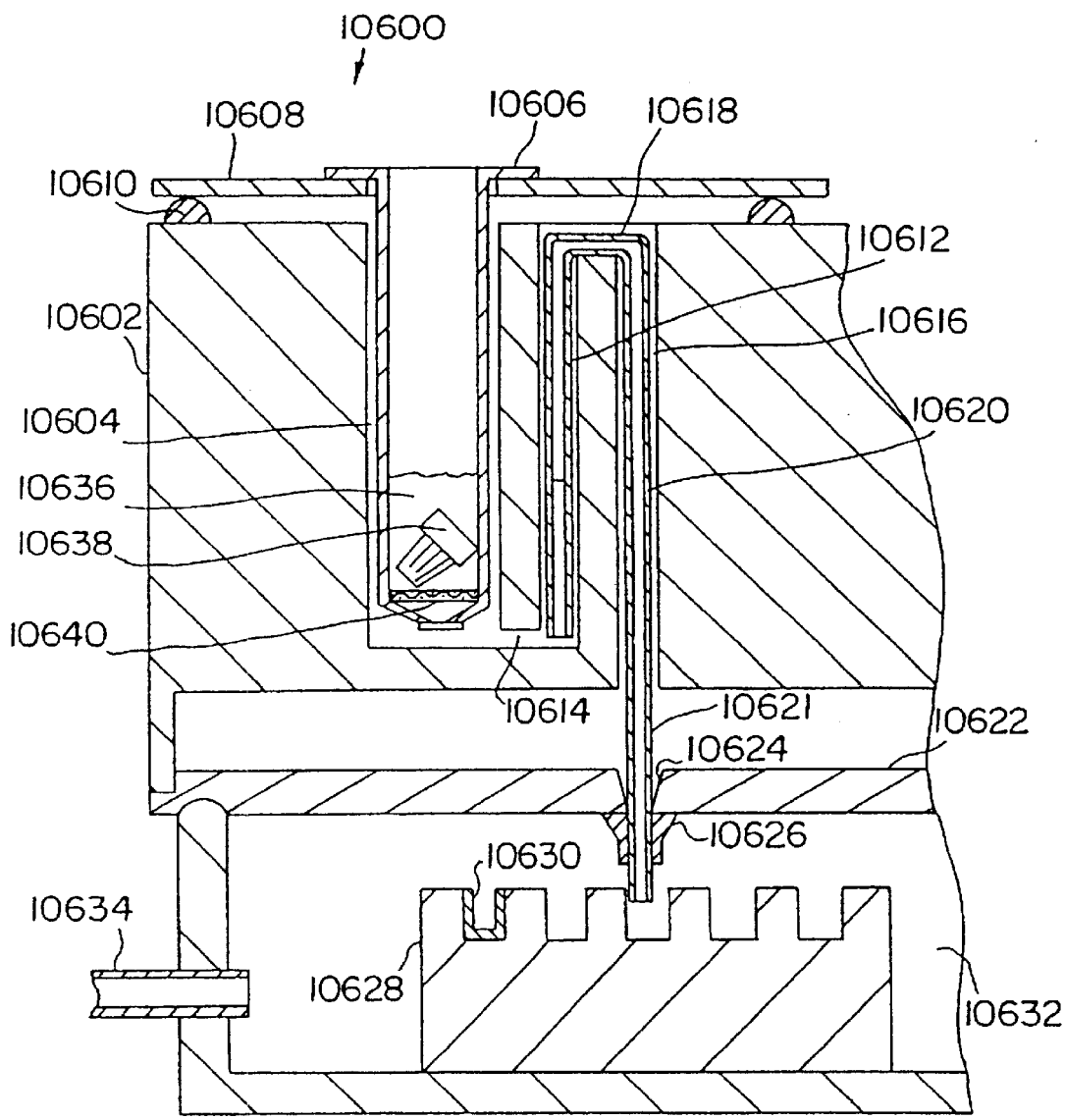
FIG. 106 is a cross-sectional view of another alternative embodiment of the automated cleaving station, showing a pre-formed U-tube which is inserted into a pair of bores within the cleaving block.

Still referring to FIG. 118, within the vacuum chamber 11036 are vial racks 11038, 11040, 11042 and 11044. As illustrated, each vial rack holds a 4-by-6 array of collection vials 11058, however, such an arrangement and quantity is exemplary only, and other arrangements of vials may be used. For example, the cleaving block 11026 may be formed with any number of bores 11024, and the location and quantity of vials and/or vial racks will be selected to correspond with the cleaving block and the number of samples to be created. Referring briefly back to FIG. 106, cleaving block 10602 is shown to be in fluid communication with collection rack 10628 via U-tube 10621. This U-tube configuration may also used in conjunction with the embodiment shown in FIG. 118, allowing the transfer of the cleaved compounds or biological particles from the microreactor carriers to the vials 11058.

Figure 120:
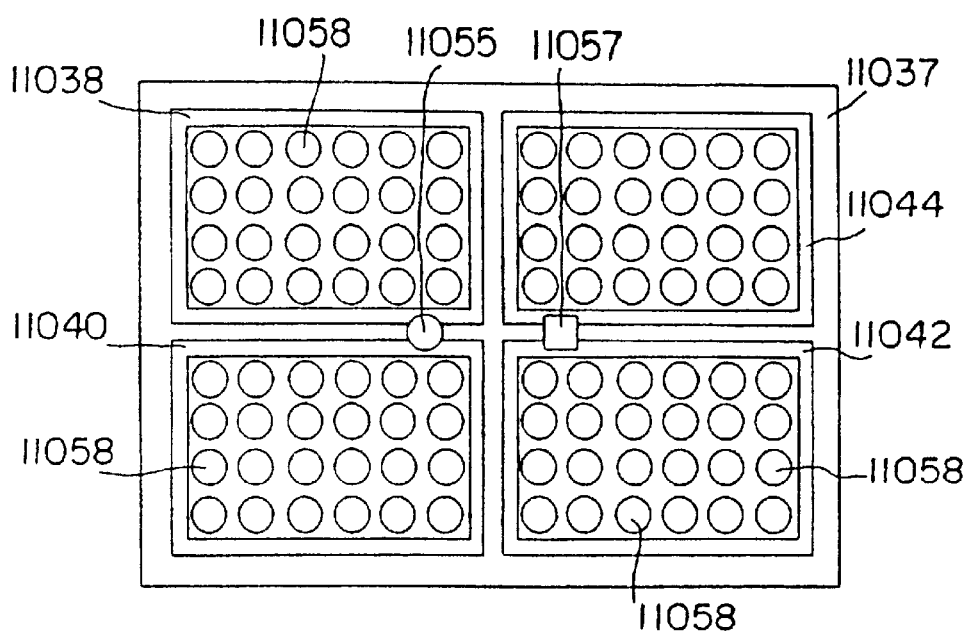

Each vial rack 11038, 11040, 11042, 11044 is equipped with a keyway for orienting and positioning the racks within vacuum chamber 11036. As illustrated in FIG. 118, keyways 11054 and 11056 are visible in vial racks 11038 and 11044. Keyways 11054, 11056 are shown in more detail in FIGS. 120 and 121, in which the vial racks are viewed from above. Collection rack locator tray 11037 is formed with four quadrants which are sized to receive vial racks 11038, 11040, 11042, and 11044. Locator tray 11037 will have raised ridges or some other form of demarcation to indicate the footprint of the vial racks for general guidance as to where the vial racks are to be placed. Each vial rack is formed with a keyway to restrict the position of the rack to only one location within the collection rack locator tray 11037. As shown, keyways 11053, 11054, 11056 and 11059 are grooves or channels formed in the center-facing side of each vial rack. Each keyway mates with only one key in rack locator tray 11037, and only when the vial rack is correctly oriented. In FIG. 120, keys 11055 and 11057 are a round peg and a square peg, respectively. Thus, in order to fit in locator tray 11037, keyways 11054 and 11059 are formed as rounded channels, while keyways 11053 and 11056 are formed as squared channels.

Figure 121:
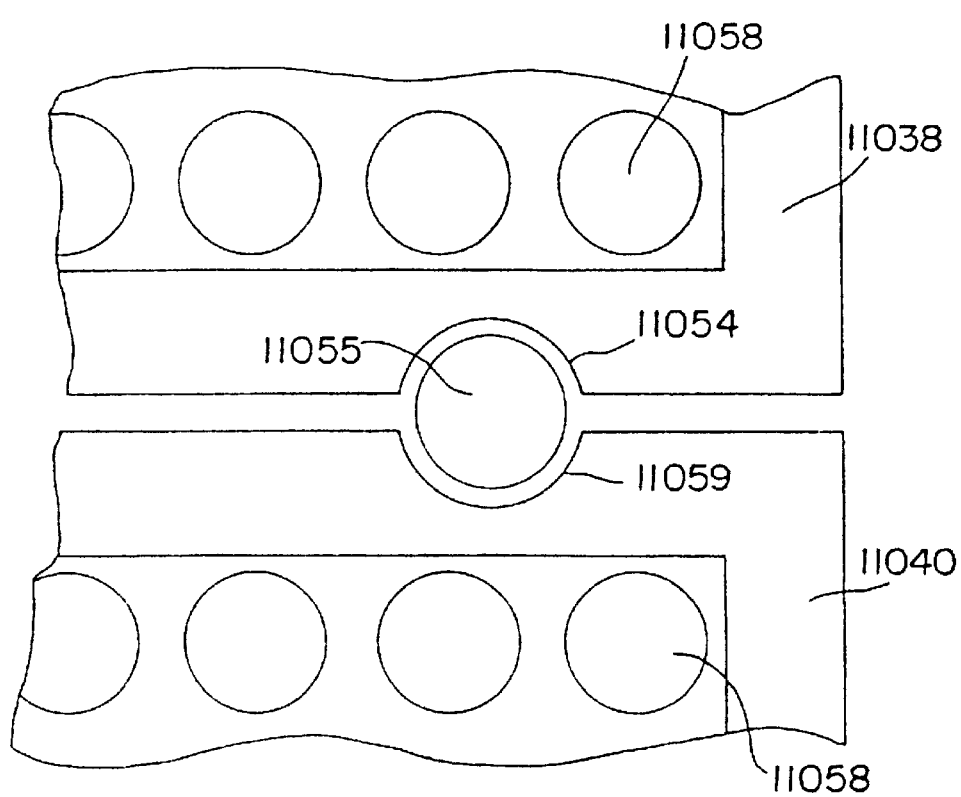

Referring to FIG. 121 for a more detailed view, vial rack 11038 is formed with a keyway 11054 sized and positioned to receive key 11055. This ensures that vial rack 11038 will only be able to be positioned within the locator place 11037 in one location and in one orientation. Similarly, vial rack 11040 is formed with keyway 11059 which is also sized and positioned to receive key 11055, yet maintaining a distinction between vial rack 11038 and vial rack 11040. Such distinction may be accomplished by offsetting the keyways such that even if the vial rack was rotated or orientated in a different position, it would not be possible to position the vial rack in the wrong position within the locator tray 11037. It should be noted that the keying shown and described herein is merely exemplary, and that other methods of uniquely orienting and positioning the vial racks within the vacuum chamber may be used.

Referring again to FIG. 118, vial racks 11038, 11040, 11042 and 11044 are shown having identification tags 11046, 11048, 11050 and 11052, respectively. The identification tags allow for the unique identification of each vial rack. In combination with the specific orientation of the vial rack within the vacuum chamber, the identification tags in the vial racks permit the unique identification of each vial 11058 within the vial rack. The vials may be identified either by tracking their physical position, by including a memory at each location, or combinations thereof.

To facilitate such identification, a vacuum chamber may be equipped with an identification station in close proximity to each vial rack position within the vacuum chamber. Using the identification station, each vial rack can be identified as it is placed into the vacuum chamber, further facilitating the tracking of the compounds from the microreactor carriers by eliminating the need for manual tracking of the vial racks within the vacuum chamber.

The unique identification and orientation of each vial rack ensures that each individual matrix-with-memory and the respective cleaved compound may be effectively tracked from the microreactor in the automated sorting device to its microreactor carrier in the microreactor carrier tray, through the cleaving assembly, and eventually to the vial rack after the sorting process.

Referring still to FIG. 118, once the vial racks 11038, 11040, 11042, and 11044 are in position within the vacuum chamber 11036, a vacuum is created in the vacuum chamber to draw the cleaved compound from each microreactor carrier, through its corresponding U-tube, and into its respective vial 11058 within a vial rack. It is not necessary for a direct mapping from microreactor carrier to vial to occur within the nozzle array interface tray, and such mapping may have virtually any configuration. For example, it is possible for a mapping configuration to allow for the transfer of a compound from a single microreactor carrier to be divided and mapped to more than one vial. Alternatively, it may be possible to map the compounds from more than one microreactor carrier into a single vial, such as for combining the compounds following the cleaving process.

Figure 119:
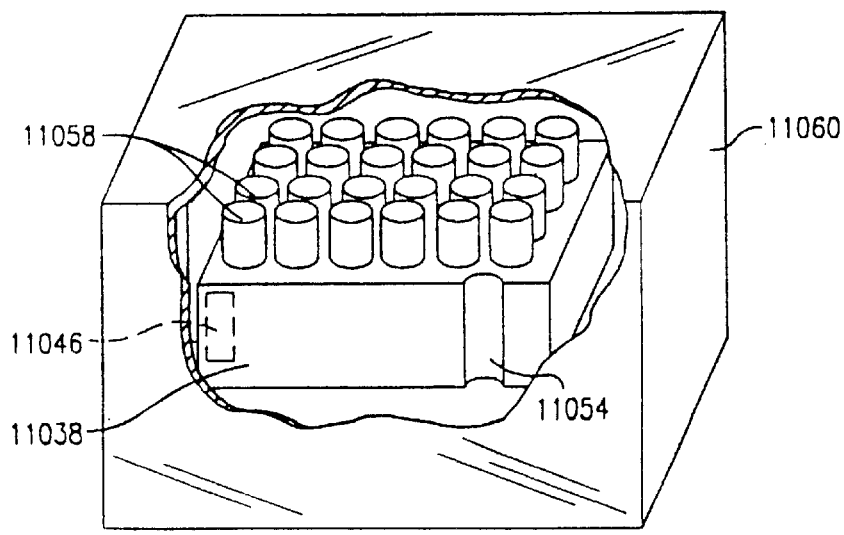

Once the compounds have been drawn from the microreactor carriers in the cleaving assembly 11029 into the vial racks, each vial rack is typically placed in a speed-vacuum 11060, as shown in FIG. 119. The speed-vacuum, or speed-vac, facilitates the evaporation of a cleaving agent, such as TFA, leaving only the cleaved compound in the vials 11058. Speed-vacuums are well known in the art, and will not be discussed in detail here.

G. Tools and Applications Using Matrices with Memories

1. Tools

The matrix with memory and associated system as described herein is the basic tool that can be used in a multitude of applications, including any reaction that incorporates a functionally specific (i.e. in the reaction) interaction, such as receptor binding. This tool is then combined with existing technologies or can be modified to produce additional tools.

For example, the matrix with memory combination, can be designed as a single analyte test or as a multianalyte test and also as a multiplexed assay that is readily automated. The ability to add one or a mixture of matrices with memories, each with linked or proximate molecule or biological particle to a sample, provides that ability to simultaneously determine multiple analytes and to also avoid multiple pipetting steps. The ability to add a matrix with memory and linked molecules or particles with additional reagents, such as scintillants, provides the ability to multiplex assays.

As discussed herein, in one preferred embodiment the matrices are particulate and include adsorbed, absorbed, or otherwise linked or proximate, molecules, such as peptides or oligonucleotides, or biological particles, such as cells. Assays using such particulate memories with matrices may be conduced "on bead" or "off bead". On bead assays are suitable for multianalyte assays in which mixtures of matrices with linked molecules are used and screened against a labeled known. Off bead assays may also be performed; in these instances the identity of the linked molecule or biological particle must be known prior to cleavage or the molecule or biological particle must be in some manner associated with the memory.

In other embodiments the matrices with memories use matrices that are continuous, such as microplates, and include a plurality of memories, preferably one memory/well. Of particular interest herein are matrices, such as Flash Plates™ [NEN, Dupont], that are coated or impregnated with scintillant or fluophore or other luminescent moiety or combination thereof, modified by including a memory in each well. The resulting matrix with memory is herein referred to as a luminescing matrix with memory. Other formats of interest that can be modified by including a memory in a matrix include the Multiscreen Assay System [Millipore] and gel permeation technology. Again it is noted that the memories may be replaced with or supplemented with engraved code, preferably at the base of each well [outer surface preferred] that is either precoded or added prior to or during use. The memory, in these instances, is then remote from the matrix.

Preferred plates are those that contain a microplate type frame and removable wells or strips. Each well or strip can contain a memory and/or can be engraved with a code.

2. Scintillation proximity assays (SPAs) and scintillant-containing matrices with memories Scintillation proximity assays are well known in the art [see, e.g., U.S. Pat. No. 4,271,139; U.S. Pat. No. 4,382,074; U.S. Pat. No. 4,687,636; U.S. Pat. No. 4,568,649; U.S. Pat. No. 4,388,296; U.S. Pat. No. 5,246,869; International PCT. application No. WO 96/211 56, International PCT Application No. WO 94/26413; International PCT Application No. WO 90/03844; European Patent Application No. 0 556 005 A1; European Patent Application No. 0 301 769 A1; Hart et al. (1979) *Molec. Immunol.* 16:265–267; Udenfriend et al. (1985) *Proc. Natl. Acad. Sci. U.S.A.* 82:8672–8676; Nelson et al. (1987) *Analyt. Biochem* 165:287–293; Heath, et al. (1991) *Methodol. Surv. Biochem. Anal.* 21:193–194; Mattingly et al. (1995) *J. Memb. Sci.* 98:275–280; Pernelle (1993) *Biochemistry* 32:11682–116878; Bosworth et al. (1989) *Nature* 341:167–168; and Hart et al. (1989) *Nature* 341:265]. Beads [particles] and other formats, such as plates and membranes have been developed.

SPA assays refer to homogeneous assays in which quantifiable light energy produced and is related to the amount of radioactively labeled products in the medium. The light is produced by a scintillant that is incorporated or impregnated or otherwise a part of a support matrix. The support matrix is coated with a receptor, ligand or other capture molecule that can specifically bind to a radiolabeled analyte, such as a ligand.

a. Matrices

Typically, SPA uses fluomicrospheres, such as diphenyloxazole-latex, polyacrylamide-containing a fluophore, and polyvinyltoluene [PVT] plastic scintillator beads, and they are prepared for use by adsorbing compounds into the matrix. Also fluomicrospheres based on organic phosphors have been developed. Microplates made from scintillation plastic, such as PVT, have also been used [see, e.g., International PCT Application No. WO 90/03844]. Numerous other formats are presently available, and any format may be modified for use herein by including one or more recording devices.

Typically the fluomicrospheres or plates are coated with acceptor molecules, such as receptors or antibodies to which ligand binds selectively and reversibly. Initially these assays were performed using glass beads containing fluors and functionalized with recognition groups for binding specific ligands [or receptors], such as organic molecules, proteins, antibodies, and other such molecules. Generally the support bodies used in these assays are prepared by forming a porous amorphous microscopic particle, referred to as a bead [see, e.g., European Patent Application No. 0 154,734 and International PCT Application No. WO 91/08489]. The bead is formed from a matrix material such as acrylamide, acrylic acid, polymers of styrene, agar, agarose, polystyrene, and other such materials, such as those set forth above. Cyanogen bromide has been incorporated into the bead into to provide moieties for linkage of capture molecules or biological particles to the surface. Scintillant material is impregnated or incorporated into the bead by precipitation or other suitable method. Alternatively, the matrices are formed from scintillating material [see, e.g., International PCT Application No. WO 91/08489, which is based on U.S. application Ser. No. 07/444,297; see, also U.S. Pat. No. 5,198,670], such as yttrium silicates and other glasses, which when activated or doped respond as scintillators. Dopants include Mn, Cu, Pb, Sn, Au, Ag, Sm, and Ce. These materials can be formed into particles or into continuous matrices. For purposes herein, the are used to coat, encase or otherwise be in contact with one or a plurality of recording devices.

Assays are conducted in normal assay buffers and require the use of a ligand labeled with an isotope, such as $^3$H and $^{125}$I, that emits low-energy radiation that is readily dissipated easily an aqueous medium. Because $^3$H β particles and $^{125}$I Auger electrons have average energies of 6 and 35 keV, respectively, their energies are absorbed by the aqueous solutions within very small distances (~4 μm for $^3$H β particles and 35 μm for $^{125}$I Auger electrons).

Thus, in a typical reaction of 0.1 ml to 0.4 ml the majority of unbound labeled ligands will be too far from the fluoromicrosphere to activate the fluor. Bound ligands, however, will be in sufficiently close proximity to the fluomicrospheres to allow the emitted energy to activate the fluor and produce light. As a result bound ligands produce light, but free ligands do not. Thus, assay beads emit light when they are exposed to the radioactive energy from the label bound to the beads through the antigen-antibody linkage, but the unreacted radioactive species in solution is too far from the bead to elicit light. The light from the beads will be measured in a liquid scintillation counter and will be a measure of the bound label.

Matrices with memories for use in scintillation proximity assays [SPA] are prepared by associating a memory [or engraved or imprinted code or symbology] with a matrix that includes a scintillant. In the most simple embodiment, matrix particles with scintillant [fluomicrospheres] are purchased from Amersham, Packard, NE Technologies [(formerly Nuclear Enterprises, Inc.) San Carlos, Calif.] or other such source and are associated with a memory, such as by including one or more of such beads in a MICROKAN™ microvessel with a recording device. Typically, such beads as purchased are derivatized and coated with selected moieties, such as streptavidin, protein A, biotin, wheat germ agglutinin [WGA], and polylysine, to which the target ligand will be attached. Streptavidin (or avidin) and biotin, because of their high affinity for each other, are particularly useful for forming such linkage. Among the commercially available and known SPA assays are those in which the target moiety includes biotin attached to the target ligand and these are linked to the streptavidin-coated support. Also available are inorganic fluomicrospheres based on cerium-doped yttrium silicate or polyvinyltoluene (PVT). These contain scintillant and may be coated and derivatized. Because the number of compounds that can be biotinylated other linkage methods and moieties have been developed. For example, International PCT application No. Wo 96/21156 describes a method for immobilizing an assay target on a fluorescent support by expressing a fusion protein that contains a linking domain for attaching the fusion protein to the fluorescent support, and a functional domain that includes the assay target or a protein that can attach to the assay target. The linking domain is, for example, a biotin-accepting domain, such as the biotin carboxylate carrier protein from *Propionibacterium shrmanii*. The functional domains are also used to link whole cells or membrane vesicles to supports.

Alternatively, small particles of PVT impregnated with scintillant are used to coat recording devices, such as the IPTT-100 devices [Bio Medic Data Systems, Inc., Maywood, N.J.; see, also U.S. Pat. Nos. 5,422,636, 5,420,579, 5,262,772, 5,252,962, 5,250,962, 5,074,318, and RE 34,936] that have been coated with a protective material, such as polystyrene, TEFLON, a ceramic or anything that does not interfere with the reading and writing EM frequency(ies). Such PVT particles may be manufactured or purchased from commercial sources such as NE TECHNOLOGY, INC. [e.g., catalog #191A, 1–10 μm particles]. These particles are mixed with agarose or acrylamide, styrene, vinyl or other suitable monomer that will polymerize or gel to form a layer of this material, which is coated on polystyrene or other protective layer on the recording device. The thickness of the layers may be empirically determined, but they must be sufficiently thin for the scintillant to detect proximate radiolabels. To make the resulting particles resistant to chemical reaction they may be coated with polymers such as polyvinyltoluene or polystyrene, which can then be further derivatized for linkage and/or synthesis of molecules and biological particles. The resulting beads are herein called luminescing matrices with memories, and when used in SPA formats are herein referred to as scintillating matrices with memories.

The scintillating matrices with memories beads can be formed by manufacturing a bead containing a recording device and including scintillant, such as 2,5-diphenyloxazole [PPO] and/or 1,4-bis-[5-phenyl-(oxazolyl)]benzene [POPOP] as a coating. These particles or beads are then coated with derivatized polyvinyl benzene or other suitable matrix on which organic synthesis, protein synthesis or other synthesis can be performed or to which organic molecules, proteins, nucleic acids, biological particles or other such materials can be attached. Attachment may be effected using any of the methods known to those of skill in the art, including methods described herein, and include covalent, non-covalent, direct and indirect linkages.

Alternatively or additionally, each bead or tube may be engraved with a code. Preferably the beads are of such geometry that they can be readily oriented for reading. Also the beads or tubes may be engraved and also include a data storage device.

Molecules, such as ligands or receptors or biological particles are covalently coupled thereto, and their identity is recorded in the memory. Alternatively, molecules, such as small organics, peptides and oligonucleoties, are synthesized on the beads as described herein so that history of synthesis and/or identity of the linked molecule is recorded in the memory. The resulting matrices with memory particles with linked molecules or biological particles may be used in any application in which SPA is appropriate. Such applications, include, but are not limited to: radioimmunoassays, receptor binding assays, enzyme assays and cell biochemistry assays.

For use herein, the beads, plates and membranes are either combined with a recording device or a plurality of devices, or the materials used in preparing the beads, plates or membranes is used to coat, encase or contact a recording device and/or engraved with a code. Thus, microvessels, such as MICROTUBE™ microreactors, MICROKAN™ microreactors containing SPA beads coated with a molecule or biological particle of interest; microplates impregnated with or coated with scintillant, and recording devices otherwise coated with, impregnated with or contacted with scintillant are provided.

To increase photon yield and remove the possibility of loss of fluor, derivatized fluomicrospheres based on yttrium silicate, that is doped selectively with rare earth elements to facilitate production of light with optimum emission characteristics for photomultipliers and electronic circuitry have been developed [see, e.g., European Patent Application No. 0 378 059 B1; U.S. Pat. No. 5,246,869]. In practice, solid scintillant fibers, such as cerium-loaded glass or based on rare earths, such as yttrium silicate, are formed into a matrix. The glasses may also include activators, such as terbium, europium or lithium. Alternatively, the fiber matrix may be made from a scintillant loaded polymer, such as polyvinyltoluene. Molecules and biological particles can be adsorbed to the resulting matrix.

For use herein, these fibers may be combined in a microvessel with a recording device [i.e., to form a MICROKAN™ microreactor]. Alternatively, the fibers are used to coat a recording device or to coat or form a microplate containing recording devices in each well. The resulting combinations are used as supports for synthesis of molecules or for linking biological particles or molecules. The identity and/or location and/or other information about the particles is encoded in the memory and the resulting combinations are used in scintillation proximity assays.

Scintillation plates [e.g., FlashPlates™, NEN Dupont, and other such plates] and membranes have also been developed [see, Mattingly et al. (1995) *J. Memb. Sci.* 98:275–280] that may be modified by including a memory for use as described herein. The membranes, which can contain polysulfone resin M.W. 752 kD, polyvinylpyrrolidone MW 40 kDA, sulfonated polysulfone, fluor, such as p-bis-o-methylstyrylbenzene, POP and POPOP, may be prepared as described by Mattingly, but used to coat, encase or contact a recording device. Thus, instead of applying the polymer solution to a glass plate the polymer solution is applied to the recording device, which, if need is pre-coated with a protective coating, such as a glass, TEFLON or other such coating.

Further, as shown in the Examples, the recording device may be coated with glass, etched and the coated with a layer of scintillant. The scintillant may be formed from a polymer, such as polyacrylamide, gelatin, agarose or other suitable material, containing fluophors, a scintillation cocktail, FlexiScint [Packard Instrument Co., Inc., Downers Grove, Ill.] NE Technology beads [see, e.g., U.S. Pat. No. 4,588,698 for a description of the preparation of such mixtures]. Alternatively, microplates that contain recording devices in one or more wells may be coated with or impregnated with a scintillant or microplates containing scintillant plastic may be manufactured with recording devices in each well. If necessary, the resulting bead, particle or continuous matrix, such as a microplate, may be coated with a thin layer polystyrene, TEFLON or other suitable material. In all embodiments it is critical that the scintillant be in sufficient proximity to the linked molecule or biological particle to detect proximate radioactivity upon interaction of labeled molecules or labeled particles with the linked molecule or biological particle.

The resulting scintillating matrices may be used in any application for which scintillation proximity assays are used. These include, ligand identification, single assays, multianalyte assays, including multi-ligand and multi-receptor assays, radioimmunoassays [RIAs], enzyme assays, and cell bio-chemistry assays [see, e.g., International PCT Application No. WO 93/19175, U.S. Pat. No. 5,430,150, Whitford et al. (1991) *Phytochemical Analysis* 2:134–136; Fenwick et al. (1994) *Anal. Proc. Including Anal. Commun.* 31:103–106; Skinner et al. (1994) *Anal. Biochem.* 223:259–265; Matsumura et al. (1992) *Life Sciences* 51:1603–1611; Cook et al. (1991) *Structure and Function of the Aspartic Proteinases*, Dunn, ed., Penum Press, New York, pp. 525–528; Bazendale et al. in (1990) *Advances in Prostaglandin, Thromboxane and Leukotriene Research*, Vol. 21, Samuelsson et al., eds., Raven Press, New York, pp 302–306].

The MICROTUBE microreactor provided herein offers a convenient format for the memory technology. The grafted surface polymer is suitable for synthesizing and screening large numbers of compounds. Procedures used to covalently link small organic molecules (e.g. biotin) to the MICROTUBE™ microreactor and other radiation grafted surfaces under aqueous and organic conditions are provided [see, EXAMPLES]. Methods for removing nonspecifically adsorbed organic molecules on the radiation grafted surface have been developed [see, EXAMPLES]. As a result the signal/noise ration has been substantially increased. As described in the EXAMPLES, the biotin/streptavidin system was used to demonstrate these procedures. Biotin was covalently linked to the surface of the radiation grafted surface in aqueous buffer or organic solvents. The biotin on the surface was detected with $^{125}$I-streptavidin using a SPA format. Microreactors biotinylated in aqueous buffer always generated higher signals compared to those biotinylated in organic solvents. Organic material is adsorbed into the polymer matrix during synthesis, and these adsorbed molecules may later interact with the applied $^{125}$I-streptavidin, lowering or blocking measurable signal.

Using an iminobiotin agarose gel assay, a variety of wash procedures for removing molecules that are not covalently bound to the surface of the microreactor were compared. The effects of washing biotinylated MICROTUBE microreactors with PBS buffer containing one of several detergents [CHAPS(zwitterionic), Triton-X100 (non-ionic), sodium dodecyl sulfate (SDS, anionic), benzalkonium chloride (BAC, cationic)] or charcoal, as well as dialysis against PBS containing avidin were. MICROTUBE™ microreactors biontinylated either in aqueous buffer or organic solvent were washed using these methods. After washing, $^{125}$I-streptavidin was added and the MICROTUBE microreactors were counted by SPA format.

The results showed that, for micreators biotinylated in aqueous solution, all wash conditions improved the signal. For those biotinylated in organic solvents, only those that were washed with SDS, BAC or charcoal had an improved signal. Additional wash studies with tube biotinylated in organic solvents were performed with either SDS and/or charcoal in wash buffer because MICROTUBE microreactors washed with BAC had greater variation in the signal. Various concentrations of SDS (including 0.75% SDS) in the wash buffer improved the results. Finally the optimal wash period was determined by comparing the signal of biotinylated MICROTUBE microreactors washed in this buffer for up to 5 days. Washing these MICROTUBE microreactors for two days most efficiently removes noncovalently bound small molecules that interfere with the desired interaction with $^{125}$I-streptavidin. This washing procedure dramatically improved the interaction of the tubes biotinylated in organic solvents with $^{125}$I-streptavidin. A 45-fold higher signal than background as measured by SPA was observed.

b. Assays (1) Receptor Binding Assays

Scintillating matrices with memories beads can be used, for example, in assays screening test compounds as agonists or antagonists of receptors or ion channels or other such cell surface protein. Test compounds of interest are synthesized on the beads or linked thereto, the identity of the linked compounds is encoded in the memory either during or following synthesis, linkage or coating. The scintillating matrices with memories are then incubated with radiolabeled [$^{125}$I, $^3$H, or other suitable radiolabel] receptor of interest and counted in a liquid scintillation counter. When radiolabeled receptor binds to any of the structure(s) synthesized or linked to the bead, the radioisotope is in sufficient proximity to the bead to stimulate the scintillant to emit light. In contrast, if a receptor does not bind, less or no radioactivity is associated with the bead, and consequently less light is emitted. Thus, at equilibrium, the presence of molecules that are able to bind the receptor may be detected. When the reading is completed, the memory in each bead that emits light [or more light than a control] queried and the host computer, decoder/encoder, or scanner can interpret the memory in the bead and identify the active ligand.

(a) Multi-ligand assay

Mixtures of scintillating matrices with memories with a variety of linked ligands, which were synthesized on the matrices or linked thereto and their identities encoded in each memory, are incubated with a single receptor. The memory in each light-emitting scintillating matrix with memory is queried and the identity of the binding ligand is determined.

(b) Multi-receptor assays

Similar to conventional indirect or competitive receptor binding assays that are based on the competition between unlabeled ligand and a fixed quantity of radiolabeled ligand for a limited number of binding sites, the scintillating matrices with memories permit the simultaneous screening of a number of ligands for a number of receptor subtypes.

Mixtures of receptor coated beads [one receptor type/per bead; each memory encoded with the identity of the linked receptor] are reacted with labeled ligands specific for each receptor. After the reaction has reached equilibrium, all beads that emit light are reacted with a test compound. Beads that no longer emit light are read.

For example receptor isoforms, such as retinoic acid receptor isoforms, are each linked to a different batch of scintillating matrix with memory beads, and the identity of each isoform is encoded in the memories of linked matrices. After addition of the radiolabeled ligand(s), such as $^3$H-retinoic acid, a sample of test compounds [natural, synthetic, combinatorial, etc.] is added to the reaction mixture, mixed and incubated for sufficient time to allow the reaction to reach equilibrium. The radiolabeled ligand binds to its receptor, which has been covalently linked to the bead and which the emitted short range electrons will excite the fluophor or scintillant in the beads, producing light. When unlabelled ligand from test mixture is added, if it displaces the labeled ligand it will diminish or stop the fluorescent light signal. At the end of incubation period, the tube can be measured in a liquid scintillation counter to demonstrate if any of the test material reacted with receptor family. Positive samples [reduced or no fluorescence] will be further analyzed for receptor subtyping by querying their memories with the RF detector. In preferred embodiments, each bead will be read and with a fluorescence detector and RF scanner. Those that have a reduced fluorescent signal will be identified and the linked receptor determined by the results from querying the memory.

The same concept can be used to screen for ligands for a number of receptors. In one example, FGF receptor, EGF receptor, and PDGF receptor are each covalently linked to a different batch of scintillating matrix with memory beads. The identity of each receptor is encoded in each memory. After addition of the $^{125}$I-ligands [$^{125}$I-FGF, $^{125}$I-EGF, and $^{125}$I-PDGF] a sample of test compounds [natural, synthetic, combinatorial, etc.) is added to the tube containing $^{125}$I-ligand-receptor-beads, m mixed and incubated for sufficient time to allow the reaction to reach equilibrium. The radiolabeled ligands bind to their respective receptors receptor that been covalently linked to the bead. By virtue of proximity of the label to the bead, the emitted short range electrons will excite the fluophor in the beads. When unlabelled ligand from test mixture is added, if it displaces the any of the labeled ligand it will diminish or stop the fluorescent signal. At the end of incubation period, the tube can be measured in a liquid scintillation counter to demonstrate if any of the test material reacted with the selected receptor family. Positive samples will be further analyzed for receptor type by passing the resulting complexes measuring the fluorescence of each bead and querying the memories by exposing them to RF or the selected EM radiation. The specificity of test ligand is determined by identifying beads with reduced fluorescence that and determining the identity of the linked receptor by querying the memory.

(c) Other formats

Microspheres, generally polystyrene typically about 0.3 µm–3.9 µm, are synthesized with scintillant inside can either be purchased or prepared by covalently linking scintillant to the monomer prior to polymerization of the polystyrene or other material. They can then be derivatized [or purchased with chemical functional groups], such as —COOH, and —CH$_2$OH. Selected compounds or libraries are synthesized on the resulting microspheres linked via the functional groups, as described herein, or receptor, such as radiolabeled receptor, can be coated on the microsphere. The resulting "bead" with linked compounds, can used in a variety of SPA and related assays, including immunoassays, receptor binding assays, protein:protein interaction assays, and other such assays in which the ligands linked to the scintillant-containing microspheres are reacted with memories with matrices that are coated with a selected receptor.

For example, $^{125}$I-labeled receptor is passively coated on the memory with matrix and then mixed with ligand that is linked to a the scintillant-containing microspheres. Upon binding the radioisotope into is brought into close proximity to the scintillant in which effective energy transfer from the β particle will occur, resulting in emission of light.

Alternatively, the memory with matrix [containing scintillant] can also be coated with $^3$H-containing polymer on which the biological target [i.e., receptor, protein, antibody, antigen] can be linked [via adsorption or via a functional group]. Binding of the ligand brings the scintillant into close proximity to the label, resulting in light emission.

(2) Cell-based Assays

Cell-based assays, which are fundamental for understanding of the biochemical events in cells, have been used with increasing frequency in biology, pharmacology, toxicology, genetics, and oncology [see, e.g., Benjamin et al. (1992) *Mol. Cell. Biol.* 12:2730–2738] Such cell lines may be constructed or purchased [see, e.g., the Pro-Tox Kit available from Xenometrix, Boulder Colo.; see, also International PCT Application No. WO 94/7208 cell lines]. Established cell lines, primary cell culture, reporter gene systems in recombinant cells, cells transfected with gene of interest, and recombinant mammalian cell lines have been used to set up cell-based assays. For example Xenometrix, Inc. [Boulder, Colo.] provides kits for screening compounds for toxicological endpoints and metabolic profiles using bacteria and human cell lines. Screening is effected by assessing activation of regulatory elements of stress genes fused to reporter genes in bacteria, human liver or colon cell lines and provide information on the cytotoxicity and permeability of test compounds.

In any drug discovery program, cell-based assays offer a broad range of potential targets as well as information on cytotoxicity and permeability. The ability to test large numbers of compounds quickly and efficiently provides a competitive advantage in pharmaceutical lead identification.

High throughput screening with cell-based assays is often limited by the need to use separation, wash, and disruptive processes that compromise the functional integrity of the cells and performance of the assay. Homogeneous or mix-and-measure type assays simplify investigation of various biochemical events in whole cells and have been developed using scintillation microplates [see, e.g., International PCT Application No. WO 94/26413, which describes scintillant plates that are adapted for attachment and/or growth of cells and proximity assays using such cells]. In certain embodiment herein, cell lines such as those described in International PCT Application No. WO 94/17208 are be plated on scintillant plates, and screened against compounds synthesized on matrices with memories. Matrices with memories encoded with the identity of the linked molecule will be introduced into the plates, the linkages cleaved and the effects of the compounds assessed. Positive compounds will be identified by querying the associated memory.

The scintillant base plate is preferably optically transparent to selected wavelengths that allow cells in culture to be viewed using an inverted phase contrast microscope, and permit the material to transmit light at a given wavelength with maximum efficiency. In addition the base retains its optical properties even after exposure to incident beta radiation from radioisotopes as well as under stringent radiation conditions required for sterilization of the plates. The base plate can be composed of any such optically transparent material containing scintillant, e.g., a scintillant glass based on lanthanide metal compounds. Typically, the base plate is composed of any plastic material, generally formed from monomer units that include phenyl or naphthyl moieties in order to absorb incident radiation energy from radionuclides which are in close proximity with the surface. Preferably the plastic base plate is composed of polystyrene or polyvinyltoluene, into which the scintillant is incorporated. The scintillant includes, but is not limited to: aromatic hydrocarbons such as p-terphenyl, p-quaterphenyl and their derivatives, as well as derivatives of the oxazoles and 1,3,4-oxadiazoles, such as 2-(4-t-butylphenyl)-5-(4-biphenyl)-1,3,4-oxadiazole and 2,5-diphenyloxazole. Also included in the polymeric composition may be a wavelength shifter such as 1,4-bis(5-phenyl-2-oxazolyl)benzene, 9,10-diphenylanthracene, 1,4-bis(2-methylstyryl)-benzene, and other such compounds. The function of the wavelength shifter is to absorb the light emitted by the scintillant substance and re-emit longer wavelength light which is a better match to the photo-sensitive detectors used in scintillation counters. Other scintillant substances and polymer bodies containing them are known to those of skill in this art [see, e.g., European Patent Application No. 0 556 005 A1].

The scintillant substances can be incorporated into the plastic material of the base by a variety of methods. For example, the scintillators may be dissolved into the monomer mix prior to polymerization, so that they are distributed evenly throughout the resultant polymer. Alternatively the scintillant substances may be dissolved in a solution of the polymer and the solvent removed to leave a homogeneous mixture. The base plate of disc may be bonded to the main body of the well or array of wells, which itself may be composed of a plastic material including polystyrene, polyvinyltoluene, or other such polymers. In the case of the multi-well array, the body of the plate may be made opaque, i.e., non-transparent and internally reflective, in order to completely exclude transmission of light and hence minimize "cross-talk." This is accomplished by incorporating into the plastic at the polymerization stage a white dye or pigment, for example, titanium dioxide. Bonding of the base plate to the main body of the device can be accomplished by any suitable bonding technique, for example, heat welding, injection molding or ultrasonic welding.

For example, a 96-well plate is constructed to the standard dimensions of 96-well microtiter plates 12.8 cm×8.6 cm×1.45 cm with wells in an array of 8 rows of 12 wells each. The main body of the plate is constructed by injection molding of polystyrene containing a loading of white titanium oxide pigment at 12%. At this stage, the wells of the microtiter plate are cylindrical tubes with no closed end. A base plate is formed by injection molding of polystyrene containing 2-(4-t-butylphenyl)-5-(4-biphenyl)-1,3,4-oxadiazole (2%) and 9,10-diphenylanthracene (0.5%). The base plate has been silk screen printed with a grid array to further reduce crosstalk. The base plate is then fused in a separate operation to the body by ultrasonic welding, such that the grid array overlies the portions of the microtiter plate between the wells.

A 24-well device is constructed to the dimensions 12.8× 8.6×1.4 cm with 24 wells in an array of 4 rows of 6 wells. The main body of the plate [not including the base of each well] is constructed by injection molding of polystyrene containing 12% white titanium oxide pigment. The base 24 of each well is injection molded with polystyrene containing 2-(4-t-butylphenyl)-5-(4-biphenylyl)-1,3,4-oxadizaole [2%] and 9,10-diphenylanthracene [0.5%]. The heat from the injected base plastic results in fusion to the main body giving an optically transparent base to the well.

The plates may contain multiple wells that are continuous or that are each discontinuous from the other wells in the array, or they may be single vessels that have, for example, an open top, side walls and an optically transparent scintillant plastic base sealed around the lower edge of the side walls.

In another format the plate, is a single well or tube. The tube may be constructed from a hollow cylinder made from optically transparent plastic material and a circular, scintillant containing, plastic disc. The two components are welded together so as to form a single well or tube suitable for growing cells in culture. As in the plate format, bonding of the circular base plate to the cylindrical portion is achieved by any conventional bonding technique, such as ultrasonic welding. The single well or tube may be any convenient size, suitable for scintillation counting. In use, the single well may either be counted as an insert in a scintillation vial, or alternatively as an insert in a scintillation vial, or alternatively as an insert in a multi-well plate of a flat bed scintillation counter. In this latter case, the main body of the multi-well plate would need to be opaque for reasons given earlier.

The various formats are selected according to use. They may be used for growing cells and studying cellular biochemical processes in living cells or cell fragments. The 96-well plate is a standard format used in experimental cell biology and one that is suitable for use in a flat bed scintillation counter [e.g., Wallac Microbeta or Packard Top Count]. In the multi-well format, it is an advantage to be able to prevent "cross talk" between different wells of the plate that may be used for monitoring different biological processes using different amounts or types of radioisotope. Therefore the main body of the plate can be made from opaque plastic material. The 24-well plate format is commonly used for cell culture. This type of plate is also suitable for counting in a flat bed scintillation counter. The dimensions of the wells will be larger.

As an alternative format, the transparent, scintillant containing plastic disc is made to be of suitable dimensions so as to fit into the bottom of a counting vessel. The counting vessel is made from non-scintillant containing material such as glass or plastic and should be sterile in order to allow cells to grow and the corresponding cellular metabolic processes to continue. Cells are first cultured on the disc, which is then transferred to the counting vessel for the purposes of monitoring cellular biochemical processes.

The culture of cells on the scintillation plastic base plate of the wells (or the disc) involves the use of standard cell culture procedures, e.g., cells are cultured in a sterile environment at 37° C. in an incubator containing a humidified 95% air/5% $CO_2$ atmosphere. Various cell culture media may be used including media containing undefined biological fluids such as fetal calf serum, or media which is fully defined and serum-free. For example, MCDB 153 is a selective medium for the culture of human keratinocytes [Tsao et al. (1982) *J. Cell. Physiol.* 110:219–229].

These plates are suitable for use with any adherent cell type that can be cultured on standard tissue culture plasticware, including culture of primary cells, normal and transformed cells derived from recognized sources species and tissue sources. In addition, cells that have been transfected with the recombinant genes may also be cultured using the invention. There are established protocols available for the culture of many of these diverse cell types [see, e.g., Freshney et al. (1987) *Culture of Animal Cells: A Manual of Basic Technique*, 2nd Edition, Alan R. Liss Inc.]. These protocols may require the use of specialized coatings and selective media to enable cell growth and the expression of specialized cellular functions.

The scintillating base plate or disc, like all plastic tissue culture ware, requires surface modification in order to be adapted for the attachment and/or growth of cells. Treatment can involves the use of high voltage plasma discharge, a well established method for creating a negatively charged plastic surface [see, e.g., Amstein et al. (1975) *J. Clinical Microbiol.* 2:46–54]. Cell attachment, growth and the expression of specialized functions can be further improved by applying a range of additional coatings to the culture surface of the device. These can include: (i) positively or negatively charged chemical coatings such as poly-lysine or other biopolymers [McKeehan et al. (1976) *J. Cell Biol.* 71:727–734 (1976)]; (ii) components of the extracellular matrix including collagen, laminin, fibronectin [ see, e.g., Kleinman et al. (1987) *Anal. Biochem.* 166:1–13]; and (iii) naturally secreted extracellular matrix laid down by cells cultured on the plastic surface [ Freshney et al. et al. (1987) *Culture of Animal Cells: A Manual of Basic Technique*, 2nd Edition, Alan R. Liss Inc.]. Furthermore, the scintillating base plate may be coated with agents, such as lectins, or adhesion molecules for attachment of cell membranes or cell types that normally grow in suspension. Methods for the coating of plasticware with such agents are known [see, e.g., Boldt et al. (1979) *J. Immunol.* 123:808].

In addition, the surface of the scintillating layer may be coated with living or dead cells, cellular material, or other coatings of biological relevance. The interaction of radiolabeled living cells, or other structures with this layer can be monitored with time allowing processes such as binding, movement to or from or through the layer to be measured.

Virtually all types of biological molecules can be studied. A any molecule or complex of molecules that interact with the cell surface or that can be taken up, transported and metabolized by the cells, can be examined using real time analysis. Examples of biomolecules will include receptor ligands, protein and lipid metabolite precursors (e.g., amino acids, fatty acids), nucleosides and any molecule that can be radiolabeled. This would also include ions such as calcium, potassium, sodium and chloride, that are functionally important in cellular homeostasis, and which exist as radioactive isotopes. Furthermore, viruses and bacteria and other cell types, which can be radiolabeled as intact moieties, can be examined for their interaction with monolayer adherent cells grown in the scintillant well format.

The type of radioactive isotope that can be used with this system will typically include any of the group of isotopes that emit electrons having a mean range up to 2000 µm in aqueous medium. These will include isotopes commonly used in biochemistry such as [$^3$H], [$^{125}$I], [$^{14}$C], [$^{35}$S], [$^{45}$Ca], [$^{33}$p], and [$^{32}$p], but does not preclude the use of other isotopes, such as [$^{55}$Fe], [$^{109}$Cd] and [$^{51}$Cr] that also emit electrons within this range. The wide utility of the invention for isotopes of different emission energy is due to the fact that the current formats envisaged would allow changes to the thickness of the layer containing a scintillant substance, thereby ensuring that all the electron energy is absorbed by the scintillant substance. Furthermore, cross-talk correction software is available which can be utilized with all high energy emitters. Applications using these plates include protein synthesis, $Ca^{2+}$ transport, receptor-ligand binding, cell adhesion, sugar transport and metabolism, hormonal stimulation, growth factor regulation and stimulation of motility, thymidine transport, and protein synthesis.

For use in accord with the methods herein, the scintillant plates can include a memory in each well, or alternatively, memory with matrix-linked compounds will be added to each well. The recording device with memory may be impregnated or encased or placed in wells of the plate, typically during manufacture. In preferred embodiments, however, the memories are added to the wells with adsorbed or linked molecules.

In one embodiment, matrices with memories with linked molecules are introduced into scintillant plates in which cells have been cultured [see, e.g., International PCT Application No. WO 94/26413]. For example, cells will be plated on the transparent scintillant base 96-well microplate that permits examination of cells in culture by inverted phase contrast microscope and permits the material to transmit light at a given wavelength with maximum efficiency. Matrices with memories to which test compounds linked by preferably a photocleaveable linker are added to the wells. The identity of each test compound is encoded in the memory of the matrix during synthesis if the compound is synthesized on the matrix with memory or when the compound is linked to the matrix.

Following addition of matrix with memory to the well and release of chemical entities synthesized on the beads by exposure to light or other procedures, the effects of the chemical released from the beads on the selected biochemical events, such as signal transduction, cell proliferation, protein or DNA synthesis, in the cells can be assessed. In this format receptor binding Such events include, but are not limited to: whole cell receptor-ligand binding [agonist or antagonist], thymidine or uridine transport, protein synthesis (using, for example, labeled cysteine, methionine, leucine or proline], hormone and growth factor induced stimulation and motility, and calcium uptake.

In another embodiment, the memories are included in the plates either placed in the plates or manufactured in the wells of the plates. In these formats, the identities of the contents of the well is encoded into the memory. Of course it is understood, that the information encoded and selection of encased or added memories depends upon the selected protocol.

In another format, cells will be plated on the tissue culture plate, after transferring the matrices with memories and release of compounds synthesized on the beads in the well. Cytostatic, cytotoxic and proliferative effects of the compounds will be measured using colorimetric [MTT, XTT, MTS, Alamar blue, and Sulforhodamine B], fluorimetric [carboxyfluorescein diacetate] , or chemiluminescent reagents [i.e., CytoLite™, Packard Instruments, which is used in a homogeneous luminescent assay for cell proliferation, cell toxicity and multi-drug resistance].

For example, cells that have been stably or transiently transfected with a specific gene reporter construct containing an inducible promoter operatively linked to a reporter gene that encodes an indicator protein can be calorimetrically monitored for promoter induction. Cells will be plated on the tissue culture 96-well microtiter plate and after addition of memories with matrices in the wells and release of chemical entities synthesized on the matrices, the effect of the compound released from the beads on the gene expression will be assessed. The Cytosensor Microphysiometer [Molecular Devices] evaluates cellular responses that are mediated by G protein-linked receptors, tyrosine kinase-linked receptors, and ligand-gated ion channels. It measures extracellular pH to assess profiles of compounds assessed for the ability to modulate activities of any of the these cell surface proteins by detecting secretion of acid metabolites as a result of altered metabolic states, particularly changes in metabolic rate. Receptor activation requires use of ATP and other energy resources of the cell thereby leading to increased intracellular metabolic rate. For embodiments herein, the memories with matrices, particularly those modified for measuring pH, and including linked test compounds, can be used to track and identify the added test compound added and also to detect changes in pH, thereby identifying linked molecules that modulate receptor activities.

3. Memories with matrices for non-radioactive energy transfer proximity assays

Non-radioactive energy transfer reactions, such as FET or FRET, FP and HTRF assays, are homogeneous luminescence assays based on energy transfer are carried out between a donor luminescent label and an acceptor label [see, e.g., Cardullo et al. (1988) Proc. Natl. Acad. Sci. U.S.A. 85:8790–8794; Peerce et al. (1986) Proc. Natl. Acad. Sci. U.S.A. 83:8092–8096; U.S. Pat. No. 4,777,128; U.S. Pat. No. 5,162,508; U.S. Pat. No. 4,927,923; U.S. Pat. No. 5,279,943; and International PCT Application No. WO 92/01225]. The donor label is usually a rare earth metal cryptate, particularly europium trisbipyridine diamine [EuTBP] or terbium trisbipyridine diamine [TbTBP] and an acceptor luminescent, presently fluorescent, label. When the donor is EuTBP, the acceptor is preferably allopycocyanin [APC], allophycocyanin B, phycocyanin C or phycocyanin R, and when the donor is TbTBP, the acceptor is a rhodamine, thiomine, phycocyanin R, phycoerythrocyanin, phycoerythrin C, phycoerythrin B or phycoerythrin R.

Energy transfer between such donors and acceptors is highly efficient, giving an amplified signal and thereby improving the precision and sensitivity of the assay. Within distances characteristic of interactions between biological molecules, the excitation of a fluorescent label (donor) is transferred non radiatively to a second fluorescent label (acceptor). When using europium cryptate as the donor, APC, a phycobiliprotein of 5 kDa, is presently the preferred acceptor because it has high molar absorptivity at the cryptate emission wavelength providing a high transfer efficiency, emission in a spectral range in which the cryptate signal is insignificant, emission that is not quenched by presence of sera, and a high quantum yield. When using $Eu^{3+}$ cryptate as donor, an amplification of emitted fluorescence is obtained by measuring APC emission.

The rare earth cryptates are formed by the inclusion of a luminescence lanthanide ion in the cavity of a macropolycyclic ligand containing 2,2'-biphyridine groups as light absorbers [see, e.g., U.S. Pat. No. 5,162,508; U.S. Pat. No. 4,927,923; U.S. Pat. No. 5,279,943; and International PCT Application No. WO 92/01225]. Preferably the $Eu3^+$ tris-bypryidine diamine derivative, although the acceptor may be used as the label, is cross-linked to antigens, antibodies, proteins, peptides, and oligonucleotides and other molecules of interest.

For use herein, matrices with memories are prepared that incorporate either the donor or, preferably the acceptor, into or on the matrix. In practice, as with the scintillating matrices with memories, the matrices may be of any format, i.e. particulate, or continuous, and used in any assay described above for the scintillating matrices. For example, the recording device is coated with a protective coating, such as glass or polystyrene. If glass it can be etched. As with preparation of the scintillating matrices with memories, compositions containing the donor or preferably acceptor, such as APC, and typically a polymer or gel, are coated on the recording device or the device is mixed with the composition to produce a fluorescing matrix with memory. To make these matrices resistant to chemical reaction, if needed, they may be coated with polymers such as polyvinylbenzene or polystyrene. Molecules, such as the constituents of combinatorial libraries, are synthesized on the fluorescing matrices with memories, or molecules or biological particles are linked thereto, the identity of the synthesized molecules or linked molecules or biological particles is encoded in memory, and the resulting matrices with memories employed in any suitable assay, including any of those described for the scintillating memories with matrices. In particular, these homogeneous assays using long-lived fluorescence rare earth cryptates and amplification by non radiative energy transfer have been adapted to use in numerous assays including assays employing ligand receptor interaction, signal transduction, transcription factors (protein-protein interaction), enzyme substrate assays and DNA hybridization and analysis [see, Nowak (1993) Science 270:368; see, also, Velculescu et al. (1995) Science 270:484–487, and Schena et al. (1995) Science 270:467–470, which describe methods quantitative and simultaneous analysis of a large number of transcripts that are particularly suited for modification using matrices with memories]. Each of these assays may be modified using the fluorescing matrices with memories provided herein.

For example, a receptor will be labeled with a europium cryptate [where the matrices with memories incorporate, for example allophycocyanin (APC)] or will be labeled with APC, where the matrices incorporate a europium cryptate. After mixing receptor and mixtures of matrices with different ligands, the mixture is exposed to laser excitation at 337 nm, and, if reaction has occurred, typical signals of europium cryptate and APC over background are emitted. Measurement with an interference filter centered at 665 nm selects the signal of the APC labeled receptor from that of europium cryptate labeled ligand on the beads. If particulate, the memories of matrices that emit at 665, can be queried to identify linked ligands.

4. Other applications using memories with matrices and luminescing memories with matrices a. Natural product screening In the past, the vast majority of mainline pharmaceuticals have been isolated form natural products such as plants, bacteria, fungus, and marine microorganisms. Natural products include microbials, botanicals, animal and marine products. Extracts of such sources are screened for desired activities and products. Selected products include enzymes [e.g., hyaluronidase], industrial chemicals [e.g., petroleum emulsifying agents], and antibiotics [e.g., penicillin]. It is generally considered that a wealth of new agents still exist within the natural products pool. Large mixtures of natural products, even within a fermentation broth, can be screened using the matrices with memory combinations linked, for example, to peptides, such as antigens or antibody fragments or receptors, of selected and known sequences or specificities, or to other biologically active compounds, such as neurotransmitters, cell surface receptors, enzymes, or any other identified biological target of interest. Mixtures of these peptides linked to memory matrices can be introduced into the natural product mixture. Individual binding matrices, detected by an indicator, such as a fluorometric dye, can be isolated and the memory queried to determine which linked molecule or biological particle is bound to a natural product.

b. Immunoassays and immunodiagnostics

The combinations and methods provided herein represent major advances in immunodiagnostics. Immunoassays [such as ELISAs, RIAs and EIAs (enzyme immunoassays)] are used to detect and quantify antigens or antibodies.

(1) Immunoassays

Immunoassays detect or quantify very small concentrations of analytes in biological samples. Many immunoassays use solid supports in which antigen or antibody is covalently, non-covalently, or otherwise, such as via a linker, attached to a solid support matrix. The support-bound antigen or antibody is then used as an analyte in the assay. As with nucleic acid analysis, the resulting antibody-antigen complexes or other complexes, depending upon the format used, rely on radiolabels or enzyme labels to detect such complexes.

The use of antibodies to detect and/or quantitate reagents ["antigens"] in blood or other body fluids has been widely practiced for many years. Two methods have been most broadly adopted. The first such procedure is the competitive binding assay, in which conditions of limiting antibody are established such that only a fraction [usually 30–50%] of a labeled [e.g., radioisotope, fluophore or enzyme] antigen can bind to the amount of antibody in the assay medium. Under those conditions, the addition of unlabeled antigen [e.g., in a serum sample to be tested] then competes with the labeled antigen for the limiting antibody binding sites and reduces the amount of labeled antigen that can bind. The degree to which the labeled antigen is able to bind is inversely proportional to the amount of unlabeled antigen present. By separating the antibody-bound from the unbound labeled antigen and then determining the amount of labeled reagent present, the amount of unlabeled antigen in the sample [e.g., serum] can be determined.

As an alternative to the competitive binding assay, in the labeled antibody, or "immunometric" assay [also known as "sandwich" assay], an antigen present in the assay fluid is specifically bound to a solid substrate and the amount of antigen bound is then detected by a labeled antibody [see, eg., Miles et al. (1968) Nature 29:186–189; U.S. Pat. No. 3,867,517; U.S. Pat. No. 4,376,110]. Using monoclonal antibodies two-site immunometric assays are available [see, e.g., U.S. Pat. No. 4,376,110]. The "sandwich" assay has been broadly adopted in clinical medicine. With increasing interest in "panels" of diagnostic tests, in which a number of different antigens in a fluid are measured, the need to carry out each immunoassay separately becomes a serious limitation of current quantitative assay technology.

Some semi-quantitative detection systems have been developed [see, e.g., Buechler et al. (1992) Clin. Chem. 38:1678–1684; and U.S. Pat. No. 5,089,391] for use with immunoassays, but no good technologies yet exist to carefully quantitate a large number of analytes simultaneously [see, eg., Ekins et al. (1990) J. Clin. Immunoassay 13:169–181] or to rapidly and conveniently track, identify and quantitate detected analytes.

The methods and memories with matrices provided herein provide a means to quantitate a large number of analytes simultaneously and to rapidly and conveniently track, identify and quantitate detected analytes.

(2) Multianalyte immunoassays

The combinations of matrix with memories provided herein permits the simultaneous assay of large numbers of analytes in any format. In general, the sample that contains an analyte, such as a ligand or any substance of interest, to be detected or quantitated, is incubated with and bound to a protein, such as receptor or antibody, or nucleic acid or other molecule to which the analyte of interest binds. In one embodiment, the protein or nucleic acid or other molecule to which the analyte of interest binds has been linked to a matrix with memory prior to incubation; in another embodiment, complex of analyte or ligand and protein, nucleic acid or other molecule to which the analyte of interest binds is linked to the matrix with memory after the incubation; and in a third embodiment, incubation to form complexes and attachment of the complexes to the matrix with memory are simultaneous. In any embodiment, attachment is effected, for example, by direct covalent attachment, by kinetically inert attachment, by noncovalent linkage, or by indirect linkage, such as through a second binding reaction [ie., biotin-avidin, Protein A-antibody, antibody-hapten, hybridization to form nucleic acid duplexes of oligonucleotides, and other such reactions and interactions]. The complexes are detected and quantitated on the solid phase by virtue of a label, such as radiolabel, fluorescent label, luminophore label, enzyme label or any other such label. The information that is encoded in the matrix with memory depends upon the selected embodiment. If, for example, the target molecule, such as the protein or receptor is bound to the solid phase, prior to complexation, the identity of the receptor and/or source of the receptor may be encoded in the memory in the matrix.

For example, the combinations provided herein are particularly suitable for analyses of multianalytes in a fluid, and particularly for multianalyte immunoassays. In one example, monoclonal antibodies very specific for carcinoembryonic antigen [CEA], prostate specific antigen [PSA], CA-125, alphafetoprotein [AFP], TGF-β, IL-2, IL-8 and IL-10 are each covalently attached to a different batch of matrices with memories using well-established procedures and matrices for solid phase antibody assays. Each antibody-matrix with memory complex is given a specific identification tag, as described herein.

A sample of serum from a patient to be screened for the presence or concentration of these antigens is added to a tube containing two of each antibody-matrix with memory complex [a total of 16 beads, or duplicates of each kind of bead]. A mixture of monoclonal antibodies, previously conjugated to fluorescent dyes, such as fluorescein or phenyl-EDTA-Eu chelate, reactive with different epitopes on each of the antigens is then added. The tubes are then sealed and the contents are mixed for sufficient time [typically one hour] to allow any antigens present to bind to their specific antibody-matrix with memory-antigen complex to produce antibody-matrix with memory-antigen-labeled antibody complexes. At the end of the time period, these resulting complexes are briefly rinsed and passed through an apparatus, such as that set forth in FIG. 7, but with an additional light source. As each complex passes through a light source, such as a laser emitting at the excitation wavelength of fluorescein, about 494 nm, or 340 nm for the Eu chelate complex, its fluorescence is measured and quantitated by reading the emitted photons at about 518 nm for fluorescein or 613 nm for phenyl-EDTA-Eu, and as its identity is determined by the specific signal received by the RF detector. In this manner, eight different antigens are simultaneously detected and quantitated in duplicate.

In another embodiment, the electromagnetically tagged matrices with recorded information regarding linked antibodies can be used with other multianalyte assays, such as those described by Ekins et al. [(1990) J. Clin. Immunoassay 13:169–181; see, also International PCT Applications Nos. 89/01157 and 93/08472, and U.S. Pat. Nos. 4,745,072, 5,171,695 and 5,304,498]. These methods rely on the use of small concentrations of sensor-antibodies within a few $\mu m^2$ area. Individual memories with matrices, or an array of memories embedded in a matrix are used. Different antibodies are linked to each memory, which is programmed to record the identity of the linked antibody. Alternatively, the antibody can be linked, and its identity or binding sites identified, and the information recorded in the memory. Linkage of the antibodies can be effected by any method known to those of skill in this art, but is preferably effected using cobalt-iminodiacetate coated memories [see, Hale (1995) *Analytical Biochem.* 231:46–49, which describes means for immobilization of antibodies to cobalt-iminodiacetate resin] mediated linkage particularly advantageous. Antibodies that are reversibly bound to a cobalt-iminodiacetate resin are attached in exchange insert manner when the cobalt is oxidized from the +2 to +3 state. In this state the antibodies are not removed by metal chelating regents, high salt, detergents or chaotropic agents. They are only removed by reducing agents. In addition, since the metal binding site in antibodies is in the C-terminus heavy chain, antibodies so-bound are oriented with the combining site directed away from the resin.

In particular antibodies are linked to the matrices with memories. The matrices are either in particular form or in the form of a slab with an array of recording devices linked to the matrices or microtiter dish or the like with a recording device in each well. Antibodies are then linked either to each matrix particle or to discrete "microspots" on the slab or in the microtiter wells.

In one application, prior to use of these matrices with memories, they are bound to a relatively low affinity anti-idiotype antibody [or other species that specifically recognizes the antibody binding site, such as a single chain antibody or peptidomimetic] labeled with a fluophore [e.g., Texas Red, acridine, fluorescein, ellipticine, rhodamine, Lissamine rhodamine B, Malachite Green, erythrosin, tetramethylrhodamine, eosin, pyrene, anthracene, methidium, ethydium, phenanthroline, 4-dimethylaminonaphthalene, quinoxaline, 2-dimethylaminonaphthalene, 7-dimethylamino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarine, isoluminol, benzophenone, dansyl, dabsyl, mansyl, sulfo rhodamine, 4-acetamido-4'-stilbene-2, 2'-disulfonic acid disodium salt, 4-benzamido-4'-stilbene-2, 2'-disulfonic acid disodium salt] to measure the concentration of and number of available binding sites present on each matrix with memory particle or each microspot, which information is then encoded into each memory for each microspot or each particle [see, Ekins et al. (1990) *J. Clin. Immunoassay* 13:169–181]. These low affinity antibodies are then eluted, and the matrices can be dried and stored until used.

Alternatively or additionally, the memories in the particles or at each microspot could be programmed with the identity or specificity of the linked antibody, so that after reaction with the test sample and identification of complexed antibodies, the presence and concentration of particular analytes in the sample can be determined. They can be used for multianalyte analyses as described above.

After reaction with the test sample, the matrices with memories are reacted with a second antibody, preferably, although not necessarily, labeled with a different label, such as a different fluophore, such as fluorescein. After this incubation, the microspots or each matrix particle is read by passing the particle through a laser scanner [such as a confocal microscope, see, e.g., Ekins et al. (1990) *J. Clin. Immunoassay* 13:169–181; see also, U.S. Pat. No. 5,342,633] to determine the fluorescence intensity. The memories at each spot or linked to each particle are queried to determine the total number of available binding sites, thereby permitting calculation of the ratio of occupied to unoccupied binding sites.

Equilibrium dialysis and modifications thereof has been used to study the interaction of antibody or receptor or other protein or nucleic acid with low molecular weight dialyzable molecules that bind to the antibody or receptor or other protein or nucleic acid. For applications herein, the antibody, receptor, protein or nucleic acid is linked to solid support (matrix with memory) and is incubated with the ligand.

In particular, this method may be used for analysis of multiple binding agents [receptors], linked to matrices with memories, that compete for available ligand, which is present in limiting concentration. After reaction, the matrices with memories linked to the binding agents [receptors] with the greatest amount of bound ligand, are the binding agents [receptors] that have the greatest affinity for the ligand.

The use of matrices with memories also permits simultaneous determination of $K_a$ values of multiple binding agents [receptors] or have multiple ligands. For example, a low concentration of labeled ligand is mixed with a batch of different antibodies bound to matrices with memories. The mixture is flowed through a reader [i.e., a Coulter counter or other such instrument that reads RF and the label] could simultaneously measure the ligand [by virtue of the label] and identity of each linked binding agent [or linked ligand] as the chip is read. After the reaction equilibrium [determined by monitoring progress of the reaction] labeled ligand is added and the process of reading label and the chips repeated. This process is repeated until all binding sites on the binding agent [or ligand] approach saturation, thereby permitting calculation of $K_a$ values and binding sites that were available.

C. Selection of antibodies and other screening methods
(1) Antibody selection

In hybridoma preparation and selection, fused cells are plated into, for example, microtiter wells with the matrices with memory-tagged antibody binding reagent [such as protein A or Co-chelate [see, e.g., Smith et al. (1992) *Methods: A Companion to Methods in Enzymology* 4, 73 (1992); III et al. (1993) *Biophys J.* 64:919; Loetscher et al. (1992) *J. Chromatography* 595:113–199; U.S. Pat. No. 5,443,816; Hale (1995) *Analytical Biochem.* 231:46–49]. The solid phase is removed, pooled and processed batchwise to identify the cells that produce antibodies that are the greatest binders [see, e.g., U.S. Pat. No. 5,324,633 for methods and device for measuring the binding affinity of a receptor to a ligand; or the above method by which phage libraries are screened for highest $K_A$ phage, i.e., limiting labeled antigen].

(2) Antibody panning

Memories with matrices with antibody attached thereto [e.g., particularly embodiments in which the matrix is a plate] may be used in antibody panning [see, e.g., Wysocki et al. (1978) *Proc. Natl. Acad. Sci. U.S.A.* 75:2844–48; Basch et al. (1983) *J. Immunol. Methods* 56:269; Thiele et al. (1986) *J. Immunol.* 136:1038–1048; Mage et al. (1981) *Eur. J. Immunol.* 11:226; Mage et al. (1977) *J. Immunol. Methods* 15:47–56; see, also, U.S. Pat. Nos. 5,217,870 and 5,087,570, for descriptions of the panning method]. Antibody panning was developed as a means to fractionate lymphocytes on the basis of surface phenotype based on the ability of antibody molecules to adsorb onto polystyrene surfaces and retain the ability to bind antigen. Originally [Wysocki et al. (1978) *Proc. Natl. Acad. Sci. U.S.A.*

75:2844–2848] polystyrene dishes coated with antibodies specific for cell surface antigens and permit cells to bind to the dishes, thereby fractionating cells. In embodiments herein, polystyrene or other suitable matrix is associated with a memory device and coated with an antibody, whose identity is recorded in the memory. Mixtures of these antibody coated memories with matrices can be mixed with cells, and multiple cell types can be sorted and identified by querying the memories to which cells have bound.

d. Phage display

Phage, viruses, bacteria and other such manipulable hosts and vectors [referred to as biological particles] can be modified to express selected antigens [peptides or polypeptides] on their surfaces by, for example, inserting DNA encoding the antigen into the host or vector genome, at a site such as in the DNA encoding the coat protein, such that upon expression the antigen [peptide or polypeptide] is presented on the surface of the virus, phage or bacterial host. Libraries of such particles that express diverse or families of proteins on their surfaces have been prepared. The resulting library is then screened with a targeted antigen [receptor or ligand] and those viruses with the highest affinity for the targeted antigen [receptor or ligand] are selected [see, e.g., U.S. Pat. Nos. 5,403,484, 5,395,750, 5,382,513, 5,316,922, 5,288,622, 5,223,409, 5,223,408 and 5,348,867].

Libraries of antibodies expressed on the surfaces of such packages have been prepared from spleens of immunized and unimmunized animals and from humans. In the embodiment in which a library of phage displaying antibodies from unimmunized human spleens is prepared, it is often of interest to screen this library against a large number of different antigens to identify a number of useful human antibodies for medical applications. Phage displaying antibody binding sites derived from single or small numbers of spleen cells can be separately produced, expanded into large batches, and bound to matrices with memories, such as programmable PROM or EEPROM memories, and identified according to phage batch number recorded in the memory. Each antigen can then be exposed to a large number of different phage-containing memory devices, and those that bind the antigen can be identified by one of several means, including radiolabeled, fluorescent labeled, enzyme labeled or alternate (e.g., mouse) tagged antibody labeled antigen. The encoded information in the thus identified phage-containing devices, relates to the batch of phage reactive with the antigen.

Libraries can also be prepared that contain modified binding sites or synthetic antibodies. DNA molecules, each encoding proteins containing a family of similar potential binding domains and a structural signal calling for the display of the protein on the outer surface of a selected viral or bacterial or other package, such as a bacterial cell, bacterial spore, phage, or virus are introduced into the bacterial host, virus or phage. The protein is expressed and the potential binding domain is displayed on the outer surface of the particle. The cells or viruses bearing the binding domains to which target molecules bind are isolated and amplified, and then are characterized. In one embodiment, one or more of these successful binding domains is used as a model for the design of a new family of potential binding domains, and the process is repeated until a novel binding domain having a desired affinity for the target molecule is obtained. For example, libraries of de novo synthesized synthetic antibody library containing antibody fragments expressed on the surface have been prepared. DNA encoding synthetic antibodies, which have the structure of antibodies, specifically Fab or Fv fragments, and contain randomized binding sequences that may correspond in length to hypervariable regions [CDRs] can be inserted into such vectors and screened with an antigen of choice.

Synthetic binding site libraries can be manipulated and modified for use in combinatorial type approaches in which the heavy and light chain variable regions are shuffled and exchanged between synthetic antibodies in order to affect specificities and affinities. This enables the production of antibodies that bind to a selected antigen with a selected affinity. The approach of constructing synthetic single chain antibodies is directly applicable to constructing synthetic Fab fragments which can also be easily displayed and screened. The diversity of the synthetic antibody libraries can be increased by altering the chain lengths of the CDRs and also by incorporating changes in the framework regions that may affect antibody affinity. In addition, alternative libraries can be generated with varying degrees of randomness or diversity by limiting the amount of degeneracy at certain positions within the CDRs. The synthetic binding site can be modified further by varying the chain lengths of the CDRs and adjusting amino acids at defined positions in the CDRs or the framework region which may affect affinities. Antibodies identified from the synthetic antibody library can easily be manipulated to adjust their affinity and or effector functions. In addition, the synthetic antibody library is amenable to use in other combinatorial type approaches. Also, nucleic acid amplification techniques have made it possible to engineer humanized antibodies and to clone the immunoglobulin [antibody] repertoire of an immunized mouse from spleen cells into phage expression vectors and identify expressed antibody fragments specific to the antigen used for immunization [see, e.g., U.S. Pat. No. 5,395,750].

The phage or other particles, containing libraries of modified binding sites, can be prepared in batches and linked to matrices that identify the DNA that has been inserted into the phage. The matrices are then mixed and screened with labeled antigen [e.g., fluorescent or enzymatic] or hapten, using an assay carried out with limiting quantities of the antigen, thereby selecting for higher affinity phage. Thus, libraries of phage linked to matrix particles with memories can be prepared. The matrices are encoded to identify the batch number of the phage, a sublibrary, or to identify a unique sequence of nucleotides or amino acids in the antibody or antibody fragment expressed on its surface. The library is then screened with labeled antigens. The antigens are labeled with enzyme labels or radiolabels or with the antigen bound with a second binding reagent, such as a second antibody specific for a second epitope to which a fluorescent antigen binds.

Following identification of antigen bound phage, the matrix particle can be queried and the identity of the phage or expressed surface protein or peptide determined. The resulting information represents a profile of the sequence that binds to the antigen. This information can be analyzed using methods known to those of skill in this art.

e. Combinatorial Biology: Target discovery and identification

Methods for identifying targets for receptors and for identifying functon of proteins encoded by open reading frames using libraries on matrices with memories, preferably scintillating matrices with memories. In particular methods for target identification by screening selected targets with a library of combination of a matrix with a memory and linked compounds or biological particles. The target may be a cell or tissue extract, and the library, prepared on the matrix contains known compounds, whose identity is stored in the associated memory. Positive signals will identify compounds specific for the known compounds.

In certain embodiments, the target is cell or tissue extract in which the cells or cells in the tissue contain heterologous DNA that encodes a protein of unknown function. In other embodiments, whole cells can be screened against a library of compounds linked to matrices with memories. Targeted receptors, for example, will be those implicated in a disorder and agents that interact with or somehow modulate that activity of the receptor are identified.

The preferred matrix with memory for this embodiment are the MICROTUBE microreactors, preferably those that include scintillant. The SPA format or HTRF format is the preferred format for identification of positives. Positive MICROTUBE microreactors will emit a light. The extract or cells will be labeled with a suitable label for each format (i.e. tritium or $^{125}$I for SPA).

f. Anti-microbial assays and mutagenicity assays

Compounds are synthesized or linked to matrix with memory. The linkage is preferably a photocleavable linkage or other readily cleavable linkage. The matrices with memories with linked compounds, whose identities are programmed into each memory are the placed on, for example, 10-cm culture plates, containing different bacteria, fungi, or other microorganism. After release of the test compounds the anti-microbial effects of the chemical will be assessed by looking for lysis or other indicia of anti-microbial activity. In preferred embodiments, arrays of memories with matrices can be introduced into plates. The memories are encoded with the identity of the linked or associated test compound and the position on the array.

The AMES test is the most widely used mutagen/carcinogen screening assay [see, e.g., Ames et al. (1975) *Mutation Res.* 31:347–364; Ames et al. (1973) *Proc. Natl. Acad. Sci. U.S.A.* 70:782–786.; Maron et al., (1983) *Mutation Research* 113:173; Ames (1971) in *Chemical Mutagens, Principles and Methods for their Detection*, Vol. 1, Plenum Press, New York, pp 267–282]. This test uses several unique strains of *Salmonella typhimurium* that are histidine-dependent for growth and that lack the usual DNA repair enzymes. The frequency of normal mutations that render the bacteria independent of histidine [i.e., the frequency of spontaneous revertants] is low. The test evaluates the impact of a compound on this revertant frequency. Because some substances are converted to a mutagen by metabolic action, the compound to be tested is mixed with the bacteria on agar plates along with the liver extract. The liver extract serves to mimic metabolic action in an animal. Control plates have only the bacteria and the extract. The mixtures are allowed to incubate. Growth of bacteria is checked by counting colonies. A test is positive where the number of colonies on the plates with mixtures containing a test compound significantly exceeds the number on the corresponding control plates.

A second type of Ames test [see, International PCT Application No. WO 95/10629, which is based on U.S. application Ser. No. 08/011,617; and Gee et al. (1994) *Proc. Natl. Acad. Sci. U.S.A.* 91:11606–11610; commercially avail from Xenometrix, Boulder Colo.] is of interest herein. This test provides a panel of *Salmonella typhimurium* strains for use as a detection system for mutagens that also identifies mutagenic changes. Although a direct descendant of the traditional Ames Salmonella reverse mutation assay in concept, the Ames II assay provides the means to rapidly screen for base mutations through the use of a mixture of six different Salmonella strains.

These new strains carry his mutations listed in the table below. All are deleted for uvrB and are deficient therefore in excision repair. In addition, all six have lipopolysaccharide [rfa] mutations rendering them more permeable, and all contain the pKM$^{101}$ plasmid conferring enhanced mutability.

| STRAIN | BASE CHANGE | MUTATION |
|---|---|---|
| TA7001 | A:T → G:C | hisG1775 |
| TA7002 | T:A → A:T | hisC9138 |
| TA7003 | T:A → G:C | hisG9074 |
| TA7004 | G:C → A:T | hisG9133 |
| TA7005 | G:C → A:T | hisG9130 |
| TA7006 | G:C → C:G | hisC9070 |

These strains, which revert at similar spontaneous frequencies [approximately 1 to $10 \times 10^8$] can be exposed and plated separately for determining mutational spectra, or mixed and exposed together to assess broad mutagenic potential. The assay takes 3 days from start to finish and can be performed in 96 well- or 384 well-microtiter plates. Revertant colonies are scored using bromo-cresol purple indicator dye in the growth medium. The mixed strains can be assayed first as part of a rapid screening program. Since this six strain mixture is slightly less sensitive than individual strains tested alone, compounds which are negative for the mix can be retested using all six strains. For all but the weakest mutagens, the Ames II strain mixture appears to be capable of detecting reversion events even if only one strain is induced to revert. The mixed strains provide a means to perform rapid initial screening for genotoxins, while the battery of base-specific tester strains permit mutational spectra analysis.

As modified herein, the test compounds are linked to matrices with memories, that have been encoded with the identity of the test compounds. The assays can be performed on multiple test compounds simultaneously using arrays of matrices with memories or multiple matrices with memories encoded with the identity of the linked test compound and the array position or plate number into which the compound is introduced.

g. Hybridization assays and reactions
(1) Hybridization reactions

It is often desirable to detect or quantify very small concentrations of nucleic acids in biological samples. Typically, to perform such measurements, the nucleic acid in the sample [i.e., the target nucleic acid] is hybridized to a detection oligonucleotide. In order to obtain a detectable signal proportional to the concentration of the target nucleic acid, either the target nucleic acid in the sample or the detection oligonucleotide is associated with a signal generating reporter element, such as a radioactive atom, a chromogenic or fluorogenic molecule, or an enzyme [such as alkaline phosphatase] that catalyzes a reaction that produces a detectable product. Numerous methods are available for detecting and quantifying the signal.

Following hybridization of a detection oligonucleotide with a target, the resulting signal-generating hybrid molecules must be separated from unreacted target and detection oligonucleotides. In order to do so, many of the commonly used assays immobilize the target nucleic acids or detection oligonucleotides on solid supports. Presently available solid supports to which oligonucleotides are linked include nitrocellulose or nylon membranes, activated agarose supports, diazotized cellulose supports and non-porous polystyrene latex solid microspheres. Linkage to a solid support permits fractionation and subsequent identification of the hybridized nucleic acids, since the target nucleic acid may be directly captured by oligonucleotides immobilized on solid supports.

More frequently, so-called "sandwich" hybridization systems are used. These systems employ a capture oligonucleotide covalently or otherwise attached to a solid support for capturing detection oligonucleotide-target nucleic acid adducts formed in solution [see, e.g., EP 276,302 and Gingeras et al. (1989) Proc. Natl. Acad. Sci. USA 86:1173]. Solid supports with linked oligonucleotides are also used in methods of affinity purification. Following hybridization or affinity purification, however, if identification of the linked molecule or biological material is required, the resulting complexes or hybrids or compounds must be subjected to analyses, such as sequencing. The combinations and methods herein eliminate the need for such analyses.

Use of matrices with memories in place of the solid support matrices used in the prior hybridization methods permits rapid identification of hybridizing molecules. The identity of the linked oligonucleotide is written or encoded into the memory. After reaction, hybrids are identified, such as by radioactivity or separation, and the identify of hybridizing molecules are determined by querying the memories.

(2) Hybridization assays

Mixtures nucleic acid probes linked to the matrices with memories can be used for screening in assays that heretofore had to be done with one probe at a time or with mixtures of probes followed by sequencing the hybridizing probes. There are numerous examples of such assays [see, e.g., U.S. Pat. No. 5,292,874, "Nucleic acid probes to *Staphylococcus aureus*" to Milliman, and U.S. Pat. No. 5,232,831, "Nucleic acid probes to *Streptococcus pyogenes*" to Milliman, et al.; see, also, U.S. Pat. Nos. 5,216,143, 5,284,747 5,352,579 and 5,374,718]. For example, U.S. Pat. No. 5,232,831 provides probes for the detection of particular Streptococcus species from among related species and methods using the probes. These probes are based on regions of Streptococcus rRNA that are not conserved among related Streptococcus species. Particular species are identified by hybridizing with mixtures of probes and ascertaining which probe(s) hybridize. By virtue of the instant matrices with memories, following hybridization, the identity of the hybridizing probes can be determined by querying the memories, and thereby identifying the hybridizing probe.

h. Combinatorial libraries and other libraries and screening methodologies

The combinations of matrices with memories are applicable to virtually any synthetic scheme and library preparation and screening protocol. These include, those discussed herein, and also methodologies and devices, such as the Chiron "pin" technology [see, e.g., International PCT application No. WO 94/11388; Geysen et al. (1985) *Proc. Natl. Acad. Sci. U.S.A.* 82:178; Geysen et al. (1987) *J. Immunol. Meth.* 102:259–274; Maeji et al. (1994) *Reactive Polymers* 22:203–21 2], which relies on a support composed of annular synthesis components that have an active surface for synthesis of a modular polymer and an inert support rod that is positioned axially to the annular synthesis components. This pin technology was developed for the simultaneous synthesis of multiple peptides. In particular the peptides are synthesized on polyacrylic acid grafted on the tip of polyethylene pins, typically arranged in a microtiter format. Amino acid coupling is effected by immersing the pins in a microtiter plate. The resulting peptides remain bound to the pins and can be reused.

As provided herein, "pins" may be linked to a memory or recording device, preferably encasing the device, or each pin may be coded and the code and the identity of the associated linked molecule(s) stored in a remote memory. As a result it will not be necessary to physically array the pins, rather the pins can be removed and mixed or sorted.

Also of interest herein, are DIVERSOMER™ technology libraries produced by simultaneous parallel synthesis schemes for production of nonoligomeric chemical diversity [see, e.g., U.S. Pat. No. 5,424,483; Hobbs DeWitt et al. (1994) *Drug Devel. Res.* 33:116–124; Czarnik et al. (1994) *Polym. Prepr.* 35:985; Stankovic et al. (1994) in *Innovation Perspect. Solid Phase Synth. Collect. Pap., Int. Symp.*, 3rd Epton, R. (Ed), pp. 391–6; DeWitt et al. (1994) *Drug Dev. Res.* 33:116–124; Hobbs DeWitt et al. (1993) *Proc. Natl. Acad. Sci. U.S.A.* 90:6909–6913]. In this technology a starting material is bonded to a solid phase, such as a matrix material, and is subsequently treated with reagents in a stepwise fashion. Because the products are linked to the solid support, multistep syntheses can be automated and multiple reactions can be performed simultaneously to produce libraries of small molecules. This technology can be readily improved by combining the matrices with memories or encoding the matrix supports in accord with the methods herein.

The matrices with memories, either those with memories in proximity or those in which the matrix includes a code stored in a remote memory, can be used in virtually any combinatorial library protocol. These protocols or methodologies and libraries, include but are not limited to those described in any of following references: Zuckermann et al. (1994) *J. Med. Chem.* 37:2678; Martin et al. (1995) *J. Med. Chem.* 38:1431; Campbell et al. (1995) *J. Am. Chem. Soc.* 117:5381; Salmon et al. (1993) *Proc. Natl. Acad. Sci. U.S.A.* 90:11708; Patek et al. (1994) *Tetrahedron Lett.* 35:9169; Patek et al. (1995) *Tetrahedron Lett.* 36:2227; Hobbs DeWitt et al. (1993) *Proc. Natl. Acad. Sci. U.S.A.* 90:6906; Baldwin et al. (1995) *J. Am. Chem. Soc.* 117:5588; and others.

i. Nucleic Acid Sequencing

Methods of DNA sequencing based on hybridization of DNA fragments with a complete set of fixed length oligonucleotides [usually 8-mers] that are immobilized individually as dots in a 2-dimensional matrix is sufficient for computer-assisted reconstruction of the sequences of fragments up to 200 bases long [International PCT Application WO 92/10588]. The nucleic acid probes are of a length shorter than a target, which is hybridized to the probes under conditions such that only those probes having an exact complementary sequence are hybridized maximally, but those with mismatches in specific locations hybridize with a reduced affinity, as can be determined by conditions necessary to dissociate the pairs of hybrids. Alignment of overlapping sequences from the hybridizing probes reconstructs the complement of the target [see, EP 0 535 242 A1, International PCT Application WO 95/00530, and Khrapko et al. (1989) *FEBS Lttrs.* 256:118–122]. The target fragment with the sequence of interest is hybridized, generally under highly stringent conditions that tolerate no mismatches or as described below a selected number of mismatches, with mixtures of oligonucleotides [typically a mixture of octomers of all possible sequences] that are each immobilized on a matrix with memory that is encoded with the sequence of the probe. Upon hybridization, hybridizing probes are identified by routine methods, such as OD or using labeled probe, and the sequences of the hybridizing probes can be determined by retrieving the sequences from the linked memories. When hybridization is carried out under conditions in which no mismatches are tolerated, the sequence of the target can then be determined by aligning overlapping sequences of the hybridizing probes.

Previous methods used to accomplish this process have incorporated microscopic arrays of nucleotide oligomers synthesized on small silicon based chips. It is difficult to synthesize such arrays and quality control the large number of spots on each chip [about 64,000 spots for 8-mer oligonucleotides, that number necessary to accomplish sequencing by hybridization].

In the present method, each oligomer is independently synthesized on a batch of individual chips, those chips are tested for accuracy and purity of their respective oligomers, then one chip from each batch is added to a large pool containing oligomers having all possible sequences. After hybridization in batch mode with the gene segment to be sequenced, usually amplified by a method such as PCR, using appropriate primers, and labeled with a detectable [such as fluorescent] tag, the chips can be passed through a detector, such as described above for processing multiplexed assays, including multiplexed immunoassays, and the degree of binding to each oligomer can be determined. After exposing the batch to varying degrees of dissociating conditions, the devices can again be assayed for degree of binding, and the strength of binding to related sequences will relate the sequence of the gene segment [see, e.g., International PCT Application WO 95/00530].

An exemplary method for synthesizing an oligonucleotide library, preferably hexamers or octomers, for use in sequencing methods, or other methods, is set forth in the EXAMPLES and depicted in FIG. 33, in which the oligonucleotides are synthesized on optical memory devices that are each uniquely encoded either before, during or after synthesis with a code. The identity of the oligomer associated with each code is stored in a remote memory, generally a computer. Other memory with matrices, such as the MICROTUBE™ and MICROKAN™ microreactors and other such combination, may be used in place of the optical memory devices In particular this library of microreactors [oligonucleotides-linked to memory with matrix] can be used in methods for DNA sequencing by primer walking using capillary electrophoresis (CE) and ultrathin slab gels for separation [see, e., Ruiz-Martinez et al. (1996) *Biotechniques* 20:1058–1069; Kieleczawa et al. (1992) *Science* 258:1787–1791; McCombie et al. (1994) *BioTechniques* 17:574–5790]. Such methods rely on the use of oligonucleotide libraries, containing all permutations of pentamer or hexamers, which are used as primers. The identity of each oligonucleotide will be encoded in the associated memory or stored in the proximate or linked memory. A synthetic protocol is depicted in FIG. 33.

j. Separations, physical mapping and measurements of kinetics of binding and binding affinities Multiple blots [i.e., Western, Northern, Southern and/or dot blots] may be simultaneously reacted and processed. Each memory, in the form of a rectangle or other suitable, is linked or coated on one surface with material, such as nitrocellulose, to which or the analyte of interest binds or with which it reacts. The chips are arranged in an array, such as in strips that can be formed into rectangles or suitable other shapes, circles, or in other geometries, and the respective x-y coordinate or other position-identifying coordinate (s), and, if needed, sheet number and/or other identifying information, is programmed into each memory. Alternatively, they may be programmed with this identification, then positioned robotically or manually into an array configuration. They are preferably linked together, such as by reversible glue, or placing them in agarose, or by any suitable method as long as the reactive surface is not disturbed. Following transfer of the material, such as transfer of protein from a Western Blot, nucleic acid from a Southern or Northern blot, dot blots, replica plated bacterial culture, or viral plaques, the memories are separated and mixed for reaction with a traditionally labeled, such as a fluorescent label, detection nucleic acid, protein, antibody or receptor of interest. Complexes are identified, and their origin in the blot determined by retrieving the stored information in each chip. Quantitation may also be effected based on the amount of label bound.

A series of appropriately activated matrices with memories are arranged in an array, one or, preferably two dimensional. In one configuration, each chip is pre-programmed and placed in a specific location that is entered into its memory, such as an x-y coordinate. At least one surface of the memory with matrix is treated so that the transferred reagent binds. For example, a piece of nitrocellulose can be fixed to one side of the memory device. The resulting array is then contacted with a separation medium whereby each reagent of interest is transferred to and bound to the end of the matrix with memory such that the reagent location is known. The matrices are separated and pooled; multiple arrays may be pooled as long as source information is recorded in each memory. All matrices with memories are then contacted with detection agents that specifically bind to reagents in the mixture. The matrices with memories are passed through a reading device, either after an incubation for end point determinations or continuously for kinetic measurements. The reading devices is a device that can detect label, such as fluorescence, and an reader, such as an RF ready, that can query the memory and identify each matrix. The rate of binding and maximum binding and identify of bound reagents can be determined.

Dot blots, for example, can be used in hybridoma analysis to identify clones that secrete antibodies of desired reactivity and to determine the relative affinities of antibodies secreted by different cell lines. Matrices with memories that are activated to bind immunoglobulins and with on-board information specifying their relative locations in the array are dipped in an array into the wells of microplates containing hybridoma cells. After incubation, they are withdrawn, rinsed, removed and exposed to labeled antigen. Matrices of desired specificity and affinity are selected and read thereby identifying the original wells containing the hybridoma cells that produce the selected antibodies.

In other embodiments, the transfer medium [i.e., the nitrocellulose or other such medium] may be part of the surface of the chip or array of chips that can bind to the separated species subsequent to separation. For example, the separation system, such as the agarose or polyacrylamide gel, can be included on the surface(s) of the matrix with memories in the array. After separation the surface will be activated with a photoactivatable linker or suitable activating agent to thereby covalently link, such as by a photoflash, the separated molecules to the matrices in the array.

Alternatively, each matrix with memory may have one or more specific binding agents, such as an antibody or nucleic acid probe, attached (adsorbed, absorbed, or otherwise in physical contact) to matrix with memory. The matrix with memory and linked binding agent is then contacted with a medium containing the target(s). After contacting, which permits binding of any targets to which the linked binding agents specifically bind, the matrix with memory is processed to identify memories with matrices to which target has specifically bound via interaction with the binding agent. For example, the (1) the target is labeled, thereby permitted direct detection of complexes; (2) the memory with matrix is then contacted with a developing agent, such as a second antibody or detection probe, whereby binding agent-target complexes are detected; or (3) the detection agent is present during the reaction, such as non-specifically attached to the matrix with memory or by other method [thin film, coated on the matrix with memory, coated on nitrocellulose].

Such support bound analytes may also be used to analyze the kinetics of binding by continuously passing the supports through a label reading device during the reaction, and identify the labeled complexes. The binding agents can be eluted, either in a kinetically readable manner or in batch. In addition, since the recording devices may also include components that record reaction conditions, such as temperature and pH, kinetics, which are temperature and pH dependent, may be accurately calculated.

After elution, the support bound analytes may be identified to analyze kinetics of binding to the binding agent. Such binding and elution protocols may also be adapted to affinity purification methodologies.

k. Cell Sorting

The devices herein may also be used in methods of cell sorting. For example, the memory with matrix combinations are linked to selected antigens, information regarding the antigens is encoded into the memories, the resulting combinations are used in multi-analyte analyses of cells.

It is possible to identify a profile of cells exhibiting different surface markers [antigens, for example, or other ligands or receptor molecules] by using combinations of labeled and matrix memory-bound binding agents. In one embodiment, each agent, such as an antibody, capable of binding specifically to one of many different surface markers is bound to a different matrix with a memory. The nature of the recognized marker is recorded in the memory of each matrix-binding agent complex, and the mixture of binding-agent-matrix memory complexes is reacted with a mixture of cells. The cell-matrix complexes that result from binding agents attaching cells to the surfaces of the respective matrices are then reacted with a labeled [for example, fluorescent] reagent or mixture of reagents which also reacts with the cells. These labeled reagents can be the same or different from those coupled to the memory matrices. When the matrices are passed through a reader [to read the label and the memory], those that have bound cells can be identified and if necessary isolated. This application is particularly useful for screening for rare cells, for example stem cells in a bone marrow or peripheral lymphocyte sample, for detecting tumor cells in a bone marrow sample to be used for autologous transplantation, or for fetal cells in a maternal circulation.

In these embodiments, the memory with matrices herein can be counted and read with instruments, such as a device that operates on the principles of a Coulter counter, that are designed to count cells or particles. In using a Coulter Counter, a suspension of cells or particles is sucked through a minute hole in a glass tube. One electrode is placed within the tube and another is outside of the tube in the suspension. The passage of a particle through the hole temporarily interrupts the current; the number of interruptions is determined by a conventional scaling unit.

For use herein, such instruments are modified by including an RF reader [or other reader if another frequency or memory means is selected] so that the identity of the particle or cell [or antigen on the cell or other encoded information] can be determined as the particle or cell passes through the hole and interrupts the current, and also, if needed, a means to detect label, such as fluorescent label. As the particle passes through the hole the RF reader will read the memory in the matrix that is linked to the particle. The particles also may be counted concurrently with the determination of the identity of the particle. Among the applications of this device and method, is a means to sort multiple types of cells at once.

I. Multiplexed or coupled protocols in which the synthesis steps [the chemistry] is coupled to subsequent uses of the synthesized molecules Multiplexed or multiple step processes in which compounds are synthesized and then assayed without any intermediate identification steps are provided herein. Since the memories with matrices permit identification of linked or proximate or associated molecules or biological particles, there is no need to identify such molecules or biological particles during any preparative and subsequent assaying steps or processing steps. Thus, the chemistry [synthesis] can be directly coupled to the biology [assaying, screening or any other application disclosed herein]. For purposes herein this coupling is referred to as multiplexing. Thus, high speed synthesis can be coupled to high throughput screening protocols.

As described elsewhere herein, automated and tagged laboratories are also provided. Tags are combined with containers, tubes and instruments used in processing the products; as a product is moved from one container to another the identifying information and/or other associated information becomes associated with or written to a tag combined with the next vessel used in the process. As a result the information remains associated with the products. Ultimately, the tag is associated with the product when and if it is stored for later use.

H. Applications of the Memories with Matrices and Luminescing and Scintillating Matrices with Memories in Combinatorial Syntheses and Preparation of Libraries Libraries of diverse molecules are critical for identification of new pharmaceuticals. A diversity library has three components: solid support matrix, linker and synthetic target. The support is a matrix material as described herein that is stable to a wide range of reaction conditions and solvents; the linker is selectively cleavable and does not leave a functionalized appendage on the synthetic target; and the target is synthesized in high yield and purity. For use herein, the diversity library further includes a memory or recording device in combination with the support matrix. The memory is linked, encased, in proximity with or otherwise associate with each matrix particle, whereby the identify of synthesized targets is written into the memory.

The matrices with memories are linked to molecules and particles that are components of libraries to electronically tagged combinatorial libraries. Particularly preferred libraries are the combinatorial libraries that containing matrices with memories that employ radio frequencies for reading and writing.

1. Oligomer and polypeptide libraries
   a. Bio-oligomer libraries

One exemplary method for generating a library [see, U.S. Pat. No. 5,382,513] involves repeating the steps of (1) providing at least two aliquots of a solid phase support; separately introducing a set of subunits to the aliquots of the solid phase support; completely coupling the subunit to substantially all sites of the solid phase support to form a solid phase support/new subunit combination, assessing the completeness of coupling and if necessary, forcing the reaction to completeness; thoroughly mixing the aliquots of solid phase support/new subunit combination; and, after repeating the foregoing steps the desired number of times, removing protecting groups such that the bio-oligomer remains linked to the solid phase support. In one embodiment, the subunit may be an amino acid, and the bio-oligomer may be a peptide. In another embodiment, the subunit may be a nucleoside and the bio-oligomer may be an oligonucleotide. In a further embodiment, the nucleoside is deoxyribonucleic acid; in yet another embodiment, the nucleoside is ribonucleic acid. In a further embodiment, the subunit may be an amino acid, oligosaccharide, oligoglycosides or a nucleoside, and the bio-oligomer may be a peptide-oligonucleotide chimera or other chimera. Each solid phase support is attached to a single bio-oligomer species and all possible combinations of monomer [or multimers in certain embodiments] subunits of which the bio-oligomers are composed are included in the collection.

In practicing this method herein, the support matrix has a recording device with programmable memory, encased, linked or otherwise attached to the matrix material, and at each step in the synthesis the support matrix to which the nascent polymer is attached is programmed to record the identity of the subunit that is added. At the completion of synthesis of each biopolymer, the resulting biopolymers linked to the supports are mixed.

After mixing an acceptor molecule or substrate molecule of interest is added. The acceptor molecule is one that recognizes and binds to one or more solid phase matrices with memory/bio-oligomer species within the mixture or the substrate molecule will undergo a chemical reaction catalyzed by one or more solid phase matrix with memory/bio-oligomer species within the library. The resulting combinations that bind to the acceptor molecule or catalyze reaction are selected. The memory in the matrix-memory combination is read and the identity of the active bio-oligomer species is determined.

b. Split Bead Sequential Syntheses

Figure 3:
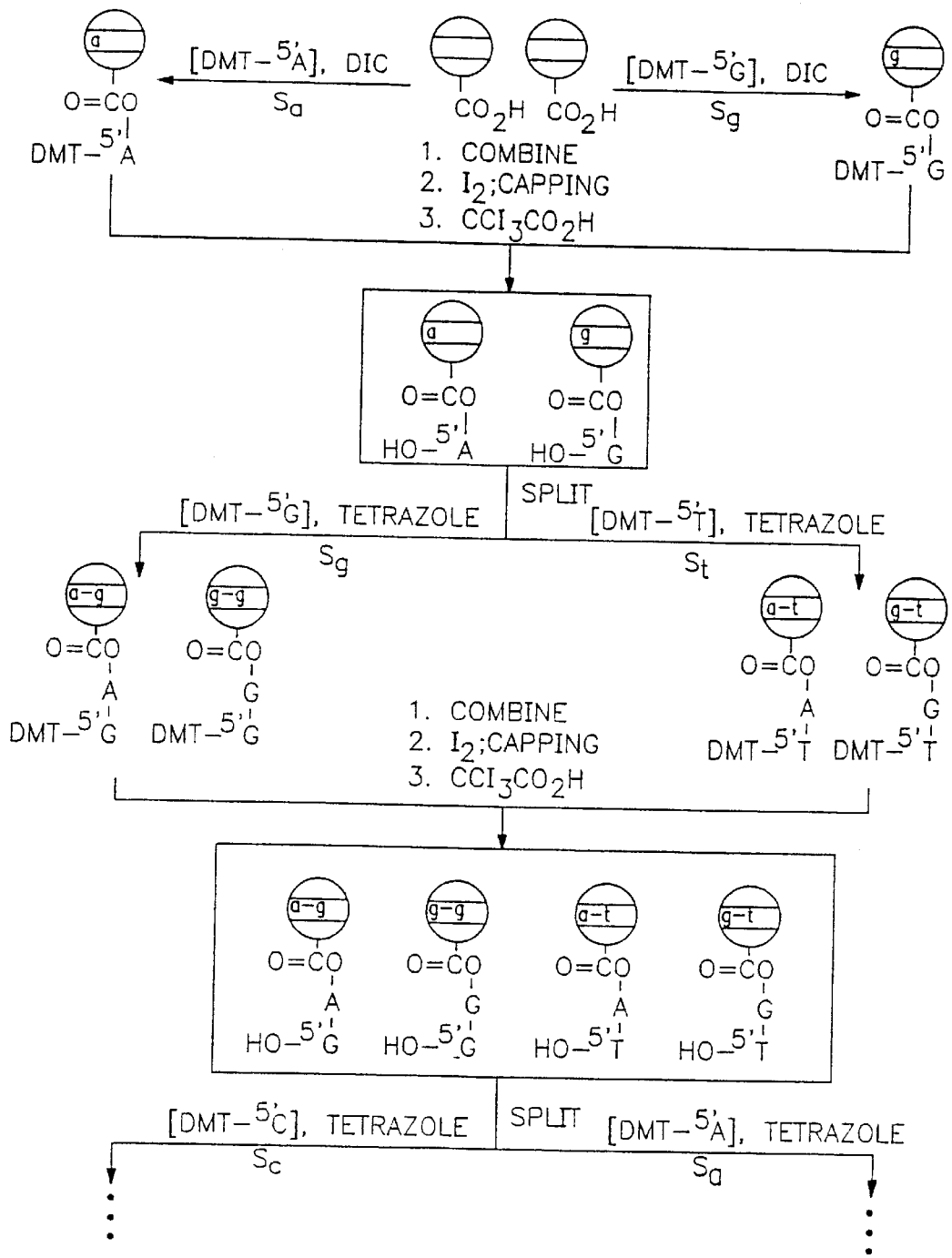
FIG. 3 depicts combinatorial synthesis of oligonucleotides on matrix supports with memories. A, G, T and C represent nucleotides, and a, g, t, and c represent the electronic codes stored in memory that correspond to each of A, G T and C, respectively. The phosphoramidite method of oligonucleotide synthesis is performed by methods known to those of skill in the art [see, e.g., Brown et al. (1991) "Modern machine-aided methods of oligodeoxyribonucleotide synthesis" in Oligonucleotides Analogues EDITOR: Eckstein, Fritz (Ed), IRL, Oxford, UK., pp. 1–24, esp. pp. 4–7]. As in FIGS. 1 and 2, the matrix may alternatively, or additionally, have symbology engraved thereon.
Figure 4:
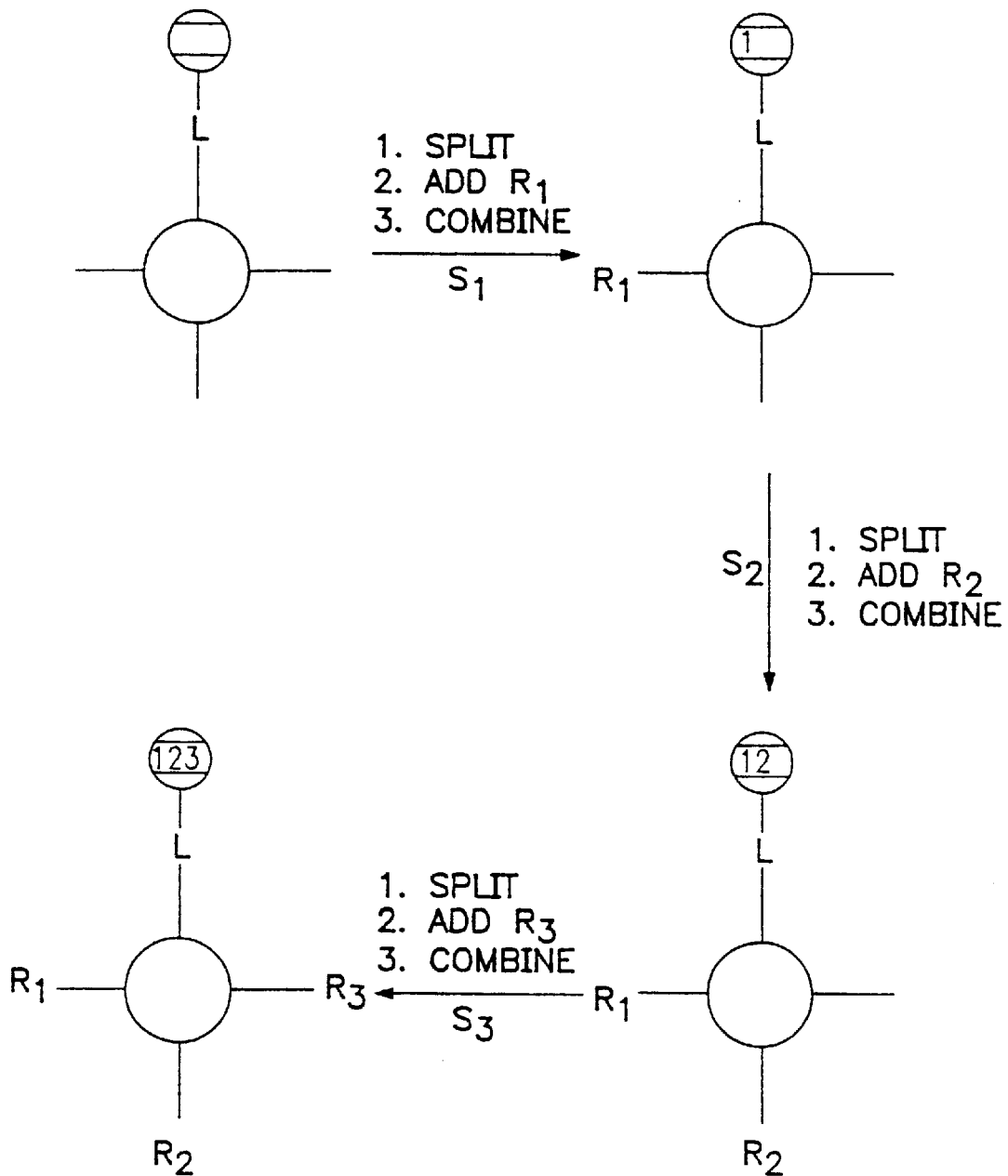
FIG. 4 depicts generation of a chemical library, such as a library of organic molecules, in which $R_1$, $R_2$, $R_3$ are substituents on selected molecule, such as a pharmacophore monomer, each identified with a different signal, depicted as 1, 2, or 3, from the classes $S_1$, $S_2$, $S_3$, respectively. The circle represents an organic pharmacophore. If $R_1$–$R_3$ are the same, and selected from among the same 50 choices, then the complete library contains $50^3$=125,000 members. If $R_1$–$R_3$ selected from among different sets of choices, then the resulting library has correspondingly more members. Each optical memory device can be encoded with information that represents the $R_n$ added and class $[S_n]$ thereby providing a unique code for each library member. As in FIGS. 1–3, the matrix may be engraved with symbology, such as a two-dimensional bar code.

Various schemes for split bead syntheses of polymers [FIG. 1], peptides [FIG. 2], nucleic acids [FIG. 3] and organic molecules based on a pharmacophore monomer [FIG. 4] are provided. Selected matrices with memory particles are placed in a suitable separation system, such as a funnel [see, FIG. 5]. After each synthetic step, each particle is scanned [i.e., read] as it passes the RF transmitter, and information identifying the added component or class of components is stored in memory. For each type of synthesis a code can be programmed [i.e., a 1 at position 1,1 in the memory could, for example, represent alanine at the first position in the peptide]. A host computer or decoder/encoder is programmed to send the appropriate signal to a transmitter that results in the appropriate information stored in the memory [i e for alanine as amino acid 1, a 1 stored at position 1,1]. When read, the host computer or decoder/encoder can interpret the signal read from and transmitted from the memory.

In an exemplary embodiment, a selected number of beads [i.e., particulate matrices with memories [matrix particles linked to recording devices], typically at least $10^3$, more often $10^4$, and desirably at least $10^5$ or more up to and perhaps exceeding $10^{15}$, are selected or prepared. The beads are then divided into groups, depending upon the number of choices for the first component of the molecule. They are divided into a number of containers equal to or less than [for pooled screening, nested libraries or the other such methods] the number of choices. The containers can be microtiter wells, Merrifield synthesis vessels, columns, test tubes, gels, etc. The appropriate reagents and monomer are added to each container and the beads in the first container are scanned with electromagnetic with radiation, preferably high frequency radio waves, to transmit information and encode the memory to identify the first monomer. The beads in the second container are so treated. The beads are then combined and separated according to the combinatorial protocol, and at each stage of added monomer each separate group is labeled by inputting data specific to the monomer. At the end of the synthesis protocol each bead has an oligomer attached and information identifying the oligomer stored in memory in a form that can be retrieved and decoded to reveal the identity of each oligomer.

An 8-member decapeptide library was designed, synthesized, and screened against an antibody specifically generated against one of the library members using the matrices with memories. Rapid and clean encoding and decoding of structural information using radio frequency signals, coupling of combinatorial chemical synthesis to biological assay protocols, and potential to sense and measure biodata using suitable biosensors, such as a temperature thermistor or pH electrode, embedded within the devices have been demonstrated. The "split and pool" method [see, e.g., Furka et al. (19910 *Int. J. Pept. Protein Res.* 37:487–493; Lam et al. (1991) *Nature* 354:82–84; and Sebestyen et al. (1993) *Bioorg. Med. Chem. Lett.* 3:413–418] was used to generate the library. An ELISA [see e.g., Harlow et al. (1988) *Antibodies, a laboratory manual*, Cold Spring Harbor, N.Y.] was used to screen the library for the peptide specific for the antibody.

2. "Nested" combinatorial library protocols

In this type of protocol libraries of sublibraries are screened, and a sublibrary selected for further screening [see, e.g., Zuckermann et al. (1994) *J. Med. Chem.* 37:2678–2685; and Zuckermann et al. (1992) *J. Am. Chem. Soc.* 114:10646–10647]. In this method, three sets of monomers were chosen from commercially available monomers, a set of four aromatic hydrophobic monomers, a set of three hydroxylic monomers, a set of seventeen diverse monomers, and three N-termini were selected. The selection was based on an analysis of the target receptor and known ligands. A library containing eighteen mixtures, generated from the six permutations of the three monomer sets, times three N-termini was prepared. Each mixture of all combinations of the three sets of amines, four sets of hydrophobic monomers and seventeen diverse monomers was then assayed. The most potent mixture was selected for deconvolution by synthesis of pools of combinatorial mixtures of the components of the selected pool This process was repeated, until individual compounds were selected.

Tagging the mixtures with the matrices with memories will greatly simplify the above protocol. Instead of screening each mixture separately, each matrix particle with memory will be prepared with sets of the compounds, analogous to the mixtures of compounds. The resulting matrix particles with memories and linked compounds can be combined and then assayed. As with any of the methods provided herein, the linked compounds [molecules or biological particles] can be cleaved from the matrix with memory prior to assaying or anytime thereafter, as long as the cleaved molecules remain in proximity to the device or in some manner can be identified as the molecules or particles that were linked to the device. The matrix particle (s) with memories that exhibit the highest affinity [bind the greatest amount of sample at equilibrium] are selected and identified by querying the memory to identify the group of compounds. This group of compounds is then deconvoluted and further screened by repeating this process, on or off the matrices with memories, until high affinity compounds are selected.

3. Other combinatorial protocols

The matrices with memories provided herein may be used as supports in any synthetic scheme and for any protocol, including protocols for synthesis of solid state materials, polymers and industrial chemicals and other compounds and materials of interest. For example, combinatorial approaches have been developed for parallel synthesis of libraries of solid state materials [see, e.g., Xiang et al. (1995) *Science* 268:1738–1740]. In particular, arrays containing different combinations, stoichiometries, and deposition sequences of inorganics, such as $BaCO_3$, $BiO_3$, CaO, CuO, PbO, $SrCO_3$ and $Y_2O_3$, for screening as superconductors have been prepared. These arrays may be combined with memories that identify position and the array and/or deposited material.

I. Microvessel Opening and Closing Devices

In order to facilitate the opening and closing, and particularly to prevent damaging the contents and/or structure, of a MICROKAN microvessel or other such microvessel or microreactor, a pair of hand tools is provided herein. More specifically, and with reference to U.S Pat. Nos. 4,651,598 and 4,662,252, each of the hand tools includes a pliers body that has been adapted to accept various portions of the microvessel. Referring to FIG. 44, the cap sealing tool is shown and generally designated 4600. As shown, the tool 4600 includes a pair of elongated handle portions 4602 and 4604. These handle portions articulate about a sliding pivot disc 4605 that engages any one of the teeth 4607 such that when the handles are forced together, the opposite ends of the handle portions also move towards each other. On the ends of the elongated handle members, the traditional pliers are modified to have a striking plate 4610 and a receiving cylinder. The receiving cylinder is pivotally attached to the end of member 4602 such that the cylinder may swing out away from the pliers, to facilitate loading and unloading the cylinder 4608. On the upper member 4612, the striking plate 4610 is attached to be positioned directly above the cylinder when the cylinder is in its raised position.

FIG. 45 is a front cross-sectional view showing the placement of the microvessel within the cylinder such that the lid 4620 is positioned over the tube 4616. Referring to FIG. 46, the striking plate 4610 and cylinder 4622 are shown in lateral cross-section. From this view it is clear that the inside of the cylinder 4622 is formed to accept a MICROKAN microvessel. As can be appreciated, however, the cylinder may be formed to accept virtually a container of any geometry or size, preferably a container with a volume of 1 ml or less, that is sealed as provided herein. The MICROKAN microvessel shown here contains a tag 4618, such as, for exemplification purposes, an RF tag in the shape of a capsule, such as that available from IDTag, described elsewhere herein. As with the microvessel, the tags may be formed in a variety of shapes and sizes, as long as it is insertable into the container. FIG. 45 shows the lid 4620 of the tube 4616 positioned above the tube such that when the handle portions are squeezed together, the lid 4620 is forced into the container to seal the tag therein.

Moving now to FIG. 47, the cylinder 4622 is shown forced against the striking plate 4610 to press the lid 4614 into the microvessel 4616. Once the tag is contained within the microvessel, the pliers are opened and the cylinder is articulated outwards about the pinion 4626 in direction 4628 such that the tang 4624 strikes the bottom 4630 of the microvessel 4616 to push the microvessel out of the cylinder. Once the cylinder is articulated, the microvessel may be easily removed from the cylinder. As can be seen from this view, the tag 4618 is sealed inside the microvessel to prevent exposure of the tag to environmental contaminates. Moreover, by placing the tag in a sealable container, the tag may be reused.

Because the tag 4618 may be reused, another tool has been created to facilitate removing it from the microvessel.

Referring now to FIG. 49, a similar plier-like tool is formed with a striking plate 4610, and a fork 4634. The fork is attached to the end of elongated handle 4604 and has two prongs 4632 which are connected to define an arc shaped wedge. This arc shaped wedge can be positioned against the side of the microvessel where the lid 4614 joins the microvessel, and upon actuating the pliers, the prongs slide between the lid and the microvessel to remove the lid.

As perhaps more clearly shown in FIG. 50, the prongs 4632 are wedge shaped such that the more the pliers are closed, the more the lid is urged out of the microvessel. From this view, the shape of the striking plate 4610 can be easily seen. It is to be appreciated that any number of striking plate shapes could be used. In fact, because a container of any shape could be used to hold the tag, it should be appreciated that the striking plate could be shaped to accommodate those shapes. Further, the prongs 4632 on the fork 4634 could be shaped to more closely fit an alternatively shaped container. Once the lid is removed, the tag can also be removed from the microvessel and reused in another microvessel.

FIG. 111 shows another embodiment of a hand tool in cross-section which is generally designated 10928. This permits assembly of various configurations of the MICROKAN microreactor. Hand tool 10928 includes a first piece 10930 and a second piece 10932 which cooperate to facilitate the assembly of the MICROKAN microreactors disclosed herein. First piece 10930 is formed with a junction receiver 10934 and a body receiver 10936. Junction receiver 10934 is sized to accept a junction tube 10924, and may be closely sized to provide a friction force to hold the junction tube 10924 within the junction receiver 10934 while first piece 10934 is handled. The opposite end of first piece 10934 is formed with a body receiver 10936 sized to receive a body 10902, such that the portion of the body 10902 which receives the cap 10904 is flush with the end of the first piece 10930.

Second piece 10932 is formed with a cap receiver 10938 and a body receiver 10940. Cap receiver 10938 is sized to accept the cap 10904, and may provide a frictional retaining force present between the cap 10904 and the cap receiver 10938. Such retaining force would allow handling of the second piece while the cap 10904 is installed within the second piece 10932.

Assembly of a single-bodied MICROKAN microreactor 10900 is accomplished using the hand tool 10928 by placing a cap 10904 in the cap receiver 10938 in the second piece 10932, and by placing a body 10902 in the body receiver 10936 of the first piece 10930. Once the cap and body are in place, the first piece 10930 and the second piece 10932 are aligned such that the cap 10904 is positioned adjacent to the body 10902. Once aligned, the first piece is urged in direction 10944, and the second piece is urged in direction 10946, thereby forcing the cap 10904 held in second piece 10932 into body 10902 held in first piece 10930 to engage tab portions 10910 into channel portion of 10908 formed in body 10902 in microreactor 10900. It should be noted that prior to the capping of the MICROKAN microreactor, any matrix material and/or identification tags can be inserted into the body 10902.

Assembly of a double-bodied MICROKAN microreactor 10920 is accomplished using hand tool 10928 in a two-step process. The assembly of a double-bodied MICROKAN microreactor 10920 begins with the placement of a body 10902 into the body receiver 10940 of the second piece 10932, and placement of a junction tube 10924 in junction receiver 10934 in first piece 10930. Once the junction tube and body are in place, the first and second pieces 10930 and 10932 are aligned such that the junction tube 10924 is positioned adjacent to the body 10902. Once aligned, the second piece is urged in direction 10948 and the first piece is urged in direction 10950, thereby forcing junction tube 10924 into body 10902 held in second piece 10932 to engage tab portions 10926 into channel portion 10908 in body 10902 of microreactor 10900.

In order to aid in the secure gripping of the hand tool 10928 by a user, both the first piece 10930 and the second piece 10932 are formed with a number of grip ridges 10942. An alternative to such ridges would be to cut circumferential channels onto the outer surface of the hand tool, or to alter the external shape of the hand tool 10928 to a more grippable contour, such as a cylinder having a larger gripping channel for each finger. Additionally, the ability of a user to securely hold the hand tool may be improved by coating the pieces of the hand tool with slip-resistant materials, such as cork or rubber.

J. Sleeves with Memories

In another embodiment provided herein, depicted in FIGS. 35–43, a sleeve, containing a remotely programmable memory with a coiled antenna, that is specially adapted to fit on a tube, such as an Hewlett Packard HPLC tube. The sleeve fits tightly on the tube, thereby permitting the tube to be tracked and information about the contents, source or other some information, to be stored in the memory in the sleeve or in a remote computer that associates the memory with such information.

Figure 35:
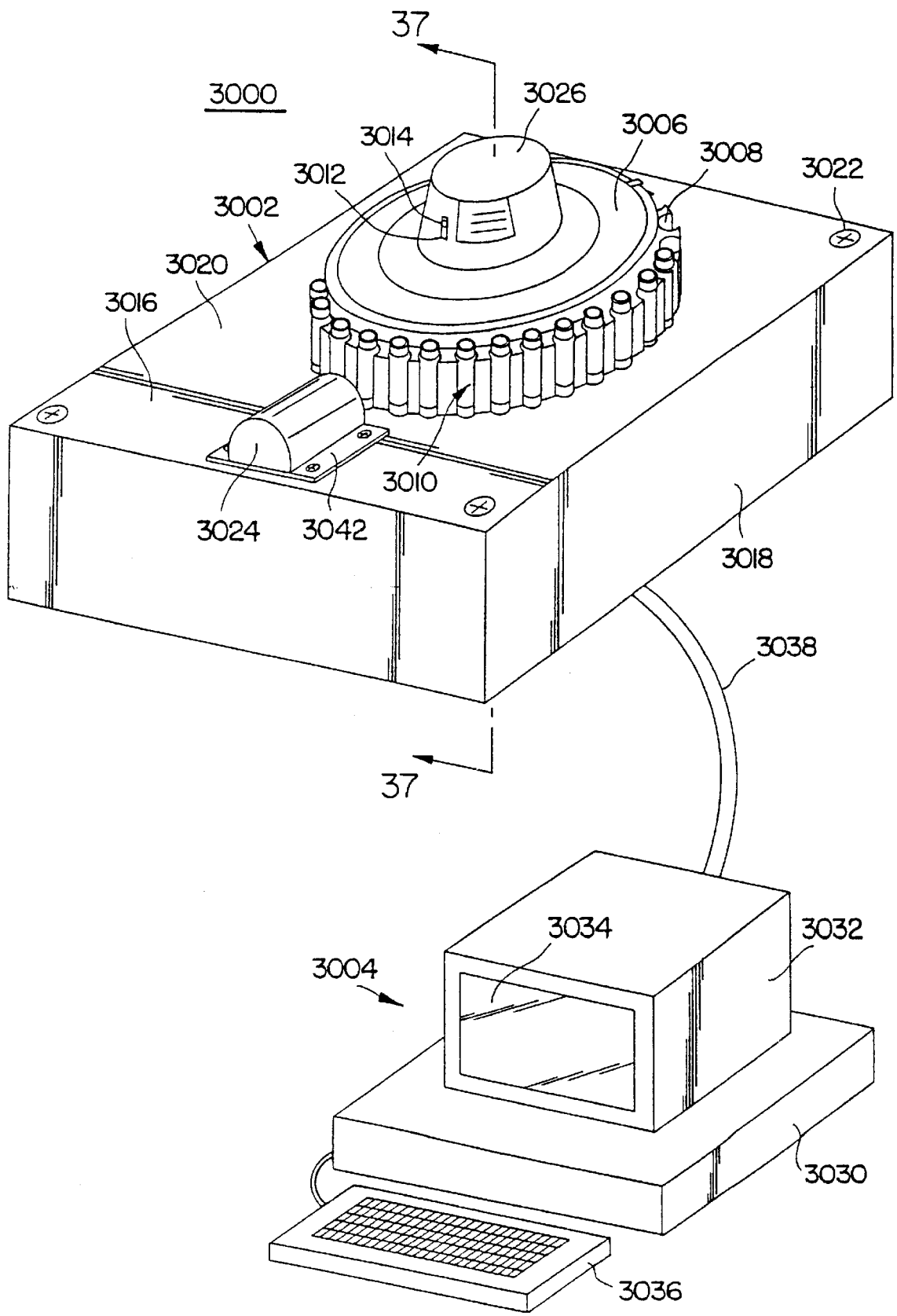
FIG. 35 is a perspective view of an alternative embodiment of a exemplary read/write station.

Referring to FIG. 35, the identification system is shown and generally designated 3000. The system 3000 includes a read/write controller 3002 that includes a housing 3018 that supports a carousel 3006, and a computer system 3004. The carousel 3006 as shown is mounted to rest on the top surface 3020 of the housing 3018. As will be further discussed below in connection with FIG. 36, the carousel rotates about its vertical axis so that as it rotates, each of the ports 3008 will rotate in front of the plunger 3024. The carousel is formed with a number of the ports 3008 that are sized to receive a vial 3010. Although the carousel is shown to contain 21 different ports, a carousel having any number of ports could be formed. The carousel may be of any geometry, including square, oval, oblong and rectangular.

Formed in the carousel is a keyway 3012 that is sized to accept a key 3014. While not shown in this figure, this key is attached to a hub 3056 (shown in FIG. 37). In order to stop the carousel from freely rotating, the plunger 3024 is positioned on the top surface 3020 so that its slide 3044 (shown in FIG. 36) strikes the outside rim of the carousel.

The computer system 3004 includes a central processing unit 3030 that has a serial port to accept a serial cable 3038, a monitor 3032 having a screen 3034, and a keyboard 3036. While a traditional computer is shown to include separate parts, a laptop computer would be equally acceptable so long as it is equipped with a serial port to accept cable 3038.

Figure 36:
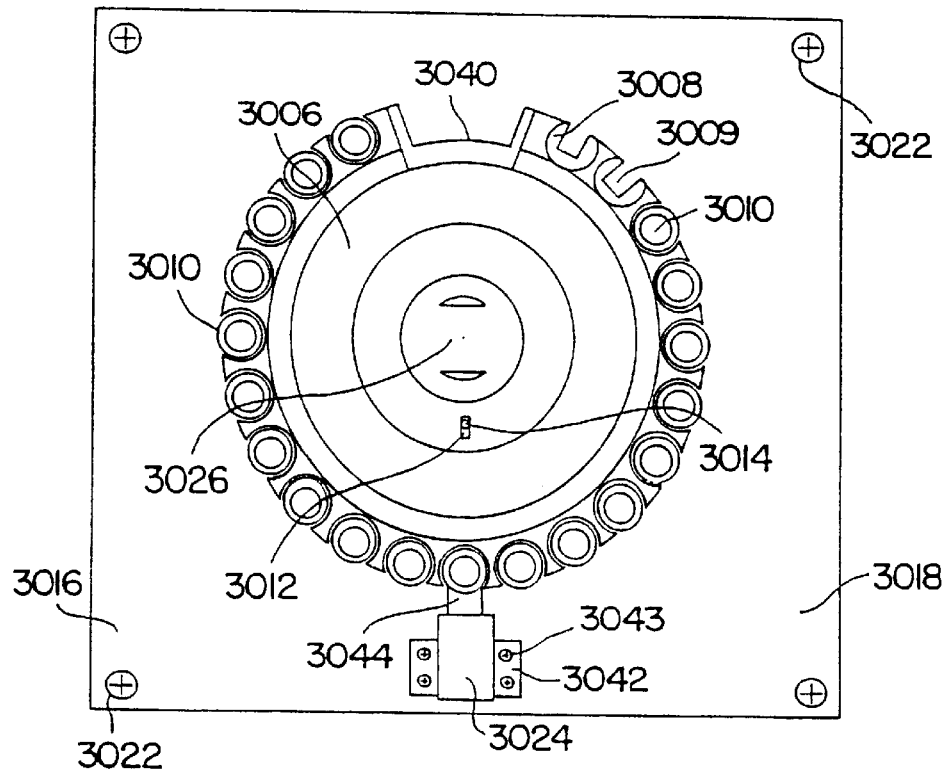
FIG. 36 is a plan view of the read/write station shown in FIG. 35.

Referring now to FIG. 36, the read/write controller is shown from the top thereby providing a more detailed view of the rotational positioning of the carousel 3006 and the plunger 3024. The plunger is attached to the top surface 3020 of the housing 3018 with a flange 3042. The positioning of the plunger is important because the plunger slide 3044 must hit the outer rim of the carousel in a location that will provide a stopping pressure against the carousel. This stopping pressure acts to prevent any spinning of the carousel unless there is a turning force placed on the carousel itself. It will be appreciated that the strike of the plunger could be replaced by a more precise stopping member, such as a post. The post, like the slide, would strike the outer surface of the carousel. If the post is significantly smaller than the slide, the carousel may be formed with a number of holes spaced along the rim of the carousel so that when activated, the plunger would urge the post into the hole to securely stop the carousel from spinning. In addition, any other method of orienting the carousel on the housing could be used, so long as the carousel could be rotated.

The surface 3016 of housing 3018 is attached using screws 3022. Instead of using screws, virtually any manner of attaching the housing together may be used. The housing 301 8 may be formed from one single piece of material that is either bored or machined to have a hollow inside for holding the necessary electronics discussed below.

Also from FIG. 36, the interaction between the key 3014 and keyway 3012 is clearly shown. The carousel can be lifted off of the housing and keyway and replaced with another carousel that was oriented such that the keyway in the new carousel would match the position of the key on the housing. In such a manner, virtually any number of carousels could be placed on the housing.

The outer surface of the carousel is formed with 21 ports 3008. Each of these ports is formed with a cutout 3009. As easily appreciated from this view, the carousel could be made to have a larger diameter to accommodate a larger number of vials, or the vials could be smaller to accomplish the same quantity of vials. In other words, by making the carousel and vials of differing sizes, a virtually unlimited number of vials could be accommodated. Moreover, because the carousels are removable, a large number of vials could be processed through the read/write controller in a short period of time. Although the carousel is formed with a handle 3026, it could instead be formed with a grip that would be easily mated with some automated handling device, such as a robotic arm (not shown). This robotic arm could be independently operated, or could be controlled by the computer system 3004.

There is a notch 3040 formed in the outer edge of the carousel that is particularly useful for aligning with the plunger 3024 when installing or removing the carousel from the read/write controller. When the carousel is rotated such that the notch is adjacent to the plunger 3024, the slide 3044 will not strike the carousel. As a result, the carousel may be easily lifted up and off of the read/write controller. Such simple removal is particularly useful when there are a large number of vials present on the carousel that would add a significant weight to the carousel, making removal more strenuous, or when they are robotically removed.

Figure 37:
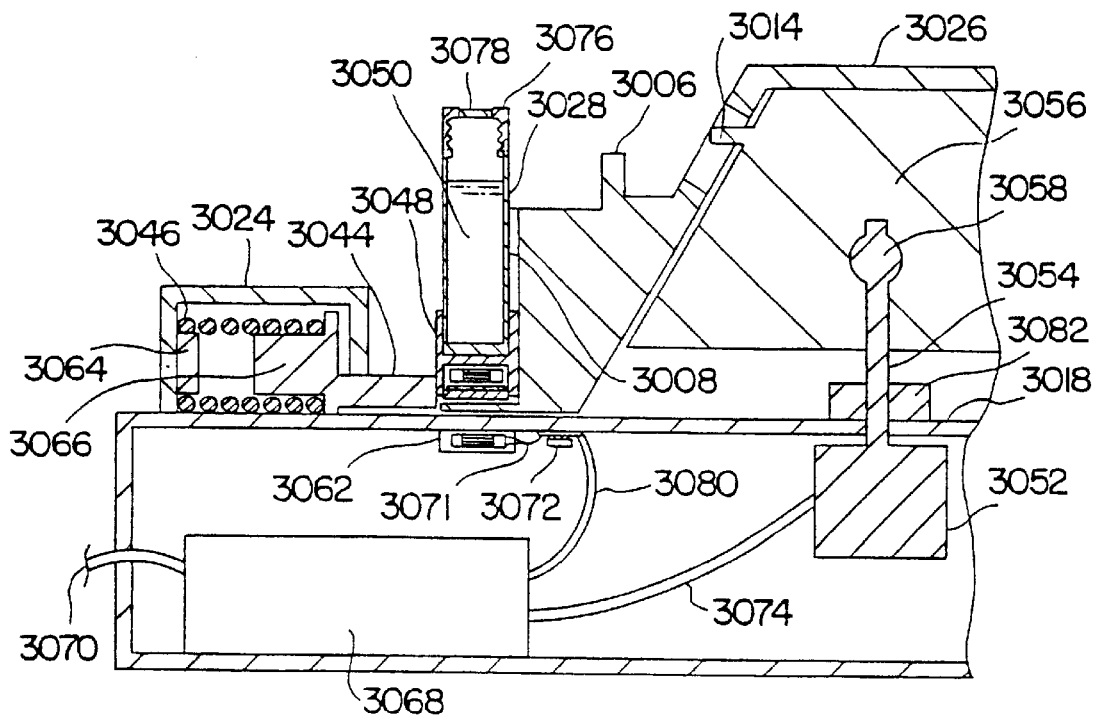
FIG. 37 is a cross-sectional view of the read/write station taken along line 37—37 of FIG. 35.

Referring now to FIG. 37, the housing 3018, carousel 3006, vial 3010, and plunger 3024 are shown in cross-section. The housing is shown having a module 3068 that includes the majority of the electronics needed to operate the system 3000, with the exception of the computer system 3004. Mounted and extending through the housing 3018 is a motor 3052. The motor is positioned to extend vertically upwards from the housing and into a hub 3056 that is sized to receive the carousel 3006. Specifically, the shaft 3054 of the motor extends upwards and is formed with a locking tab 3058 that is intended to keep the hub properly positioned on the shaft. In other words, the tab 3058 engages the hub to prevent the hub from rotating when the shaft 3054 is not rotating. To assist the shaft in maintaining a proper vertical alignment, a bearing 3082 is mounted to the housing 3018.

Any type of bearing could be used for this application, including but not limited to ball bearings or roller bearings. In fact, a grease bearing, if providing sufficient stability, could be used. In the event that the carousel is to be manually rotated, there would be no need for the motor 3052 and, as a result, the bearing 3082 would be of a different type to give support to the carousel itself. In such an instance, the shaft would be fixed to the housing, or to a bearing mounted on the housing, and the carousel would rotate freely about the shaft. Thus, in such an instance where no motor is used, the tabs 3058 would not be formed on the shaft 3054.

In order to control the motor 3052, if used, a control wire 3074 extends from the motor to the module 3068. One function of this module would be to receive an electronic signal from the computer system and command the motor to a particular rotational position. In order to achieve this positional accuracy, the motor may be a stepper motor, or may be equipped with either a synchro or resolver that would be used to determine the angular position of the carousel 3006. Briefly, and as is generally known in the art, a synchro or resolver would provide a three-phase electrical signal that would represent the angular position of the carousel. This three-phase signal can be decoded using a synchro or resolver-to-digital converter to determine the angular position of the carousel in digital representation, or the signal can be a quadrature output with Z pulse shaft encoder. Alternatively, the carousel could be formed with angular markings on the outer surface of the carousel that could be read by either a mechanical or optical device common for use in such positioning systems. Such an optical system could use a decoding scheme based on a binary-coded-decimal representation in a bar-code form that could be easily marked on the outer surface of the carousel.

Plunger 3024 is shown with slide 3044 striking the outer surface of vial 3010 to hold the rotational position of the carousel. As shown, the plunger 3024 has a slide 3044 that is urged towards the carousel by a spring 3046. As a result of the expansion of the spring, the slide is urged gently against the surface of the carousel. Thus, in order to adjust the force with that the slide strikes the carousel, the spring 3046 may be selected to have a different spring constant. In other words, the higher the spring constant, the more force the slide will strike the carousel with. Alternatively, the plunger could be formed with slots that would allow the screws 3043 to be loosened to adjust the plunger position either towards or away from the carousel to effectively adjust the force with which the slide strikes the carousel. The spring 3046 is retained in place within the plunger 3024 by the combination of nipple 3066 and nipple 3064. The diameter of the nipples is to be selected to match the diameter of the spring. As such, the diameter of the spring and nipples will likely change to reflect springs having different spring constants and dimensions.

In an alternative embodiment, the spring 3046 could be substituted with a solenoid that could be electrically activatable to force the slide either towards or away from the carousel. Such electrical control could easily come from the module 3068, in combination, or acting independently, with computer 3004. Also, if the slide is replaced with the post as mentioned above, the accuracy of the positioning could be increased while not increasing the level of human intervention required to position the carousel on the housing.

A vial 3010 is shown placed in a port 3008 of the carousel, and aligned with a receiving coil 3062. Importantly, the slide 3024 holds the vial 3010 directly over the antenna coil 3062. While this is not particularly necessary to insure proper communication between the vial and the antenna coil, the need for accuracy of the positioning increases when the distance between the vials is decreased. As discussed above, where there is a large number of vials held on a single carousel, there is a need to properly position the vial so that there is limited, or no, interference between the intended vial and any neighboring vials. This problem would be particularly noticeable in carousels where there is minimal space between the vials, or when the vials have been miniaturized.

Figure 38:
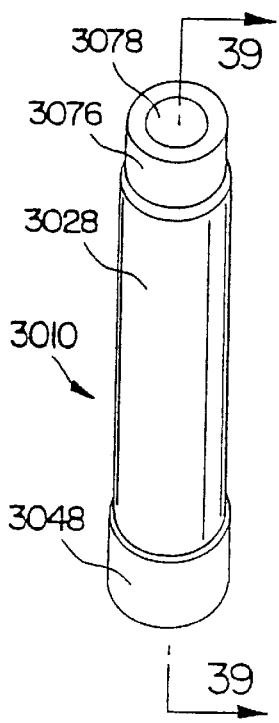
FIG. 38 is a perspective view of a cylindrical tube having a read/write device attached to its lower end.
Figure 39:
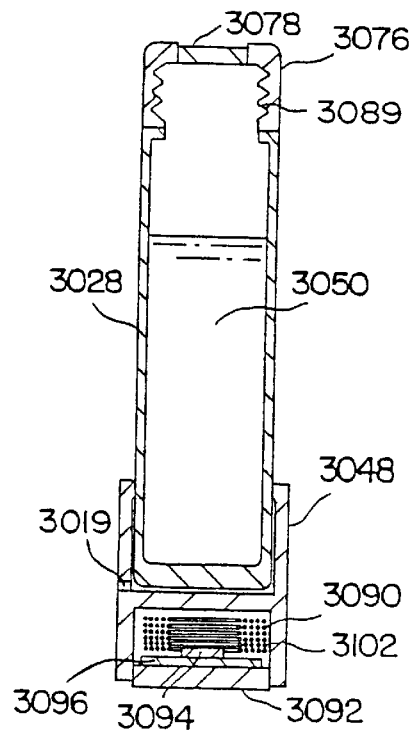
FIG. 39 is a cross-sectional view of the cylindrical tube and read/write device taken along line 39—39 of FIG. 38.

Referring now to FIG. 38, a vial is shown in perspective and generally designated 3010. Vial 3010 has three portions: a lid 3076, a cylinder 3028, and a sleeve. The vial is shown in cross-section in FIG. 39. As shown, the lid 3076 is held on the cylinder 3028 by threads 3089 that are formed on the cylinder and the lid. Although threads provide for an easy installation and removal of the lid, a snap-type attachment could also be used. Moreover, any type of lid could be used and it would not affect the utility of this system 3000. It will be appreciated by those skilled in the art that the ability to add and remove materials from the cylinder is determined by the type of lid that is used. This preferred embodiment uses a lid 3076 that is formed with a membrane window 3078 that is preferably made of a puncturable material. This puncturable material would allow a syringe to puncture the membrane to inject or remove materials from the cylinder, removing the syringe when finished, allowing the membrane to re-seal itself. Such materials are well known in the art and are not discussed further here.

The cylinder 3028 is shown filled with material 3050. While this is shown as a fluid, it is to be appreciated that any number of materials, such as polystyrene beads, patient samples and other materials, could be placed in these cylinders. A sleeve 3048 is attached to the bottom of the cylinder 3028 and is formed with an upper orifice 3116 and a lower chamber 3117. The sleeve 3048 is shown in greater detail in FIG. 40. The upper orifice 3116 is formed with a circumferential ridge 3110 that is adjacent to the upper end of the sleeve. This ridge 3110 is sized to have a distance 3118 between them that is slightly smaller than the diameter of the cylinder 3028. This diameter difference is important to insure that the sleeve, once positioned, will not slide off of the cylinder. This is particularly important when it is critical to track the placement and location of a vial. In order to achieve the resilience needed to allow the insertion of the cylinder into the sleeve. The sleeve is fabricated from a suitable inert material, such as polypropylene material, that is also substantially transparent to the selected signal, such as an RF or microwave signal, passing through the sleeve. While this material is fairly pliable, it is also sufficiently rigid to retain its shape. As a result, the polypropylene is particularly suited to such an application where there is a need to securely mount the sleeve to an object, while providing sufficient pliability to avoid cracking the cylinder if made of a fragile material such as glass. In situations where the cylinder is more rigid and less fragile, the sleeve could be attached using a variety of other manners. More specifically, elastic bands or adhesive straps could be used to hold the sleeve in position over the cylinder.

In order to facilitate the insertion of the cylinder 3028 into the orifice 3116 in the sleeve 3048, a vent hole 3019 is formed in the wall of the sleeve adjacent to the divider 3114 of the orifice 3116. This vent hole allows the air trapped inside the orifice while the cylinder is being inserted to escape into the atmosphere since a considerable pressure could build within the orifice and prevent the insertion of the cylinder.

On the underside of the sleeve, a chamber is formed between the plug 3092, sleeve wall 3112, and divider 3114.

Within this chamber is the sleeve antenna 3090, a microchip 3094, both mounted on a substrate 3096. The sleeve antenna 3090 includes multiple windings of a fine gauge, insulated wire to form an inductive proximity antenna. The antenna is an important feature of the data transmission process between the read/write controller and read/write device. The antenna in this embodiment has a outer coil diameter of 0.420 inches and an inner coil diameter of 0.260 inches. The coils includes approximately 305 turns of wire having a diameter of 0.015 inches. In any case, the inductance of the antenna once formed should be on the order of 7.92 mH, with a series resistance of no more than 850 ohms at 1 volt and 100 KHz. Coil antennas of differing sizes can be used in this embodiment, but the number of turns of wire will change with the size of the coil, the size of the wire, and the overall diameter of the coil. To determine the proper number of turns given a different dimensioned antenna, the following equation must be used:

$$L = 2*a*\ln\left(\frac{a}{D} - K\right)*N^{1.9}$$

where "L" is the desired inductance in nH, "a" is the antenna circumference in centimeters, "D" is the wire diameter in centimeters, "N" is the number of windings, "K" is the geometrical constant that for a circular antenna is 1.01, and for a square antenna is 1.47. Because the value of "K" for a circular antenna is approximately and is normally much smaller than a/D, it can be left out, yielding a simpler equation:

$$N \approx 1.9\sqrt{\frac{L}{2*a*\ln(a/D)}}$$

Thus, once the inductance desired, diameter of the wire and circumference of the antenna are known, the proper number of windings can be determined. Conversely, any one variable can be determined from the equations above to yield the characteristics of the antenna.

In this particular embodiment, the cylinders are vials fabricated from glass. The cylinder could be made of virtually any material, including a suitable metal or any other inert material, so long as it or the memory device is configured to avoid detrimentally interfering with any data-carrying signals. They may also be made of matrices that include at least a portion of a surface suitable for linking biological particles or molecules. In the event metal is used, there may be a need to elongate the sleeve to insure that the metal is distanced from the antenna. In addition to the cylinder being made of a variety of materials, the sleeve can be used with any number of containment devices. Of these devices, the discussed above would be a particularly well suited container for attachment to the sleeve. In fact, the sleeve could be reformed to a substantially different structure that, nonetheless, would work equally as well as the sleeve and cylinder embodiment. Moreover, any other containment device or matrix support that is provided herein is capable of being equipped with the sleeve with memory with the exception that particularly small-sized read/write devices would require a miniaturized design having a smaller sleeve antenna. In environments where a sleeve is not practical, the read/write device may be made in the form of a submersible chamber or embedded in the structure of the containment device as described herein.

Also within the chamber 3117 is the microcircuit 3094 and substrate 3096. The microcircuit includes a rectifier, voltage regulator, reset generator, demodulator, clock extractor, modulator, control unit, and memory [see, U.S. Pat. No. 5,345,231]. Referring briefly to FIG. 2 in the U.S. Pat. No. 5,345,231 patent, the overall system architecture of the semiconductor is identified. This circuitry derives its power from rectifying an incoming signal that is received by the antenna. The rectified signal is conditioned with the voltage regulator and fed to all other circuitry on the semiconductor.

The microcircuit 3094 is attached to the substrate 3096 using a bonding adhesive as is common in the art. Any number of attachment methods could be used, however, and would achieve the same result The substrate is preferably made of alumina that would provide a stable platform that would have dielectric constants approximately equal to those of the silicon wafer of the microcircuit. As is common in the industry, by matching the dielectric constants of the materials, as well as the thermal expansion coefficients of the various materials, there is less of a likelihood that there will be cracking on the microcircuit. Moreover, because the thermal coefficients of the microcircuit are approximately the same as the alumina substrate, thermal stresses that are present on the microcircuit are greatly reduced.

Figure 41:
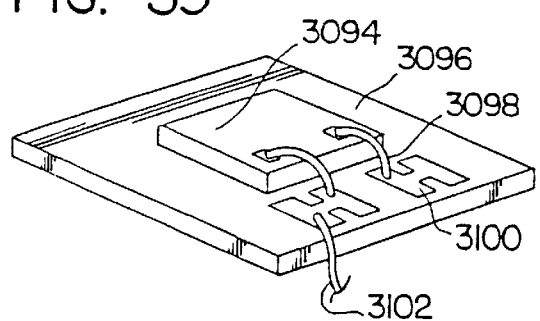
FIG. 41 is a perspective view of the microcircuit shown attached to a substrate.

Referring now to FIG. 41, the substrate 3096 is shown with the microcircuit 3094 firmly attached. In addition to having the microcircuit mounted to it, the substrate 3096 is also formed with a copper layer that is intended to be the bonding points for the antenna leads 3102. More specifically, the substrate 3096 is formed with a pair of pads 3100. Each of these pads is securely attached to the surface of the substrate to allow the wires 3098 from the microcircuit, called bonding wires, to be easily attached to the antenna wires 3102. Attachment between the two wires is made by soldering or brazing one of the wires, preferably the most delicate wire that would be the bonding wire 3102, from the microcircuit to the pad 3100. Once the most delicate wire is attached, the more robust and durable wire is attached to the pad. In this instance, the antenna wire is significantly thicker than the bonding wire and, thus, is connected last. In order to simplify the attachment of the antenna wire and to reduce the heat to which the microcircuit is exposed to, the pad may be tinned. A lead is "tinned" when covered with a slight layer of solder to which the antenna wire can be more easily attached.

Figure 40:
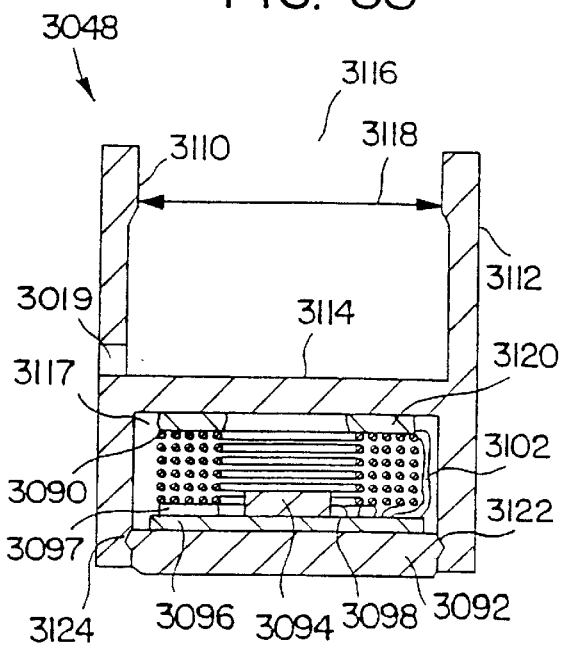
FIG. 40 is an enlarged cross-sectional view of the read/write device showing the coil antenna, microcircuit, and housing.

Once the sleeve antenna 3090 is formed and electrically connected to the substrate 3096, the substrate is attached to the antenna using an adhesive 3097. This adhesive may be of any kind known in the art and is selected so that it produces very little radio frequency [or other frequency when other frequencies are used] interference. In this embodiment, silicone is used to secure the substrate to the sleeve antenna 3090. It is important to note that the microcircuit 3094 in the present embodiment fits nicely within the internal diameter of the sleeve antenna. Such positioning effectively reduces the combined height of the antenna, substrate, and microcircuit. Once the substrate is firmly attached to the sleeve antenna, the combination is inserted into the chamber 3117 and held against the divider 3114 by an adhesive. Again, silicone is used to hold the sleeve antenna in place against the divider. As shown in FIG. 40, there is little space remaining following the insertion of the sleeve antenna and substrate into the chamber.

Figure 42:
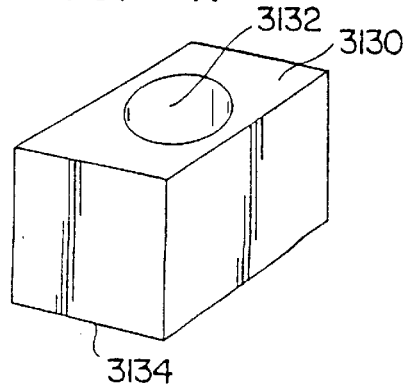
FIG. 42 is a perspective view of the sealing apparatus which is used to create an environmental on the lower end of the housing.

Once the sleeve antenna is positioned within the chamber, the plug 3092 is inserted into the sleeve 3048 to seal the chamber 3117. The plug is formed with a circumferential ring 3124 which engages to a circumferential slot 3122 formed in the sleeve wall. The ring and slot engage each other to retain the plug and avoid exposing the delicate electronics to the environment. To provide even greater protection, particularly when the environment is damaging to the electronics (e.g. wet), the plug can be fused with the sleeve. Referring to FIG. 42, a heating tool is shown that contains a thermally conducting block 3134 that is formed with a hole 3132 for receiving the sleeve. Once the plug has been inserted into the sleeve to seal the chamber, the entire device is inserted into the heated block 3134, allowing the sleeve to be easily melted so that the plug is fused to the sleeve to create an environmental seal. This seal is capable of withstanding even the most harsh environment, while maintaining the electronics in a dry location within the chamber.

Referring back to FIG. 37, and having review all necessary structural components of the system 3000, the operation of the system is more easily understood. A vial is either filled with a substance, or has been purchased with a substance already in it. In either case, this vial is inserted into a sleeve. As the sleeve is inserted over the vial, the polyethylene yields to provide a solid connection between the sleeve and the cylinder wall 3028. Preferably, at the time of mating the cylinder with the sleeve, the microcircuit has no memory stored on it which represents an identification tag. Thus, once the vial and sleeve have been combined, the combination is placed in a port 3008 of the carousel 3006. Once inserted in the port, the carousel is then placed on the housing with the notch 3040 adjacent to the plunger 3024. Then, the carousel is rotated such that the vial is directly in front of the plunger, and thus, immediately over the base antenna 3062. Once in position, the base antenna 3062 is excited with a high frequency (HF) signal from the base antenna 3062 [see, U.S. Pat. No. 5,345,231], which activates the microcircuit in the chamber 3117. As stated above, this HF signal is rectified and filtered to provide power to the microcircuit. Additionally, a clock signal is removed from the HF signal radiating from the base antenna, and used to coordinate operations within the microcircuit to the operations within the housing and module 3068. It should be appreciated that any other manner of exciting a non-powered microcircuit, or accessing identification data from a powered microcircuit, including other frequencies, is contemplated by this disclosure.

Once rectified, the microcircuit (rwd) is powered on and proceeds through its set-up routine which places the microcircuit in a condition wherein it can be programmed by the read/write controller. The read/write controller senses that the read/write device is not programmed and, as a result, selects an identification number for programming. As mentioned above, it is possible to program all of the microcircuits when the sleeves are made. In such an instance, the precoded information will be stored in a remote computer and associated with information regarding the contents of the vial or container. Thus, when the microcircuit is precoded, that identification code is incorporated into a database that identifies the contents of the cylinder [or other container] with the identification code. As is customary in the industry, a variety of information fields could be used to accomplish a variety of informational purposes. The identification code programmed into the microchip could be matched with a database that includes all patient information for the sample contained within the cylinder. For example, if the sample was blood, the database could include the patient's name as well as other aspects of the patient's file. In addition, in an automated process, the computer system where the database is maintained could be continually updated to monitor the current status of the sample or specimen contained in the cylinder associated with the particular sleeve and identification number.

Once programmed, the sleeve and vial can be removed from the carousel, or the carousel may be rotated so that a different sleeve may be inserted into a different port. In this manner, an entire carousel may be loaded and programmed within a short period of time. Despite requiring a short program period, the cylinder will never have to be re-programmed. In fact, many of the microcircuits are one-time-programmable (OTP) which removes any problem with erasing the identification code from the microcircuit. The vials with sleeve may be further processed in accord with methods described herein or other methods. The sleeve permits the vials to be readily identified and tracked.

The base antenna is substantially shaped like the sleeve antenna. Specifically, The ratio between the diameter of the sleeve antenna and the base antenna should be approximately 1:1. In certain circumstances, the ratio can be as much as 3:1, where there is sufficient distance between the vial being identified and the neighboring vials. Matching the base antenna to the sleeve antenna is an important aspect of the inductive communication which passes between the two antennas. More particularly, in order for the communication between the two antennas to be optimized, the antennas must be properly matched and positioned. While it is not critical that the antennas be precisely matched, it is important to maintain the ratio of 3:1 or less for the difference in sizes between the two antenna.

A pair of leads 3071 pass from the base antenna to a filter board 3072 which is intended to adjust the frequency range of the base coil to match the frequency range of the sleeve coil. In the present embodiment where the base antenna and the sleeve antenna are similarly shaped, the filter board 3072 only includes a capacitive adjustment. In this particular embodiment, the capacitance needed to match the two antenna was on the order of 20 pF.

From the filter board 3072, the electronic signal to and from the base antenna passes through wire 3080. This wire handles all communications between the module 3068 and the read/write device. Inside the module is a circuit board which includes those components shown in FIG. 1, U.S. Pat. No. 5,345,231. The circuit within the module includes an oscillator, modulator, demodulator, clock extractor, control unit, and interface. In particular, the modulator and demodulator are matched to the modulator and demodulator housed on the microchip. The control chip essentially coordinates all activity between the computer system 3004 and the module [see, U.S. Pat. No. 5,345,231, which describes the operation of the circuitry within the module].

Wire 3070 passes from the control module 3068 to the computer system 3004. This connection is a standard serial communication channel that is readily accepted into virtually all modern computer systems. In this embodiment, the computer system is equipped with a program that is designed to receive the serial digital information from the module that represents the identification code of the microcircuit in the read/write device. This program is included in Software Appendix II attached to this application and is incorporated herein. In addition to decoding the identification number, the computer system can be provided with positioning information that identifies the location within the carousel of the particular sleeve and vial. Because the motor is electrically actuatable, the particular vial can be identified and repeatedly accessed without having to redecode the identification code for each instance.

Although the positioning of the sleeves had been discussed in terms of being mounted on a containment device of one sort or another, it is to be appreciated that virtually anything could be identified with such a read/write device. More specifically, in the instance of the preferred embodiment, the carousel itself could be equipped with a read/write device that would enable the read/write controller to identify which carousel out of a number of carrousels was actually installed on the system 3000. To this end, it is to be appreciated that the housing 3018 could be equipped with a number of base antenna that could simultaneously read a number of sleeve antennae and read/write device, as well as those read/write devices located within the carousel itself.

Figure 43:
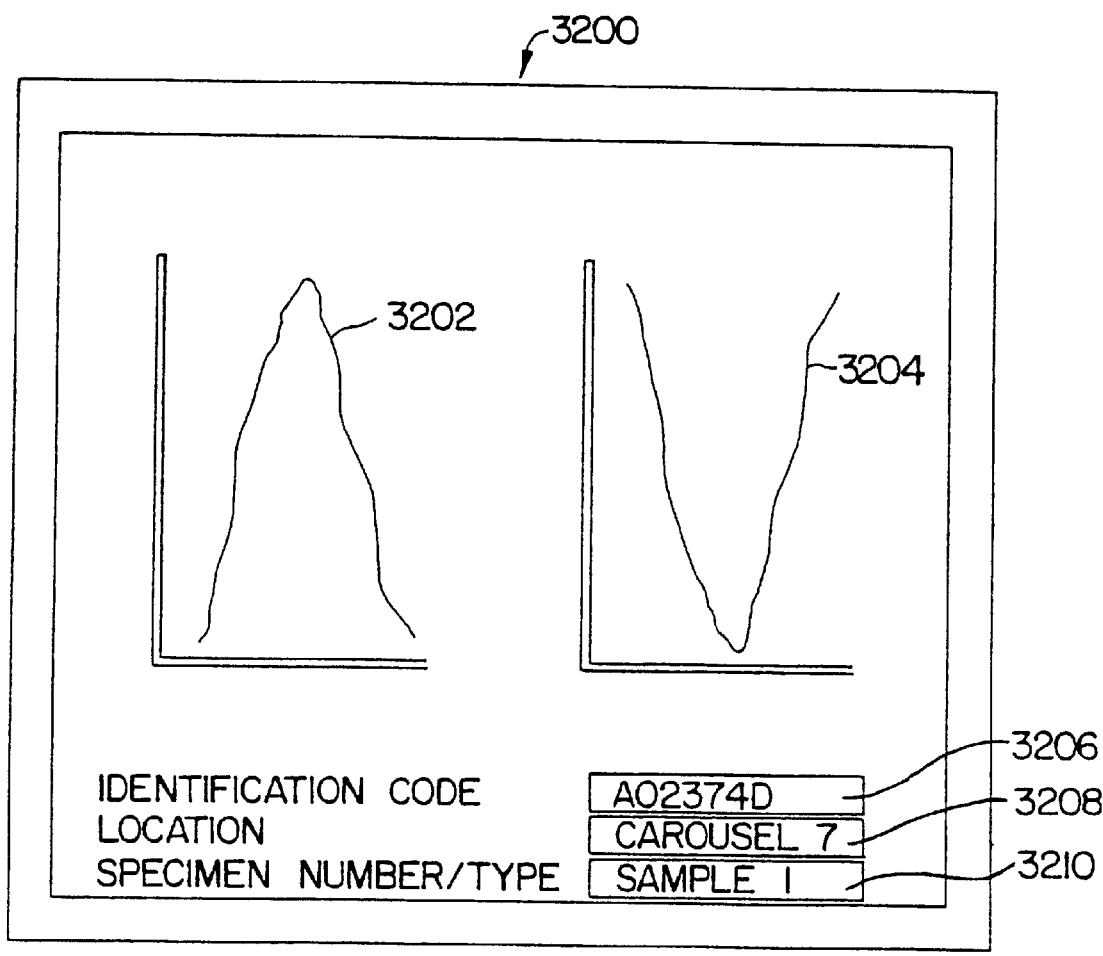
FIG. 43 is a view of a typical program output to the screen showing the decoded identification code, in combination with a graphical representation of the contents of the cylindrical tube.
Figure 54:
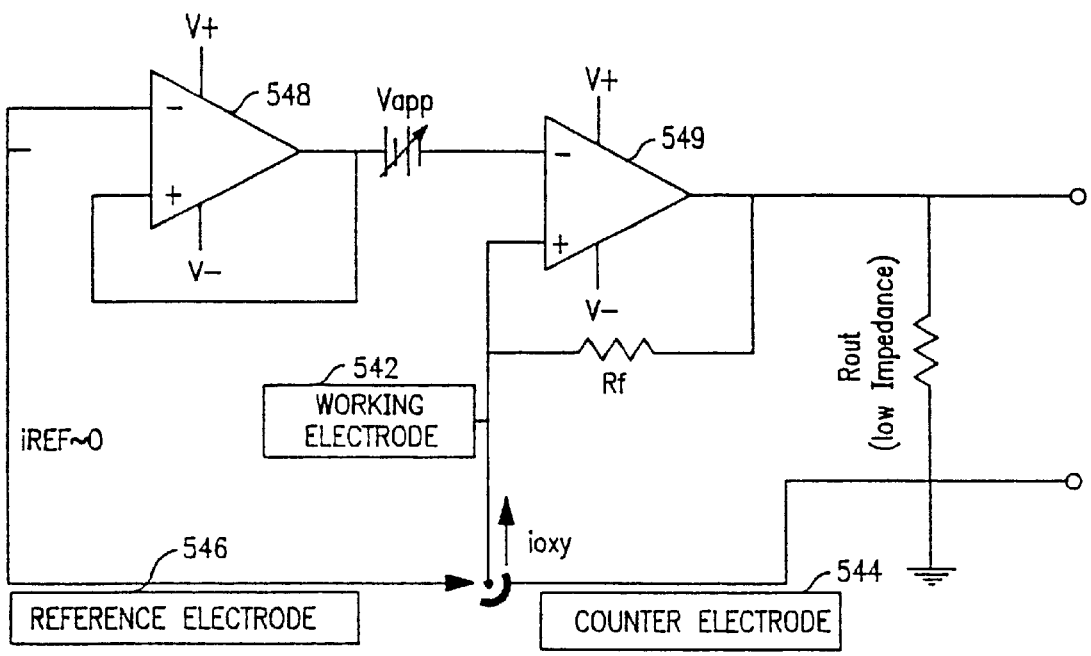
FIG. 54 is a circuit diagram of the basic components and interconnection of an exemplary sensor with memory.
Figure 55:
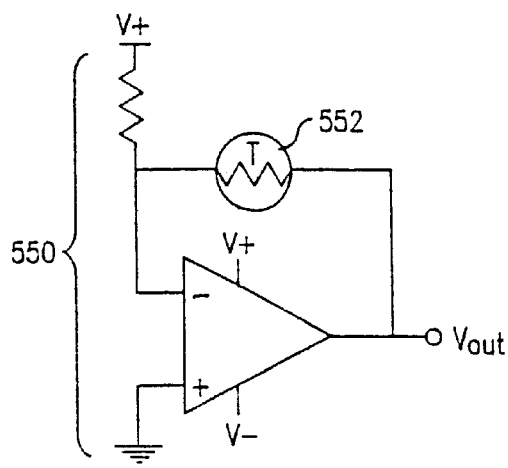
FIG. 55 is a simple circuit diagram for a temperature sensor.
Figure 56:
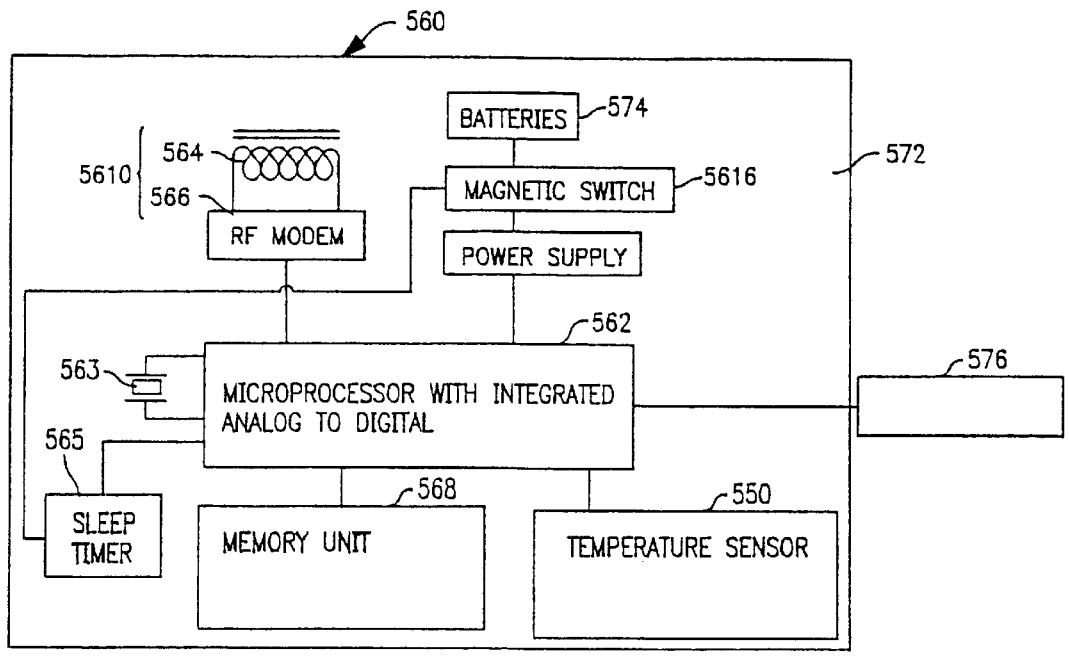
FIG. 56 is a block diagram of the components of an exemplary implantable glucose sensing system.
Figure 57:
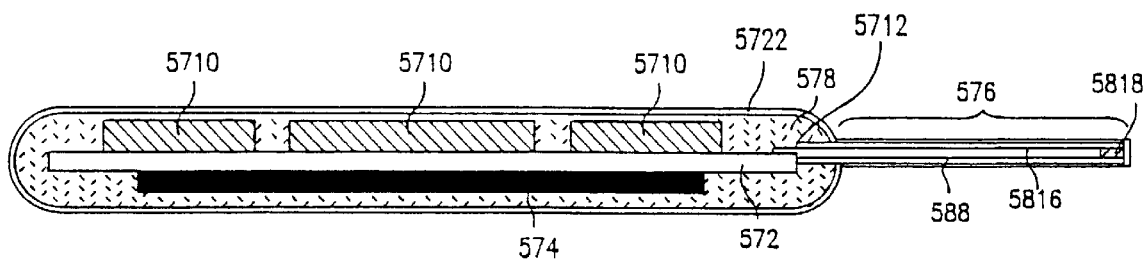
FIG. 57 is a cross-section of an exemplary implantable device with logic, power and communication electronics with electrode sensors.
Figure 58:
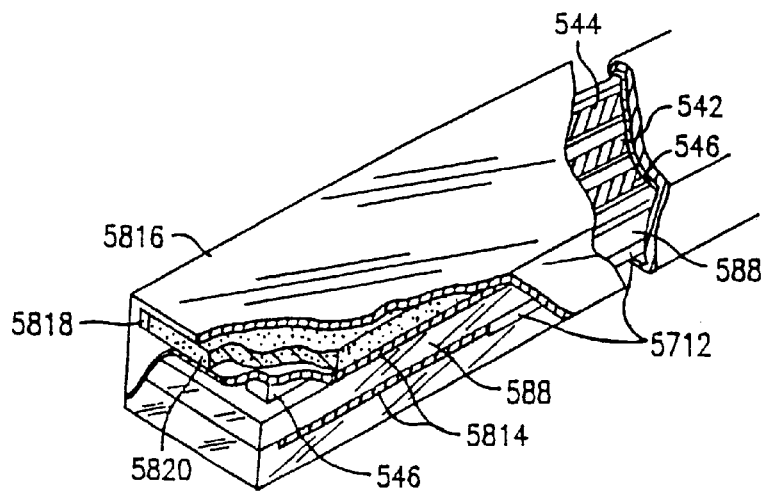
FIG. 58 is a perspective diagrammatic view of the sensor assembly of an exemplary implantable glucose sensing system.
Figure 59:
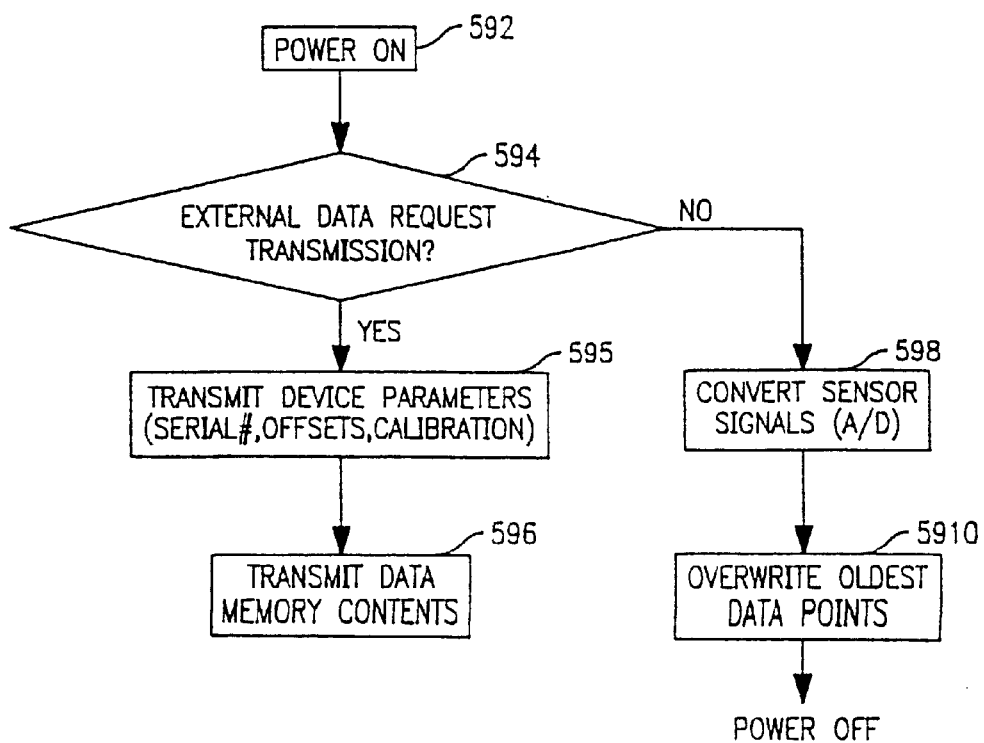
FIG. 59 is a flow diagram the basic control software for the exemplary implantable glucose sensing system.

Referring now to FIG. 43, a typical display 3200 is shown that is generated from software, such as that provided in Appendix II or such as software that one of skill in the art could design based on the disclosure herein. As shown, the screen has a number of graphical plots 3202, 3204 that may be used to show any number of characteristics of the sample contained within the vial. In this display, the identification code 3206 is shown at the lower left as read from the read/write controller and decoded by the computer system 3004. While this display shows various data fields, it is to be appreciated that virtually an unlimited number of data fields 3210 could be incorporated into a series of displays associated or linked with a single identification code. More particularly, the identification code could be linked to a database that indicates the contents of the cylinder as well as the location of the cylinder, as well as any number of other features that are also relevant to the contents of the cylinder. For example, the graphs shown here depict various levels of a substance which either varies over time, or following a series of tests.

The following examples are included for illustrative purposes only and are not intended to limit the scope of the invention.

EXAMPLE 1

Formation of a Polystyrene Polymer on Glass and Derivatization of Polystyrene

A glass surface of any conformation [beads for exemplification purposes (1) that contain a selected memory device or that are to be engraved with a 2-D optical bar code or that include a 3-D memory] that coat the device or that can be used in proximity to the device or subsequently linked to the device is coated with a layer of polystyrene that is derivatized so that it contains a cleavable linker, such as an acid cleavable linker. To effect such coating a bead, for example, is coated with a layer of a solution of styrene, chloromethylated styrene, divinyl benzene, benzoyl peroxide [88/10/1/1/, molar ratio] and heated at 70° C. for 24 h. The result is a cross-linked chloromethylated polystyrene on glass (2). Treatment of (2) with ammonia [2 M in 1,4-dioxane, overnight] produces aminomethylated coated beads (3). The amino group on (3) is coupled with polyethylene glycol dicarboxymethyl ether (4) [n≈20] under standard conditions [PyBop/DIEA] to yield carboxylic acid derivatized beads (5). Coupling of (5) with modified PAL [PAL is pyridylalanine] linker (6) under the same conditions produces a bead that is coated with polystyrene that has an acid cleavable linker (7).

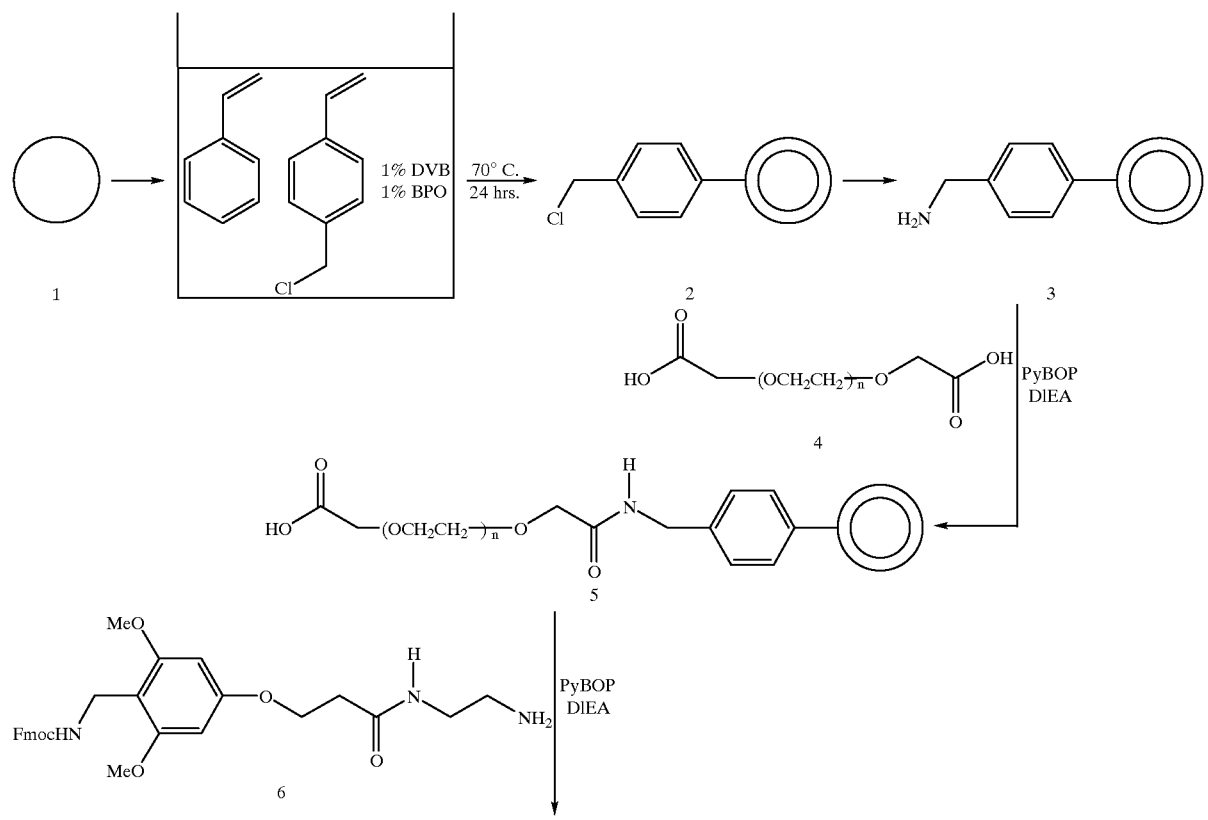

-continued

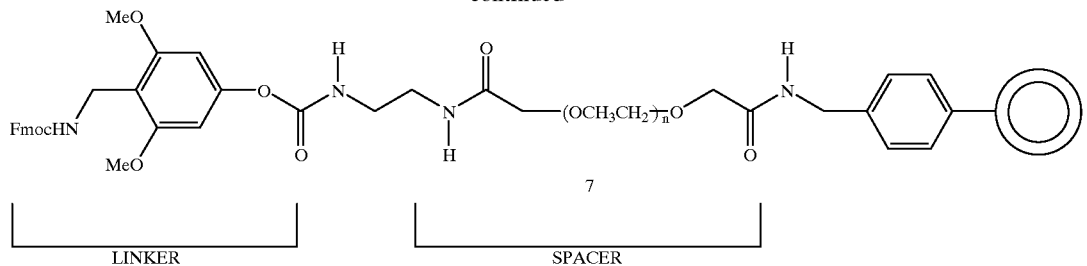

LINKER · SPACER

The resulting coated beads with memories are then used as solid support for molecular syntheses or for linkage of any desired substrate.

EXAMPLE 2

Microvessels and Use Thereof

A. FIGS. 11–13

Figure 11:
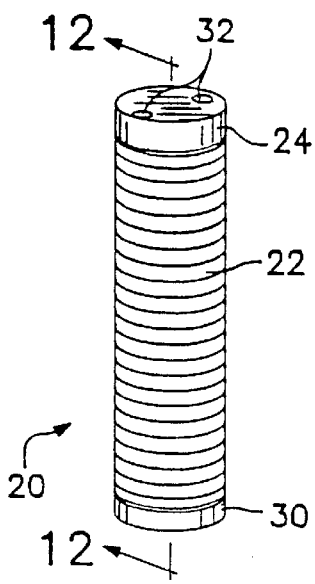
FIG. 11 is a side elevation of a preferred embodiment of a microvessel.
Figure 13:
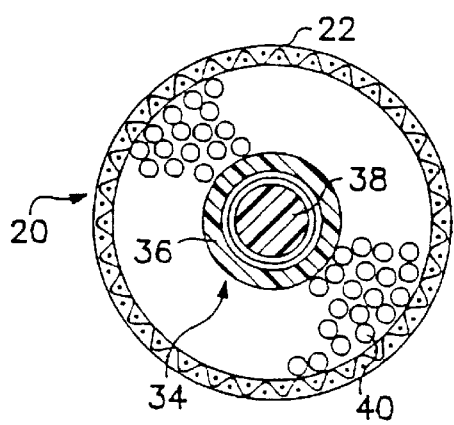
FIG. 13 is a sectional view taken along line 13—13 of FIG. 12.
Figure 12:
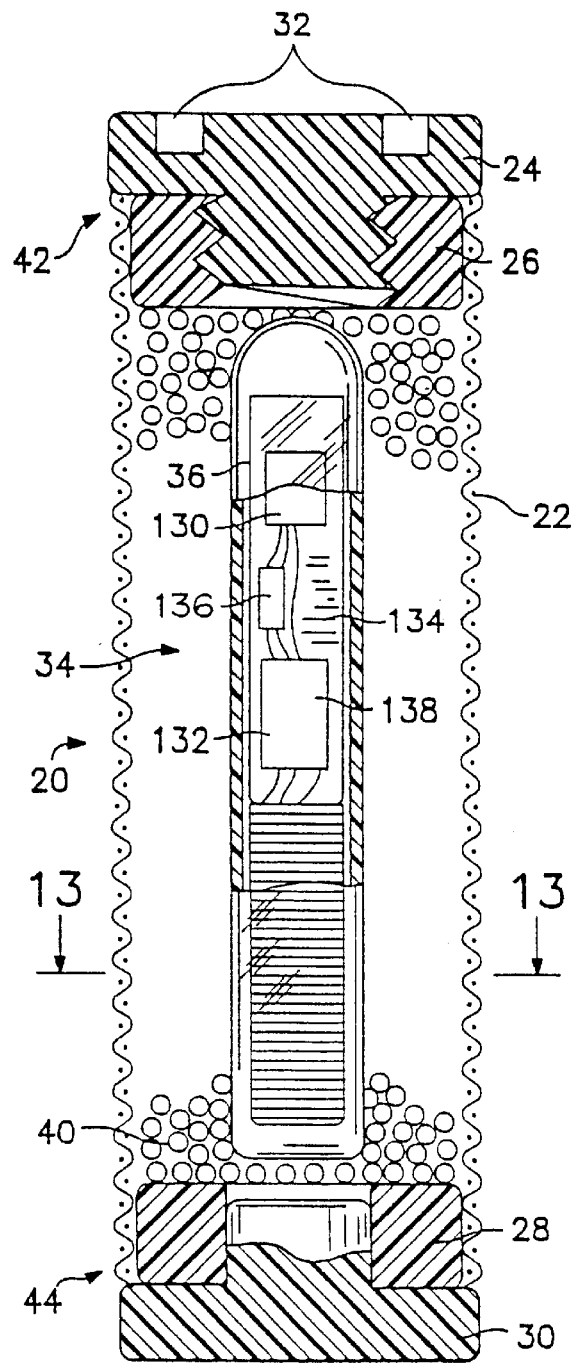
FIG. 12 is a sectional view, with portions cut away, taken along line 12—12 of FIG. 11.

FIGS. 11–13 illustrate an embodiment of a microvessel 20 provided herein [see, also FIGS. 45–50 for an alternative embodiment]. The microvessel 20 is a generally elongated body with walls 22 of porous or semi-permeable non-reactive material which are sealed at both ends with one or more solid-material cap assemblies 42, 44. The microvessel 20 retains particulate matrix materials 40 and can, as depicted in the Figure, contain one or more recording devices 34 or alternatively is engraved or imprinted with a symbology, particularly, the 2-D optical bar code provided herein. In the embodiment illustrated in FIGS. 11–13, the recording device includes a shell 36 that is impervious to the processing steps or solutions with which the microvessel may come into contact, but which permits transmission of electromagnetic signals, including radiofrequency, magnetic or optical signals, to and from the memory engraved on or in the device.

The microvessel 20 is generally cylindrically shaped and has two solid-material cap assemblies 42, 44. The cap assemblies may be formed of any material that is non-reactive with the solutions with which the microvessel will come into contact. Such appropriate materials include, for example, plastic, TEFLON, polytetrafluoroethylene (hereinafter, PTFE) or polypropylene. Each cap assembly 42, 44 preferably includes a support base 26, 28, respectively, and an end cap 24, 30, respectively. Each support base 26, 28 is permanently attached to the walls 22 of the vessel by known means such as bonding with appropriate adhesives or heat treatment, either by heat-shrinking the wall material onto the lower portions of the support bases 26,28, or by fusing the wall material with the support base material.

Preferably, at least one of the caps 24,30 is removably attached to its cap base 26, for example by providing complementary threads on the support base and the end cap so that the end cap can be screwed into the support base, as illustrated in FIG. 12. Other possible means for attaching the end cap to the support base will be apparent to those in the art, and can include snap rings, spring tabs, and bayonet connectors, among others. The end cap 24 has one or more slots, bores, or recesses 32 formed in its outer surface to facilitate removal or replacement, with the user's fingers and/or by use of an appropriate tool. For the example illustrated, a spanner wrench having pegs spaced at the same separation as the recesses 32 can be used by inserting the pegs into the recesses. For a single slot, removal and replacement of the end cap could be achieved by using a screwdriver. Protruding tabs, rims, knurled edges or other means to enhance the ability to grasp the end cap can be used for manual assembly/disassembly of the microvessel. The cap assembly 42 at the opposite end of the microvessel can be permanently sealed using an adhesive or heat treatment to attach the support base 28 to the end cap 30, or the cap assembly 42 can be molded as a single piece, combining the support base 28 and the end cap 30.

Retained within the microvessel 20 are particle matrix materials 40 and, as depicted a memory device 34. In embodiments herein, the memory device will be a symbology engraved on the device, such as on the cap.

The illustrated microvessel, as illustrated in FIGS. 11–13, is of a size sufficient to contain at least one recording device and one matrix particle, such as a TENTAGEL™ bead. The device is typically 20 mm in length [i.e., the largest dimension] or smaller, with a diameter of approximately 5 mm or less, although other sizes are also contemplated. These sizes are sufficient to contain form about 1 mg up to about 1 g of matrix particle, and thus range from about 1 mm up 100 mm in the largest dimension, typically about 5 mm to about 50 mm, preferably 10 mm to 30 mm, and most preferably about 15 to 25 mm. The size, of course can be smaller than those specified or larger. The wall material of the microvessel is PTFE mesh or other chemically inert surrounding porous support [polypropylene AA, SPEConn.RUM, Houston, Tex.], or other suitable material, having a preferably about 50 μM to 200 μM, generally 50 to 100 μM, more preferably 50 μm–70 μm hole size that is commercially available. The size of course is selected to be sufficiently small to retain the matrix particles. The cap apparatus is machined rod PTFE [commercially available from McMaster Carr, as Part #8546K11].

The matrix material is selected based upon the particular use of the microvessel; for example, a functionalized resin, such as TENTAGEL™ resin [e.g., TENTAGEL™ polymer beads carrying an acid-cleavable linker, from TENTAGEL S Am cat # S30 022, RAPP Polymer, Tubingen, Germany]. The matrix material may also include fluophores or scintillants as described herein.

Alternative embodiments of the microvessel will be appreciated and include, for example, a pouch, including porous or semi-permeable material, which is permanently sealed to itself and contains matrix material and one or more memories.

About 20 mg of the derivatized TENTAGEL™ beads have been sealed in a small [of a size just sufficient to hold the beads] porous polypropylene microvessel [see, Examples, below].

In alternative embodiments, microvessels in which the tube [or other geometry] is solid [not porous], such as polypropylene, PTFE or other inert surface that has been radiation grafted, as described herein, may also be used.

With these devices syntheses are performed on the surface and the solid tube is engraved with a symbology or includes an optical memory or other tag or combinations thereof, which may be permanently or removably sealed inside. These devices, herein denoted the MICROTUBE microreacters [or microvesses], may be used in the methods herein interchangeably with the MICROKAN microreactor type of device. In addition, these may also be advantageously use in the optical embodiments.

Figure 109:
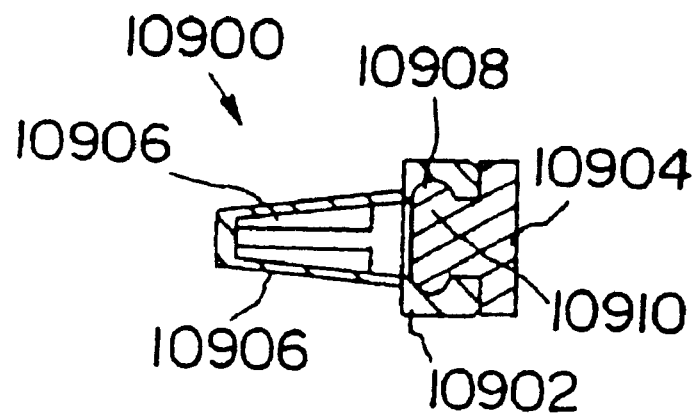
FIG. 109 is a cross-sectional view of a typical MICROKCAN microreactor showing the interaction between the body of the MICROKAN microreactor and the cap.

Referring now to FIG. 109 an alternative embodiment of a MICROKAN microreactor is shown in cross-section and generally designated 10900. MICROKAN microreactor 10900 includes a body 10902 and a cap 10904. Body 10902 is formed with porous portions 10906, which are intended to allow the free diffusion of solutions, while retaining the resins used for synthesis within the MICROKAN 10900. Once inserted into the MICROKAN 19099, cap 10904 is retained in body 10902 by a retention force exerted by the tab portion 10910 of cap 10904 against the channel portion 10908 formed in body 10902.

Figure 110:
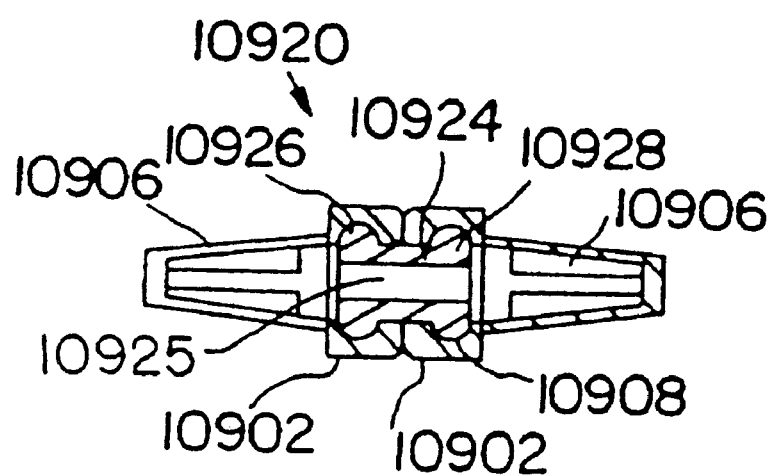
FIG. 110 is a cross-sectional view of a back-to-back MICROKAN microreactor showing the two MICROKAN microreactor bodies and the connecting spacer.

Referring now to FIG. 110, an alterative embodiment of a MICROKAN microreactor is shown in cross-section and generally designated 10920 (a back-to-back or dual MICROKAN microreactor). MICROKAN 10920 is a double-bodied reactor, also referred to as the back-to-back MICROKAN, which includes two bodies 10902 separated by a hollow junction tube 10924 which allows the free flow of reagents and resin particles between the two bodies 10902. The back-to-back MICROKAN microreactor is held together by a retention force, similar to the force holding the cap on the single body microreactor 10900. For example, the junction tube 10924 is formed with a pair of tab portions 10926 and 10928 which engage channel portions 10908 on bodies 10902. The combination of multiple microreactors bodies provides for the use of a larger quantity of matrices, as well as the combination of matrices which originate from two separate bodies 10902.

B. Tagging

By pooling and splitting matrix with memory microreactors [rather than individual solid phase resin beads] by a process known as "directed sorting", one discrete compound is synthesized in each matrix with memory reactor or microreactor. Each microreactor contains a memory, such as an optical memory, that is a unique label or tag used to identify it during the sorting processes that occur between chemical synthesis steps.

The memory tag provides a unique ID for each matrix with memory reactor and therefore each compound. This unique ID allows each microreactor to be identified during the combinatorial directed sorting process.

C. The "Directed Sorting™" Approach to Solid Phase Combinatorial Chemistry

The "directed sorting" approach to combinatorial chemistry is made possible by splitting and pooling matrix with memory microreactors rather than individual solid phase resin beads. During the first directed sorting step each microreactor is assigned to one specific compound. This assignment is maintained during all subsequent directed sorting and synthesis steps.

Tagging with a memory that is either engraved or imprinted during processing, subsequent to or pre-encoded [with decoding information stored remotely and associated with identifying information] of microreactors provides convenient and positive identification of compounds for archival and storage purposes. Such tagging permits the microreactors to be sorted between the individual steps in the synthesis.

Traditional split-and-pool methodology relies on a statistical distribution of resin beads between each step in the chemical synthesis. Typically, a large number of resin beads are used for each compound being synthesized to ensure an adequate statistical distribution of compounds. A consequence of this approach is that individual compounds are synthesized on multiple solid phase resin beads. These multiple copies of each compound are mixed together with multiple copies of all the other compounds. These mixtures need to be deconvoluted during screening. In contrast, the directed sorting approach ensures that:

1. Every compound is synthesized
2. Only one copy of each compound is synthesized
3. All compounds are present as discrete entities (no mixtures).

D. Software

Software, described below [see, also, Appendix III] provides:

1. A repository for the chemical synthesis information—primarily the building blocks and reaction steps. Other information, such a pre-reaction procedures and reaction work-up procedures ban also be stored.
2. Explicit directions teaching how to sort the microreactors between each reaction step to ensure that all compounds, and no duplicates, are synthesized.
3. An interface from the chemical synthesis environment and format (individual compounds in microreactors) to the biological screening environment and format (cleaved compounds in 96-well microplates).

E. FIGS. 14–16

Figure 14:
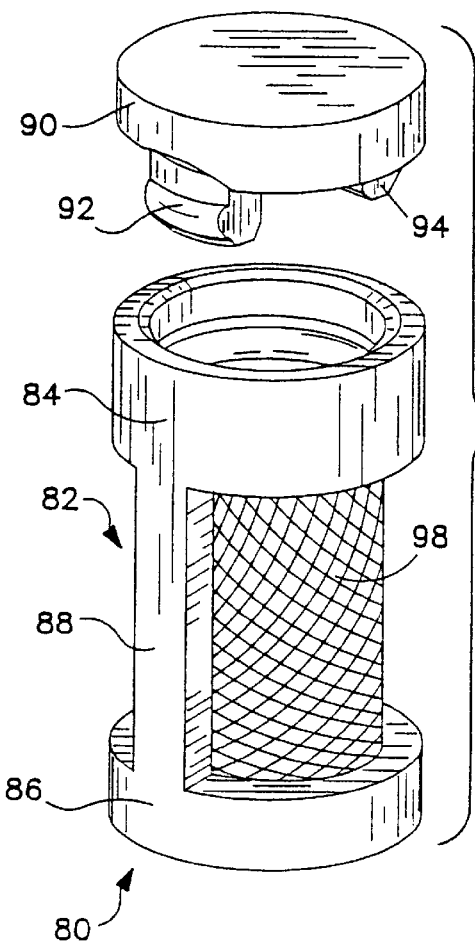
FIG. 14 is a perspective view of an alternative embodiment of a microvessel, with the end cap separated.
Figure 15:
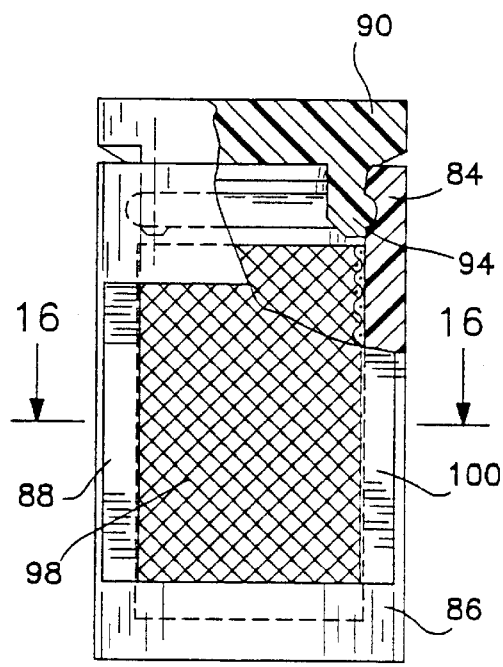
FIG. 15 is a side elevation view of the microvessel of FIG. 14, with a portion cut away.
Figure 16:
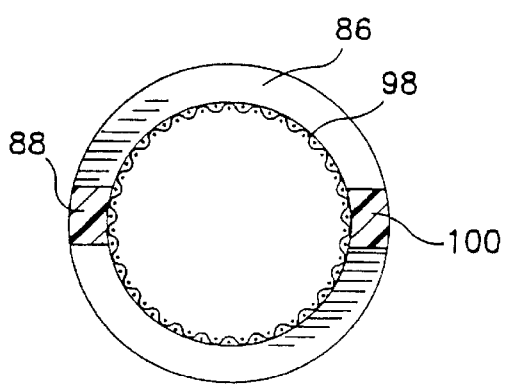
FIG. 16 is a sectional view taken along line 16—16 of FIG. 15.

FIGS. 14–16 illustrate an alternate embodiment of a microvessel provided herein. Like the microvessel described in Example 3, this embodiment of the microvessel also retains particulate matrix materials and can be imprinted with a symbology or will contain one or more recording devices (not illustrated). The microvessel has a single-piece solid material frame 82, including a top ring 84, two support ribs 88, 100 disposed diametrically opposite each other and a bottom cap 86. The solid material frame 82 may be constructed of any material which is non-reactive with the solutions with which the microvessel will come into contact. Such appropriate materials include, for example, plastic, polytetrafluoroethylene (hereinafter, PTFE), TEFLON or polypropylene, and formation may be by molding or machining of the selected material, with the former being preferred for economy of manufacture.

The sidewall of the microvessel 98 is formed of porous or semi-permeable non-reactive material, such as PTFE mesh, preferably having a 70$\mu$M pore size. The sidewall is preferably attached to the top ring 84 and bottom cap 86 of the solid material frame 82. Such attachment may be by known means such as bonding with appropriate glues or other chemicals or heat, with heat being preferred.

In the embodiment of FIGS. 14–16, the two support ribs 88, 100 are positioned opposite one another, however, any number of support ribs, i.e., one or more, may be provided. The microvessel sidewall 98 need not be fully attached to the support ribs 88, 100, however, the molding process by which the microvessels are formed may result in attachment at all contact points between the frame and the sidewall.

In the preferred manufacturing process, the sidewall material, a flat sheet of mesh, is rolled into a cylinder and placed inside the mold. The frame material is injected into the mold around the mesh, causing the frame to fuse to the mesh at all contact points, and sealing the edges of the mesh to close the cylinder.

In the embodiment illustrated in FIGS. 14–15, the microvessel is configured with a removable end cap 90. The end cap 90 is preferably constructed of the same material as the solid material frame 82. A snap ring, or, as illustrated, projections 92, 94 extend downward from the inside surface of the end cap 90. The projections 92, 94 have a flange which mates with a groove 96 formed in the inner wall of top ring 84 when pressed into the top ring to releasable secure the end cap 90 to the microvessel 80. As will be apparent, other means for releasably securing the end cap 90 to the top ring 84 can be used, including, but not limited to, those alternatives stated for the embodiment of FIGS. 11–13. The dimensions vary as described for the microvessel of FIGS. 11–13 and elsewhere herein.

In other embodiments, these vessels fabricated in any desired or convenient geometry, such as conical shapes. They can be solid at one end, and only require a single cap or sealable end.

These microvessels are preferably fabricated as follows. The solid portions, such as the solid cap and body, are fabricated from a polypropylene resin, Moplen resin [e.g., V29G PP resin from Montell, Newark Del., a distributor for Himont, Italy]. The mesh portion is fabricated from a polypropylene, polyester, polyethylene or fluorophore-containing mesh [e.g., PROPYLTEX®, FLUORTEX®, and other such meshes, including cat. no. 9-70/22 available from TETKO® Inc, Briarcliff Manor, N.Y., which prepares woven screening media, polypropylene mesh, ETF mesh, PTFE mesh, polymers from W. L. Gore. The pores are any suitable size [typically about 50–100 $\mu$M, depending upon the size of the particulate matrix material] that permits contact with the synthetic components in the medium, but retains the particulate matrix particles.

EXAMPLE 3

Systems for Sythesis, Screening and Sorting

A. Manual system

Illustrated in FIG. 17 is a program/read station for writing to and reading from the memory devices in the microvessel. The electronic components are commercially available from the same supplier of the memory devices, e.g., BMDS or ID TAG or the monolithic memory provided herein [Bracknell Berks RG12 3XQ, UK], so that the basic operations and frequency are compatible. The basic controller 170 and the transceiver 172 are disposed within a housing 174 which has a recessed area 176 positioned within the transmission range of coil 178. The microvessel 180 may be placed anywhere within recessed area 176, in any orientation, for programming and reading functions. Basic controller 170 is connected to the system controller 182, illustrated here as a functional block, which provides the commands and encoded data for writing to the memory device in the microvessel and which receives and decodes data from the memory device during the read function. System controller 182 is typically a PC or lap top computer which has been programmed with control software 184 for the various write and read functions.

An example of the operation of the system of FIG. 17 is illustrated in FIG. 18. When power is supplied to the system, transceiver 172 emits an interrogation signal 185 to test for the presence of a memory device, i.e., a responder, within its detection range. The interrogation signal 185 is essentially a read signal that is continuously transmitted until a response 186 is received. The user manually places a microvessel 180 within the recessed area 176 so that the interrogation signal 185 provides a response to the controllers indicating the presence on the microvessel. The system receives the interrogation signal and performs a decode operation 187 to determine the data on the memory device within the microvessel, which data may include identification of the device and data concerning prior operations to which the microvessel has been exposed. Based upon the data obtained, the system makes a determination 188 of whether additional information is to be written. The system then performs a write operation 189 to record the immediately preceding operation. The write operation 189 involves modulating the transmitted signal as a series of "0's" and "1's", which are recorded on the memory chip, which typically has a 128 bit capacity. After completion of the programming step 189, an error check 190 is performed wherein a second read signal is emitted to verify the data that was written for integrity and correct content. If the correct data is not verified, the system may attempt to perform the write operation 189 again. After verification of the correct data, if the microvessel is one that should proceed to another operation, the system controller 182 will display instructions 192 for direction of the microvessel to the next process step.

The read operation is the same as the beginning of the write operation, with the interrogation signal being continuously transmitted, or transmitted at regular intervals, until a response is received. The response signal from the memory device in the microvessel 180 is conducted to system controller 182 for decoding and output of the data that is stored on the memory device. Software within the system controller 182 includes a data base mapping function which provides an index for identifying the process step associated with data written at one or more locations in the memory device. The system memory within the system controller 182 will retain the identification and process steps for each microvessel, and an output display of the information relating to each microvessel can indicate where the microvessel has been, and where it should go in subsequent steps, if any. After the data stored within the microvessel has been read, it is removed from the interrogation field and advanced to its next process step.

Referring to FIG. 67, a manual sorting device is shown and generally designated 6700. As shown, the manual sorting device contains an identification station 6702, a computer system 6706, a number of visual cue devices 6740 mounted on an equal number of destination beakers 6720.

The identification station 6702 is a memory-reading and/or writing device which is capable of accessing the memory within the matrix-with-memory. The identification station is similar to or is the read/write station identified and discussed in conjunction with FIG. 17. As will be apparent to those skilled in the art, any variety of optical or RF reading and or writing devices may be used as long as the identification station had a data output channel. This channel is represented by the cable 6712 which passes between the identification station 6702 and the computer system 6706. The cable 6712, in addition to carrying the data to and from the identification station, provides any necessary power that the identification station should require.

In embodiments in which the memory in the matrix-with-memory is an optical bar code, the identification station 6702 includes a light emitter and detector capable of transmitting light away from the station, and receiving reflected light from the bar code or similar marking, on the memory device. Thus, by passing the memory device over the sensor portion of the identification station, the identifying marking is illuminated and reflected back onto the identification station. Then, by receiving and decoding the markings, the identification station provides information from the memory device to the computer system.

In embodiments in which the memory in the matrix-with-memory is an electronic memory, such as an RF tag, the identification station 6702 includes a RF emitter and detector 6705. This emitter and detector operates in the same manner as those described herein. More specifically, for example, when the tag is an RF tag, the identification station emits an RF signal in about the 125 KHz range that creates an electromagnetic field in a region surrounding the station. When the matrix-with-memory with memory 6704 is passed in proximity of the station, the electromagnetic energy from the station excites a coil which is either part of, or attached to, the memory device. Once excited, a voltage is induced in the coil which, once rectified within the memory, powers the memory device. Once powered, and in response to the electromagnetic field, the memory device, of the RF tag or other type described in this application, transmits a data signal back to the identification station. This data signal can include many pieces of information. For instance, each memory device has its own identification code, or serial number. In association with that number, a variety of other information may be associated. This other information can include the source of the memory device, the characteristics of any molecules or biological particles linked to or associated with the memory device, other information, including the destination of the memory device [which, however, will generally be provided by the software that directs the protocol], or any other information relevant to the procedure or test in progress.

The identification station 6702 is attached to the computer system 6706 via cable 6712. This cable is typically a serial data channel that provides serial communication between the identification station and the computer, where the identification number, serial number, and any other information can be communicated to the computer system. As a result of this information transfer, the computer system may use a large data base which accumulates information about all of the matrices-with-memories, and can monitor the location of the various matrices-with-memories and otherwise coordinate their movement. For instance, the matrices-with-memories can be accessed and programmed in accord with the procedures set forth elsewhere herein, and can be identified using a serial number that was either programmed, or pre-programmed during the manufacturing process of the memory. In any case, once accessed, the memory device, whether attached to a matrix-with-memory, a container, or completely unattached, can be identified and tracked by updating the information in the computer data base entry that corresponds to the particular memory device.

The computer system 6706 has a video display 6710 which is capable of displaying the identification number of the memory device, the destination of the memory device, the source of the memory device, and various other features of the device, such as the contents of the matrix-with-memory, or the contents of a vial, or other vessel attached to the memory device. Data fields 6711 can be used to display the data fields discussed above. The ability to create an appropriate data base is generally within the level of skill in the programming art. The data base for monitoring and directing the locations of memories could include a virtually unlimited number of data fields, and could correspondingly maintain a data field for a virtually unlimited number of memory devices. For example, a numeric serial number having six characters would accommodate $10^6$ memory devices, ranging from number 000000 to 999999. Using conventional computing capabilities, an almost unlimited number of matrices-with-memories could be simultaneously monitored and tracked throughout a protocol or series of protocols.

In accordance with the tracking and location functions of the data base and computer system, it is advantageous to provide the ability to direct the placement of a matrix-with-memory to a particular location or destination. For example, when testing a number of assays with a particular series of matrices-with-memories, it may be useful to coordinate the movement of the matrices throughout the laboratory. When handling large quantities of matrices-with-memories, the likelihood of error or failure increases. To minimize the chance of error, the computer system and database can be used to assist and/or direct the user in the placement of the various matrices-with-memories in solutions for the various reaction vessels or vessels containing reagents for screening. With such a system, it would be possible to coordinate the movement of virtually any objects with the assistance of the computer and data base.

The computer-aided direction can be achieved using a variety of humanly perceptible cues which can be generated to direct the placement of the matrices-with-memories. Such cues may include displaying the destination location on the computer graphic display screen 6710, such as in a location 6711. As another example, a speech synthesizer could be connected to the computer for generating human-sounding voice patterns to verbally instruct the user to place a given memory device in a particular destination, such as a beaker, container, or other location suitable for testing purposes. A voice message could provide an instruction such as: "Memory Identification Number 123456, place in beaker number 23." Alternatively, the voice message may simply say "23". In either case, the user would know to place the memory device in beaker number 23. The spoken verbal assistance could minimize errors resulting from misreading the displayed location 6711.

Other audible signals, such as those from a simple audio generator, could be used for guiding the user to the correct destination for placement of a given memory device by using patterns of audible signals. Piezoelectric transducers which generate audible tones could be placed on or near each of a group of containers into which the memory devices are to be placed. In operation, the memory device would be read using the identification station and the computer to determine its identification information, then, the computer would activate the audio transducer located on the correct container.

An optical guidance device could be integrated with the computer system 6706 and used alone or in combination with an audible system. A optical system could include a separate alphanumeric indicator, independent of a graphic display on the computer monitor. For example, a conventional digital LED alphanumeric display could display "BEAKER 23" to indicate the correct destination beaker. However, since the need to read the display can lead to error, an alternative or supplementary optical guidance device consisting of a number of independent LEDs could be used, with at least one LED corresponding to each destination option. Using the second optical guidance device in an array of destination options, a memory device would be identified as above, then the computer would determine the proper destination for the memory device and cause an LED corresponding to the proper destination, e.g., beaker #23, to be activated, thus guiding the user to the proper destination.

Continuing the description of the exemplary embodiment of a manual sorter as illustrated in FIG. 67. A cable 6716 extends from an output of computer 6708 for providing the electrical signals to the visual indicators 6740. As illustrated, the cable 6716 includes eight individual lead wires 6718, and a common ground wire. The interface for connecting cable 6716 to computer 6708 may be provided using a digital input/output (I/O) card [not shown]. The particular card selected for this embodiment was manufactured by COMPUTER BOARDS, of 125 High Street, Mansfield Mass. 02048, and was model number C10/D10 48H. The selected I/O card is capable of driving forty-eight different electrical output lines, each of which can be switched between about a 5 volt level and a 0 volt level, and have the capability to drive the LEDs without any interface driving buffers. (It should be noted that the system is illustrated with one cable 6716 with eight lead wires 6718 for simplicity only, and that the I/O card is capable of supporting forty-eight signal wires.) Each lead wire 6718 consists of a signal wire and a ground wire, which may be in the form of a twisted pair. Connected at the end of each lead wire 6718 is a visual indicator 6740. This visual indicator is configured for placement on the rim of a beaker 6720.

Shown in greater detail in FIGS. 68 and 69, visual indicator 6740 comprises an inverted U-shaped bracket 6742 and a light emitting diode (LED) 6752. LED 6752 is disposed at an upper portion of the bracket so that it is visible from the front of the bracket. The bracket is formed with a slanted portion 6750 which causes LED 6752 to be directed slightly upwards at an angle from the bracket to optimize its visibility to the user, who will typically be viewing the system from in front of and above the set-up.

Inverted U-shaped bracket 6742 has a first leg 6744 and a second leg 6746, with a gap 6748 being formed between them. As shown in FIG. 67, bracket 6742 is hung over the rim of a beaker 6720 so that the bracket is held in place by gravity and/or friction between the inner surfaces of legs 6744 and 6746 and the beaker wall, making positioning and removal of the bracket from the beaker simple and quick, requiring only minimal time to set up the manual sorter.

Referring now to FIG. 69, visual indicator 6740 is shown in cross-section. This view shows the relative position of the LED 6752 within a bore 6758 formed in the bracket. LED 6752 may extend slightly beyond the face of slanted portion 6750 so that it may be more readily seen from oblique angles as well as from directly in the front of the bracket. Epoxy or silicone 6760 may be used to secure the LED within the bore, however, by forming the bore with the appropriate inner diameter relative to the LED outer diameter, the LED may be retained frictionally using a slight interference fit. Lead 6756 extends out the back of bracket 6740 for attachment to lead 6718. In the instant embodiment of indicator, LED 6752 is available from Chicago Lamp Company as part number CMD531D-5V, and is powered with 5 volts at 12 mA, and generates 40 micro-candela ($\mu$Cd). An LED with these operating parameters can be connected directly to the output of the I/O card without the need for current-limiting resistors. Other LEDs may be used with appropriate current compensation.

Leads 6718 and cable 6716 may be wrapped in shrink tubing and can also be shielded against electromagnetic interference. The electrical shielding can be a wire braid, or a full or partial foil, terminated to the computer chassis via cable 6716. Electromagnetic radiation-inhibiting ferrite beads may also be used. Such shielding will minimize interference caused by electromagnetic radiation emitted from the manual sorting system 6702 that may be located in relatively close proximity to the leads 6718 and cables 6716.

Manual Cleaving Station

Referring now to FIG. 97, a manual cleaving station is shown and generally designated 9700. Manual cleaving station 9700 includes a cleaving block 9702 formed with an array of bores 9704 and having a number of standoffs 9706 and sleeves 9708. Manual cleaving station 9700 also includes a top plate, or tray, 9710 which is formed with four mounting holes 9712 aligned with the standoff pegs 9706, and an array of holes 9714 aligned with bores 9704. As shown, microreactor carrier, such as a syringe body or similar funnel-ended cylindrical tube 9716 and 9718 are removably inserted into holes 9714.

FIG. 98 illustrates a section of the manual cleaving station 9700 in cross-section with the top plate 9710 mounted on standoff pegs 9706 with removable sleeves 9708 suspending the top plate 9710, with microreactor carrier 9716, above one of the bores 9704. Microreactor carrier 9716 preferably includes a filter or frit 9720 at its lower end to prevent particles from microreactor 9722 from exiting through the opening in the lower end and passing into the cleaved solution. Frit 9720 is preferably made from polyethylene or polypropylene, and has filtering properties for particles sized above 10–20 microns.

Details of standoff pegs 9706 and sleeves 9708 are illustrated in FIG. 99. Sleeve 9708 is formed from a flexible, resilient material and is adapted to be press fit over standoff peg 9706. Sleeve 9708 is placed of peg 9706 by pressing sleeve gap 9728 against peg 9706 in a direction perpendicular to peg 9706, causing sleeve gap 9728 to expand until it snaps into position as indicated by dashed lines 9732. Sleeve 9708 is removable from peg 9706 pressing the edges of sleeve gap 9728 in a perpendicular direction away from the peg, causing sleeve gap 9728 to expand until it clears peg 9706. Referring back to FIG. 98, the top plate 9710 may be lowered in direction 9724 against the cleaving block 9702 by removing sleeve 9708.

Referring now to FIG. 100, top plate 9710 is shown resting on the upper surface of the cleaving block 9702, with microreactor carrier 9716 extending fully into the bore 9704. In this position, the microreactor 9722 is typically bathed in a cleaving reagent such as TFA solution 9726, and the entire cleaving station may be agitated using a standard chemistry lab agitator to enhance the cleaving process. After the cleaving is completed, the top plate 9710 is lifted to its original position and sleeves 9708 are installed over standoffs 9706. In the raised position, microreactor carrier 9716 and microreactor 9722 are suspended above the level of solution 9726 to drain. If desired, the cleaving process may be repeated as needed by again removing sleeves 9708 to lower top plate 9710, washing the microreactor with a solution of TFA, raising the top plate and re-installing the sleeves 9708 to allow the microreactor and microreactor carrier to drain. Once the microreactor and microreactor carrier have been sufficiently cleaved and drained, the solution 9726 within the bore 9704 is then removed with a pipet for placement on a standard microtiter plate for drying and further processing.

Cleaving block 9702 is typically manufactured from polypropylene or TEFLON™, however, other materials may be used provided they are non-porous, washable to remove all residues, and can withstand exposure to the chemicals used in the cleaving process. Such other materials could include various glasses, for example. As shown, manual cleaving station 9700 has an array of 3×9 bores, however, a cleaving block may be formed having any number of bores in any variety of arrays. For use with an automated sorter, the cleaving block should be compatible with the configuration of the sorter tray.

B. Software

Software for aiding in the steps in combinatorial synthesis schemes has been developed. The software, which is exemplified by the code provided in Appendix ll, but which in light of the description herein could be developed without reference to the Appendix, facilitates the process of creating chemical libraries with the systems provided herein. Exemplary software, now available under the name ACCUTAG™ SYNTHESIS MANAGER Software as a part of the AccuTag™-100 Combinatorial Chemistry System [e.g., an embodiment of the system provided herein]. These systems exemplified with the device of FIG. 17 [e.g., sold under the name ACCUTAG™], computer-based hardware, and the matrix with memories used therewith, such as the MICRO-KAN™ matrix-with-memory device and the MICRO-TUBE™ matrix-with-memory device [see, e.g., FIGS. 11–15 and 21].

The software is organized into the following sections. These sections represent the normal sequence of activities that go into building a library with the system provided herein.

1. Define Building Blocks. The user enters the names of the chemical building blocks to be used. For brevity of reference, a code letter is assigned to each building block. An example of a screen that will be generated by the software and displayed in a WINDOWS™ format is provided in FIG. 135, showing the button bar 13501 with the button for selecting the first step "Define Building Blocks" 13502, with the user selecting the step using a mouse or the keyboard.

2. Plan Steps.

a. Number of Steps. The user specifies the number of steps 13503 as shown in the upper left portion of the screen. In a given step, a building block, such as a monomer, amino acid, nucleotide, will be chemically added to each compound that is being synthesized.

b. Building Blocks To Use. The user specifies which of the defined building blocks 13504 will be used in each step. If, for example, there are 3 steps and the user specifies building blocks A, B, C in step 1, building blocks D, and number in step 2, and building blocks F, G, H, I in step 3, then the resulting library will contain 24 unique compounds because there are 3×2×4=24 combinations of building blocks. Pre-reaction procedure 13505, and work-up procedures 13506 are also stored for each step.

c. Procedural information. The user optionally enters "recipe" information such as reaction times, temperatures, molarities, and reagents to use for each building block's reactions as well as procedures common to all building blocks. At the appropriate times during the "Perform Synthesis" section of the program, which is shown in FIG. 136, the pre-procedure information is "played back" to the user.

3. Perform Synthesis. Using a virtual library database of all the involved building blocks, reactions, process and compound tracking data, the software facilitates the step-by-step synthesis of the chemical library using memories with matrices, such as a MICROKAN™ OR MICRO-TUBE™ microreactor. For each step specified in Plan Steps (above) the following four tasks are performed.

a. Pre-Procedure 13601. Any preliminary procedures that the user entered are displayed. Typically these will involve chemical "deprotection" of the reaction site associated with this step.

b. Sorting 13602. The "directed sorting" process for the current step is administered by the software. The user is prompted to place a memory with matrix on the scanning station 13605[see, e.g., FIG. 17], which is connected to a computer. The memory in the matrix, i.e., the tags, identification [ID] is read. The software does a database look up, seeking this unique ID. On the first step, the tag's ID is not found in the data base, so the software assigns it to the first compound in the library, which has not yet been associated with a tag. The user is instructed to place the device into the reaction vessel for the appropriate building block. From this point on, when this tag is read, the user is instructed to put the device into the reaction that will add the building block planned for this step for this specific compound.

c. Reactions 13603. Through directed sorting, all the devices in the library are now in reaction vessels. These is one vessel for each building block in the current step. The user is now prompted to perform the synthetic chemistry that will add each vessel's building block to the compounds it contains. The software displays any procedure information pertaining to reaction conditions that the user entered in Plan Steps.

d. Work Up 13604. The user is prompted to perform the "work up" [follow-up] task. Any work-up procedures the user entered in Plan Steps are displayed. Typically these involve rinsing and drying the reactor devices.

4. Archive. Archive refers to the process of transferring the completely synthesized compound from matrices-with-memories to a storage medium, such as a 96 well microplate or vials of any shape or size. This works as follows.

a. User chooses either vials or microplates [or other container]. These containers or vials may include memories into which identifying information can be entered, such as by scanning the first memory and then entering the scanned information into the memory in the matrix [container] into which the compounds are transferred. Using a template function appropriate for the containers to be used, a map 13701 can be generated and displayed by pressing button 13702 in button bar 13501, as shown in FIG. 137. Here, a 96 well template is used. Specific columns, designated 1–12, rows, designated A–H, or individual wells within the plate can be protected or pre-assigned to accommodate the need for standards and controls.

b. User places device on memory with matrix reader, a scanning station [see, e.g., FIG. 17].

c. User selects a placement location: a well in a plate or a specific vial number.

d. User affirms placement location and the database is updated to document this. Chemically, the user typically cleaves the compound from the solid phase support and deposits only the synthesized compound in the storage media, while salvaging the reusable tag device for reuse on a another library.

e. The software automatically selects the next available storage location. The user may override this, and make another selection.

While not required part of the process, additional functions, such as the following functions are provided.

1. Utility Functions.

a. Decode Tags. Using this function, at any time, the user can place a tag on the Scanning Station. If the tag has been assigned to a compound in the library, then information about that compound 13803 is displayed, as shown in FIG. 138. To select this utility, the user first selects button 13801 on the button bar, the selects folder 13802 for "Decode Tag".

b. Find Compound. The user can specify a combination of building blocks by selecting folder 13804 for "Find Compound." The software looks up this combination, and if it exists, it displays information about the compound and its tag.

c. Status. Spreadsheets showing all devices, their building block assignments and process status (which steps have been sorted) may be displayed by selecting folder 13805 for "Device Status".

2. Printing. The user can print out report describing:
   a. Building Blocks
   b. Steps planned.
   c. List of All Compounds.
3. On Line Help. The user can get context-sensitive assistance and a hypertext version of the System's User's Guide.

This system and software can be used in combination with a sorting system that provides the user with destinations for each matrix-with-memory during synthesis, screening or other protocols. FIGS. 67–69 set forth an exemplary embodiment of a manual sorting system.

Also provided is a wedge program [see, e.g., Appendix V] intended to be used to receive tags, particularly read-only tags, and perform in a manner similar to the SYNTHESIS MANAGER™ program in Appendix III (see, also Appendix VI). This program, referred to as TAGGER, is a "keyboard wedge" program. It receives data via a communications ports from a scanning station or other form reader and operates on the received data in the same manner as SYNTHESIS MANAGER. TAGGER sends the data to whatever program is active. The data appears as keystrokes to the receiving program. The receiving program cannot distinguish between human-generated keystrokes and the synthesized "keystrokes", thereby providing a "wedge" function. For example, a bioassay program could be the active program. The user will select a field in the program into which an ID code, for example for a microplate, can be typed. Instead of typing in the information, an tag is scanned. Tagger sends this information as keystrokes to the program. Thus, the ID of the plate is deftly scanned right into the bioassay program. TAGGER also provides a find function. The user specifies a tag ID that is sought and scans the tags. When the tag with the sought for ID is scanned, TAGGER generates a visual and audible annunciation.

C. Automated system-Sorter (1) A first embodiment

Figure 70:
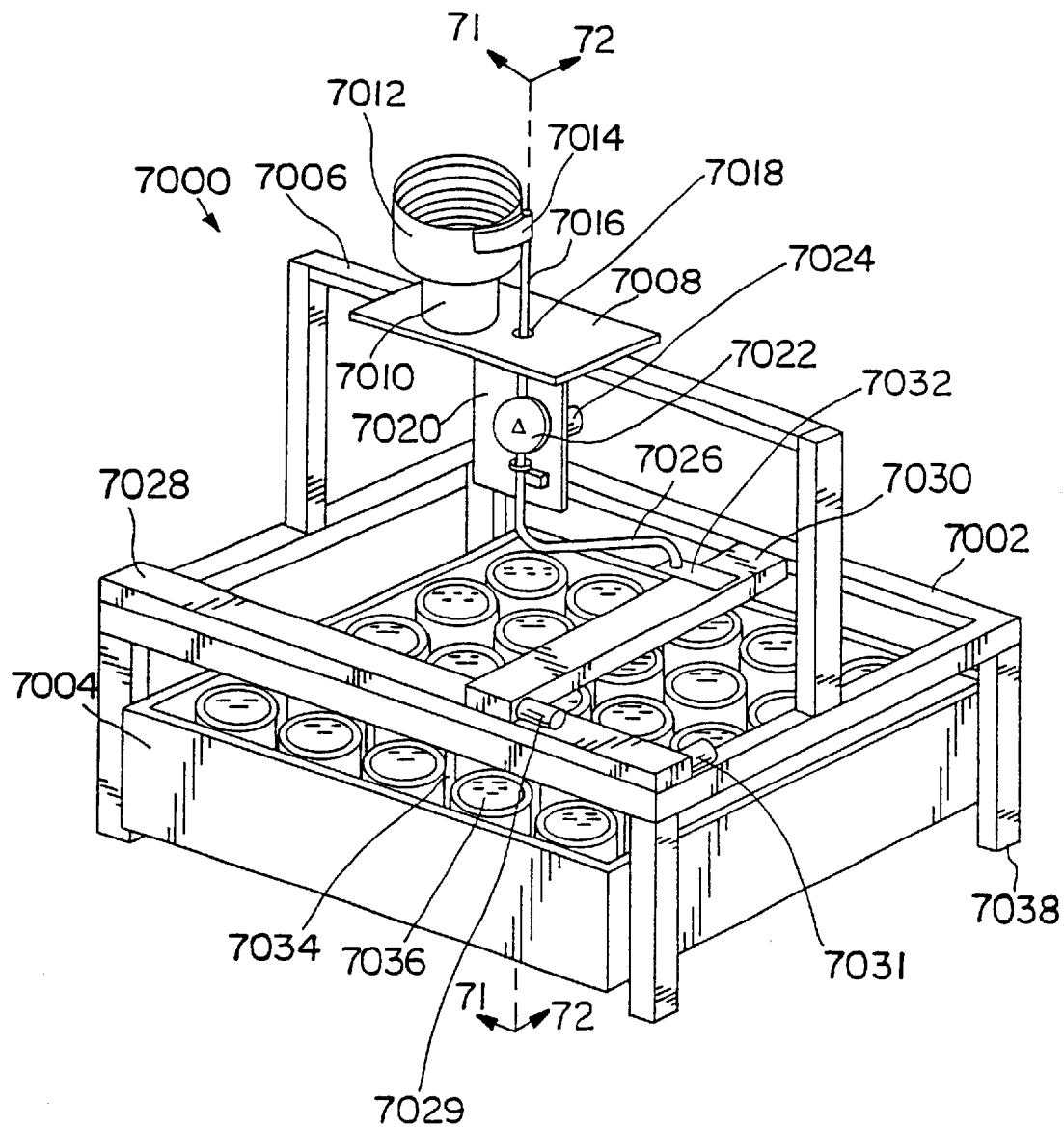
FIG. 70 is a perspective view of an automated sorting device showing the vibratory feeder, turnstile, positioning means, and a drawer holding a number of containers.

Referring first to FIG. 70, one exemplary automated sorting device is shown and generally designated 7000. Automated sorting device 7000 includes a frame 7002 that is supported by legs 7038 to provide an area for a drawer 7004 to slide in and out from beneath the frame 7002. Drawer 7004 is shown having a number of containers 7034, in this case, beakers, which are distributed evenly within the drawer. The actual number and distribution of the containers will depend on the sizes of the containers and the drawer and, thus, may vary from the arrangement illustrated. Depending upon the nature of the container used, appropriate supporting means, such as a rack or tray, will be required if the container is not free-standing and/or is likely to shift when the drawer is moved.

Extending upwards from the frame 7002 is an upper frame 7006 that attaches to two opposite sides of the frame 7002 to span the width of the frame. Attached to upper frame 7006 is supporting table 7008, which supports vibratory feeder 7010. Vibratory feeder 7010 is equipped with a sorting bowl 7012 that has a spiral ramp on its inside surface, which is described below with reference to FIG. 71. Vibratory feeders are well known in the art and are commercially available from manufacturers including Automation Devices, Inc., and Hoppmann Corporation of Chantilly, Va. In the present application, feeder 7010 is selected to minimize the vibration experienced by the matrix-with-memory devices that will pass through the sorter. The preferred feeder, from Automation Devices, moves the parts within the bowl 7012 using a sawtooth-type oscillation which gradually lifts and advances the devices within the feeder, thus minimizing exposure of the matrix-with-memory devices to extreme vibrations.

Figure 71:
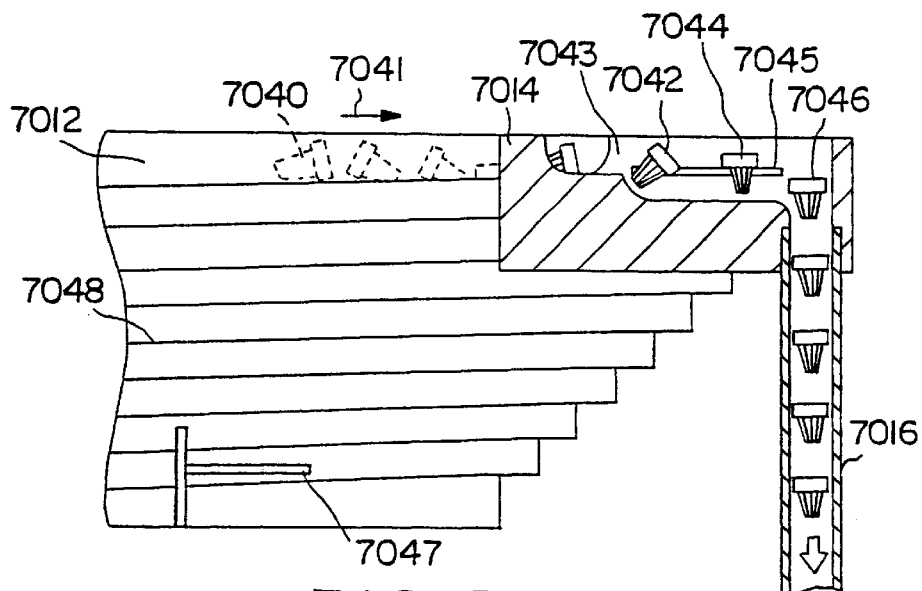
FIG. 71 is a cross-sectional view of the vibratory feeder taken along line 71—71 of FIG. 70 showing the circular ramp and delivery bracket, with devices in transit to the supply tube.

Delivery from vibratory feeder 7010 to supply tube 7016 is achieved via delivery bracket 7014. Referring to FIG. 71, delivery bracket 7016 is shown in detail using a cross-section of a portion of vibratory feeder 7010. The inner surface of bowl 7012 is formed as a spiral ramp 7048. When bowl 7012 is oscillated, devices 7040 "climb" up the ramp 7048, eventually reaching bracket 7014. At this point, as the devices 7040 proceed in direction 7041, they are not oriented any particular direction. Bracket 7014, which has a width just slightly larger that the diameter of the upper portion of the memory devices is formed with a chute 7043 that provides enough room for the device to orient itself so that the larger, upper portion of the matrix-with-memory device 7040 is facing upwards. Orientation is achieved as the device 7040 advances into the bracket 7014, so that its upper portion strikes ridge 7045. Note that there are preferably two ridges 7045, one on each side of chute 7043. Ridge 7045 extends inwardly to decrease the inside width of bracket 7014, thus preventing the device 7040 from moving further down into the chute 7043 if it is not properly oriented. Now looking at device 7042, which has partially progressed into chute 7043, it begins to rotate counterclockwise so that its upper portion is in contact with the upper edge of ridge 7045, and gravity pulls its lower end downward. As the device continues to advance, looking now at device 7044, it is oriented vertically, with the larger portion facing upwards. As the device continues to advance to the end of bracket 7014, device 7046 passes the end of ridge 7045 and falls downwards into supply tube 7016.

In addition to the sawtooth vibration of the bowl 7012, an arm 7047 is located at the center of the bowl to prevent devices from sinking to the center of the bowl so that they remain within the bowl. The positioning of arm 7047 within bowl 7012 is not critical as long as the arm extends through the center to prevent a device from achieving equilibrium within the bowl 7012.

Supply tube 7016 is a hollow tube having approximately a one half inch internal diameter. Tube 7016 may be formed from polyvinyl chloride (PVC), or a variety of other plastics or polymers, such as Tygon™, or may be metal or metal-coated tubing. In some cases, a metallic material could assist in protecting the memory devices against stray electromagnetic radiation. Supply tube 7016 is preferably at least partially clear, which may include metal tubing with a clear window, to permit visual inspection of the tube and observation of the flow of devices through it without requiring disassembly.

Figure 72:
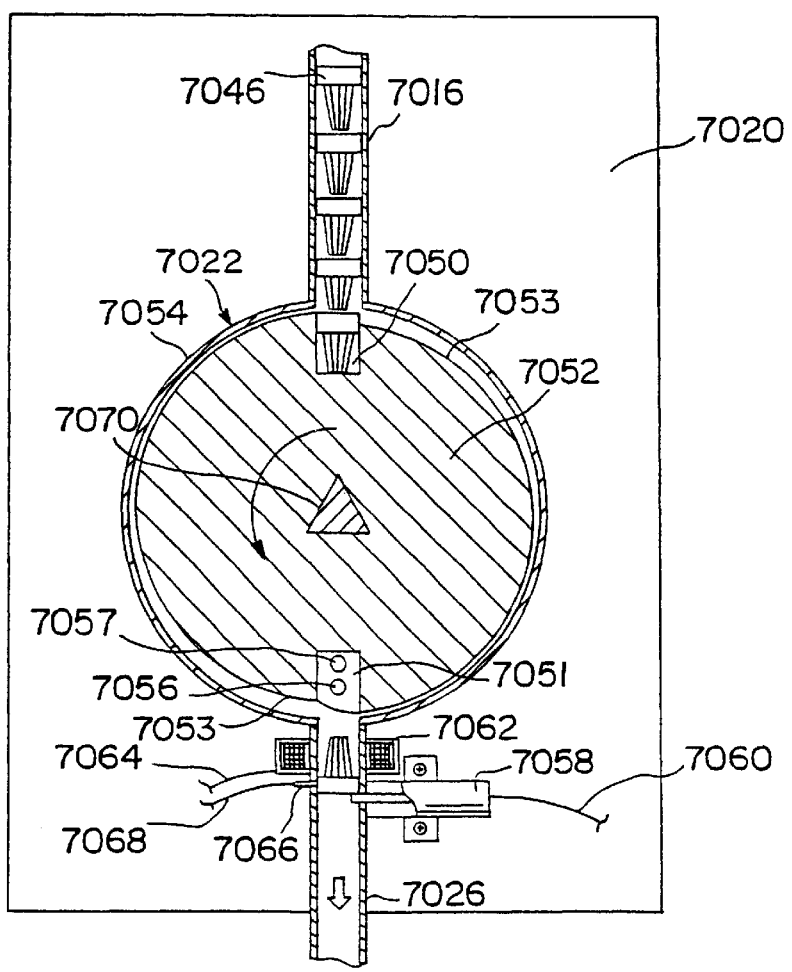
FIG. 72 is a cross-sectional view of the turnstile taken along line 72—72 of FIG. 70 showing the rotating hub, optical sensors, stopping solenoid, and antenna coil.

Referring again to FIG. 70, supply tube 7016 passes through an opening 7018 formed in supporting table 7008. Mounted on upper frame 7006 and extending downward from supporting table 7016, is mounting plate 7020. Mounting plate 7020 includes mounting means, such as a plurality of mounting holes (not shown) for receiving screws or bolts (not shown), for attachment of the turnstile 7022, solenoid 7058, and antenna 7062. FIG. 72 provides a more detailed view of this assembly.

As shown in FIG. 72, supply tube 7016, with a number of devices 7046 stacked within it, terminates at turnstile 7020.

This cross-sectional view shows that the turnstile 7020 includes a hub 7052 and a housing 7054. The hub is formed with a pair of slots 7050, 7051 that are sized to receive the sorted memory with matrix device. In the present case, the hub is formed with a pair of slots sized to receive the MICROKAN matrix-with-memory device. The hub is formed with a triangular hole for positioning over the shaft 7070 of motor 7024 (shown in FIG. 70). Such a configuration allows the hub to be changed easily in order to install a hub having either more slots, or a different size slot, or a combination of a different quantity of either larger or smaller sized slots. Thus, by replacing the turnstile hub 7052, a device of virtually any size could be sorted.

The hub 7052 is substantially circular shaped, except for the slight arcuate portions 7053 adjacent to each slot. This arcuate portion 7053 is shaped to minimize the likelihood of damaging the device as the hub is turned. More specifically, as the hub receives one device and then begins to turn, it would be possible for the next device to become caught in the same slot. As a result, the slot is followed with an arc 7053 such that there will not be any trailing edge of the slot to catch the device. As the hub continues to rotate, the device will be pushed upwards back into the supply tube slightly until the next slot is in sufficiently position under the supply tube 7016 to catch to the device.

At that time, the raised device falls into the slot 7050 in the hub.

In order to determine whether the device is positioned in the slot, or whether the slot is empty, the hub 7052 is formed with at least one optical detector hole 7056, 7057 in each slot. As shown in FIG. 72, the hole 7056 is adjacent to a device such that the optical detector could sense whether there is a device within the slot. This information is particularly useful in order to optimize the sorting process. More specifically, if there are no devices in the supply tube 7016, then the sensors located near the higher portion of the hub would detect that there was no device in the slot 7050. Once a device falls down through the supply hose and lands within the slot, the sensor will sense the presence of a device and the hub is then allowed to rotate. Similarly, when it is time for the hub to drop a device, the sensors located towards the lower portion of the hub verify that the device did indeed fall prior to rotational movement of the hub 7052.

Once a device falls downwards from the turnstile and into the positioning tube 7026, the device is stopped by solenoid 7058 that is positioned such that the plunger of the solenoid extends into the positioning tube 7026. Antenna 7062 is positioned around the positioning tube 7026 such that the device is within the electromagnetic field generated by the antenna. In this particular embodiment, the antenna 7062 is made from approximately 75 turns of 28 gauge epoxy coated wire on a bobbin having an internal diameter of one half inch, yielding an antenna having about 87 micro Henries of inductance at a resonant frequency of approximately 125 kilohertz. Antenna 7062 is attached via wire 7064 to a read/write station as discussed above in this application. As the device is being held, the matrix-with-memory device is accessed using the antenna 7062.

While the device is being held in place by the solenoid, an additional optical sensor senses that the device is present. More specifically, optical sensor 7066, such as part number E32D32, from Omron, and electrically attached to a controller module E3XNM11, is positioned to sense the presence of a device when the solenoid 7058 is engaged. Solenoid 7058 is a linear solenoid, part number F13038L.9224, and is available from Shindengen America, Inc., located at 2985 E. Hillcrest Drive, Westlake Village, Calif. 91362. This solenoid is activated by 24 volts used to draw the plunger into the solenoid. Because the solenoid is at rest with the plunger extended, there is very little power required to control the solenoid. More specifically, because the only time the solenoid requires power is when, momentarily, the plunger must be retracted to allow passage of a device. Referring to FIG. 70, the positioning tube 7026 extends downwards and is attached to a clamping plate 7032 that in turn is attached to the frame by a pair of arms configured in an X and Y axis. More specifically, arm 7028 attaches to the frame 7002 to provide linear movement of a platform in the X axis direction. Attached to the arm 7028 is arm 7030, also capable of providing linear movement in a Y direction. As can be appreciated from this Figure, any location within the frame 7002 may be reached using an X and Y coordinate system. To facilitate movement of the various arms, motors 7029 and 7030 can be activated either independently or together to get X, Y or combined X-Y movement within the frame 7002. Suitable motors are available. For example, in the exemplary embodiment, the motors are available from Mycom as part number PS4913M-02A, which is a high resolution size 34 frame size, triple stack stepper motor and is used on the X axis, and part number Y PS499M-02, which is a two stack high resolution stepper motor is used on the Y axis. The motors are driven by a SD-45-230 motor driver also available from Mycom. Using the X-Y translation, any location within the frame can be accessed quickly and repeatably, by designating a particular X and Y coordinate.

Motors 7029 and 7031 are stepper motors capable of precisely moving the plate 7030 within the frame to a coordinate with a tolerance of less than 0.10 inches. As a result, as discussed above, a variety of container sizes could be used within the drawer 7004. One way to facilitate the adaptability of the automated sorting device to a variety of containers is to create a container and drawer size library that will effectively map the coordinates of each container within the drawer. Such a mapping would expedite the loading of a different size container because the device would effectively know the location of each container without having to calculate it, or have the user of the system program the location. In any event, having a coordinate mapping scheme increases the efficiency and throughput of the sorting device.

In the exemplary embodiment, the arms 7028 and 7030 are part numbers GL15B-500L for the Y axis, and GL20B-1000L for the X-axis [available from THK America, Inc., 200 E. Commerce Drive, Schaumberg, Ill., 60173]. As the frame is constructed, it is wider than deep, resulting in a rectangular area for locating containers. It is understood that given a different shaped frame, one of skill in the are could select suitable arms to facilitate access to every portion of the useful frame area.

Once the matrix-with-memory device is accessed and identified, the X and Y destination coordinates are determined either from calculation or from accessing a look-up table or database, and the solenoid is activated to retract from the positioning tube, thereby releasing the device to fall downwards through the positioning tube and into the appropriate container.

As noted above, in order for the automated sorting device to automatically determine the proper container or location in X-Y coordinates to position the arms and drop the device, the library of container locations within a given drawer may be created and entered into the computer's memory. Alternatively, a standard configuration for a particular automated sorting device may be adopted. A memory device, such as an RF tag or bar code, may be placed on the drawer and programmed with information regarding the drawer and/or its contents, so a record can be created for the drawer. For example, for a five by five array of beakers in the drawer, the associated memory device can be encoded with positioning information for each beaker, or the memory device could include a precoded identification number that would identify the drawer associated with a particular beaker configuration. With the ability to individually identify each drawer, numerous different testing configurations could be set up in multiple drawers to permit a large number of tests to be performed in rapid succession. With a positional accuracy of within 0.10 inches, the X-Y translator enables the loading and recording of information for a drawer containing a very high density of containers.

In addition to the various sensors and solenoids discussed above in connection with FIGS. 70–72, there are also numerous interlock and safety devices that are not depicted and that are contemplated. For example, there is at least one emergency disable switch that will instantaneously halt the operation of the system. This can be activated either by entering a command via the host computer, or by a safety switch located on the automated sorting device frame. Such switches should be readily accessible while the system is in operation.

Interlock switches may also be used to ensure the proper sequence of events occur prior to, or during, a sorting procedure. For example, the drawer can be equipped with a microswitch or other position-sensitive switch to prevent operation of the sorter if the drawer is not properly seated within the frame. Such an interlock avoids any offsets or inaccuracies that might occur if the drawer is offset from its correct position.

Figure 73:
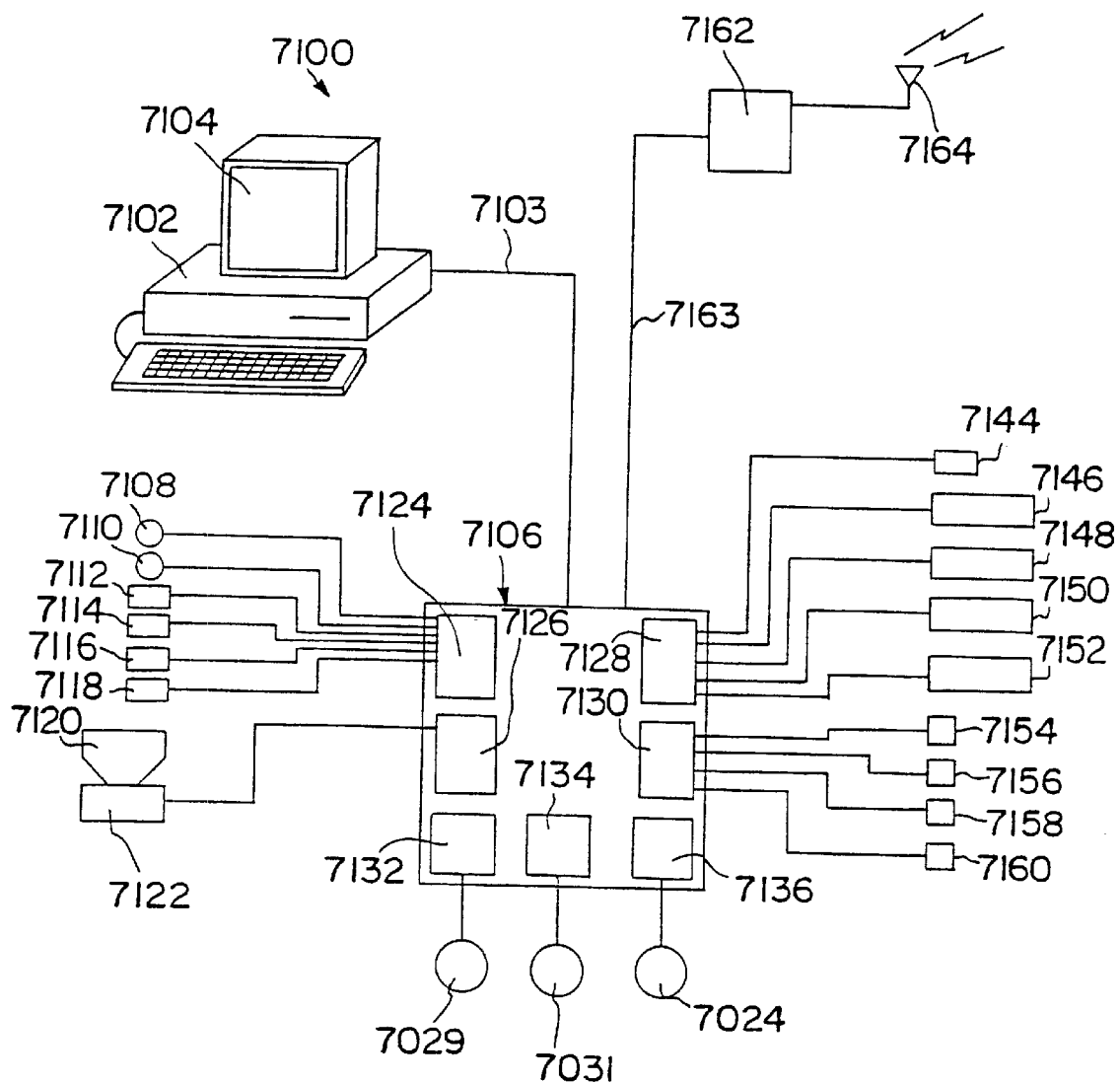
FIG. 73 is a block diagram of an automated sorting device showing the host computer, Programmable Logic Controller (PLC), and other electronic sensors and devices used in the sorting device.

Referring now to FIG. 73, a block diagram of the manual sorting device 7000 is shown and generally designated 7100. A host computer 7102 contains the database and other controlling software [see, e.g., Appendix IV]. This software controls all aspects of the operation of the automated sorting device, with the exception of embedded software that may be housed within the PLC 7106. The host computer attaches to the PLC with a serial communication link 7103 that allows communication and data exchange between the computer and PLC. In order for the user of the automated sorting device to properly operate the device, a display 7104 is provided that instructs the user in the proper placement of the various containers within the drawer, or the particular batch of devices to place in the vibratory feeder 7012, or other helpful or troubleshooting information to assist the user in performance of the sorting process. Alternatively, as noted above, placement may be preprogrammed and each drawer prepared prior to use.

The serial link 7103 links the computer to the PLC. The PLC contains a variety of digital and analog motion control communication modules, such as part numbers ID216 and OD 218 supplied by Omron, Inc., connected to a controller module (CPU), such as part number C200HS also from Omron. Beginning with the digital input sensors, an digital input module 7124 is used to interconnect the panic switches 7108, 7110 to the PLC and computer. Additionally, a number of limit switches 7112,7114, 7116, and 7118 are positioned around the automated sorter and electrically connected to the PLC through the digital input module 7124. Analog output module 7126 is used to control the vibratory feeder in order to turn the feeder on and off, depending on the number of devices used in a particular sorting task. This analog output module accepts the information from the PLC and computer, and with either a relay or other switching device, turns the feeder on or off, depending on the current need for more devices.

The motor 7029 for the X arm 7028, the motor 7031 for the Y arm 7030, and the motor 7024 for the turnstile 7022 are controlled by motor controllers 7132, 7134, and 7136. These motor controllers activate the stepper motors in very small increments, and at a variety of speeds. As a result, the positioning ability of the X and Y arms is sufficient for the arms to be positioned from one corner of the drawer to the opposite corner of the drawer within one second. This provides for a quick, accurate, and error-free placement and sorting of the devices with the automated sorting device.

To identify the matrix-with-memory device on the device, the read/write station 7162 is attached to the PLC with a serial link 7163. This serial link allows the identification information received by antenna 7164 to be communicated to the PLC and back to the host computer. As a result of this link, the read/write station will be activated at intervals when there is a device in place near the antenna, and will be de-activated when not in use.

Numerous optical sensors can be attached to analog input module 7130 for monitoring of the sorter operation. By polling module 7130, the PLC can verify the presence of devices at various stages within the automated sorting device. When the sensors indicate that a step has been missed, the PLC can repeat the missed step, thus providing for the continued operation of the sorter without human intervention. To provide an example, optical sensors could be placed in the turnstile to confirm the presence of the devices within the turnstile prior to its rotation. An optical sensor can also be installed close to the antenna in the positioning tube to trigger activation of the read/write station. Additional optical sensors could be used at various locations throughout the sorter for virtually error-free sorting. Implementation of such additional sensors is within the level of skill in the art.

In addition to the sensor discussed above, a number of other sensors could be used. For example, a Hall-effect sensor 7144 can be used to sense the presence of a device or container. Additionally, limit switches 7146, 7148. 7150, and 7152 can be used to effectively monitor the accuracy of the X and Y arms. For example, upon start-up of the sorting device, the X and Y arms can be operated to their limits, tripping the limit switches at either end of the travel so that the full range of travel of the arms can be verified. In this way, the sorting device will be continuously and reliably capable of reaching the extents of the frame and drawer.

The software for controlling the operation of this sorting device includes a high-level language which implements "ladder-logic" [see, Appendix IV, especially pages 1, 2 and 3 of that appendix]. The ladder logic is a Boolean representation of a state machine which allows the programmer to graphically implement a variety of control parameters. The development tool "Syswin" is available from Omron and is used to implement the particular logic and control parameters necessary to control the sorting device using the PLC. These control parameters are defined and ordered on pages 4 and 5 of the Appendix and represent hardware addresses in the PLC, or other memory locations. The sorting process is controlled by the statements contained within and defined by the ladder logic. This process, as discussed below, controls and monitors the various electronic and mechanical parts of the sorting device.

Figure 74A:
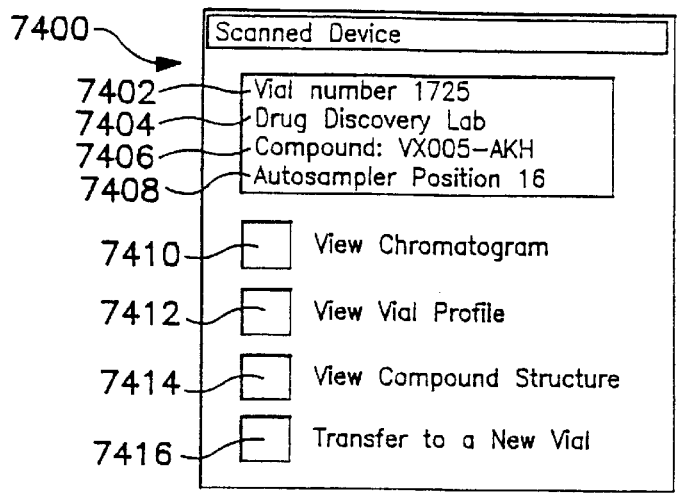
FIG. 74(*a–c*) depicts exemplary images displayed on the host computer that assist the user in selecting the various locations, containers, or devices, and viewing the contents thereof.

Referring now to FIG. 74*a*, a typical display is shown and generally designated 7400. This display is a computer generated display and is shown in the monitor 7104 of the host computer 7102 as discussed above with reference to FIG. 73. As shown, this display has several fields which are visible by the user. Generally, this format of display may be used in conjunction with any of the sorting devices or other identification devices discussed in this application, and will be discussed here only as an example. This type of display could also contain a variety of other fields which contain information about the date of last access, the source of the contents of the vessel, or other pertinent information. FIG. 74a shows the vial identification number 7402, the particular location 7404 of the scanned device, shown here as the "Drug Discovery Lab", the contents 7406 of the scanned device, shown here as Compound VX005-AKH (which can either be a compound name, identification code, or other identifying information), and the position within the autosampler 7408, shown here as position 16. Position 16 could represent a position with a drawer, or any other location within the laboratory environment.

In addition to the identification information shown in portions 7402, 7404, 7406, and 7408, additional options can be provided to the user. More specifically, options 7410 allows the user to view the chromatogram of the contents of the scanned device, option 7412 allow the user to view the vial profile, option 7414 allows the user to view the compound structure, and options 7416 allows the user the option of transferring the contents of the vial to a new vial. Thus, this display would be most often used when the device scanned is an HPLC type sample vial.

Figure 74B:
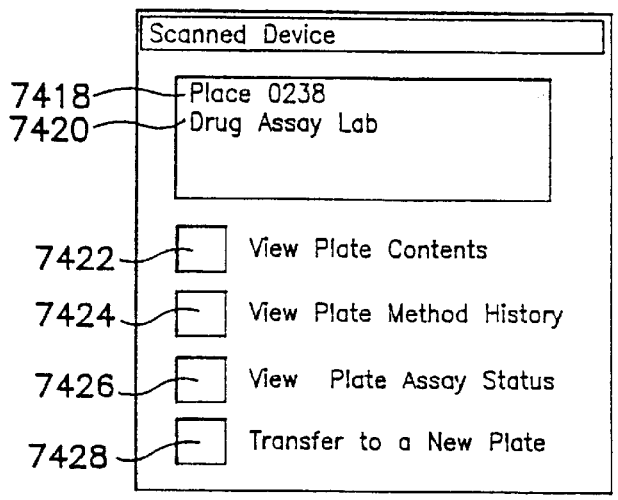

FIG. 74b shows a similar display having an identification code 7418 which indicates that this is a plate number 0238. Such identification code would most likely be used in conjunction with a Microplate, but could be used with other, less widely known plate configurations. The location field 7420 of the display shows that the microplate is located in the Drug Assay Lab. As with the display discussed above, this display also has different options that are consistent with the type of device. Specifically, the options include the ability to view the plate contents 7422, view the plate method history 7424, view the plate assay status 7426, and transfer the contents to a new plate 7428.

Figure 74C:
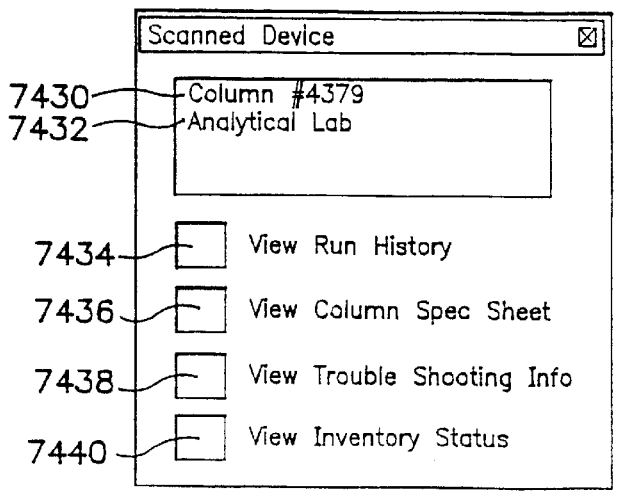

FIG. 74c shows yet another similar display most useful for identification and tracking of a GC Column. This display has an identification code 7430 showing the Column #4379, with a location code 7432 identifying the Analytical Lab. Like the other displays, the options on this display allow the user to view the run history 7434, view the column specification sheet 7436, view trouble shooting information pertinent to that column 7438, and to view the inventory status 7440.

Operation of the automated sorting device begins with the loading of the drawer 7004 with a collection of containers. As described above, virtually any number or size of container could be placed in the drawer, or the drawer itself could be the containers. For example, the drawer could be formed with a number of wells, or other fluid-tight containers so that the drawers could be used instead of having to place a number of containers within the drawer. Once the containers or wells are positioned within the drawer, the drawer slides under the X and Y arms within the frame 7002. Once the drawer has been placed in position with the containers, the user places a quantity of devices in the vibratory feeder bowl 7012. Once the devices are in place, the host computer is engaged to control the operation and sorting of the devices to different locations within the drawer.

As the devices are fed from the vibratory bowl 7012 to the supply tube 7016, they fall into position above the turnstile 7022. As the turnstile rotates, a single component is passed through the turnstile and downward into the positioning tube 7026. As the device drops, the piston from the solenoid 7058 stops its fall and holds the device in position until the antenna is activated and the device's matrix-with-memory device is accessed. Once accessed and identified, the matrix-with-memory device can be written to or can be logged into the computer data base which is maintained within the host computer 7102. After identification and writing, if necessary, the X arm 7028 and Y arm 7030 are moved into position where the device shall be placed, preferably over a container within the drawer identified by the host computer The solenoid 7058 is then activated to drop the device through the positioning tube 7026 and into the appropriate container.

When using devices having a lighter weight, it may be desirable to assist the passage through the various tubes. To affect such a passage, compressed air can be used to assist in the movement of the device. This is particularly useful when handling and sorting devices having low weight to size ratio. The addition of compressed air to a laboratory environment is sometimes not desirable. In those instances, it is possible to utilize a conveyor belt, or other means for advancing the devices, into the various containers. A person skilled in the art would be able to identify and implement alternatives to the supply tube and positioning tube described above. Once the device has been placed within the proper container, the process can be repeated. The vibratory bowl has a capacity for holding several hundred devices, allowing the automated sorting device to be used to sort hundreds of devices into the various containers. In addition, the vibratory bowl can be equipped with a hopper which would effectively increase the quantity of devices into thousands that can be sorted without human intervention.

The drawer discussed above could be replaced with a conveyor belt having a replaceable number of containers that would be passed under the X and Y positioning arms. In this embodiment, the containers could be either manually or automatically placed on the conveyor belt which, when passed under the frame 7002, would be available for placement of devices by the automated sorting device.

In summary, the process of automated sorting can be expanded to control not only the position of a device within a container, but can also be used to monitor and control the movement of various devices between containers, as well as other machines or devices typically found in a laboratory environment. Such a sorting and inventory maintenance system could include a number of RF decoding stations, or read/write stations, a number of auto samplers, fraction collectors, plate readers, reagent carriers, microplates, collection vials, auto sampler carousels, HPLC columns, GC columns, and CE columns. It will be apparent that virtually any device, machine, reagent source, or other device can be identified, tagged with a matrix-with-memory device, and used in an automated sorting system. Such universal tagging of all relevant devices and machines within a laboratory can provide a nearly fully automated laboratory, removing much, if not all, human interaction required for testing and synthesis operations.

(2) A second embodiment

Figure 76:
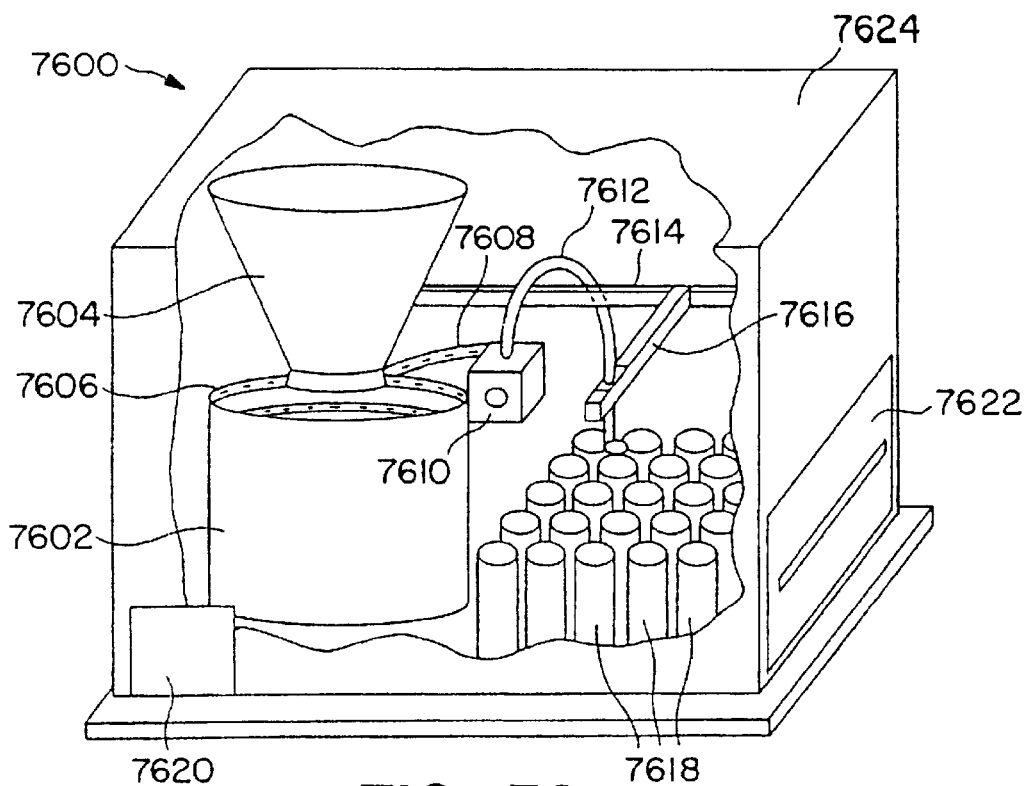
FIG. 76 is a perspective view of an alternative embodiment of an automated sorting device, with portions cut away for clarity.

Referring initially to FIG. 76, an alternative embodiment of an automated sorting device is shown and generally designated 7600. Sorting device 7600 includes a vibratory feeder 7602 which has a hopper 7604 for holding a large quantity of microreactors. Typically, the hopper can hold in excess of 10,000 microreactors, allowing the automated operation of the sorting device for extended period of time. The microreactors are advanced through the feeder 7602 to the supply tube 7608 and to the singulator 7610. The singulator 7610 isolates a single microreactor from the stream of microreactors 7606 for identification of the microreactor which is positioned within delivery tube 7612. Once the microreactor is within the delivery tube 7612, it is identified by control electronics 7620 and the x-axis robotic arm 7614 and the y-axis robotic arm are manipulated such that the delivery tube is positioned immediately above the appropriate container 7618. Container 7618 is typically a synthesis vessel, or cleavage well, or any other vessel described herein. In order to facilitate the positioning and removal of the containers 7618, a drawer 7622 is provided. Also, cover 7624 may be used to prevent the introduction of contaminates into the containers, as well as to protect the sorting device 7600 from damage. Additionally, the cover 7624 may be formed with an opening on its top surface (not shown) such that microreactors may be added to the hopper 7604 without the need for removing the cover.

Figure 77:
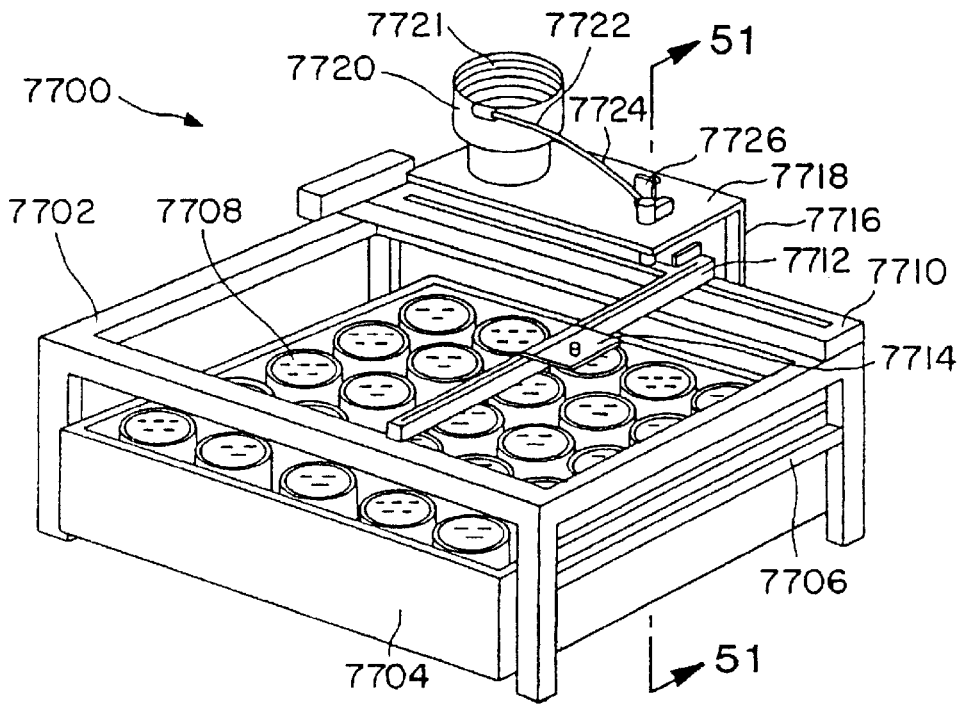
FIG. 77 is a perspective view of yet another alternative embodiment of an automated sorting device.

Referring now to FIG. 77, yet another alternative embodiment of an automated sorting device is provided and generally designated 7700. Sorting device 7700 includes a frame 7702 which is equipped with a drawer 7704 that is slidable outwards from the frame on slides 7706. The drawer 7704 is sized to receive a number of containers 7708 which are typically filled with a solution. In general, the number of containers 7708 within drawer 7704 may be varied, and may range from one or two containers, to a 96 well titre plate, 384 well titre plate, or any other container or array of containers described herein.

Frame 7702 is equipped with an x-axis positioning slide 7710, and a y-axis positioning slide 7712. Specifically, the x-axis slide 7710 is attached directly to the surface of the frame 7702, and the y-axis slide 7712 is attached directly to the surface of the x-axis slide 7710. Thus, by combining the movement of both the x-axis slide 7710 and the y-axis slide 7712, any location within the range of the x and y axes may be accessed with the dynamic dropper 7714. A typical axis slide is a member of the FS series of timing belt actuators available from Intelligent Actuator, Inc. of 3302 South New Hope Rd. #200F., Gastonia, N.C. 28056. This family of actuators is capable of linear positioning within 0.003 inches, providing accurate access to any location within the drawer 7704. This is particularly important when sorting microreactors to containers which have a relatively high density, as well as a small opening or neck.

Frame 7716 extends upwards from the frame 7702 and supports a platform 7718. Platform 7718 is sized to accommodate placement of a vibratory feeder 7720 which receives and advances microreactors 7721, and a singulation device 7726. The microreactors 7721 are advanced from the vibratory feeder 7720 along orientator 7722 to delivery slide 7724 which holds the microreactors 7721 until the singulator 7726 identifies and advances the microreactors individually for dropping into the dynamic dropper 7714. Once within the dynamic dropper 7714, the dynamic dropper is moved along the x-axis 7710 and the y-axis 7712 such that the dynamic dropper and corresponding microreactor are positioned above the container 7708. Once in position, the dynamic dropper 714 drops the microreactor into the container, and returns to the initialization location immediately under the platform 7718 and singulation device 7726.

Figure 78:
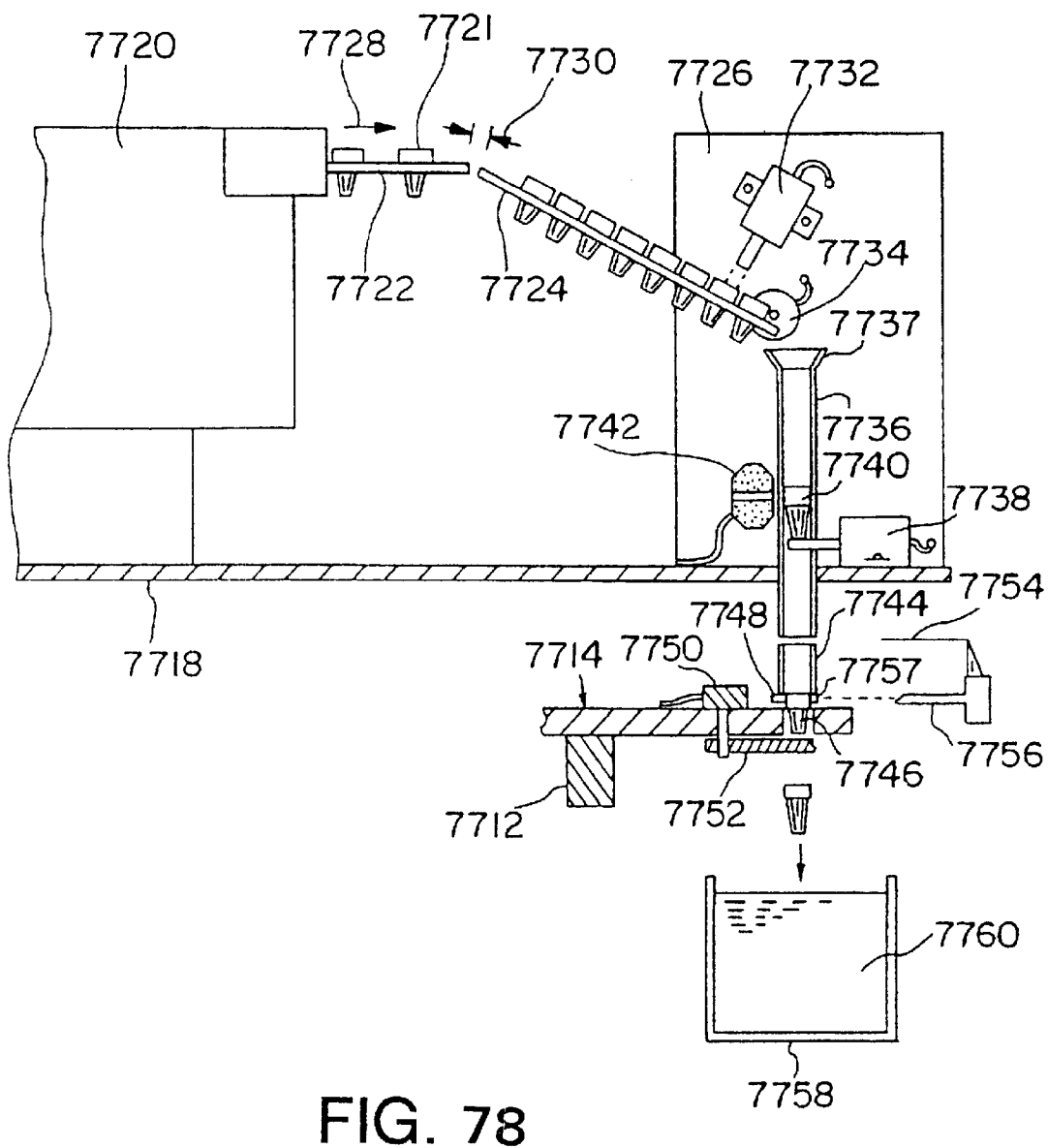
FIG. 78 is a cross-sectional view of the automated sorting device of FIG. 77 taken along line 78—78.

Referring to FIG. 78, the automated sorting device 7700 is shown in with portions in cross-section for clarity. As shown, the vibratory feeder 7720 is mounted on platform 7718 with the orientator 7722 extending from the feeder 7720. Microreactors are advanced in direction 7728 such that when they reach the orientator 7722, the microreactors are properly oriented. This orientation is accomplished with the aid of gravity acting on the microreactor. Specifically, orientator 7722 includes two parallel supports which are spaced apart a distance slightly larger than the diameter of the lower portion of the microreactor, and less than the diameter of the upper portion of the microreactor. As a result, as the microreactor is advanced in direction 7728, gravity pulls the lower portion of the microreactor downwards between the two parallel supports, with the upper portion of the microreactor resting on the supports. In this manner, the microreactor will be oriented upright, regardless of the orientation with which the microreactor is advanced from the vibratory feeder 7720.

Delivery slide 7724 is positioned adjacent to the end of the orientator 7722 and is also formed from a pair or parallel supports. The delivery slide 7724 and the orientator 7722 are separated by a gap 7730. Gap 7730 is important as the gap prevents the propagation of the vibrations generated form the vibratory feeder 7720 into the remainder of the automated sorting device 7700. Typically, gap 7730 is on the order of 2 to 3 millimeters, but any gap distance would suffice so long as the orientator 7722 and the delivery slide 7724 do not strike each other.

Deliver slide 7724 is at an incline from the orientator 7722. The inclined configuration eliminates the need for a supply tube which was shown in FIGS. 71 and 72. Elimination of the supply tube allows for the minimization of the height of the system 7700, which given the density of lab equipment and limited space within most laboratories, is critically important. As the microreactors are advancing downwards along delivery slide 7724, a pair of singulation solenoids 7732 and 7734 prevent the continued downward movement of the microreactors. More specifically, singulation solenoid 7732 is a linearly actuated solenoid which is positioned on mounting plate 7726 such that the solenoid, when activated, strikes the upper surface of a microreactor. Singulation solenoid 7734 is positioned to prevent the advancement of a microreactor from the end of the delivery slide 7724. In operation of the singulator, a number of microreactors 7721 are positioned on the delivery slide 7724. Singulation solenoid 7734 is activated to prevent the lower-most microreactor from falling from the end of the delivery slide. When it is time to advance a single microreactor, the singulation solenoid 7732 is activated to prevent the microreactor adjacent to the lower-most reactor from moving, and the singulation solenoid 7734 is deactivated allowing the lower-most microreactor to slide down delivery slide 7724 and dropped into tube 7736. Tube 7736 may be formed with a funnel portion 7737 to ensure the microreactor is properly positioned within the tube. Once the lower-most microreactor has been delivered, the singulation solenoid 7734 is again activated, and the singulation solenoid 7732 is de-activated allowing the remaining microreactors to slide down the delivery slide until striking the singulation solenoid 7734. This process may be repeated as necessary.

Once the microreactor has been singulated into the tube 7736, the microreactor is held in position by a stopping solenoid 7738. Stopping solenoid 7738 is positioned on platform 7718 to that when activated, the solenoid shaft extends into a hole in the tube 7736 to prevent the passage of the microreactor through the tube and into the dynamic dropper 7714. Alternatively, stopping solenoid 7738 may be a rotating solenoid which rotates a stopping door (not shown) into and out of the tube 7736. While the microreactor is being held in position by the solenoid 7738, antenna 7742 accesses the memory device within the microreactor to identify the memory device, as well as access any additional information related to the device, as described elsewhere herein. Antenna 7742 may be orientated in a variety of directions, with such orientation only slightly affecting the operation of the antenna. As shown, antenna 7742 is oriented perpendicularly to the tube 7736, such that the microreactor will lie within the electromagnet field generated by the antenna. Generally, the antenna may be positioned anywhere within the electromagnetic field of the antenna, as will be recognized by one skilled in the art. Although depicted in a perpendicular orientation, it is, however, preferable for it to be at an angle other than perpendicular to the tag. For example, antenna 7742 may be oriented at about a 45° angle with respect to the tag to ensure that the radiation pattern surrounding the microreactor is sufficiently powerful to excite the coil in the tag.

By positioning the antenna close to tube 7736, instead of around the tube as in FIG. 72, the same antenna may be used regardless of the tube size and material. This is particularly advantageous when changing the diameter of tube 7736 to accommodate microreactors having various sizes. By changing the diameter of the tube 7736, a variety of devices containing memory devices can be used.

Once the memory device within the microreactor has been identified, and the dynamic dropper is in its original position under the tube 7736, the microreactor is released from solenoid 7738 thereby dropping into the dynamic dropper 7714. Specifically, the microreactor drops from tube 7736 into the drop tube 7744 and retained within the drop tube by rotating door 7752 which is positioned to obstruct the passage of the microreactor through the drop tube 7744. Positioning of the rotating door is achieved by rotating solenoid 7750 which, when de-activated, holds the door to cover the exit to the drop tube 7744. When the solenoid 7750 is activated, the rotating door 7752 is rotated out of the path of the microreactor which in turn drops out of the drop tube 7744. A rotating door is particularly advantageous for this embodiment as it will accommodate microreactors having a variety of sizes, as well as other devices incorporating a memory device.

The dynamic dropper 7714 is equipped with at least one optical sensor 7748 which is positioned to provide a signal which indicates the presence of a microreactor within the drop tube 7744. This sensor 7748 provides feedback to the host computer, as shown and described in conjunction with FIG. 73. Once the optical sensor 7748 identifies the presence of the microreactor within the drop tube 7744, the x-axis 7710 and y-axis 7712 are controlled to position the dynamic dropper directly above the proper container 7758. Once in position, solenoid 7750 is activated to open door 7752, thereby allowing the microreactor 7746 to fall into container 7758 and solution 7760.

In an effort to improve the exposure of the contents of the microreactors to the solution within container 7758, the lid to the microreactor may be removed. Lid removal is particularly helpful in applications involving cleaving steps because the contents of the microreactor are more easily agitated when outside the microreactor. Such lid removal is accomplished by directing a microreactor within the drop tube 7744 to be struck against punch 7756. Punch 7756 is mounted on frame 7702 such that dynamic dropper 7714 may be positioned such that aperture 7757 in drop tube 7744 is aligned with punch 7756. Thus, by moving the dynamic dropper 7714 with the microreactor 7746 with the drop tube 7744 against the punch, the lid is ejected from the microreactor. Because the lid removal process can require that the microreactor strike the punch with considerable force, a lid 7754 is provided which prevents the upward ejection of the lid from the drop tube 7744. This prevents the hazard of having a large number of microreactor lids being ejected from the system 7700, and also prevents the cross-contamination between containers which could be caused by introducing the lid of one microreactor to a solution containing another microreactor.

The automated sorting device 7700 as shown in FIGS. 77 and 78 is representative of a preferred embodiment. System 7700 also includes a host computer, such as the host computer 7102 shown and described in conjunction with FIG. 73.

Operation of automated sorting device 7700 includes placing a number of microreactors 7721 into vibratory feeder 7720. Vibratory feeder 7720 advances microreactors which are then properly oriented by passing through orientator 7722, and advanced to delivery slide 7724. At the end of the delivery slide, the microreactors are singulated by selective activation of solenoids 7732 and 7734. A single microreactor 7740 is provided to tube 7736 and held in place by solenoid 7738 while the memory device within the microreactor is accessed using antenna 7742 and the host computer (not shown in this FIGURE). Once identified, the destination location for the microreactor is determined and the microreactor is released by solenoid 7738 to allow it to fall into the dynamic dropper 7714. Dynamic dropper 7714 has a drop tube 7744 which receives the dropped microreactor and holds it in place with solenoid 7750 and door 7752. Upon receiving the microreactor, the x-axis and y-axis are activated to first remove the lid from the microreactor by urging the dynamic dropper and microreactor against the punch 7756. Following lid removal, the host computer then re-positions the dynamic dropper immediately over the designated container 7758, and the door 7752 is moved using solenoid 7750 to allow the microreactor 7746 to drop into the container 7758. Once the microreactor has been successfully delivered to the appropriate container, the dynamic dropper is re-located underneath the tube 7736 to receive another microreactor for placement in another, or perhaps the same, container.

The automated sorting device shown in FIGS. 77 and 78 is significantly shorter than the sorting device of FIG. 70, permitting this embodiment of the automated sorter to be placed within an area having decreased vertical clearance. Additionally, because the path of the microreactor from the vibratory feeder to the placement within the container is significantly shorter in device 7700 than in device 7000, the microreactors may be sorted more rapidly. Device 7700 is capable of sorting over one thousand microreactors per hour, depending on the size of the drawer, since the longer the potential travel distance for the x-axis and y-axis, the more time it will take to reposition the dynamic dropper. The positioning actuators provided by Intelligent Actuator are capable of traversing approximately a five foot distance within one second. Thus, the positioning of the dynamic dropper within a drawer having dimensions of three feet square, would take less than one second, providing for a sorting rate of approximately thirty microreactors per minute, when taking into account the longest positioning and return paths.

In an effort to minimize the travel time for placement of the microreactors within the drawer, the initialization point for the dynamic dropper 7714 could be adjacent to the punch 7756. This would effectively limit the distance traveled to the location of the container only, eliminating the need to repeatedly travel to the punch location.

(3) A third embodiment

Figure 125:
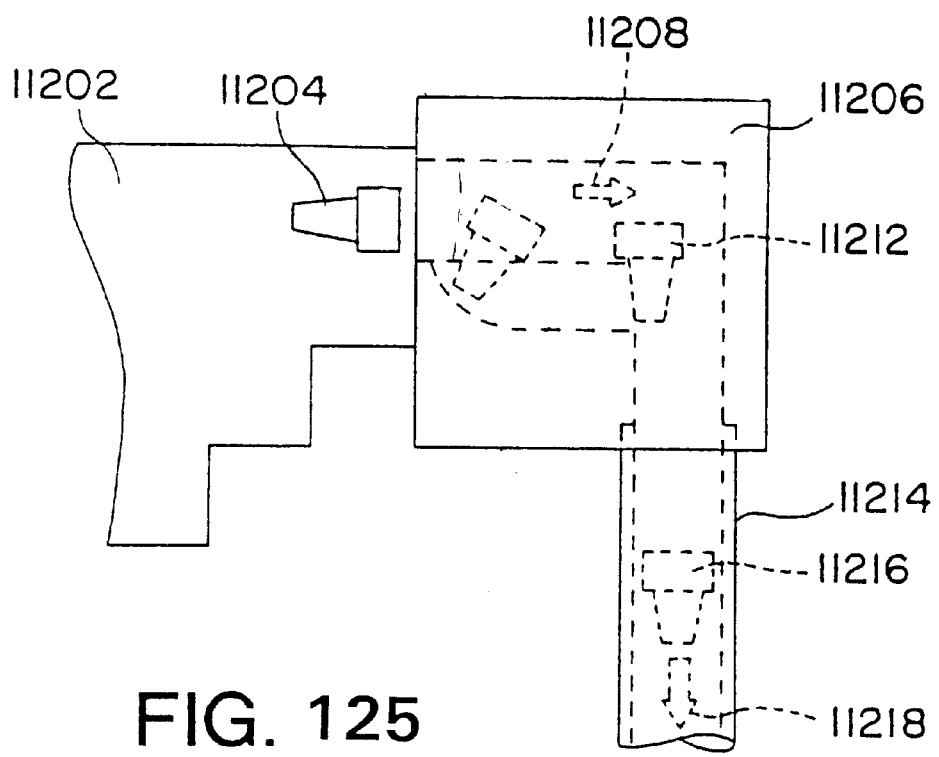
Figure 126:
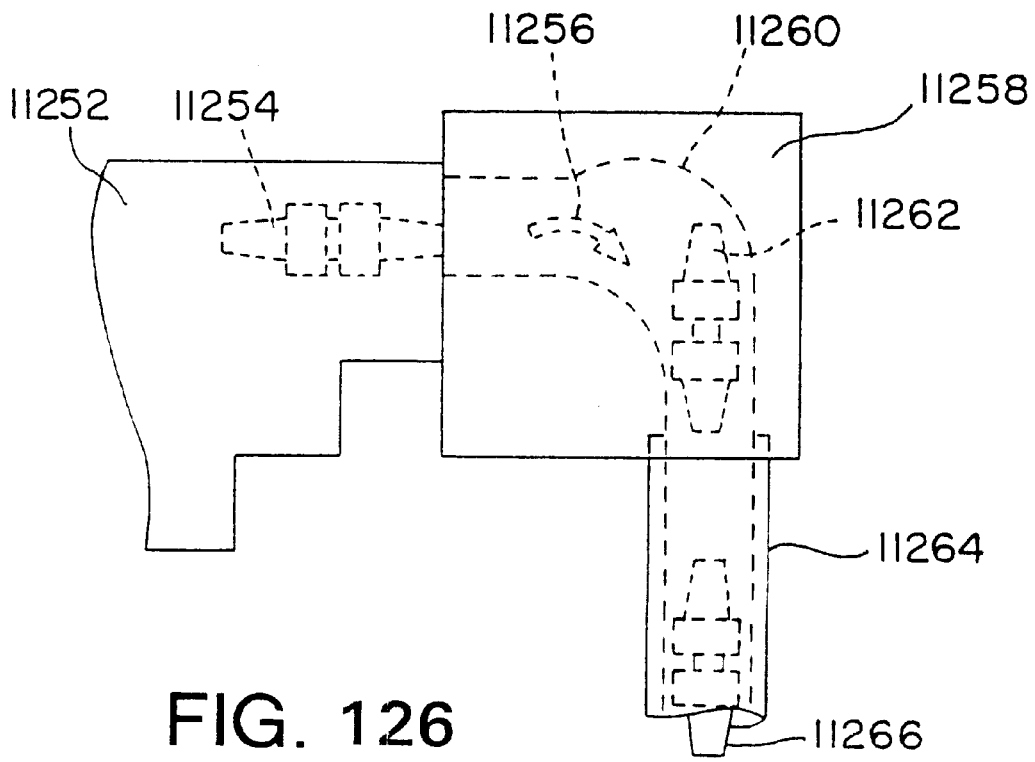

Orientator 7014 of FIG. 71, and orientator 7722 of FIG. 77 provide alternative embodiments of a structure for assisting in the proper alignment and orientation of matrices-with-memories, such as MICROKAN™ or MICROTUBE™ microreactors, as they traverse through the automated sorting device. An additional embodiment of an orientator is shown in FIGS. 125 and 126. The embodiments of FIGS. 125 and 126 are interchangeable so that the automated sorting device may be used for virtually any embodiment of matrix-with-memory, including for example, the MICROKAN and MICROTUBE microreactors.

Referring to FIG. 125, orientator 11206 is shown attached to a vibratory feeder 11202 such that as a single-bodied MICROKAN™ microreactor 11204 advances in direction 11208 from feeder 11202, orientator 11206 orientates microreactor 11204 in a vertical orientation. Once the microreactor reaches position 11212, it drops downward in direction 11218 into feeder tube 11214, as shown by microreactor 11216.

Referring now to FIG. 126, an alternative embodiment of an orientator is shown and generally designated 11258. As double-bodied microreactor 11254 advances from vibratory feeder 11252, it rotates in direction 11256 within curved opening 11260 to position 11262 and falls downwards into feeder tube 11264 as shown by microreactor 11266. Generally, orientator 11258 can be used for a variety of matrices-with-memories, such as double-bodied microreactors, MICROTUBE™ microreactors, and any other embodiment, particularly those that do not require a particular orientation other than a vertical orientation.

(4) A fourth embodiment

Figure 127:
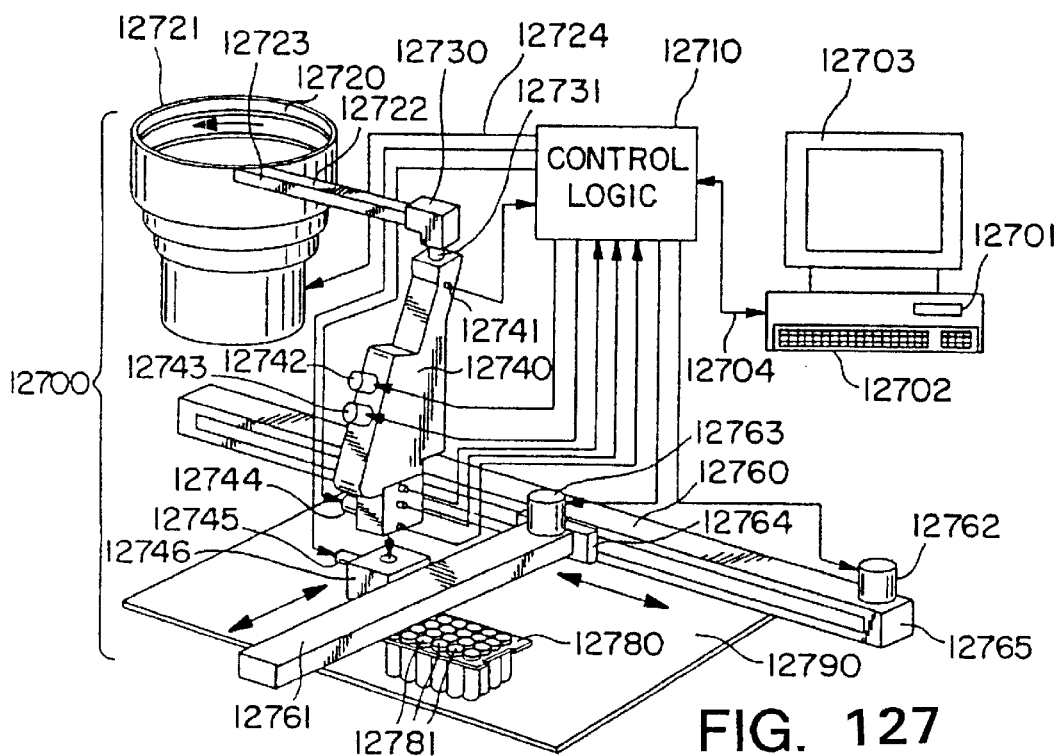

A fourth embodiment of the automated sorting system 12700 is illustrated in FIG. 127. As in the previous embodiments of automated sorters, the basic components of the system 12700 are a host controller 12701 which interacts with control logic 12710, a vibratory feeder 12720, an orientator 12730, a metering device 12740, an X-Y translation system 12760, and a container tray 12780. Container tray 12780 may be supported by a frame, as in previously-described sorter embodiments, or may be placed on deck 12790, i.e., the bottom of the sorter.

Host controller 12701 is an IBM-type PC with processor such as a Pentium® (Intel Corporation) processor which has a speed of 100 MHZ or faster. The preferred PC is the Vectra Pentium® PC from Hewlitt-Packard Corporation. The PC should be equipped with 16 MB or higher RAM (random-access memory), a 1 GB or higher hard drive, a CD/ROM and/or disk drive, and should run on the Windows 95™ operating system from Microsoft Corporation. User interfaces include a mouse or similar pointer (not shown), a keyboard 12702, and parallel and serial ports, including two RS-232 high speed UART (universal asynchronous receiver/transmitter) links 12704. Monitor 12703 provides means for displaying instructions and information to the user.

The basic architecture for the software that is run in host controller 12701 is illustrated in FIG. 134. The source code for the following programs is filed herewith as Appendices 6, 7 and 8. The SYNTHESIS MANAGER™ program 12705, which has been previously described relative to the manual sorting system, reads the sorter files and uses the information to present sorting options to the user, and facilitates the overall synthesis and cleavage processes. The analytical operations performed and the graphical displayed provided by the SYNTHESIS MANAGER™ software in the present automated sorting system are the same as those used in the manual system, see, e.g., FIGS. 135–138 and the description therefor. The primary difference is that interface capabilities are provided for providing interaction between the SYNTHESIS MANAGER™ software and operation and control of the sorter.

Sorter server 12706, using the combined source code listed in Appendix ("Sorter Server") and Appendix 8 (Sorter operation code ("Sorter.ocx") provides communication services to and from the sorter, sending commands, including operational commands and status inquiries, to logic controller 12710 and communications with the SYNTHESIS MANAGER™ program 12705. Sorter server 12706 operates on a separate thread from applications software so that it can operate independently, without being interrupted by input or other operations within an application.

Sorter Command Test Utility 12707 is a debugging tool which allows the user to enter the command portion of Host-Link command strings, send it to logic controller 12710, then view the response from the logic controller 12710. Sorter test and calibration (CalTest) program 12708 is used for set-up and alignment of the sorter. The various configuration and calibration files are created, viewed and edited using program 12708. Access to the CalTest program 12708 is preferably controlled using a multi-tier password, limiting access to only those personnel who are sufficiently trained for making changes to the calibrated parameters. Configuration, template and calibration test files 12709 are created, edited and/or read using the CalTest program 12708. Configuration files, which are created, edited and viewed using the CalTest program, contain deck/X-Y arm calibration data as well as calibration data for any other deck-based features such as the reject and recycle bins. A separate configuration file is created for each sorter in set-ups where a host controller is used for controlling a network of sorting systems. The configuration file will include the identity of the specific sorter for which is was created.

Template files serve as templates for defining allowable sort target arrangements. Target arrangements will include variables of organization, size, and spacing for a plurality of containers, and can include sorting patterns for using less than a full tray or other array of containers. One template file will be created for each possible arrangement variation, however, in most cases, only a few template files will be required. Template files may be read, but are not modified, by the CalTest program 12708:

Calibration files are created by the template files and the configuration files in the course of calibrating the frames, carriers and other features of the sorter. The calibration files provide a translation from a template file location to a corresponding X-Y location for a selected sorting arrangement, thus mapping the features defined in the template file to the X-Y locations.

An optional program, the Simulator Utility program 12711 allows the user to send commands to sorter server program 12706 and receive responses from it for testing the sorter server program 12706 and the sorter 12700. Simulator Utility program 12711 simulates a data base look-up of a data for a memory device and may include a user-settable delay to simulate the data base look up time.

Logic controller 12710 is generated by a PLC (programmable logic controller) and provides local control over all motion and functions of the sorter 12700. Logic controller 12710 operates as a slave to host controller 12701, responding only to received commands, and does not initiate transmissions. As in previous embodiments, the PLC is programmable in relay ladder logic using a personal computer with a ladder support software package, and is available from Omron Electronics, Inc. of Schaumburg, Ill. Communication between the host controller 12701 and logic controller 12710 is provided by RS-232 link 12704 using the serial communication protocol described in the Omron Sysmac C-Series Rack PC's Host Link Units System Manual, Catalog No. W143-E3-1.

As in the previous embodiments, vibratory feeder 12720 is used to feed the memory devices for reading and sorting. Briefly, feeder 12720 is a conventional vibratory bowl feeder which has a helical track 12721 climbing the inside wall of bowl 12722, generally in a counterclockwise direction. By applying a circular vibratory motion to bowl 12722, the memory devices that are dumped into bowl 12722 will climb helical track 12721 in single file. Feeder 12720 is connected to and receive control commands from PLC 12710 via connector 12724.

Once the memory devices reach the top of bowl 12722 they proceed through feed channel 12723 to orientator 12730. Depending on the configuration of the memory devices, e.g., single- or double-bodied MICROKAN™ reactors, orientator 12730 may be one of the embodiments shown in and described with reference to FIGS. 125 and 126. After the memory devices are correctly oriented they fall through vertical channel or tube 12731 and into singulator 12740 for releasing the memory devices one-at-a-time for placement in the target containers.

Figure 129:
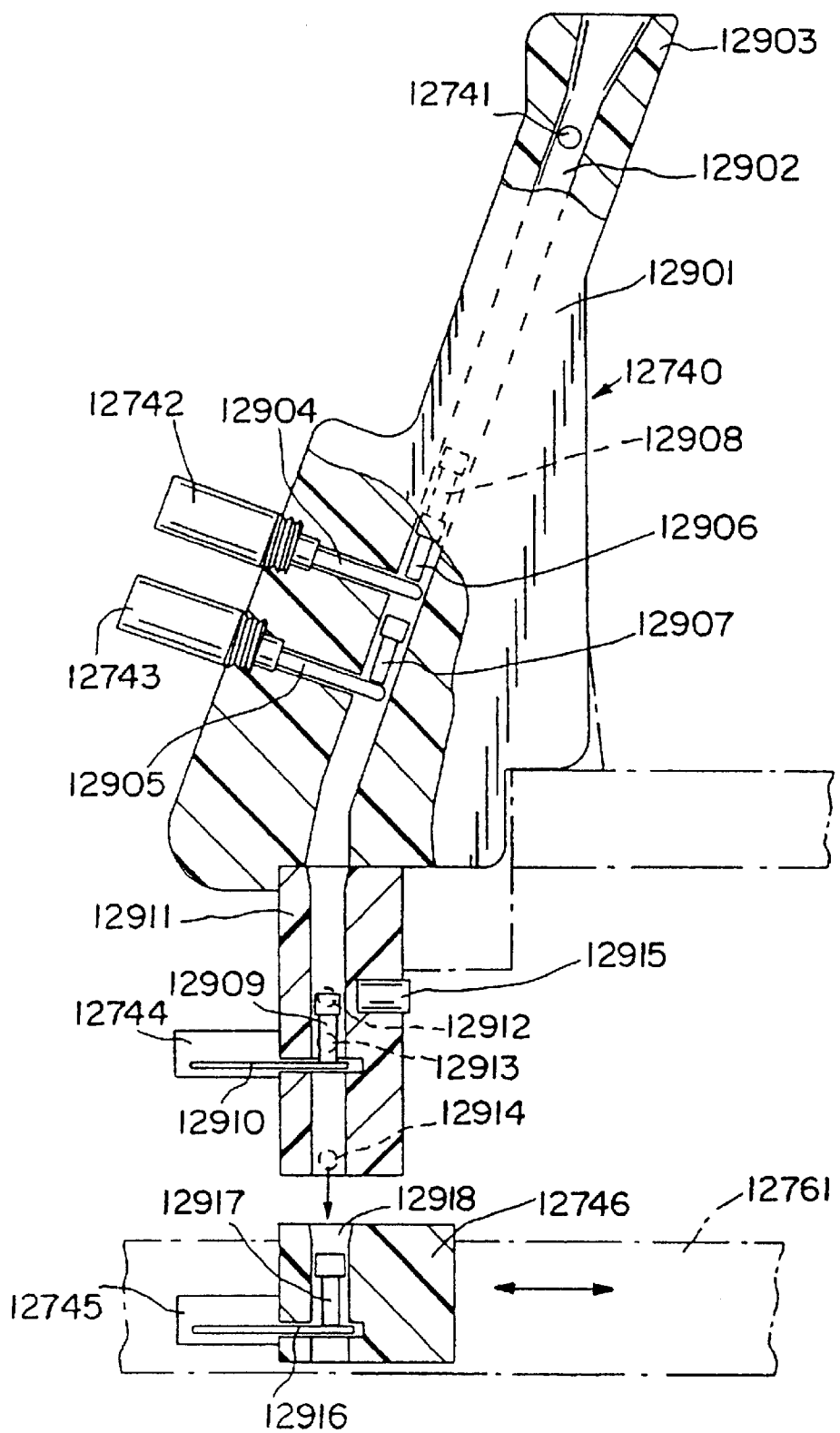

A detailed view of singulator 12740, which is mounted above and in a fixed relationship to X-axis arm 12765, is provided in FIG. 129. As shown, singulator 12740 comprises a body 12901 with a cylindrical bore 12902 running at a substantially vertical angle through the length of body 12901. Body 12901 is generally of solid construction except where bores are formed. In the exemplary embodiment, body 12901 is formed from one or more blocks of clear acrylic or Lucite material. Bore 12902 may be slightly flared at its entrance at upper end 12903 for mating with tube 12731 and to facilitate transition of the memory devices into the bore. The bore angle may be perpendicular to the surface on which the sorter is resting, or may be off-perpendicular by as much as 40°. An important consideration in selecting bore angle is that the force for advancement of the memory devices through bore 12902 is provided solely by gravity, therefore, the bore angle must be steep enough to allow gravity to overcome at least part of the friction or other possible adhesion forces between the inner walls of bore 12902 and the memory device. The bore angle must also be shallow enough to slow the progress of the memory devices to permit gating using solenoids 12742 and 12743, as described below. As illustrated, the bore angle is on the order of 25° to 30° from vertical.

At the upper end of body 12901 is sensor 12741 for monitoring the contents of bore 12902. If the memory devices becomes backed-up in bore 12902, sensor 12741 provides a signal lo PLC 12710 which may then trigger a signal to pause operation of feeder 12720 until the bottleneck at the singulator is cleared to prevent jamming that may be caused by too many memory devices being fed into channel 12722 or orientator 12730. Sensor 12741 may be an optical sensor which detects changes in light reflection or transmission caused when a memory device dwells in front of sensor 12741 for a relatively extended period of time, indicating that the memory devices has stopped moving. Sensor 12741 may also be used to generate a signal every time a memory device passes it, allowing calculation of the feed rate.

Singulation, i.e., the controlled intermittent release of individual memory devices, is effected using gating solenoids 12742 and 12743 which are mounted on body 12901 so that pistons 12904 and 12905, which are driven by the two gating solenoids project perpendicular to and at least partially into bore 12902. First gating solenoid 12742 and its corresponding piston 12904 are activated by a signal from PLC 12710 to halt memory devices as they are stacked one on top of the other within bore 12902. As shown, memory devices 12906 and 12908 are stopped above piston 12904. First gating solenoid 12742 is then quickly opened and closed to allow one memory device 12907 to pass, where it is trapped by piston 12905, driven by second gating solenoid 12743, activated by a signal from PLC 12710. The rate of opening and closing of second gating solenoid 12743 is governed by the amount of time required to read the memory devices to determine its identity and any other information pertinent to the sorting procedure. Due to the amount of heat that can be generated by the rapid and repeated activation of the two gating solenoids 12742 and 12743, it may be desirable to provide a heat sink or other cooling means to prevent the solenoids from burning out. Although not shown, in the preferred embodiment, metal radiating fins are placed in thermal communication with the two solenoids. Implementation of such heat sinks are within the level of skill in the art.

Following its release by second gating solenoid 12743, memory device 12909 is halted within the bore in the lower end 12911 of body 12901 by third gating solenoid 12744 and retractable gate 12910. Position sensors 12912 and 12913 monitoring the bore above gate 12910 to detect the presence of memory device 12909. First position sensor 12912 provides a signal to PLC 12710 to trigger the activation of a reading device 12915 which queries memory device 12909 to determine its identity and obtain any other pertinent information In the exemplary embodiment, reading device 12915 is an RF antenna connected to an RF reader (not shown) which provides input to host computer 12701. Examples of such systems are described above. Other types of readers, including optical readers are also described above and may be utilized in the present embodiment with appropriate adaptations. Second position sensor 12913 provides a signal to PLC 12710 confirming the presence of memory device 12909 at the reading position. Once the reading operation is complete, host computer 12701 provides a signal to PLC 12710 which, in turn, causes solenoid 12744 to be activated, opening gate 12910, dropping the memory device past third position sensor 12914 to generate a signal to PLC 12710 to confirm release of the device.

After exiting from lower portion 12911 of body 12901, memory device 12917, which has now been identified by the reader, drops into bore 12918 within loading block 12746. While the calibration and set-up procedures will provide for alignment of singulator 12740 and loading block 12746, any minor offset can be alleviated by providing a slight flare in the entrance to bore 12918. Fourth gating solenoid 12745 and retractable gate 12916 retain memory device 12917 within bore 12918 until it is properly positioned over the target container.

Referring again to FIG. 127, loading block 12746 is slidably mounted on arm 12761 of X-Y positioner 12760. After memory device 12917 has been received in bore 12918 and the host computer 12701 and its associated software for managing the synthesis process, e.g., the SYNTHESIS MANAGER software, have determined the desired target location for memory device 12917, X-Y positioner 12760 will move loading block 12746 into position over the target container.

As described with regard to other embodiments of the automated sorter, X-Y positioner 12760 comprises an X-axis arm 12765, X-axis high speed stepper motor 12762 mounted on arm 12765, Y-axis mounting plate 12764 slidably mounted on X-axis arm 12765 and connected to X-axis motor 12762 for translation along the X-axis, and Y-axis arm 12761 attached to Y-axis mounting plate 12764. Loading block 12746 is movable along Y-axis arm 12761 and is driven by high speed Y-axis motor 12763. Movement of loading block 12746 is guided by X-Y position sensors, as previously described, the SYNTHESIS MANAGER software, the sorter server, and the calibration files to identify the exact target position.

As illustrated in FIG. 127, and as described with reference to other embodiments of the automated sorter, the containers 12781 into which the memory devices are to be placed are microreactor carriers. The carriers 12781 are retained within microreactor carrier tray 12780 which is supported on a tray frame (not shown). Only one carrier tray 12780 is illustrated in the figure for simplicity, however, configurations of multiple carrier trays 12780 may be used with an appropriate sorting template.

Once the position of the target microreactor carrier 12781 is determined, loading block 12746 is moved to the specified position and, after confirming the position, PLC 12710 sends a release signal to fourth gating solenoid 12745, causing gate 12916 to open, dropping memory device 12917 into the target microreactor carrier 12781. After placement of every memory device in its target microreactor carrier, loading block 12746 returns to its starting position below singulator 12740 to receive the next microreactor carrier.

C. Automated system-Cleaver (1) A first embodiment

Figure 101:
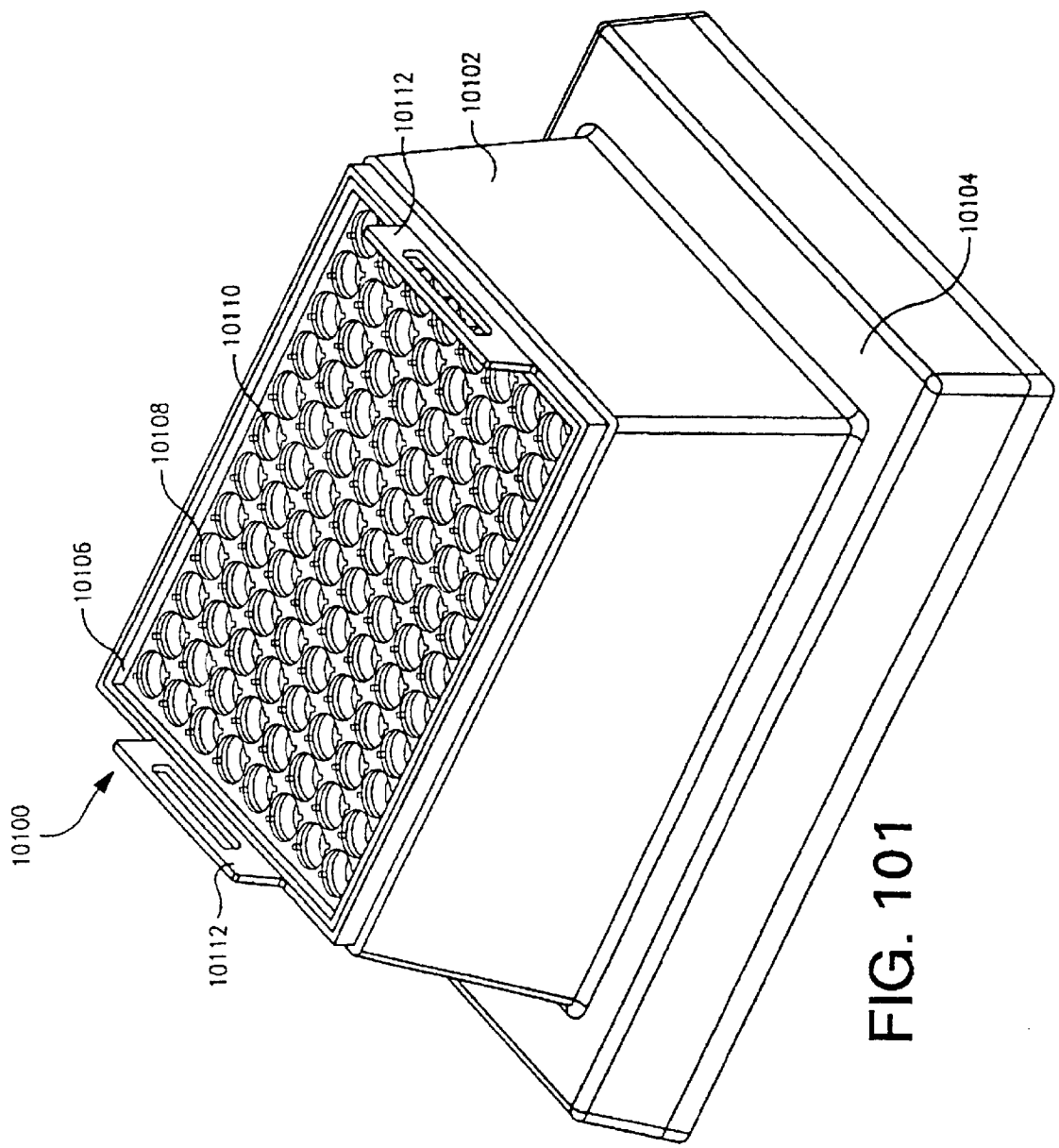
FIG. 101 is a perspective view of a preferred embodiment of an automated cleaving station.

Referring now to FIG. 101, an exemplary automated cleaving station is shown and generally designated 10100. Automated cleaving station 10100 includes a cleaving block 10102 mounted to a base 10104. A tray 10106 is attached to the top of the cleaving block 10102 and is formed with an array of holes 10108, with each hole being loaded with a disposable microreactor carrier 10110. Optional handles 10112 are provided for tray 10106 in order to easily raise and lower the tray from the cleaving block, as described in conjunction with the manual cleaving station shown in FIGS. 97 through 100, and to remove the microreactor carriers from the station 10100.

Figure 102:
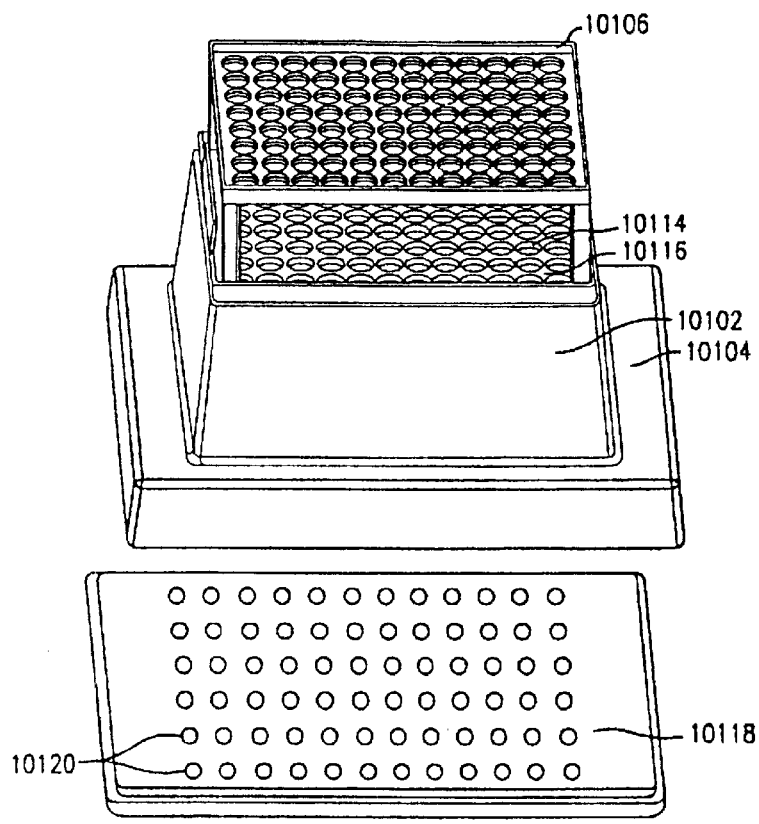
FIG. 102 is a perspective view of the automated cleaving station of FIG. 101 with the top plate raised, and the nozzle array interface plate separated from the cleaving block.

FIG. 102 shows the automated cleaving station 10100 in an exploded format detailing the movement of tray 10106 from the cleaving block 10102, and the interaction of the nozzle array interface plate 10118 to the base 10104. As shown, the nozzle array interface plate 10118 is attached to the base 10104 such that the outlets from each of the bores 10116 may be routed to the plate 10118 to accommodate a variety of patterns, as will be discussed in more detail in conjunction with FIGS. 105 and 106.

Figure 103:
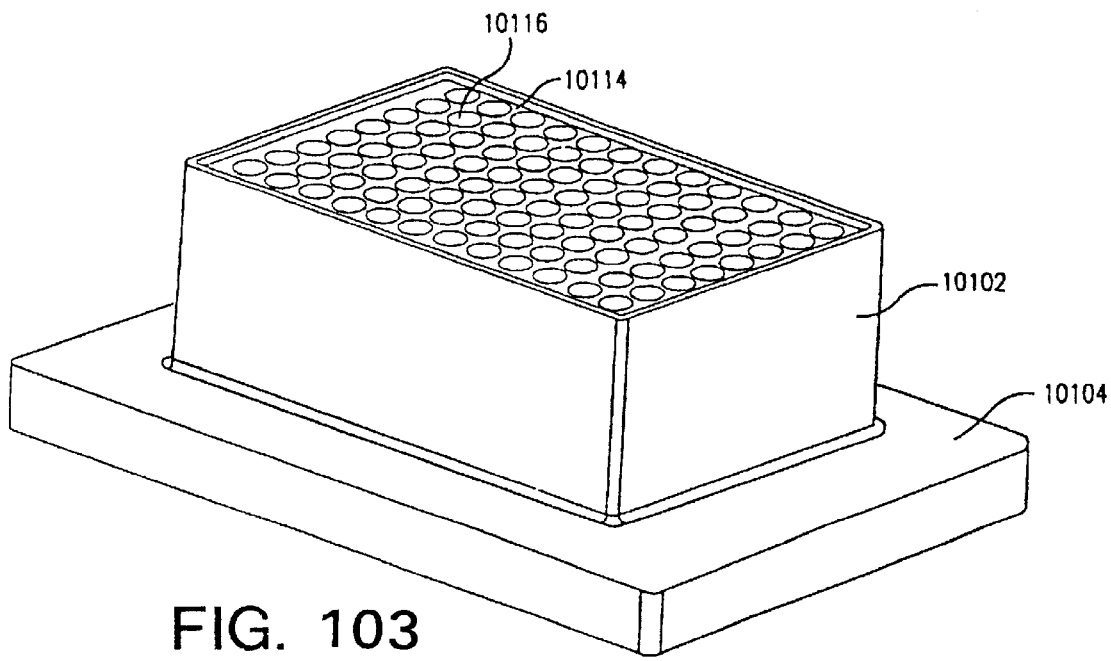
FIG. 103 is a perspective view of the cleaving block of the automated cleaving station of FIG. 101.
Figure 104:
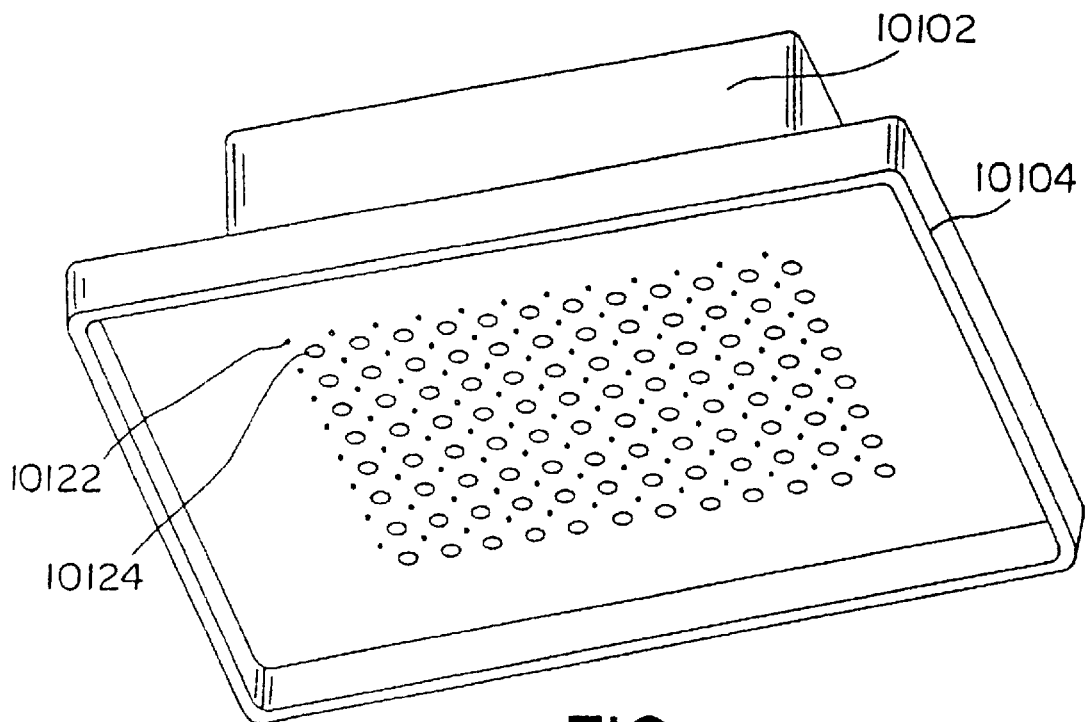
FIG. 104 is a perspective view of the bottom surface of the cleaving block of the automated cleaving station of FIG. 101 showing the exits from the cylinders and the U-tube insertion bores.

Referring now to FIG. 103, the cleaving block 10102 is shown with the tray 10106 removed from upper surface 10114. Cleaving block 10102 is formed with an array of 96 bores 10116 which are sized only slightly larger than the disposable microreactor carriers 10110. While cleaving block 10102 is shown as described as being formed with 96 bores, any number of bores may be formed in the cleaving block, corresponding to standard microtiter formats, or custom formats. FIG. 104 is a view of the bottom side of base 10104 showing an array of drains 10122, and a corresponding array of tube bores 10124 which are formed in the cleaving block 10102. From this view it can be appreciated that the drain 10122 is axially aligned with the bore 10116, and that the tube bores 10124 are formed within the interstitial space between the bores 10116.

Figure 105:
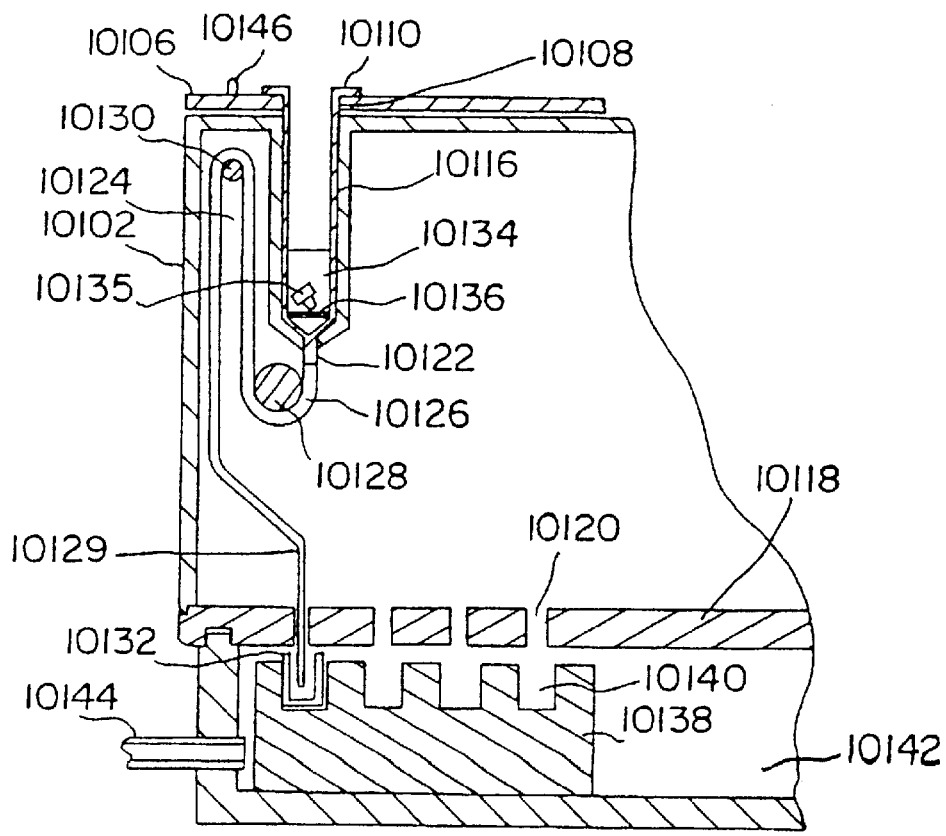
FIG. 105 is a cross-sectional view of an alternative embodiment of the automated cleaving station showing a U-tube which is routed over a pair of retaining pins to the nozzle array interface plate.

Referring to FIG. 105, a preferred embodiment of the present automated cleaving station is shown. The cleaving station of FIG. 105 includes a cleaving block 10102 which is formed with bores 10116 which are sized to receive a microreactor carrier 10110 that is resting in a hole 10108 in ray 10106. To assist in locating the tray 10106 on cleaving block 10102, an alignment pin 10146 is provided which mates with an alignment hole in the tray (not shown).

Bore 10116 has a drain 10122 which leads to a U-tube 10126 which is shaped to form a trap. For example, U-tube 10126 extends downwards from the drain 10122 and rounds pin 10128 to lead upwards around pin 10130, returning in a downward direction. Because the location of the pin 10130 is substantially the same height of the bore 10116, any fluid 10134 which is in the microreactor carrier and/or bore will be prevented from leaking out of the cleaving block. Typically, the U-tube is made of a TEFLON™ (PTFE) which has an outer diameter of approximately 1–3 mm, preferably about 2 mm. As a result of the small diameter of the U-tube 10126, it may be easily routed to any number of locations underneath the cleaving block 10102.

Referring back to FIG. 104 for an alternative to the pins 10128 and 10130, bores 10124 are formed in the cleaving block 10102 and are sized to have an approximate diameter of 6 millimeters which allows the U-tube 10126 to be folded over and inserted into the bore 10124. Because the diameter of the hole 10124 (6 millimeters) is over twice the diameter of the U-tube 10126 (1.6 millimeters) the U-tube will not pinch together to prevent the flow of fluid through the U-tube. For example, referring to FIG. 107 for clarity, cleaving block 10102 is shown having a bore 10116 formed with a drain 10122. U-tube 10126 is attached to the drain 10122, bent upon itself and is inserted into bore 10124 to form a trap. Bend 10127 is shown inserted into bore 10124 and does not show any pinching, or otherwise substantial narrowing of the U-tube.

Figure 107:
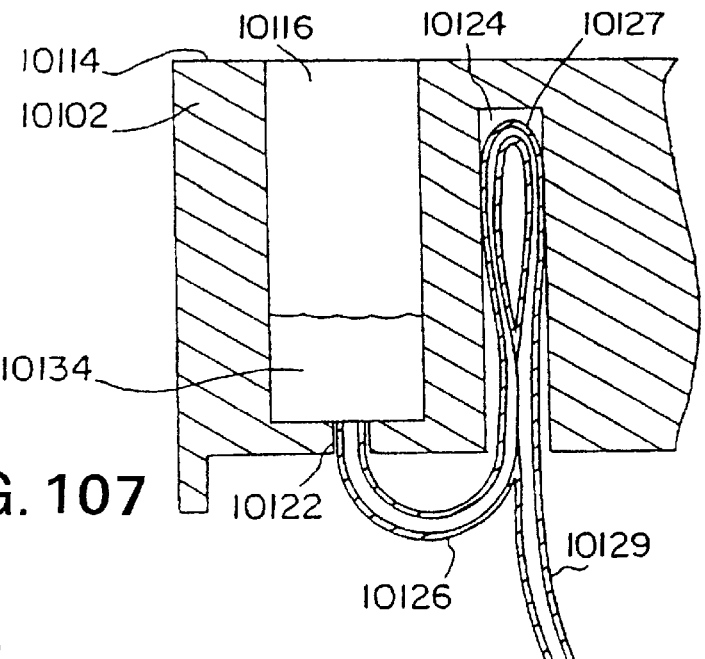
FIG. 107 is a detail view of an alternative embodiment of the automated cleaving station showing the placement of the U-tube within the cleaving block.

Regardless of whether the pins 10128 and 10130 of FIG. 105, or the bores 10124 of FIGS. 104 and 107 are used, following formation of the trap with U-tube 10126, the pigtail 10129 is routed to a port 10120 in the nozzle array interface plate 10118 shown in FIG. 105. The nozzle array interface plate 10118 is formed with an array of ports 10120 such that a variety of routing options may be accommodated. For example, such routing may be from the bores 10116 to the interface plate 10118 in order to be able to map to either in a standard microtiter plate footprint with 3×4, 4×6, 6×8, or 8×12 or other configuration of wells. Alternatively the routing may be a format to accommodate a standard vial rack, or may be a custom routing. Because of the flexibility of the U-tube 10126, and the length of the pigtail 10129, virtually any routing configuration may be accomplished.

Referring again to FIG. 105, cleaving block 10102 is shown with its U-tube 10126 routed to a position on the nozzle array interface plate 10118. The cleaving block 10102 and nozzle array interface 10118 are positioned over a vacuum chamber 10142 and a seal 10131 establishes an airtight seal between the interface plate and vacuum chamber to prevent the entry of air into the vacuum chamber, except through the U-tubes 10126. The pigtail 10129 extends through the interface plate 10118 for alignment with a vessel 10132 in a desired collection rack 10138. It is not necessary to include a vessel 10132 in addition to wells 10140, but each is included for clarity. It should be appreciated that any variety of containers could be positioned within vacuum chamber for alignment with the interface plate and protruding pigtail 10129.

Once the cleaving block 10102 is in position over the vacuum chamber 10142, a vacuum is created within that chamber by activating a vacuum generating device (not shown) which attached to vacuum hose 10144. The vacuum which is created within the vacuum chamber 10142 in turn draws the fluid 10134 from microreactor carrier 10110 and/or bore 10116 through drain 10122, through U-tube 10126, and out the pigtail 10129 into vessel 10132. Thus, the fluid within the bore 10116 and microreactor carrier 10110 is effectively drawn into the appropriate vessel without any manual intervention, aside from activation of the vacuum source. While not shown in FIG. 105, it will be apparent that the fluid 10134 from any number of bores 10116 may be drawn into a multi-well container simultaneously. Effectively providing for an automated one step fluid transfer from cleaving station to microtiter plate, for example.

As a result of the vacuum transfer from the cleaving station 10100 to the subsequent processing platform, such as a collection rack, the need for a manual transfer of the fluid is eliminated. Because the entire process is controlled by a vacuum, there is no need for a valve in the system thereby improving the performance and life of an automated cleaving station. Further, the valveless automated cleaving station is capable of cleaving 96 or more compounds simultaneously, eliminating the otherwise necessary step-and-repeat process of cleaving with a traditional pipet, or pipet-like device. In fact, because it is possible to map the pigtails to any location within the nozzle array interface plate, it is possible to accommodate standard microtitre plate formats, or any other custom format, including for example vials and vessels.

Another benefit of the valveless automated cleaving station is the leak-proof nature of the U-tube design. For example, a U-tube design includes no connectors which can corrode over time, and thus the durability and reliability of the automated cleaving station is enhanced. Also, because there are no valves or connectors to leak, the likelihood of contamination of one solution from another is minimal. Because of the absence of valves and connectors, cleaning of the automated cleaving station includes simply filling the bores 10116 with a cleaning solution, and drawing the solution through the system using the vacuum chamber, resulting in a cleaving station which is effectively self-washing.

Vacuum chamber 10142 is typically made from glass, which provides the ability to visually verify the proper cleaving process is completed, as well as resist corrosion from such materials as TFA. In addition to a vacuum chamber 10632, a vacuum generator (not shown) may include a vacuum trap to eliminate the destructive effect of TFA on the vacuum generator itself. Such a vacuum trap is generally known in the art as a standard bench chemist's trap, or "cold trap".

Referring now to FIG. 106, an alternative embodiment of the automated cleaving station is provided and generally designated 10600. Automated cleaving station 10600 is functionally similar to station 10100, yet structurally distinct. Station 10600 includes a cleaving block 10602 formed with a well 10602 sized to receive a microreactor carrier 10606 that is positioned on top plate 10608 which is resting on supports 10610. A lower connecting bore 10614 is formed at the base of the well 10604 and extends horizontally towards a first vertical bore 10612. First vertical bore 10612 extends upwards from the lower connecting bore 10614 to an upper connecting channel 10618. Upper connecting channel 10618 extends from the first vertical bore 10612 to a second vertical bore 10616 which extends downwards through the cleaving block 10602.

A U-tube is inserted into both the first and second vertical bores 10612 and 10616, and through the upper connecting channel 10618 such that one end of the U-tube is positioned near the lower connecting bore 10614, and the other end, pigtail 10621, extends out the bottom of the cleaving block 10602 for routing to an appropriate port on the nozzle array interface plate 10622. This U-tube may be preformed in a u-shape, or may be placed into position. In order to ensure that the end of the U-tube within the first vertical bore 10612 does not seal itself against the cleaving block 10602, a small notch [not shown, but see, e.g., FIG. 122, which shows a U-tube having an angled cut 11130] may be cut at the end of the U-tube to prevent such sealing.

To facilitate the routing of the pigtail 10621, the ports on the nozzle array interface plate 10622 may be formed with a tapered portion 10624 which assists in inserting the small-diameter pigtail 10621 through the plate. In addition, a support flange 10626 may be attached to, or formed integrally to, the interface plate 10622.

The operation of the automated cleaving station 10600 is substantially similar to the operation of the other automated cleaving station discussed above, including the use of a vacuum chamber 10632 to draw solution 10636 from microreactor carrier 10606 and/or well 10604 into a suitably positioned container, such as a collection rack 10628, or a well 10630. Due to the manner in which the U-tube is integrated into the cleaving block, the manufacturing of this embodiment is substantially easier. For example, the cleaving block will be typically formed by traditional machining techniques, such as injection molding or any other manner as is known in the art. As a result, well 10604, first vertical bore 10612, upper connecting channel 10618, and second vertical bore 10616 may be formed in a single injection molding step. Lower connecting bore 10614 may also be formed during the injection molding process, or by a simple end-mill machining process following the injection molding. Once these passageways have been formed, it is a simple process to simply drop a pre-formed U-tube 10620 into position within the bores. Once positioned, a simple routing procedure may be implemented to map the pigtail 10621 to the appropriate port on the nozzle array interface adapter 10622. Because there are no pins to route the U-tube through, or any bores to insert the U-tube into, this alternative embodiment is easier to assemble, particularly when configuring the nozzle array interface plate with 96 Teflon tubes having a small diameter.

In addition to the manufacturing advantages listed above, the automated cleaving station 10600 utilizes any available solution 10636 more efficiently. For example, instead of having a drain 10122 which retains an amount of uncirculated solution, or "dead" solution, the automated cleaving station 10600 has a lower connecting bore 10614 which minimizes the uncirculated fluid. This is particularly important when attempting to cleave a microreactor 10638 with the minimal amount of solution as possible.

Figure 108:
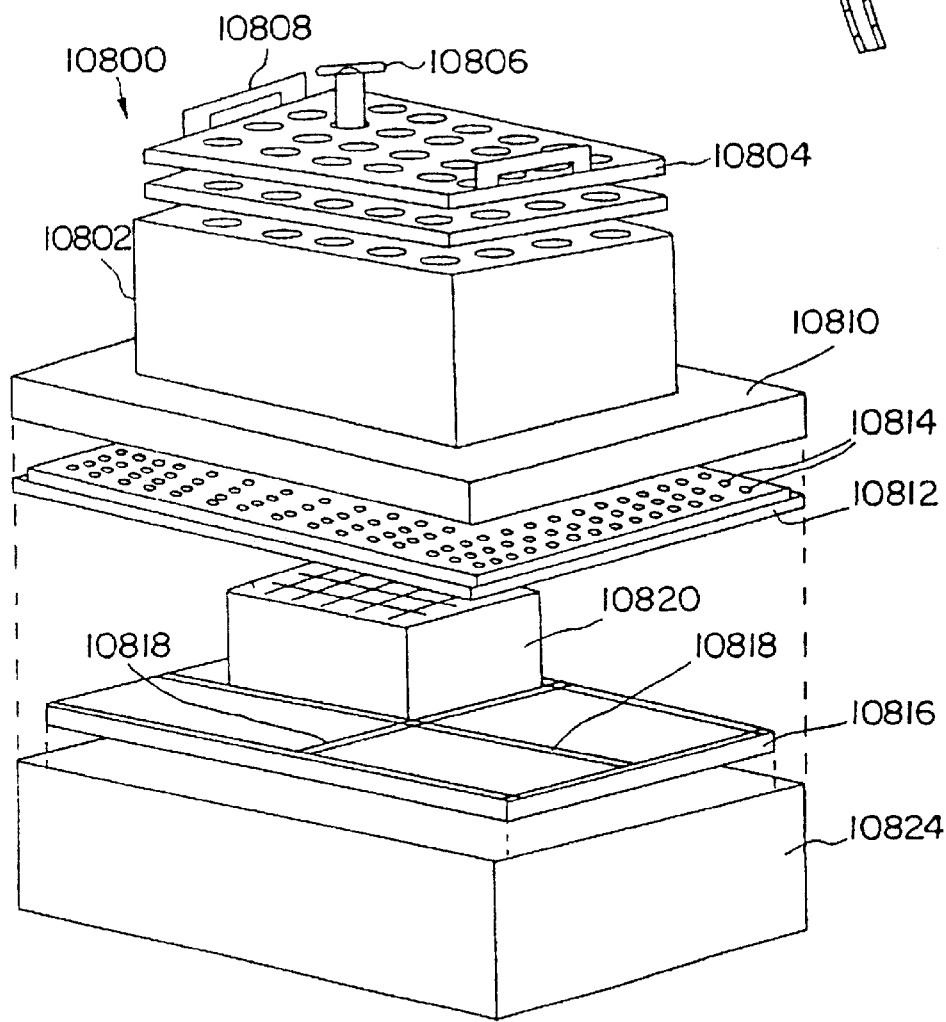
FIG. 108 is a perspective view of an alternative embodiment of the automated cleaving station shown in exploded format for clarity.

Referring now to FIG. 108, yet another alternative embodiment of an automated cleaving station is shown and generally designated 10800. The cleaving station 10800 includes a cleaving block 10802 with a top plate 10804, or carrier trays, which are formed with an array of holes to receive microreactor carriers 10806. The top plate 10804 is equipped with handles 10808 to simplify the movement and positioning of the tray on the cleaving block 10802. Cleaving block 10802 is attached to a base 10810 that fits together with a nozzle array interface plate 10812 having an array of ports 10814. The routing of the U-tubes for this embodiment is identical to the routing of the previously described embodiments, and will not be discussed again for this embodiment.

The automated cleaving station 10800 has a vacuum chamber 10824 which receives a collection rack locator plate 10816 which is formed with guide ridges 10818 which are sized to accept a variety of standard high-density collection racks, such as a 12, 24, 48, 96, and 384 microtitre plate. It should be appreciated, however, that the collection rack locator plate 10816 may be customized for a particular application, or may be generic to a family of collection racks as shown.

The operation of the automated cleaving station 10800 includes placing the appropriate number of microreactor carriers 10806, or barrels, into carrier trays 10804, sorting the desired number of MICROKAN microreactors (not shown) into the appropriate microreactor carriers, place the carrier trays in onto cleaving block 10802, fill the wells with cleaving solvent, place any necessary upper and lower spill sheets onto station, cleave on a standard platform shaker for an appropriate period of time, draw a vacuum within the vacuum chamber to transfer the compounds to the collection rack of the proper format, such as a standard microtiter plate, or vial rack.

Figure 122:
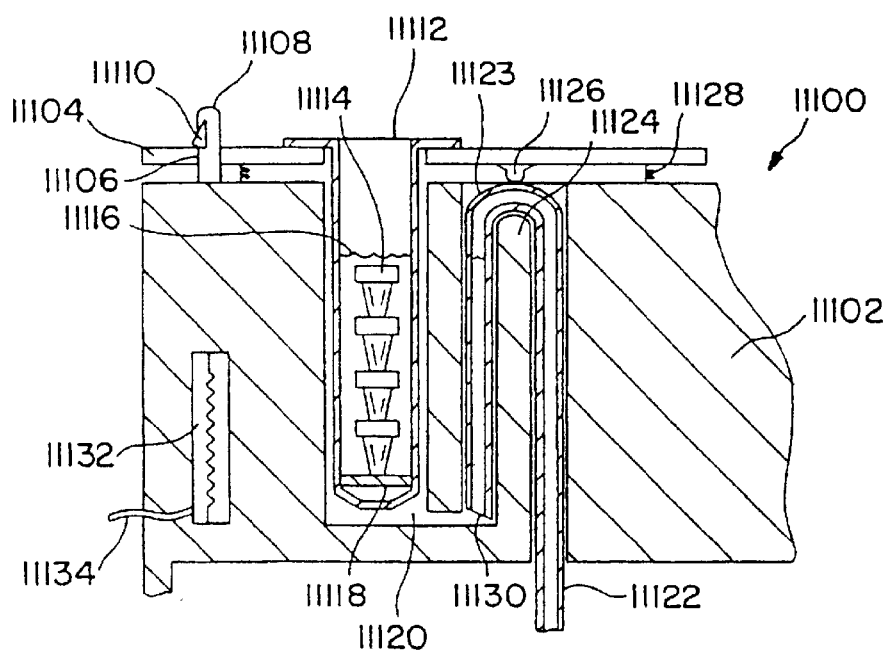

Referring now to FIG. 122, an alternative embodiment of a cleaving block having a valve is shown and generally designated 11100. Cleaving block 11100 has a body 11102 formed with bores 11120 which are similar to those discussed in conjunction with FIG. 106. A microreactor carrier 11104 is formed with alignment holes 11106 to receive an alignment and retaining pin 11108 to ensure the proper orientation and positioning of the microreactors 11112. Moveable tab 11110 is formed on the upper portion of pin 11108 to allow for the positioning of the microreactor carrier tray 11104, and its associated microreactor carriers 11112 in a raised or lowered position. Each microreactor carrier may hold one or more microreactors, such as the MICROKAN microreactors 11114 shown, and they may be immersed in a quantity of a cleaving agent 11116, such as TFA.

Cleaving block 11102 is formed with a curved portion 11124 and is equipped with a modified U-tube 11122 having a curved portion 11123. These curved portions slightly raise the U-tube upwards towards the microreactor carrier tray 11104. In a corresponding location on the underside of the microreactor carrier tray 11104, a nipple 11126 is formed to align with the uppermost portion of the curved U-tube. Cleaving block 11102 may also have a number of springs 11128 which maintain the microreactor carrier at a predetermined height such that the nipple 11126 is not pressing on U-tube 11122.

Figures 123, 124:
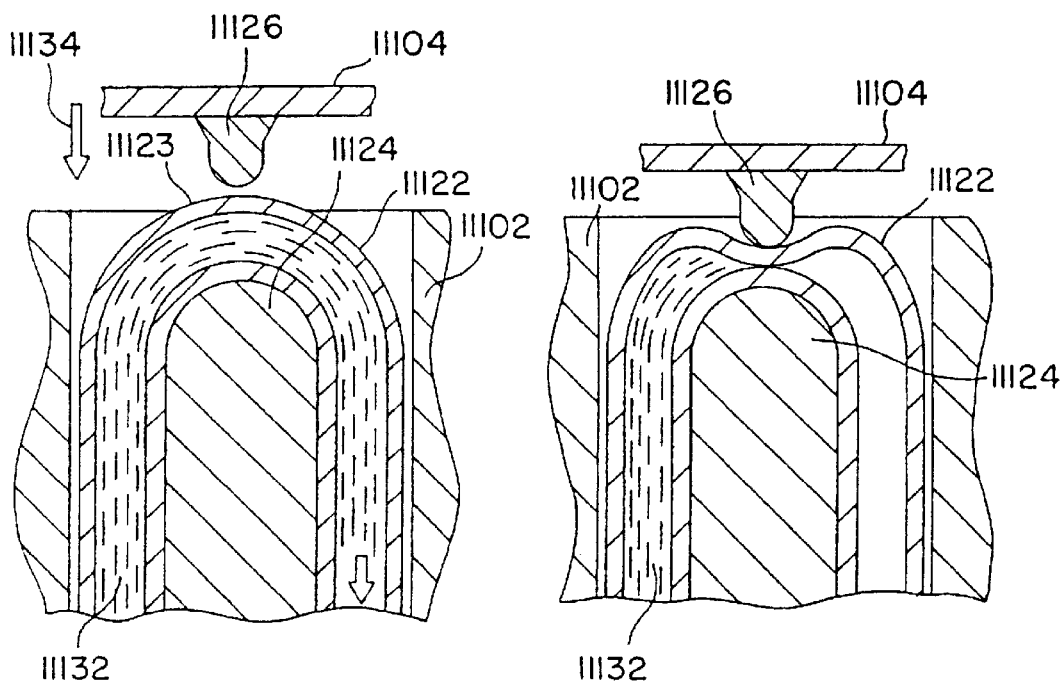

Referring now to FIGS. 123 and 124, the implementation of the valving is perhaps more clearly shown. For example, in FIG. 123, microreactor carrier tray 111 04 is shown with nipple 11126 being held above U-tube 11122 such that the fluids 11132, or other compounds, may easily flow through the U-tube 11122, such as when the compounds are drawn from the microreactors into the vials within the vacuum chamber, as discussed elsewhere herein. More specifically, the curved portion 11123 of U-tube 11122 is not squeezed in any way as it passes over curved portion 11124 of cleaving block 11102. However, by pressing downward in direction 11134 on the microreactor carrier 11126, nipple 11126 presses downward on curved portion 11123 of U-tube 11122. Referring now to FIG. 124, the U-tube may be successfully compressed between the nipple 11126 and the curved portion 11124 of cleaving block 11120 to effectively stop the flow of all fluid 11132 through the U-tube 11122.

By pressing downward sufficiently to prevent the flow of fluid through the U-tube, moveable tab 11110 will spring outward from pin 11108 to retain the microreactor carrier tray in its lowered position. Once treatment of the matrix within the microreactor, such as cleaving, is completed, the moveable tabs 11110 may be depressed into the pins 11108 allowing the microreactor carrier tray 11104 to be forced upwards to its predetermined position by springs 11128. As will be apparent to those skilled in the art, the movable tabs and springs discussed herein are exemplary only, and other valving methods may be used.

To facilitate the cleaving process, cleaving block 11102 may be equipped with heaters 11132, as shown in FIG. 122, to increase its temperature during the cleaving process. Heater 11132 can be an electrically-controlled resistive heating element which is implemented by embedding or otherwise inserting wire 11134 into the block and applying a controlled electrical current to establish the proper temperature of the cleaving block. The heater as described, as well as alternative heating elements, are well known and may be readily adapted for use in a similar manner.

(2) A second embodiment

Figure 128:
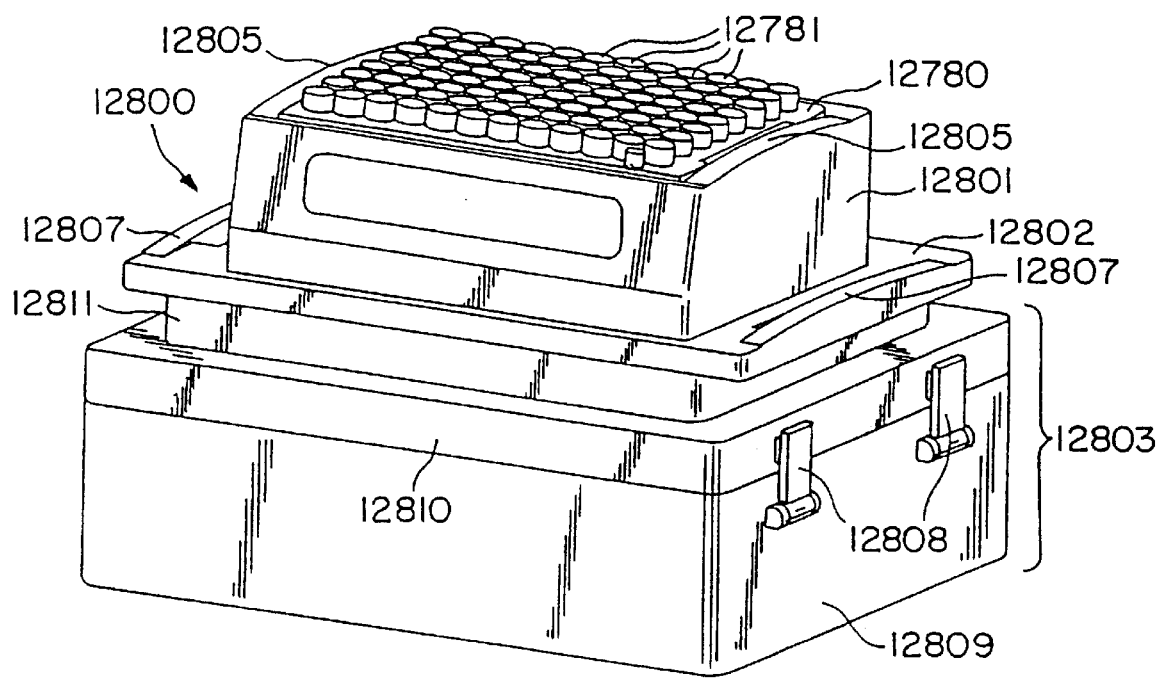

The cleaving assembly 12800 illustrated in FIG. 128 provides an alternate embodiment for cleavage of synthetic compounds. Microreactor carrier tray 12780 is removed from sorter assembly 12700 after the microreactor carriers 12871 have received the appropriate memory devices and is placed on cleaving block 12801.

Cleaving block 12801 is shown with the tray 12780 disposed on its upper surface, positioned within the recessed area between guide rails 12805. As in the previous embodiment, exemplary cleaving block 12801 is formed with an array of ninety-six wells 13001 having dimensions to provide a small clearance fit between microreactor carriers 12780 and well walls 13002, the detail of which is shown in FIG. 131. Cleaving block 12780 may be formed with any number of wells 13001 for compatibility with standard microtitre formats or custom formats. The lower portion of cleaving block 12780 is formed as a flange 12802 which overhangs a recess 12811, to facilitate raising and lowering the upper portion of cleaving assembly 12800. Stepped or recessed areas 12807 in the outer side edges of flange 12802 may be formed to enhance the ability to grasp flange 12802. Below recess 12811 is a base portion 12810 which provides the upper sealing portion for vacuum chamber 12809. As shown in FIG. 130, cleaving block 12801 is formed as an outer shell 13001, which includes ridges 12805, flange 12802, recess 12811 and base portion 12810, which surrounds center block 13003 into which wells 13001 are formed. Wells 13001 may be formed by machining bores into the material from which center block 13003 is formed, which, as in the previous embodiment, may be TEFLON™ or polypropylene. Referring to FIG. 132, in addition to the bores, a lateral extension 13004 is created in the bottom of well 13001 to provide fluid communication with the lower end of a second bore 13017 into which the ascending portion 13008 of a U-tube is inserted. The bottoms of wells 13001 are sealed by plate 13006, which is attached to the lower surface of center block 13003.

As previously described with regard to other embodiments of the cleaving assembly, U-tubes are used to draw the cleaved fluid from wells 13001 into vials 13020 located within vacuum chamber 12809, as shown in FIG. 130. Referring again to FIG. 132, ascending portion 13008 of U-tube closely fits within second bore 13017. The relative dimensions of the lower end 13021 of the U-tube and the lower end of second bore 13017 are such that an interference fit is provided to create a tight vacuum seal for drawing the liquid in the bottom of well 13001 through bore 13017 and into the U-tube. The details of the interference fit and the slanted cut of lower end 13021 are provided in FIG. 133.

Referring again to FIG. 132, at the top of bore 13017, U-tube 13014 bends and turns downward into third bore 13010, which continues through center block 13003 and lower plate 13006, allowing descending portion 13009 of the U-tube to extend beyond the bottom surface of the cleaving block. Using the same interrelationship described with reference to FIGS. 123 and 124, as shown in FIG. 132, the combination of the bend 13014 in the U-tube and the nipple 13023 which extends downward from the bottom of carrier tray 12780 provide a valve for preventing the flow of fluids through the U-tube when downward pressure is applied to the carrier tray 12780 by pinching bend 13014 between nipple 13023 and bridge 13015, which is located between the tops of second bore 13017 and third bore 13010. A top view showing the relative positioning of wells 13001 and bend 13014 in the U-tube for a plurality of wells 13001 is provided in FIG. 131. As previously described with reference to other embodiments, the U-tube is formed from resilient material with provides can be compressed under external pressure to cut fluid flow therethrough, but resides to re-open when the external pressure is released.

Referring again to FIG. 132, The descending portion 13012 of the U-tube extends beyond the bottom surface of plate 13006 via third bore 13010, across gap 13011, and through nozzle array interface plate 13022, in which is formed an array of ports 13007. Gap 13011 is provided to permit the routing of the exiting U-tubes 13012 to various ports 13007 in plate 13022, allowing a variety of routing options to be selected. It should be noted that the direct vertical correspondence between the exiting U-tubes 13012 and the feeding end 13016 of the U-tubes is shown for simplicity, and that exiting U-tubes may be passed laterally within gap 13011 so that it is directed toward a different vial or vials 13020 within vacuum chamber 12803. Vials 13020 are retained within vial tray 13025, which is positioned on the inside of vacuum chamber bottom 12809.

In order to provide a good quality seal against the loss of vacuum within vacuum chamber 12803, the upper inside edge 13024 of vacuum chamber 12809 should create an interference fit with the lower edge of interface place 13022. Referring back to FIG. 129, the vacuum seal is also enhanced by the use of latches 12808, which pull and lock base 12811 and vacuum chamber bottom 12809 together. The vacuum tubing 13026 is connected to a vacuum pump or other conventional means for drawing a vacuum on vacuum chamber 12803.

EXAMPLE 4

Preparation of a Library and Encoding the Matrices with Memories

A typical matrix with memory, such as the MICROKAN matrix with memory reactor will provide the following yield:
Resin loading: 0.5–1.0 μmol/mg resin
Using 30 mg of resin: 15–30 μmol compound
For a 500 MW compound: 7.5–15 mg of compound.

A pool of the matrices with memories prepared as in EXAMPLE 2 was split into two equal groups. Each group was then addressed and write-encoded with a unique radio frequency signal corresponding to the building block, in this instance an amino acid, to be added to that group.

The matrices with memories were then pooled, and common reactions and manipulations such as washing and drying, were performed. The pool was then re-split and each group was encoded with a second set of radio frequency signals corresponding to the next set of building blocks to be introduced, and the reactions were performed accordingly. This process was repeated until the synthesis was completed. The semiconductor devices also recorded temperature and can be modified to record other reaction conditions and parameters for each synthetic step for storage and future retrieval.

Ninety-six matrices with memories were used to construct a 24-member peptide library using a 3×2×2×2 "split and pool" strategy. The reactions, standard Fmoc peptide syntheses [see, e.g., Barany et al. (1987) Int. J. Peptide Protein Res. 30:705–739] were carried out separately with each group. All reactions were performed at ambient temperature; fmoc deprotection steps were run for 0.5 h; coupling steps were run for 1 h; and cleavage for 2 h. This number was selected to ensure the statistical formation of a 24-member library [see, Burgess et al. (1994) J. Med. Chem. 37:2985].

Each matrix with memory in the 96-member pool was decoded using a specifically designed radio frequency memory retrieving device [Bio Medic Data Systems Inc. DAS-5001 CONSOLE™ System, see, also U.S. Pat. No. 5,252,962 and U.S. Pat. No. 5,262,7721 the identity of the peptide on each matrix with memory. The structural identity of each peptide was confirmed by mass spectrometry and $^1$H NMR spectroscopy. The content of peptide in each crude sample was determined by HPLC to be higher than 90% prior to any purification and could be increased further by standard chromatographic techniques.

Detailed exemplification of the use of the combinations for synthesis of libraries is described in co-pending, co-owned application U.S. application Ser. No. 08/881,248, filed Jun. 24, 1997, which is incorporated by reference in its entirety.

EXAMPLE 5

Synthesis of Oligonucleotide Libraries on OMDs

Oligonucleotide libraries are synthesized on OMDS [described above, see, e.g., FIGS. 22–30 and 33]. Referring to FIG. 33, polypropylene sheets [(10×10×1 mm) the Moplen resin e.g., V29G PP resin from Montell, Newark Del., a distributor for Himont, Italy] are radiation grafted with polystyrene to give the surface modified devices 1 [MACROCUBES™ or MACROBEADS™]. Each such device is imprinted with a unique symbology, such as the two-dimensional optical bar code using the methods described herein. The OMDs [also called laser optical synthesis chips] are then subjected [see, FIG. 33] to a modified aminomethylation procedure [Mitchell et al. (1978) J. Org. Chem. 43:2845; Mitchell et al. (1976) J. Org. Chem. Soc. 98:7357; or other procedures to obtain other functional groups (Farrall et al. (1976) J. Org. Chem. 41:3877; Merrifield et al. (1985) Angew. Chem. Int. Ed. Engl. 24:799])] to functionalize the polystyrene surface graft. Procedures are exemplified in the examples.

Figure 33A:
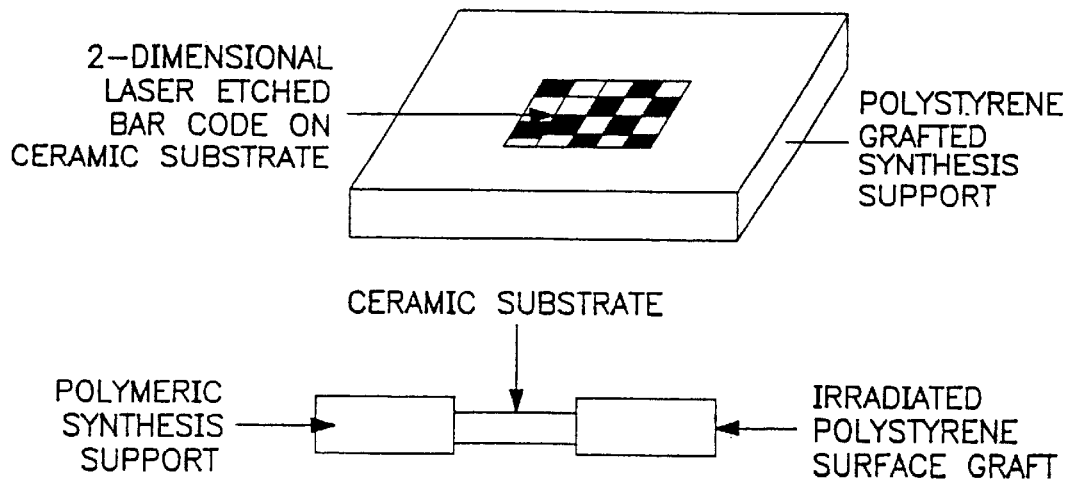
FIG. 33A illustrates an exemplary OMD.
Figure 33B:
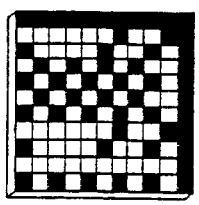
FIG. 33B depicts a close-up of a 2-D laser etched bar code that is read by the software described herein that reads the code in two dimensions, horizontally and vertically simultaneously using a camera and pattern recognition software described herein. With reference to the exemplified embodiment [see EXAMPLES], the code in this figure is 0409AA55AA550409. The blacked out and whitened squares represent data units. Etching of the entire 2-D bar code by a $CO_2$ laser can be accomplished with a resolution below about 0.5 mm.
Figure 33C:
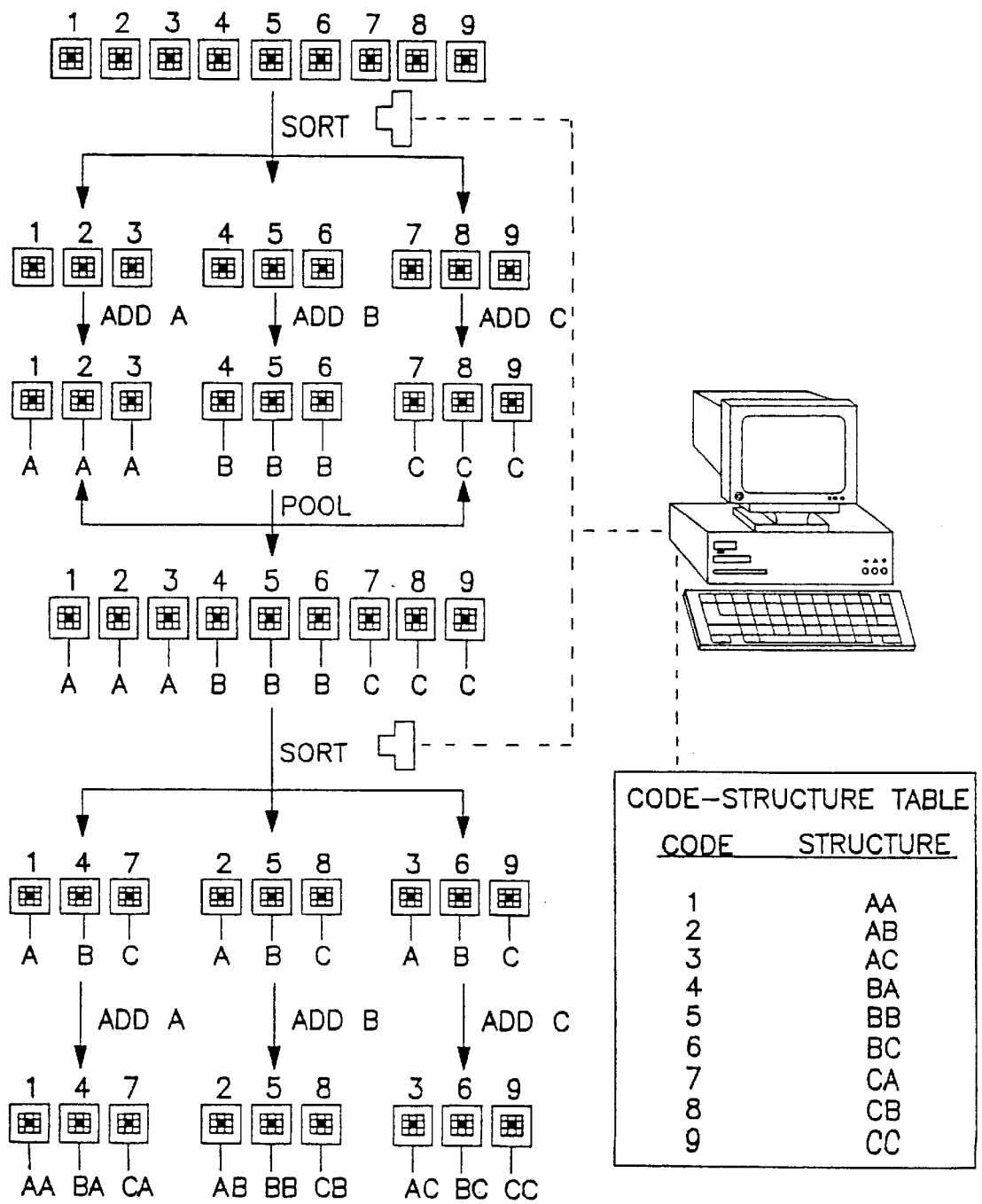
FIG. 33C depicts a split and pool combinatorial synthesis protocol using the OMDs and directed sorting. A, B and C represent building blocks, and the numbers above each OMD represent a 2-D optical bar code [single digits are used merely for exemplification].

A laser optical memory device is shown in FIG. 33A and 33B. It was fabricated by combining two components: a 2-dimensional (2-D) 16 digit bar code for encoding and a separate polymeric support for synthesis. The 2-D bar codes were laser-etched by a $CO_2$ laser on 6×6 segments of a chemically inert alumina ceramic plate (Coors Ceramics, thickness=0.5 mm; the actual size of each 2-D bar code is 3×3 mm). The surrounding synthesis support is a stable polypropylene or fluoropolymer square (10×10×2 mm) radiologically grafted [as describe herein] with low cross-linking polystyrene [Battered, G. W. Tregear, (1967) in Graft Copolymers, John Wiley & Sons, Interscience, New York] and designed with a square hole (6×6 mm) in the middle. The etched ceramic block is securely inserted within the hole to form the entire OMD. Very small size OMDS can be manufactured as the laser etching optical resolution of an entire 2-D bar code can extend well below 0,5 mm in total diameter. 2-D bar coding has the advantage over regular linear bar coding of more data compression in a much smaller surface area (FIG. 33B).

A loading of a 5–8 µmol/device was typically obtained as measured by Fmoc analysis. At this point, the OMDS are ready for use in combinatorial or standard chemical synthesis.

A directed sorting strategy [instead of statistical pool and splitting] was used in the construction of combinatorial libraries with zero redundancy [i.e., the number of OMDs is equal to the number of the library members]. In an example of a 3×3 directed sorting synthesis [FIG 33C), nine OMDs are first scanned optically using a small camera [ i.e., such as the QuickCam™] linked to the pattern recognition software [see, Appendix I and description above and FIG. 31] on a computer, and each device [with a unique 2-D bar-code], i.e., 1–9, for exemplification, is assigned to one of the nine members in the library [a Code-Structure Table] by the software that directs the synthesis, such as the Synthesis Manager software, [see Appendix III and description above and in the EXAMPLES]. The OMDs are then split [sorted], using software for synthesis and for decoding the 2-D code pattern [see Appendix I and description herein] into three groups according to the first building block (A, B, or C) for each structure as pre-assigned in the Code-Structure Table. A reaction with building block A, B, or C is then performed on each specific group. The OMDs are then pooled, washed, subjected to common reactions, scanned and re-sorted into three new groups according to the second building block (A, B, or C). A second reaction with building block A, B, or C is then performed with each group of OMDs. The OMDs can then be pooled again, subjected to common manipulations, and sorted. The process is repeated until the synthesis is completed. The structure of the compound synthesized on each OMD can then be decoded by optically reading the 2-D image with synthesis software via the camera and the decoding software and correlating the bar code with the structures in the Code-Structure Table.

Figure 33D:
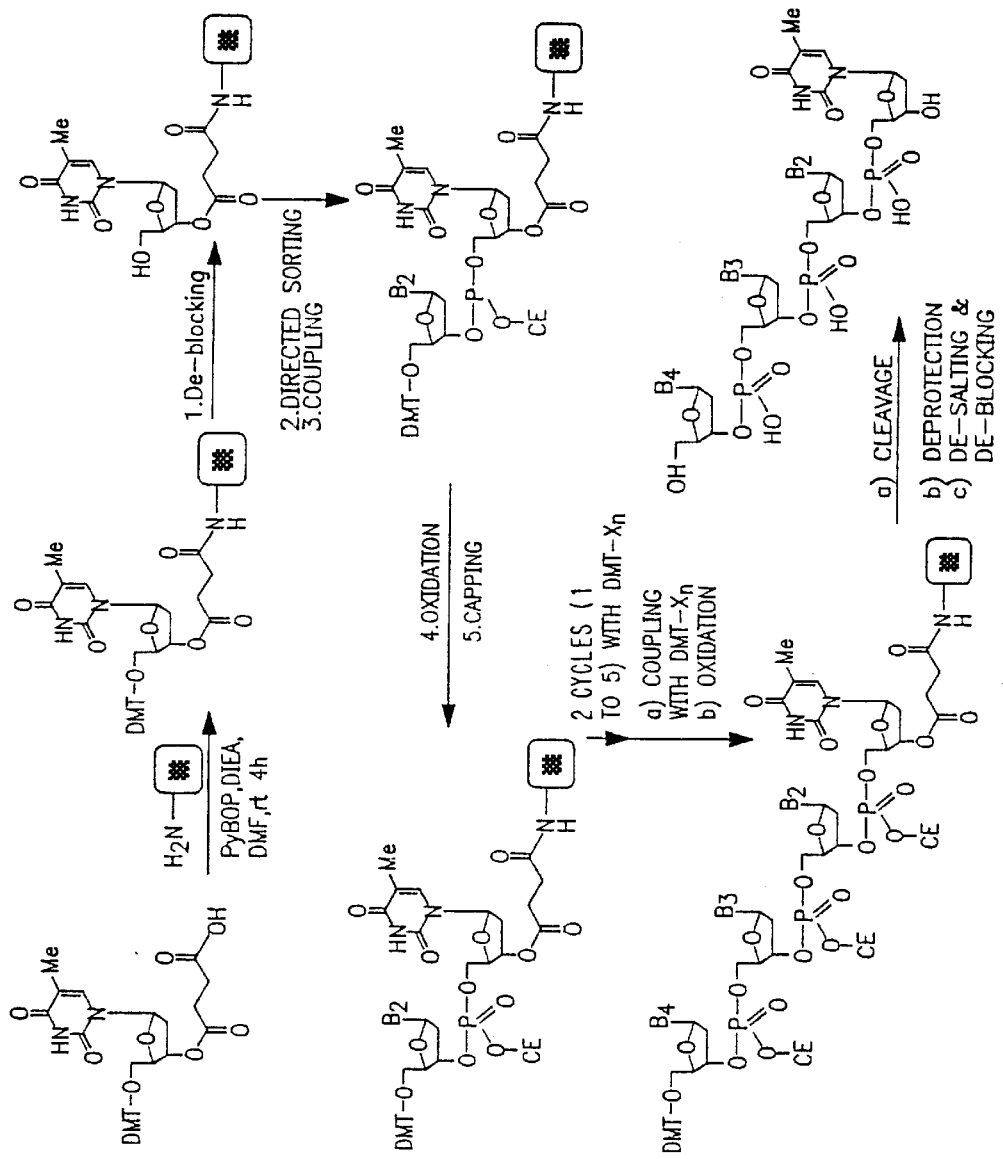
FIG. 33D depicts synthesis of a 3×3×3 oligonucleotide library using the OMDs and directed sorting [reaction conditions are described in the EXAMPLES; DMT-$X_2$, $X_3$ or $X_4$ is 5'-O-DMT-2'deoxyadenosine-3'-O-phosphoramidite, 5'-O-DMT-2'deoxycytidine-3'-O-phosphoramidite, 5'-O-DMT-2'deoxyguanosine-3'-O-phosphoramidite; $B_2$, $B_3$ or $B_4$ is adenine, cytosine or guanine.
Figure 33E:
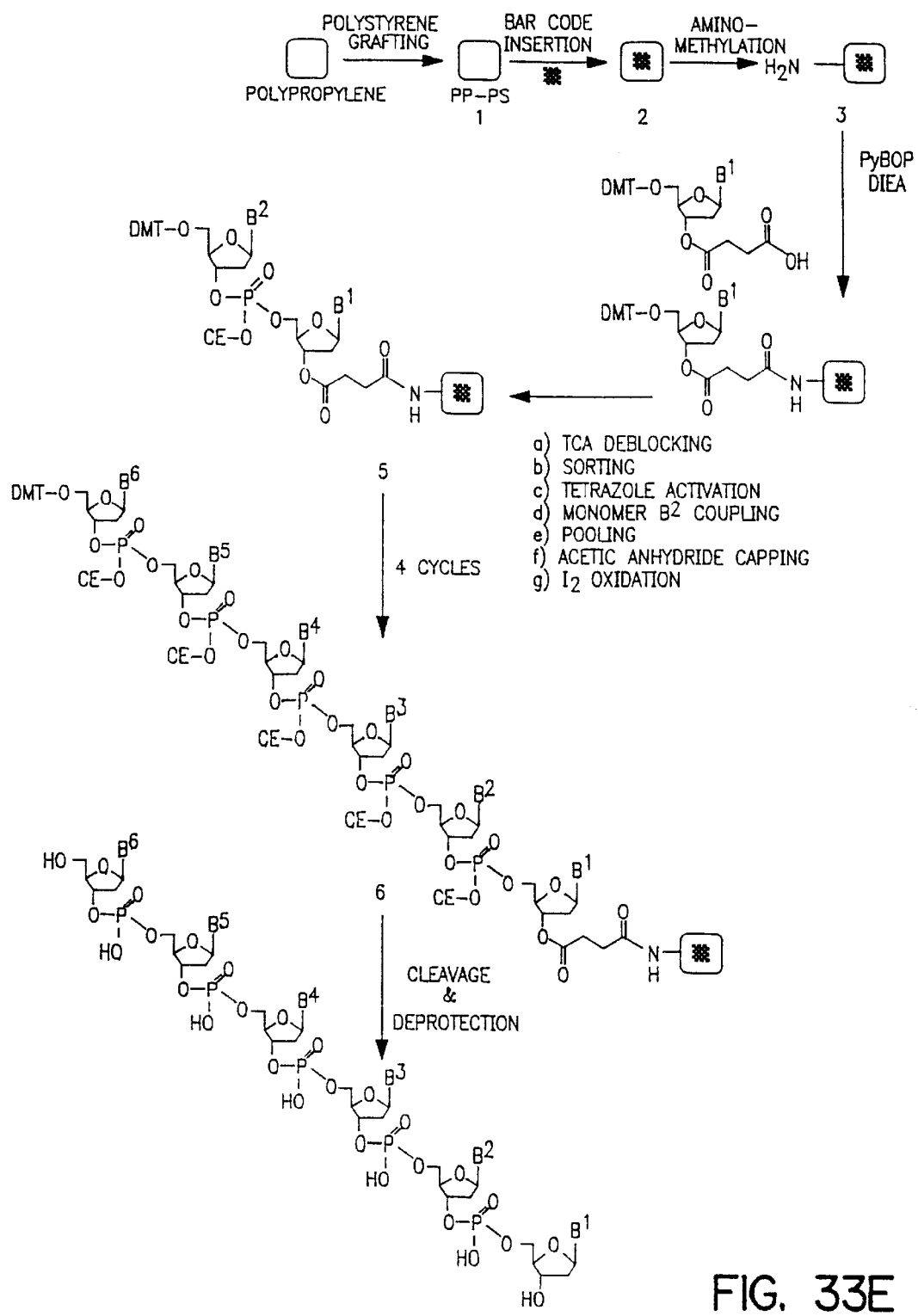
FIG. 33E depicts an oligonucleotide hexamer library using the optical memory device. Each B" refers to a nucleoside base, and the resulting library, where n=6, will contain 4096 unique members [$4^6$=4096].

To demonstrate the utility of the laser optical synthesis OMDs in the large scale synthesis of oligonucleotides, a library of 27 oligonucleotides with a general structure of $X_4$-$X_3$-$X_2$-T was constructed using the above described Directed Sorting strategy (FIG. 33D). Since polystyrene does not completely swell in acetonitrile or water, which are the solvents for the coupling and cleavage steps in a standard oligonucleotide synthesis cycle[Gait et al. (1990) in *Oligonucleotide Synthesis, A Practical Approach*, Gait, Ed., IRL Press, Oxford], reaction conditions were modified to accommodate the polystyrene support. Among the range of solvents and co-solvents investigated, it was found that a mixture of acetonitrile and dichloromethane (2:3, v/v) for the coupling reaction gave the highest coupling efficiency, and water/1,4-dioxane (1:1, v/v) performed best as the solvents for the cleavage step. The standard conditions for the de-blocking step (3% trichloroacetic acid/dichloromethane) and the oxidation step (0.1 M $I_2$/THF) are directly applicable. All reactions [see FIG. 33D] were performed in appropriate size glass bottles with Teflon-lined screw caps, and all the washings are performed using acetonitrile and dichloromethane alternately.

Reaction conditions were as follows:
de-blocking, 3% TCA/DCM, rt, 2 min, repeat 2 times, coupling, 0.1 M DMT-$X_n$, 0.3 M tetrazole, ACN/DCM (2:3 v/v), rt, 1 h; oxidation, 0.1 M $I_2$, THF/pyridine/$H_2O$ (40:10:1, v/v/v), rt, 20 min; capping, 0.5 M $Ac_2O$, 0.5 M 1-methylimidazole, 0.45 M 2, 6-lutidine, THF, rt, 20 min.; cleavage, concentrated ammonia/1,4-dioxane (1:1 v/v), rt, 20 h; deprotection, concentrated ammonia, 55° C., 20 h,; de-salting (and de-blocking) on Poly Pak cartridges (according to manufacturer's instructions).

Twenty-seven amino-functionalized OMDs were first reacted with 0.1 M 5'-O-DMT-3'-succinic acid-2'-deoxythymidine/0.1 M PyBop/0.2 M DIEA/DMF (30 ml) at room temperature for 4 hours. The OMDs were washed (acetonitrile and dichloromethane alternately, 30 ml×4 for each solvent) and dried under vacuum at room temperature for 30 min (all subsequent reactions were followed by the same washing and drying procedures). The OMDs were then capped with $Ac_2O$/1-methylimidazole/2,6-lutidine/THF (0.5 M for each, 30 ml) at room temperature for 20 min., and de-blocked with 3% trichloracetic acid/dichloromethane (30 ml, rt, 2 min, repeated two times). UV measurement of the de-blocking solution indicated an average loading of 7.0 µmol per OMD. The OMDs were then scanned and each OMD was assigned to one of the 27 oligonucleotide sequences in the library (Code-Structure Table) using software, such as the Synthesis Manager software described herein, and a camera, such as the QUICKCAM camera. The OMDs were sorted into three groups according to the second residue assignment (A, G, or C) and coupled with one of the corresponding β-cyanoethyl phosphoramidites (0.1 M) in acetonitrile/dichloromethane (2:3, v/v, 10 ml, with 0.3 M tetrazole) at room temperature for 60 min. The OMDs were then pooled together, oxidized (0.1 $MI_2$/THF/pyridine/$H_2O$, 30 ml, rt, 20 min), capped, and de-blocked. Next, the OMDs were subjected to another cycle of sorting→coupling→oxidation→capping→de-blocking according to the third residue ($X_3$) in their assigned structures. After the third residue, the OMDs were scanned, sorted into three groups according to their last residues ($X_4$), coupled to the corresponding phosphoramidites, and oxidized. The capping and de-blocking steps were omitted in this cycle.

The washed OMDs were then scanned with the QUICKCAM™ and the sequence of the oligonucleotides on each OMD was de-coded. Each OMD was put into a 5 ml glass vial labeled with the corresponding oligonucleotide sequence. Concentrated ammonia and 1,4-dioxane (2 ml, 1:1, v/v) was added to each vial and the vials were sealed with Teflon-lined screw caps. The vials were shaken at room temperature for 20 hours to cleave the oligonucleotides from the support. The OMDs were then removed from the vials and rinsed with aqueous dioxane (0.5 ml×2) and the vials were evaporated to dryness under vacuum. Next, fresh concentrated ammonia (2 ml each) was added to each vial. The vials were capped tightly and heated in an oil bath (55° C.) for 20 hours to removed the cyanoethyl, isobutyryl, and benzoyl groups. An aliquot (10 µl) of the crude oligonucleotide solution from each vial was saved for HPLC analysis and the rest of the solutions were evaporated under vacuum. The crude oligonucleotides were then de-blocked and de-salted with Poly Pak™ cartridges (Glenn Research) using standardized procedures [User Guide for Poly Pak Cartridges from Glenn Research]. The fully de-protected oligonucotides were lyophilized from 20% acetonitrile/water (white solids), weighed, and analyzed by MS, $^1$H NMR:

[Selective $^1$H NMR spectra data (500 MHz, $D_2O$). ACCT: s=8.47 (s, 1 H, CH-adenine), 8.37 (s, 1 H CH-adenine), 8.09 (d, J=7.8 Hz, 1 H, CH-cytosine), 8.06 (d, J=7.8 Hz, 1 H, CH-cytosine), 7.68 (s, 1 H, CH-thymine), 6.15–6.32 (3 multiplets, 6 H, CH-cytosine and O—C (N)H), 3.81–5.03 (6 multiplets, 16 H, O—$CH_2$ and O—CH), 2.28–2.92 (4 multiplets, 8 H, CH$_2$), 1.87 (s, 3 H, CH$_3$). ACAT: s=8.47 (s, 1 H, CH-adenine), 8.44 (s, 1 H CH-adenine), 8.35 (s, 1 H, CH-adenine), 8.34 (s, 1 H, CH-adenine), 8.05 (d, J=8.0 Hz, 1 H, CH-cytosine), 7.59 (s, 1 H, CH-thymine), 6.15–6.43 (3 multiplets, 5 H CH-cytosine and O—C(N)H), 3.78–5.1 (7 multiplets, 15 H, O—CH$_2$ and O—CH), 2.17–2.87 (5 multiplets, 8 H CH$_2$), 1.79 (s, 3 H, CH$_3$).]

The OMDs were also analyzed by sequence analysis. Oligonucleotide sequence analysis was performed using electrospray and EM mass spectrometry [ES MS-MS; see, e.g., Siuzdak (1966) in Mass Spectrometry for Biotechnology, Academic Press, San Diego; Metzger et al. (1994) Anal. Biochem. 219:261; Ni et al. (1996) Anal. Chem. 68:1989].

Each oligonucleotide gave the expected molecular ion in mass spectroscopy analysis as configured by the 2-D encoding. Sequence analysis of two oligonucleotides with the same molecular weight showed that they had the expected sequences. The crude products had good to excellent purity as analyzed by reverse phase HPLC. A quick, standard de-salting procedure using Ply Pak cartridges yielded 27 pure (>95% by HPLC) oligonucleotides with good overall isolated yields (while solid, 2–7 mg each). These data show that the combinatorial strategy of oligonucleotide synthesis using the laser optical synthesis (LOSC) technology should produce a large number and quantity of oligonucleotides with high purity.

EXAMPLE 6

Radiation Grafting of a Polymer on a Insert Surface for Preparation of Matrices with Memories Matrices for use as supports for synthesis and for use in coupled [single platform] protocols have been prepared using radiation grafting. These supports include any inert surface, including PTFE [TEFLON®], which heretofore does not appear to have been used for radiation grafting. The methods exemplified below with reference to FIGS. 34 have been designed for use with PTFE as well as other surfaces. A method of radiation-induced grafted copolymerization of styrene to Teflon (PTFE) has been developed.

A. Scheme 1

1. Preparation of polymer

Scheme 1 shows the preparation of polymer. Polystyrene is radiation grafted onto polypropylene or TEFLON® tubes, an RF tag, such as the BMDS tag, or IDTAG transponder, was inserted into the tube to produce what will be provided under the name MICROTUBE. The polystyrene is then functionalized with selected functional groups [i.e., such as "A" in FIG. 34A]. Scintillant is covalently linked onto the polystyrene through "A", and bioactive molecules, such as, for example, biotin, can be synthesized on the surface using the remaining "A" functionalities.

2. Radiation

The Teflon (PTFE) tube was radiated under a Co$^{60}$ source at a dose rate of 0.1×10$^5$ r/h; the total dose is typically 2.6–2.9×10$^6$r.

3. Polymers

Using radiation-induced grafting polymerization techniques, a variety of monomers such as styrene, acrylic acid, methylacrylic acid, 2-hydroxy-methylacrylate, and other such monomers can be used to produce different polymeric surfaces with different functional groups on polypropylene (PP), polyethylene (PE) and fluoropolymers. Polyethylene oxide (PEG) may be grafted onto the surface to change the hydrophilicity and reduce the steric-hindrance to antibodies or receptors. Functional groups such as amines, alcohols and phenols, carboxylic acids, halides, aldehydes, nitrites and other such groups can be introduced.

It was found that dilution of monomers, such as styrene, with methanol enhanced the rate of grafting PP and PTFE tubes have demonstrated highest styrene grafting at styrene concentrations of about 25 to 50%.

4. Functionalization

The functionalization was performed using the readily available N-(hydroxymethyl) phthalimide, with trifluoromethanesulfonic acid as catalyst. The polystyrene grafted tubes is thoroughly washed before use to remove residual monomer, non-attached polystyrene and additives remaining from radiation grafting. The amidoalkylation proceeds smoothly in the 50% (v/v) trifluoroacetic acid-dichloromethane as solvent at room temperature for 24 hours. The predetermined loading can be obtained by changing the concentrations of reagent, catalyst and reaction time. The hydrazinolysis in refluxing ethanol gives the aminomethyl polystyrene grafted PTFE tube.

The MICROTUBE microreactors were prepared in different sizes (2–12 mm) with loading capacity range from 0.5–15 ymol per tube.

5. Fluorophores

The scintillants, which are chemical stable, were chosen to match the energy gap from radiation energy of radioisotopes. Scintillants such as 9-anthracenepropionoc acid, 1-pyrenebutanoic acid and their derivatives are matched to the energy transfer for different radioisotopes, in including $^{125}$I, $^3$H, $^{14}$C and others. Care should be taken when selecting combinations of scintillants and radioisotopes to match so that energy transfer from isotope to scintillant is matched.

A portion of the functional groups were covalently linked to the mixture of primary fluor (S1, molecules that emit light following interaction with radiation) and secondary fluor (S2, wavelength shifter). Experiments were performed with mixture of S1/S2 at the ratio ranging from 20:1 to 100:1 for S1 and S2 respectively, with optimum ratio of 40:1 for most of the experiments presented here. Conditions in which 20% to 80% of the functional groups were occupied with mixture of S1/S2 were evaluated. The optimum number of the functional group linked to primary and secondary fluors for most of the experiments was 50%.

The remaining of the functional groups (20% to 80%) were used for chemical synthesis. Small molecules (e.g., biotin) were synthesized on the solid support as described in the scheme 2.

6. Chemical synthesis on the surface of MICROTUBE:

A variety of small molecules, such as biotin, peptides, and oligonucleotides, may be synthesized on the MICROTUBE microvessel [see, e.g., scheme 2 (biotin), below]. In order to reduce steric hindrance and improve the interaction of labeled biological target (e.g. antibody, receptor, and complementary DNA or RNA, labeled probe), and depending on the size and nature of the small molecule, different percentages of the functional groups were used for chemical synthesis while the remaining functional group(s) were blocked with Boc. Conditions in which 0.25% to 100% of the functional groups were used for chemical synthesis were evaluated. The results indicated that use of 25% of the functional groups for chemical synthesis is optimal.

B. Scheme 2: Biotin synthesis

In order to reduce steric hindrance and improve the interaction of labeled biological target [e.g., $^{125}$I-receptor), and depending on the size and nature of the small molecule, a different percentage of the functional groups was utilized for chemical synthesis, while the remaining functional group were blocked with Boc. The experiments indicate that optimum results are obtainable with 25% of the functional group dedicated for chemical synthesis.

1. Synthesis

Fmoc (Fmoc-Gly-OH) and Boc(Boc-Gly-OH) linked amino acids were used to control the loading of scintillants and remaining amines. The Fmoc groups were removed using 20 piperidine in DMF, and Boc groups were removed using 1:1 ratio of TFA and dimethylmethane. 50% amine groups were covalently linked to scintillants. The remaining 50% amine were used to synthesize biotin.

2. Assays

The activity of molecules synthesized on the surface of the microvessels may be evaluated in a variety of solid based assay formats.

a. SPA Assay

The biological activity of small molecules synthesized on the surface of the matrices with memories with scintillant may be evaluated in a variety of scintillation proximity assay formats as described herein. For example, biotin and its derivative (2-imidazolidone-4-carboxylic acid) were synthesized on the tube and the binding characteristics of the synthesized molecules on the solid support to $^{125}$I-streptavidin in scintillation proximity assay were evaluated. The results demonstrated that biotin derivative (2-imidazolidone-4-carboxylic acid) that has much lower affinity for streptavidin exhibited a lower signal.

b. ELISA type assay

ELISAs can be performed using antibodies to small molecules, such as a peptide. For example metenkephalin was synthesized on the MICROTUBE micro-vessel, and anti-metenkephalin antibody was used. As an example of nonpeptide small molecule biotin was synthesized and an anti-biotin antibody labeled with alkaline phosphatase was used to detect by calorimetric, fluorometric or luminescent means.

C. Radio-immunoassay

Using radio-labeled antibody or receptor, a variety of radio-immunoassays may be designed using the microvessels, such as the MICROTUBE microreactors.

d. Detection of the oligonucleotides

A variety of the labeled probes (e.g., fluorescence and radiolabels) may be used to detect the identity of a synthesized oligonucleotide on the surface of the polymer, which has been radiation grafted [see, below] on the MICROTUBE microvessel (or on a particle in a MICROKAN microreactor]. Oligonucleotides may be also characterized using a labeled complementary DNA or RNA in a hybridization assay.

C. Radiation grafting

Figure 34A:
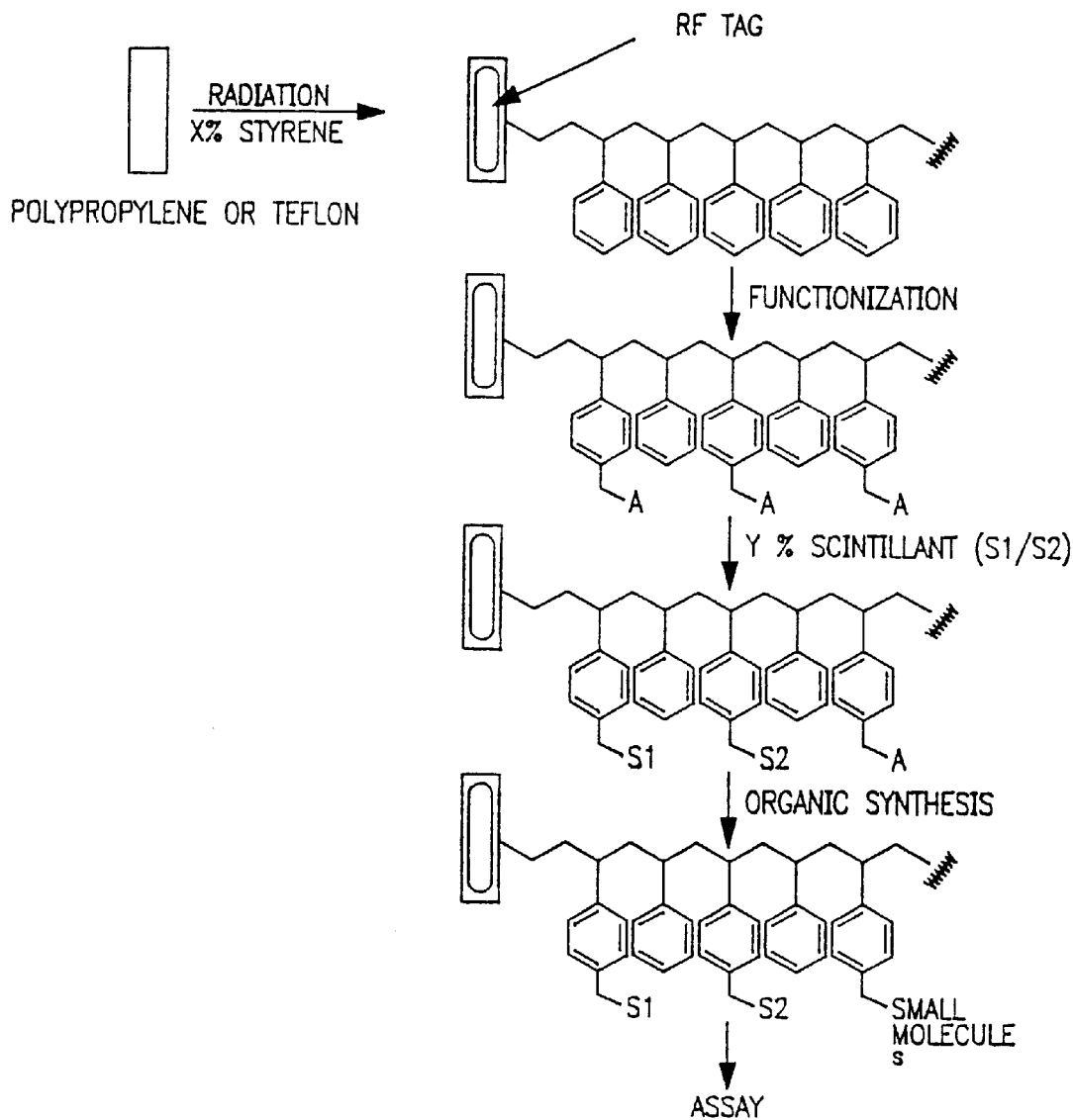
FIG. 34A exemplifies the grafting of a polymer to a tube containing an RF tag, linkage of scintillant to the surface, organic synthesis and then use of the resulting compound linked to the support in an assay. Thus, all steps are performed on the same platform.
Figure 34B:
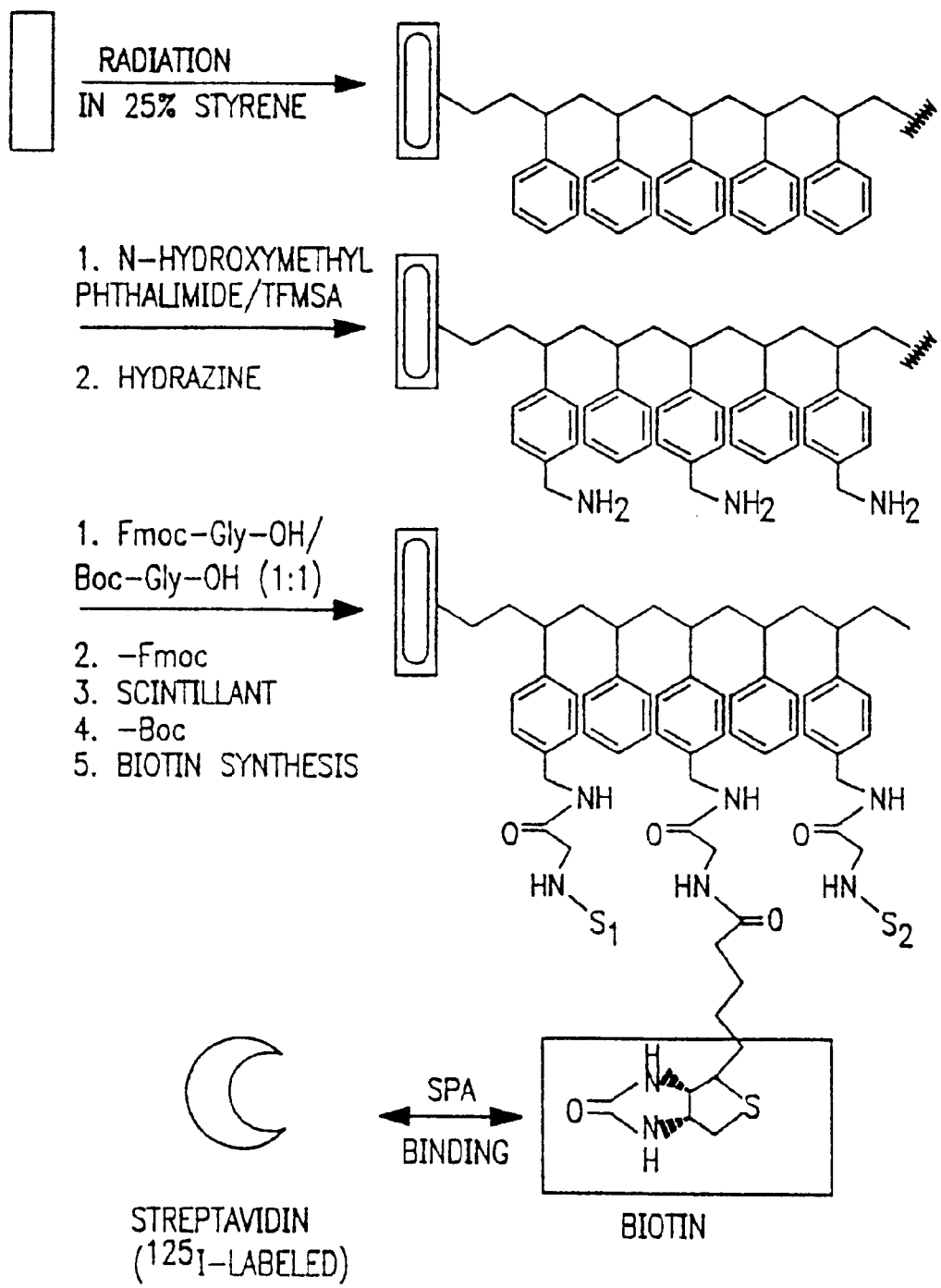
FIG. 34B also exemplifies a single platform protocol.
Figure 34C:
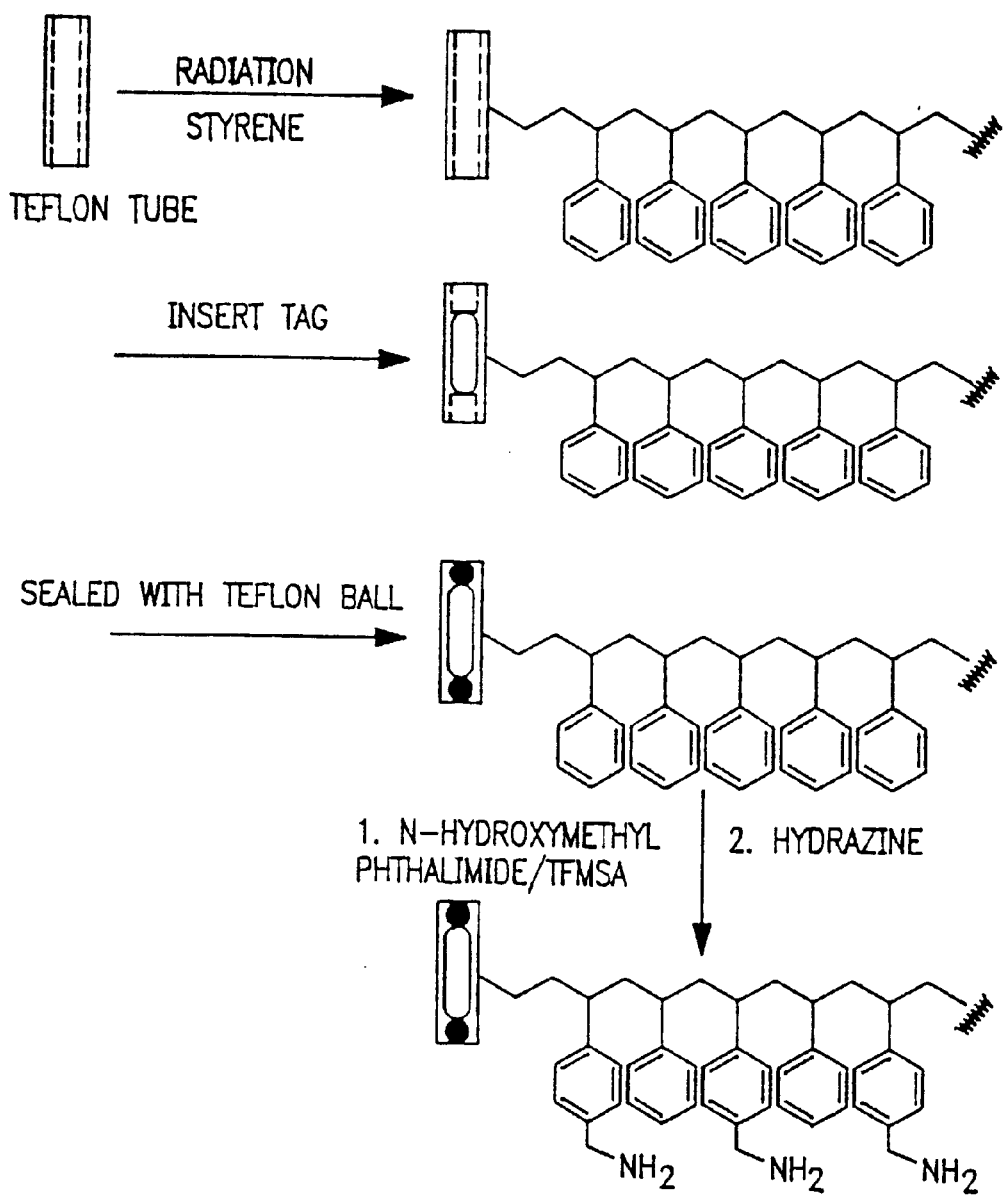
FIG. 34C depicts the preparation of a tubular devices in which the matrix is the radiation grafted PTFE and the memory is a transponder, such as the BMDS transponder or IDTAG™ transponder [such as a MICROTUBE], described herein.
Figure 34D:
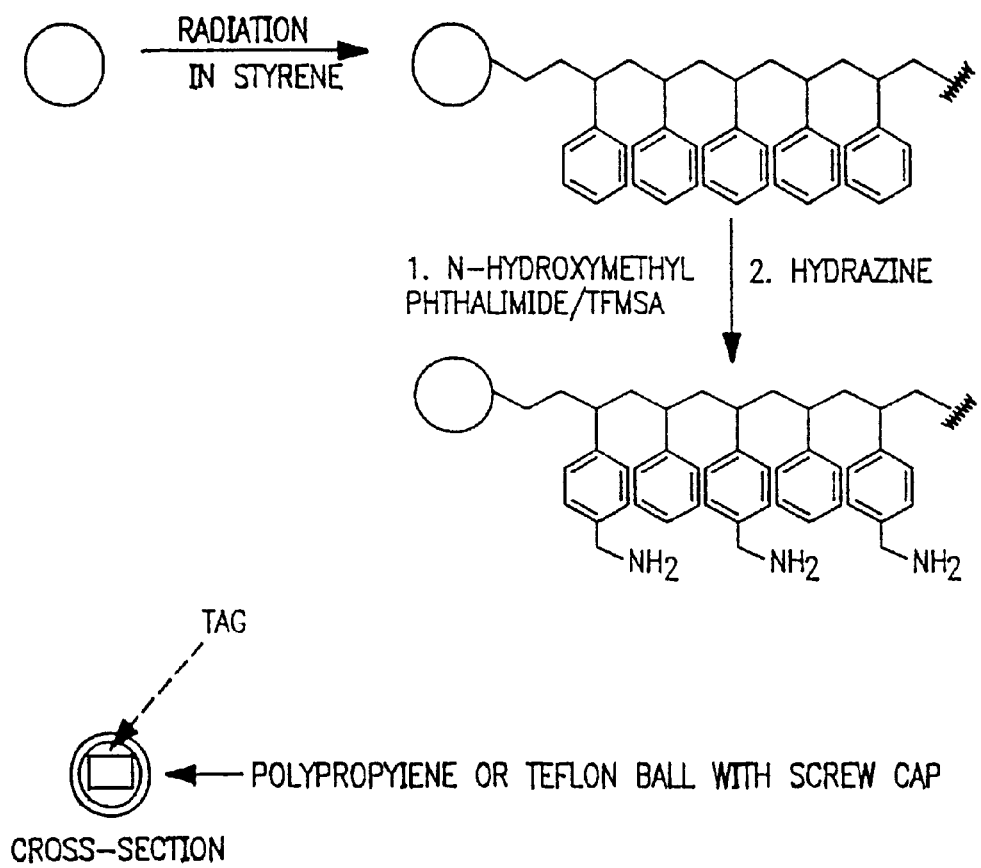
FIG. 34D depicts a small chip [2 mm×2 mm×0.1 mm] encased in a radiation grafted polypropylene or Teflon ball [ball or bead or other such geometry] with a screw cap [such as a MICROBALL or MICROBEAD]. It is understood herein that microvessels, such as the MICROBEAD, are not necessarily tubular in shape, but may be any geometry.

Teflon tube [19 mm, long, OD:5 mm, ID:2 mm; see FIGS. 34C and 34D] were radiation grafted. It was found that dilution of styrene with methanol enhances the rate of grafting. Dilutions of from 5% to 70% were tested. The PTFE tube has the highest styrene grafting at 50% dilution. The polypropylene tube has the best performance at 35% dilution. The Teflon (PTFE) tube is radiated under Co$^{60}$ source at a dose rate of 0.1×10$^6$ r/h; the total dose of 2.6–2.9×10$^6$ r.

Functionalization was performed using N-(hydroxymethyl) phthalimide, with trifluoromethanesulfonic acid [TFMSA] as a catalyst. The polystyrene grafted PTFE tube is thoroughly washed before use to remove residual monomer, non-attached polystyrene and additives remaining from radiation grafting. The amidoalkylation proceeds smoothly in the 50% (v/v) trifluoroacetic acid—dichloromethane solvent at room temperature for 24 hours. The predetermined loading can be obtained by changing the concentrations of reagent, catalyst and reaction time. The hydrazinolysis in refluxing ethanol gives the aminomethyl polystyrene grafted PTFE tube.

FIG. 34 depicts the protocol for radiation grafting of polymers to the surface of TEFLON® [or other suitable surface]. FIG. 34C depicts the preparation of a tubular devices in which the matrix is the radiation grafted PTFE and the memory is a transponder, such as the monolithic device provided herein, the BMDS transponder or IDTAG™ transponder [such as a MICROTUBE], described herein; and FIG. 34D depicts the small chip [2 mm×2 mm×0.1 mm, see, FIGS. 51 and 51] encased in a radiation grafted polypropylene or Teflon ball [or bead, conical tube or other such geometry] with a screw cap or snap on lid [such as device provided herein that will be provided under the name MICROBALL or MICROBEAD or MICROTUBE]. These devices may have removable lids, such as a snap on lid, preferably a snap on lid, or a screw top, so that the memory device can be removed and reused, and can be added after radiation grafting. Loading on the grafted tubes and balls is adjustable can was typically about 0.5–15 μmol per tube. The amount can be varied by altering the size of the tube or balls. A variety of selected functional groups are available. Any known to those of skill in the art may be used, including any described herein. PTFE devices are particularly suitable for high temperature reactions [loading was less than or about 3 μmol per device].

D. Protocol for Increasing Loading on Fluoropolymer

Dilution of styrene with methanol enhances the rate of grafting. In the radiation-induced grafted copolymerization of styrene to ETFE and Teflon (PTFE) tube (21 mm long, OD:6 mm, ID: 4 mm), dilutions of from 5% to 70% were tested. The PTFE tube had the highest styrene grafting at a 50% dilution. By adding a mineral acid such as sulfuric acid and nitric acid (concentrations from 0.01–0.5 M), the polystyrene grafting was increased from 50–200%. See Table below. Loading was further improved by machining the ETFE/PTFE tubes from rods rather than extruding the tubes from ETFE/PTFE resin beads at high temperatures. The machined tubes, which as a result of the crimping introduced by machining are about 4 mm shorter than the extruded tubes, have more rough surfaces than the extruded tubes.

| Sulfuric Acid (M) | Polystyrene amount (mg) loaded per tube | | |
|---|---|---|---|
| | extruded ETFE tube | machined PTFE tube | machined ETFE tube |
| 0 | 17 | 10 | 19 |
| 0.05 | — | 12 | 32 |
| 0.1 | 38 | 24 | 48 |
| 0.2 | — | 38 | 56 |

In addition, adjusting the polystyrene concentration in combination with the use of acid increased the loading. The best increase was observed at a concentration of about 45% styrene in methanol. At 45% styrene grafted in the presence of acid, the amount of polystyrene loaded per tube was almost 70 mg, compared to in the absence of acid (less than about 20 mg loaded). At other concentrations of styrene in acid the amount loaded varied from about 30 mg to the high of 70 mg. In the absence of acid, loading is substantially independent of polystyrene concentration for the tested concentration range (25% to 50%).

The functionalization was performed as described above, using N-(hydroxymethyl) phthalimide, with trifluoromethanesulfonic acid as catalyst. The polystyrene grafted PTFE tube was thoroughly washed before use to remove residual monomer, non-attached polystyrene and additives remaining from radiation grafting. The amidoalkylation proceeded smoothly in the 50% (v/v) trifluoracetic acid-dichloromethane as the solvent at room temperature for 24 hours.

A predetermined loading can be obtained by changing the concentrations of reagent catalyst and reaction time. The hydrazinolysis in refluxing ethanol gave the aminomethyl polystyrene grafted PTFE or ETFE tube. The loading of amine groups on a PTFE tube was about 41 micromol, and on an ETFE was as high as 52 micromol.

| Acid Concentration (M) | Polystyrene attached on tube surface (mg) PTFE | Polystyrene which attached on tube surface (mg) |
| --- | --- | --- |
| 0 | 10 | 19 |
| 0.05 | 12 | 32 |
| 0.1 | 12 | 33 |
| 0.2 | 20 | 35 |

The two modifications to the procedure using acid and also machining the polymer substantially increased polystyrene radiation grafting loadings. Adding a mineral acid such as sulfuric or nitric (concentrations 0.01 M to 0.5 M) increased the grafted polystyrene from about 20 to 200%. Using a rough surface further increased the loading.

EXAMPLE 7

Wash and SPA Assay Procedure Using MICROTUBE Microreactors

1. Covalently linking scintillant to the surface of the MICROTUBE microreactor

Scintillants (pyrenebutyric acic and 9-anthracenepropionic acid) were covalently linked to the grafted polystyrene on the surface of the polymer. The Fluorophore was linked to 50% of the available functional groups as described above (see polymer preparation).

2. Synthesizing biotin on the MICROTUBE microreactor

The remaining 50% functional amine groups on the surface of the MICROTUBE microreactor was estimated by Fmoc to be ~1.8 μmol/tube. The amine group was covalently linked to biotin under conditions described below. 0.012 M biotin, 0.024 MDiEA (diisopropylethylamine), 0.012 M PYBOP (Benzotriazol-1-yl-oxy-tris-pyrrollidino-phophonium hexafluorophosphate) in DMF (N,N-Dimethyl foramide) at room temperature for 1 hour.

3. Washing protocol for MICROTUBE microreactors

A. Development and Optimization of wash procedure.

The MICROTUBE microreactors were washed with various detergents (SDS, CHAPS, Triton X-100, or Benzalchonium Chloride) or charcoal. The effects of detergents were evaluated by washing the microreactors with different concentrations of detergents (0.5 to 5% in PBS) for 24 hours on an orbital shaker at room temperature. The charcoal wash was done by dialysis against PBS containing 10–35% charcoal (4–8 mesh)

It was found that the MICROTUBE microreactors that had been washed with SDS, Benzalchonium Chloride or charcoal had an improved signal. Additional wash studies were performed with either SDS and/or charcoal in wash buffer. The effect of SDS concentration was assessed by washing the tube with 0.25, 0.5, 0.75, or 1% SDS in PBS for 24 hours. Results of this experiment indicated that microreactors that had been washed with 0.5%–0.75% SDS and/or charcoal in PBS yielded a better signal.

Finally, the optimal wash period was determined by washing microreactors with 0.75% SDS/charcoal for 1, 2, 3, 4, or 5 days at room temperature on an orbital shaker. The results of this experiment revealed that washing tubes for 2 days efficiently removes undesirable material which interfere with the SPA signal.

B. Optimized Wash Procedure.

After synthesis of small molecules (biotin) on the MICROTUBE microreactors were washed as described above. The MICROTUBE microreactors were placed in a dialysis bag and were dialyzed against PBS containing 0.75% SDS +/–35% charcoal for 2 days at room temperature on an orbital shaker. At the end of SDS wash, microreactors were rinsed with PBS (10 ml/MICROTUBE) 2 times.

Thus, performance of assays on solid supports can be improved by washing the solid support with linked biological particle or molecule with 0.75% SDS with or without 35% charcoal in PBS (pH 7.2) for about 2 days.

2. Blocking

The MICROTUBE microreactors were placed in PBS (pH 7.2) buffer containing 3% BSA (bovine serum albumin) and incubated overnight at 40° C.

3. SPA Detection.

Biotin was detected in the SPA format. MICROTUBE microreactors were placed in 24 well plate containing 1 ml of Assay Buffer [10 mM Sodium Phosphate pH 7.2, 150 mM NaCl, 0.5% BSA, 0.05% Tween 20, and $^{125}$I streptavidin (244 ng/ml, specific activity 0.291 μCi/μg)]. MICROTUBE microreactors were incubated at room temperature on an orbital shaker for 2 hours. The extent of $^{125}$I streptavidin binding on the MICROTUBE microreactors was assessed in a Wallac MicroBeta Trilux scintillation counter.

EXAMPLE 8

Assembly System for the MICROTUBE Microreactors

As described elsewhere herein, microvessels that are hollow, preferably tubular, devices fabricated from a polymeric material, such as PTFE, ETFE, or other such material as set forth herein, and treated to render the outer surface suitable for linking biological particles or molecules are provided herein. These microvessels include the MICROTUBE microreactors. An assembly system for preparation of these microreactors, with reference to the MICROTUBE microreactors is provided herein.

Figure 79:
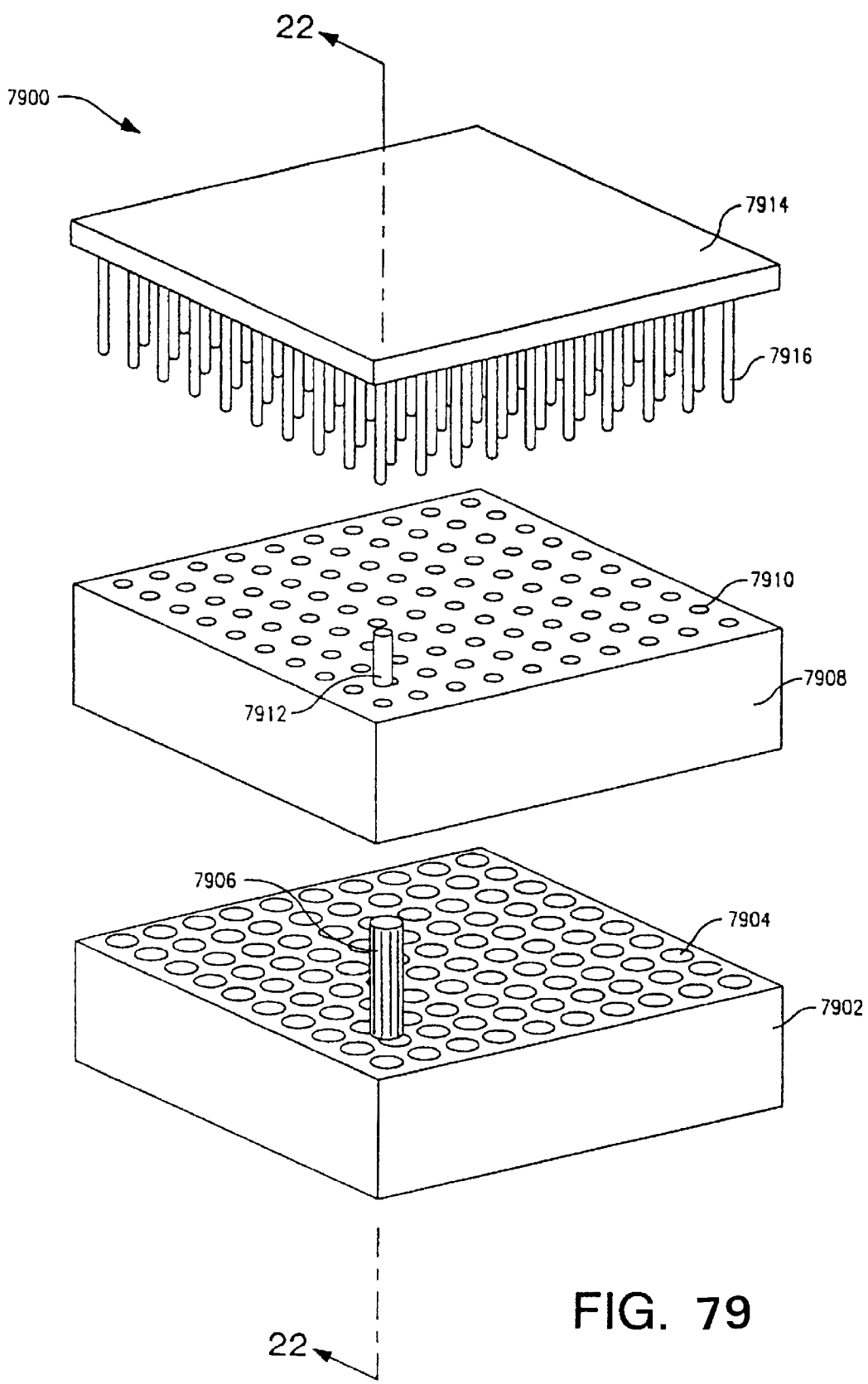
FIG. 79 is a perspective view of a MICROTUBE microreactor or assembly system showing the insertion of a microtag into a MICROTUBE microreactor.

Referring now to FIG. 79, a MICROTUBE microreactor assembly system is shown and generally designated 7900. System 7900 includes a MICROTUBE microreactor loading block 7902, a microtag holding block 7908, and a plunger plate 7914. The MICROTUBE microreactor loading block 7902 is formed with an array of bores 7904 which are each sized to receive a substantially cylindrical MICROTUBE microreactor, with each bore being formed with a narrow ejection port 7928 to prevent the passage of the MICROTUBE microreactor through the loading block 7902. The MICROTUBE microreactor, and variations thereon, will be more fully described in conjunction with FIGS. 83 through 96. The microtag holding block 7908 is formed with an array of bores 7910 which extend through the block 7908, and each of which are sized and formed to receive and retain a microtag 7912. The plunger plate 7914 includes an array of plungers 7916 which are aligned with the array pattern of bores 7910 and 7904 in the microtag holding block 7908 and MICROTUBE microreactor loading block 7902, respectively.

Figure 80:
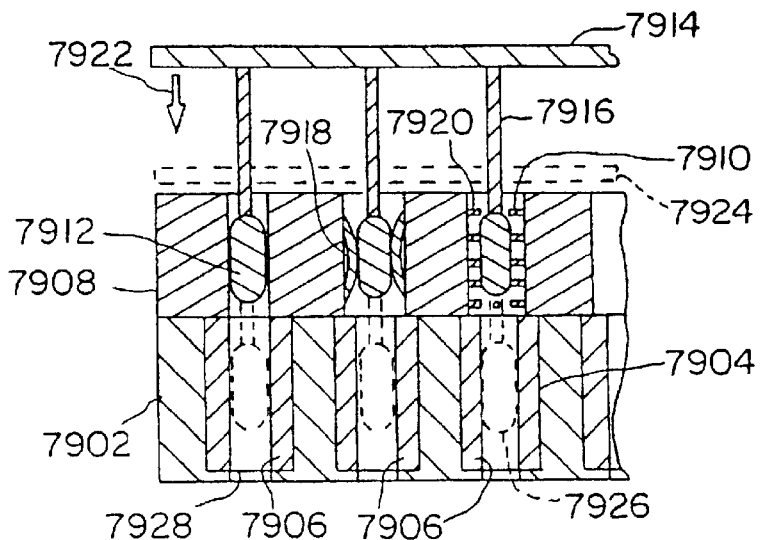
FIG. 80 is a cross-sectional view of the MICROTUBE microreactor assembly system of FIG. 79, showing the insertion of the microtag into the MICROTUBE microreactor.

FIG. 80 is a cross-sectional view of the system 7900 showing the insertion of microtags into a number of MICROTUBE microreactors with MICROTUBE microreactor loading block 7902. In the insertion configuration for this preferred embodiment, loading block 7902 is pre-loaded with a MICROTUBE microreactor 7906 in each bore 7904. Immediately adjacent to the top surface of loading block 7902 is the holding block 7908 which is pre-loaded with a microtag 7912 in each bore 7910. Importantly, each bore 7910 in the holding block 7908 is substantially aligned with a corresponding bore 7904 in loading block 7902. Plunger plate 7914 is positioned with each of its plungers 7916 inside a corresponding bore 7910 of the holding block 7908. As shown, the plunger plate 7914 is moved in direction 7922 to second position 7924 such that each of the plungers 7916 simultaneously urges its respective microtag 7912 from the holding block 7908 into a second position 7926 within the loading block 7902. Following the insertion of the microtags 7912 into a respective MICROTUBE microreactor 7906, the plunger plate 7914 and holding block 7908 are removed from loading block 7902. The MICROTUBE microreactors may then me removed from the loading block, and used for solid phase synthesis and screening and the other applications, including as described elsewhere herein.

The holding block as shown in FIG. 80 has a number of bores 7910. Each of these bores are shown having a different retaining device to retain the microtag within the bore 7910. For example, the left-most bore 7910 is sized to retain microtag 7912 by friction generated between the microtag and the inside wall of the bore 7910. Additionally, the holding block may be manufactured from a pliable material which would be sufficiently resilient to allow the easy insertion and removal of the microtags, however, also provide sufficient contact force to hold the microtag securely within the bore 7910. Such a material, for example, could include vinyl or Teflon, or any other materials which exhibit similar strength and rigidity.

The center bore 7910 shown in FIG. 80 includes a pair of flexible members 7918 which are either pre-formed within the bore, or are inserted after manufacturing of the holding block. Alternatively, the right-most bore 7910 includes a number of pliable fingers 7920 which are positioned within the bore to allow easy insertion and removal of the microtag, while retaining the microtag in position during the assembly process. In any case, it should be appreciated that any variety of retaining techniques are contemplated herein, so long as the microtags are retained in place pending insertion into the MICROTUBE microreactors, or other vessels disclosed herein.

Figure 81:
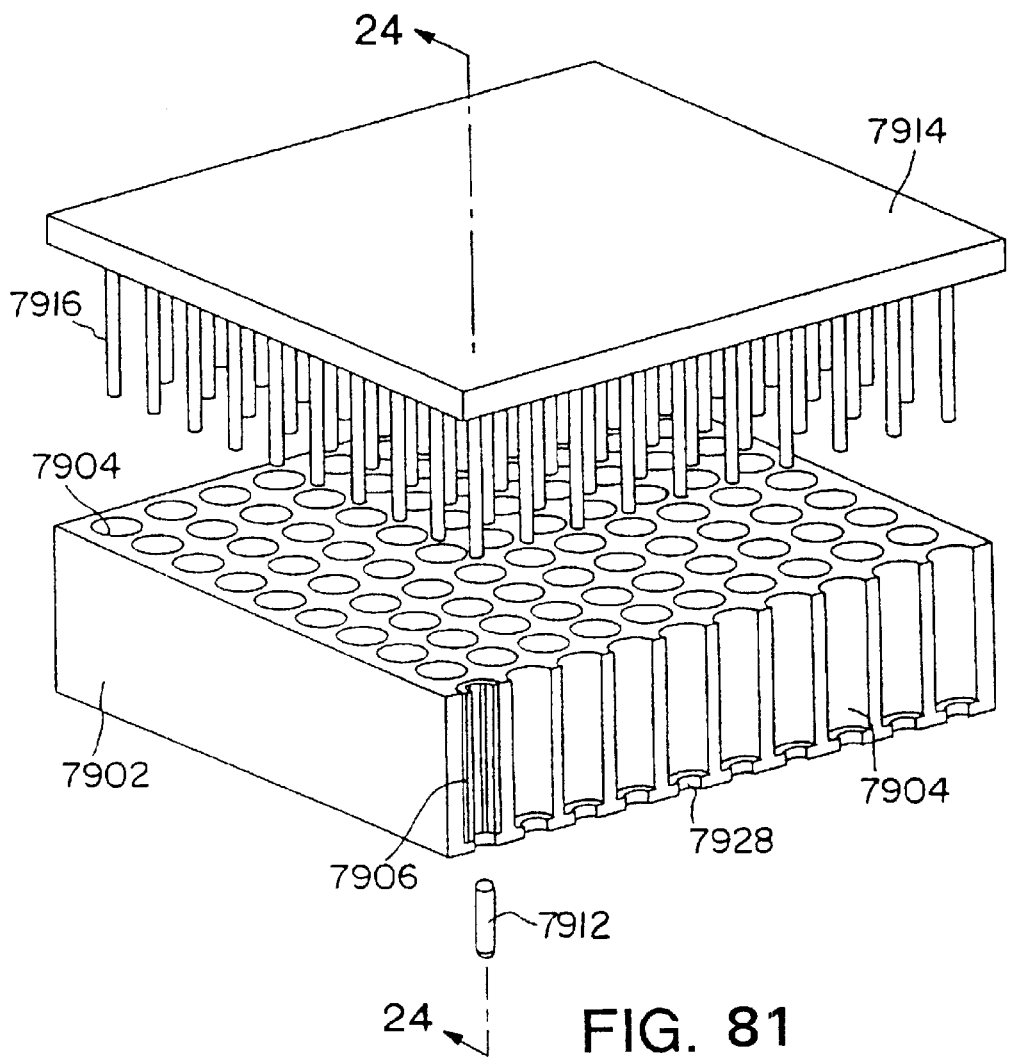
FIG. 81 is a cross-sectional view of the MICROTUBE microreactor assembly system of FIG. 79, showing the removal of a microtag from a MICROTUBE microreactor.

Referring now to FIG. 81, the MICROTUBE microreactor assembly system 7900 is shown in the ejection configuration with portions of the loading block 7902 cut away for clarity. Loading lock 7902 is shown having a MICROTUBE microreactor 7906 installed in a bore 7904. Plunger plate 7914 is positioned above the loading block 7902 such that the plungers 7916 align with a corresponding bore 7904 and MICROTUBE microreactor 7906.

Figure 82:
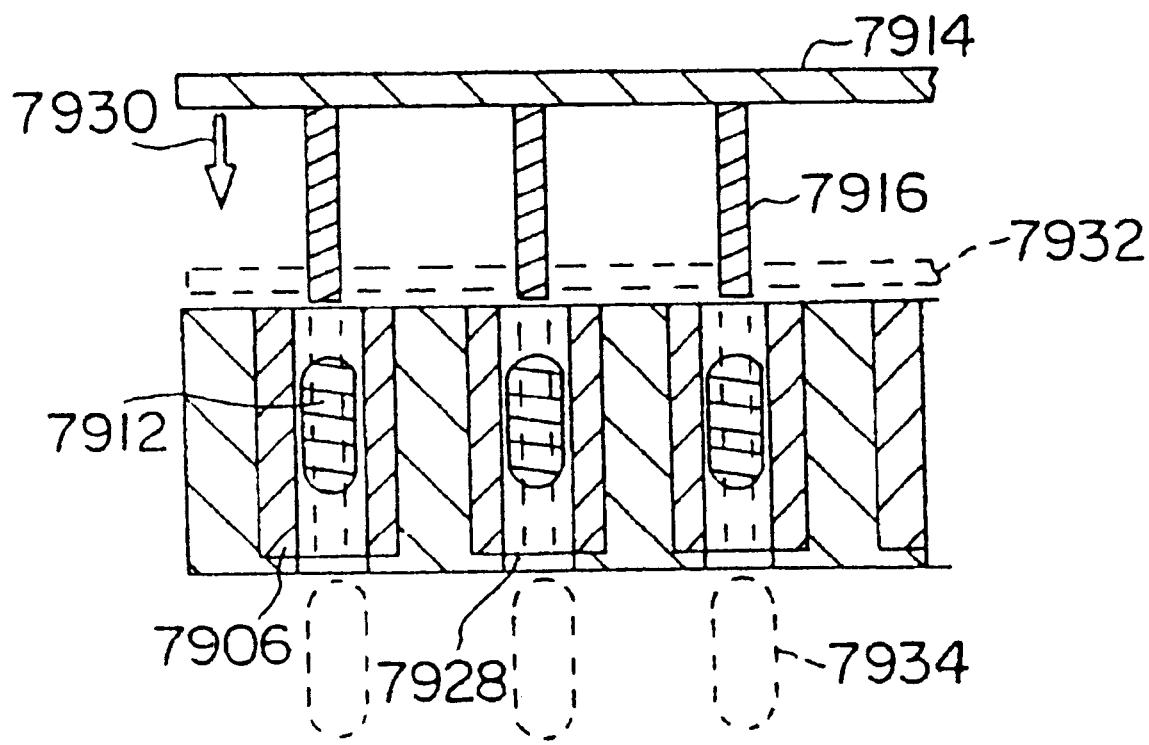
FIG. 82 is a cross-sectional view of the MICROTUBE microreactor assembly system of FIG. 81, showing the removal process for removing a microtag from a MICROTUBE microreactor.

FIG. 82 is a cross-sectional view of the loading block 7902 and plunger plate 7914 which shows the positioning of the plungers 7916 inside bore 7904 and MICROTUBE microreactor 7906. As the plunger plate is advanced in direction 7930 towards the loading block to second position 7932, plungers 7916 enter MICROTUBE microreactor 7906 and strike microtag 7912 which is thereby advanced from its position within the MICROTUBE microreactor 7906, through the ejection port 7928, and to an ejected position 7934.

The pre-loading of the holding block 7908 may be accomplished by manually inserting a microtag into each bore 7910, or the holding block may be provided from the manufacture pre-loaded with the microtags. Similarly, the loading block may be loaded with the necessary MICROTUBE microreactors manually, or may also be provided pre-loaded from the manufacturer.

Since modifications will be apparent to those of skill in this art, it is intended that this invention be limited only by the scope of the appended claims.

What is claimed:

1. A system for use in solid phase synthesis comprising:
   a plurality of combinations of matrices with memories, each combination of matrix with memory comprising a combination of a matrix material for supporting solid phase synthesis and a remotely-accessible memory containing encoded data for uniquely identifying each matrix with memory;
   an identification station for identifying each matrix with memory when the matrix with memory is disposed within a reading range of the identification station;
   a plurality of synthesis containers, each synthesis container adapted for receiving one or more selected matrices with memories, each synthesis container containing a solution comprising a building block for solid phase synthesis on the selected matrices with memories;
   a host computer in electrical communication with the identification station and having a database comprising a plurality of synthesis sequences, each synthesis sequence comprising a plurality of steps for synthesizing a molecule or biological particle from a plurality of building blocks and, each synthesis sequence corresponding to an identified matrix with memory, wherein the host computer determines a destination of the identified matrix with memory, the destination comprising a pre-determined synthesis container of the plurality of synthesis containers; and
   a positioning means responsive to the host computer for moving the matrix with memory to the predetermined destination.

2. The system of claim 1, further comprising means for generating a cue that identifies the pre-determined synthesis container to the positioning means.

3. The system of claim 2, wherein the means for generating the cue is removably mounted on the destination container.

4. The system of claim 1, wherein the remotely-accessible memory comprises an optically-readable symbol and the identification station comprises:
   a light emitter and a light detector, wherein by placing a matrix with memory near the light emitter, light is reflected from the optically-readable symbol to the light detector which decodes the reflected light and yields the unique identity of the matrix with memory.

5. The system of claim 1, wherein the remotely-accessible memory comprises an electronic memory connected to a transceiver and the identification station comprises:
   an electromagnetic transmitter for generating an electromagnetic field;
   and an electromagnetic receiver, wherein placing a matrix with memory within the electromagnetic field activates the memory which in turn transmits information included within the memory to the electromagnetic receiver.

6. The system of claim 1, further comprising a data base within the host computer having a plurality of data fields comprising records of the matrices with memories and records of the plurality of synthesis containers, wherein the host computer contains links between the data fields whereby the synthesis container is determined by reading data contained within the memory of the matrix with memory.

7. The system of claim 6, wherein the plurality of data fields further includes a data field comprising records containing identifying or historical information pertaining to the matrix with memory.

8. The system of claim 2, further comprising:
   a feeding means for separating a single matrix with memory from a plurality of matrices with memories and disposing the single matrix with memory within the reading range of the identification station for identification of the single matrix with memory, wherein the feeding means is connected to the positioning means.

9. The system of claim 8, further comprising a removable drawer disposed adjacent the positioning means for containing an array of synthesis containers, wherein the positioning means has a range of movement adapted to cover the array of synthesis containers in the drawer.

10. The system of claim 8, wherein the feeding means comprises a vibratory feeder.

11. The system of claim 8, further comprising a programmable logic controller for controlling communication between the host computer and each of the identification station, the positioning means, and the feeding means.

12. The system of claim 11, wherein the programmable logic controller is programmed:
   (a) to receive a feed signal from the host computer and direct the vibratory feeder to advance the matrix with memory to the identification station, and
   (b) following identification of the matrix with memory, to receive a location signal from the host computer and direct the positioning means to place the matrix with memory in the pre-determined synthesis container.

13. The system of claim 11, wherein the positioning means further comprises:
   a first motor attached to a first arm for moving along one of an X-axis and a Y-axis; and
   a second motor attached to a second arm that is further attached to the first arm for moving along the other of the X-axis and the Y-axis.

14. The system of claim 12, further comprising a feedback means for providing feedback to the programmable logic controller to monitor the identification station, the positioning means, and the feeding means.

15. The system of claim 1, wherein the matrix material is of a size such that at least one dimension is no more than about 20 mm, or the matrix material is in the form of a container or solid surface used for chemical syntheses, or the matrix material comprises a plurality of solid support particles contained within a microvessel.

16. The system of claim 15, wherein the remotely-accessible memory is an electronic memory.

17. The system of claim 15, wherein the remotely-accessible memory is an optical memory.

18. The system of claim 17, wherein the optical memory is an optically-readable symbol imprinted on the matrix material.

19. The system of claim 18, wherein the optically-readable symbol is a bar code.

20. The system of claim 19, wherein the bar code is a two-dimensional bar code.

21. The system of claim 15, wherein at least one surface of the matrix material or portion thereof that is sufficient to serve as a support is derivatized for linking molecules or biological particles.

22. The system claim 15, wherein the matrix with memory further comprises a molecule, a biological particle, a mixture of molecules, a mixture of biological particles, or a mixture of both molecules and biological particles.

23. The system of claim 15, wherein the matrix material comprises a plurality of solid support particles contained within a structure with a cavity formed therein for retaining the plurality of solid support particles and having at least one porous wall enclosing the cavity for permitting the building block to enter the cavity.

24. The system of claim 15, wherein the matrix with memory is about 20 mm or less in size in the largest dimension.

25. The system of claim 15, wherein the matrix material comprises an elongated tube.

26. The system of claim 15, wherein the elongated tube has two ends and walls of porous or semi-permeable non-reactive material and the two ends are sealed.

27. The system of claim 24, wherein each solid support particle is about 50 $\mu$m–200 $\mu$m in its largest dimension or smaller.

28. The system of claim 15, wherein the matrix material further comprises associated luminescent moieties.

29. The system of claim 1, wherein
   at least a portion of the matrix material is treated to render it suitable for use as a support matrix for molecules or biological particles.

30. The system of claim 1, wherein the remotely-readable memory comprises an optically-readable symbol imprinted on the matrix material, wherein:
   the optical memory is readable by an optical detector;
   the optical memory is in contact with or is part of the matrix material;
   at least a portion of the matrix material is treated to render it suitable for use as a support matrix for molecules or biological particles.

31. The system of claim 1, where a surface or a portion thereof of the matrix material is radiation grafted with a monomer that is derivatized for linking molecules or biological particles.

32. The system of claim 2, wherein the cue includes an audible signal.

33. The system of claim 2, wherein the cue includes a visually-detectable signal.

34. The system of claim 2, wherein the visually-detectable signal is light from a light emitting diode and the diode is selectively illuminated to indicate a proper destination or an improper destination.

35. The system of claim 15, wherein the matrix material is in the form of a cube or other parallelopiped having an outer surface wherein at least a portion of the outer surface has been treated for linkage of molecules or biological particles.

36. An automated system for use in solid phase synthesis comprising:
   a plurality of matrices with memories, each matrix with memory comprising a combination of a matrix material for supporting solid phase chemical synthesis and a remotely-accessible memory containing encoded data for uniquely identifying each matrix with memory;
   a vibratory feeder having a bowl for retaining a plurality of matrices with memories, the vibratory feeder having an output for feeding matrices with memories out of the bowl;

a supply tube having a first end disposed at the output for receiving matrices with memories, and a second end;

a turnstile disposed at the second end of the supply tube adapted to receive the matrices with memories, the turnstile being rotatable to isolate a single matrix with memory for release from a turnstile release;

a positioning tube disposed at the turnstile release for receiving the matrix with memory;

a releasable stop for temporarily retaining the matrix with memory within the positioning tube;

an identification station adjacent the releasable stop having an antenna adapted to interrogate the matrix with memory when the releasable stop is activated;

a plurality of synthesis containers, each synthesis container adapted for receiving one or more selected matrices with memories, each synthesis container containing a solution comprising a building block for solid phase synthesis on the selected matrices with memories;

a positioner adapted for placing the matrix with memory into a pre-determined synthesis container of the plurality of synthesis containers; and a computer in electrical communication with the identification station, the positioner, the turnstile and the releasable stop, the computer having a database comprising a plurality of synthesis sequences, each synthesis sequence comprising a plurality of steps for synthesizing a molecule or biological particle from a plurality of building blocks, wherein each synthesis sequence corresponds to an identified matrix with memory and the computer identifies the predetermined synthesis container for placement of the identified matrix with memory for performing the next step in the synthesis sequence.

37. The automated sorter of claim 36, wherein the releasable stop comprises a gating solenoid having a plunger adapted to penetrate the positioning tube so as to prevent the passage of the matrix with memory when the solenoid is activated.

38. The automated sorter of claim 37, wherein the positioner further comprises a first linear translator connected to the positioning tube for translating the positioning tube to a location over the designated container.

39. The automated sorter of claim 36, wherein the positioner comprises:

a first arm for providing movement along one of an X-axis and a Y-axis; and a second arm connected to the first arm for providing movement along the other of the X-axis and the Y-axis, the second arm being attached to the positioning tube;

wherein movement along the first arm and the second arm provide for two dimensional positioning of the positioning tube over the designated container.

40. The automated sorter of claim 39, further comprising:

a programmable logic controller in electrical communication with the positioner;

a first motor driver in electrical communication with the programmable logic controller for controlling translation of the first arm in response to a first signal from the programmable logic controller;

a second motor driver in electrical communication with the programmable logic controller for controlling translation of the second arm in response to a second signal from the programmable logic controller; and a solenoid for retracting the releasable stop to release the memory system in response to a third signal from the programmable logic controller.

41. An automated system for use in solid phase synthesis comprising:

a plurality of matrices-with-memories, each matrix-with-memory comprising a matrix material for supporting solid phase synthesis in physical contact with a remotely-accessible memory containing encoded data for uniquely identifying each matrix with memory;

an array of synthesis containers adapted for receiving one or more selected matrices with memories, each synthesis container containing a solution comprising a building block for solid phase synthesis on the selected matrices with memories;

a feeder having a vessel for receiving the plurality of matrices-with-memories and a vessel outlet for feeding the plurality of matrices-with-memories one at a time out of the vessel;

a singulator means connected to vessel outlet for receiving the plurality of matrices-with-memories and dispensing a single matrix-with-memory of the plurality of matrices-with-memories;

a positioning means disposed for receiving the matrix-with-memory dispensed from the singulator means, wherein the positioning means holds the matrix-with-memory until a release signal is received;

a gating means within the positioning means responsive to the release signal for retaining the matrix-with-memory within the positioning means and releasing the matrix-with-memory when the release signal is received;

an identification station disposed within a reading distance of the positioning means for reading data stored within the matrix-with-memory when the matrix-with memory is held within the positioning means, wherein the identification station generates a data signal comprising information corresponding to the matrix-with-memory;

a translator for moving the positioning means in response to a positioning signal for positioning the matrix-with-memory over a pre-determined synthesis container within the array of synthesis containers; and a system controller in electrical communication with the positioning means, the gating means, the translator and the identification station, the system controller having a database comprising a plurality of synthesis sequences, each synthesis sequence comprising a plurality of steps for synthesizing a molecule or biological particle from a plurality of building blocks and each synthesis sequence corresponding to an identified matrix with memory, wherein the system controller receives the data signal and associates the information therein with a corresponding synthesis sequence of the plurality of synthesis sequences to determine a next step within the synthesis sequence, identifies the pre-determined synthesis container corresponding to the next step within the synthesis sequence, generates the positioning signal for moving the positioning means to the pre-determined synthesis container, and generates the release signal for releasing the matrix-with-memory from the positioning means into the pre-determined synthesis container.

42. An automated system for use in solid phase synthesis comprising:

a plurality of matrices with memories, each matrix with memory comprising a combination of a matrix material for supporting solid phase synthesis and a remotely-accessible memory containing encoded data for uniquely identifying each matrix with memory;

a plurality of synthesis containers adapted for receiving one or more selected matrices with memories, each synthesis container containing a solution comprising a building block for solid phase synthesis on the selected matrices with memories;

a singulator for advancing a single matrix with memory;

a dynamic dropper for receiving the matrix with memory from the singulator;

an identification station for reading data stored within the matrix-with-memory when the matrix-with memory is held within the dynamic dropper, wherein the identification station generates a data signal comprising information corresponding to the matrix-with-memory;

a means for positioning the dynamic dropper above a pre-determined synthesis container corresponding to a next step in a solid phase synthesis sequence, wherein the matrix with memory is dropped into the pre-determined synthesis container; and a computer in electrical communication with the identification station and the positioning means and having a database comprising a plurality of synthesis sequences, each synthesis sequence comprising a plurality of steps for synthesizing a molecule or biological particle from a plurality of building blocks and each synthesis sequence corresponding to an identified matrix with memory, wherein the host computer determines a destination of the identified matrix with memory, the destination comprising a pre-determined synthesis container of the plurality of synthesis containers.

43. An automated system for use in solid phase synthesis comprising:

a plurality of matrices-with-memories, each matrix with memory comprising a combination of a matrix material for supporting solid phase synthesis and a remotely-accessible memory containing encoded data for uniquely identifying each matrix with memory, a feeder having a vessel for receiving the plurality of matrices-with-memories and a vessel outlet for feeding the plurality of matrices-with-memories one at a time out of the vessel;

a singulator means connected to the vessel outlet for receiving the plurality of matrices-with-memories and dispensing a single matrix-with-memory;

a positioning means disposed for receiving the matrix-with-memory dispensed from the singulator means, wherein the positioning means holds the matrix-with-memory until a release signal is received;

a gating means within the positioning means responsive to the release signal for retaining the matrix-with-memory within the positioning means and releasing the matrix-with-memory when the release signal is received;

an identification station disposed within a reading distance of the positioning means for reading data stored within the matrix-with-memory when the matrix-with memory is held within the positioning means, wherein the identification station generates a data signal comprising information corresponding to the matrix-with-memory;

a plurality of synthesis containers, each synthesis container adapted for receiving one or more selected matrices with memories after release from the positioning means, wherein each synthesis container contains a reagent comprising a building block for solid phase synthesis on the selected matrices with memories;

a controller including a database comprising a plurality of synthesis sequences, each synthesis sequence comprising a plurality of steps for synthesizing a biological particle or molecule; and an X-Y translator for moving the positioning means along an X-axis and a Y-axis in response to a positioning signal for positioning the matrix-with-memory over a pre-determined synthesis container containing the reagent corresponding to the next step in the synthesis sequence;

wherein the controller receives the data signal and associates the information therein with the next step in the solid phase synthesis sequence, for identifying a location of the synthesis container corresponding to the next step within the synthesis sequence, for generating the positioning signal for moving the positioning means to the synthesis container, and for generating the release signal for releasing the matrix-with-memory from the positioning means into the synthesis container.

44. The automated system of claim 43, wherein the vessel outlet includes an orientation means for feeding the plurality of matrices-with-memories to the singulator means with a pre-determined orientation.

45. The automated system of claim 43, wherein the singulator means comprises:

a body having an angled bore disposed therethrough for receiving the matrix-with-memory so that the matrix-with-memory slides from an upper end to a lower end of the angled bore; and a gating solenoid in electrical communication with the controller, the gating solenoid for gating the release of the matrix-with-memory from the angled bore in response to a gating signal generated by the controller.

46. The automated system of claim 45, wherein the gating solenoid comprises two gating solenoids, each gating solenoid receiving a separate gating signal from the controller.

47. The automated system of claim 45, wherein the singulator means further includes a plurality of position sensors for sensing a position of the matrix-with-memory within the angled bore and for generating and providing a plurality of position signals to the controller for indicating the position within the angled bore.

48. The automated system of claim 47, wherein the controller receives a first position signal of the plurality of position signals and generates the gating signal in response thereto.

49. The automated system of claim 47, wherein the identification station is disposed near an exit of the singulator means, and the controller generates a command for activating the identification station in response to a second position signal of the plurality of position signals.

50. The automated system of claim 43, wherein the singulator means comprises:

a turnstile having at least one slot for receiving the matrix-with-memory, the turnstile being rotatable around an axis so that the at least one slot for receiving the matrix-with-memory can be rotated to an exit position for releasing the matrix-with-memory; and a drive means in electrical communication with the controller for rotating the turnstile in response to a rotation signal generated by the controller.

51. The automated system of claim 43, wherein the controller comprises a programmable logic controller and a host computer for running a plurality of software programs including a synthesis manager program for associating the information for the matrix-with-memory with one or more steps in a corresponding synthesis sequence.

52. The automated system of claim 51, wherein the plurality of software programs includes a sorter interface program for controlling the programmable logic controller in coordination with the synthesis manager program.

53. The automated system of claim 51, wherein the synthesis manager program generates a searchable record corresponding to each matrix-with-memory and each compound to be synthesized in the corresponding synthesis sequence.

54. The automated system of claim 53, wherein the host computer further includes a graphic display, and the synthesis manager program generates a display of a map of the plurality of matrices-with-memories and the container associated with each matrix-with-memory.

55. The automated system of claim 53, wherein the host computer further includes a graphic display, and the synthesis manager program generates a display of the building block for each compound to be synthesized in the corresponding synthesis sequence.

56. The automated system of claim 52, wherein the plurality of software programs includes a template program for identifying a pre-determined layout for the plurality of synthesis containers, the template program being interactive with the synthesis manager program and the sorter interface program.

57. The automated system of claim 52, wherein the plurality of software programs includes a calibration program for calibrating movement of the X-Y translator for a plurality of increments along the X-axis and the Y-axis.

58. The system of claim 1, wherein the molecule or biological particle is selected from the group consisting of monomers, nucleotides, amino acids, small molecules, antigens, antibodies, ligands, proteins, nucleic acids, phage and viral particles, and cells.

* * * * *